United States Patent
Fan et al.

(10) Patent No.: US 11,773,091 B2
(45) Date of Patent: *Oct. 3, 2023

(54) 6-5 FUSED RINGS AS C5A INHIBITORS

(71) Applicant: CHEMOCENTRYX, INC., San Carlos, CA (US)

(72) Inventors: Pingchen Fan, Hayward, CA (US); Christopher W. Lange, Hayward, CA (US); Rebecca M. Lui, Mountain View, CA (US); Viengkham Malathong, Mountain View, CA (US); Venkat Reddy Mali, Cupertino, CA (US); Sreenivas Punna, Sunnyvale, CA (US); Rajinder Singh, Belmont, CA (US); Hiroko Tanaka, Mountain View, CA (US); Yibin Zeng, Foster City, CA (US); Penglie Zhang, Foster City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,283

(22) Filed: May 3, 2022

(65) Prior Publication Data

US 2023/0151002 A1    May 18, 2023

Related U.S. Application Data

(63) Continuation of application No. 16/723,433, filed on Dec. 20, 2019, now Pat. No. 11,384,079, which is a continuation of application No. 15/991,703, filed on May 29, 2018, now Pat. No. 10,562,896.

(60) Provisional application No. 62/513,010, filed on May 31, 2017.

(51) Int. Cl.
| C07D 471/04 | (2006.01) |
| A61P 37/02 | (2006.01) |
| C07D 519/00 | (2006.01) |

(52) U.S. Cl.
CPC ............ C07D 471/04 (2013.01); A61P 37/02 (2018.01); C07D 519/00 (2013.01)

(58) Field of Classification Search
CPC ...... C07D 471/04; C07D 519/00; A61P 37/02
See application file for complete search history.

(56) References Cited

U.S. PATENT DOCUMENTS

| 4,500,525 | A | 2/1985 | Winters et al. |
| 4,925,846 | A | 5/1990 | Deacon et al. |
| 6,893,659 | B2 | 5/2005 | Abramovici et al. |
| 7,145,012 | B2 | 12/2006 | Carpino |
| 7,230,024 | B2 | 6/2007 | Carpino et al. |
| 7,531,531 | B2 | 5/2009 | Fancelli et al. |
| 7,541,354 | B2 | 6/2009 | Fancelli et al. |
| 7,902,179 | B2 | 3/2011 | Tanaka et al. |
| 8,445,515 | B2 | 5/2013 | Fan et al. |
| 8,846,949 | B2 | 9/2014 | Winters et al. |
| 8,883,808 | B2 | 11/2014 | Bonaventure et al. |
| 8,906,938 | B2 | 12/2014 | Fan et al. |
| 9,126,939 | B2 | 9/2015 | Fan et al. |
| 9,573,897 | B2 | 2/2017 | Fan et al. |
| 10,035,768 | B2 | 7/2018 | Fan et al. |
| 10,329,314 | B2 | 6/2019 | Fan et al. |
| 10,562,896 | B2 * | 2/2020 | Fan .................. A61P 37/02 |
| 10,683,294 | B2 | 6/2020 | Fan et al. |
| 10,759,807 | B2 | 9/2020 | Fan et al. |
| 10,828,285 | B2 | 11/2020 | Fan et al. |
| 11,384,079 | B2 * | 7/2022 | Fan .................. C07D 471/04 |

(Continued)

FOREIGN PATENT DOCUMENTS

| CN | 103421006 | 12/2013 |
| RU | 2550508 C2 | 5/2015 |

(Continued)

OTHER PUBLICATIONS

U.S. Appl. No. 11/485,737, filed Nov. 1, 2022, Fan et al.

(Continued)

*Primary Examiner* — D Margaret M Seaman

(74) *Attorney, Agent, or Firm* — Mintz Levin Cohn Ferris Glovsky and Popeo PC

(57) ABSTRACT

The present disclosure provides, inter alia, Compounds of Formula (I)

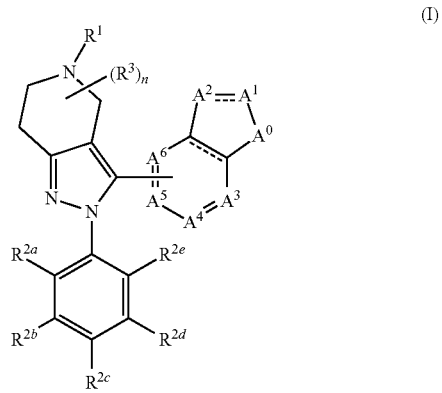

or pharmaceutically acceptable salts thereof that are modulators of the C5a receptor. Also provided are pharmaceutical compositions and methods of use including the treatment of diseases or disorders involving pathologic activation from C5a and non-pharmaceutical applications.

20 Claims, No Drawings

(56) References Cited

U.S. PATENT DOCUMENTS

| | | |
|---|---|---|
| 11,478,460 B2 | 10/2022 | Fan et al. |
| 11,479,553 B2 | 10/2022 | Fan et al. |
| 2004/0116425 A1 | 6/2004 | Li et al. |
| 2004/0147546 A1 | 7/2004 | Tanaka et al. |
| 2004/0214855 A1 | 10/2004 | Carpino et al. |
| 2004/0214856 A1 | 10/2004 | Carpino et al. |
| 2006/0205948 A1 | 9/2006 | Carpino et al. |
| 2007/0112015 A1 | 5/2007 | Hurt et al. |
| 2008/0267887 A1 | 10/2008 | Yuan et al. |
| 2010/0311753 A1 | 12/2010 | Fan et al. |
| 2011/0275639 A1 | 11/2011 | Fan et al. |
| 2012/0149734 A1 | 6/2012 | Biftu et al. |
| 2013/0184253 A1 | 7/2013 | Adams et al. |
| 2014/0051688 A1 | 2/2014 | Winters et al. |
| 2015/0141425 A1 | 5/2015 | Fan et al. |
| 2017/0065604 A1 | 3/2017 | Fan et al. |
| 2017/0114017 A1 | 4/2017 | Fan et al. |
| 2019/0060321 A1 | 2/2019 | Fan et al. |
| 2019/0062275 A1 | 2/2019 | Fan et al. |
| 2019/0300526 A1 | 10/2019 | Fan et al. |
| 2021/0052612 A1 | 2/2021 | Fan et al. |
| 2023/0115912 A1 | 4/2023 | Fan et al. |

FOREIGN PATENT DOCUMENTS

| | | |
|---|---|---|
| TW | 201803850 A | 2/2018 |
| WO | 02/049993 A2 | 6/2002 |
| WO | 02/049993 A3 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/018460 A1 | 3/2004 |
| WO | 2004/043925 A2 | 5/2004 |
| WO | 2004/043925 A3 | 5/2004 |
| WO | 2004/094421 A1 | 11/2004 |
| WO | 2004/094429 A1 | 11/2004 |
| WO | 2004/100975 A1 | 11/2004 |
| WO | 2005/007087 A2 | 1/2005 |
| WO | 2005/007087 A3 | 1/2005 |
| WO | 2007/019083 A1 | 2/2007 |
| WO | 2008/024978 A2 | 2/2008 |
| WO | 2009/155565 | 12/2009 |
| WO | 2010/075257 A1 | 7/2010 |
| WO | 2011/163640 A2 | 12/2011 |
| WO | 2013/016197 A1 | 1/2013 |
| WO | 2014/028805 A1 | 2/2014 |
| WO | 2015/086512 A1 | 6/2015 |
| WO | 2017/176620 A2 | 10/2017 |
| WO | 2019/126424 A1 | 6/2019 |
| WO | 2019/126431 A1 | 6/2019 |
| WO | 2019/195159 A1 | 10/2019 |

OTHER PUBLICATIONS

International Search Report and Written Opinion dated Aug. 24, 2018 corresponding to PCT/US2018/034905 filed May 29, 2018 (13 pages).

International Search Report and Written Opinion dated Aug. 23, 2018 corresponding to PCT/US2018/034908 filed May 29, 2018 (13 pages).

International Search Report and Written Opinion dated Mar. 25, 2019 corresponding to PCT/US2018/066667 filed Dec. 20, 2018 (7 pages).

International Search Report and Written Opinion dated Mar. 22, 2019 corresponding to PCT/US2018/066677 filed Dec. 20, 2018 (7 pages).

Extended European Search Report completed Aug. 27, 2020 corresponding to EP 18809537 (4 pages).

Extended European Search Report completed Aug. 27, 2020 corresponding to EP 18809125 (4 pages).

Extended European Search Report completed Apr. 19, 2021 corresponding to EP 18890906 (6 pages).

Extended European Search Report completed May 7, 2021 corresponding to EP 18890906 (8 pages).

An, GuiPeng et al., "Role of C5a-C5aR axis in the development of atherosclerosis," *Sci China Life Sci* (2014; accepted Jul. 8, 2014) 57:790-794.

Bao, Lihua et al., "C5a promotes development of experimental lupus nephritis which can be blocked with a specific receptor antagonist," *Eur. J. Immunol.* (Jun. 20, 2005); 35:2496-2506.

Cravedi, P. et al., "Immune Cell-Derived C3a and C5a Costimulate Human T Cell Alloimmunity," *Am. J. Transplant* (Jun. 27, 2013); 13(10):2530-2539.

Darling, Victoria R. et al., "Immunological Effects and Therapeutic Role of C5a in Cancer," *Expert Rev Clin Immunol.* (Feb. 1, 2015); 11(2):255-263.

Guo, Ren-Feng et al., "Role of C5a in Inflammatory Responses," *Annu. Rev. Immunol.* (Jan. 7, 2005); 23:821-852.

Huber-Lang, Markus S. et al., "Role of Complement in Multi-Organ Dysfunction," *The Complement System*, Abstract, (@ 2004; Print/DOI: 10.1007/1-4020-8056-5_22); pp. 465-480.

Lee, Hyun et al., "Receptors for complement C5a. The importance of C5aR and the enigmatic role of C5L2," *Immunology and Cell Biology* (Jan. 29, 2008); 86:153-160.

Lu, Yi et al., "C5a stimulates the proliferation of breast cancer cells via akt-dependent RGC-32 gene activation," *Oncology Reports* (2014; Accepted Aug. 14, 2014); 32:2817-2823.

Pandey, Manoj Kumar, "Molecular Basis for Downregulation of C5a-Mediated Inflammation by IgG1 Immune Complexes in Allergy and Asthma," *Curr Allergy Asthma Rep* (Sep. 8, 2013) 13:596-606.

Seow, Vernon et al., "Inflammatory Responses Induced by Lipopolysaccharide Are Amplified in Primary Human Monocytes but Suppressed in Macrophages by Complement Protein C5a," *J Immunol* (2013; prepublished online Sep. 16, 2013) 191:4308-4316.

Strachan A.J. et al., "A New Small Molecule C5a Receptor Antagonist Inhibits the Reverse-Passive Arthus Reaction and Endotoxic Shock in Rats," *The Journal of Immunology*, (Apr. 6, 2000); 164:6560-6565.

Winters, Michael P. et al., "Discovery and SAR of novel tetrahydropyrrolo[3,4-c]pyrazoles as inhibitors of the N-type calcium channel," *Bioorg. Med. Chem. Lett.* (avail online Mar. 27, 2014); 24:2053-2056.

Woodruff T.M. et al., "A Potent Human C5a Receptor Antagonist Protects against Disease Pathology in a Rat Model of Inflammatory Bowel Disease," *The Journal of Immunology* (Nov. 15, 2003); 171:5514-5520.

U.S. Appl. No. 17/931,801, filed Sep. 13, 2022, Fan et al.

International Search Report dated Jul. 19, 2019 corresponding to PCT/US2019/025165 filed Apr. 1, 2019; 14 pages.

Extended European Search Report dated Dec. 1, 2021 corresponding to EP19782402.2 filed Apr. 1, 2019; 8 pages.

\* cited by examiner

6-5 FUSED RINGS AS C5A INHIBITORS

CROSS-REFERENCES TO RELATED APPLICATIONS

This application is a continuation of U.S. patent application Ser. No. 16/723,433 filed Dec. 20, 2019 which is a continuation of Ser. No. 15/991,703 filed May 29, 2018 which is an application claiming benefit under 35 U.S.C. § 119(e) of U.S. Provisional Application No. 62/513,010 filed on May 31, 2017, each of which is herein incorporated by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The complement system plays a central role in the clearance of immune complexes and in immune responses to infectious agents, foreign antigens, virus infected cells and tumor cells.

Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, *In Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, a and P, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498 (1980)).

C5 is cleaved into the C5a and C5b fragments during activation of the complement pathways. The convertase enzymes responsible for C5 activation are multi-subunit complexes of C4b, C2a, and C3b for the classical pathway and of $(C3b)_2$, Bb, and P for the alternative pathway (Goldlust, M. B. et al., *J. Immunol.* 113: 998-1007 (1974); Schreiber, R. D. et al, *Proc. Natl. Acad. Sci.* 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. Both C5a and C3a are potent stimulators of neutrophils and monocytes (Schindler, R. et al., *Blood* 76: 1631-1638 (1990); Haeffner-Cavaillon, N. et al., *J. Immunol.* 138: 794-700 (1987); Cavaillon, J. M. et al., *Eur. J. Immunol.* 20: 253-257 (1990)).

In addition to its anaphylatoxic properties, C5a induces chemotactic migration of neutrophils (Ward, P. A. et al., *J. Immunol.* 102: 93-99 (1969)), eosinophils (Kay, A. B. et al., *Immunol.* 24: 969-976 (1973)), basophils (Lett-Brown, M. A. et al., *J. Immunol.* 117: 246-252 1976)), and monocytes (Snyderman, R. et al., *Proc. Soc. Exp. Biol. Med.* 138: 387-390 1971)). Both C5a and C5b-9 activate endothelial cells to express adhesion molecules essential for sequestration of activated leukocytes, which mediate tissue inflammation and injury (Foreman, K. E. et al., *J. Clin. Invest.* 94: 1147-1155 (1994); Foreman, K. E. et al., *Inflammation* 20: 1-9 (1996); Rollins, S. A. et al., *Transplantation* 69: 1959-1967 (2000)). C5a also mediates inflammatory reactions by causing smooth muscle contraction, increasing vascular permeability, inducing basophil and mast cell degranulation and inducing release of lysosomal proteases and oxidative free radicals (Gerard, C. et al., *Ann. Rev. Immunol.* 12: 775-808 (1994)). Furthermore, C5a modulates the hepatic acute-phase gene expression and augments the overall immune response by increasing the production of TNF-α, IL-1-β, IL-6, IL-8, prostaglandins and leukotrienes (Lambris, J. D. et al., *In: The Human Complement System in Health and Disease*, Volanakis, J. E. ed., Marcel Dekker, New York, pp. 83-118).

The anaphylactic and chemotactic effects of C5a are believed to be mediated through its interaction with the C5a receptor. The human C5a receptor (C5aR) is a 52 kD membrane bound G protein-coupled receptor, and is expressed on neutrophils, monocytes, basophils, eosinophils, hepatocytes, lung smooth muscle and endothelial cells, and renal glomerular tissues (Van-Epps, D. E. et al., *J. Immunol.* 132: 2862-2867 (1984); Haviland, D. L. et al., *J Immunol.* 154:1861-1869 (1995); Wetsel, R. A., *Immunol.*

Leff. 44: 183-187 (1995); Buchner, R. R. et al., 25 *J. Immunol.* 155: 308-315 (1995); Chenoweth, D. E. et al., *Proc. Natl. Acad. Sci.* 75: 3943-3947 (1978); Zwirner, J. et al., *Mol. Immunol.* 36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxy-terminal end (amino acids 62-74) (Wetsel, R. A., *Curr. Opin. Immunol.* 7: 48-53 (1995)).

C5a plays important roles in inflammation and tissue injury. In cardiopulmonary bypass and hemodialysis, C5a is formed as a result of activation of the alternative complement pathway when human blood makes contact with the artificial surface of the heart-lung machine or kidney dialysis machine (Howard, R. J. et al., *Arch. Surg.* 123: 1496-1501 (1988); Kirklin, J. K. et al., *J. Cardiovasc. Surg.* 86: 845-857 (1983); Craddock, P. R. et al., *N. Engl. J. Med.* 296: 769-774 (1977)). C5a causes increased capillary permeability and edema, bronchoconstriction, pulmonary vasoconstriction, leukocyte and platelet activation and infiltration to tissues, in particular the lung (Czermak, B. J. et al., *J. Leukoc. Biol.* 64: 40-48 (1998)). Administration of an anti-C5a monoclonal antibody was shown to reduce cardiopulmonary bypass and cardioplegia-induced coronary endothelial dysfunction (Tofukuji, M. et al., *J. Thorac. Cardiovasc. Surg.* 116: 1060-1068 (1998)).

C5a is also involved in acute respiratory distress syndrome (ARDS), Chronic Obstructive Pulmonary Disorder (COPD) and multiple organ failure (MOF) (Hack, C. E. et al., *Am. J. Med.* 1989: 86: 20-26; Hammerschmidt DE et al. *Lancet* 1980; 1: 947-949; Heideman M. et al. *J. Trauma* 1984; 4: 1038-1043; Marc, M M, et al., *Am. J. Respir. Cell andMol. Biol.*, 2004: 31: 216-219). C5a augments monocyte production of two important pro-inflammatory cytokines, TNF-α and IL-1. C5a has also been shown to play an important role in the development of tissue injury, and particularly pulmonary injury, in animal models of septic shock (Smedegard G et al. *Am. J. Pathol.* 1989; 135: 489-497; Markus, S., et al., *FASEB Journal* (2001), 15: 568-570). In sepsis models using rats, pigs and non-human primates, anti-C5a antibodies administered to the animals before treatment with endotoxin or *E. coli* resulted in decreased tissue injury, as well as decreased production of IL-6 (Smedegard, G. et al., *Am. J. Pathol.* 135: 489-497 (1989); Hopken, U. et al., *Eur. J. Immunol.* 26: 1103-1109 (1996); Stevens, J. H. et al., *J. Clin. Invest.* 77: 1812-1816 (1986)). More importantly, blockade or C5a with anti-C5a polyclonal antibodies has been shown to significantly improve survival rates in a caecal ligation/puncture model of sepsis in rats (Czermak, B. J. et al., *Nat. Med.* 5: 788-792 (1999)). This model share many aspects of the clinical manifestation of sepsis in humans. (Parker, S. J. et al., *Br. J. Surg.* 88: 22-30 (2001)). In the same sepsis model, anti-C5a antibodies were shown to inhibit apoptosis of thymocytes (Guo, R. F. et al., *J. Clin. Invest.* 106: 1271-1280 (2000)) and prevent MOF (Huber-Lang, M. et al., *J. Immunol.* 166: 1193-1199 (2001)). Anti-C5a antibodies were also protective in a cobra venom factor model of lung injury in rats, and in immune complex-induced lung injury (Mulligan, M. S. et al. *J. Clin. Invest.* 98: 503-512 (1996)). The importance of C5a in immune complex-mediated lung injury was later confirmed in mice (Bozic, C. R. et al., *Science* 26: 1103-1109 (1996)).

C5a is found to be a major mediator in myocardial ischemia-reperfusion injury. Complement depletion reduced myocardial infarct size in mice (Weisman, H. F. et al., *Science* 249: 146-151 (1990)), and treatment with anti-C5a antibodies reduced injury in a rat model of hindlimb ischemia-reperfusion (Bless, N. M. et al., *Am. J. Physiol.* 276: L57-L63 (1999)). Reperfusion injury during myocardial infarction was also markedly reduced in pigs that were retreated with a monoclonal anti-C5a IgG (Amsterdam, E. A. et al., *Am. J. Physiol.* 268:H448-H457 (1995)). A recombinant human C5aR antagonist reduces infarct size in a porcine model of surgical revascularization (Riley, R. D. et al., *J. Thorac. Cardiovasc. Surg.* 120: 350-358 (2000)).

C5a driven neutrophils also contribute to many bullous diseases (e.g., bullous pemphigoid, *Pemphigus vulgaris* and *Pemphigus foliaceus*). These are chronic and recurring inflammatory disorders clinically characterized by sterile blisters that appear in the sub-epidermal space of the skin and mucosa. While autoantibodies to keratinocytes located at the cutaneous basement membranes are believed to underlie the detachment of epidermal basal keratinocytes from the underlying basement membrane, blisters are also characterized by accumulation of neutrophils in both the upper dermal layers and within the blister cavities. In experimental models a reduction of neutrophils or absence of complement (total or C5-selective) can inhibit formation of sub-epidermal blisters, even in the presence of high auto-antibody titers.

Complement levels are elevated in patients with rheumatoid arthritis (Jose, P. J. et al., *Ann. Rheum. Dis.* 49: 747-752 (1990); Grant, E. P., et al., *J. of Exp. Med.*, 196(11): 1461-1471, (2002)), lupus nephritis (Bao, L., et al., *Eur. J. of Immunol.*, 35(8), 2496-2506, (2005)) and systemic lupus erythematosus (SLE) (Porcel, J. M. et al., *Clin. Immunol. Immunopathol.* 74: 283-288 (1995)). C5a levels correlate with the severity of the disease state. Collagen-induced arthritis in mice and rats resembles the rheumatoid arthritic disease in human. Mice deficient in the C5a receptor demonstrated a complete protection from arthritis induced by injection of monoclonal anti-collagen Abs (Banda, N. K., et al., J. of Immunol., 2003, 171: 2109-2115). Therefore, inhibition of C5a and/or C5a receptor (C5aR) could be useful in treating these chronic diseases.

The complement system is believed to be activated in patients with inflammatory bowel disease (IBD) and is thought to play a role in the disease pathogenesis. Activated complement products were found at the luminal face of surface epithelial cells, as well as in the muscularis mucosa and submucosal blood vessels in IBD patients (Woodruff, T. M., et al., *J of lmmunol.*, 2003, 171: 5514-5520).

C5aR expression is upregulated on reactive astrocytes, microglia, and endothelial cells in an inflamed human central nervous system (Gasque, P. et al., *Am. J. Pathol.* 150: 31-41 (1997)). C5a might be involved in neurodegenerative diseases, such as Alzheimer disease (Mukherjee, P. et al., *J. Neuroimmunol.* 105: 124-130 (2000); O'Barr, S. et al., *J. Neuroimmunol.* (2000) 105: 87-94; Farkas, I., et al. *J. Immunol.* (2003) 170:5764-5771), Parkinson's disease, Pick disease and transmissible spongiform encephalopathies. Activation of neuronal C5aR may induce apoptosis (Farkas I et al. *J. Physiol.* 1998; 507: 679-687). Therefore, inhibition of C5a and/or C5aR could also be useful in treating neurodegenerative diseases.

There is some evidence that C5a production worsens inflammation associated with atopic dermatitis (Neuber, K., et al., *Immunology* 73:83-87, (1991)), and chronic urticaria (Kaplan, A. P., *J. Allergy Clin. Immunol.* 114; 465-474, (2004).

Psoriasis is now known to be a T cell-mediated disease (Gottlieb, E. L. et al., *Nat. Med.* 1: 442-447 (1995)). However, neutrophils and mast cells may also be involved in the pathogenesis of the disease (Terui, T. et al., *Exp. Dermatol.* 9: 1-10; 2000); Werfel, T. et al., *Arch. Dermatol. Res.* 289: 83-86 (1997)). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. T cells and neutrophils are chemo-attracted by C5a (Nataf, S. et al., *J. Immunol.* 162: 4018-4023 (1999); Tsuji, R. F. et al., *J. Immunol.* 165: 1588-1598 (2000); Cavaillon, J. M. et al., *Eur. J. Immunol.* 20: 253-257 (1990)). Additionally expression of C5aR has been demonstrated in plasmacytoid dendritic cells (pDC) isolated from lesions of cutaneous lupus erythematous and these cells were shown to display chemotactic behavior towards C5a, suggesting that blockade of C5aR on pDC might be efficacious in reducing pDC infiltration into inflamed skin in both SLE and psoriasis. Therefore C5a could be an important therapeutic target for treatment of psoriasis.

Immunoglobulin G-containing immune complexes (IC) contribute to the pathophysiology in a number of autoimmune diseases, such as systemic lupus erthyematosus, rheumatoid arthritis, Sjögren's disease, Goodpasture's syndrome, and hypersensitivity pneumonitis (Madaio, M. P., *Semin. Nephrol.* 19: 48-56 (1999); Korganow, A. S. et al., *Immunity* 10: 451-459 (1999); Bolten, W. K., *Kidney Int.* 50: 1754-1760 (1996); Ando, M. et al., *Curr. Opin. Pulm. Med.* 3: 391-399 (1997)). These diseases are highly heterogeneous and generally affect one or more of the following organs: skin, blood vessels, joints, kidneys, heart, lungs, nervous system and liver (including cirrhosis and liver fibrosis). The classical animal model for the inflammatory response in these IC diseases is the Arthus reaction, which features the infiltration of polymorphonuclear cells, hemorrhage, and plasma exudation (Arthus, M., C. R. Soc. Biol. 55: 817-824 (1903)). Recent studies show that C5aR deficient mice are protected from tissue injury induced by IC (Kohl, J. et al., *Mol. Immunol.* 36: 893-903 (1999); Baumann, U. et al., *J. Immunol.* 164: 1065-1070 (2000)). The results are consistent with the observation that a small peptidic anti-C5aR antagonist inhibits the inflammatory response caused by IC deposition (Strachan, A. J. et al., *J. Immunol.* 164: 6560-6565 (2000)). Together with its receptor, C5a plays an important role in the pathogenesis of IC diseases. Inhibitors of C5a and C5aR could be useful to treat these diseases.

DESCRIPTION OF RELATED ART

Non-peptide based C5a receptor antagonist have been reported as being effective for treating endotoxic shock in rats (Stracham, A. J., et al., *J. of Immunol.* (2000), 164(12): 6560-6565); and for treating IBD in a rat model (Woodruff, T. M., et al., *J of Immunol.*, 2003, 171: 5514-5520). Non-peptide based C5a receptor modulators also have been described in the patent literature by Neurogen Corporation, (e.g., WO2004/043925, WO2004/018460, WO2005/007087, WO03/082826, WO03/08828, WO02/49993, WO03/084524); Dompe S.P.A. (WO02/029187); The University of Queenland (WO2004/100975); and ChemoCentryx (WO2010/075257).

There is considerable experimental evidence in the literature that implicates increased levels of C5a with a number of diseases and disorders, in particular in autoimmune and inflammatory diseases and disorders. Thus, there remains a need in the art for new small organic molecule modulators, e.g., agonists, preferably antagonists, partial agonists, of the C5a receptor (C5aR) that are useful for inhibiting pathogenic events, e.g., chemotaxis, associated with increased levels anaphylatoxin activity. The present invention fulfills this and other needs.

BRIEF SUMMARY OF THE INVENTION

In one aspect, the present invention provide compounds of Formula (I):

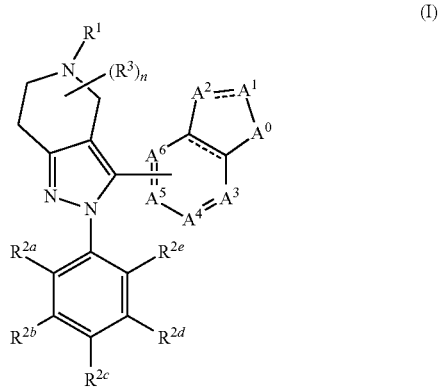

or a pharmaceutically acceptable salt thereof, wherein,
ring vertex $A^0$ is NH or C(O);
each of ring vertices $A^1$ and $A^3$ are independently selected from the group consisting of N, NH, CH, C(O) and C($R^4$);
each of ring vertices $A^2$, $A^5$ and $A^6$ is independently selected from the group consisting of N, CH, and C($R^4$);
ring vertex $A^4$ is selected from the group consisting of N, N($C_{1-4}$ alkyl), CH, and C($R^4$); and no more than two of $A^3$, $A^4$, $A^5$ and $A^6$ are N;
each of the dashed bonds independently is a single or double bond;
$R^1$ is selected from the group consisting of heteroaryl, $C_{6-10}$ aryl, —$C_{1-8}$ alkylene-heteroaryl, —$C_{1-8}$alkylene-$C_{6-10}$aryl, $C_{3-5}$ cycloalkyl, four to eight membered heterocycloalkyl, $C_{1-8}$ alkyl, $C_{1-8}$ haloalkyl, —C(O)NR$^{1a}$R$^{1b}$, and —CO$_2$R$^{1a}$; wherein the heterocycloalkyl group is a 4 to 8 membered ring having from 1 to 3 heteroatoms as ring vertices selected from N, O and S; the heteroaryl group is a 5 to 10 membered aromatic ring having from 1 to 3 heteroatoms as ring vertices selected from N, O and S;
wherein $R^{1a}$ and $R^{1b}$ are each independently selected from the group consisting of hydrogen, $C_{1-8}$ alkyl, $C_{6-10}$aryl, and —$C_{1-6}$ alkylene-$C_{6-10}$aryl;
wherein $R^1$ is optionally substituted with 1 to 5 $R^5$ substituents;
$R^{2a}$ and $R^{2e}$ are each independently selected from the group consisting of $C_{1-6}$ alkyl, $C_{1-6}$ alkoxy, $C_{1-6}$haloalkyl, —O—$C_{1-6}$ haloalkyl, —S—$C_{1-6}$ alkyl, —$C_{1-6}$ alkyl-O—$C_{1-6}$ alkyl, —$C_{1-6}$alkyl-S—$C_{1-6}$ alkyl, CN, and halogen;
$R^{2b}$, $R^{2c}$, and $R^{2d}$ are each independently selected from the group consisting of hydrogen, $C_{1-6}$alkyl, $C_{1-6}$alkoxy, $C_{1-6}$ haloalkyl,—O—$C_{1-6}$haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, cyano, and halogen;

each $R^3$ is independently selected from the group consisting of $C_{1-4}$ alkyl, $C_{1-4}$haloalkyl and hydroxyl, and optionally two $R^3$ groups on the same carbon atom are combined to form oxo (=O);

each $R^4$ is independently selected from the group consisting of $C_{1-6}$ alkyl, $C_{1-6}$ alkoxy, $C_{1-6}$hydroxyalkyl, $C_{1-6}$ haloalkyl, $C_{1-6}$ haloalkoxy, —O—$C_{1-6}$ haloalkyl, halogen, cyano, hydroxyl, —S—$C_{1-6}$ alkyl, —$C_{1-6}$ alkyl-O—$C_{1-6}$ alkyl, —$C_{1-6}$ alkyl-S—$C_{1-6}$ alkyl, —$NR^{4a}R^{4b}$, —$CONR^{4a}R^{4b}$, —$CO_2R^{4a}$, —$COR^{4a}$, —OC(O)$NR^{4a}R^{4b}$, —$NR^{4a}C(O)R^{4b}$, —$NR^{4a}C(O)_2R^{4b}$, and —$NR^{4a}$—$C(O)NR^{4a}R^{4b}$; each $R^{4a}$ and $R^{4b}$ is independently selected from the group consisting of hydrogen, $C_{1-4}$ alkyl, and $C_{1-4}$ haloalkyl;

each $R^5$ is independently selected from the group consisting of $C_{1-8}$ alkyl, $C_{1-8}$ alkoxy, $C_{1-8}$ haloalkyl, $C_{1-8}$ haloalkoxy, $C_{1-8}$ hydroxyalkyl, —$C_{1-8}$ alkyl-heterocycloalkyl, —$C_{1-8}$ alkyl-$C_{3-8}$ cycloalkyl, $C_{3-6}$ cycloalkyl, heterocycloalkyl, halogen, OH, $C_{2-8}$ alkenyl, $C_{2-8}$ alkynyl, CN, $C(O)R^{5a}$, —$NR^{5b}C(O)R^{5a}$, —$CONR^{5a}R^{5b}$, —$NR^{5a}R^{5b}$, —$C_{1-8}$ alkylene-$NR^{5a}R^{5b}$, —S—$C_{1-6}$alkyl, —$C_{1-6}$ alkyl-O—$C_{1-6}$ alkyl, —$C_{1-6}$ alkyl-S—$C_{1-6}$alkyl, —$OC(O)NR^{5a}R^{5b}$, —$NR^{5a}C(O)_2R^{5b}$, —$NR^{5a}$—$C(O)NR^{5b}R^{5b}$ and $CO_2R^{5a}$; wherein the heterocycloalkyl group is a 4 to 8 membered ring having from 1 to 3 heteroatoms as ring vertices selected from N, O and S; wherein each $R^{5a}$ and $R^{5b}$ is independently selected from the group consisting of hydrogen, $C_{1-4}$ alkyl, and $C_{1-4}$ haloalkyl, or when attached to the same nitrogen atom $R^{5a}$ and $R^{5b}$ are combined with the nitrogen atom to form a five or six-membered ring having from 0 to 1 additional heteroatoms as ring vertices selected from N, O, or S; and the subscript n is 0, 1, 2 or 3.

In addition to the compounds provided herein, the present invention further provides pharmaceutical compositions containing one or more of these compounds, as well as methods for the use of these compounds in therapeutic methods, primarily to treat diseases associated C5a signaling activity.

In yet another aspect, the present invention provides methods of diagnosing disease in an individual. In these methods, the compounds provided herein are administered in labeled form to a subject, followed by diagnostic imaging to determine the presence or absence of C5aR and/or the localization of cells expressing a C5aR receptor. In a related aspect, a method of diagnosing disease is carried out by contacting a tissue or blood sample with a labeled compound as provided herein and determining the presence, absence, amount, or localization of C5aR in the sample.

BRIEF DESCRIPTION OF THE DRAWINGS

NOT APPLICABLE

DETAILED DESCRIPTION OF THE INVENTION

Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), isobutenyl, 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2] octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The term "hydroxyalkyl" is used in its conventional sense, and refers to branched or straight chain alkyl group substituted with at least one hydroxyl group. The hydroxyl group may be at any position in the alkyl group. For example, the term "$C_{1-4}$hydroxylalkyl" is meant to include hydroxymethyl, hydroxyethyl, hydroxypropyl, hydroxyisopropyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzooxazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, pyrrolopyridyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, a wavy line, "~", that intersects a single, double or triple bond in any chemical structure depicted herein, represent the point attachment of the single, double, or triple bond to the remainder of the molecule.

DESCRIPTION OF THE EMBODIMENTS

Compounds

In one aspect, the present invention provides compounds of Formula (I):

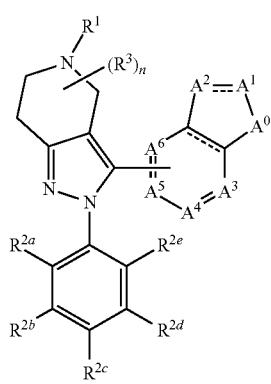

or a pharmaceutically acceptable salt thereof, wherein,
ring vertex $A^0$ is NH or C(O);
each of ring vertices $A^1$ and $A^3$ are independently selected from the group consisting of N, NH, CH, C(O) and C($R^4$);
each of ring vertices $A^2$, $A^5$ and $A^6$ is independently selected from the group consisting of N, CH, and C($R^4$);
ring vertex $A^4$ is selected from the group consisting of N, N($C_{1-4}$ alkyl), CH, and C($R^4$); and no more than two of $A^3$, $A^4$, $A^5$ and $A^6$ are N;
each of the dashed bonds independently is a single or double bond;
$R^1$ is selected from the group consisting of heteroaryl, $C_{6-10}$ aryl, —$C_{1-8}$ alkylene-heteroaryl, —$C_{1-8}$alkylene-$C_{6-10}$aryl, $C_{3-8}$ cycloalkyl, four to eight membered heterocycloalkyl, $C_{1-8}$ alkyl, $C_{1-8}$ haloalkyl, —C(O)N$R^{1a}R^{1b}$, and —$CO_2R^{1a}$; wherein the heterocycloalkyl group is a 4 to 8 membered ring having from 1 to 3 heteroatoms as ring vertices selected from N, O and S; the heteroaryl group is a 5 to 10 membered aromatic ring having from 1 to 3 heteroatoms as ring vertices selected from N, O and S;
wherein $R^{1a}$ and $R^{1b}$ are each independently selected from the group consisting of hydrogen, $C_{1-8}$ alkyl, $C_{6-10}$aryl, and —$C_{1-6}$ alkylene-$C_{6-10}$aryl;
wherein $R^1$ is optionally substituted with 1 to 5 $R^5$ substituents;
$R^2a$ and $R^{2e}$ are each independently selected from the group consisting of $C_{1-6}$ alkyl, $C_{1-6}$ alkoxy, $C_{1-6}$haloalkyl, —O—$C_{1-6}$ haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, CN, and halogen;
$R^{2b}$, $R^{2c}$, and $R^{2d}$ are each independently selected from the group consisting of hydrogen, $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl-O—$C_{1-6}$ alkyl, —$C_{1-6}$alkyl-S—C1.6 alkyl, cyano, and halogen;
each $R^3$ is independently selected from the group consisting of $C_{1-4}$ alkyl, $C_{1-4}$haloalkyl and hydroxyl, and optionally two $R^3$ groups on the same carbon atom are combined to form oxo (=O);
each $R^4$ is independently selected from the group consisting of $C_{1-6}$ alkyl, $C_{1-6}$ alkoxy, $C_{1-6}$hydroxyalkyl, $C_{1-6}$ haloalkyl, $C_{1-6}$ haloalkoxy, —O—$C_{1-6}$haloalkyl, halogen, cyano, hydroxyl, —S—$C_{1-6}$ alkyl, —$C_{1-6}$ alkyl-O—$C_{1-6}$ alkyl, —$C_{1-6}$ alkyl-S—$C_{1-6}$ alkyl, —N$R^{4a}R^{4b}$, —CON$R^{4a}R^{4b}$, —$CO_2R^{4a}$, —CO$R^{4a}$, —OC(O)N$R^{4a}R^{4b}$, —N$R^{4a}$C(O)$R^{4b}$, —N$R^{4a}$C(O)$_2R^{4b}$, and —N$R^{4a}$—C(O)N$R^{4a}R^{4b}$;
each $R^{4a}$ and $R^{4b}$ is independently selected from the group consisting of hydrogen, $C_{1-4}$ alkyl, and $C_{1-4}$ haloalkyl;
each $R^5$ is independently selected from the group consisting of $C_{1-8}$ alkyl, $C_{1-8}$ alkoxy, $C_{1-8}$haloalkyl, $C_{1-8}$ haloalkoxy, $C_{1-8}$ hydroxyalkyl, —$C_{1-8}$ alkyl-heterocycloalkyl, —$C_{1-8}$alkyl-$C_{3-8}$cycloalkyl, $C_{3-6}$ cycloalkyl, heterocycloalkyl, halogen, OH, $C_{2-8}$ alkenyl, $C_{2-8}$ alkynyl, CN, C(O)$R^{5a}$, —N$R^{5b}$C(O)$R^{5a}$, —CON$R^{5a}R^{5b}$, —N$R^{5a}R^{5b}$, —$C_{1-8}$ alkylene-N$R^{5a}R^{5b}$, —S—$C_{1-6}$alkyl, —$C_{1-6}$alkyl-O—$C_{1-6}$ alkyl, —$C_{1-6}$ alkyl-S—$C_{1-6}$ alkyl, —OC(O)N$R^{5a}R^{5b}$, —N$R^{5a}$C(O)$_2R^{5b}$, —N$R^{5a}$—C(O)N$R^{5b}R^{5b}$ and —$CO_2R^{5a}$; wherein the heterocycloalkyl group is a 4 to 8 membered ring having from 1 to 3 heteroatoms as ring vertices selected from N, O and S;
wherein each $R^{5a}$ and $R^{5b}$ is independently selected from the group consisting of hydrogen, $C_{1-4}$ alkyl, and $C_{1-4}$ haloalkyl, or when attached to the same nitrogen atom $R^{5a}$ and $R^{5b}$ are combined with the nitrogen atom to form a five or six-membered ring having from 0 to 1 additional heteroatoms as ring vertices selected from N, O, or S; and the subscript n is 0, 1, 2 or 3.

Focusing on the ring portion having $A^0$, $A^1$, $A^2$, $A^3$, $A^4$, $A^5$, and $A^6$, in some embodiments, the ring portion having $A^0$, $A^1$, $A^2$, $A^3$, $A^4$, $A^5$, and $A^6$ as ring vertices is a bicyclic heteroaryl selected from

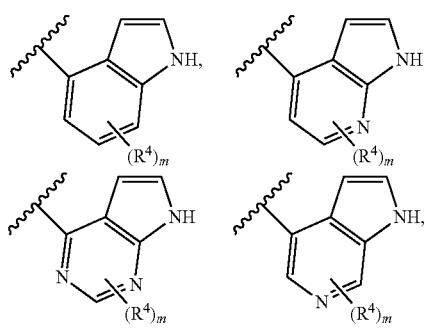

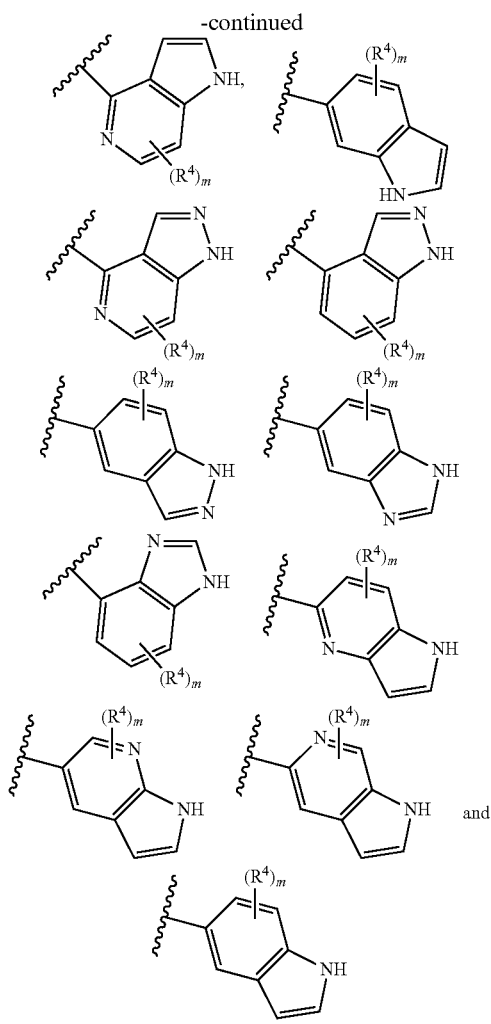

wherein m is 0, 1, 2 or 3; and wherein the $R^4$ substituents may be attached to any suitable carbon ring vertex of the bicyclic heteroaryl.

In some embodiments, the ring portion having $A^0$, $A^1$, $A^2$, $A^3$, $A^4$, $A^5$, and $A^6$ as ring vertices is a bicyclic heteroaryl selected from

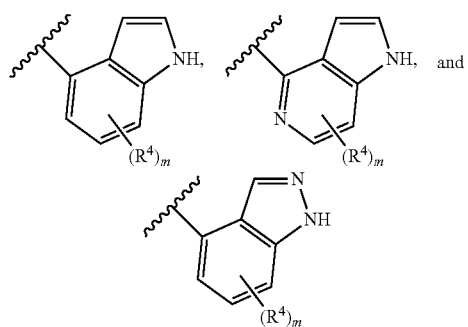

wherein m is 0, 1, 2, or 3.

In some embodiments, the each $R^4$ is independently selected from the group consisting of $C_{1-4}$ alkyl, $C_{1-4}$ alkoxy, $C_{1-6}$ hydroxyalkyl, $C_{1-4}$ haloalkyl, halogen, cyano, hydroxyl, —$NH_2$, —$CONR^{4a}R^{4b}$, and —$CO_2R^{4a}$; wherein $R^{4a}$ and $R^{4b}$ are as defined above, and wherein the $R^4$ substituents may be attached to any suitable carbon ring vertex of the bicyclic heteroaryl.

A person of skill in the art will recognize that particular carbon atoms of the ring portion having $A^0$, $A^1$, $A^2$, $A^3$, $A^4$, $A^5$, and $A^6$ cannot be substituted with $R^4$. For example, the carbon atom linking the bicyclic heteroaryl moiety (i.e. the ring portion having $A^0$, $A^1$, $A^2$, $A^3$, $A^4$, $A^5$, and $A^6$) to the remainder of the molecule and the carbon atoms that are members of both ring systems in the fused bicyclic heteroaryl moiety (i.e. the two carbon atoms that are ring vertices in both the benzene and five-membered ring system) cannot be substituted with $R^4$ because an additional substituent will exceed the valence of these carbon atoms.

In some embodiments, the ring portion having $A^0$, $A^1$, $A^2$, $A^3$, $A^4$, $A^5$, and $A^6$ as ring vertices is a bicyclic heteroaryl selected from

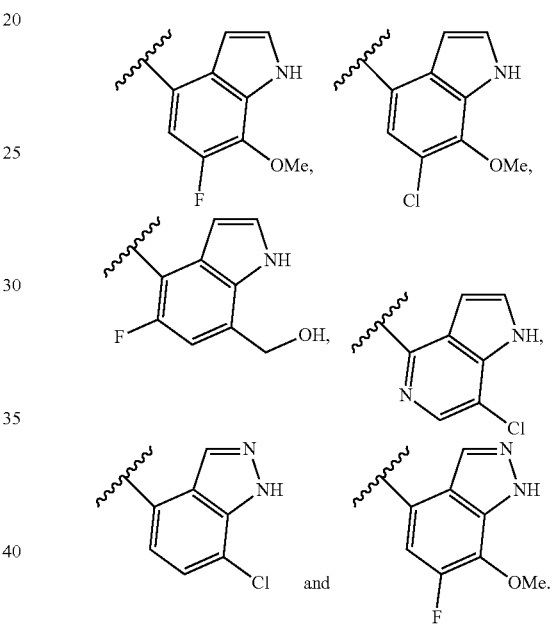

Turning to $R^1$ and optional substituent(s), in some embodiments, $R^1$ is heteroaryl, $C_{6-10}$ aryl, —$C_{1-6}$ alkylene-heteroaryl, —$C_{1-6}$ alkylene-$C_{6-10}$ aryl, four to eight membered heterocycloalkyl, $C_{3-8}$ cycloalkyl, $C_{1-8}$ alkyl, —C(O)NR$^{1a}$R$^{1b}$, and —CO$_2$R$^{1a}$, wherein $R^{1a}$ and $R^{1b}$ and heterocycloalkyl are as defined above; the heteroaryl group is a 5 or 6 membered aromatic ring having from 1 to 3 heteroatoms as ring vertices selected from N, O and S, and wherein $R^1$ is optionally substituted with 1 to 3 $R^5$ substituents.

In some embodiments, heterocycloalkyl groups of $R^1$ or $R^5$ are from 4 to 6 membered rings having from 1 to 3 heteroatoms as ring vertices selected from N, O, and S. In some embodiments, the heteroaryl groups of $R^1$ or $R^5$ are 5 to 6 membered aromatic rings having from 1 to 3 heteroatoms as ring vertices selected from N, O, and S. In some embodiments, the $C_{6-10}$ aryl group of $R^1$ is phenyl.

In some embodiments, $R^1$ is pyridyl, pyrimidyl, pyrazinyl, thiadiazolyl, phenyl, benzyl, cyclopentyl, tetrahydropyranyl, —C(O)NR$^{1a}$R$^{1b}$, —CO$_2$R$^{1a}$, or $C_{1-8}$ alkyl, wherein $R^{1a}$ and $R^{1b}$ are as defined above for Formula I, and wherein $R^1$ is optionally substituted with 1 to 3 $R^5$ substituents.

In some embodiments, $R^1$ is

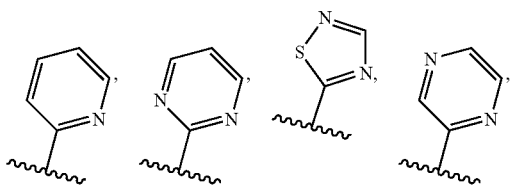

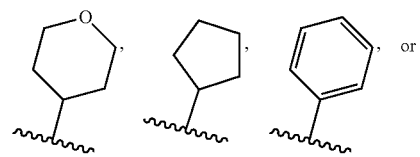

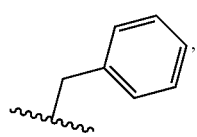

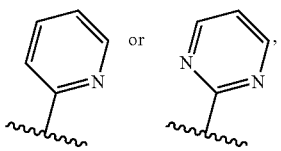 [SMILES: *c1ccccn1 ; *c1ncccn1]

each of which is optionally substituted with 1 to 3 $R^5$ substituents.

In some embodiments, $R^1$ is

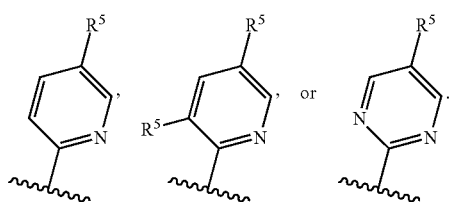

each of which is optionally substituted with 1 or 2 $R^5$ substituents.

In some embodiments, $R^1$ is

In each of the described embodiments of $R^1$, $R^5$ can be as defined above or as further defined as follows.

In some embodiments, each $R^5$ is independently $C_{1-8}$ alkyl, $C_{1-8}$ alkoxy, $C_{1-8}$haloalkyl, $C_{1-8}$ haloalkoxy, $C_{1-8}$ hydroxyalkyl, —$C_{1-8}$ alkyl-heterocycloalkyl, $C_{3-6}$ cycloalkyl, halogen, —$CONR^{5a}R^{5b}$, —$NR^{5a}R^{5b}$, or —$C_{1-8}$ alkylene-$NR^{5a}R^{5b}$, each $R^{5a}$ and $R^{5b}$ is independently selected from the group consisting of hydrogen and $C_{1-4}$ alkyl, or when attached to the same nitrogen atom can be combined with the nitrogen atom to form a 5 or 6-membered ring; and the heterocycloalkyl group is a 4 to 6 membered ring having from 1 to 3 heteroatoms as ring vertices selected from N, O and S.

In some embodiments, $R^5$ is halogen, $C_{1-8}$ alkyl, $C_{1-8}$ haloalkyl, $C_{3-6}$ cycloalkyl, —$C(O)NR^{5a}R^{5b}$, and —$CO_2R^{5a}$, wherein $R^{5a}$ and $R^{5b}$ are as defined above (with reference to Formula I).

In some embodiments, $R^5$ is cyclopropyl, isopropyl, isopropyloxy, OMe, Me, Cl, F, —$CONH_2$, —$CF_3$, —O—$CF_3$

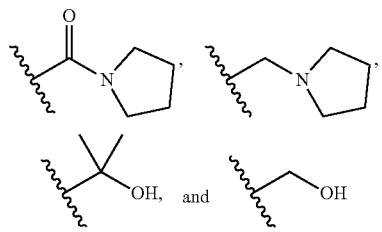

In some embodiments, $R^1$ is

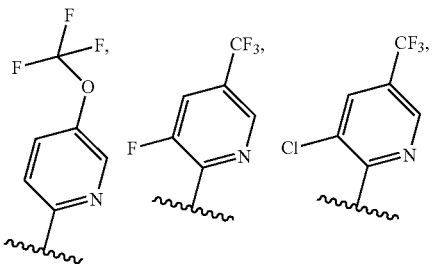

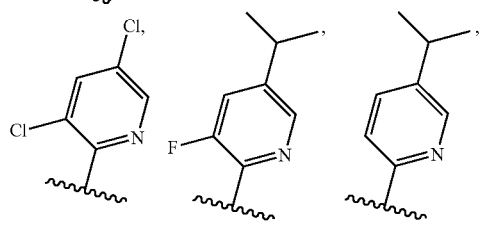

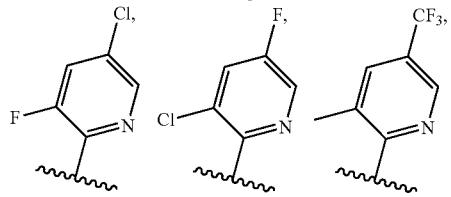

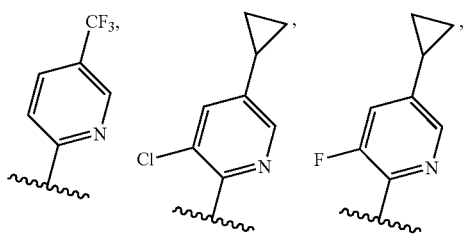

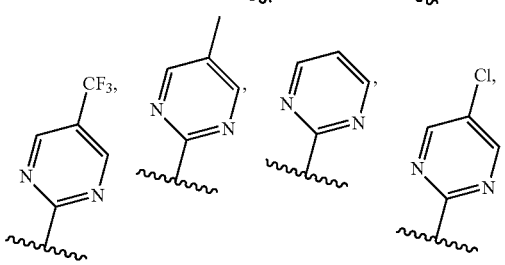

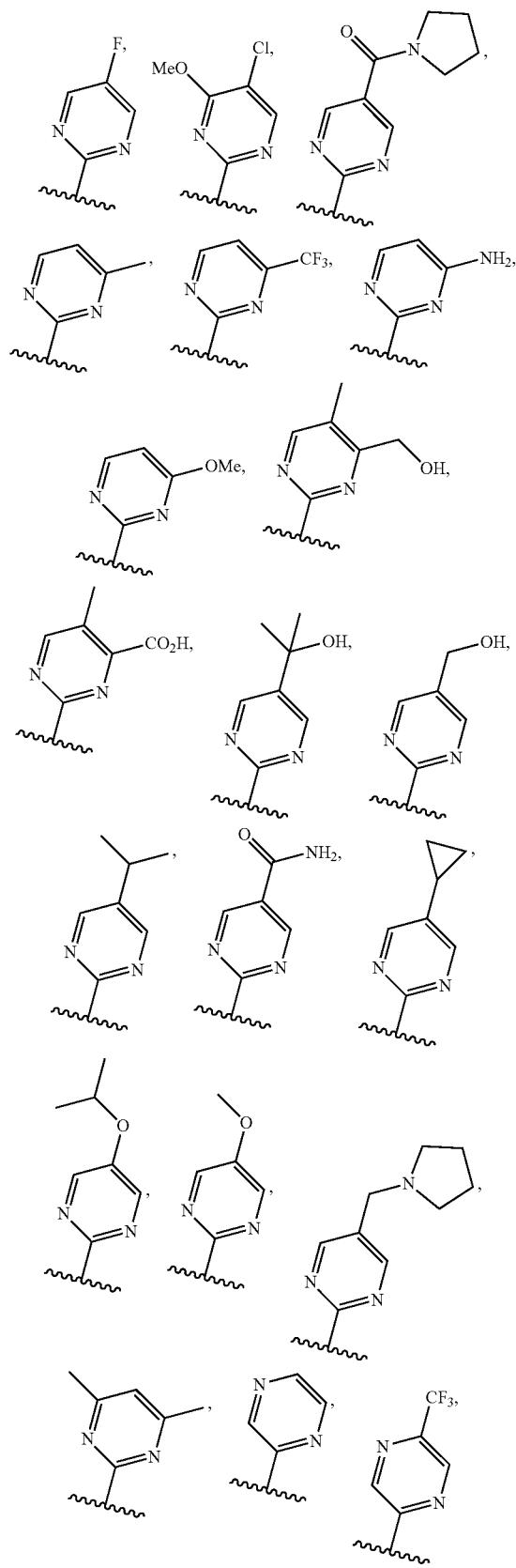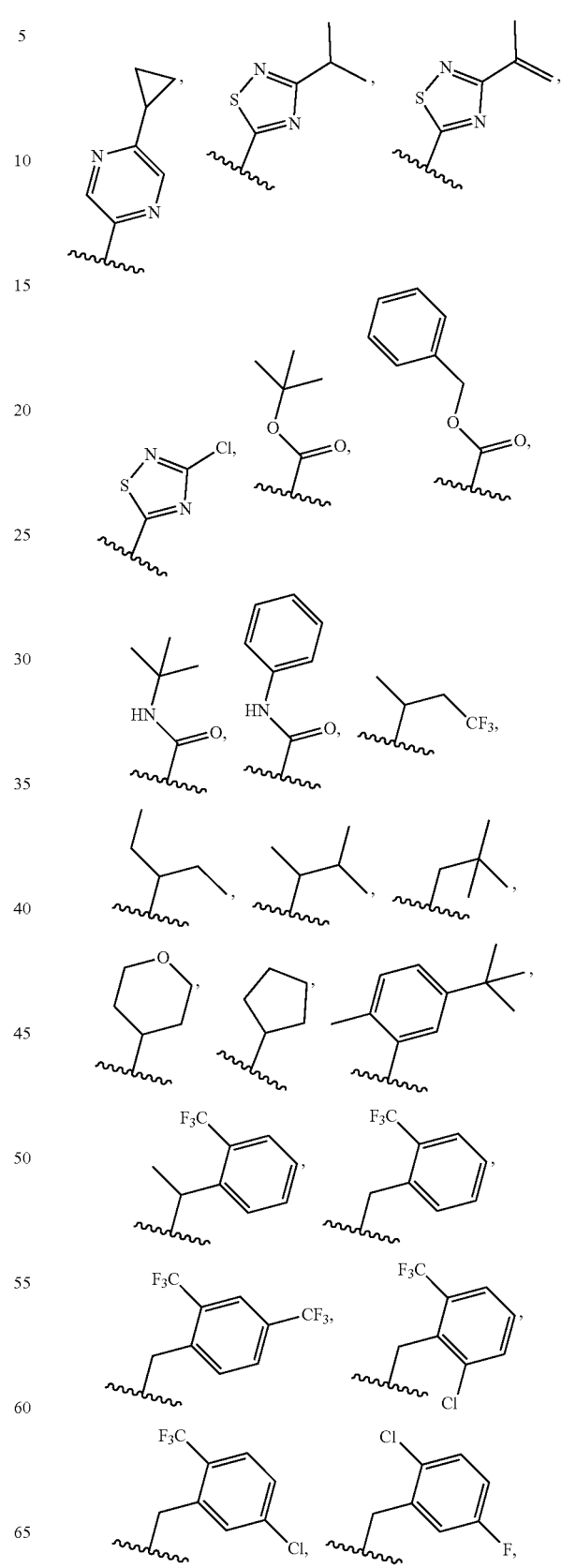

-continued

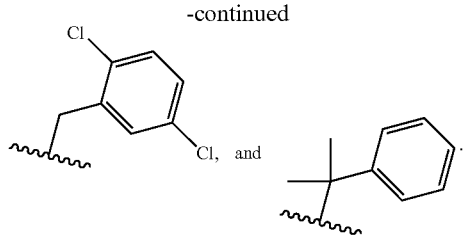

In some embodiments, R¹ is

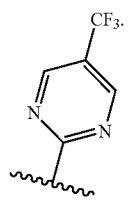

Returning to Formula I and substituents $R^{2a}$, $R^{2b}$, $R^{2c}$, $R^{2d}$, and $R^{2e}$, in some embodiments, $R^{2a}$ and $R^{2e}$ are each independently $C_{1-6}$ alkyl, $C_{1-6}$ alkoxy, $C_{1-6}$ haloalkyl, —O—$C_{1-6}$ haloalkyl, or halogen. In some embodiments, $R^{2b}$, $R^{2c}$, and $R^{2d}$ are independently H, $C_{1-4}$ alkyl, $C_{1-4}$ haloalkyl, or halogen.

In some embodiments, $R^{2b}$, $R^{2c}$, and $R^{2d}$ are each H.

In some embodiments, $R^{2a}$ and $R^{2e}$ are each independently Me, Et, F, Cl, OMe, OCF₃, and

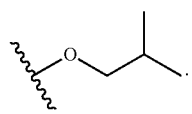 [SMILES: *OCC(C)C]

In some embodiments, $R^{2a}$ and $R^{2e}$ are each independently $C_{1-6}$ alkyl or $C_{1-6}$ haloalkyl.

In some embodiments, $R^{2a}$ and $R^{2e}$ are each independently methyl or ethyl. In some embodiments, $R^{2a}$ and $R^{2e}$ are both methyl or are both ethyl.

In some embodiments, the portion of Formula I represented by

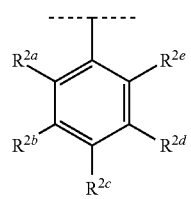

is

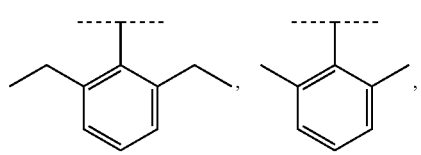

-continued

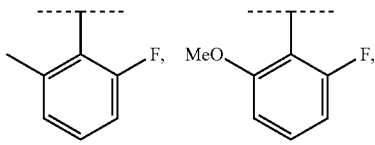

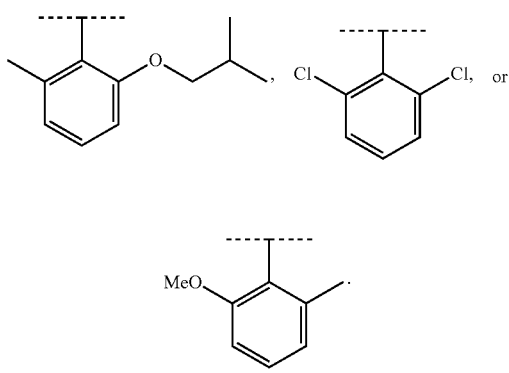

Each R³ of Formula I, in some embodiments, is independently $C_{1-4}$ alkyl, or when two R³ groups are on the same carbon atom, they are combined to form oxo (=O).

In some embodiments, n, the subscript of R³, is 0. In some embodiments n is 2 and the two R³ groups are on the same carbon atom and are combined to form oxo (=O).

In some embodiments, the portion of Formula (I) represented by

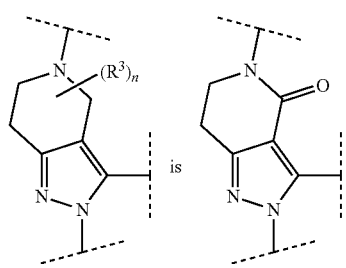

is

In some embodiments, the compound of Formula I is represented by Formula (Ia) or (Ib).

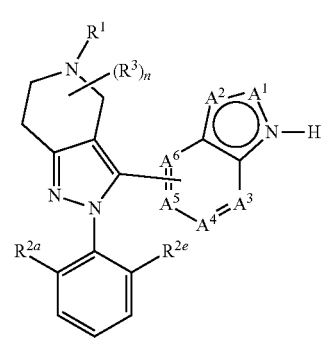

(Ia)

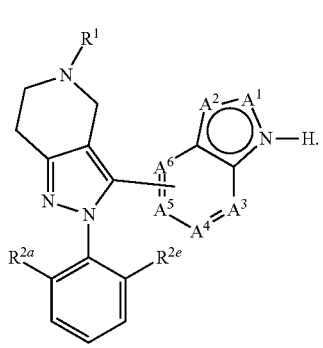
(Ib)

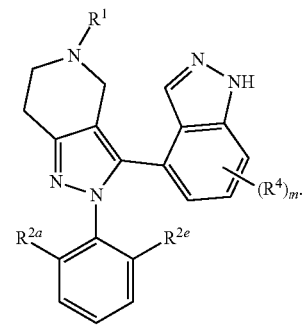
(Ie)

In embodiments where the compound of Formula (I) is represented by Formula (Ia), $R^1$, $R^3$, n, $R^{2a}$, $R^{2e}$, and the ring portion having $A^1$, $A^2$, $A^3$, $A^4$, $A^5$, and $A^6$ as ring vertices are as defined above for Formula (I).

In embodiments where the compound of Formula (I) is represented by Formula (Ib), $R^1$, $R^{2a}$, $R^{2e}$, and the ring portion having $A^1$, $A^2$, $A^3$, $A^4$, $A^5$, and $A^6$ as ring vertices are as defined above for Formula (I).

In some embodiments, the compound of Formula (I) is represented by Formula (Ic), (Id), or (Ie)

In embodiments where the compound of Formula (I) is represented by Formula (Ic), (Id) or (Ie), $R^1$, $R^4$, m, $R^{2a}$, and $R^{2e}$ are as defined above for Formula (I).

In some embodiments, the compound of Formula (I) is represented by Formula (If), (Ig), (Ih), or (Ii)

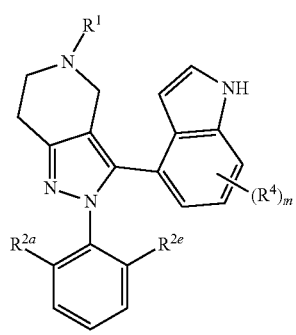
(Ic)

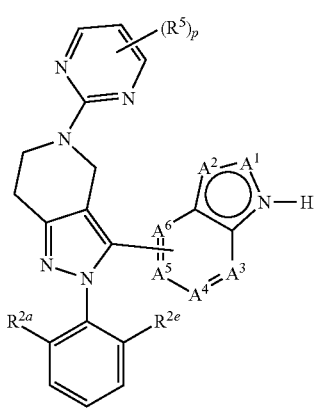
(If)

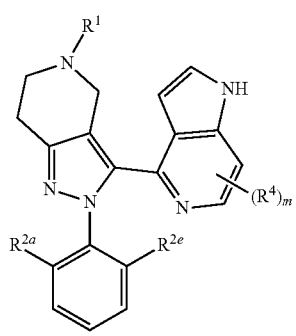
(Id)

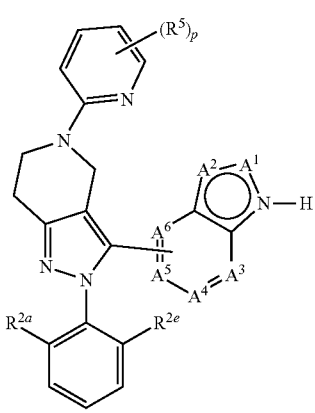
(Ig)

(Ih)

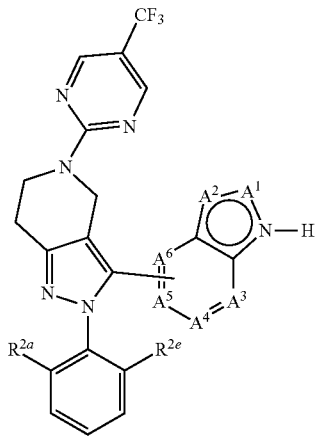

(Ii)

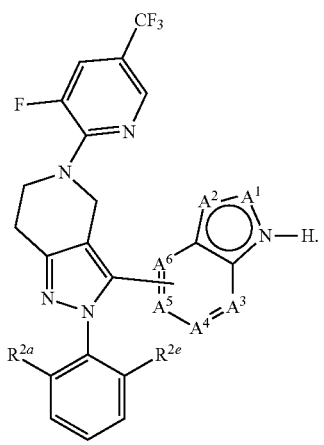

In embodiments where the compound of Formula (I) is represented by Formula (If), (Ig), (Ih), or (Ii), the ring portion having $A^1$, $A^2$, $A^3$, $A^4$, $A^5$, and $A^6$ as ring vertices, $R^{2a}$, $R^{2e}$, and $R^5$ are as defined above for Formula (I), and p is 0, 1 or 2.

In some embodiments, the compound of Formula (I) is represented by Formula (Ik), (Il), or (Im)

(Ik)

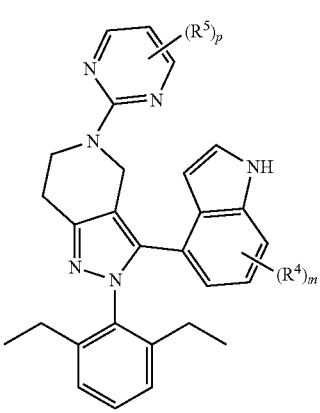

(Il)

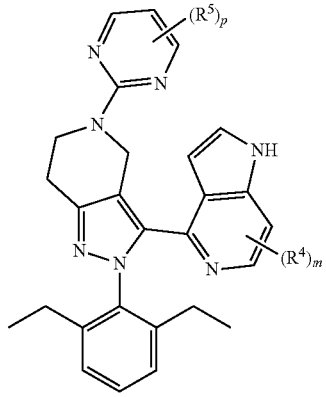

(Im)

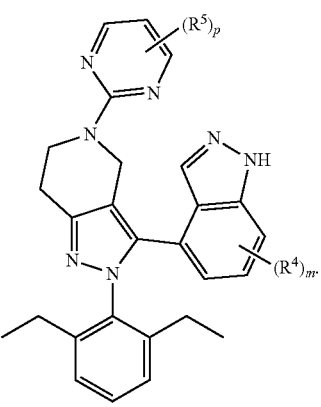

In embodiments where the compound of Formula (I) is represented by Formula (Ik), (Il) or (Im), $R^4$, m, and $R^5$ are as defined above for Formula (I), and p is 0, 1, or 2.

In some embodiments of Formulas (Ik), (Il), and (Im),
p is 1 or 2;
m is 1 or 2;
each $R^5$ is independently $C_{1-8}$ alkyl, $C_{1-8}$ alkoxy, $C_{1-8}$ haloalkyl, $C_{1-8}$ haloalkoxy, $C_{1-8}$hydroxyalkyl, —$C_{1-8}$ alkyl-heterocycloalkyl, $C_{3-6}$cycloalkyl, halogen, —CONR$^{5a}$R$^{5b}$, —NR$^{5a}$R$^{5b}$, and —$C_{1-8}$ alkylene-NR$^{5a}$R$^{5b}$, wherein each R$^{5a}$ and R$^{5b}$ is independently selected from the group consisting of hydrogen and $C_{1-4}$ alkyl, or when attached to the same nitrogen atom can be combined with the nitrogen atom to form a 5 or 6-membered ring, wherein the heterocycloalkyl group is a 4 to 6 membered ring having from 1 to 3 heteroatoms as ring vertices selected from N, O, and S; and
each $R^4$ is independently $C_{1-4}$ alkyl, $C_{1-4}$ alkoxy, $C_{1-6}$ hydroxyalkyl, $C_{1-4}$ haloalkyl, halogen, cyano, hydroxyl, —NH$_2$, —CONR$^{4a}$R$^{4b}$, and —CO$_2$R$^{4a}$, wherein R$^{4a}$ and R$^{4b}$ are as defined above.

In some embodiments, the compound of Formula (I) is a compound described in the Examples section.

Preparation of Compounds

Certain compounds of the invention can be prepared following methodology as described in the Examples section of this document. In addition, the syntheses of certain intermediate compounds that are useful in the preparation of compounds of the invention are also described.

Pharmaceutical Compositions

In addition to the compounds provided above, compositions for modulating C5a activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3- butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug.

Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

The pharmaceutical compositions of the present disclosure may be formulated with one or more additional therapeutic agents. The one or more additional therapeutic agents can include corticosteroids, steroids, immunosuppressants, or CD 20 inhibitors. In some embodiments, the one or more additional therapeutic agents include obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate. Further discussions of combination therapy are included in the "Methods of Use" section of this application.

Methods of Use

The compounds of the invention may be used as agonists, (preferably) antagonists, partial agonists, inverse agonists, of C5a receptors in a variety of contexts, both in vitro and in vivo. In one embodiment, the compounds of the invention are C5aR antagonist that can be used to inhibit the binding of C5a receptor ligand (e.g., C5a) to C5a receptor in vitro or in vivo. In general, such methods comprise the step of contacting a C5a receptor with a sufficient amount of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), in a cultured or isolated cell, or in a tissue or organ.

Preferably, the amount of C5a receptor modulator contacted with the receptor should be sufficient to inhibit C5a binding to C5a receptor in vitro as measured, for example, using a radioligand binding assay, calcium mobilization assay, or chemotaxis assay as described herein.

In one embodiment of the invention, the C5a modulators of the invention are used to modulate, preferably inhibit, the signal-transducing activity of a C5a receptor, for example, by contacting one or more compound(s) of the invention with a C5a receptor (either in vitro or in vivo) under conditions suitable for binding of the modulator(s) to the receptor. The receptor may be present in solution or suspension, in a cultured or isolated cell preparation or within a patient. Any modulation of the signal transducing activity may be assessed by detecting an effect on calcium ion calcium mobilization or by detecting an effect on C5a receptor-mediated cellular chemotaxis. In general, an effective amount of C5a modulator(s) is an amount sufficient to modulate C5a receptor signal transducing activity in vitro within a calcium mobilization assay or C5a receptor-mediated cellular chemotaxis within a migration assay.

When compounds of the invention are used to inhibit C5a receptor-mediated cellular chemotaxis, preferably leukocyte (e.g., neutrophil) chemotaxis, in an in vitro chemotaxis assay, such methods comprise contacting white blood cells (particularly primate white blood cells, especially human white blood cells) with one or more compounds of the invention. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound of the invention has been added.

In another embodiment, the compounds of the present invention further can be used for treating patients suffering from conditions that are responsive to C5a receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to C5a receptor modulation" if modulation of C5a receptor activity results in the reduction of inappropriate activity of a C5a receptor. As used herein, the term "patients" include primates (especially humans), domesticated companion animals (such as dogs, cats, horses, and the like) and livestock (such as cattle, pigs, sheep, and the like), with dosages as described herein.

Conditions that can be Treated by C5a Modulation:

Autoimmune disorders—e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, dense deposit disease, pemphigus, pemphigoid, scleroderma, myasthenia gravis, autoimmune hemolytic and thrombocytopenic states, Goodpasture's syndrome (and associated glomerulonephritis and pulmonary hemorrhage), C3-glomerulopathy, C3-glomerulonephritis, membranoproliferative glomerulonephritis, Kawasaki disease, IGs nephropathy, immunovasculitis, tissue graft rejection, graft versus host disease, hyperacute rejection of transplanted organs; and the like.

Inflammatory disorders and related conditions—e.g., Neutropenia, sepsis, septic shock, Alzheimer's disease, multiple sclerosis, neutrophilia, stroke, inflammatory bowel disease (IBD), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS) Hemolytic uremic syndrome, atypical hemolytic uremic syndrome (aHUS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant invention may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the invention may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Oncologic Diseases or Disorders—e.g., melanoma, lung cancer, lymphoma, sarcoma, carcinoma, fibrosarcoma, liposarcoma, chondrosarcoma, osteogenic sarcoma, angiosarcoma, lymphangiosarcoma, synovioma, mesothelioma, meningioma, leukemia, lymphoma, leiomyosarcoma, rhabdomyosarcoma, squamous cell carcinoma, basal cell carcinoma, adenocarcinoma, papillary carcinoma, cystadenocarcinoma, bronchogenic carcinoma, renal cell carcinoma, hepatocellular carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

Diseases of Vasculitis—Vasculitic dseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present invention can be used to treat leukoclastic vasculitis, Anti-neutrophil cytoplasmic antibody (ANCA) associated vasculitis, immune vasculitis Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS —C5a receptor modulators provided herein may be used to inhibit HIV infection, delay AIDS progression or decrease the severity of symptoms or HIV infection and AIDS.

Neurodegenerative disorders and related diseases— Within further aspects, C5a antagonists provided herein may be used to treat Alzheimer's disease, multiple sclerosis, and cognitive function decline associated with cardiopulmonary bypass surgery and related procedures.

In one embodiment of the invention, the compounds of the invention can be used for the treatment of diseases selected from the group consisting of sepsis (and associated disorders), COPD, rheumatoid arthritis, lupus nephritis and multiple sclerosis.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally or topically. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Combination Therapy

The presently disclosed compounds may be used in combination with one or more additional therapeutic agents that are used in the treatment, prevention, suppression or amelioration of the diseases or conditions for which compounds and compositions of the present invention are useful. Such one or more additional therapeutic agents may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention.

Examples of the one or more additional therapeutic agents that may be combined with a compound or composition of the present invention, either administered separately or in the same pharmaceutical compositions, include, but are not limited to: (a) VLA-4 antagonists, (b) steroids and corticosteroids, such as beclomethasone, betamethasone (including betamethasone sodium phosphate, betamethasone valerate, betamethasone dipropionate) prednisone, prenisolone, methylprednisolone, mometasone, dexamethasone (including dexamethasone sodium phosphate), fluticasone, cortisone (including cortisone acetate) hydrocortisone (including hydrocortisone acetate, hydrocortisone-17-valerate, hydrocortisone-17-butyrate, hydrocortisone-17-aceponate, hydrocortisone-17-buteprate), budesonide, desonide, fluocinonide (including fluocinolone acetonide), triamcinolone (including triamcinolone acetonide and triamcinolone alcohol), tixocortol (including tixocortol pivalate) fluocortolone (including fluocortolone caproate and fluocortolone pivalate), amcinonide, halcinonide, halometasone, fluprednidene acetate, salmeterol, salmeterol, salbutamol, ciclesonide, formeterol, alclometasone (including alclometasone dipropionate), prednicarbate, clobetasone (including clobetasone-17-butrate), clobetasol (including clobetasol-17-propionate); (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and rnycophenolate, e.g., mycophenolate mofetil (CellCept8); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbre10), (k) cyclophosphamide, (l) antibody therapies such as orthoclone (OKT3), daclizumab (Zenapax®), basiliximab (Simulect®) and infliximab (Remicade®), (m) antibody therapies targeting CD20 such as obinutuzumab, rituximab, or ocrelizumab; (n) chemotherapeutic agents such anthracyclines (e.g., daunorubicin (daunomycin; rubidomycin), doxorubicin, epirubicin, idarubicin, and valrubicin), mitoxantrone, and pixantrone; platinum-based agents (e.g., cisplatin, carboplatin, oxaliplatin, satraplatin, picoplatin, nedaplatin, triplatin, and lipoplatin); tamoxifen and metabolites thereof such as 4-hydroxytamoxifen (afimoxifene) and N-desmethyl-4-hydroxytamoxifen (endoxifen); taxanes such as paclitaxel (taxol) and docetaxel; alkylating agents (e.g., nitrogen mustards such as mechlorethamine (HN2), cyclophosphamide, ifosfamide, melphalan (L-sarcolysin), and chlorambucil); ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)); antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)); (o) other antagonists of the chemokine receptors, especially CXCR2, CXCR3, CCR2, CCR3, CCR4, CCR7, CX3CR1 and CXCR6.

The disease or disorder being treated will determine which additional therapeutic agent or therapeutic agents are most appropriately administered in combination with the compounds of the present invention—such determination can be made by a person of skill in the art.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Non-Pharmaceutical Applications

In another aspect of the invention, the compounds of the invention can be used in a variety of non-pharmaceutical in vitro and in vivo application. For example, the compounds of the invention may be labeled and used as probes for the detection and localization of C5a receptor (cell preparations or tissue sections samples). The compounds of the invention may also be used as positive controls in assays for C5a receptor activity, i.e., as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

The compounds provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

EXAMPLES

The following examples are offered to illustrate, but not to limit the claimed invention.

Reagents and solvents used below can be obtained from commercial sources such as Aldrich Chemical Co. (Milwaukee, Wisconsin, USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:
EtOH: Ethanol
EtONa: Sodium ethoxide
THF: Tetrahydrofuran
TLC: Thin layer chromatography
MeOH: Methanol Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

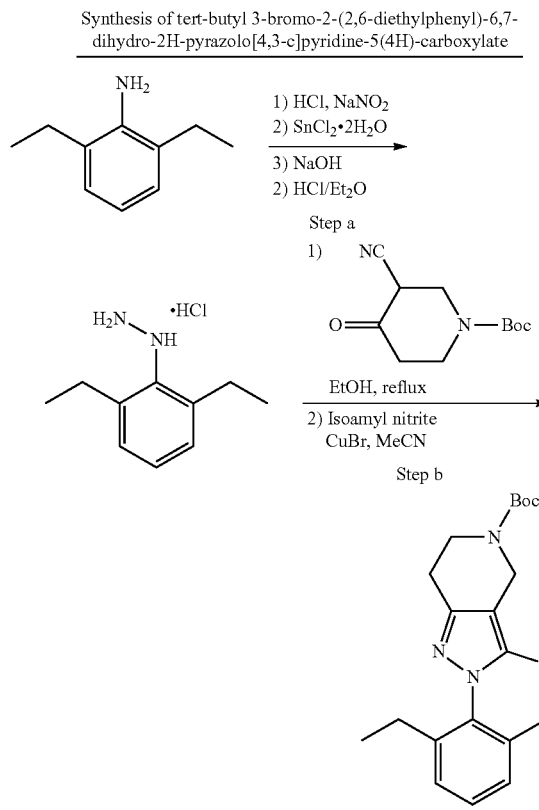

Synthesis of tert-butyl 3-bromo-2-(2,6-diethylphenyl)-6,7-dihydro-2H-pyrazolo[4,3-c]pyridine-5(4H)-carboxylate Caution: Diazonium formation could be potentially dangerous, please handle with care and wear proper personal protection equipment!

Step a: To a 250 mL flask charged with 90 mL of concentrated hydrochloric acid under magnetic stirring was added 2,6-diethylaniline (10 g, 67 mmol). The resulting mixture was stirred for 30 min and cooled with an ice salt bath until the internal temperature reached −5° C. A solution of sodium nitrite (5.5 g, 80 mmol) in water (60 mL) was added slowly to the above mixture while maintaining the internal temperature below 5° C.

Separately, tin(II) chloride dihydrate (31.6 g, 140 mmol) was added to a 500 mL 3-neck round bottom flask charged with concentrated hydrochloric acid (60 mL) under mechanical stirring. The resulting solution was then cooled with an ice bath.

The diazonium slurry was then filtered into the 500 mL flask containing the cooled tin chloride solution with vigorous stirring. After 90 min, the reaction mixture was transferred to a 500 mL Erlenmeyer flask and the flask was rinsed with water (20 mL) and chloroform (8 mL). The combined mixture was stirred overnight at room temperature. The entire liquid layer was decanted to give a wet solid. The material thus recovered was dried in vacuo for one day and then transferred to a 500 mL 3-neck round bottom flask equipped with an overhead mechanical stirrer and stirred with ether (180 mL). The resulting mixture was cooled in an ice bath, and NaOH solution (10 N, 30 mL) was added slowly to the above mixture while maintaining the inner temperature below 12° C. After the addition, the mixture was allowed to stand for 2 h on ice. The ether layer was decanted into a 500 mL flask, and a stream of hydrogen chloride gas was bubbled into the ether solution while stirring. The resulting precipitate was collected by filtration to afford (2,6-diethylphenyl)hydrazine hydrochloride. MS: (ES) m z calculated for $C_{100}H_{17}N_2[M+H]^+$ 165.1, found 165.1.

Step b: N,N-diisopropylethylamine (8 mL, 46.0 mmol) was added to a mixture of (2,6-diethylphenyl)hydrazine hydrochloride (8 g, 39.9 mmol), tert-butyl 3-cyano-4-oxopiperidine-1-carboxylate (5 g, 22.3 mmol) and EtOH (60 mL) in a 250 mL round bottom flask under magnetic stirring. The resulting mixture was stirred under reflux for 3 h. Glacial acetic acid (12 mL, 208 mmol) was added and the mixture was stirred under reflux for another 2 h. The solvent was removed under reduced pressure and the residue was dissolved in EtOAc and washed with NaOH solution (2N), brine, and dried over $MgSO_4$. The solvent was removed under reduced pressure and the residue was purified by silica gel flash chromatography (5 to 55% EtOAc in hexanes) to give tert-butyl 3-amino-2-(2,6-diethylphenyl)-6,7-dihydro-2H-pyrazolo[4,3-c]pyridine-5(4H)-carboxylate. MS: (ES) m z calculated for $C_{21}H_{31}N_4O_2$ $[M+H]^+$ 371.2, found 371.2.

Caution: Diazonium formation could be potentially dangerous, please handle with care and wear proper personal protection equipment!

Isopentyl nitrite (4 mL, 28.6 mmol) was added slowly at room temperature to a mixture of tert-butyl 3-amino-2-(2,6-diethylphenyl)-6,7-dihydro-2H-pyrazolo[4,3-c]pyridine-5(4H)-carboxylate (3 g, 8.1 mmol), CuBr (4 g, 27.9 mmol) and MeCN (50 mL) in a 250 mL round bottom flask under magnetic stirring. The resulting mixture was stirred at room temperature for 1 h, diluted with EtOAc, filtered through Celite, washed with saturated $NH_4Cl$ solution, and dried over $MgSO_4$. The solvent was removed under reduced pressure and the residue was purified by silica gel flash chromatography (2 to 25% EtOAc in hexanes) to give tert-butyl 3-bromo-2-(2,6-diethylphenyl)-6,7-dihydro-2H-pyrazolo[4,3-c]pyridine-5(4H)-carboxylate. MS: (ES) m z calculated for $C_{21}H_{29}BrN_3O_2$ $[M+H]^+$ 434.1, found 434.2.

Synthesis of 7-chloro-4-(4,4,5,5-tetramethyl-1,3,2-dioxaborolan-2-yl)-1H-indole

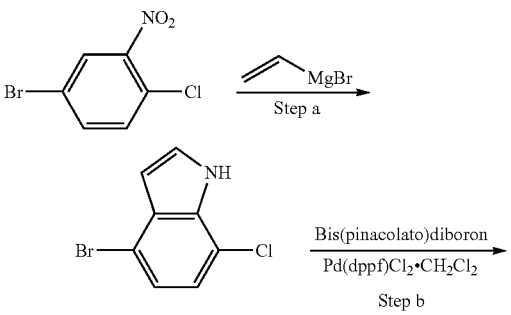

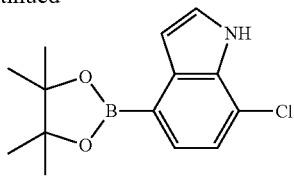

Step a: A solution of vinylmagenesium bromide in THF (1 M, 60 mL, 60 mmol) was added rapidly to a solution of 4-bromo-1-chloro-2-nitrobenzene (4.7 g, 19.9 mmol) in anhydrous THF (50 mL) under $N_2$ and vigorously stirring at −60° C. The reaction mixture was stirred at the same temperature and allowed to warm to −30° C. over 1.5 h. The reaction was quenched with saturated $NH_4Cl$ solution and the mixture was allowed to warm up to room temperature over 1 h. The reaction mixture was diluted with EtOAc, washed with brine and dried over $MgSO_4$. The solvent was removed under reduced pressure and the residue was purified by silica gel flash chromatography (2 to 20% EtOAc in hexanes) to give 4-bromo-7-chloro-1H-indole. MS: (ES) m z calculated for $C_8H_6BrClN$ [M+H]$^+$229.9, found 229.9.

Step b: To a suspension of 4-bromo-7-chloro-1H-indole (1.7 g, 7.4 mmol), 4,4,4',4',5,5,5',5'-octamethyl-2,2'-bi(1,3,2-dioxaborolane) (3.4 g, 13.4 mmol), and KOAc (3 g, 30.6 mmol) in p-dioxane (12 mL) was added Pd(dppf)Cl$_2$ complex with dichloromethane (800 mg, 0.97 mmol). The reaction mixture was degassed ($N_2$) for 2 min and stirred at 100° C. for 3 h. The reaction mixture was diluted with EtOAc, filtered through Celite. The solvent was removed under reduced pressure and the residue was purified by silica gel flash chromatography (5 to 20% EtOAc in hexanes) to give 7-chloro-4-(4,4,5,5-tetramethyl-1,3,2-dioxaborolan-2-yl)-1H-indole. MS: (ES) m z calculated for $C_{15}H_{20}BFNO_2$ [M+H]$^+$276.1, found 276.1.

Synthesis of 2,3-difluoro-5-(1-methylethyl)pyridine

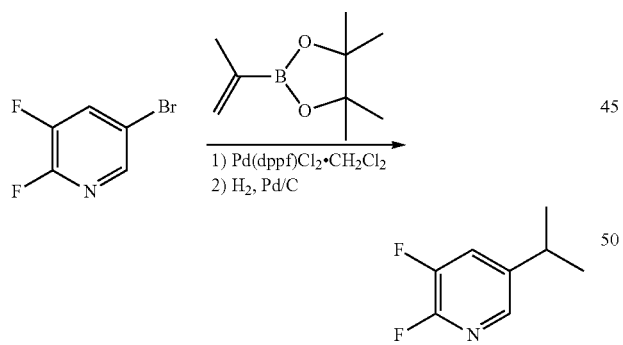

To a suspension of 5-bromo-2,3-difluoropyridine (9.0 g, 46 mmol), 4,4,5,5-tetramethyl-2-(1-methylethenyl)-1,3,2-dioxaborolane (11 g, 65 mmol), and sodium carbonate (15 g, 140 mmol) in a mixture of dioxane (150 mL) and water (40 mL) was added Pd(dppf)Cl$_2$ complex with dichloromethane (2.0 g, 2.4 mmol). The reaction mixture was degassed ($N_2$) for 2 min and refluxed for 1 h. Dioxane was removed in vacuo and the residue was taken up in dichloromethane and water. The organic phase was separated, filtered through Celite, and the solvent was removed under reduced pressure. The residue was purified by silica gel flash chromatography (5% EtOAc in hexanes) to obtain 2,3-difluoro-5-(1-methylethenyl)pyridine. $^1$H NMR (400 MHz, CDCl$_3$) δ 8.04 (t, J=1.9 Hz, 1H), 7.58-7.65 (m, 1H), 5.39 (s, 1H), 5.22 (s, 1H), 2.14 (s, 3H).

To the above 2,3-difluoro-5-(1-methylethenyl)pyridine (5.9 g, 38 mmol) dissolved in EtOAc (100 mL) was added 10% Pd/C (Degussa type E101 NE/W, 420 mg). The mixture was stirred under one atmosphere of hydrogen for 17 h. When the reaction was complete, the mixture was filtered through Celite and solvent was removed in vacuo to give 2,3-difluoro-5-(1-methylethyl)pyridine. $^1$H NMR (400 MHz, CDCl$_3$) δ 7.82 (t, J=1.7 Hz, 1H), 7.38-7.45 (m, 1H), 2.91-3.10 (m, 1H), 1.27 (d, J=7.2 Hz, 6H).

Synthesis of tert-butyl 4-bromo-6-fluoro-7-(hydroxymethyl)-1H-benzo[d]imidazole-1-carboxylate

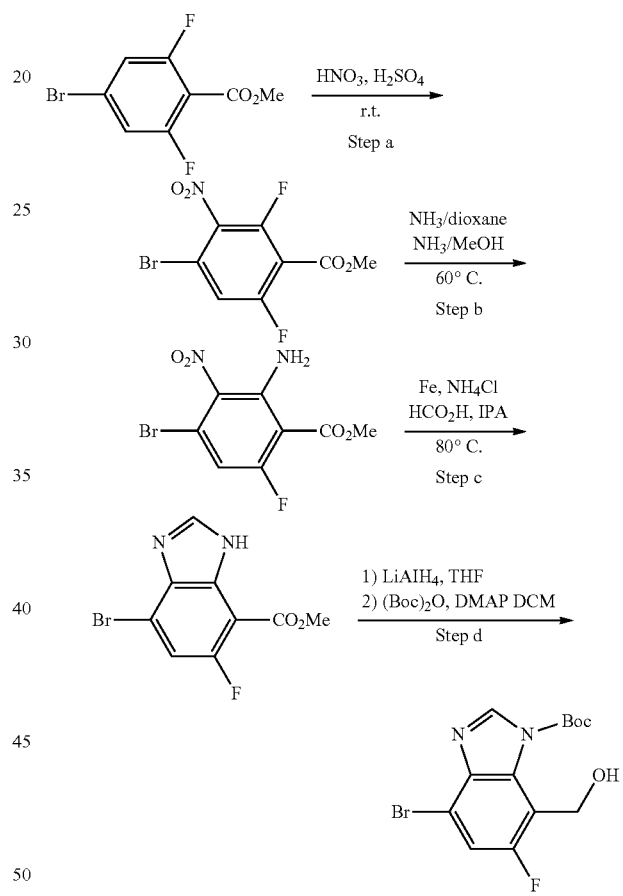

Step a: A mixture of methyl 4-bromo-2,6-difluorobenzoate (5.5 g, 21.9 mmol), conc. H$_2$SO$_4$ (25 mL) and HNO$_3$ (25 mL) was stirred at room temperature for 0.5 hr. It was then poured onto ice and extracted withEtOAc. The organic layer was separated, dried over Na$_2$SO$_4$, concentrated on a rotary evaporator under reduced pressure and the residue was purified by silica gel flash chromatograph (0 to 40% EtOAc/hexanes) to give methyl 4-bromo-2,6-difluoro-3-nitrobenzoate. MS: (ES) m z calculated for $C_8H_4BrF_2NO_4$ [M+H]$^+$ 295.1, found 295.1.

Step b: A mixture of methyl 4-bromo-2,6-difluoro-3-nitrobenzoate (6.0 g, 20.2 mmol) and NH$_3$/dioxane (0.5M, 200 mL, 100 mmol) was stirred at 60° C. for 1 hr. To the mixture was then added NH$_3$/MeOH (1.0 M, 100 mL, 100 mmol) and heating continued for another 15 min at the same temperature. It was then cooled to room temperature, poured into water and extracted withEtOAc. The organic layer was separated, dried over Na$_2$SO$_4$, concentrated on a rotary evaporator under reduced pressure and the residue was purified by silica gel flash chromatograph (0 to 100% EtOAc/hexanes) to give methyl 2-amino-4-bromo-6-fluoro-3-nitrobenzoate. MS: (ES) m z calculated for C$_8$H$_6$BrFN$_2$O$_4$ [M+H]$^+$292.0, found 292.0.

Step c: A mixture of methyl 2-amino-4-bromo-6-fluoro-3-nitrobenzoate (3.6 g, 12.2 mmol), Fe (25 g, 447 mmol), NH$_4$Cl (30 g, 560 mmol), trimethyl orthoformate (50 mL), formic acid (70 mL) and IPA (120 mL) conc. H$_2$SO$_4$ (25 mL) and HNO$_3$ (25 mL) was stirred at 80° C. for 5 hours. It was then cooled to room temperature, diluted with 20% MeOH/DCM and filtered through celite. The filtrate was collected, concentrated on a rotary evaporator under reduced pressure and the residue was purified by silica gel flash chromatograph (0 to 100% EtOAc/hexanes) to give methyl 4-bromo-6-fluoro-1H-benzo[d]imidazole-7-carboxylate. MS: (ES) m z calculated for C$_9$H$_6$BrFN$_2$O$_2$[M+H]$^+$272.2, found 272.2.

Step d: A mixture of methyl 4-bromo-6-fluoro-1H-benzo[d]imidazole-7-carboxylate (0.64 g, 2.35 mmol) and LiAlH$_4$ (3.3 mL, 1M/ether, 3.3 mmol) in THF (7 mL) was stirred at 0° C. for 1 hr. It was then poured into aq. NH$_4$OH and extracted withIPA/CHCl$_3$. The organic layer was separated, dried over Na$_2$SO$_4$, concentrated on a rotary evaporator under reduced pressure. The residue was purified by silica gel flash chromatograph (0 to 30% MeOH/EtOAc) to give (4-bromo-6-fluoro-1H-benzo[d]imidazol-7-yl)methanol. MS: (ES) m z calculated for C$_8$H$_6$BrFN$_2$O [M+H]$^+$ 243.9, found 243.9.

A mixture of (4-bromo-6-fluoro-1H-benzo[d]imidazol-7-yl)methanol (0.48 g, 1.96 mmol), (BOC)$_2$O (2.0 g, 9.2 mmol) and DMAP (0.36 g, 3 mmol) in DCM (25 mL) was stirred at room temperature for 1 hr. It was then poured into aq. NaHCO$_3$ and extracted with DCM. The organic layer was separated, dried over Na$_2$SO$_4$, concentrated on a rotary evaporator under reduced pressure. The residue was purified by silica gel flash chromatography (0 to 60% EtOAc/hexanes) to give tert-butyl 4-bromo-6-fluoro-7-(hydroxymethyl)-1H-benzo[d]imidazole-1-carboxylate. MS: (ES) m z calculated for C$_{13}$H$_{14}$BrFN$_2$O$_3$[M+H]$^+$344.0, found 344.0.

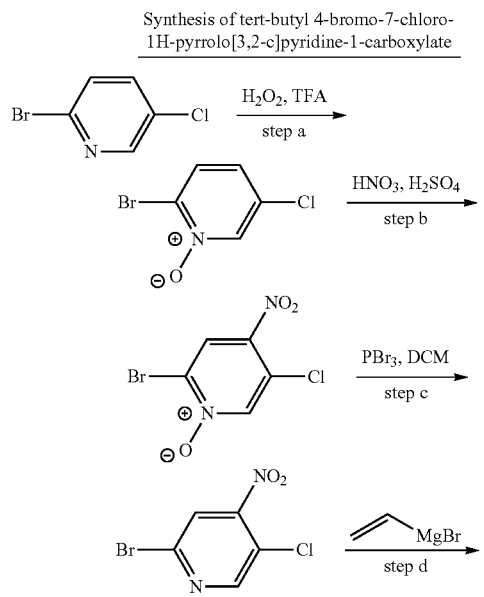

Synthesis of tert-butyl 4-bromo-7-chloro-1H-pyrrolo[3,2-c]pyridine-1-carboxylate

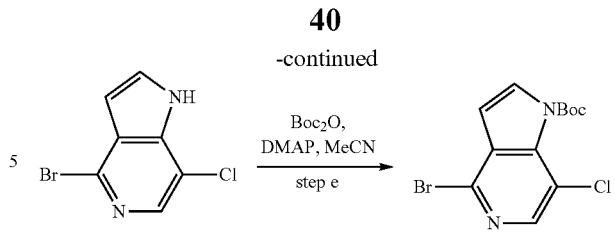

Step a: To solution of 2-bromo-5-chloropyridine (25 g, 0.13 mol) in 70 mL of TFA was added dropwise a 35% wt/wt aqueous solution of H$_2$O$_2$. The solution was heated at 70° C. for 16 hrs then quenched with a saturated solution of sodium sulfite. The mixture was extracted with ethyl acetate and the organic layers were combined, dried with sodium sulfate, filtered and concentrated in vacuo. The residue was purified by silica gel column chromatography (70% EtOAc in hexanes) to afford 2-bromo-5-chloropyridine 1-oxide. MS: (ES) m z calculated for C$_5$H$_3$BrClNO [M+H]$^+$207.9, found 207.9.

Step b: To a solution of 2-bromo-5-chloropyridine 1-oxide in 100 mL of H$_2$SO$_4$ at 0° C. was added dropwise 46 mL of HNO$_3$. The solution was heated at 65° C. for 16 hrs then quenched with 250 mL of H$_2$O. The mixture was stirred at room temperature overnight and the precipitate was filtered and collected. The solid was further purified on silica gel column chromatography to yield 2-bromo-5-chloro-4-nitropyridine 1-oxide 2-bromo-5-chloropyridine 1-oxide. MS: (ES) m z calculated for C$_5$H$_2$BrClN$_2$O$_3$[M+H]$^+$252.9, found 252.9.

Step c: To a solution of PBr$_3$ (1.32 mL, 14.3 mmol) in 3 mL of DCM was added portion-wise 2-bromo-5-chloro-4-nitropyridine 1-oxide 2-bromo-5-chloropyridine 1-oxide (1.5 g, 6.0 mmol). The mixture was stirred at room temperature for 30 min, then cooled to 0° C. and quenched slowly with ice water. The aqueous layer was extracted with ethyl acetate and the combined organic layers was dried with sodium sulfate, filtered and concentrated. The residue was purified by silica gel column chromatography (10% ethyl acetate in hexanes) to give 2-bromo-5-chloro-4-nitropyridine.

Step d: To a solution of 2-bromo-5-chloro-4-nitropyridine (1.6 g, 6.6 mmol) in 26 mL of THF at −78° C. was added dropwise a solution of 1.0 M vinylmagnesium bromide in THE (23.2 mL, 23.2 mmol). The solution was stirred at −78° C. for 30 min then quenched slowly with a solution of 1 N HCl. The aqueous and organic layers were separated and the aqueous layer was washed with ethyl acetate. The combined organic layers was dried with sodium sulfate, filtered and concentrated. The residue was purified by silica gel column chromatography (40% ethyl acetate in hexanes) to afford 4-bromo-7-chloro-1H-pyrrolo[3,2-c]pyridine. MS: (ES) m z calculated for C$_7$H$_4$BrClN$_2$ [M+H]$^+$230.9, found 230.9.

Step e: To a solution of 4-bromo-7-chloro-1H-pyrrolo[3,2-c]pyridine (0.3 g, 1.3 mmol) in 2.6 mL of acetonitrile was added di-tert-butyl dicarbonate (0.6 mL, 2.6 mmol) followed by DMAP (0.16 g, 1.3 mmol). The solution was stirred at room temperature for 15 min. The mixture was concentrated in vacuo and the residue was purified by silica gel column chromatography (10% ethylacetate in hexanes) to provide tert-butyl 4-bromo-7-chloro-1H-pyrrolo[3,2-c]pyridine-1-carboxylate. MS: (ES) m z calculated for C$_{12}$H$_{12}$BrClN$_2$O$_2$ [M+H]$^+$ 331.0, found 331.0.

Example 1

Synthesis of 3-(6-chloro-7-methoxy-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine

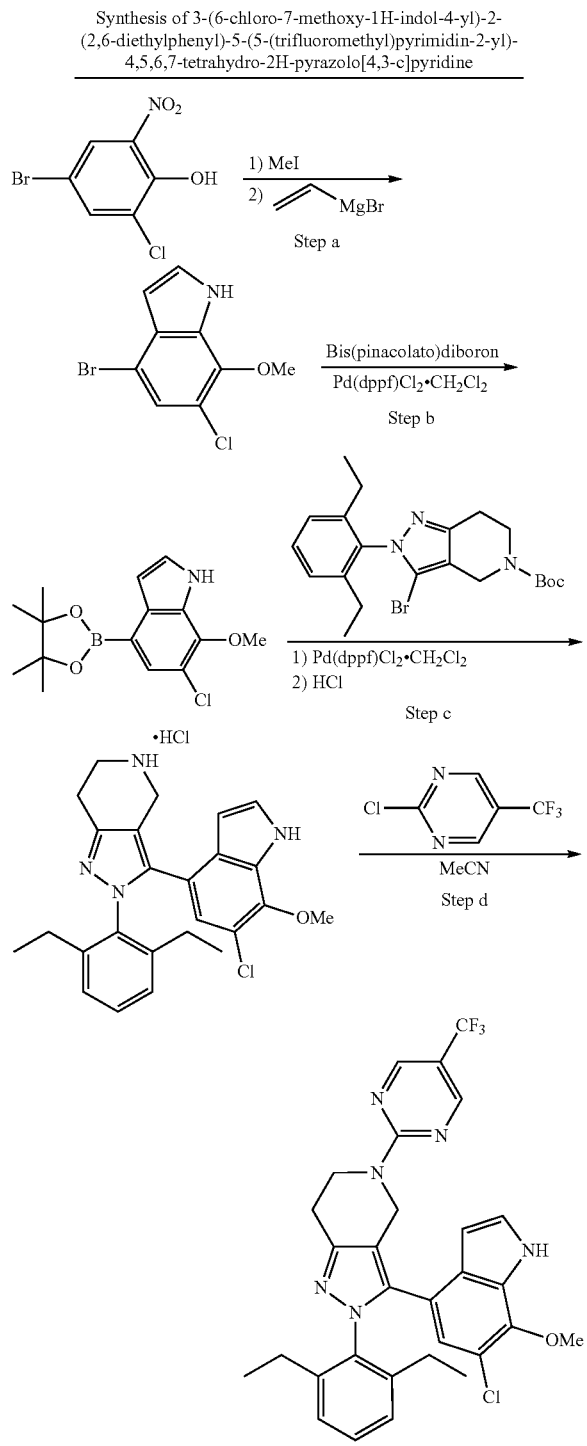

Step a: Iodomethane (1.5 mL, 24 mmol) was added to a suspension of 4-bromo-2-chloro-6-nitrophenol (3.2 g, 12.7 mmol) and $K_2CO_3$ (3 g, 21.7 mmol) in DMF (40 mL) in a 250 mL round bottom flask under magnetic stirring. The resulting mixture was stirred at 45° C. for 4 h, diluted with EtOAc, washed with brine, and dried over $MgSO_4$. The solvent was removed under reduced pressure and the residue was purified by silica gel flash chromatography (2 to 25% EtOAc in hexanes) to give 5-bromo-1-chloro-2-methoxy-3-nitrobenzene. MS: (ES) m z calculated for $C_7H_6BrClNO_3$ [M+H]$^+$265.9, found 265.9.

A solution of vinylmagenesium bromide in THE (1 M, 40 mL, 40 mmol) was added rapidly to a solution of 5-bromo-1-chloro-2-methoxy-3-nitrobenzene (3.2 g, 12 mmol) in anhydrous THF (40 mL) under $N_2$ and vigorously stirring at −60° C. The reaction mixture was allowed to warm to −30° C. over 1.5 h. The reaction was quenched with saturated $NH_4Cl$ solution and the mixture was allowed to warm up to room temperature over 1 h. The reaction mixture was diluted with EtOAc, washed with brine and dried over $MgSO_4$. The solvent was removed under reduced pressure and the residue was purified by silica gel flash chromatography (2 to 20% EtOAc in hexanes) to give 4-bromo-6-chloro-7-methoxy-1H-indole. MS: (ES) m z calculated for $C_9H_8BrClNO$ [M+H]$^+$259.9, found 259.9.

Step b: To a suspension of 4-bromo-6-chloro-7-methoxy-1H-indole (1.2 g, 4.6 mmol), 4,4,4',4',5,5,5',5'-octamethyl-2,2'-bi(1,3,2-dioxaborolane) (2.4 g, 9.5 mmol), and KOAc (2.3 g, 23.4 mmol) in DMSO (10 mL) was added Pd(dppf)Cl$_2$ complex with dichloromethane (600 mg, 0.73 mmol). The reaction mixture was degassed ($N_2$) for 2 min and stirred at 120° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) to give 6-chloro-7-methoxy-4-(4,4,5,5-tetramethyl-1,3,2-dioxaborolan-2-yl)-1H-indole. MS: (ES) m z calculated for $C_{15}H_{20}BClNO_3$ [M+H]$^+$308.1, found 308.1.

Step c: To a suspension of tert-butyl 3-bromo-2-(2,6-diethylphenyl)-6,7-dihydro-2H-pyrazolo[4,3-c]pyridine-5(4H)-carboxylate (600 mg, 1.4 mmol), 6-chloro-7-methoxy-4-(4,4,5,5-tetramethyl-1,3,2-dioxaborolan-2-yl)-1H-indole (550 mg, 1.8 mmol), $K_2CO_3$ (500 mg, 3.6 mmol) in p-dioxane (6 mL) and water (1 mL) was added Pd(dppf)Cl$_2$ complex with dichloromethane (300 mg, 0.37 mmol). The reaction mixture was degassed ($N_2$) for 2 min and stirred under $N_2$ at 100° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) to give tert-butyl 3-(6-chloro-7-methoxy-1H-indol-4-yl)-2-(2,6-diethylphenyl)-6,7-dihydro-2H-pyrazolo[4,3-c]pyridine-5(4H)-carboxylate. MS: (ES) m z calculated for $C_{30}H_{36}ClN_4O_3$[M+H]$^+$535.2.1, found 535.2.

The above tert-butyl 3-(6-chloro-7-methoxy-1H-indol-4-yl)-2-(2,6-diethylphenyl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 3-(6-chloro-7-methoxy-1H-indol-4-yl)-2-(2,6-diethylphenyl)-4,5,6,7-tetrahydro-2H-pyrazolo[4,3-c]pyridine hydrochloride. MS: (ES) m z calculated for $C_{25}H_{29}ClN_4O$ [M+H]$^+$435.2, found 435.2.

Step d: N,N-diisopropylethylamine (0.2 mL, 1.15 mmol) was added to a suspension of 3-(6-chloro-7-methoxy-1H-indol-4-yl)-2-(2,6-diethylphenyl)-4,5,6,7-tetrahydro-2H-pyrazolo[4,3-c]pyridine hydrochloride (100 mg, 0.21 mmol), 2-chloro-5-(trifluoromethyl)pyrimidine (45 mg, 0.25 mmol), and $Li_2CO_3$ (20 mg, 0.27 mmol) in MeCN (10 mL) under magnetic stirring. The resulting mixture was stirred at 75° C. for 30 min. After cooling to room temperature, the reaction mixture was diluted with EtOAc, washed with brine and dried over MgSO$_4$. The solvent was removed under reduced pressure and the residue was purified by preparative TLC (40% EtOAc in hexanes) followed by trituration in MeOH to afford 3-(6-chloro-7-methoxy-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.48 (s, 2H), 8.46 (s, 1H), 7.06-7.27 (m, 4H), 6.62 (d, J=1.0 Hz, 1H), 6.42-6.49 (m, 1H), 4.83 (s, 2H), 4.36 (t, J=5.7 Hz, 2H), 4.00 (s, 3H), 3.03 (t, J=5.7 Hz, 2H), 2.10-2.40 (m, 4H), 0.80-1.08 (m, 6H). MS: (ES) m z calculated for C$_{30}$H$_{29}$ClF$_3$N$_6$O [M+H]$^+$ 581.2, found 581.2.

Example 2

Synthesis of 2-(2,6-diethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine

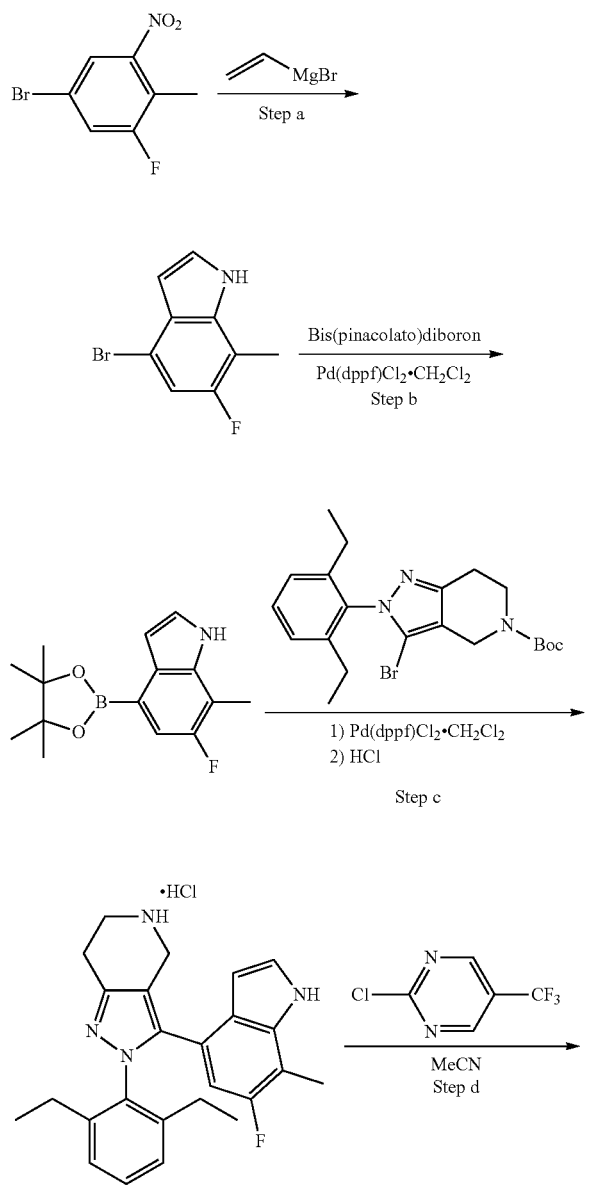

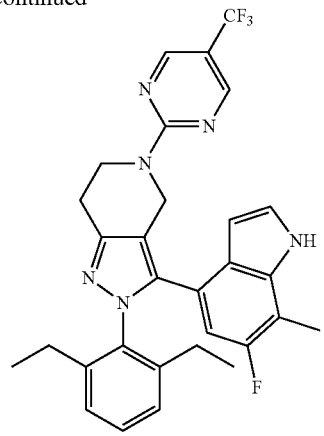

Step a: A solution of vinylmagenesium bromide in THF (1 M, 70 mL, 70 mmol) was added rapidly to a solution of 5-bromo-1-fluoro-2-methyl-3-nitrobenzene (5.0 g, 21.3 mmol) in anhydrous THF (40 mL) under N$_2$ and vigorously stirred at −60° C. The reaction mixture was allowed to warm up to −30° C. over 1.5 h. The reaction was quenched with saturated NH$_4$Cl solution and the mixture was allowed to warm up to room temperature over 1 h. The reaction mixture was diluted with EtOAc, washed with brine, and dried over MgSO$_4$. The solvent was removed under reduced pressure and the residue was purified by silica gel flash chromatography (2 to 20% EtOAc in hexanes) to give 4-bromo-6-fluoro-7-methyl-1H-indole. MS: (ES) m z calculated for C$_9$H$_8$BrFN [M+H]$^+$227.9, found 227.9.

Step b: To a suspension of 4-bromo-6-fluoro-7-methyl-1H-indole (1.0 g, 4.4 mmol), 4,4,4',4',5,5,5',5'-octamethyl-2,2'-bi(1,3,2-dioxaborolane) (2.0 g, 7.9 mmol), and KOAc (2 g, 20.4 mmol) in p-dioxane (12 mL) was added Pd(dppf)Cl$_2$ complex with dichloromethane (600 mg, 0.73 mmol). The reaction mixture was degassed (N$_2$) for 2 min and stirred at 100° C. for 3 h. The reaction mixture was diluted with EtOAc, filtered through Celite. The solvent was removed under reduced pressure and the residue was purified by silica gel flash chromatography (5 to 20% EtOAc in hexanes) to give 6-fluoro-7-methyl-4-(4,4,5,5-tetramethyl-1,3,2-dioxaborolan-2-yl)-1H-indole. MS: (ES) m z calculated for C$_{15}$H$_{20}$BFNO$_2$ [M+H]$^+$276.1, found 276.1.

Step c: To a suspension of tert-butyl 3-bromo-2-(2,6-diethylphenyl)-6,7-dihydro-2H-pyrazolo[4,3-c]pyridine-5(4H)-carboxylate (500 mg, 1.2 mmol), 6-fluoro-7-methyl-4-(4,4,5,5-tetramethyl-1,3,2-dioxaborolan-2-yl)-1H-indole (260 mg, 0.94 mmol), K$_2$CO$_3$ (500 mg, 3.6 mmol) in p-dioxane (6 mL) and water (1 mL) was added Pd(dppf)Cl$_2$ complex with dichloromethane (100 mg, 0.12 mmol). The reaction mixture was degassed (N$_2$) for 2 min and stirred under N$_2$ at 100° C. for 2 h. The reaction mixture was diluted with EtOAc, filtered through Celite, washed with brine, and dried over MgSO$_4$. The solvent was removed under reduced pressure and the residue was purified by silica gel flash chromatography (5 to 20% EtOAc in hexanes) to give tert-butyl 2-(2,6-diethylphenyl)-3-(6-fluoro-7-methyl-1H-indol-4-yl)-6,7-dihydro-2H-pyrazolo[4,3-c]pyridine-5(4H)-carboxylate. MS: (ES) m z calculated for C$_{30}$H$_{36}$FN$_4$O$_2$[M+H]$^+$503.2, found 503.2.

The above tert-butyl 2-(2,6-diethylphenyl)-3-(6-fluoro-7-methyl-1H-indol-4-yl)-6,7-dihydro-2H-pyrazolo[4,3-c]pyridine-5(4H)-carboxylate was dissolved in dichloromethane (5 mL) and charged with HCl in dioxane (4N, 5 mL).

The resulting mixture was stirred at room temperature for 2 h. After the reaction was complete, the solvent was evaporated in vacuo to give 2-(2,6-diethylphenyl)-3-(6-fluoro-7-methyl-1H-indol-4-yl)-4,5, 6,7-tetrahydro-2H-pyrazolo[4,3-c]pyridine hydrochloride. MS: (ES) m z calculated for $C_{25}H_{28}FN_4$ [M+H]$^+$ 403.2, found 403.2.

Step d: N,N-diisopropylethylamine (0.2 mL, 1.15 mmol) was added to a suspension of 2-(2,6-diethylphenyl)-3-(6-fluoro-7-methyl-1H-indol-4-yl)-4,5, 6,7-tetrahydro-2H-pyrazolo[4,3-c]pyridine hydrochloride (50 mg, 0.11 mmol), 2-chloro-5-(trifluoromethyl)pyrimidine (45 mg, 0.25 mmol), and $Li_2CO_3$ (20 mg, 0.27 mmol) in DMSO (5 mL) under magnetic stirring. The resulting mixture was stirred at 75° C. for 30 min. After cooling to room temperature, the reaction mixture was diluted with EtOAc, washed with brine and dried over $MgSO_4$. The solvent was removed under reduced pressure and the residue was purified by Preparative TLC (40% EtOAc in hexanes) followed by trituration in MeOH to afford 2-(2,6-diethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine. $^1$H NMR (400 MHz, $CDCl_3$) δ 8.48 (s, 2H), 8.17 (s, 1H), 7.18-7.29 (m, 2H), 7.05 (d, J=7.8 Hz, 2H), 6.37-6.49 (m, 2H), 4.84 (s, 2H), 4.35 (t, J=5.9 Hz, 2H), 3.04 (t, J=5.9 Hz, 2H), 2.34 (d, J=1.5 Hz, 3H), 2.10-2.33 (m, 4H), 0.80-1.08 (m, 6H). MS: (ES) m z calculated $C_{30}H_{29}F_4N_6$ [M+H]$^+$ 549.2, found 549.2.

Example 3

Synthesis of 2-(2,6-diethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine

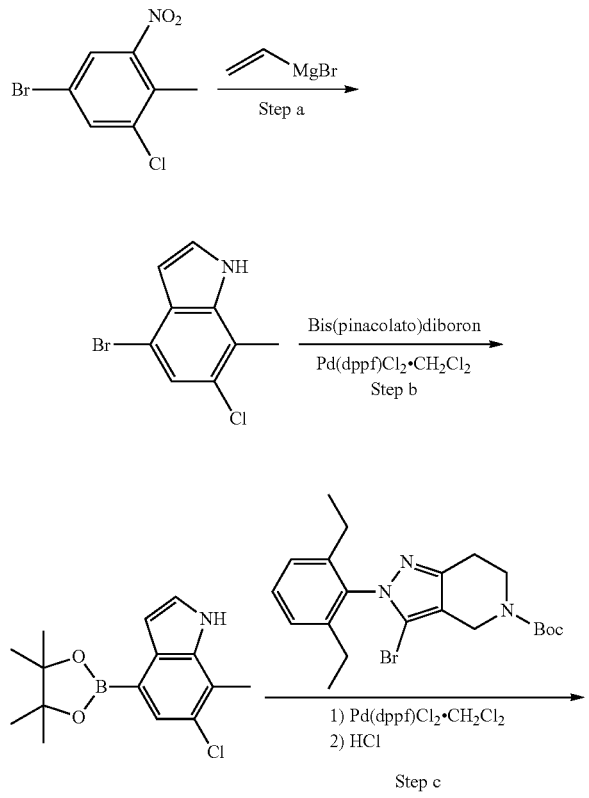

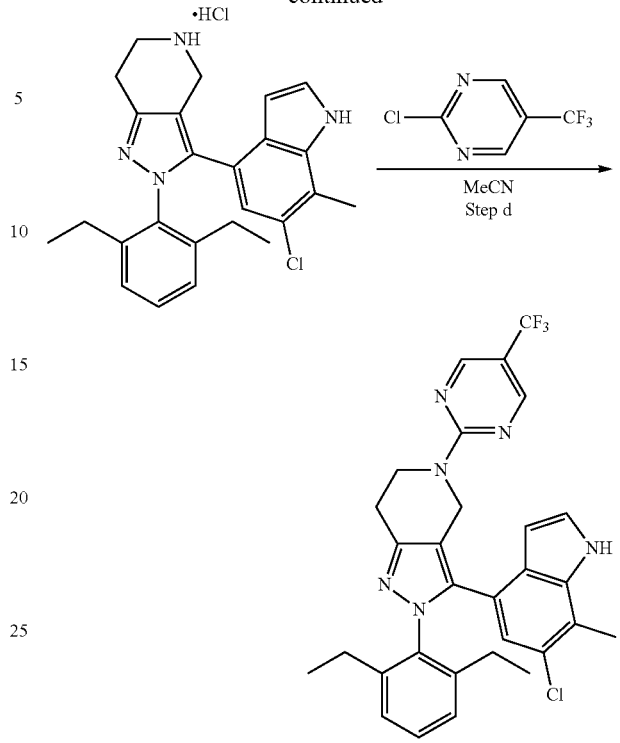

Step a: A solution of vinylmagenesium bromide in THF (1 M, 60 mL, 60 mmol) was added rapidly to a solution of 5-bromo-1-chloro-2-methyl-3-nitrobenzene (5.0 g, 20 mmol) in anhydrous THF (100 mL) under $N_2$ and vigorously stirred at −40° C. The reaction mixture was stirred at the same temperature for 1.5 h. The reaction was quenched with saturated $NH_4Cl$ solution and the mixture was allowed to warm up to room temperature over 1 h. The reaction mixture was diluted with EtOAc, washed with brine and dried over $MgSO_4$. The solvent was removed under reduced pressure and the residue was purified by silica gel flash chromatography (4 to 6% methyl tert-butyl ether/hexane) to give 4-bromo-6-chloro-7-methyl-1H-indole. MS: (ES) m z calculated for $C_9H_8BrClN$ [M+H]$^+$243.9, found 243.9.

Step b: To a suspension of 4-bromo-6-chloro-7-methyl-1H-indole (1.0 g, 4.1 mmol), 4,4,4',4',5,5,5',5'-octamethyl-2,2'-bi(1,3,2-dioxaborolane) (2.0 g, 7.9 mmol), and KOAc (2 g, 20.4 mmol) in p-dioxane (12 mL) was added Pd(dppf)Cl$_2$ complex with dichloromethane (600 mg, 0.73 mmol). The reaction mixture was degassed ($N_2$) for 2 min and stirred at 100° C. for 3 h.

The reaction mixture was diluted with EtOAc, filtered through Celite. The solvent was removed under reduced pressure and the residue was purified by silica gel flash chromatography (5 to 20% EtOAc in hexanes) to give 6-chloro-7-methyl-4-(4,4,5,5-tetramethyl-1,3,2-dioxaborolan-2-yl)-1H-indole. MS: (ES) m z calculated for $C_{15}H_{20}BClNO_2$ [M+H]$^+$ 292.1, found 292.1.

Step c: To a suspension of tert-butyl 3-bromo-2-(2,6-diethylphenyl)-6,7-dihydro-2H-pyrazolo[4,3-c]pyridine-5(4H)-carboxylate (380 mg, 0.87 mmol), 6-chloro-7-methyl-4-(4,4,5,5-tetramethyl-1,3,2-dioxaborolan-2-yl)-1H-indole (250 mg, 0.86 mmol), $K_2CO_3$ (290 mg, 2.1 mmol) in p-dioxane (6 mL) and water (1 mL) was added Pd(dppf)Cl$_2$ complex with dichloromethane (160 mg, 0.19 mmol). The reaction mixture was degassed ($N_2$) for 2 min and stirred under $N_2$ at 100° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) to give tert-butyl 3-(6-chloro-7-methyl-1H-indol-4-yl)-2-(2,6-diethylphenyl)-6,7-dihydro-2H-pyrazolo[4,3-c]pyridine-5 (4H)-carboxylate. MS: (ES) m z calculated for $C_{30}H_{36}ClN_4O_2[M+H]^+$ 519.2, found 519.2.

The above tert-butyl 3-(6-chloro-7-methyl-1H-indol-4-yl)-2-(2,6-diethylphenyl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 3-(6-chloro-7-methyl-1H-indol-4-yl)-2-(2,6-diethylphenyl)-4,5,6,7-tetrahydro-2H-pyrazolo[4,3-c]pyridine hydrochloride. MS: (ES) m z calculated for $C_{25}H_{28}FN_4$ $[M+H]^+$ 419.2, found 419.2.

Step d: N,N-diisopropylethylamine (0.1 mL, 0.58 mmol) was added to a suspension of 3-(6-chloro-7-methyl-1H-indol-4-yl)-2-(2,6-diethylphenyl)-4,5,6,7-tetrahydro-2H-pyrazolo[4,3-c]pyridine hydrochloride (46 mg, 0.10 mmol), 2-chloro-5-(trifluoromethyl)pyrimidine (45 mg, 0.25 mmol), and $Li_2CO_3$ (20 mg, 0.27 mmol) in DMSO (5 mL) under magnetic stirring. The resulting mixture was stirred at 75° C. for 2 h. After cooling to room temperature, the reaction mixture was diluted with EtOAc, washed with brine and dried over $MgSO_4$. The solvent was removed under reduced pressure and the residue was purified by Preparative TLC (40% EtOAc in hexanes) followed by trituration in MeOH to afford 2-(2,6-diethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine. $^1$H NMR (400 MHz, $CDCl_3$) δ 8.49 (s, 2H), 8.21 (s, 1H), 7.06-7.36 (m, 4H), 6.69 (s, 1H), 6.47 (d, J=3.1 Hz, 1H), 4.84 (s, 2H), 4.37 (t, J=5.9 Hz, 2H), 3.04 (t, J=5.9 Hz, 2H), 2.34 (s, 3H), 2.10-2.33 (m, 4H), 0.80-1.08 (m, 6H). MS: (ES) m z calculated $C_{30}H_{29}ClF_3N_6[M+H]^+$ 565.2, found 565.2.

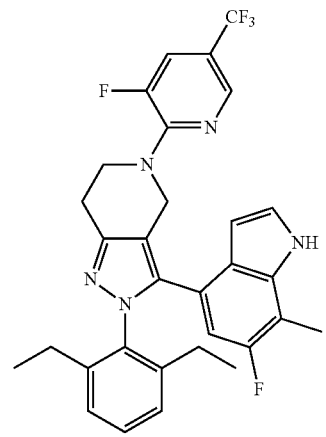

N,N-diisopropylethylamine (0.1 mL, 0.58 mmol) was added to a suspension of 3-(6-chloro-7-methyl-1H-indol-4-yl)-2-(2,6-diethylphenyl)-4,5,6,7-tetrahydro-2H-pyrazolo[4,3-c]pyridine hydrochloride (46 mg, 0.10 mmol), 2,3-difluoro-5-(trifluoromethyl)pyridine (20 mg, 0.11 mmol), and $Li_2CO_3$ (20 mg, 0.27 mmol) in MeCN (5 mL) under magnetic stirring. The resulting mixture was stirred at 75° C. for 2 h. After cooling to room temperature, the reaction mixture was diluted with EtOAc, washed with brine and dried over $MgSO_4$. The solvent was removed under reduced pressure and the residue was purified by Preparative TLC (40% EtOAc in hexanes) followed by trituration in MeOH to afford 3-(6-chloro-7-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, $CDCl_3$) δ 8.16-8.21 (m, 2H), 7.03-7.40 (m, 5H), 6.67 (d, J=0.6 Hz, 1H), 6.48 (dd, J=2.1, 3.3 Hz, 1H), 4.63 (br s, 2H), 4.07 (t, J=5.8 Hz, 2H), 3.11 (t, J=5.8 Hz, 2H), 2.45 (s, 3H), 2.10-2.33 (m, 4H), 0.80-1.08 (m, 6H). MS. (ES) m z calculated $C_{31}H_{29}ClF_4N_5$ $[M+H]^+$ 582.2, found 582.2.

Example 5

Synthesis of 2-(2,6-diethylphenyl)-3-(7-fluoro-1H-indol-4-yl)-5-(5-isopropylpyrimidin-2-yl)-6,7-dihydro-4H-pyrazolo[4,3-c]pyridine

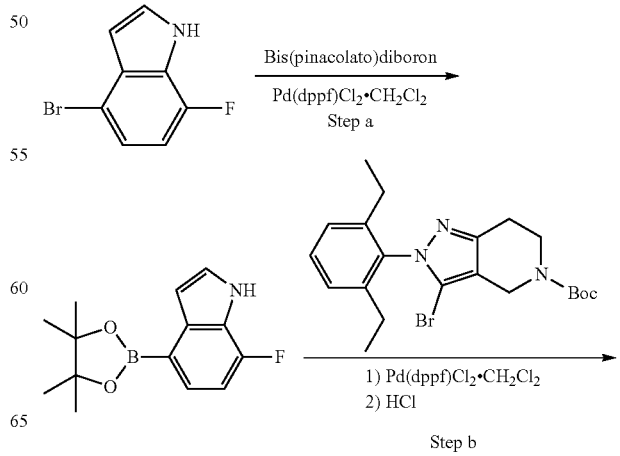

Example 4

Synthesis of 3-(6-chloro-7-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine

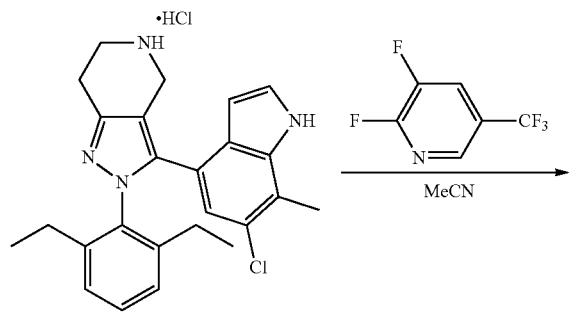

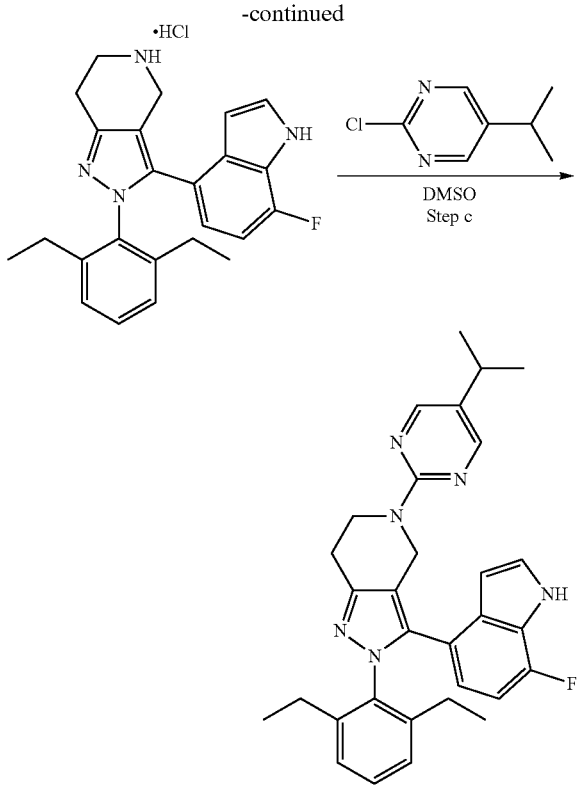

Step a: To a suspension of 4-bromo-7-fluoro-1H-indole (1.00 g, 4.67 mmol), 4,4,4',4',5,5,5',5'-octamethyl-2,2'-bi(1,3,2-dioxaborolane) (1.31 g, 5.14 mmol) and KOAc (1.15 g, 11.7 mmol) in dioxane (15 mL) was added Pd(dppf)Cl$_2$·CH$_2$Cl$_2$ (416 mg, 0.51 mmol). The reaction mixture was degassed (N$_2$) for 2 min and stirred at 100° C. for 2 h. The reaction mixture was cooled to room temperature, diluted with EtOAc and filtered through Celite. The solvent was removed under reduced pressure and the residue was purified by silica gel flash chromatography (0 to 30% EtOAc in hexanes) to give 7-fluoro-4-(4,4,5,5-tetramethyl-1,3,2-dioxaborolan-2-yl)-1H-indole. MS: (ES) m z calculated for C$_{14}$H$_{18}$BFNO$_2$ [M+H]$^+$ 262.1, found 262.1.

Step b: To a suspension of tert-butyl 3-bromo-2-(2,6-diethylphenyl)-6,7-dihydro-2H-pyrazolo[4,3-c]pyridine-5(4H)-carboxylate (490 mg, 1.13 mmol), 7-fluoro-4-(4,4,5,5-tetramethyl-1,3,2-dioxaborolan-2-yl)-1H-indole (350 mg, 1.34 mmol), and K$_2$CO$_3$ (830 mg, 6.78 mmol) in p-dioxane (12 mL) and water (3 mL) was added Pd(dppf)Cl$_2$ complex with dichloromethane (200 mg, 0.32 mmol). The reaction mixture was degassed (N$_2$) for 2 min and stirred under N$_2$ at 100° C. for 2 h. The reaction mixture was cooled to room temperature, diluted with EtOAc, washed with aqueous NaHCO$_3$ and dried over Na$_2$SO$_4$. The solvent was removed under reduced pressure and the residue was purified by silica gel flash chromatography (0 to 40% EtOAc in hexanes) to give tert-butyl 3-(7-fluoro-1H-indol-4-yl)-2-(2,6-diethylphenyl)-6,7-dihydro-4H-pyrazolo[4,3-c]pyridine-5-carboxylate. MS: (ES) m z calculated for C$_{29}$H$_{35}$FN$_4$O$_2$ [M+H]$^+$ 489.3, found 489.3.

The above tert-butyl 3-(7-fluoro-1H-indol-4-yl)-2-(2,6-diethylphenyl)-6,7-dihydro-4H-pyrazolo[4,3-c]pyridine-5-carboxylate (0.350 g, 0.71 mmol) was dissolved in dichloromethane (5 mL) and charged with HCl in dioxane (4N, 5 mL). The resulting mixture was stirred at room temperature for 2 h. The solvent was evaporated in vacuo to give 3-(7-fluoro-1H-indol-4-yl)-2-(2,6-diethylphenyl)-4,5,6,7-tetrahydropyrazolo[4,3-c]pyridine hydrochloride. MS: (ES) m z calculated for C$_{24}$H$_{26}$FN$_4$ [M+H]$^+$ 389.2, found 389.2.

Step c: Triethylamine (0.13 mL, 0.93 mmol) was added to a suspension of 3-(7-fluoro-1H-indol-4-yl)-2-(2,6-diethylphenyl)-4,5,6,7-tetrahydropyrazolo[4,3-c]pyridine hydrochloride (0.040 g, 0.094 mmol), 2-chloro-5-isopropylpyrimidine (70 mg, 0.44 mmol) and Li$_2$CO$_3$ (0.143 g, 1.76 mmol) in DMSO (1.5 mL). The resulting mixture was stirred at 110° C. for 3 h. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 40% EtOAc in hexanes) to afford 2-(2,6-diethylphenyl)-3-(7-fluoro-1H-indol-4-yl)-5-(5-isopropylpyrimidin-2-yl)-6,7-dihydro-4H-pyrazolo[4,3-c]pyridine. $^1$H NMR (400 MHz, CDCl$_3$) δ 8.86 (br s, 1H), 8.49 (s, 2H), 7.20 (t, J=7.6 Hz, 1H), 7.15 (t, J=2.6 Hz, 1H), 7.02 (d, J=6.8 Hz, 2H), 6.64 (m, 1H), 6.51 (m, 2H), 4.75 (s, 2H), 4.30 (br s, 2H), 3.03 (t, J=5.8 Hz, 2H), 2.76 (septet, J=7.0 Hz, 1H), 2.10-2.40 (two br, 4H), 1.21 (d, J=7.2 Hz, 6H), 0.98 (br s, 6H). MS: (ES) m z calculated for C$_{31}$H$_{34}$FN$_6$ [M+H]$^+$ 509.3, found 509.3.

Example 6

Synthesis of 5-[3-chloro-5-(trifluoromethyl)-2-pyridyl]-2-(2,6-diethylphenyl)-3-(7-fluoro-1H-indol-4-yl)-6,7-dihydro-4H-pyrazolo[4,3-c]pyridine

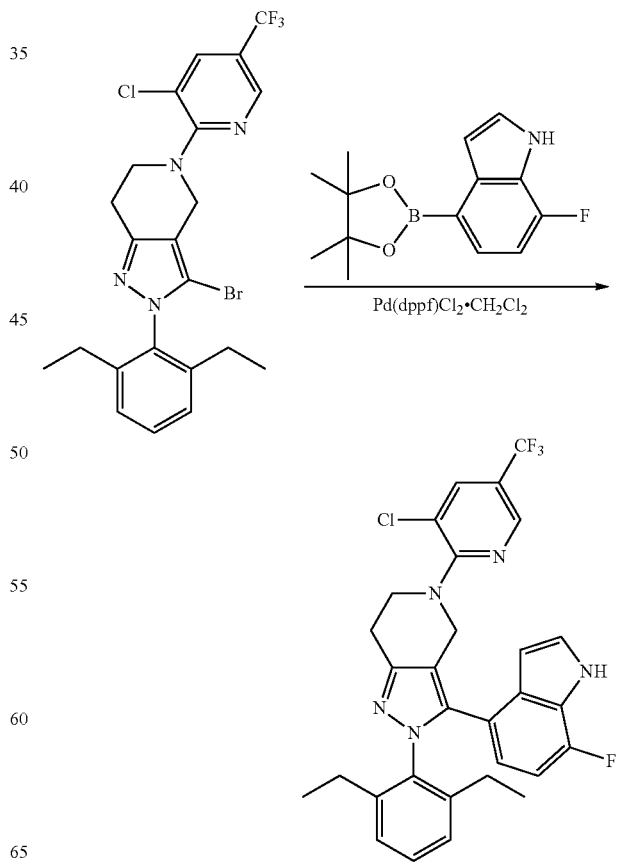

To a suspension of 3-bromo-2-(2,6-diethylphenyl)-5-[3-chloro-5-(trifluoromethyl)-2-pyridyl]-6,7-dihydro-4H-pyrazolo[4,3-c]pyridine (60 mg, 0.12 mmol), 7-fluoro-4-(4,4,5,5-tetramethyl-1,3,2-dioxaborolan-2-yl)-1H-indole (60 mg, 0.24 mmol) and $K_2CO_3$ (180 mg, 1.30 mmol) in p-dioxane (3.2 mL) and water (0.6 mL) was added Pd(dppf)Cl$_2$ complex with dichloromethane (80 mg, 0.098 mmol). The reaction mixture was degassed (N$_2$) for 2 min and stirred under N$_2$ at 100° C. for 2 h. The reaction mixture was cooled to room temperature, diluted with EtOAc, washed with brine and dried over Na$_2$SO$_4$. The solvent was removed under reduced pressure. The obtained residue was purified by silica gel flash chromatography (0-100% DCM/hexanes followed by 0 to 40% EtOAc in hexanes) followed by preparative HPLC to yield 5-[3-chloro-5-(trifluoromethyl)-2-pyridyl]-2-(2,6-diethylphenyl)-3-(7-fluoro-1H-indol-4-yl)-6,7-dihydro-4H-pyrazolo[4,3-c]pyridine. $^1$H NMR (400 MHz, CD$_3$OD) δ 11.31 (br s, 1H), 8.36 (d, J=1.2 Hz, 1H), 7.97 (d, J=2.0 Hz, 1H), 7.39 (m, 1H), 7.27 (t, J=7.6 Hz, 1H), 7.11 (br s, 2H), 6.64 (m, 1H), 6.52 (m, 1H), 6.45 (t, J=3.2 Hz, 1H), 4.47 (br s, 2H), 3.98 (t, J=5.6 Hz, 2H), 3.15 (t, J=5.6 Hz, 2H), 2.31 (br s, 4H), 1.01 (br s, 6H). MS: (ES) m z calculated for $C_{30}H_{27}ClF_4N_5[M+H]^+$ 568.2, found 568.2.

Example 7

Synthesis of 5-(3,5-dichloro-2-pyridyl)-2-(2,6-diethylphenyl)-3-(7-fluoro-1H-indol-4-yl)-6,7-dihydro-4H-pyrazolo[4,3-c]pyridine

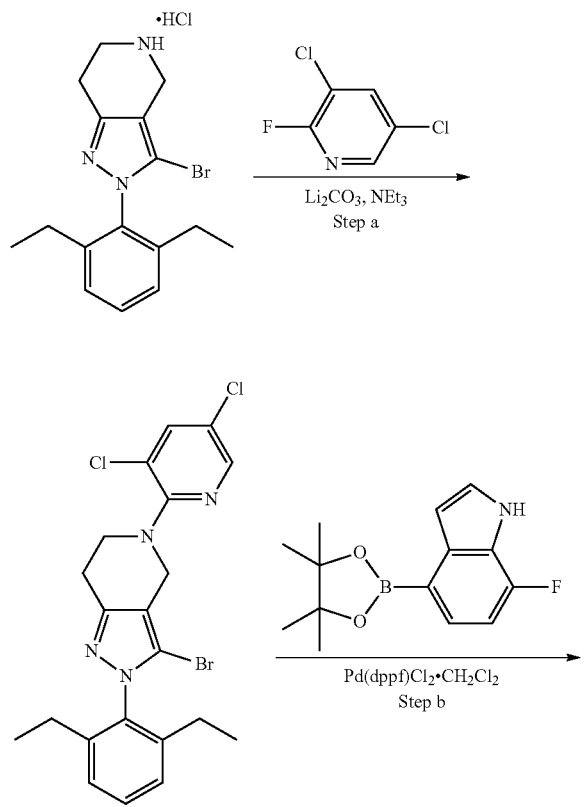

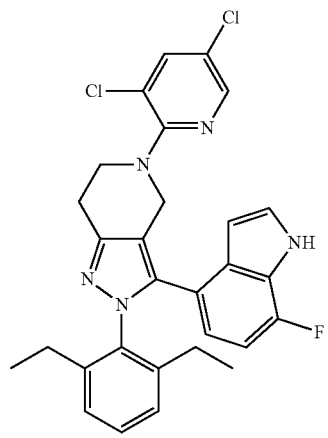

Step a: A mixture of 3-bromo-2-(2,6-diethylphenyl)-4,5,6,7-tetrahydropyrazolo[4,3-c]pyridine hydrochloride (100 mg, 0.27 mmol), 3,5-dichloro-2-fluoro-pyridine (150 mg, 0.90 mmol), Li$_2$CO$_3$ (200 mg, 2.7 mmol) and NEt$_3$ (0.20 mL, 1.42 mmol) in DMSO (3 mL) was stirred at 100° C. for 3 h. It was then cooled to room temperature, diluted with EtOAc and water. The organic layer was separated, dried over Na$_2$SO$_4$, concentrated on a rotary evaporator under reduced pressure and purified by silica gel flash chromatography (0 to 30% EtOAc in hexanes) to afford 3-bromo-5-(3,5-dichloro-2-pyridyl)-2-(2,6-diethylphenyl)-6,7-dihydro-4H-pyrazolo[4,3-c]pyridine.

Step b: To a suspension of 3-bromo-5-(3,5-dichloro-2-pyridyl)-2-(2,6-diethylphenyl)-6,7-dihydro-4H-pyrazolo[4,3-c]pyridine (60 mg, 0.12 mmol), 7-fluoro-4-(4,4,5,5-tetramethyl-1,3,2-dioxaborolan-2-yl)-1H-indole (63 mg, 0.24 mmol), and K$_2$CO$_3$ (140 mg, 1.0 mmol) in p-dioxane (3 mL) and water (0.6 mL) was added Pd(dppf)Cl$_2$ complex with dichloromethane (60 mg, 0.073 mmol). The reaction mixture was degassed (N$_2$) for 2 min and stirred under N$_2$ at 100° C. for 2 h. The reaction mixture was cooled to room temperature, diluted with EtOAc, washed with brine and dried over Na$_2$SO$_4$. The solvent was removed under reduced pressure. The obtained residue was purified by silica gel flash chromatography (0 to 100% DCM/hexanes followed by 0 to 35% EtOAc in hexanes) followed by preparative HPLC to yield 5-(3,5-dichloro-2-pyridyl)-2-(2,6-diethylphenyl)-3-(7-fluoro-1H-indol-4-yl)-6,7-dihydro-4H-pyrazolo[4,3-c]pyridine. $^1$H NMR (400 MHz, CD$_3$OD-CDCl$_3$) δ 11.03 (br s, 1H), 8.02 (d, J=2.4 Hz, 1H), 7.68 (d, J=2.0 Hz, 1H), 7.30 (t, J=2.6 Hz, 1H), 7.21 (t, J=7.6 Hz, 1H), 7.06 (br s, 2H), 6.59 (m, 1H), 6.47 (t, J=8.0 Hz, 1H), 6.44 (m, 1H), 4.29 (br s, 2H), 3.78 (t, J=5.6, 2H), 3.09 (t, J=5.6, 2H), 2.10-2.42 (2 br s, 4H), 0.399 (br s, 6H). MS: (ES) m z calculated for $C_{29}H_{27}Cl_2FN_5 [M+H]^+$ 534.2, found 534.2.

Example 8

Synthesis of 2-(2,6-diethylphenyl)-3-(7-fluoro-1H-indol-4-yl)-5-[3-fluoro-5-(trifluoromethyl)-2-pyridyl]-6,7-dihydro-4H-pyrazolo[4,3-c]pyridine

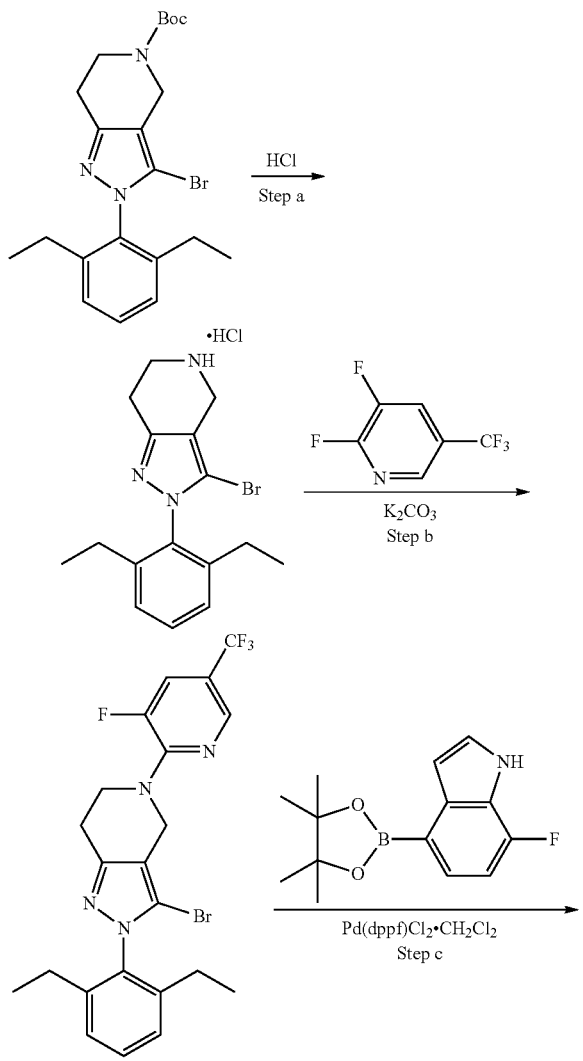

Step a: tert-Butyl 3-bromo-2-(2,6-diethylphenyl)-6,7-dihydro-4H-pyrazolo[4,3-c]pyridine-5-carboxylate (400 mg, 0.92 mmol) was dissolved in dichloromethane (4 mL) and charged with HCl in dioxane (4N, 6 mL). The resulting mixture was stirred at room temperature for 1.5 h. The solvent was evaporated in vacuo to give 3-bromo-2-(2,6-diethylphenyl)-4,5,6,7-tetrahydropyrazolo[4,3-c]pyridine hydrochloride.

Step b: A mixture of 3-bromo-2-(2,6-diethylphenyl)-4,5,6,7-tetrahydropyrazolo[4,3-c]pyridine hydrochloride (100 mg, 0.27 mmol), 2,3-difluoro-5-(trifluoromethyl)pyridine (100 mg, 0.54 mmol) and $K_2CO_3$ (150 mg, 1.08 mmol) in $CH_3CN$ (3 mL) was stirred at 80° C. for 2 h. After cooling to room temperature, the reaction mixture was diluted with EtOAc, washed with aqueous $NaHCO_3$ and dried over $Na_2SO_4$. The solvent was removed under reduced pressure and the residue was purified by silica gel flash chromatography (0 to 30% EtOAc in hexanes) to afford 3-bromo-2-(2,6-diethylphenyl)-5-[3-fluoro-5-(trifluoromethyl)-2-pyridyl]-6,7-dihydro-4H-pyrazolo[4,3-c]pyridine. MS: (ES) m z calculated for $C_{22}H_{22}BrF_4N_4[M+H]^+$ 497.1, found 497.1.

Step c: To a suspension of 3-bromo-2-(2,6-diethylphenyl)-5-[3-fluoro-5-(trifluoromethyl)-2-pyridyl]-6,7-dihydro-4H-pyrazolo[4,3-c]pyridine (60 mg, 0.12 mmol), 7-fluoro-4-(4,4,5,5-tetramethyl-1,3,2-dioxaborolan-2-yl)-1H-indole (45 mg, 0.17 mmol), and $K_2CO_3$ (120 mg, 0.86 mmol) in p-dioxane (3 mL) and water (0.6 mL) was added Pd(dppf)$Cl_2$ complex with dichloromethane (120 mg, 0.15 mmol). The reaction mixture was degassed ($N_2$) for 2 min and stirred under $N_2$ at 100° C. for 1 h. The reaction mixture was cooled to room temperature, diluted with EtOAc, washed with brine, and dried over $Na_2SO_4$. The solvent was removed under reduced pressure and the residue was purified by silica gel flash chromatography (0 to 100% DCM in hexanes followed by 0 to 50% EtOAc in hexanes) to give 2-(2,6-diethylphenyl)-3-(7-fluoro-1H-indol-4-yl)-5-[3-fluoro-5-(trifluoromethyl)-2-pyridyl]-6,7-dihydro-4H-pyrazolo[4,3-c]pyridine. $^1$H NMR (400 MHz, CDCl$_3$) δ 8.70 (br s, 1H), 8.19 (s, 1H), 7.39 (dd, J=2, 13 Hz, 1H), 7.20 (m, 2H), 7.03 (d, J=7.2 Hz, 2H), 6.67 (m, 1H), 6.52 (m, 2H), 4.64 (br s, 2H), 4.07 (t, J=5.6 Hz, 2H), 3.12 (t, J=5.6 Hz, 2H), 2.1-2.4 (two br s, 4H), 0.98 (br s, 6H). MS: (ES) m z calculated for $C_{30}H_{27}F_5N_5$ $[M+H]^+$552.2, found 552.2.

Example 9

Synthesis of 2-(2,6-diethylphenyl)-3-(7-methoxy-1H-indol-4-yl)-5-(5-(trifluoromethyl)pyrimidin-2-yl)-4,5,6,7-tetrahydro-2H-pyrazolo[4,3-c]pyridine

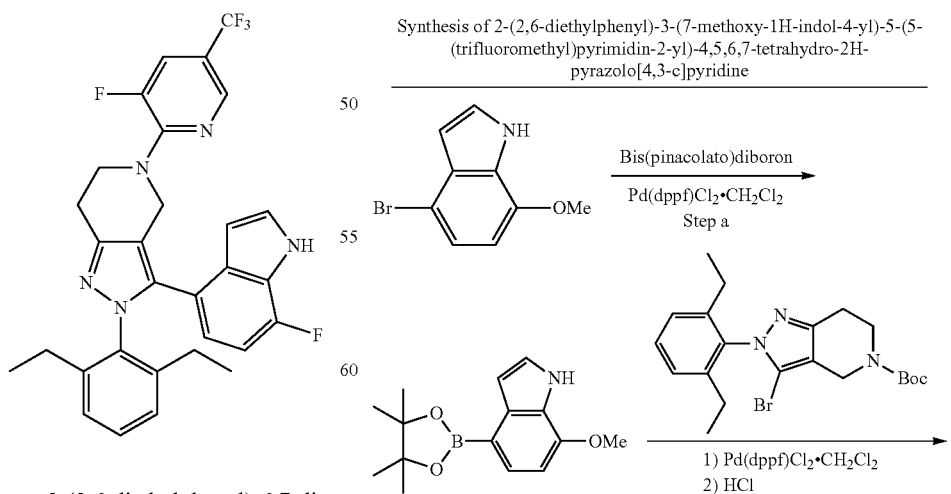

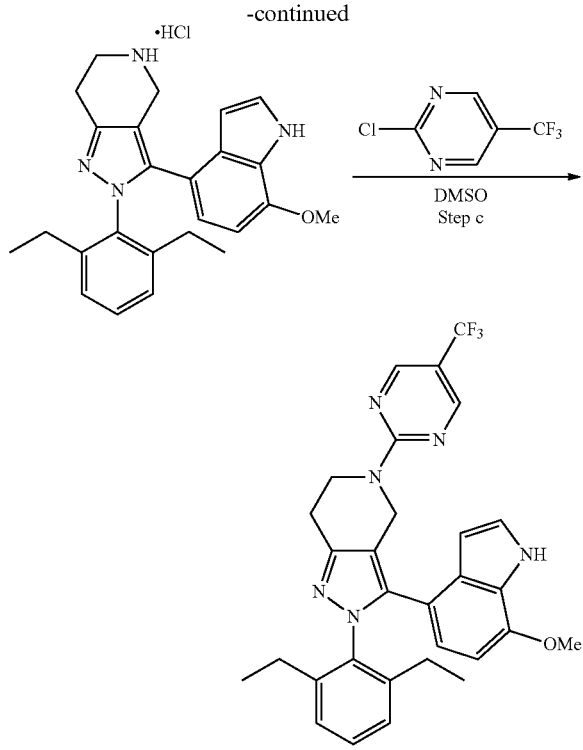

Step a: To a suspension of 4-bromo-7-methoxy-1H-indole (800 mg, 3.5 mmol), 4,4,4',4',5,5,5',5'-octamethyl-2,2'-bi(1,3,2-dioxaborolane) (1.6 g, 6.3 mmol), and KOAc (1.6 g, 16.3 mmol) in p-dioxane (10 mL) was added Pd(dppf)Cl$_2$ complex with dichloromethane (800 mg, 0.97 mmol). The reaction mixture was degassed (N$_2$) for 2 min and stirred at 100° C. for 3 h. The reaction mixture was diluted with EtOAc, filtered through Celite. The solvent was removed under reduced pressure and the residue was purified by silica gel flash chromatography (5 to 25% EtOAc in hexanes) to give 7-methoxy-4-(4,4,5,5-tetramethyl-1,3,2-dioxaborolan-2-yl)-1H-indole. MS: (ES) m z calculated for C$_{15}$H$_{21}$BNO$_3$ [M+H]$^+$ 274.2, found 274.2.

Step b: To a suspension of tert-butyl 3-bromo-2-(2,6-diethylphenyl)-6,7-dihydro-2H-pyrazolo[4,3-c]pyridine-5(4H)-carboxylate (300 mg, 0.72 mmol), 7-methoxy-4-(4,4,5,5-tetramethyl-1,3,2-dioxaborolan-2-yl)-1H-indole (200 mg, 0.73 mmol), and K$_2$CO$_3$ (300 mg, 2.2 mmol) in p-dioxane (6 mL) and water (1 mL) was added Pd(dppf)Cl$_2$ complex with dichloromethane (100 mg, 0.12 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 20% EtOAc in hexanes) to give tert-butyl 2-(2,6-diethylphenyl)-3-(7-methoxy-1H-indol-4-yl)-6,7-dihydro-2H-pyrazolo[4,3-c]pyridine-5(4H)-carboxylate. MS: (ES) m z calculated for C$_{30}$H$_{37}$N$_4$O$_3$ [M+H]$^+$ 501.2, found 501.2.

The above tert-butyl 2-(2,6-diethylphenyl)-3-(7-methoxy-1H-indol-4-yl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 2-(2,6-diethylphenyl)-3-(7-methoxy-1H-indol-4-yl)-4,5,6,7-tetrahydro-2H-pyrazolo[4,3-c]pyridine hydrochloride. MS: (ES) m z calculated for C$_{25}$H$_{29}$N$_4$O [M+H]$^+$ 401.2, found 401.2.

Step c: N,N-diisopropylethylamine (0.1 mL, 0.58 mmol) was added to a suspension of 2-(2,6-diethylphenyl)-3-(7-methoxy-1H-indol-4-yl)-4,5,6,7-tetrahydro-2H-pyrazolo[4,3-c]pyridine hydrochloride (50 mg, 0.11 mmol), 2-chloro-5-(trifluoromethyl)pyrimidine (50 mg, 0.27 mmol), and Li$_2$CO$_3$ (20 mg, 0.27 mmol) in DMSO (10 mL) under magnetic stirring. The resulting mixture was stirred at 75° C. for 1 h. After cooling to room temperature, the reaction mixture was diluted with EtOAc, washed with brine and dried over MgSO$_4$. The solvent was removed under reduced pressure and the residue was purified by Preparative TLC (40% EtOAc in hexanes) followed by trituration in MeOH to afford 2-(2,6-diethylphenyl)-3-(7-methoxy-1H-indol-4-yl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.45 (s, 2H), 8.18 (dt, J=1.0, 2.0 Hz, 2H), 7.37 (dd, J=2.0, 13.2 Hz, 1H), 7.03-7.30 (m, 4H), 6.54 (dd, J=0.8, 8.0 Hz, 1H), 6.37-6.49 (m, 2H), 4.65 (s, 2H), 4.07 (t, J=5.8 Hz, 2H), 3.88 (s, 3H), 3.11 (t, J=5.8 Hz, 2H), 2.10-2.35 (br m, 4H), 0.85-1.03 (br m, 6H). MS: (ES) m z calculated C$_{30}$H$_{30}$F$_3$N$_6$O [M+H]$^+$ 547.2, found 547.2.

Example 10

Synthesis of 2-(2,6-diethylphenyl)-5-(3-fluoro-5-(trifluoromethyl)pyridin-2-yl)-3-(7-methoxy-1H-indol-4-yl)-4,5,6,7-tetrahydro-2H-pyrazolo[4,3-c]pyridine

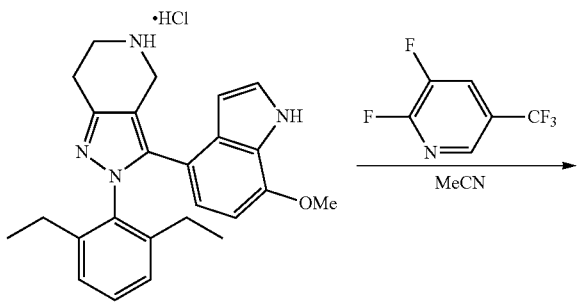

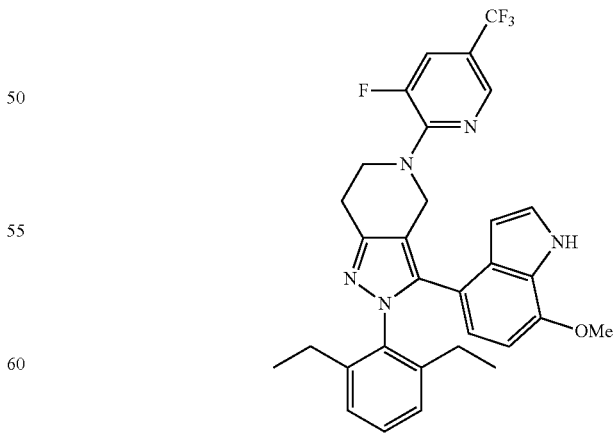

N,N-diisopropylethylamine (0.1 mL, 0.58 mmol) was added to a suspension of 2-(2,6-diethylphenyl)-3-(7-methoxy-1H-indol-4-yl)-4,5,6,7-tetrahydro-2H-pyrazolo[4, 3-c]pyridine hydrochloride (50 mg, 0.11 mmol), 2,3-difluoro-5-(trifluoromethyl)pyridine (60 mg, 0.33 mmol), and Li$_2$CO$_3$ (20 mg, 0.27 mmol) in MeCN (5 mL) under magnetic stirring. The resulting mixture was stirred at 80° C. for 2 h. After cooling to room temperature, the reaction mixture was diluted with EtOAc, washed with brine and dried over MgSO$_4$. The solvent was removed under reduced pressure and the residue was purified by Preparative TLC (40% EtOAc in hexanes) followed by trituration in MeOH to afford 2-(2,6-diethylphenyl)-5-(3-fluoro-5-(trifluoromethyl)pyridin-2-yl)-3-(7-methoxy-1H-indol-4-yl)-4,5,6,7-tetrahydro-2H-pyrazolo[4,3-c]pyridine. $^1$H NMR (400 MHz, CDCl$_3$) δ 8.46 (d, J=11.4 Hz, 2H), 7.16-7.31 (m, 4H), 7.02 (d, J=7.7 Hz, 1H), 6.40-6.55 (m, 3H), 4.85 (s, 2H), 4.36 (t, J=5.9 Hz, 2H), 3.89 (s, 3H), 3.03 (t, J=5.9 Hz, 2H), 2.10-2.35 (br m, 4H), 0.85-1.03 (br m, 6H). MS: (ES) m z calculated C$_{31}$H$_{30}$F$_4$N$_5$O [M+H]$^+$ 564.2, found 564.2.

Example 11

Synthesis of 3-(7-chloro-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine

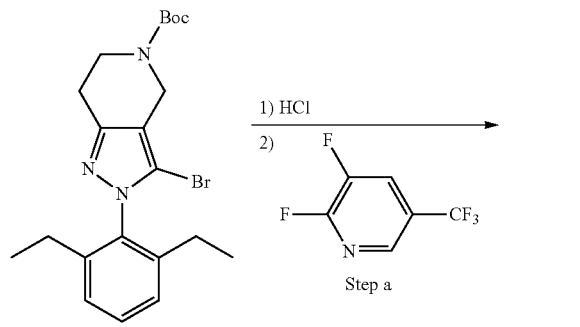

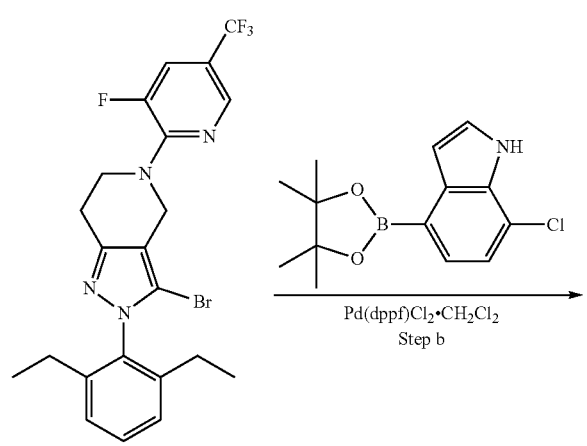

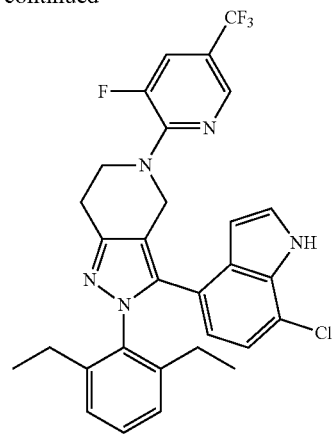

Step a: tert-butyl 3-bromo-2-(2,6-diethylphenyl)-6,7-dihydro-2H-pyrazolo[4,3-c]pyridine-5(4H)-carboxylate (1.5 g, 3.6 mmol), was dissolved in dichloromethane (10 mL) and charged with HCl in dioxane (4N, 5 mL). The resulting mixture was stirred at room temperature for 2 h. After the reaction was complete, the solvent was evaporated in vacuo to give 3-bromo-2-(2,6-diethylphenyl)-4,5,6,7-tetrahydro-2H-pyrazolo[4,3-c]pyridine hydrochloride. MS: (ES) m z calculated for C$_{16}$H$_{21}$BrN$_3$ [M+H]$^+$ 334.1, found 334.1.

N,N-diisopropylethylamine (0.2 mL, 1.15 mmol) was added to a suspension of 3-bromo-2-(2,6-diethylphenyl)-4,5,6,7-tetrahydro-2H-pyrazolo[4,3-c]pyridine hydrochloride (750 mg, 2.02 mmol), 2,3-difluoro-5-(trifluoromethyl)pyridine (800 mg, 4.37 mmol), and K$_2$CO$_3$ (800 mg, 5.79 mmol) in MeCN (10 mL) under magnetic stirring. The resulting mixture was stirred at 85° C. for 2 h. After cooling to room temperature, the reaction mixture was diluted with EtOAc, washed with brine and dried over MgSO$_4$. The solvent was removed under reduced pressure and the residue was purified by silica gel flash chromatography (2 to 15% EtOAc in hexanes) to afford 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine. MS: (ES) m z calculated for C$_{22}$H$_{22}$BrF$_4$N$_4$[M+H]$^+$497.1, found 497.1.

Step b. To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (50 mg, 0.1 mmol), 7-chloro-4-(4,4,5,5-tetramethyl-1,3,2-dioxaborolan-2-yl)-1H-indole (50 mg, 0.18 mmol), and K$_2$CO$_3$ (180 mg, 1.3 mmol) in p-dioxane (6 mL) and water (1 mL) was added Pd(dppf)Cl$_2$ complex with dichloromethane (40 mg, 0.05 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 20% EtOAc in hexanes) to give 3-(7-chloro-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, CDCl$_3$) δ 8.46 (s, 1H), 8.18 (s, 1H), 7.04-7.43 (m, 5H), 6.97 (d, J=7.9 Hz, 1H), 6.52-6.59 (m, 2H), 4.63 (s, 2H), 4.07 (t, J=5.8 Hz, 2H), 3.11 (t, J=5.8 Hz, 2H), 2.10-2.40 (m, 4H), 0.80-1.08 (m, 6H). MS: (ES) m z calculated C$_{30}$H$_{27}$ClF$_4$N$_5$ [M+H]$^+$ 568.2, found 568.2.

Example 12

Synthesis of 2-(2,6-diethylphenyl)-5-(3-fluoro-5-(trifluoromethyl)pyridin-2-yl)-3-(5-fluoro-7-methyl-1H-indol-4-yl)-4,5,6,7-tetrahydro-2H-pyrazolo[4,3-c]pyridine

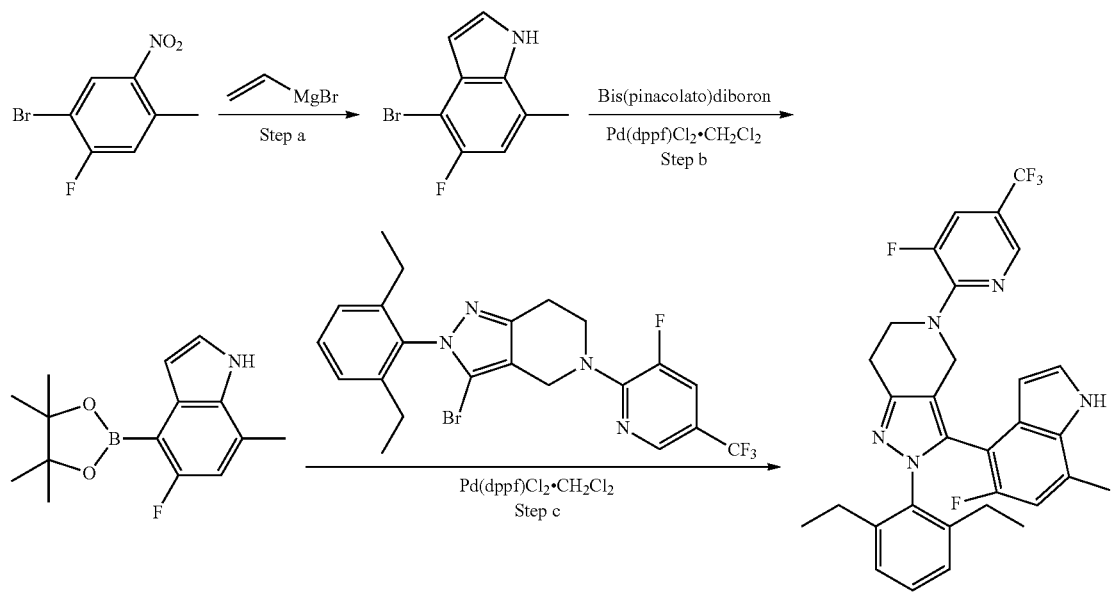

Step a: A solution of vinylmagenesium bromide in THE (1 M, 66 mL, 66 mmol) was added rapidly to a solution of 1-bromo-2-fluoro-4-methyl-5-nitrobenzene (5.0 g, 21.4 mmol) in anhydrous THF (50 mL) under $N_2$ and vigorously stirring at −60° C. The reaction mixture was stirred at the same temperature and allowed to warm to −35° C. over 1.5 h. The reaction was quenched with saturated $NH_4Cl$ solution and the mixture was allowed to warm up to room temperature over 1 h. The reaction mixture was diluted with EtOAc, washed with brine and dried over $MgSO_4$. The solvent was removed under reduced pressure and the residue was purified by silica gel flash chromatography (2 to 20% EtOAc in hexanes) to give 4-bromo-5-fluoro-7-methyl-1H-indole. MS: (ES) m z calculated for $C_9H_8BrFN$ [M+H]$^+$227.9, found 227.9.

Step b: To a suspension of 4-bromo-5-fluoro-7-methyl-1H-indole (1.6 g, 7.0 mmol), 4,4,4',4',5,5,5',5'-octamethyl-2,2'-bi(1,3,2-dioxaborolane) (3.2 g, 12.6 mmol), and KOAc (3 g, 30.6 mmol) in p-dioxane (10 mL) was added Pd(dppf)Cl$_2$ complex with dichloromethane (800 mg, 0.97 mmol). The reaction mixture was degassed ($N_2$) for 2 min and stirred at 95° C. for 5 h. The reaction mixture was diluted with EtOAc, filtered through Celite. The solvent was removed under reduced pressure and the residue was purified by silica gel flash chromatography (5 to 30% EtOAc in hexanes) to give 5-fluoro-7-methyl-4-(4,4,5,5-tetramethyl-1,3,2-dioxaborolan-2-yl)-1H-indole. MS: (ES) m z calculated for $C_{15}H_{20}BFNO_2$ [M+H]$^+$276.2, found 276.2.

Step c: To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (80 mg, 0.16 mmol), 5-fluoro-7-methyl-4-(4,4,5,5-tetramethyl-1,3,2-dioxaborolan-2-yl)-1H-indole (80 mg, 0.29 mmol), and $K_2CO_3$ (180 mg, 1.3 mmol) in p-dioxane (6 mL) and water (1 mL) was added Pd(dppf)Cl$_2$ complex with dichloromethane (40 mg, 0.05 mmol). The reaction mixture was degassed ($N_2$) for 2 min and stirred under $N_2$ at 100° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) followed by HPLC (MeCN/H$_2$O, with 1% TFA) to give 2-(2,6-diethylphenyl)-5-(3-fluoro-5-(trifluoromethyl)pyridin-2-yl)-3-(5-fluoro-7-methyl-1H-indol-4-yl)-4,5,6,7-tetrahydro-2H-pyrazolo[4,3-c]pyridine. $^1$H NMR (400 MHz, CDCl$_3$) δ 8.13-8.20 (m, 2H), 7.38 (dd, J=2.0 Hz, 13.0,1H), 7.10-7.29 (m, 3H), 6.84-6.91 (m, 1H), 6.60 (dd, J=0.9, 10.8 Hz, 1H), 6.39 (dd, J=2.1 3.2 Hz, 1H), 4.75 (d, J=15.7 Hz, 1H), 4.45 (d, J=15.7 Hz, 1H), 4.02-4.09 (m, 2H), 3.12 (t, J=5.8, 2H), 2.41-2.54 (m, 2H), 2.43 (s, 3H), 1.96-2.21 (m, 2H), 1.22 (t, J=7.5 Hz, 3H), 0.75 (t, J=7.5 Hz, 3H). MS: (ES) m z calculated C$_{31}$H$_{29}$F$_5$N$_5$ [M+H]$^+$ 566.2, found 566.2.

Example 13

Synthesis of 3-(7-chloro-1H-indol-4-yl)-2-(2,6-diethylphenyl)-5-(5-(trifluoromethyl)pyridin-2-yl)-4,5,6,7-tetrahydro-2H-pyrazolo[4,3-c]pyridine

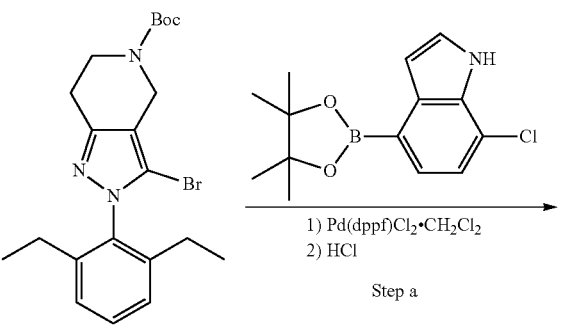

1) Pd(dppf)Cl$_2$•CH$_2$Cl$_2$
2) HCl

Step a

-continued

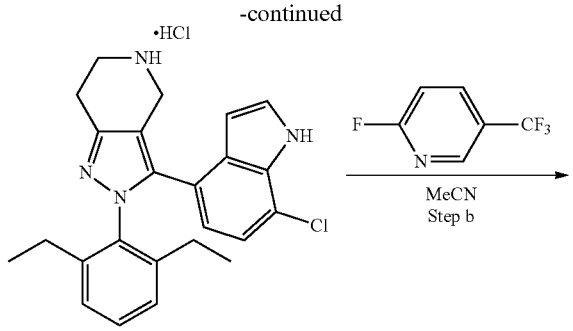

Step a: To a suspension of tert-butyl 3-bromo-2-(2,6-diethylphenyl)-6,7-dihydro-2H-pyrazolo[4,3-c]pyridine-5(4H)-carboxylate (500 mg, 1.2 mmol), 7-chloro-4-(4,4,5,5-tetramethyl-1,3,2-dioxaborolan-2-yl)-1H-indole (400 mg, 1.44 mmol), and K₂CO₃ (500 mg, 3.6 mmol) in p-dioxane (6 mL) and water (1 mL) was added Pd(dppf)Cl₂ complex with dichloromethane (200 mg, 0.24 mmol). The reaction mixture was degassed (N₂) for 2 min and stirred under N₂ at 100° C. for 2 h. The reaction mixture was diluted with EtOAc, filtered through Celite, washed with brine and dried over MgSO₄. The solvent was removed under reduced pressure and the residue was purified by silica gel flash chromatography (5 to 35% EtOAc in hexanes) to give tert-butyl 3-(7-chloro-1H-indol-4-yl)-2-(2,6-diethylphenyl)-6,7-dihydro-2H-pyrazolo[4,3-c]pyridine-5(4H)-carboxylate. MS: (ES) m z calculated for C₂₉H₃₄ClN₄O₂[M+H]⁺ 505.2, found 505.2.

The above tert-butyl 3-(7-chloro-1H-indol-4-yl)-2-(2,6-diethylphenyl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 3-(7-chloro-1H-indol-4-yl)-2-(2,6-diethylphenyl)-4,5,6,7-tetrahydro-2H-pyrazolo[4,3-c]pyridine hydrochloride. MS: (ES) m z calculated for C₂₅H₂₈FN₄ [M+H]⁺ 403.2, found 403.2.

Step b: N,N-diisopropylethylamine (0.2 mL, 1.15 mmol) was added to a suspension of 3-(7-chloro-1H-indol-4-yl)-2-(2,6-diethylphenyl)-4,5,6,7-tetrahydro-2H-pyrazolo[4,3-c]pyridine hydrochloride (50 mg, 0.11 mmol), 2-fluoro-5-(trifluoromethyl)pyridine (50 mg, 0.31 mmol), and Li₂CO₃ (20 mg, 0.27 mmol) in MeCN (5 mL) under magnetic stirring. The resulting mixture was stirred at 85° C. for 5 h. After cooling to room temperature, the reaction mixture was diluted with EtOAc, washed with brine and dried over MgSO₄. The solvent was removed under reduced pressure and the residue was purified by Preparative TLC (40% EtOAc in hexanes) followed by trituration in MeOH to afford 3-(7-chloro-1H-indol-4-yl)-2-(2,6-diethylphenyl)-5-(5-(trifluoromethyl)pyridin-2-yl)-4,5,6,7-tetrahydro-2H-pyrazolo[4,3-c]pyridine. ¹H NMR (400 MHz, CDCl₃) δ 8.29-8.37 (m, 2H), 7.70 (ddt, J=0.6, 2.6, 9.1 Hz, 1H), 7.46 (d, J=3.2 Hz, 1H), 7.27 (t, J=7.7 Hz, 1H), 7.11 (br, 2H), 6.84-6.93 (m, 2H), 6.51-6.55 (m, 2H), 4.65 (s, 2H), 4.19 (t, J=5.8 Hz, 2H), 3.01 (t, J=5.8 Hz, 2H), 2.10-2.33 (br,m, 4H), 0.80-1.08 (br,m, 6H). MS: (ES) m z calculated C₃₀H₂₈ClF₃N₅[M+H]⁺ 550.2, found 550.2.

Example 14

Synthesis of 3-(7-chloro-1H-indol-4-yl)-2-(2,6-diethylphenyl)-5-(3-methyl-5-(trifluoromethyl)pyridin-2-yl)-4,5,6,7-tetrahydro-2H-pyrazolo[4,3-c]pyridine

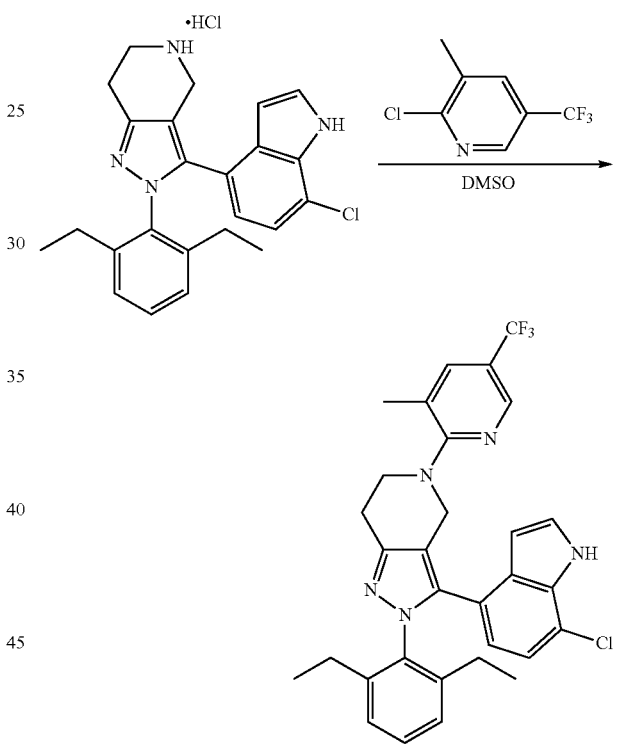

N,N-diisopropylethylamine (0.1 mL, 0.58 mmol) was added to a suspension of 3-(7-chloro-1H-indol-4-yl)-2-(2,6-diethylphenyl)-4,5,6,7-tetrahydro-2H-pyrazolo[4,3-c]pyridine hydrochloride (25 mg, 0.06 mmol), 2-chloro-3-methyl-5-(trifluoromethyl)pyridine (40 mg, 0.20 mmol), and Li₂CO₃ (20 mg, 0.27 mmol) in DMSO (5 mL) under magnetic stirring. The resulting mixture was stirred at 155° C. for 6 h. After cooling to room temperature, the reaction mixture was diluted with EtOAc, washed with brine and dried over MgSO₄. The solvent was removed under reduced pressure and the residue was purified by HPLC (MeCN/H₂O, with 0.1% TFA) to afford 3-(7-chloro-1H-indol-4-yl)-2-(2,6-diethylphenyl)-5-(3-methyl-5-(trifluoromethyl)pyridin-2-yl)-4,5,6,7-tetrahydro-2H-pyrazolo[4,3-c]pyridine. ¹H NMR (400 MHz, CDCl₃) δ 8.48 (s, 1H), 8.31 (dt, J=0.9, 1.7 Hz, 1H), 7.57 (tt, J=0.8, 1.7 Hz, 1H), 7.19-7.29 (m, 2H), 7.04 (d, J=7.7 Hz, 2H), 6.95 (dd, J=0.7, 7.7 Hz, 1H), 6.51-6.57 (m, 2H), 4.32 (s, 2H), 3.66 (t, J=5.8 Hz, 2H), 3.14 (t, J=5.8 Hz, 2H), 2.40 (s, 3H), 2.10-2.38 (br,m, 4H), 0.88-1.08 (br,m, 6H) MS: (ES) m z calculated $C_{31}H_{30}ClF_3N_5[M+H]^+$ 564.2, found 564.2.

Example 15

Synthesis of 3-(7-chloro-1H-indol-4-yl)-2-(2,6-diethylphenyl)-5-(3-methyl-5-(trifluoromethyl)pyridin-2-yl)-4,5,6,7-tetrahydro-2H-pyrazolo[4,3-c]pyridine

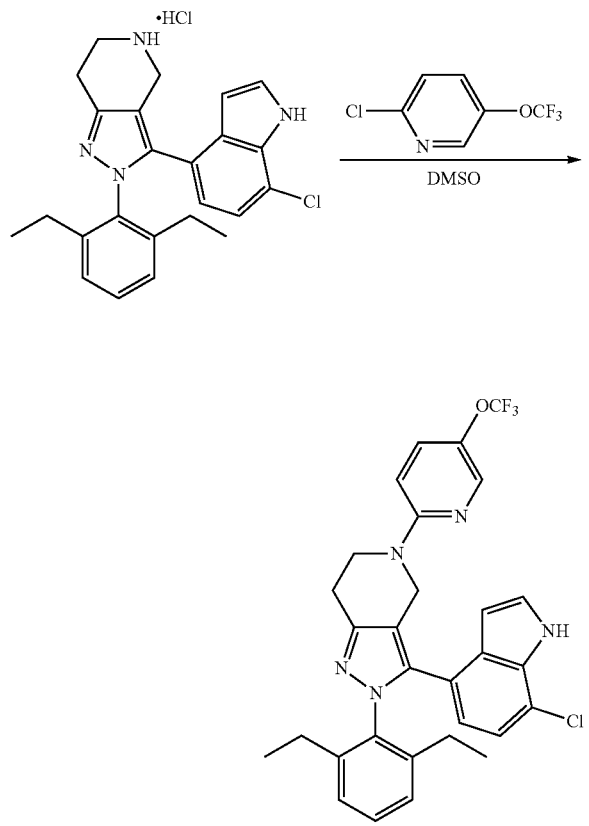

N,N-diisopropylethylamine (0.1 mL, 0.58 mmol) was added to a suspension of 3-(7-chloro-1H-indol-4-yl)-2-(2,6-diethylphenyl)-4,5,6,7-tetrahydro-2H-pyrazolo[4,3-c]pyridine hydrochloride (25 mg, 0.06 mmol), 2-chloro-5-(trifluoromethoxy)pyridine (30 mg, 0.15 mmol), and $Li_2CO_3$ (20 mg, 0.27 mmol) in DMSO (5 mL) under magnetic stirring. The resulting mixture was stirred at 155° C. for 4 h. After cooling to room temperature, the reaction mixture was diluted with EtOAc, washed with brine and dried over $MgSO_4$. The solvent was removed under reduced pressure and the residue was purified by HPLC (MeCN/$H_2O$, with 1% TFA) to afford 3-(7-chloro-1H-indol-4-yl)-2-(2,6-diethylphenyl)-5-(5-(trifluoromethoxy)pyridin-2-yl)-4,5,6,7-tetrahydro-2H-pyrazolo[4,3-c]pyridine. $^1$H NMR (400 MHz, CDCl$_3$) δ 8.49 (s, 1H), 8.09 (dd, J=1.0, 2.9 Hz, 1H), 7.02-7.34 (m, 5H), 6.98 (dd, J=8.0 Hz, 1H), 6.54-6.66 (m, 3H), 4.50 (s, 2H), 4.11 (t, J=5.8 Hz, 2H), 3.05 (t, J=5.8 Hz, 2H), 2.14-2.32 (br,m, 4H), 0.88-1.08 (br,m, 6H). MS: (ES) m z calculated $C_{30}H_{28}ClF_3N_5O$ [M+H]$^+$ 566.2, found 566.2.

Example 16

Synthesis of 3-(7-chloro-1H-indol-4-yl)-5-(3-chloro-5-fluoropyridin-2-yl)-2-(2,6-diethylphenyl)-4,5,6,7-tetrahydro-2H-pyrazolo[4,3-c]pyridine

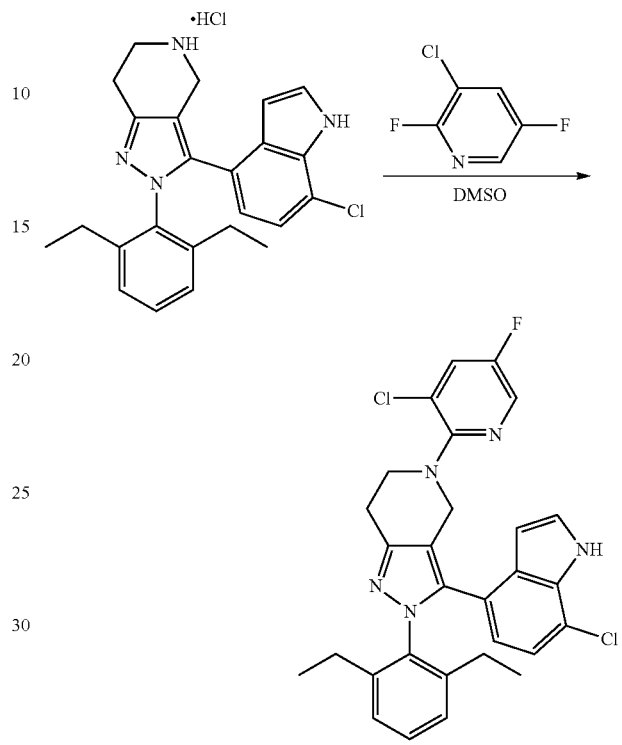

N,N-diisopropylethylamine (0.1 mL, 0.58 mmol) was added to a suspension of 3-(7-chloro-1H-indol-4-yl)-2-(2,6-diethylphenyl)-4,5,6,7-tetrahydro-2H-pyrazolo[4,3-c]pyridine hydrochloride (45 mg, 0.10 mmol), 3-chloro-2,5-difluoropyridine (60 mg, 0.40 mmol), and $K_2CO_3$ (100 mg, 0.72 mmol) in DMSO (5 mL) under magnetic stirring. The resulting mixture was stirred at 120° C. for 6 h. After cooling to room temperature, the reaction mixture was diluted with EtOAc, washed with brine and dried over $MgSO_4$. The solvent was removed under reduced pressure and the residue was purified by HPLC (MeCN/$H_2O$, with 0.1% TFA) to afford 3-(7-chloro-1H-indol-4-yl)-5-(3-chloro-5-fluoropyridin-2-yl)-2-(2,6-diethylphenyl)-4,5,6,7-tetrahydro-2H-pyrazolo[4,3-c]pyridine. $^1$H NMR (400 MHz, CDCl$_3$) δ 8.42 (s, 1H), 8.00 (dd, J=0.5, 2.7 Hz, 1H), 7.45 (dd, J=2.7, 7.5 Hz, 1H), 7.19-7.30 (m, 2H), 7.03 (br, 2H), 6.95 (d, J=7.9 Hz, 1H), 6.52-6.60 (m, 2H), 4.26 (s, 2H), 3.72 (t, J=5.8 Hz, 2H), 3.15 (t, J=5.8 Hz, 2H), 2.17-2.35 (br,m, 4H), 0.88-1.08 (br,m, 6H). MS: (ES) m z calculated $C_{29}H_{27}Cl_2FN_5$ [M+H]$^+$ 534.2, found 534.2.

Example 17

Synthesis of 3-(7-chloro-1H-indol-4-yl)-5-(5-cyclopropyl-3-fluoro-2-pyridyl)-2-(2,6-diethylphenyl)-6,7-dihydro-4H-pyrazolo[4,3-c]pyridine

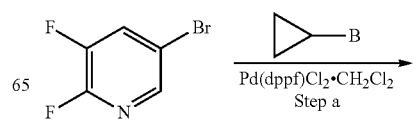

65
-continued

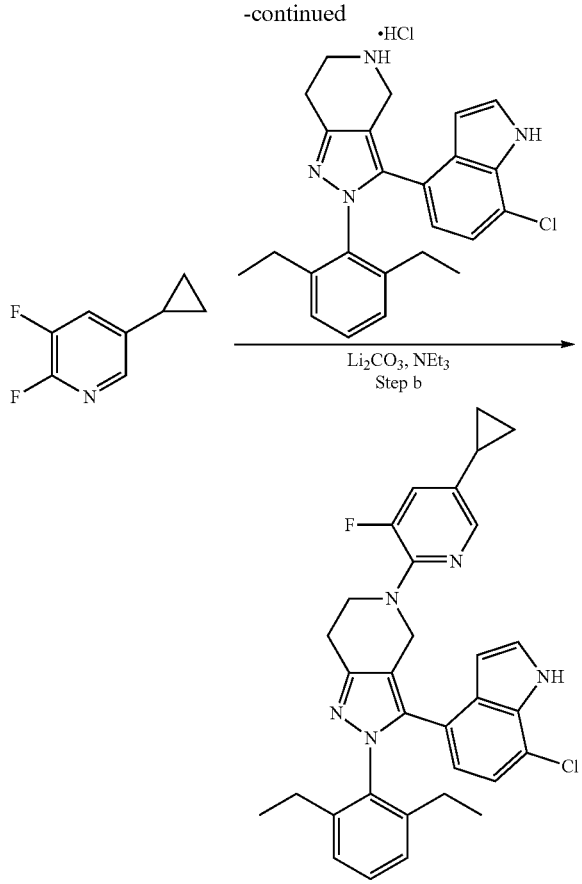

Step a: A mixture of 5-bromo-2,3-difluoropyridine (1.70 g, 8.76 mmol), cyclopropylboronic acid (1.10 g, 12.8 mmol), Cs$_2$CO$_3$ (12.0 g, 36.9 mmol) and Pd(dppf)Cl$_2$ complex with dichloromethane (250 mg, 0.30 mmol) in toluene (22 mL) and water (2 mL) was stirred at 105° C. for 1.5 h under a N$_2$ atmosphere. It was then cooled to room temperature and diluted with EtOAc, washed with aqueous NaHCO$_3$ and dried over Na$_2$SO$_4$. The solvent was removed under reduced pressure and the residue was purified by silica gel flash chromatography (0 to 100% DCM/hexanes) to give 5-cyclopropyl-2,3-difluoro-pyridine. $^1$H NMR (400 MHz, CDCl$_3$) δ 7.63 (d, J=2.0 Hz, 1H), 7.02 (m, 1H), 1.77 (m, 1H), 0.91 (m, 2H), 0.54 (m, 2H).

Step b: A mixture of 3-(7-chloro-1H-indol-4-yl)-2-(2,6-diethylphenyl)-4,5,6,7-tetrahydropyrazolo[4,3-c]pyridine hydrochloride (40 mg, 0.090 mmol), NEt$_3$ (0.15 mL, 1.07 mmol), 5-cyclopropyl-2,3-difluoro-pyridine (120 mg, 0.77 mmol) and Li$_2$CO$_3$ (120 mg, 1.62 mmol) in DMSO (2 mL) was stirred at 120° C. overnight. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 40% EtOAc in hexanes) to afford 3-(7-chloro-1H-indol-4-yl)-5-(5-cyclopropyl-3-fluoro-2-pyridyl)-2-(2,6-diethylphenyl)-6,7-dihydro-4H-pyrazolo[4,3-c]pyridine. $^1$H NMR (400 MHz, CDCl$_3$) δ 8.44 (br s, 1H), 7.66 (s, 1H), 7.07 (m, 2H), 6.89 (m, 2H), 6.78 (m, 2H), 6.42 (m, 2H), 4.26 (br s, 2H), 3.69 (t, J=5.8 Hz, 2H), 2.96 (t, J=5.8 Hz, 2H), 2.00-2.30 (m, 4H), 1.66 (m, 1H), 0.86 (br s, 6H), 0.78 (m, 2H), 0.45 (m, 2H). MS: (ES) m z calculated for C$_{32}$H$_{32}$ClFN$_5$ [M+H]$^+$ 540.2, found 540.2.

66
Example 18

Synthesis of 2-[2-[3-(7-chloro-1H-indol-4-yl)-2-(2,6-diethylphenyl)-6,7-dihydro-4H-pyrazolo[4,3-c]pyridin-5-yl]pyrimidin-5-yl]propan-2-ol

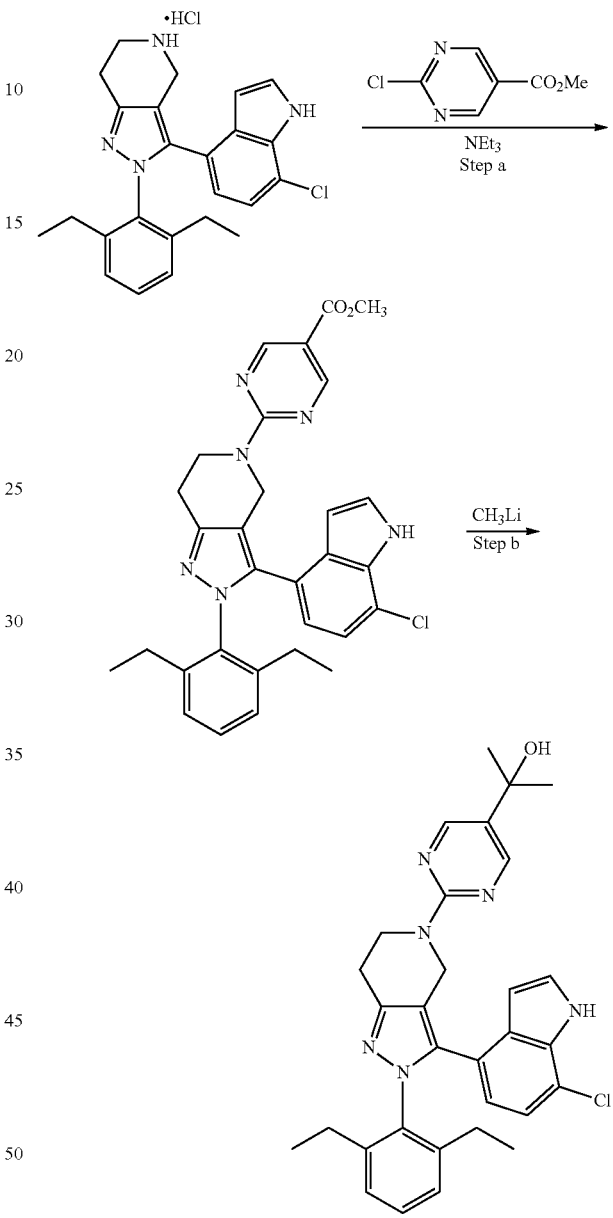

Step a: A mixture of 3-(7-chloro-1H-indol-4-yl)-2-(2,6-diethylphenyl)-4,5,6,7-tetrahydropyrazolo[4,3-c]pyridine hydrochloride (75 mg, 0.17 mmol), methyl 2-chloropyrimidine-5-carboxylate (60 mg, 0.34 mmol) and NEt$_3$ (0.12 mL, 0.85 mmol) in CH$_3$CN (2 mL) was stirred at 80° C. for 15 min. It was then cooled to room temperature, diluted with EtOAc, washed with aqueous NaHCO$_3$ and dried over Na$_2$SO$_4$. The solvent was removed under reduced pressure and the residue was purified by silica gel flash chromatography (0 to 60% EtOAc in hexanes) to afford methyl 2-[3-(7-chloro-1H-indol-4-yl)-2-(2,6-diethylphenyl)-6,7-dihydro-4H-pyrazolo[4,3-c]pyridin-5-yl]pyrimidine-5-carboxylate. MS: (ES) m z calculated for C$_{30}$H$_{30}$ClN$_6$O$_2$[M+H]$^+$ 541.2, found 541.2.

Step b: To a solution of methyl 2-[3-(7-chloro-1H-indol-4-yl)-2-(2,6-diethylphenyl)-6,7-dihydro-4H-pyrazolo[4,3-c]pyridin-5-yl]pyrimidine-5-carboxylate (35 mg, 0.064 mmol) in THF (2 mL) was added CH₃Li (0.25 mL, 0.40 mmol, 1.6 M in ether) at 0° C. The obtained mixture was stirred at the same temperature for 20 min, quenched with saturated NH₄Cl, and extracted with EtOAc. The organic layer was separated, washed with aqueous NaHCO₃, dried over Na₂SO₄, concentrated under reduced pressure and purified by silica gel flash chromatography (0 to 100% EtOAc in hexanes) to afford 2-[2-[3-(7-chloro-1H-indol-4-yl)-2-(2,6-diethylphenyl)-6,7-dihydro-4H-pyrazolo[4,3-c]pyridin-5-yl]pyrimidin-5-yl]propan-2-ol. ¹H NMR (400 MHz, CDCl₃) δ 8.41 (br s, 1H), 8.30 (m, 2H), 7.13 (m, 2H), 7.06 (t, J=7.6 Hz, 1H), 6.88 (m, 2H), 6.80 (d, J=8.4 Hz, 1H), 6.40 (m, 2H), 4.63 (br s, 2H), 4.16 (br s, 2H), 2.88 (t, J=5.8, 2H), 2.1 (m, 4H), 1.41 (m, 6H), 0.85 (br s, 6H). MS: (ES) m z calculated for C₃₁H₃₄ClN₆O [M+H]⁺ 541.2, found 541.2.

Example 19

Synthesis of 2-[3-(7-chloro-1H-indol-4-yl)-2-(2,6-diethylphenyl)-6,7-dihydro-4H-pyrazolo[4,3-c]pyridin-5-yl]pyrimidin-5-carboxamide

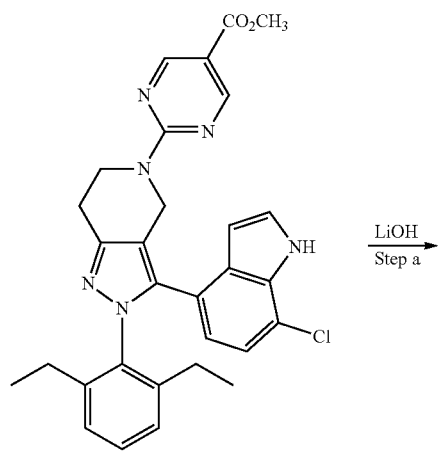

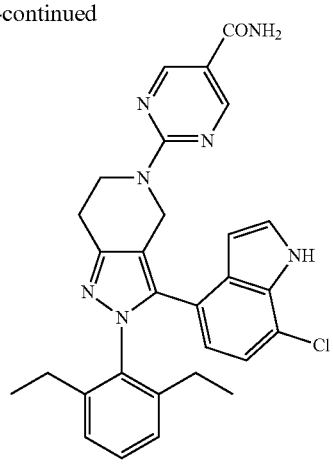

Step a: A mixture of methyl 2-[3-(7-chloro-1H-indol-4-yl)-2-(2,6-diethylphenyl)-6,7-dihydro-4H-pyrazolo[4,3-c]pyridin-5-yl]pyrimidine-5-carboxylate (40 mg, 0.074 mmol) (intermediate from Example 9) and LiOH·H₂O (100 mg, 2.5 mmol) in a mixed solvent of MeOH (1.2 mL), THF (1.2 mL) and water (0.6 mL) was stirred at 45° C. for 1 h. It was then cooled to room temperature, acidified with 1 M aqueous HCl and extracted with EtOAc. The organic layer was separated, dried over Na₂SO₄ and concentrated under reduced pressure to give 2-[3-(7-chloro-1H-indol-4-yl)-2-(2,6-diethylphenyl)-6,7-dihydro-4H-pyrazolo[4,3-c]pyridin-5-yl]pyrimidine-5-carboxylic acid.

Step b: To a mixture of 2-[3-(7-chloro-1H-indol-4-yl)-2-(2,6-diethylphenyl)-6,7-dihydro-4H-pyrazolo[4,3-c]pyridin-5-yl]pyrimidine-5-carboxylic acid (35 mg, 0.66 mmol) and HATU (100 mg, 0.26 mmol) in DMF (5 mL) was added ammonia in dioxane (0.5 M, 1 mL, 0.5 mmol). After stirring for 15 min, the reaction mixture was quenched with water and extacted with EtOAc. The organic layer was separated, dried over Na₂SO₄, concentrated under reduced pressure and purified by silica gel flash chromatography (0 to 100% EtOAc in hexanes) to yield 2-[3-(7-chloro-1H-indol-4-yl)-2-(2,6-diethylphenyl)-6,7-dihydro-4H-pyrazolo[4,3-c]pyridin-5-yl]pyrimidine-5-carboxamide. ¹H NMR (400 MHz, CD₃OD-CDCl₃) S 8.74 (br s, 1H), 7.93 (s, 1H), 7.47 (m, 1H), 7.34 (d, J=3.2 Hz, 1H), 7.21 (d, J=7.6 Hz, 1H), 7.02 (d, J=6.0 Hz, 2H), 6.90 (d, J=7.6 Hz, 1H), 6.48 (d, J=7.6 Hz, 1H), 6.45 (d, J=3.6 Hz, 1H), 4.81 (br s, 2H), 4.49 (br s, 4H), 4.35 (br s, 2H), 2.10-2.40 (m, 4H), 0.91 (br s, 6H). MS: (ES) m z calculated for C29H29ClN7O [M+H]⁺ 526.2, found 526.2.

Example 20

Synthesis of 2-[3-(7-chloro-1H-indol-4-yl)-2-(2,6-diethylphenyl)-6,7-dihydro-4H-pyrazolo[4,3-c]pyridin-5-yl]5-methyl-pyrimidine-4-carboxylic acid

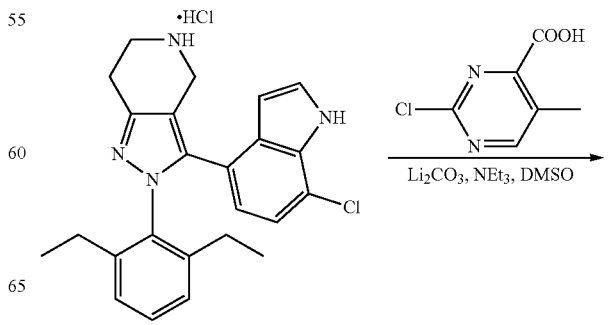

-continued

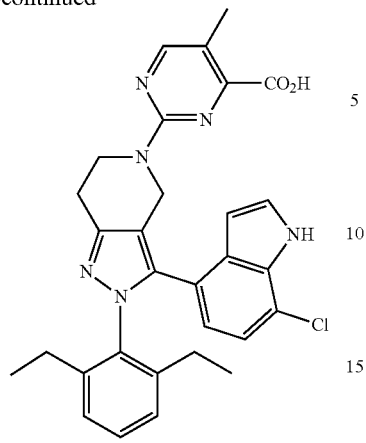

A mixture of 3-(7-chloro-1H-indol-4-yl)-2-(2,6-diethylphenyl)-4,5,6,7-tetrahydropyrazolo[4,3-c]pyridine hydrochloride (25 mg, 0.056 mmol), 2-chloro-5-methyl-pyrimidine-4-carboxylic acid (60 mg, 0.34 mmol), Li$_2$CO$_3$ (120 mg, 1.6 mmol) and NEt$_3$ (0.12 mL, 0.86 mmol) in DMSO (1.5 mL) was stirred at 120° C. for 3 h. It was then cooled to room temperature, diluted with EtOAc, and extracted with 10% aqueous HCl. The organic layer was separated, dried over Na$_2$SO$_4$, concentrated on a rotary evaporator under reduced pressure and purified by preparative HPLC to afford 2-[3-(7-chloro-1H-indol-4-yl)-2-(2,6-diethylphenyl)-6,7-dihydro-4H-pyrazolo[4,3-c]pyridin-5-yl]-5-methyl-pyrimidine-4-carboxylic acid. $^1$H NMR (400 MHz, CD$_3$OD) δ 11.27 (br s, 1H), 8.43 (br s, 1H), 7.52 (s, 1H), 7.35 (t, J=7.6 Hz, 1H), 7.18 (d, J=3.6 Hz, 2H), 6.98 (d, J=7.6 Hz, 1H), 6.66 (d, J=3.2 Hz, 1H), 6.60 (d, J=7.6 Hz, 1H), 4.90 (m, 2H), 4.39 (t, J=5.6 Hz, 2H), 3.06 (t, J=5.6 Hz, 6H), 2.38 (m, 7H), 1.06 (br s, 6H). MS: (ES) m z calculated for C$_{30}$H$_{30}$ClN$_6$O$_2$[M+H]$^+$ 541.2, found 541.2.

Example 21

Synthesis of [2-[3-(7-chloro-1H-indol-4-yl)-2-(2,6-diethylphenyl)-6,7-dihydro-4H-pyrazolo[4,3-c]pyridin-5-yl]-5-methyl-pyrimidin-4-yl]methanol

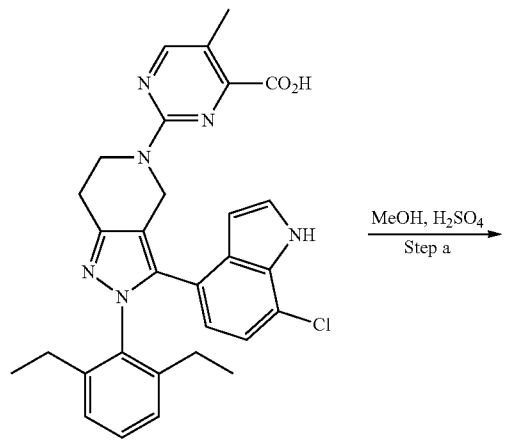

-continued

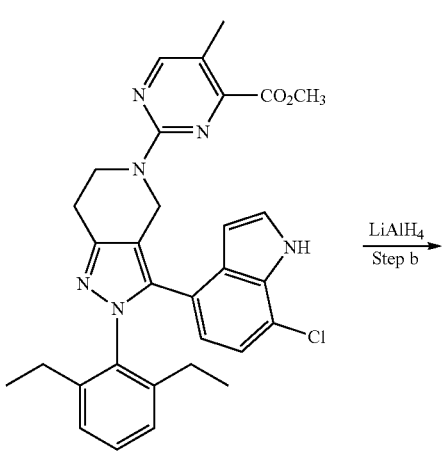

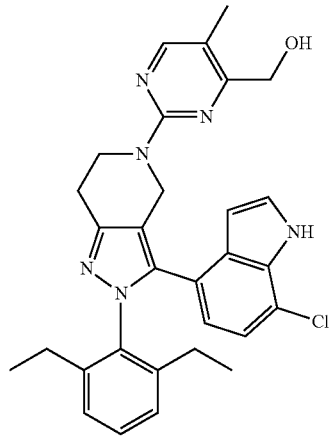

Step a: A mixture of 2-[3-(7-chloro-1H-indol-4-yl)-2-(2,6-diethylphenyl)-6,7-dihydro-4H-pyrazolo[4,3-c]pyridin-5-yl]-5-methyl-pyrimidine-4-carboxylic acid (12 mg, 0.022 mmol) and conc. H$_2$SO$_4$ (0.40 mL) in MeOH (5 mL) was refluxed for 1 h. It was then cooled to room temperature, basicified with saturated NaHCO$_3$ and extracted EtOAc. The organic layer was separated, dried over Na$_2$SO$_4$, concentrated on a rotary evaporator under reduced pressure to obtain methyl 2-[3-(7-chloro-1H-indol-4-yl)-2-(2,6-diethylphenyl)-6,7-dihydro-4H-pyrazolo[4,3-c]pyridin-5-yl]-5-methyl-pyrimidine-4-carboxylate.

Step b: The above methyl 2-[3-(7-chloro-1H-indol-4-yl)-2-(2,6-diethylphenyl)-6,7-dihydro-4H-pyrazolo[4,3-c]pyridin-5-yl]-5-methyl-pyrimidine-4-carboxylate (10 mg, 0.020 mmol) was dissolved in THF (2 mL) and charged with LiAlH$_4$ in THF (1 M, 0.07 mL, 0.14 mmol) at 0° C. The resulting mixture was stirred at 0° C. for 20 min. It was then quenched with MeOH, diluted with EtOAc, washed with brine and dried over Na₂SO₄. The solvent was removed under reduced pressure and the residue was purified by silica gel flash chromatography (0 to 80% EtOAc in hexanes) to give [2-[3-(7-chloro-1H-indol-4-yl)-2-(2,6-diethylphenyl)-6,7-dihydro-4H-pyrazolo[4,3-c]pyridin-5-yl]-5-methyl-pyrimidin-4-yl]methanol. ¹H NMR (400 MHz, CDCl₃) δ 8.38 (br s, 1H), 7.91 (s, 1H), 7.33 (br s, 1H), 7.07 (t, J=7.6 Hz, 1H), 6.90 (br s, 2H), 6.81 (d, J=7.6 Hz, 1H), 6.44 (br s, 1H), 6.40 (d, J=7.6 Hz, 1H), 4.68 (br s, 2H), 4.42 (d, J=4.2 Hz, 2H), 4.20 (t, J=4.4 Hz, 1H), 4.15 (s, 2H), 2.89 (t, J=5.6 Hz, 2H), 2.00-2.30 (2 br s, 4H), 1.87 (s, 3H), 0.85 (6H). MS: (ES) m z calculated for $C_{30}H_{32}ClN_6O$ [M+H]⁺ 527.2, found 527.2.

Example 22

Synthesis of 3-(7-chloro-1H-indol-4-yl)-2-(2,6-diethylphenyl)-N-phenyl-6,7-dihydro-2H-pyrazolo[4,3-c]pyridine-5(4H)-carboxamide

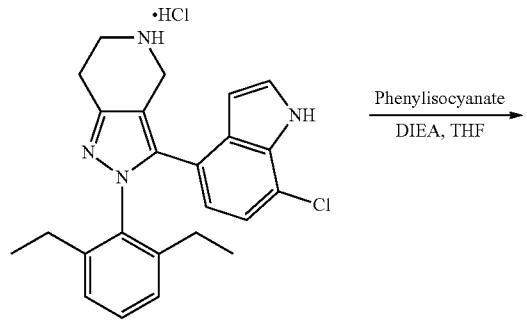

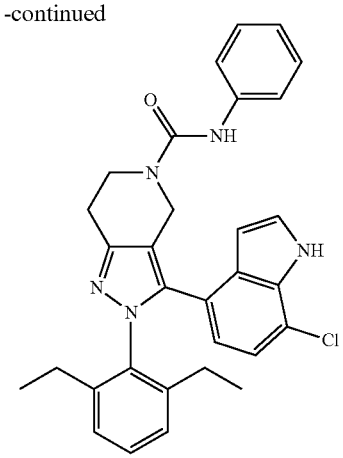

N,N-diisopropylethylamine (0.1 mL, 0.58 mmol) was added to a suspension of 3-(7-chloro-1H-indol-4-yl)-2-(2,6-diethylphenyl)-4,5,6,7-tetrahydro-2H-pyrazolo[4,3-c]pyridine hydrochloride (45 mg, 0.10 mmol), and phenyl isocyanate (0.1 mL, 0.92 mmol) in THF (5 mL) under magnetic stirring. The resulting mixture was stirred at 50° C. for 1 h and quenched with MeOH. After cooling to room temperature, the reaction mixture was diluted with EtOAc, washed with aqueous NaHCO₃ solution, brine and dried over MgSO₄. The solvent was removed under reduced pressure and the residue was purified by Preparative TLC (40% EtOAc in hexanes) followed by HPLC (MeCN/H₂O, with 1% TFA) to afford 3-(7-chloro-1H-indol-4-yl)-2-(2,6-diethylphenyl)-N-phenyl-6,7-dihydro-2H-pyrazolo[4,3-c]pyridine-5(4H)-carboxamide. ¹H NMR (400 MHz, CDCl₃) δ 8.52 (s, 1H), 7.21-7.40 (m, 5H), 6.98-7.10 (m, 4H), 6.50-6.61 (m, 2H), 6.35 (s, 1H), 4.50 (s, 2H), 3.98 (t, J=5.9 Hz, 2H), 3.05 (t, J=5.9 Hz, 2H), 2.17-2.35 (br,m, 4H), 0.88-1.08 (br,m, 6H). MS: (ES) m z calculated $C_{31}H_{31}ClN_5O$ [M+H]⁺ 524.2, found 524.2.

Example 23

Synthesis of (4-(2-(2,6-diethylphenyl)-5-(3-fluoro-5-(trifluoromethyl)pyridin-2-yl)-4,5,6,7-tetrahydro-2H-pyrazolo[4,3-c]pyridine-3-yl)-1H-indol-7-yl)methanol

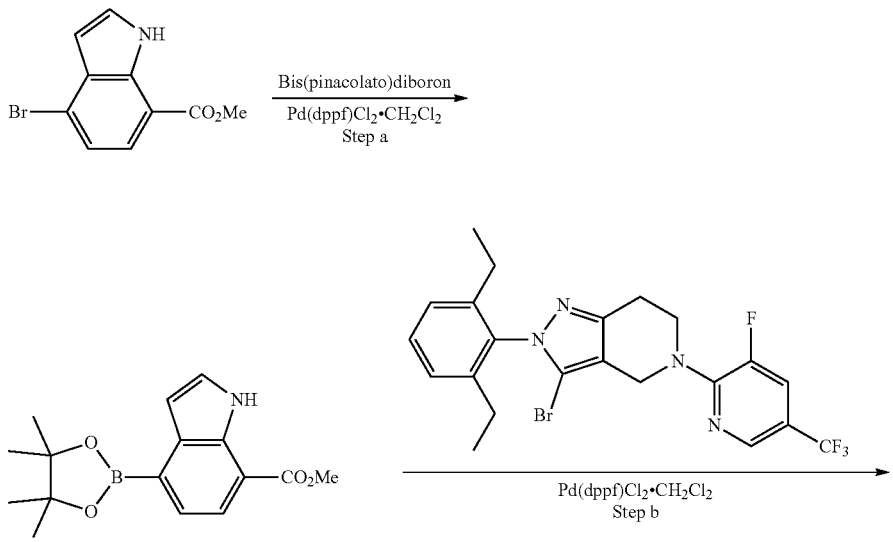

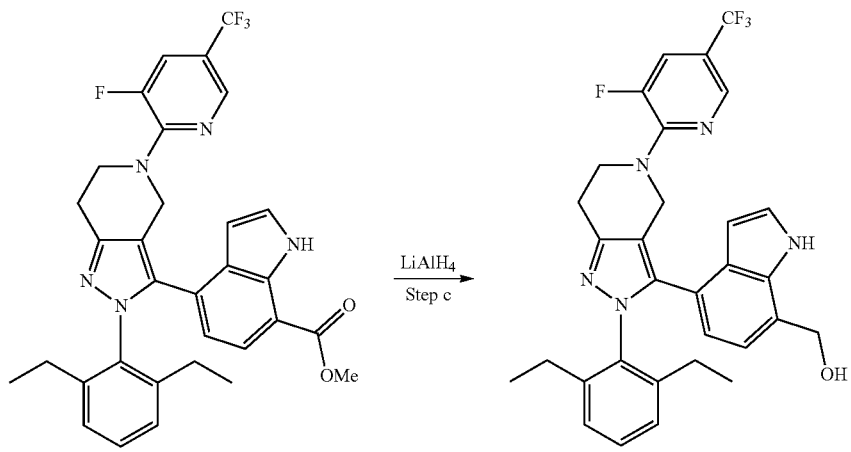

Step a: To a suspension of methyl 4-bromo-1H-indole-7-carboxylate (300 mg, 1.18 mmol), 4,4,4',4',5,5,5',5'-octamethyl-2,2'-bi(1,3,2-dioxaborolane) (330 mg, 1.30 mmol), and KOAc (290 mg, 2.96 mmol) in p-dioxane (8 mL) was added Pd(dppf)Cl$_2$ complex with dichloromethane (100 mg, 0.12 mmol). The reaction mixture was degassed (N$_2$) for 2 min and stirred at 100° C. for 1 h. The reaction mixture was diluted with EtOAc, filtered through Celite. The solvent was removed under reduced pressure and the residue was purified by silica gel flash chromatography (5 to 30% EtOAc in hexanes) to give methyl 4-(4,4,5,5-tetramethyl-1,3,2-dioxaborolan-2-yl)-1H-indole-7-carboxylate. MS: (ES) m z calculated for C$_{16}$H$_{21}$BNO$_4$ [M+H]$^+$ 302.2, found 302.2.

Step b: To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (100 mg, 0.20 mmol), methyl 4-(4,4,5,5-tetramethyl-1,3,2-dioxaborolan-2-yl)-1H-indole-7-carboxylate (100 mg, 0.33 mmol), and K$_2$CO$_3$ (180 mg, 1.3 mmol) in p-dioxane (6 mL) and water (1 mL) was added Pd(dppf)Cl$_2$ complex with dichloromethane (50 mg, 0.06 mmol). The reaction mixture was degassed (N$_2$) for 2 min and stirred under N$_2$ at 100° C. for 3 h. The reaction mixture was diluted with EtOAc, filtered through Celite, washed with brine and dried over MgSO$_4$. The solvent was removed under reduced pressure and the residue was purified by silica gel flash chromatography (5 to 35% EtOAc in hexanes) to give methyl 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylate. MS: (ES) m z calculated C$_{32}$H$_{30}$F$_4$N$_5$O$_2$[M+H]$^+$ 592.2, found 592.2.

Step c: To a solution of methyl 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylate (25 mg, 0.04 mmol) in anhydrous THF (6 mL) under ice bath was added a solution of LiAlH$_4$ in THF (2M, 0.3 mL, 0.6 mmol). The reaction mixture stirred at 0° C. for 30 min and then quenched with MeOH. The reaction mixture was diluted with EtOAc, washed with aqueous NaHCO$_3$ solution, brine and dried over MgSO$_4$. The solvent was removed under reduced pressure and the residue was purified by HPLC (MeCN/H$_2$O, with 0.1% TFA) to give (4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indol-7-yl)methanol. $^1$H NMR (400 MHz, CD$_3$OD) S 8.20 (dt, J=1.0, 1.9 Hz, 1H), 7.63 (dd, J=2.1, 13.5 Hz, 1H), 7.38 (d, J=3.2 Hz, 1H), 7.24 (t, J=7.7 Hz, 1H), 7.08 (s, 2H), 6.89 (d, J=7.4 Hz, 1H), 6.57 (d, J=7.4 Hz, 1H), 6.45 (dd, J=0.6, 3.2 Hz, 1H), 4.83-4.89 (m, 4H), 4.63 (s, 2H), 4.11 (t, J=5.7 Hz, 2H), 3.06 (t, J=5.7 Hz, 2H), 2.11-2.46 (m, 4H), 0.85-1.08 (m, 6H). MS: (ES) m z calculated C$_{31}$H$_{30}$F$_4$N$_5$O [M+H]$^+$ 564.2, found 564.2.

Example 24

Synthesis of 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxamide

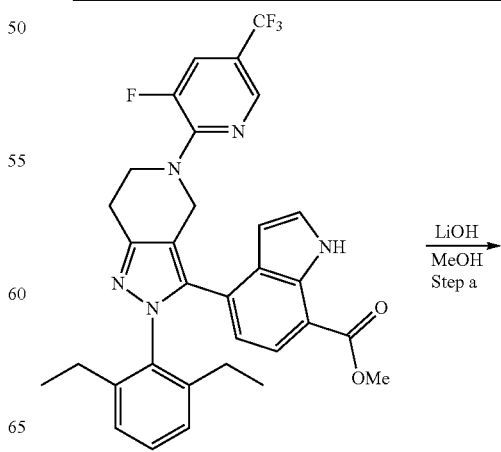

-continued

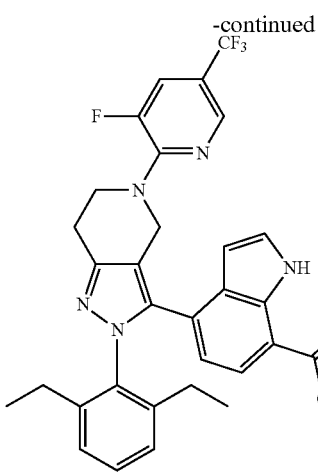

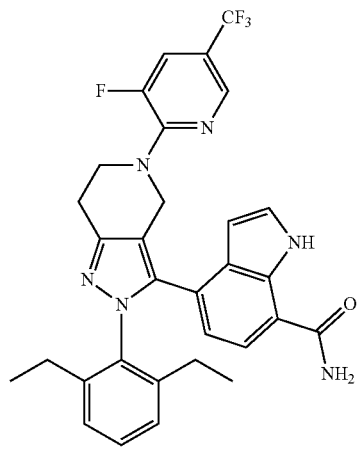

Step a: To a solution of methyl 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylate (25 mg, 0.04 mmol) in MeOH (5 mL) and water (1 mL) was added LiGH monhydrate (100 mg, 2.38 mmol). The reaction mixture stirred at 60° C. for 2 h and quenched with 1 N HCl. The reaction mixture was diluted with EtOAc, washed with brine and dried over MgSO$_4$. The solvent was removed under reduced pressure to give 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylic acid. MS: (ES) m z calculated C$_{31}$H$_{28}$F$_4$N$_5$O$_2$ [M+H]$^+$ 578.2, found 578.2.

Step b: To a solution of the above 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylic acid in DMF (5 mL) was charged with HATU (50 mg, 0.13 mmol), DIEA (0.2 mL, 1.15 mmol) and followed by ammonia in dioxane (0.5 M, 1 mL, 0.5 mmol). The reaction mixture stirred at room temperature for 2 h. The reaction mixture was diluted with EtOAc, washed with brine and dried over MgSO$_4$. The solvent was removed under reduced pressure and the residue was purified by HPLC (MeCN/H$_2$O, with 1% TFA) to give 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxamide. $^1$H NMR (400 MHz, CD$_3$OD) δ 8.21 (d, J=2.1 Hz, 1H), 7.64 (dd, J=2.0, 13.5 Hz, 1H), 7.49 (d, J=3.2 Hz, 1H), 7.40 (d, J=7.8 Hz, 1H), 7.26 (t, J=7.7 Hz, 1H), 7.11 (br, 2H), 6.62 (d, J=7.8 Hz, 1H), 6.53 (d, J=3.2 Hz, 1H), 4.67 (s, 2H), 4.13 (t, J=5.8 Hz, 2H), 3.25-3.34 (br s, 3H) 3.07 (t, J=5.8 Hz, 2H), 2.11-2.44 (m, 4H), 0.87-1.08 (m, 6H). MS: (ES) m z calculated C$_{31}$H$_{29}$F$_4$N$_6$O [M+H]$^+$ 577.2, found 577.2.

Example 25

Synthesis of 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxamide

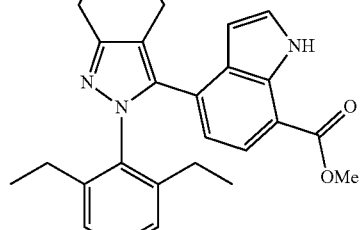

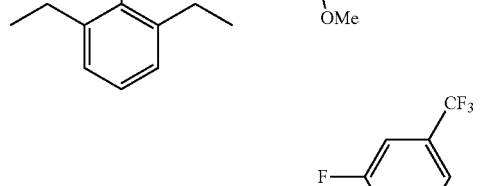

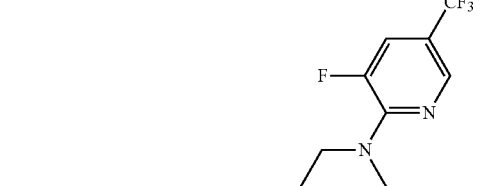

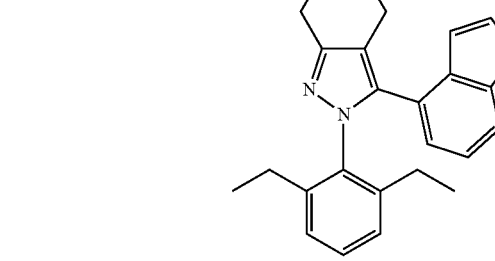

Step a: To a solution of methyl 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxylate (25 mg, 0.04 mmol) in THF (5 mL) under ice bath was added methyllithium solution in THF (3 M, 0.2 mL, 0.6 mmol). The reaction mixture stirred at 0° C. for 15 min and quenched with MeOH. The reaction mixture was diluted with EtOAc, washed with brine and dried over MgSO$_4$. The solvent was removed under reduced pressure and the residue was purified by Preparative TLC (45% EtOAc in hexanes) followed by HPLC (MeCN/H$_2$O, with 1% TFA) to give 4-(2-(2,6-diethylphenyl)-5-(3-fluoro-5-(trifluoromethyl)pyridin-2-yl)-4,5,6,7-tetrahydro-2H-pyrazolo[4,3-c]pyridin-3-yl)-1H-indole-7-carboxamide. $^1$H NMR (400 MHz, CDCl$_3$) δ 9.54 (s, 1H), 8.18 (dt, J=1.0, 2.1 Hz, 1H), 7.38 (dd, J=2.0, 13.2 Hz, 1H), 7.03-7.39 (m, 5H), 6.75 (d, J=7.6 Hz, 1H), 6.46-6.55 (m, 2H), 4.65 (br s, 2H), 4.07 (t, J=5.8 Hz, 2H), 3.11 (t, J=5.8 Hz, 2H), 2.14-2.32 (br m, 4H), 1.67 (s, 6H), 1.57 (br s, 1H), 0.88-1.28 (br m, 6H). MS: (ES) m z calculated C$_{33}$H$_{34}$F$_4$N$_5$O [M+H]$^+$ 592.2, found 592.2.

Example 26

Synthesis of 2-(2,6-diethylphenyl)-3-(6,fluoro-7-methoxy-1H-indol-4-yl)-5-(trifluoromethyl)pyrimidin-2-yl]-6,7-dihydro-4H-pyrazolo[4,3-c]pyridine

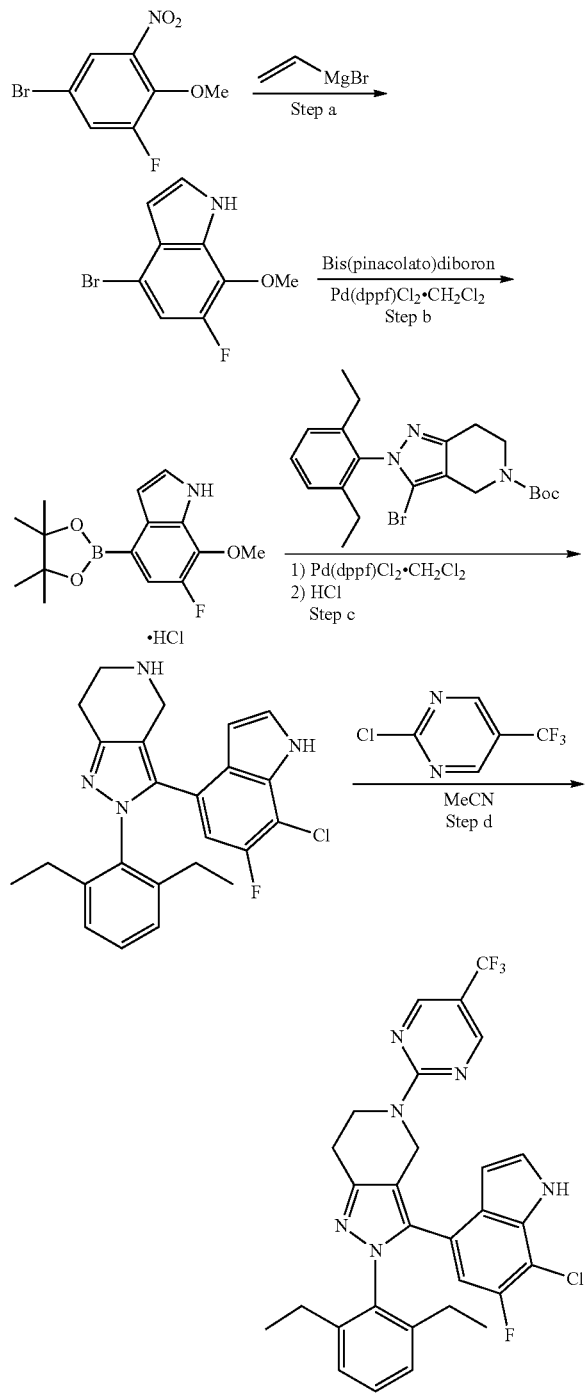

Step a: Vinylmagnesium bromide solution in THE (1 M, 70 mL, 70 mmol) was added to a solution of 4-bromo-2-fluoro-6-nitroanisole (5.0 g, 20 mmol) in anhydrous THE (70 mL) under $N_2$ at −50° C. The reaction mixture was stirred at the same temperature and allowed to warm to −30° C. over 1.5 h. The reaction mixture was quenched with saturated aqueous $NH_4Cl$ solution and allowed to warm up to room temperature over 1 h. The reaction mixture was diluted with EtOAc, washed with brine and dried over $Na_2SO_4$. The solvent was removed under reduced pressure and the residue was purified by silica gel flash chromatography (0 to 100% EtOAc in hexanes) to yield 4-bromo-6-fluoro-7-methoxy-1H-indole. MS: (ES) m z calculated for $C_9H_8BrFNO$ $[M+H]^+$ 243.9, found 243.9.

Step b: To a suspension of 4-bromo-6-fluoro-7-methoxy-1H-indole (900 mg, 3.68 mmol), 4,4,4',4',5,5,5',5'-octamethyl-2,2'-bi(1,3,2-dioxaborolane) (1.21 g, 4.8 mmol) and and KOAc (1.08 g, 11 mmol) in dioxane (16 mL) was added Pd(dppf)Cl$_2$ complex with dichloromethane (400 mg, 0.49 mmol). The reaction mixture was degassed ($N_2$) for 2 min and stirred at 100° C. for 2 h. The reaction mixture was diluted with EtOAc and filtered through Celite. The solvent was removed under reduced pressure and the residue was purified by silica gel flash chromatography (0 to 100% EtOAc in hexanes) to give 6-fluoro-7-methoxy-4-(4,4,5,5-tetramethyl-1,3,2-dioxaborolan-2-yl)-1H-indole. MS: (ES) m z calculated for $C_{15}H_{20}BFNO_3$ $[M+H]^+$ 292.1, found 292.1.

Step c: To a suspension of tert-butyl 3-bromo-2-(2,6-diethylphenyl)-6,7-dihydro-2H-pyrazolo[4,3-c]pyridine-5(4H)-carboxylate (380 mg, 0.87 mmol), 6-fluoro-7-methoxy-4-(4,4,5,5-tetramethyl-1,3,2-dioxaborolan-2-yl)-1H-indole (230 mg, 0.79 mmol) and $K_2CO_3$ (445 mg, 3.22 mmol) in p-dioxane (8 mL) and water (1.2 mL) was added Pd(dppf)Cl$_2$ complex with dichloromethane (150 mg, 0.18 mmol). The reaction mixture was degassed ($N_2$) for 2 min and stirred under $N_2$ at 100° C. for 2.5 h. The reaction mixture was diluted with EtOAc, washed with aqueous NaHCO$_3$ and dried over Na$_2$SO$_4$. The solvent was removed under reduced pressure and the residue was purified by silica gel flash chromatography (0 to 70% EtOAc in hexanes) to give tert-butyl 3-(6-fluoro-7-methoxy-1H-indol-4-yl)-2-(2,6-diethylphenyl)-6,7-dihydro-2H-pyrazolo[4,3-c]pyridine-5(4H)-carboxylate. MS: (ES) m z calculated for $C_{30}H_{36}FN_4O_3[M+H]^+$ 519.2, found 519.2.

The above tert-butyl 3-(6-fluoro-7-methoxy-1H-indol-4-yl)-2-(2,6-diethylphenyl)-6,7-dihydro-2H-pyrazolo[4,3-c]pyridine-5(4H)-carboxylate (290 mg, 0.56 mmol) was dissolved in dichloromethane (2 mL) and charged with HCl in dioxane (4N, 5 mL). The resulting mixture was stirred at room temperature for 2 h. After the reaction was complete, the solvent was evaporated in vacuo to give 3-(6-fluoro-7-methoxy-1H-indol-4-yl)-2-(2,6-diethylphenyl)-4,5,6,7-tetrahydro-2H-pyrazolo[4,3-c]pyridine hydrochloride. MS: (ES) m z calculated for $C_{25}H_{28}FN_4O$ $[M+H]^+$ 419.2, found 419.2.

Step d: Triethylamine (0.42 mL, 3 mmol) was added to a suspension of 3-(6-fluro-7-methoxy-1H-indol-4-yl)-2-(2,6-diethylphenyl)-4,5,6,7-tetrahydro-2H-pyrazolo[4,3-c]pyridine hydrochloride (350 mg, 0.77 mmol) and 2-chloro-5-(trifluoromethyl)pyrimidine (183 mg, 1.0 mmol) in MeCN (8 mL). The resulting mixture was stirred at 80° C. for 45 min. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 60% EtOAc in hexanes) to afford 3-(6-fluoro-7-methoxy-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.47 (two br s, 3H), 7.20-7.27 (m, 2H), 7.05 (d, J=7.6 Hz, 2H), 6.61 (s, 1H), 6.40-6.50 (m, 2H), 4.83 (br s, 2H), 4.36 (t, J=5.8 Hz, 2H), 4.06 (d, J=2.4 Hz, 2H), 3.03 (t, J=5.8 Hz, 2H), 2.26 (m, 4H), 1.00 (m, 6H). MS: (ES) m z calculated for $C_{30}H_{29}F_4N_6O$ [M+H]$^+$ 565.2, found 565.2.

Example 27

Synthesis of [4-[2-(2,6-diethylphenyl)-5-[5-(trifluoromethyl)pyrimidin-2-yl]-6,7-dihydro-4H-pyrazolo[4,3-c]pyridin-3-yl]-5-fluoro-1H-7-yl]methanol

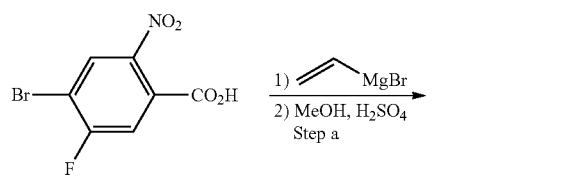

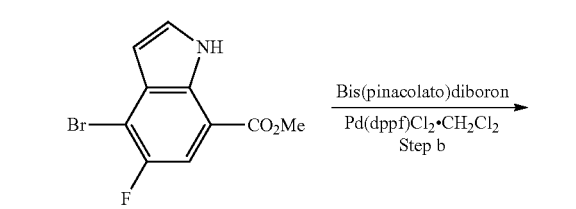

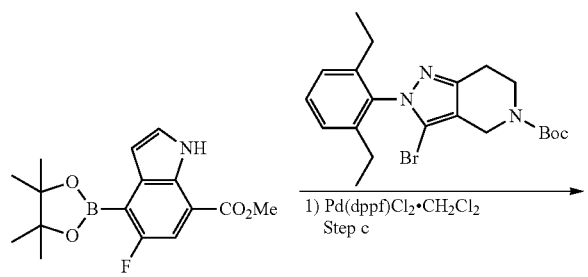

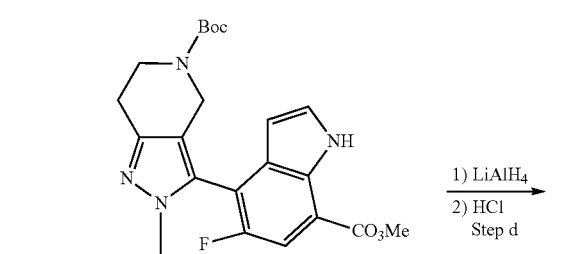

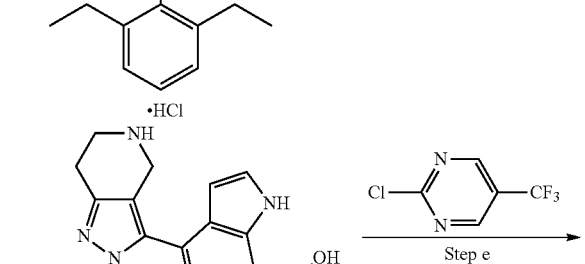

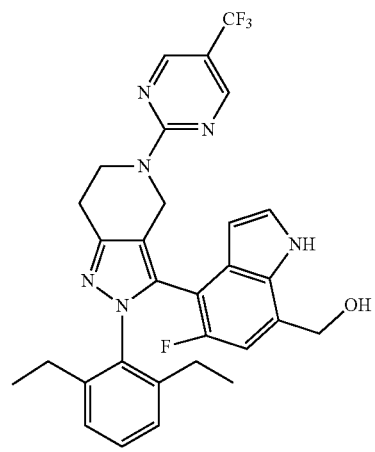

Step a: Vinylmagnesium bromide solution in THF (1 M, 341 mL, 341 mmol) was added to a solution of 4-bromo-5-fluoro-2-nitrobenzoic acid (15.0 g, 56.8 mmol) in anhydrous THF (200 mL) under $N_2$ at −50° C. The reaction mixture was stirred at the same temperature and allowed to warm to −40° C. over 1.5 h. The reaction mixture was quenched with saturated aqueous $NH_4Cl$ solution and allowed to warm up to room temperature over 1 h. The reaction mixture was acidified with 1 N aqueous HCl, diluted with EtOAc, washed with brine and dried over $Na_2SO_4$. The solvent was removed under reduced pressure to give a crude residue.

The above crude residue was stirred in a mixture of $H_2SO_4$ (25 mL) in MeOH (250 mL) at reflux for 5 h. It was then cooled to room temperature and concentrated under reduced pressure. The obtained residue was diluted with EtOAc and brine. The organic layer was separated, dried with $Na_2SO_4$, concentrated under reduced pressure and purified by silica gel flash chromatography (0 to 50% EtOAc in hexanes) to give methyl 4-bromo-5-fluoro-1H-indole-7-carboxylate. MS: (ES) m z calculated for $C_{10}H_8BrFNO_2$ [M+H]$^+$ 271.9, found 271.9.

Step b: To a suspension of methyl 4-bromo-5-fluoro-1H-indole-7-carboxylate (0.900 g, 3.3 mmol), 4,4,4',4',5,5,5',5'-octamethyl-2,2'-bi(1,3,2-dioxaborolane) (1.51 g, 5.94 mmol), and KOAc (1.62 g, 16.5 mmol) in DMSO (19 mL) was added Pd(dppf)Cl$_2$ complex with dichloromethane (400 mg, 0.49 mmol). The reaction mixture was degassed ($N_2$) for 2 min and stirred at 115° C. for 1.5 h. The reaction mixture was diluted with EtOAc, filtered through Celite, washed with brine and dried over $Na_2SO_4$. The solvent was removed under reduced pressure and the residue was purified by silica gel flash chromatography (0 to 100% $CH_2Cl_2$/hexanes) to give methyl 5-fluoro-4-(4,4,5,5-tetramethyl-1,3,2-dioxaborolan-2-yl)-1H-indole-7-carboxylate. MS: (ES) m z calculated for $C_{16}H_{20}BFNO_4$ [M+H]$^+$ 320.1, found 320.1.

Step c: To a suspension of tert-butyl 3-bromo-2-(2,6-diethylphenyl)-6,7-dihydro-2H-pyrazolo[4,3-c]pyridine-5 (4H)-carboxylate (1.00 g, 2.31 mmol), methyl 5-fluoro-4-(4,4,5,5-tetramethyl-1,3,2-dioxaborolan-2-yl)-1H-indole-7-carboxylate (740 mg, 2.31 mmol) and $K_2CO_3$ (1.28 g, 9.24 mmol) in p-dioxane (14 mL) and water (2.5 mL) was added Pd(dppf)Cl$_2$ complex with dichloromethane (400 mg, 0.49 mmol). The reaction mixture was degassed (N$_2$) for 2 min and stirred under N$_2$ at 100° C. for 2.5 h. The reaction mixture was diluted with EtOAc, washed with aqueous NaHCO$_3$ and dried over Na$_2$SO$_4$. The solvent was removed under reduced pressure and the residue was purified by silica gel flash chromatography (0 to 70% EtOAc in hexanes) to give tert-butyl 2-(2,6-diethylphenyl)-3-(5-fluoro-7-methoxycarbonyl-1H-indol-4-yl)-6,7-dihydro-4H-pyrazolo[4,3-c]pyridine-5-carboxylate. MS: (ES) m z calculated for C$_{31}$H$_{36}$FN$_4$O$_4$[M+H]$^+$ 547.2, found 547.2.

Step d: The above tert-butyl 2-(2,6-diethylphenyl)-3-(5-fluoro-7-methoxycarbonyl-1H-indol-4-yl)-6,7-dihydro-4H-pyrazolo[4,3-c]pyridine-5-carboxylate (1.00 g, 1.83 mmol) was dissolved in THF (35 mL) and charged with a solution of LiAlH$_4$ in ether (1 M, 2.7 mL) at 0° C. The resulting mixture was stirred at 0° C. for 40 min. It was then quenched with water, diluted with IPA/CHCl$_3$ (1: 3), washed with brine and dried over Na$_2$SO$_4$. The solvent was removed under reduced pressure and the residue was purified by silica gel flash chromatography (0 to 90% EtOAc in hexanes) to give tert-butyl 2-(2,6-diethylphenyl)-3-[5-fluoro-7-(hydroxymethyl)-1H-indol-4-yl]-6,7-dihydro-4H-pyrazolo[4,3-c]pyridine-5-carboxylate. MS: (ES) m z calculated for C$_{30}$H$_{36}$FN$_4$O$_3$[M+H]$^+$ 519.2, found 519.2.

The above tert-butyl 2-(2,6-diethylphenyl)-3-[5-fluoro-7-(hydroxymethyl)-1H-indol-4-yl]-6,7-dihydro-4H-pyrazolo[4,3-c]pyridine-5-carboxylate (650 mg, 1.25 mmol) was dissolved in dichloromethane (13 mL) and charged with HCl in dioxane (4N, 35 mL). The resulting mixture was stirred at room temperature for 1.5 h. After the reaction was complete, the solvent was evaporated in vacuo to give [4-[2-(2,6-diethylphenyl)-4,5,6,7-tetrahydropyrazolo[4,3-c]pyridin-3-yl]-5-fluoro-1H-indol-7-yl]methanol hydrochloride. MS: (ES) m z calculated for C$_{25}$H$_{28}$FN$_4$O [M+H]$^+$ 419.2, found 419.2.

Step e: Triethylamine (1.50 mL, 10.7 mmol) was added to a suspension of [4-[2-(2,6-diethylphenyl)-4,5,6,7-tetrahydropyrazolo[4,3-c]pyridin-3-yl]-5-fluoro-1H-indol-7-yl]methanol hydrochloride (600 mg, 1.32 mmol) and 2-chloro-5-(trifluoromethyl)pyrimidine (350 mg, 1.9 mmol) in MeCN (70 mL). The resulting mixture was stirred at 80° C. for 30 min. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 90% EtOAc in hexanes) to afford [4-[2-(2,6-diethylphenyl)-5-[5-(trifluoromethyl)pyrimidin-2-yl]-6,7-dihydro-4H-pyrazolo[4,3-c]pyridin-3-yl]-5-fluoro-1H-indol-7-yl]methanol. $^1$H NMR (400 MHz, CDCl$_3$) δ 9.05 (br s, 1H), 8.47 (br s, 2H), 7.27 (m, 1H), 7.16 (m, 2H), 6.86 (d, J=7.26 Hz, 1H), 6.56 (d, J=10.0 Hz, 1H), 6.37 (t, J=2.6 Hz, 1H), 4.88 (m, 3H), 4.68 (d, J=16.4 Hz, 1H), 4.43 (m, 1H), 4.29 (m, 1H), 3.04 (t, J=6.0 Hz, 2H), 2.38-2.58 (m, 3H), 2.17 (sextet, J=7.3 Hz, 1H), 1.94 (sextet, J=7.3 Hz, 1H), 1.21 (t, J=7.4 Hz, 3H), 0.75 (t, J=7.4 Hz, 3H). MS: (ES) m z calculated for C$_{30}$H$_{29}$F$_4$N$_6$O [M+H]$^+$ 565.2, found 565.2.

Example 28

Synthesis of [4-[5-(5-cyclopropylpyrimidin-2-yl)-2-(2,6-diethylphenyl)-6,7-dihydro-4H-pyrazolo[4,3-c]pyridin-3-yl]-5-fluoro-1H-indol-7-yl]methanol

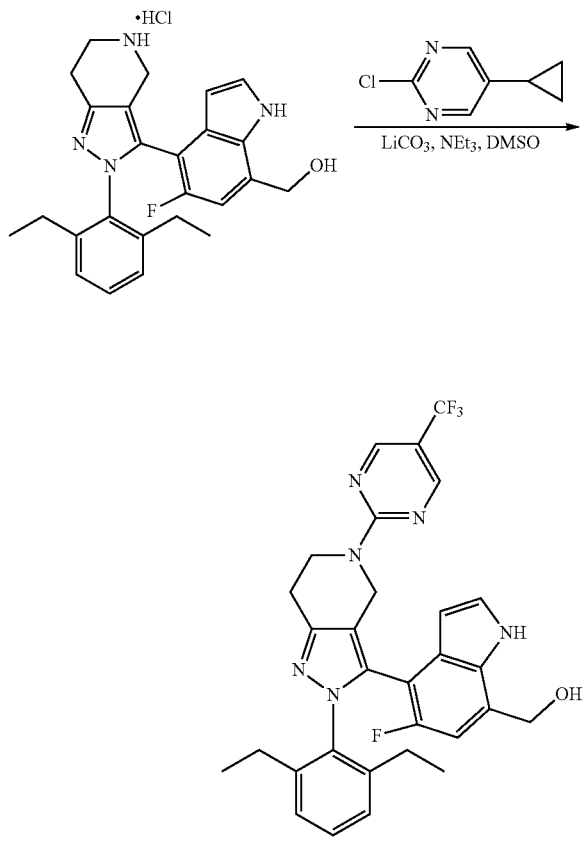

A mixture of [4-[2-(2,6-diethylphenyl)-4,5,6,7-tetrahydropyrazolo[4,3-c]pyridin-3-yl]-5-fluoro-1H-indol-7-yl]methanol hydrochloride (35 mg, 0.077 mmol) (intermediate from Example 2), NEt$_3$ (0.12 mL, 0.86 mmol), 2-chloro-5-cyclopropyl-pyrimidine (40 mg, 0.025 mmol) and Li$_2$CO$_3$ (120 mg, 1.62 mmol) in DMSO (1.5 mL) was stirred at 120° C. for 6 h. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 85% EtOAc in hexanes) to afford [4-[5-(5-cyclopropylpyrimidin-2-yl)-2-(2,6-diethylphenyl)-6,7-dihydro-4H-pyrazolo[4,3-c]pyridin-3-yl]-5-fluoro-1H-indol-7-yl]methanol. $^1$H NMR (400 MHz, CDCl$_3$) δ 8.96 (br s, 1H), 8.10 (s, 2H), 7.22 (t, J=2.8 Hz, 1H), 7.14 (m, 2H), 6.86 (dd, J=1.2, 7.2 Hz, 1H), 6.49 (d, J=10.0 Hz, 1H), 6.37 (t, J=2.6, 1H), 4.68-4.76 (m, 2H), 4.58-4.70 (m, 2H), 4.44 (m, 1H), 4.12 (quint, J=6.4 Hz, 1H), 3.10 (br s, 1H), 3.02 (d, J=5.8 Hz, 2H), 2.51 (sextet, J=7.5 Hz, 1H), 2.44 (sextet, J=7.6 Hz, 1H), 2.08 (m, 1H), 1.95 (sextet, J=7.5 Hz, 1H), 1.68 (m, 1H), 1.21 (t, J=7.6 Hz, 3H), 0.87 (m, 2H), 0.76 (t, J=7.5 Hz, 3H), 0.55 (m, 2H). MS: (ES) m z calculated for C$_{32}$H$_{34}$FN$_6$O [M+H]$^+$ 537.2, found 537.2.

Example 29

Synthesis of [4-[2-(2,6-diethylphenyl)-5-[5-(trifluoromethyl)pyrimidin-2-yl]-6,7-dihydro-4H-pyrazolo[4,3-c]pyridin-3-yl]-6-fluoro-1H-7-yl]methanol

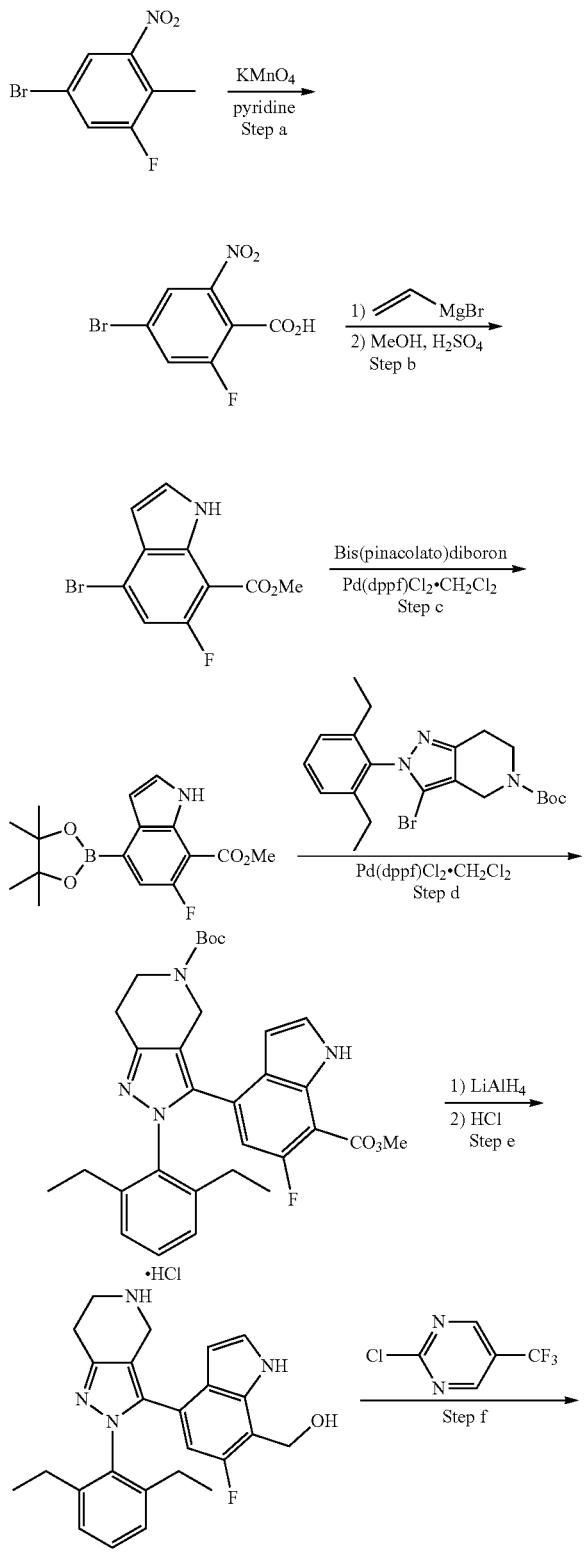

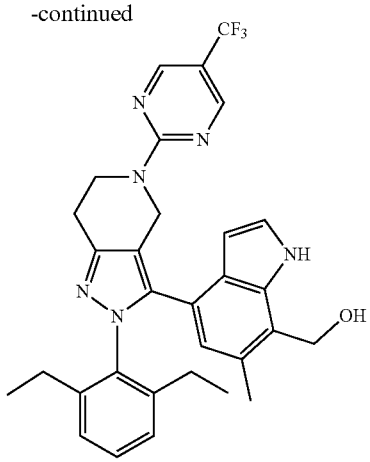

Step a: A mixture of 4-bromo-2-fluoro-6-nitrotoluene (5.50 g, 23.5 mmol), KMnO$_4$ (40 g, 253 mmol) in pyridine (100 mL) and water (75 mL) was stirred at 100° C. for 5 h. It was then cooled to room temperature, diluted with MeOH and filtered over Celite. The filtrate was acidified with 1 M aqueous HCl. The mixture was extracted with EtOAc. The organic layer was separated, dried over Na$_2$SO$_4$, concentrated under reduced pressure and purified by silica gel flash chromatography (0 to 100% EtOAc in DCM) to afford 4-bromo-2-fluoro-6-nitro-benzoic acid. $^1$H NMR (400 MHz, CDCl$_3$) δ 8.89 (br s, 1H), 8.14 (t, J=1.6 Hz, 1H), 7.70 (dd, J=1.6, 8.0 Hz, 1H).

Step b: Vinylmagnesium bromide solution in THF (1 M, 32.4 mL, 32.4 mmol) was added to a solution of 4-bromo-2-fluoro-6-nitro-benzoic acid (1.43 g, 5.4 mmol) in anhydrous THF (30 mL) under N$_2$ at −40° C. The reaction mixture was stirred at the same temperature and allowed to warm to −30° C. over 1 h. The reaction mixture was quenched with saturated aqueous NH$_4$Cl solution and allowed to warm up to room temperature over 1 h. The reaction mixture was acidified with 1 N aqueous HCl, diluted with EtOAc, washed with brine and dried over Na$_2$SO$_4$. The solvent was removed under reduced pressure to give a crude acid residue.

The above acid was stirred in a mixture of conc. H$_2$SO$_4$ (5 mL) in MeOH (100 mL) at reflux for 6 h. The mixture was then cooled to room temperature and concentrated under reduced pressure. The obtained residue was diluted with EtOAc and basified with saturated aqueous NaHCO$_3$. The organic layer was separated, washed with brine, dried with Na$_2$SO$_4$, concentrated under reduced pressure and purified by silica gel flash chromatography (0 to 100% DCM/hexanes) to afford methyl 4-bromo-6-fluoro-1H-indole-7-carboxylate. MS: (ES) m z calculated for C$_{10}$H$_8$BrFNO$_2$ [M+H]$^+$ 271.9, found 271.9.

Step c: To a suspension of methyl 4-bromo-6-fluoro-1H-indole-7-carboxylate (380 mg, 1.4 mmol), 4,4,4',4',5,5,5',5'-octamethyl-2,2'-bi(1,3,2-dioxaborolane) (461 mg, 1.8 mmol) and KOAc (412 mg, 4.2 mmol) in dioxane (9 mL) was added Pd(dppf)Cl$_2$ complex with dichloromethane (160 mg, 0.20 mmol). The reaction mixture was degassed (N$_2$) for 2 min and stirred at 115° C. for 1.5 h. The reaction mixture was diluted with EtOAc and filtered over Celite. The filtrate was concentrated under reduced pressure and the obtained residue was purified by silica gel flash chromatography (0 to 100% CH$_2$Cl$_2$/hexanes, followed by 0 to 20% EtOAc in DCM) to give methyl 6-fluoro-4-(4,4,5,5-tetramethyl-1,3,2- dioxaborolan-2-yl)-1H-indole-7-carboxylate. MS: (ES) m z calculated for $C_{16}H_{20}BFNO_4$ [M+H]$^+$ 320.1, found 320.1.

Step d: To a suspension of tert-butyl 3-bromo-2-(2,6-diethylphenyl)-6,7-dihydro-2H-pyrazolo[4,3-c]pyridine-5(4H)-carboxylate (295 mg, 0.68 mmol), methyl 6-fluoro-4-(4,4,5,5-tetramethyl-1,3,2-dioxaborolan-2-yl)-1H-indole-7-carboxylate (220 mg, 0.68 mmol), $K_2CO_3$ (400 mg, 2.9 mmol) in p-dioxane (7 mL) and water (1.4 mL) was added Pd(dppf)Cl$_2$ complex with dichloromethane (160 mg, 0.20 mmol). The reaction mixture was degassed (N$_2$) for 2 min and stirred under N$_2$ at 100° C. for 2.5 h. The reaction mixture was diluted with EtOAc, washed with aqueous NaHCO$_3$ and dried over Na$_2$SO$_4$. The solvent was removed under reduced pressure and the residue was purified by silica gel flash chromatography (0 to 50% EtOAc in hexanes) to give tert-butyl 2-(2,6-diethylphenyl)-3-(6-fluoro-7-methoxycarbonyl-1H-indol-4-yl)-6,7-dihydro-4H-pyrazolo[4,3-c]pyridine-5-carboxylate. MS: (ES) m z calculated for $C_{31}H_{36}FN_4O_4$[M+H]$^+$ 547.2, found 547.2.

Step e: The above tert-butyl 2-(2,6-diethylphenyl)-3-(6-fluoro-7-methoxycarbonyl-1H-indol-4-yl)-6,7-dihydro-4H-pyrazolo[4,3-c]pyridine-5-carboxylate (300 mg, 0.54 mmol) was dissolved in THF (4 mL) and charged with LiAlH$_4$ in ether (2 M, 0.548 mL, 1.1 mmol) at 0° C. The resulting mixture was stirred at 0° C. for 10 min. It was then quenched with methanol and diluted with EtOAc and brine. The organic layer was separated, dried over Na$_2$SO$_4$, concentrated under reduced pressure and purified by silica gel flash chromatography (0 to 100% EtOAc in hexanes) to give tert-butyl 2-(2,6-diethylphenyl)-3-[6-fluoro-7-(hydroxymethyl)-1H-indol-4-yl]-6,7-dihydro-4H-pyrazolo[4,3-c]pyridine-5-carboxylate. MS: (ES) m z calculated for $C_{30}H_{36}FN_4O_3$[M+H]$^+$ 519.2, found 519.2. The above tert-butyl 2-(2,6-diethylphenyl)-3-[6-fluoro-7-(hydroxymethyl)-1H-indol-4-yl]-6,7-dihydro-4H-pyrazolo[4,3-c]pyridine-5-carboxylate (195 mg, 0.37 mmol) was dissolved in dichloromethane (1.3 mL) and charged with HCl in dioxane (4N, 5 mL). The resulting mixture was stirred at room temperature for 1.5 h. The solvent was evaporated in vacuo to give [4-[2-(2,6-diethylphenyl)-4,5,6,7-tetrahydropyrazolo[4,3-c]pyridin-3-yl]-6-fluoro-1H-indol-7-yl]methanol hydrochloride. MS: (ES) m z calculated for $C_{25}H_{28}FN_4O$ [M+H]$^+$ 419.2, found 419.2.

Step f: Triethylamine (0.12 mL, 0.85 mmol) was added to a suspension of [4-[2-(2,6-diethylphenyl)-4,5,6,7-tetrahydropyrazolo[4,3-c]pyridin-3-yl]-6-fluoro-1H-indol-7-yl]methanol hydrochloride (25 mg, 0.055 mmol) and 2-chloro-5-(trifluoromethyl)pyrimidine (60 mg, 0.32 mmol) in MeCN (1.5 mL). The resulting mixture was stirred at 85° C. for 30 min. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 85% EtOAc in hexanes) to afford [4-[2-(2,6-diethylphenyl)-6-[5-(trifluoromethyl)pyrimidin-2-yl]-6,7-dihydro-4H-pyrazolo[4,3-c]pyridin-3-yl]-5-fluoro-1H-indol-7-yl]methanol. $^1$H NMR (400 MHz, CDCl$_3$) δ 9.17 (br s, 1H), 8.48 (br s, 2H), 7.27 (m, 1H), 7.22 (t, J=7.6 Hz, 1H), 7.04 (d, J=7.6 Hz, 2H), 6.44 (t, J=2.6 Hz, 1H), 6.37 (d, J=11.6 Hz, 1H), 5.05 (d, J=5.6 Hz, 2H), 4.84 (br s, 2H), 4.36 (br s, 2H), 3.03 (t, J=5.8 Hz, 2H), 2.10-2.40 (m, 4H), 2.15 (t, J=5.4 Hz, 1H), 1.01 (m, 6H). MS: (ES) m z calculated for $C_{30}H_{29}F_4N_6O$ [M+H]$^+$ 565.2, found 565.2.

Example 30

Synthesis of 2-[2-[2-[(2,6-diethylphenyl)-3-[6-fluoro-7-(hydroxymethyl)-1H-indol-4-yl]-6,7-dihydro-4H-pyrazolo[4,3-c]pyridin-5-yl]pyrimidin-5-yl]propan-2-ol

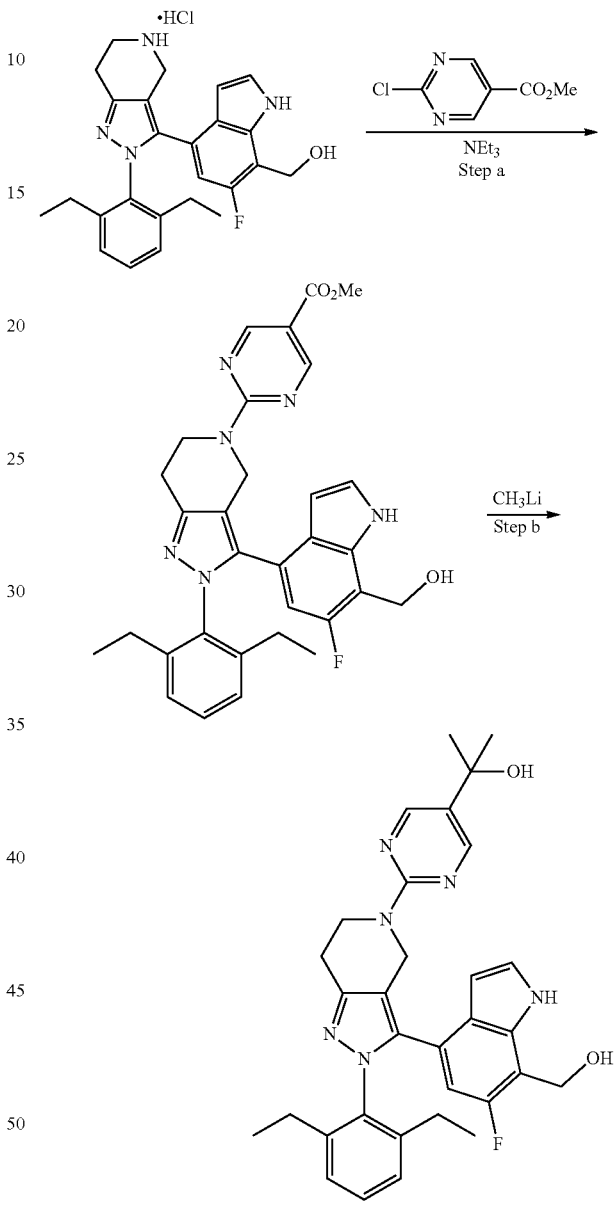

Step a: A mixture of [4-[2-(2,6-diethylphenyl)-4,5,6,7-tetrahydropyrazolo[4,3-c]pyridin-3-yl]-6-fluoro-1H-indol-7-yl]methanol hydrochloride (38 mg, 0.083 mmol) (intermediate from Example 10), methyl 2-chloropyrimidine-5-carboxylate (70 mg, 0.40 mmol) and NEt$_3$ (0.12 mL, 0.85 mmol) in CH$_3$CN (2 mL) was stirred at 80° C. for 20 min. It was then cooled to room temperature, diluted with EtOAc, washed with aqueous NaHCO$_3$ and dried over Na$_2$SO$_4$. The solvent was removed under reduced pressure and the residue was purified by silica gel flash chromatography (0 to 80% EtOAc in hexanes) to afford methyl 2-[2-(2,6-diethylphenyl)-3-[6-fluoro-7-(hydroxymethyl)-1H-indol-4-yl]-6,7-dihydro-4H-pyrazolo[4,3-c]pyridin-5-yl]pyrimidine-5-carboxylate. MS: (ES) m z calculated for $C_{31}H_{32}FN_6O_3$[M+H]$^+$ 555.2, found 555.2.

Step b: To a solution of methyl 2-[2-(2,6-diethylphenyl)-3-[6-fluoro-7-(hydroxymethyl)-1H-indol-4-yl]-6,7-dihydro-4H-pyrazolo[4,3-c]pyridin-5-yl]pyrimidine-5-carboxylate (38 mg, 0.068 mmol) in THF (2 mL) was added CH$_3$Li (0.35 mL, 0.56 mmol, 1.6 M in ether) at 0° C. The obtained mixture was stirred at the same temperature for 20 min, quenched with saturated NH$_4$Cl and extracted with EtOAc. The organic layer was separated, washed with aqueous NaHCO$_3$, dried over Na$_2$SO$_4$, concentrated under reduced pressure and purified by silica gel flash chromatography (0 to 100% EtOAc in hexanes) to afford 2-[2-[2-(2,6-diethylphenyl)-3-[6-fluoro-7-(hydroxymethyl)-1H-indol-4-yl]-6,7-dihydro-4H-pyrazolo[4,3-c]pyridin-5-yl]pyrimidin-5-yl]propan-2-ol. $^1$H NMR (400 MHz, CDCl$_3$) δ 8.91 (br s, 1H), 8.20 (br s, 2H), 6.95-7.10 (m, 2H), 6.80 (br s, 2H), 6.23 (br s, 1H), 6.14 (d, J=11.2 Hz, 1H), 4.67 (s, 2H), 4.54 (s, 2H), 4.09 (br s, 1H), 3.91 (m, 1H), 2.80 (br s, 2H), 2.71 (br s, 1H), 1.90-2.20 (br m, 4H), 1.83 (br s, 6H), 1.61 (br s, 6H). MS: (ES) m z calculated for $C_{32}H_{36}FN_6O_2$[M+H]$^+$ 555.3, found 555.3.

Example 31

Synthesis of 3-(7-chloro-6-fluoro-1H-indol-4-yl)-2-(2,6-diethylphenyl)-5-[5-(trifluoromethyl)pyrimidin-2-yl]-6,7-dihydro-4H-pyrazolo[4,3-c]pyridine

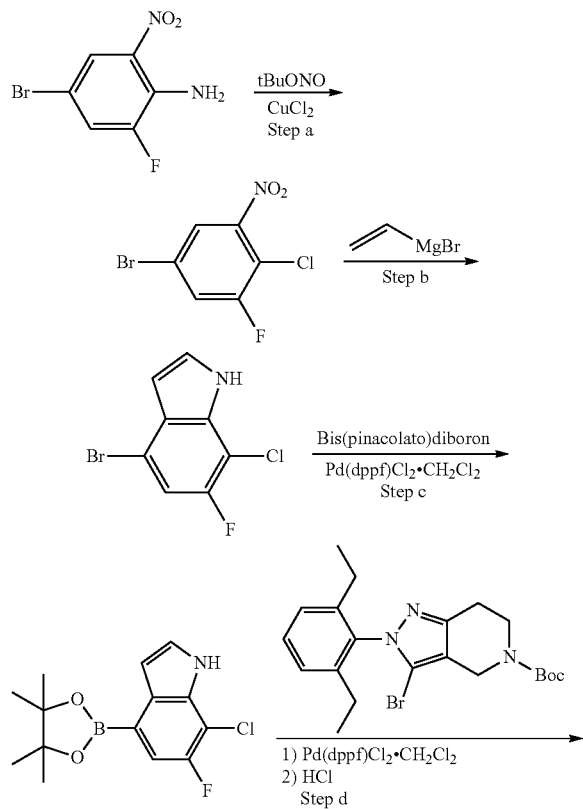

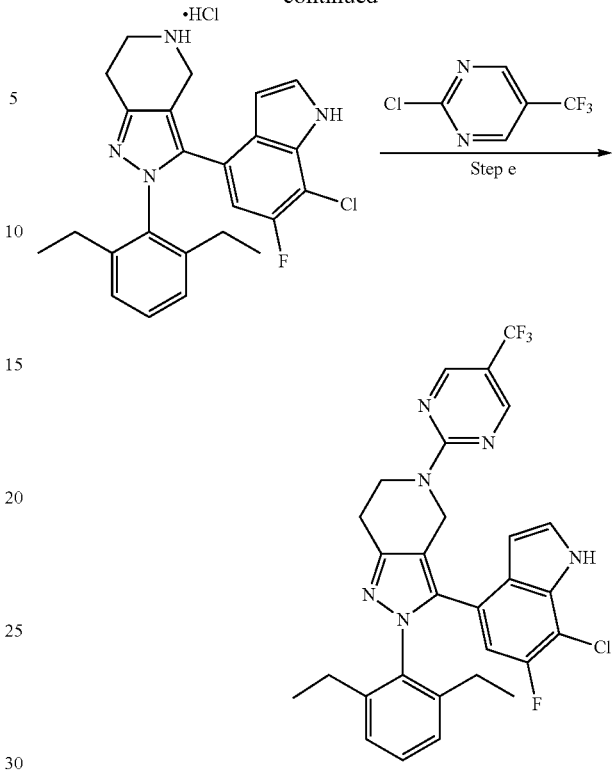

Step a: Tert-butyl nitrite (5.03 mL, 42.4 mmol) was added dropwise to a solution of 4-bromo-2-fluoro-6-nitroaniline (5.00 g, 21.2 mmol) and CuCl$_2$ (8.55 g, 63.6 mmol) in CH$_3$CN (100 mL) at room temperature. The reaction mixture was stirred at room temperature for 1 h and quenched with water. The mixture was diluted with EtOAc, washed with brine and dried over Na$_2$SO$_4$. The solvent was removed under reduced pressure and the residue was purified by silica gel flash chromatography (0 to 30% EtOAc in hexanes) to give 5-bromo-2-chloro-1-fluoro-3-nitro-benzene.

Step b: Vinylmagnesium bromide solution in THF (1 M, 56 mL, 56 mmol) was added to a solution of 5-bromo-2-chloro-1-fluoro-3-nitro-benzene (4.10 g, 16 mmol) in anhydrous THF (100 mL) under N$_2$ at −40° C. The reaction mixture was allowed to warm up to −30° C. over 1 h. The reaction mixture was quenched with saturated aqueous NH$_4$Cl solution and allowed to warm up to room temperature over 1 h. The reaction mixture was diluted with EtOAc, washed with brine and dried over Na$_2$SO$_4$. The solvent was removed under reduced pressure and the residue was purified by silica gel flash chromatography (0 to 100% DCM/hexanes) to give 4-bromo-7-chloro-6-fluoro-1H-indole. $^1$H NMR (400 MHz, CDCl$_3$) δ 7.29 (t, J=2.8 Hz, 1H), 7.20 (d, J=8.8 Hz, 1H), 6.60 (t, J=2.6 Hz, 1H).

Step c: To a suspension of 4-bromo-7-chloro-6-fluoro-1H-indole (800 mg, 3.2 mmol), 4,4,4',4',5,5,5',5'-octamethyl-2,2'-bi(1,3,2-dioxaborolane) (981 mg, 3.86 mmol), and KOAc (942 mg, 9.6 mmol) in dioxane (15 mL) was added Pd(dppf)Cl$_2$ complex with dichloromethane (300 mg, 0.37 mmol). The reaction mixture was degassed (N$_2$) for 2 min and stirred at 100° C. for 2 h. The reaction mixture was cooled to room temperature, diluted with EtOAc and filtered through Celite. The solvent was removed under reduced pressure and the residue was purified by silica gel flash chromatography (0 to 100% DCM/hexanes) to give 7-chloro-6-fluoro-4-(4,4,5,5-tetramethyl-1,3,2-dioxaborolan-2-yl)-1H-indole. MS: (ES) m z calculated for $C_{14}H_{17}BClFNO_2$ [M+H]$^+$ 296.1, found 296.1.

Step d: To a suspension of tert-butyl 3-bromo-2-(2,6-diethylphenyl)-6,7-dihydro-2H-pyrazolo[4,3-c]pyridine-5(4H)-carboxylate (293 mg, 0.67 mmol), 7-chloro-6-fluoro-4-(4,4,5,5-tetramethyl-1,3,2-dioxaborolan-2-yl)-1H-indole (200 mg, 0.67 mmol) and $K_2CO_3$ (370 mg, 2.67 mmol) in p-dioxane (6 mL) and water (0.7 mL) was added Pd(dppf)Cl$_2$ complex with dichloromethane (150 mg, 0.18 mmol). The reaction mixture was degassed (N$_2$) for 2 min and stirred under N$_2$ at 100° C. for 1.5 h. The reaction mixture was cooled to room temperature, diluted with EtOAc, washed with aqueous NaHCO$_3$ and dried over Na$_2$SO$_4$. The solvent was removed under reduced pressure and the residue was purified by silica gel flash chromatography (0 to 50% EtOAc in hexanes) to give tert-butyl 3-(7-chloro-6-fluoro-1H-indol-4-yl)-2-(2,6-diethylphenyl)-6,7-dihydro-4H-pyrazolo[4,3-c]pyridine-5-carboxylate. MS: (ES) m z calculated for $C_{29}H_{33}ClFN_4O_2$ [M+H]$^+$ 523.2, found 523.2.

The above tert-butyl 3-(7-chloro-6-fluoro-1H-indol-4-yl)-2-(2,6-diethylphenyl)-6,7-dihydro-4H-pyrazolo[4,3-c]pyridine-5-carboxylate (226 mg, 0.56 mmol) was dissolved in dichloromethane (2 mL) and charged with HCl in dioxane (4N, 7 mL). The resulting mixture was stirred at room temperature for 1 h. The solvent was evaporated in vacuo to give 3-(7-chloro-6-fluoro-1H-indol-4-yl)-2-(2,6-diethylphenyl)-4,5,6,7-tetrahydropyrazolo[4,3-c]pyridine hydrochloride. MS: (ES) m z calculated for $C_{24}H_{25}ClFN_4$ [M+H]$^+$ 423.2, found 423.2.

Step e: Triethylamine (0.49 mL, 3.48 mmol) was added to a suspension of 3-(7-chloro-6-fluoro-1H-indol-4-yl)-2-(2,6-diethylphenyl)-4,5,6,7-tetrahydropyrazolo[4,3-c]pyridine hydrochloride (400 mg, 0.87 mmol) and 2-chloro-5-(trifluoromethyl)pyrimidine (192 mg, 1.05 mmol) in MeCN (9 mL). The resulting mixture was stirred at 80° C. for 1 h. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 45% EtOAc in hexanes) to afford 3-(7-chloro-6-fluoro-1H-indol-4-yl)-2-(2,6-diethylphenyl)-5-[5-(trifluoromethyl)pyrimidin-2-yl]-6,7-dihydro-4H-pyrazolo[4,3-c]pyridine. $^1$H NMR (400 MHz, CDCl$_3$) δ 8.54 (br s, 1H), 8.49 (br s, 2H), 7.30 (d, J=2.8 Hz, 1H), 7.26 (d, J=7.0 Hz, 1H), 7.06 (d, J=7.2 Hz, 2H), 6.50 (m, 2H), 4.84 (br s, 2H), 4.36 (t, J=5.6 Hz, 2H), 3.04 (t, J=5.6 Hz, 2H), 2.25 (m, 4H), 1.01 (br s, 6H). MS: (ES) m z calculated for $C_{29}H_{26}ClF_4N_6$[M+H]$^+$ 569.2, found 569.2.

Example 32

Synthesis of 2-(2,6-diethylphenyl)-3-(5-fluoro-7-methoxy-1H-indol-4-yl)-5-[3-fluoro-5-(trifluoromethyl)-2-pyridyl]-6,7-dihydro-4h-pyrazolo[4,3-c]pyridine

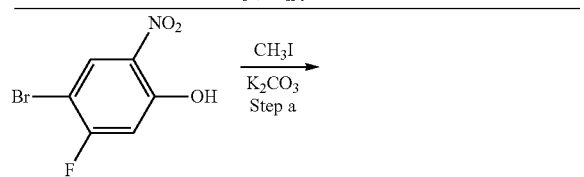

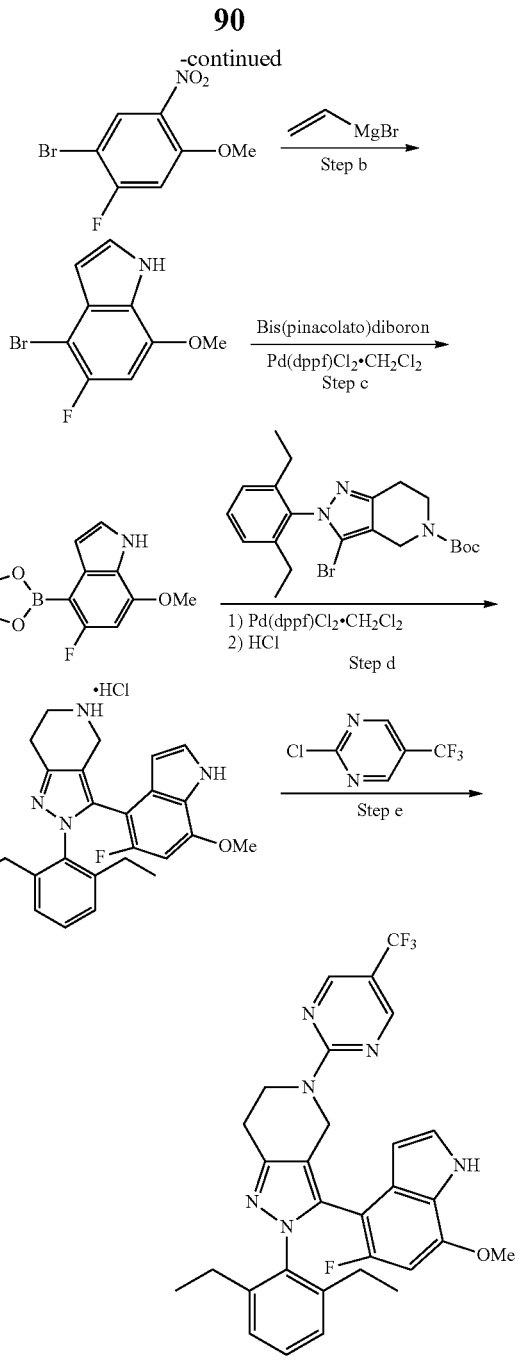

Step a: A mixture of 4-bromo-5-fluoro-2-nitrophenol (4.70 g, 19.9 mmol), CH$_3$I (3.72 mL, 59.7 mmol) and K$_2$CO$_3$ (8.25 g, 59.7 mmol) in DMF (60 mL) was stirred at 45° C. for 45 min. It was then cooled to room temperature, diluted with ether, washed with brine and dried over Na$_2$SO$_4$. The solvent was removed under reduced pressure and the residue was purified by silica gel flash chromatography (0 to 100% CH$_2$Cl$_2$/hexanes) to give 1-bromo-2-fluoro-4-methoxy-5-nitro-benzene. $^1$H NMR (400 MHz, CDCl$_3$) δ 8.16 (d, J=7.6 Hz, 1H), 6.88 (d, J=9.6 Hz, 1H), 3.96 (s, 3H).

Step b: Vinylmagnesium bromide solution in THF (1 M, 60 mL, 60 mmol) was added to a solution of 1-bromo-2-fluoro-4-methoxy-5-nitro-benzene (4.55 g, 18.2 mmol) in anhydrous THF (180 mL) under N$_2$ at −50° C. The reaction mixture was stirred at the same temperature and allowed to warm to −30° C. over 3 h. The reaction mixture was quenched with saturated aqueous NH₄Cl solution and allowed to warm up to room temperature over 1 h. The reaction mixture was diluted with EtOAc, washed with brine and dried over Na₂SO₄. The solvent was removed under reduced pressure and the residue was purified by silica gel flash chromatography (0 to 100% DCM in hexanes) to give 4-bromo-5-fluoro-7-methoxy-1H-indole. MS: (ES) m z calculated for C₉H₈BrFNO [M+H]⁺ 243.9, found 243.9.

Step c: To a suspension of 4-bromo-5-fluoro-7-methoxy-1H-indole (0.200 g, 0.82 mmol), 4,4,4',4',5,5,5',5'-octamethyl-2,2'-bi(1,3,2-dioxaborolane) (0.271 g, 1.06 mmol) and KOAc (0.241 g, 2.46 mmol) in dioxane (5 mL) was added Pd(dppf)Cl₂ complex with dichloromethane (0.130 g, 0.16 mmol). The reaction mixture was degassed (N₂) for 2 min and stirred at 100° C. for 10 h. The reaction mixture was cooled to room temperature, diluted with EtOAc and filtered through Celite. The solvent was removed under reduced pressure and the residue was purified by silica gel flash chromatography (0 to 100% DCM in hexanes) to give 5-fluoro-7-methoxy-4-(4,4,5,5-tetramethyl-1,3,2-dioxaborolan-2-yl)-1H-indole. MS: (ES) m z calculated for C₁₅H₂₀BFNO₃ [M+H]⁺ 292.1, found 292.1.

Step d: To a suspension of tert-butyl 3-bromo-2-(2,6-diethylphenyl)-6,7-dihydro-2H-pyrazolo[4,3-c]pyridine-5(4H)-carboxylate (0.060 g, 0.137 mmol), 5-fluoro-7-methoxy-4-(4,4,5,5-tetramethyl-1,3,2-dioxaborolan-2-yl)-1H-indole (0.040 g, 0.137 mmol), K₂CO₃ (0.076 g, 0.50 mmol) in p-dioxane (2 mL) and water (0.3 mL) was added Pd(dppf)Cl₂ complex with dichloromethane (0.070 g, 0.086 mmol). The reaction mixture was degassed (N₂) for 2 min and stirred under N₂ at 100° C. for 2 h. The reaction mixture was cooled to room temperature, diluted with EtOAc, washed with aqueous NaHCO₃ and dried over Na₂SO₄. The solvent was removed under reduced pressure and the residue was purified by silica gel flash chromatography (0 to 100% EtOAc in hexanes) to give tert-butyl 2-(2,6-diethylphenyl)-3-(5-fluoro-7-methoxy-1H-indol-4-yl)-6,7-dihydro-4H-pyrazolo[4,3-c]pyridine-5-carboxylate. MS: (ES) m z calculated for C₃₀H₃₆FN₄O₃[M+H]⁺ 519.2, found 519.2. The above tert-butyl 2-(2,6-diethylphenyl)-3-(5-fluoro-7-methoxy-1H-indol-4-yl)-6,7-dihydro-4H-pyrazolo[4,3-c]pyridine-5-carboxylate (0.019 g, 0.036 mmol) was dissolved in dichloromethane (1 mL) and charged with HCl in dioxane (4N, 2 mL). The resulting mixture was stirred at room temperature for 1 h. The solvent was evaporated in vacuo to give 2-(2,6-diethylphenyl)-3-(5-fluoro-7-methoxy-1H-indol-4-yl)-4,5,6,7-tetrahydropyrazolo[4,3-c]pyridine hydrochloride. MS: (ES) m z calculated for C₂₅H₂₈FN₄O[M+H]⁺ 419.2, found 419.2.

Step e: Triethylamine (0.12 mL, 0.86 mmol) was added to a suspension of 2-(2,6-diethylphenyl)-3-(5-fluoro-7-methoxy-1H-indol-4-yl)-4,5,6,7-tetrahydropyrazolo[4,3-c]pyridine hydrochloride (0.019 g, 0.034 mmol) and 2-chloro-5-(trifluoromethyl)pyrimidine (0.030 g, 0.16 mmol) in MeCN (1.5 mL). The resulting mixture was stirred at 80° C. for 0.5 h. After cooling to room temperature, the reaction mixture was diluted with EtOAc, washed with aqueous NaHCO₃ and dried over Na₂SO₄. The solvent was removed under reduced pressure and the residue was purified by silica gel flash chromatography (0 to 50% EtOAc in hexanes) to afford 2-(2,6-diethylphenyl)-3-(5-fluoro-7-methoxy-1H-indol-4-yl)-5-[3-fluoro-5-(trifluoromethyl)-2-pyridyl]-6,7-dihydro-4H-pyrazolo[4,3-c]pyridine. ¹H NMR (400 MHz, CDCl₃) δ 8.46 (two br s, 3H), 7.12-7.22 (m, 3H), 6.89 (d, J=6.0 Hz, 1H), 6.33 (t, J=2.8 Hz, 1H), 6.28 (d, J=11.6 Hz, 1H), 4.90 (d, J=16 Hz, 1H), 4.70 (d, J=16 Hz, 1H), 4.43 (quint, J=6.2 Hz, 1H), 4.29 (quint, J=6.3 Hz, 1H), 3.87 (s, 3H), 3.04 (t, J=6.0 Hz, 2H), 2.51 (sextet, J=7.4 Hz, 1H), 2.43 (sextet, J=7.6 Hz, 1H), 2.17 (sextet, J=7.5 Hz, 1H), 1.97 (sextet, J=7.5 Hz, 1H), 1.21 (t, J=7.6 Hz, 3H), 0.75 (t, J=7.6 Hz, 3H). MS: (ES) m z calculated for C₃₀H₂₉ClF₄N₆O [M+H]⁺ 565.2, found 565.2.

Example 33

Synthesis 2-(2,6-diethylphenyl)-3-(5-fluoro-7-methoxy-1H-indol-4-yl)-5-[3-fluoro-5-(trifluoromethyl)-2-pyridyl]-6,7dihydro-4H-pyrazolo[4,3-c]pyridine

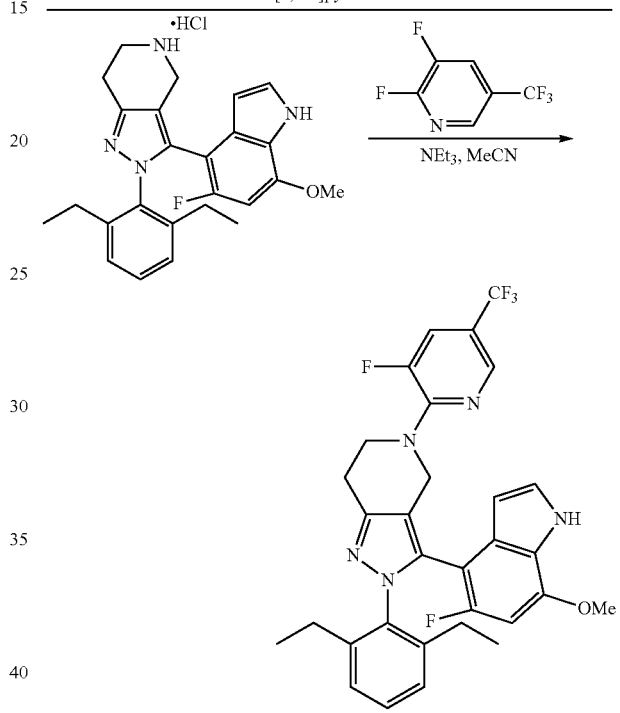

Triethylamine (0.12 mL, 0.86 mmol) was added to a suspension of 2-(2,6-diethylphenyl)-3-(5-fluoro-7-methoxy-1H-indol-4-yl)-4,5,6,7-tetrahydropyrazolo[4,3-c]pyridine hydrochloride (13 mg, 0.023 mmol) and 2,3-difluoro-5-(trifluoromethyl)pyridine (50 mg, 0.29 mmol) in MeCN (1.5 mL). The resulting mixture was stirred at 80° C. for 0.5 h. After cooling to room temperature, the reaction mixture was diluted with EtOAc, washed with aqueous NaHCO₃ and dried over Na₂SO₄. The solvent was removed under reduced pressure and the residue was purified by silica gel flash chromatography (0 to 45% EtOAc in hexanes) to afford 2-(2,6-diethylphenyl)-3-(5-fluoro-7-methoxy-1H-indol-4-yl)-5-[3-fluoro-5-(trifluoromethyl)-2-pyridyl]-6,7-dihydro-4H-pyrazolo[4,3-c]pyridine. ¹H NMR (400 MHz, CDCl₃) δ 8.44 (br s, 1H), 8.17 (d, J=0.8 Hz, 1H), 7.38 (dd, J=13.2 Hz, 1.6, 1H), 7.12-7.22 (m, 3H), 6.88 (d, J=7.6 Hz, 1H), 6.34 (t, J=2.6 Hz, 1H), 6.27 (d, J=11.6 Hz, 1H), 4.73 (d, J=16 Hz, 1H), 4.46 (d, J=16 Hz, 1H), 4.06 (m, 2H), 3.87 (s, 3H), 3.11 (t, J=5.6 Hz, 2H), 2.52 (sextet, J=7.6 Hz, 1H), 2.43 (sextet, J=7.5 Hz, 1H), 2.17 (sextet, J=7.6 Hz, 1H), 1.96 (sextet, J=7.5 Hz, 1H), 1.24 (t, J=7.6 Hz, 3H), 0.75 (t, J=7.6 Hz, 3H). MS: (ES) m z calculated for C₃₁H₂₉F₅N₅O [M+H]⁺ 582.2, found 582.2.

Example 34

Synthesis of 3-(7-chloro-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine

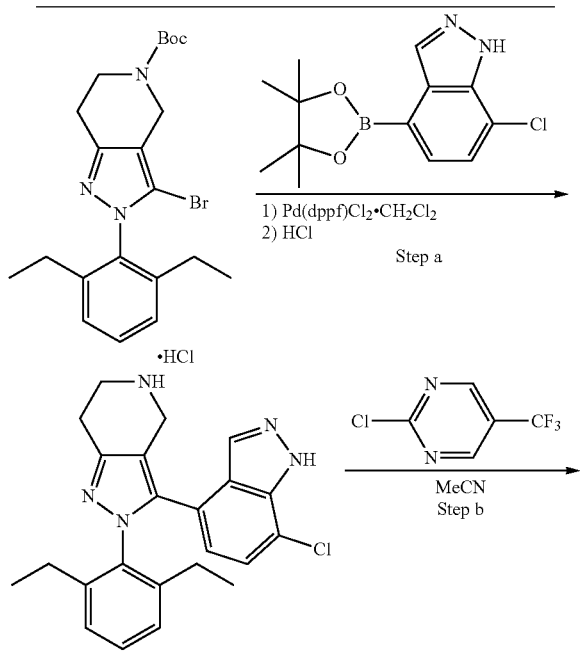

Step a: To a suspension of tert-butyl 3-bromo-2-(2,6-diethylphenyl)-6,7-dihydro-2H-pyrazolo[4,3-c]pyridine-5(4H)-carboxylate (500 mg, 1.2 mmol), 7-chloro-4-(4,4,5,5-tetramethyl-1,3,2-dioxaborolan-2-yl)-1H-indazole (350 mg, 1.26 mmol), and $K_2CO_3$ (300 mg, 2.2 mmol) in p-dioxane (6 mL) and water (1 mL) was added Pd(dppf)Cl$_2$ complex with dichloromethane (200 mg, 0.24 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 30% EtOAc in hexanes) to give tert-butyl 3-(7-chloro-1H-indazol-4-yl)-2-(2,6-diethylphenyl)-6,7-dihydro-2H-pyrazolo[4,3-c]pyridine-5(4H)-carboxylate. MS: (ES) m z calculated for $C_{28}H_{33}ClN_5O_2$[M+H]$^+$ 506.2, found 506.2. The above tert-butyl 3-(7-chloro-1H-indazol-4-yl)-2-(2,6-diethylphenyl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 3-(7-chloro-1H-indazol-4-yl)-2-(2,6-diethylphenyl)-4,5,6,7-tetrahydro-2H-pyrazolo[4,3-c]pyridine hydrochloride. MS: (ES) m z calculated for $C_{23}H_{25}ClN_5$ [M+H]$^+$ 406.2, found 406.2.

Step b: N,N-diisopropylethylamine (0.2 mL, 1.15 mmol) was added to a suspension of 3-(7-chloro-1H-indazol-4-yl)-2-(2,6-diethylphenyl)-4,5,6,7-tetrahydro-2H-pyrazolo[4,3-c]pyridine hydrochloride (50 mg, 0.11 mmol), 2-chloro-5-(trifluoromethyl)pyrimidine (20 mg, 0.11 mmol), and Li$_2$CO$_3$ (20 mg, 0.27 mmol) in DMSO (10 mL) under magnetic stirring. The resulting mixture was stirred at 65° C. for 1 h. After cooling to room temperature, the reaction mixture was diluted with EtOAc, washed with brine and dried over MgSO$_4$. The solvent was removed under reduced pressure and the residue was purified by Preparative TLC (45% EtOAc in hexanes) followed by trituration in MeOH to afford 3-(7-chloro-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 10.43 (s, 1H), 8.58 (s, 2H), 8.15 (s, 1H), 7.24-7.28 (m, 2H), 7.11 (d, J=7.7 Hz, 2H), 6.69 (d, J=7.7 Hz, 1H), 4.95 (s, 2H), 4.44 (t, J=6.0 Hz, 2H), 3.12 (t, J=6.0 Hz, 2H), 2.21-2.39 (m, 4H), 1.02-1.09 (m, 6H). MS: (ES) m z calculated $C_{28}H_{26}ClF_3N_7$[M+H]$^+$ 552.2, found 552.2.

Example 35

Synthesis of 3-(7-chloro-1H-indazol-4-yl)-5-(5-cyclopropylpyrimidin-2-yl)-2-(2,6-diethylphenyl)-4,5,6,7-tetrahydro-2H-pyrazolo[4,3-c]pyridine

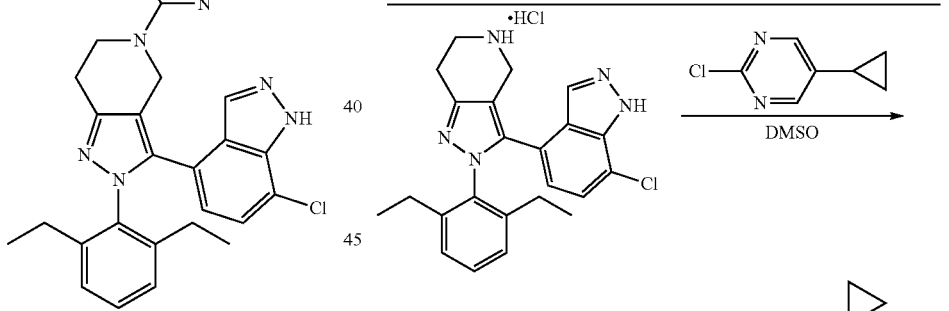

N,N-diisopropylethylamine (0.1 mL, 0.58 mmol) was added to a suspension of 3-(7-chloro-1H-indazol-4-yl)-2-(2, 6-diethylphenyl)-4,5,6,7-tetrahydro-2H-pyrazolo[4,3-c]pyridine hydrochloride (50 mg, 0.11 mmol), 2-chloro-5-cyclopropylpyrimidine (40 mg, 0.26 mmol), and Li$_2$CO$_3$ (20 mg, 0.27 mmol) in DMSO (5 mL) under magnetic stirring. The resulting mixture was stirred at 120° C. for 2 h. After cooling to room temperature, the reaction mixture was diluted with EtOAc, washed with brine and dried over MgSO$_4$. The solvent was removed under reduced pressure and the residue was purified by Preparative TLC (45% EtOAc in hexanes) to afford 3-(7-chloro-1H-indazol-4-yl)-5-(5-cyclopropylpyrimidin-2-yl)-2-(2,6-diethylphenyl)-4,5,6,7-tetrahydro-2H-pyrazolo[4,3-c]pyridine. $^1$H NMR (400 MHz, CDCl$_3$) δ 10.41 (s, 1H), 8.10-8.17 (m, 2H), 8.13 (s, 1H), 7.12-7.21 (m, 2H), 7.04 (d, J=7.7 Hz, 2H), 6.61 (d, J=7.7 Hz, 1H), 4.79 (s, 2H), 4.28 (t, J=5.9 Hz, 2H), 3.02 (t, J=5.9 Hz, 2H), 2.10-2.36 (m, 4H), 1.71 (m, 1H), 1.00 (t, J=4.0 Hz, 6H), 0.88 (m, 2H), 0.59 (m, 2H). MS: (ES) m z calculated C$_{30}$H$_{31}$ClN$_7$ [M+H]$^+$524.2, found 524.2.

Example 36

Synthesis of 2-(2,6-diethylphenyl)-3-(6-fluoro-7-methoxy-1H-indazol-4-yl)-5-(5-(trifluoromethyl)pyrimidin-2-yl)-4,5,6,7-tetrahydro-2H-pyrazolo[4,3-c]pyridine

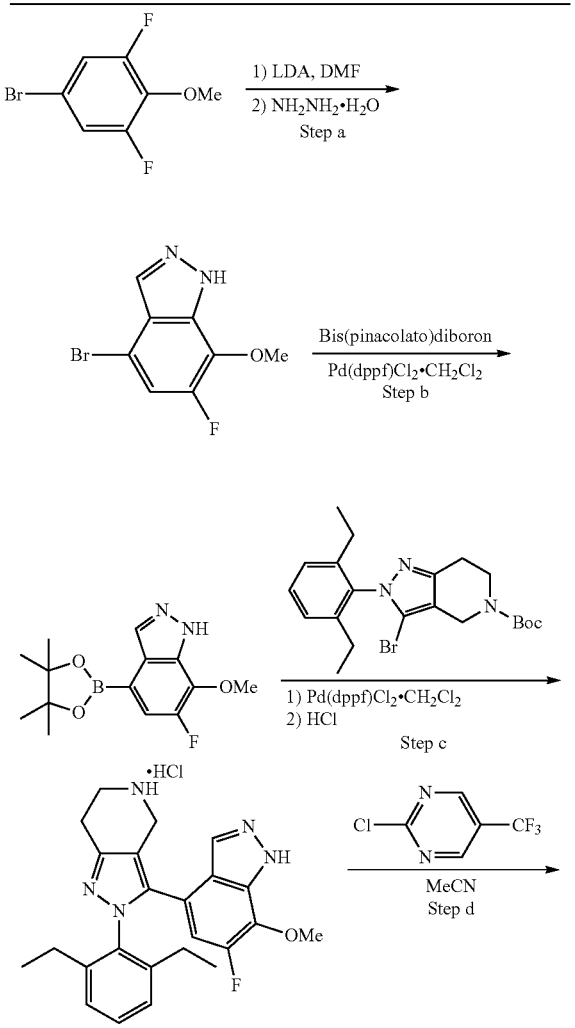

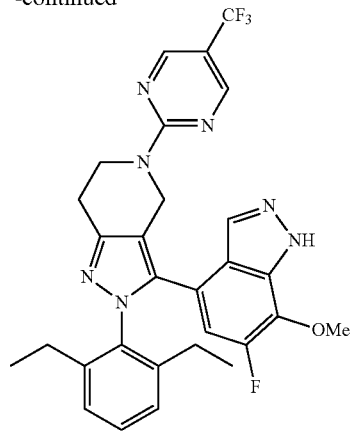

Step a: Lithium diisopropylamine solution in THF (1 M, 25 mL, 25 mmol) was added slowly to a solution of 5-bromo-1,3-difluoro-2-methoxybenzene (4.5 g, 20.2 mmol) in anhydrous THF (50 mL) under N$_2$ and vigorously stirred at −78° C. The reaction mixture was stirred at −60° C. for 1 h, followed by rapid addition of DMF (5 mL). The reaction mixture was stirred at the same temperature and allowed to warm to −50° C. over 1 h. The reaction was poured into a mixture of ice (200 g), concentrated hydrochloric acid (20 mL) and MTBE (100 mL) and the mixture was stirred and allowed to warm up to room temperature over 2 h. The oranic layer was separated, washed with brine and dried over MgSO$_4$. The solvent was removed under reduced pressure to give 6-bromo-2,4-difluoro-3-methoxybenzaldehyde. MS: (ES) m z calculated for C$_8$H$_6$BrF$_2$O$_2$ [M+H]$^+$ 250.9, found 250.9.

To the solution of the above 6-bromo-2,4-difluoro-3-methoxybenzaldehyde (1.5 g, 6.0 mmol) in DME (7 mL) was added hydrazine monohydrate (7 mL). The resulting mixture was stirred at 90° C. for 3 h. After cooling to room temperature, the reaction mixture was diluted with EtOAc, washed with brine and dried over MgSO$_4$. The solvent was removed under reduced pressure and the residue was purified by silica gel flash chromatography (5 to 40% EtOAc in hexanes) to afford 4-bromo-6-fluoro-7-methoxy-1H-indazole. MS: (ES) m z calculated for C$_8$H$_7$BrFN$_2$O [M+H]$^+$ 244.9, found 244.9.

Step b: To a suspension 4-bromo-6-fluoro-7-methoxy-1H-indazole (500 mg, 2.04 mmol), 4,4,4',4',5,5,5',5'-octamethyl-2,2'-bi(1,3,2-dioxaborolane) (1.0 g, 3.9 mmol), and KOAc (1 g, 10.2 mmol) in DMSO (12 mL) was added Pd(dppf)Cl$_2$ complex with dichloromethane (500 mg, 0.61 mmol). The reaction mixture was degassed (N$_2$) for 2 min and stirred at 120° C. for 1.5 h. The reaction mixture was diluted with EtOAc, washed with brine and dried over MgSO$_4$. The solvent was removed under reduced pressure and the residue was purified by silica gel flash chromatography (5 to 25% EtOAc in hexanes) to give 6-fluoro-7-methoxy-4-(4,4,5,5-tetramethyl-1,3,2-dioxaborolan-2-yl)-1H-indazole. MS: (ES) m z calculated for C$_{14}$H$_{19}$BFN$_2$O$_3$ [M+H]$^+$ 293.1, found 293.2.

Step c: To a suspension of tert-butyl 3-bromo-2-(2,6-diethylphenyl)-6,7-dihydro-2H-pyrazolo[4,3-c]pyridine-5(4H)-carboxylate (500 mg, 1.2 mmol), 6-fluoro-7-methoxy-4-(4,4,5,5-tetramethyl-1,3,2-dioxaborolan-2-yl)-1H-indazole (400 mg, 1.37 mmol), K$_2$CO$_3$ (600 mg, 4.4 mmol) in p-dioxane (6 mL) and water (1 mL) was added Pd(dppf)Cl$_2$ complex with dichloromethane (200 mg, 0.24 mmol).

The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 20% EtOAc in hexanes) to give tert-butyl 2-(2,6-diethylphenyl)-3-(6-fluoro-7-methoxy-1H-indazol-4-yl)-6,7-dihydro-2H-pyrazolo[4,3-c]pyridine-5(4H)-carboxylate. MS: (ES) m z calculated for C$_{29}$H$_{35}$FN$_5$O$_3$[M+H]$^+$ 520.3, found 520.3. The above tert-butyl 2-(2,6-diethylphenyl)-3-(6-fluoro-7-methoxy-1H-indazol-4-yl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 2-(2,6-diethylphenyl)-3-(6-fluoro-7-methoxy-1H-indazol-4-yl)-4,5,6,7-tetrahydro-2H-pyrazolo[4,3-c]pyridine hydrochloride. MS: (ES) m z calculated for C$_{24}$H$_{27}$FN$_5$O [M+H]$^+$ 420.2, found 420.2.

Step d: N,N-diisopropylethylamine (0.2 mL, 1.15 mmol) was added to a suspension of 2-(2,6-diethylphenyl)-3-(6-fluoro-7-methoxy-1H-indazol-4-yl)-4,5,6,7-tetrahydro-2H-pyrazolo[4,3-c]pyridine hydrochloride (50 mg, 0.11 mmol), 2-chloro-5-(trifluoromethyl)pyrimidine (20 mg, 0.11 mmol), and Li$_2$CO$_3$ (20 mg, 0.27 mmol) in DMSO (10 mL) under magnetic stirring. The resulting mixture was stirred at 65° C. for 1 h. After cooling to room temperature, the reaction mixture was diluted with EtOAc, washed with brine and dried over MgSO$_4$. The solvent was removed under reduced pressure and the residue was purified by Preparative TLC (50% EtOAc in hexanes) followed by trituration in MeOH to afford 2-(2,6-diethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 10.27 (s, 1H), 8.51 (s, 2H), 7.96 (d, J=0.6 Hz, 1H), 7.26 (m, 1H), 7.07 (d, J=7.7 Hz, 1H), 6.43-6.51 (m, 1H), 4.88 (s, 2H), 4.37 (t, J=5.9 Hz, 2H), 4.13 (dd, J=0.6, 3.0 Hz, 3H), 3.04 (t, J=5.9 Hz, 2H), 2.14-2.33 (m, 4H), 1.02 (t, J=7.5 Hz, 6H). MS: (ES) m z calculated C$_{29}$H$_{28}$F$_4$N$_7$O [M+H]$^+$ 566.2, found 566.2.

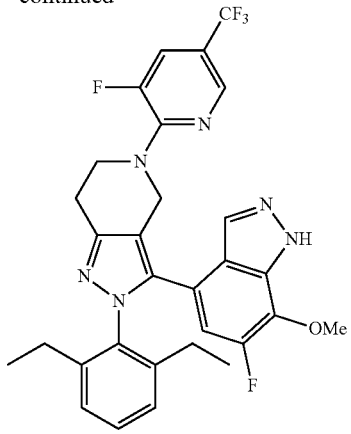

N,N-diisopropylethylamine (0.1 mL, 0.58 mmol) was added to a suspension of 2-(2,6-diethylphenyl)-3-(6-fluoro-7-methoxy-1H-indazol-4-yl)-4,5,6,7-tetrahydro-2H-pyrazolo[4,3-c]pyridine hydrochloride (30 mg, 0.07 mmol), 2,3-difluoro-5-(trifluoromethyl)pyridine (15 mg, 0.08 mmol), and Li$_2$CO$_3$ (20 mg, 0.27 mmol) in DMSO (10 mL) under magnetic stirring. The resulting mixture was stirred at 65° C. for 2 h. After cooling to room temperature, the reaction mixture was diluted with EtOAc, washed with brine and dried over MgSO$_4$. The solvent was removed under reduced pressure and the residue was purified by Preparative TLC (40% EtOAc in hexanes) followed by trituration in MeOH to afford 2-(2,6-diethylphenyl)-5-(3-fluoro-5-(trifluoromethyl)pyridin-2-yl)-3-(6-fluoro-7-methoxy-1H-indazol-4-yl)-4,5,6,7-tetrahydro-2H-pyrazolo[4,3-c]pyridine. $^1$H NMR (400 MHz, CDCl$_3$) δ 10.30 (s, 1H), 8.22 (dd, J=1.2, 2.3 Hz, 1H), 8.00 (s, 1H), 7.41 (dd, J=2.0, 13.2 Hz, 1H), 7.18-7.30 (m, 1H), 7.07 (d, J=7.7 Hz, 2H), 6.46 (d, J=13.1 Hz, 1H), 4.67 (s, 2H), 4.13 (s, 3H), 4.08 (t, J=5.9 Hz, 2H), 3.10 (t, J=5.9 Hz, 2H), 2.13-2.36 (m, 4H), 1.02 (t, J=8.0 Hz, 6H). MS: (ES) m z calculated C$_{30}$H$_{28}$F$_5$N$_6$O [M+H]$^+$ 583.2, found 583.2.

Example 38

Synthesis of 3-(7-methoxy-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine Example 37

Synthesis of 2-(2,6-diethylphenyl)-5-(3-fluoro-5-(trifluoromethyl)pyridin-2-yl)-3-(6-fluoro-7-methoxy-1H-indazol-4-yl)-4,5,6,7-tetrahydro-2H-pyrazolo[4,3-c]pyridine

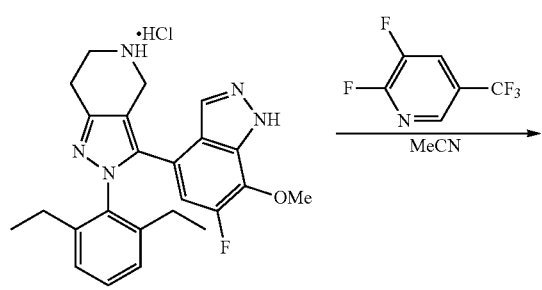

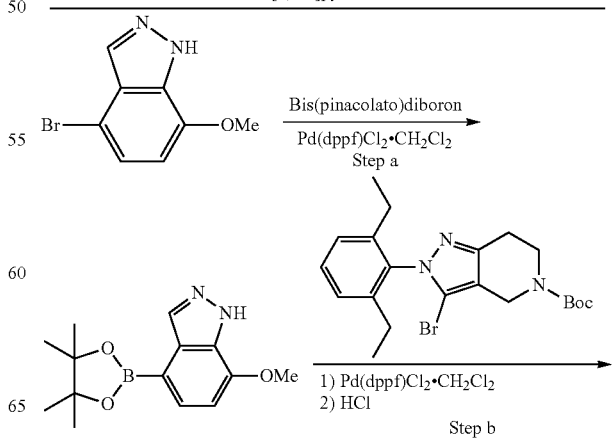

-continued

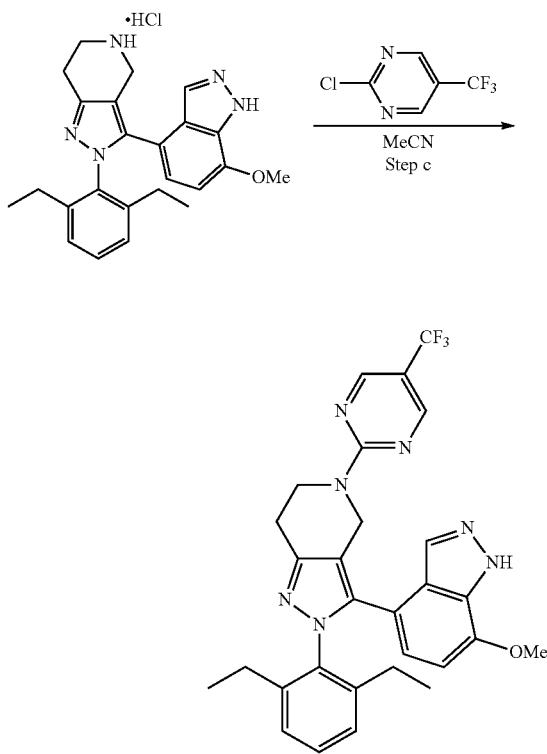

Step a: To a suspension of 4-bromo-7-methoxy-1H-indazole (500 mg, 2.2 mmol), 4,4,4',4',5,5,5',5'-octamethyl-2,2'-bi(1,3,2-dioxaborolane) (1.2 g, 2.7 mmol), and KOAc (690 mg, 7.0 mmol) in DMSO (8 mL) was added Pd(dppf)Cl$_2$ complex with dichloromethane (400 mg, 0.49 mmol). The reaction mixture was degassed (N$_2$) for 2 min and stirred at 120° C. for 2 h. The reaction mixture was diluted with EtOAc and filtered through Celite. The solvent was removed under reduced pressure and the residue was purified by silica gel flash chromatography (5 to 40% EtOAc in hexanes) to give 7-methoxy-4-(4,4,5,5-tetramethyl-1,3,2-dioxaborolan-2-yl)-1H-indazole. MS: (ES) m z calculated for C$_{14}$H$_{20}$BN$_2$O$_3$[M+H]$^+$ 275.2, found 275.2.

Step b: To a suspension of tert-butyl 3-bromo-2-(2,5-diethylphenyl)-6,7-dihydro-2H-pyrazolo[4,3-c]pyridine-5 (4H)-carboxylate (250 mg, 0.56 mmol), 7-methoxy-4-(4,4,5,5-tetramethyl-1,3,2-dioxaborolan-2-yl)-1H-indazole (310 mg, 1.1 mmol), K$_2$CO$_3$ (260 mg, 1.9 mmol) in p-dioxane (6 mL) and water (1.5 mL) was added Pd(dppf)Cl$_2$ complex with dichloromethane (200 mg, 0.25 mmol). The reaction mixture was degassed (N$_2$) for 2 min and stirred under N$_2$ at 100° C. for 3 h. The reaction mixture was diluted with EtOAc, and filtered through Celite. The solvent was removed under reduced pressure and the residue was purified by silica gel flash chromatography (10 to 80% MTBE in hexane) to give tert-butyl 3-(7-methoxy-1H-indazol-4-yl)-2-(2,6-diethylphenyl)-6,7-dihydro-2H-pyrazolo[4,3-c]pyridine-5-(4H)-carboxylate. MS: (ES) m z calculated for C$_{29}$H$_{36}$N$_5$O$_3$ [M+H]$^+$ 502.3, found 502.3.

The above tert-butyl 3-(7-methoxy-1H-indazol-4-yl)-2-(2,6-diethylphenyl)-6,7-dihydro-2H-pyrazolo[4,3-c]pyridine-5-(4H)-carboxylate was dissolved in dichloromethane (15 mL) and treated with HCl in dioxane (4N, 3 mL). The resulting mixture was stirred at room temperature for 1 h.

After the reaction was complete, the solvent was evaporated in vacuo to give 3-(7-methoxy-1H-indazol-4-yl)-2(2,6-diethylphenyl)-4,5,6,7-tetrahydro-2H-pyrazolo[4,3-c]pyridine hydrochloride. MS: (ES) m z calculated for C$_{24}$H$_{28}$N$_5$O [M+H]$^+$ 402.2, found 402.2.

Step c: N,N-diisopropylethylamine (0.040 mL, 0.23 mmol) was added to a suspension of 3-(7-methoxy-1H-indazol-4-yl)-2-(2,6-diethylphenyl)-4,5,6,7-tetrahydro-2H-pyrazolo[4,3-c]pyridine hydrochloride (52 mg, 0.11 mmol), 2-chloro-5-(trifluoromethyl)pyrimidine (25 mg, 0.14 mmol) and Li$_2$CO$_3$ (20 mg, 0.27 mmol) in DMSO (1 mL) under magnetic stirring. The resulting mixture was stirred at room temperature for 9 h. The solvent was removed in vacuo and the residue was purified by silica gel flash chromatography (4 to 40% EtOAc in hexanes) to obtain 3-(7-methoxy-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, d$_6$-DMSO) δ 8.70 (br s, 2H), 7.95 (s, 1H), 7.25 (t, J=8.0 Hz, 1H), 7.09 (d, J=8.0 Hz, 2H), 6.69 (d, J=8.0 Hz, 1H), 6.49 (d, J=8.0 Hz, 1H), 4.79 (s, 2H), 4.31 (t, J=5.6 Hz, 2H), 3.88 (s, 3H), 2.89 (t, J=5.6 Hz, 2H), 2.0-2.3 (m, 4H), 0.8-1.0 (m, 6H). MS: (ES) m z calculated for C$_{29}$H$_{29}$F$_3$N$_7$O [M+H]$^+$ 548.2, found 548.2.

Example 39

Synthesis of 2-(2,6-diethylphenyl)-3-(6,7-difluoro-1H-indol-4-yl)-5-[5-(trifluoromethyl)pyrimidin-2-yl]6,7-dihydro-4H-pyrazolo[4,3-c]pyridine

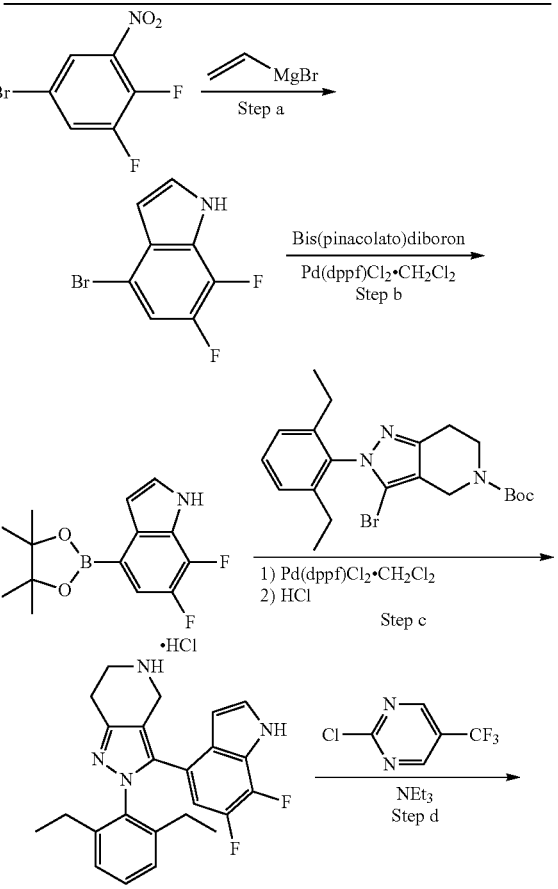

-continued

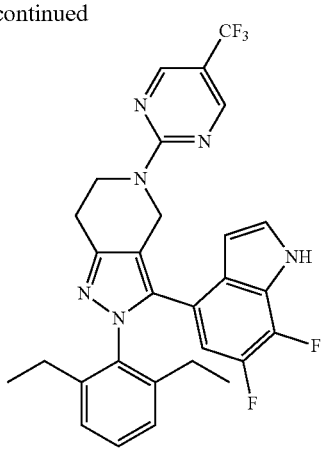

Step a: Vinylmagnesium bromide solution in THF (1 M, 65.8 mL, 65.8 mmol) was added to a solution of 5-bromo-1,2-difluoro-3-nitro-benzene (4.90 g, 20.58 mmol) in anhydrous THF (70 mL) under $N_2$ at −55° C. The reaction mixture was stirred at the same temperature and allowed to warm to −45° C. over 1.5 h. The reaction mixture was quenched with saturated aqueous $NH_4Cl$ solution and allowed to warm up to room temperature over 1 h. The reaction mixture was diluted with EtOAc, washed with brine and dried over $Na_2SO_4$. The solvent was removed under reduced pressure and the residue was purified by silica gel flash chromatography (0 to 30% EtOAc in hexanes) to give 4-bromo-6,7-difluoro-1H-indole. MS: (ES) m z calculated for $C_8H_5BrF_2N$ [M+H]$^+$ 231.9, found 231.9.

Step b: To a suspension of 4-bromo-6,7-difluoro-1H-indole (0.500 g, 2.15 mmol), 4,4,4',4',5,5,5',5'-octamethyl-2,2'-bi(1,3,2-dioxaborolane) (0.657 g, 2.6 mmol) and KOAc (0.633 g, 6.45 mmol) in dioxane (12 mL) was added Pd(dppf)Cl$_2$ complex with dichloromethane (0.200 g, 0.24 mmol). The reaction mixture was degassed ($N_2$) for 2 min and stirred at 100° C. for 1.5 h. The reaction mixture was diluted with EtOAc and filtered through Celite. The solvent was removed under reduced pressure and the residue was purified by silica gel flash chromatography (0 to 80% DCM/hexanes) to give 6,7-difluoro-4-(4,4,5,5-tetramethyl-1,3,2-dioxaborolan-2-yl)-1H-indole. MS: (ES) m z calculated for $C_{14}H_{17}BF_2NO_2$ [M+H]$^+$ 280.1, found 280.1.

Step c: To a suspension of tert-butyl 3-bromo-2-(2,6-diethylphenyl)-6,7-dihydro-2H-pyrazolo[4,3-c]pyridine-5(4H)-carboxylate (0.356 g, 0.82 mmol), 6,7-difluoro-4-(4,4,5,5-tetramethyl-1,3,2-dioxaborolan-2-yl)-1H-indole (0.230 g, 0.82 mmol), $K_2CO_3$ (0.350 g, 2.53 mmol) in p-dioxane (10 mL) and water (1.2 mL) was added Pd(dppf)Cl$_2$ complex with dichloromethane (0.150 g, 0.18 mmol). The reaction mixture was degassed ($N_2$) for 2 min and stirred under $N_2$ at 100° C. for 2 h. The reaction mixture was diluted with EtOAc, washed with aqueous $NaHCO_3$ and dried over $Na_2SO_4$. The solvent was removed under reduced pressure and the residue was purified by silica gel flash chromatography (0 to 60% EtOAc in hexanes) to give tert-butyl 2-(2,6-diethylphenyl)-3-(6,7-difluoro-1H-indol-4-yl)-6,7-dihydro-4H-pyrazolo[4,3-c]pyridine-5-carboxylate. MS: (ES) m z calculated for $C_{29}H_{33}F_2N_4O_2$[M+H]$^+$ 507.2, found 507.2.

The above tert-butyl 2-(2,6-diethylphenyl)-3-(6,7-difluoro-1H-indol-4-yl)-6,7-dihydro-4H-pyrazolo[4,3-c]pyridine-5-carboxylate (0.255 g, 0.60 mmol) was dissolved in dichloromethane (1.5 mL) and charged with HCl in dioxane (4N, 4 mL). The resulting mixture was stirred at room temperature for 1 h. The solvent was evaporated in vacuo to give 2-(2,6-diethylphenyl)-3-(6,7-difluoro-1H-indol-4-yl)-4,5,6,7-tetrahydropyrazolo[4,3-c]pyridine hydrochloride. MS: (ES) m z calculated for $C_{25}H_{27}FN_4O$ [M+H]$^+$ 407.2, found 407.2.

Step d: Triethylamine (0.12 mL, 0.86 mmol) was added to a suspension of 2-(2,6-diethylphenyl)-3-(6,7-difluoro-1H-indol-4-yl)-4,5,6,7-tetrahydropyrazolo[4,3-c]pyridine hydrochloride (0.025 g, 0.056 mmol) and 2-chloro-5-(trifluoromethyl)pyrimidine (60 mg, 0.33 mmol) in MeCN (1.5 mL). The resulting mixture was stirred at 80° C. for 45 min. After cooling to room temperature, the reaction mixture was diluted with EtOAc, washed with aqueous $NaHCO_3$ and dried over $Na_2SO_4$. The solvent was removed under reduced pressure and the residue was purified by silica gel flash chromatography (0 to 45% EtOAc in hexanes) to afford 2-(2,6-diethylphenyl)-3-(6,7-difluoro-1H-indol-4-yl)-5-[5-(trifluoromethyl)pyrimidin-2-yl]-6,7-dihydro-4H-pyrazolo[4,3-c]pyridine. $^1$H NMR (400 MHz, CDCl$_3$) δ 8.60 (br s, 1H), 8.50 (br s, 2H), 7.20-7.25 (m, 2H), 7.06 (d, J=7.2 Hz, 2H), 6.47 (m, 2H), 4.83 (br s, 2H), 4.36 (t, J=5.4 Hz, 2H), 3.04 (t, J=5.4 Hz, 2H), 2.02-2.40 (br s, 4H), 1.00 (br s, 6H). MS: (ES) m z calculated for $C_{29}H_{26}F_5N_6$ [M+H]$^+$ 553.2, found 553.2.

Example 40

Synthesis of 3-(7-chloro-5-fluoro-1H-indol-4-yl)-2-(2,6-diethylphenyl)-5-[5-(trifluoromethyl)pyrimidin-2-yl]-6,7-dihydro-4H-pyrazolo[4,3-c]pyridine

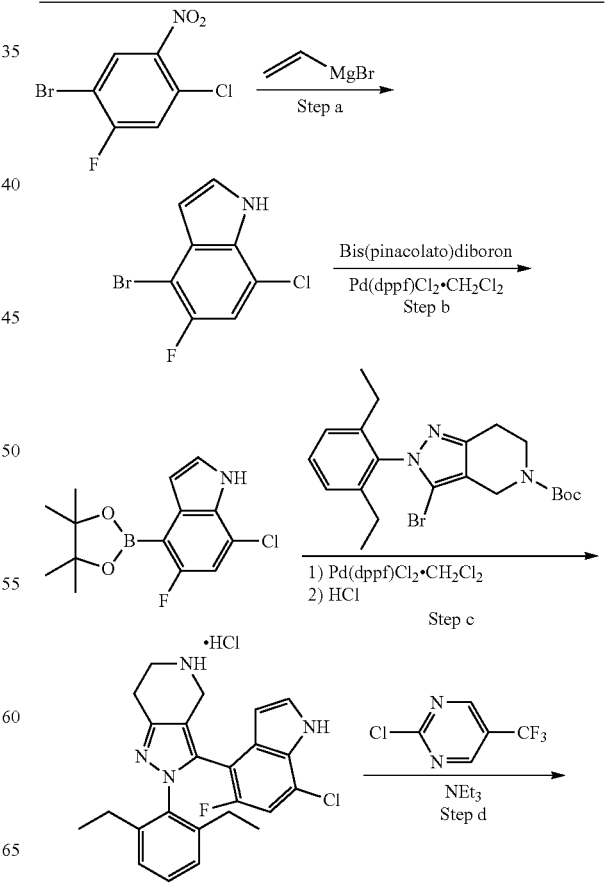

-continued

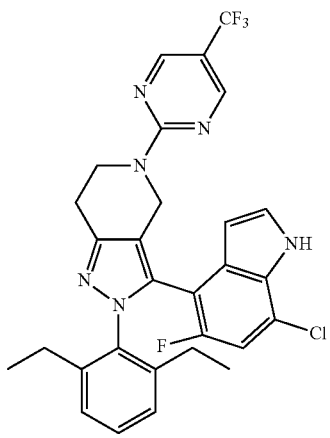

Step a: Vinylmagnesium bromide solution in THF (1 M, 37.7 mL, 37.7 mmol) was added to a solution of 1-bromo-4-chloro-2-fluoro-5-nitro-benzene (3.00 g, 11.8 mmol) in anhydrous THF (40 mL) under $N_2$ at −60° C. The reaction mixture was stirred at the same temperature and allowed to warm to −40° C. over 1.5 h. The reaction mixture was quenched with saturated aqueous $NH_4Cl$ solution and allowed to warm up to room temperature over 1 h. The reaction mixture was diluted with ether, washed with brine and dried over $Na_2SO_4$. The solvent was removed under reduced pressure and the residue was purified by silica gel flash chromatography (0 to 40% EtOAc in hexanes) to give 4-bromo-7-chloro-5-fluoro-1H-indole. MS: (ES) m z calculated for $C_8H_5BrClFN$ [M+H]$^+$ 247.9, found 247.9.

Step b: To a suspension of 4-bromo-7-chloro-5-fluoro-1H-indole (300 mg, 1.2 mmol), 4,4,4',4',5,5,5',5'-octamethyl-2,2'-bi(1,3,2-dioxaborolane) (1.44 g, 0.368 mmol), and KOAc (356 mg, 3.6 mmol) in dioxane (8 mL) was added Pd(dppf)Cl$_2$ complex with dichloromethane (120 mg, 0.15 mmol). The reaction mixture was degassed (N$_2$) for 2 min and stirred at 100° C. overnight. The reaction mixture was cooled to room temperature, diluted with EtOAc and filtered through Celite. The solvent was removed under reduced pressure and the residue was purified by silica gel flash chromatography (0 to 100% DCM in hexanes) to give 7-chloro-5-fluoro-4-(4,4,5,5-tetramethyl-1,3,2-dioxaborolan-2-yl)-1H-indole. MS: (ES) m z calculated for $C_{14}H_{17}BClFNO_2$ [M+H]$^+$ 296.1, found 296.1.

Step c: To a suspension of tert-butyl 3-bromo-2-(2,6-diethylphenyl)-6,7-dihydro-2H-pyrazolo[4,3-c]pyridine-5(4H)-carboxylate (169 mg, 0.39 mmol), 7-chloro-5-fluoro-4-(4,4,5,5-tetramethyl-1,3,2-dioxaborolan-2-yl)-1H-indole (115 mg, 0.39 mmol), K$_2$CO$_3$ (230 mg, 1.66 mmol) in p-dioxane (6 mL) and water (0.7 mL) was added Pd(dppf)Cl$_2$ complex with dichloromethane (120 mg, 0.15 mmol). The reaction mixture was degassed (N$_2$) for 2 min and stirred under N$_2$ at 100° C. for 2 h. The reaction mixture was cooled to room temperature, diluted with EtOAc, washed with aqueous NaHCO$_3$ and dried over Na$_2$SO$_4$. The solvent was removed under reduced pressure and the residue was purified by silica gel flash chromatography (0 to 50% EtOAc in hexanes) to give tert-butyl 3-(7-chloro-5-fluoro-1H-indol-4-yl)-2-(2,6-diethylphenyl)-6,7-dihydro-4H-pyrazolo[4,3-c]pyridine-5-carboxylate. MS: (ES) m z calculated for $C_{29}H_{33}ClFN_4O_2$[M+H]$^+$ 523.2, found 523.2.

The above tert-butyl 3-(7-chloro-5-fluoro-1H-indol-4-yl)-2-(2,6-diethylphenyl)-6,7-dihydro-4H-pyrazolo[4,3-c]pyridine-5-carboxylate (90 mg, 0.17 mmol) was dissolved in dichloromethane (2 mL) and charged with HCl in dioxane (4N, 4 mL). The resulting mixture was stirred at room temperature for 1 h. The solvent was evaporated in vacuo to give 3-(7-chloro-5-fluoro-1H-indol-4-yl)-2-(2,6-diethylphenyl)-4,5,6,7-tetrahydropyrazolo[4,3-c]pyridine hydrochloride. MS: (ES) m z calculated for $C_{24}H_{25}ClFN_4$ [M+H]$^+$ 423.2, found 423.2.

Step d: Triethylamine (0.12 mL, 0.86 mmol) was added to a suspension of 3-(7-chloro-5-fluoro-1H-indol-4-yl)-2-(2,6-diethylphenyl)-4,5,6,7-tetrahydropyrazolo[4,3-c]pyridine hydrochloride (23 mg, 0.05 mmol) and 2-chloro-5-(trifluoromethyl)pyrimidine (50 mg, 0.27 mmol) in MeCN (1.3 mL). The resulting mixture was stirred at 85° C. for 45 min. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 50% EtOAc in hexanes) to afford 3-(7-chloro-5-fluoro-1H-indol-4-yl)-2-(2,6-diethylphenyl)-5-[5-(trifluoromethyl)pyrimidin-2-yl]-6,7-dihydro-4H-pyrazolo[4,3-c]pyridine. $^1$H NMR (400 MHz, CDCl$_3$) δ 8.53 (br s, 1H), 8.49 (br s, 2H), 7.30 (d, J=3.0 Hz, 1H), 7.20 (t, J=7.6 Hz, 1H), 7.14 (d, J=6.4 Hz, 1H), 6.90 (d, J=7.2 Hz, 1H), 6.86 (d, J=9.6 Hz, 1H), 6.43 (t, J=2.8 Hz, 1H), 4.91 (d, J=16 Hz, 1H), 4.68 (d, J=16 Hz, 1H), 4.40 (m, 1H), 4.34 (m, 1H), 3.05 (t, J=5.8 Hz, 2H), 2.50 (m, 1H), 2.40 (m, 1H), 2.15 (sextet, J=7.5 Hz, 1H), 1.93 (sextet, J=7.5 Hz, 1H), 1.21 (t, J=7.6 Hz, 3H), 0.76 (t, J=7.4 Hz, 3H). MS: (ES) m z calculated for $C_{29}H_{26}ClF_4N_6$[M+H]$^+$ 569.2, found 569.2.

Example 41

Synthesis of 3-(7-chloro-5-fluoro-1H-indol-4-yl)-2-(2,6-diethylphenyl)-5-(5-(1-methylethyl)pyridin-2-yl)-4,5,6,7-tetrahydro-2H-pyrazolo[4,3-c]pyridine

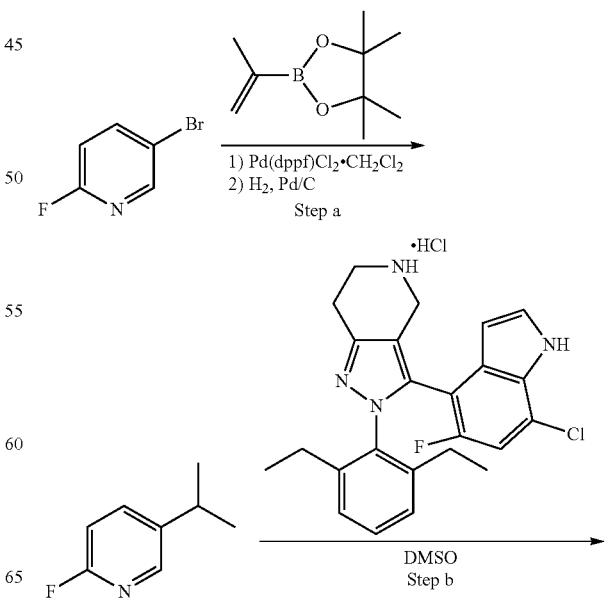

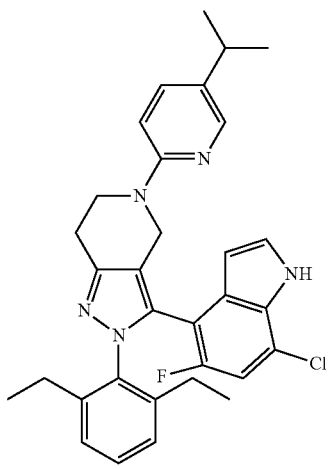

Step a: To a suspension of 5-bromo-2-fluoropyridine (10 g, 57 mmol), 4,4,5,5-tetramethyl-2-(1-methylethenyl)-1,3,2-dioxaborolane (16 g, 93 mmol), and sodium carbonate (18 g, 17 mmol) in a mixture of dioxane (150 mL) and water (45 mL) was added Pd(dppf)Cl$_2$ complex with dichloromethane (2.0 g, 2.4 mmol). The reaction mixture was degassed (N$_2$) for 2 min and refluxed for 1.5 h. Dioxane was removed in vacuo and the residue was taken up in ether and water. The organic phase was separated and washed with brine. The solvent was removed under reduced pressure and the residue was purified by silica gel flash chromatography (hexane) to obtain 2-fluoro-5-(1-methylethenyl)pyridine. $^1$H NMR (400 MHz, CDCl$_3$) δ 8.28 (d, J=2.3 Hz, 1H), 7.82-7.88 (m, 1H), 6.89 (dd, J=3.0, 8.8 Hz, 1H), 5.36 (s, 1H), 5.16 (s, 1H), 2.15 (s, 3H).

To the above 2-fluoro-5-(1-methylethenyl)pyridine (7.3 g, 53 mmol) dissolved in EtOAc (100 mL) was added 10% Pd/C (Degussa type E101 NE/W, 700 mg), and the mixture was stirred under one atmosphere of hydrogen for 4 h. Upon completion, the mixture was filtered through Celite and solvent was removed in vacuo to give 2-fluoro-5-(1-methylethyl)pyridine. $^1$H NMR (400 MHz, CDCl$_3$) δ 8.05 (s, 1H), 7.59-7.66 (dd, J=3.0, 8.4 Hz, 1H), 2.88-3.00 (m, 1H), 1.26 (d, J=6.8 Hz, 6H).

Step b: N,N-diisopropylethylamine (0.050 mL, 0.23 mmol) was added to a suspension of 3-(7-chloro-5-fluoro-1H-indol-4-yl)-2-(2,6-diethylphenyl)-4,5,6,7-tetrahydro-2H-pyrazolo[4,3-c]pyridine hydrochloride (58 mg, 0.13 mmol), 2-fluoro-5-(1-methylethyl)pyridine (240 mg, 1.7 mmol) and Li$_2$CO$_3$ (28 mg, 0.38 mmol) in DMSO (0.5 mL) under magnetic stirring. The resulting mixture was stirred at 140° C. temperature for 4 d. The solvent was removed in vacuo and the residue was purified by silica gel flash chromatography (10 to 100% MTBE in hexanes) followed by HPLC (MeCN/H$_2$O with 0.1% TFA) to obtain 3-(7-chloro-5-fluoro-1H-indol-4-yl)-2-(2,6-diethylphenyl)-5-(5-(1-methylethyl)pyridin-2-yl)-4,5,6,7-tetrahydro-2H-pyrazolo[4,3-c]pyridine. $^1$H NMR (400 MHz, CD$_3$OD) S 7.92 (d, J=2.5 Hz, 1H), 7.45-7.52 (m, 2H), 7.18-7.28 (m, 2H), 6.94 (d, J=7.2 Hz, 1H), 6.86 (d, J=10 Hz, 1H), 6.82 (d, J=9.2 Hz, 1H), 6.42 (d, J=3.1 Hz, 1H), 4.58 (d, J=16 Hz, 1H), 4.27 (d, J-16 Hz, 1H), 4.03 (t, J=6.0 Hz, 2H), 3.01 (t, J=6.0 Hz, 2H), 2.76-2.87 (m, 1H), 1.86-2.5 (m, 4H), 1.18-1.26 (m, 9H), 0.72 (t, J=7.6 Hz, 3H)). MS: (ES) m z calculated for C$_{32}$H$_{34}$ClFN$_5$ [M+H]$^+$ 542.2, found 542.2.

Example 42

Synthesis of 3-(7-chloro-5-fluoro-1H-indol-4-yl)-2-(2,6-diethylphenyl)-5-(1-methylethyl)pyridin-2-yl)-4,5,6,7-tetrahydro-2H-pyrazolo[4,3-c]pyridine

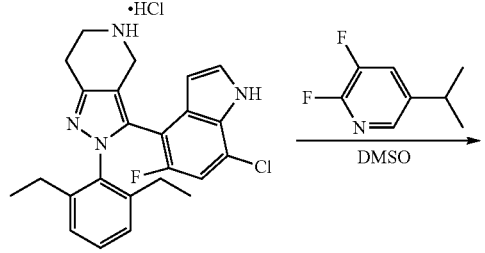

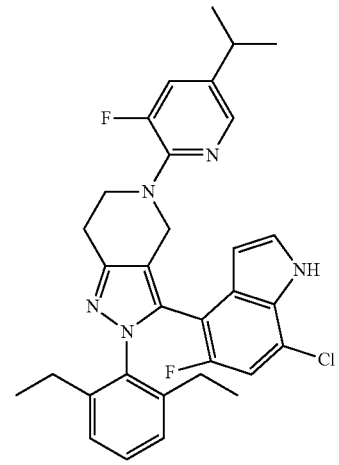

N,N-diisopropylethylamine (0.050 mL, 0.29 mmol) was added to a suspension of 3-(7-chloro-5-fluoro-1H-indol-4-yl)-2-(2,6-diethylphenyl)-4,5,6,7-tetrahydro-2H-pyrazolo[4,3-c]pyridine hydrochloride (77 mg, 0.17 mmol), 2,3-difluoro-5-(1-methylethyl)pyridine (200 mg, 1.3 mmol) and Li$_2$CO$_3$ (42 mg, 0.30 mmol) in DMSO (0.5 mL) under magnetic stirring. The resulting mixture was stirred at 140° C. temperature for 6 h. The solvent was removed in vacuo and the residue was purified by silica gel flash chromatography (4 to 60% MTBE in hexanes) to obtain 3-(7-chloro-5-fluoro-1H-indol-4-yl)-2-(2,6-diethylphenyl)-5-(3-fluoro-5-(1-methylethyl)pyridin-2-yl)-4,5,6,7-tetrahydro-2H-pyrazolo[4,3-c]pyridine. $^1$H NMR (400 MHz, CD$_3$OD) δ 7.89 (s, 1H), 7.54 (d, J=3.2 Hz, 1H), 7.43 (d, J=14 Hz, 1H), 7.27-7.37 (m, 2H), 7.03 (d, J=6.8 Hz, 1H), 6.93 (d, J=10 Hz, 1H), 6.56 (d, J=3.0 Hz, 1H), 4.63 (d, J=16 Hz, 1H), 4.23 (d, J=16 Hz, 1H), 3.83-4.05 (m, 2H), 3.12 (t, J=6.0 Hz, 2H), 1.96-2.5 (m, 4H), 1.25-1.37 (m, 9H), 0.81 (t, J=7.2 Hz, 3H). MS: (ES) m z calculated for C$_{32}$H$_{33}$ClF$_2$N$_5$[M+H]$^+$ 560.2, found 560.2.

Example 43

Synthesis of 3-(7-chloro-5-fluoro-1H-indol-4-yl)-5-(5-cyclopropylpyrimidin-2-yl)-2-(2,6-diethylphenyl)-4,5,6,7-tetrahydro-2H-pyrazolo[4,3-c]pyridine

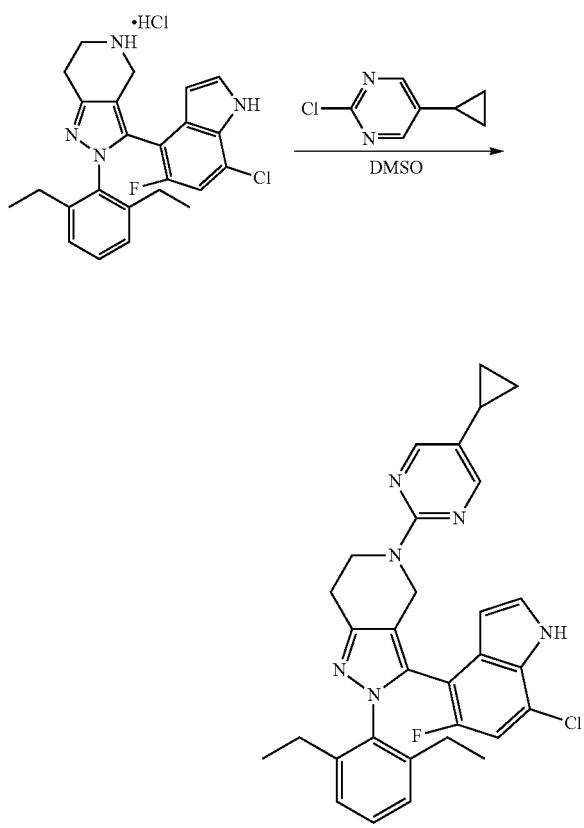

N,N-diisopropylethylamine (0.1 mL, 0.58 mmol) was added to a suspension of 3-(7-chloro-5-fluoro-1H-indol-4-yl)-2-(2,6-diethylphenyl)-4,5,6,7-tetrahydro-2H-pyrazolo[4,3-c]pyridine hydrochloride (30 mg, 0.07 mmol), 2-chloro-5-cyclopropylpyrimidine (20 mg, 0.13 mmol), and Li$_2$CO$_3$ (20 mg, 0.27 mmol) in DMSO (5 mL) under magnetic stirring. The resulting mixture was stirred at 100° C. for 2 h. After cooling to room temperature, the reaction mixture was diluted with EtOAc, washed with brine and dried over MgSO$_4$. The solvent was removed under reduced pressure and the residue was purified by Preparative TLC (45% EtOAc in hexanes) followed by trituration in MeOH to afford 3-(7-chloro-5-fluoro-1H-indol-4-yl)-5-(5-cyclopropylpyrimidin-2-yl)-2-(2,6-diethylphenyl)-4,5,6,7-tetrahydro-2H-pyrazolo[4,3-c]pyridine. $^1$H NMR (400 MHz, CDCl$_3$) δ 8.44 (d, J=2.7 Hz, 1H), 8.12 (s, 2H), 7.12-7.32 (m, 5H), 6.87 (dd, J=8.5, 15.4 Hz, 1H), 6.47 (t, J=2.5 Hz, 1H), 4.76 (d, J=15.9 Hz, 1H), 4.61 (d, J=15.9 Hz, 1H), 4.38 (m, 1H), 4.18 (m, 1H), 3.03 (t, J=5.9 Hz, 2H), 1.91-2.54 (br,m, 4H), 1.66 (m, 1H), 1.23 (t, J=7.5 Hz, 3H), 0.89 (m, 2H), 0.76 (t, J=7.5 Hz, 3H), 0.58 (m, 2H). MS: (ES) m z calculated C$_{31}$H$_{31}$ClFN$_6$ [M+H]$^+$ 541.2, found 541.2.

Example 44

Synthesis of (2-(3-(7-chloro-5-fluoro-1H-indol-4-yl)-2-(2,6-diethylphenyl)-6,7-dihydro-2H-pyrazolo[4,3-c]pyridin-5(4H)-yl)pyrimidin-5-yl)(pyrrolidin-1-yl)methanone

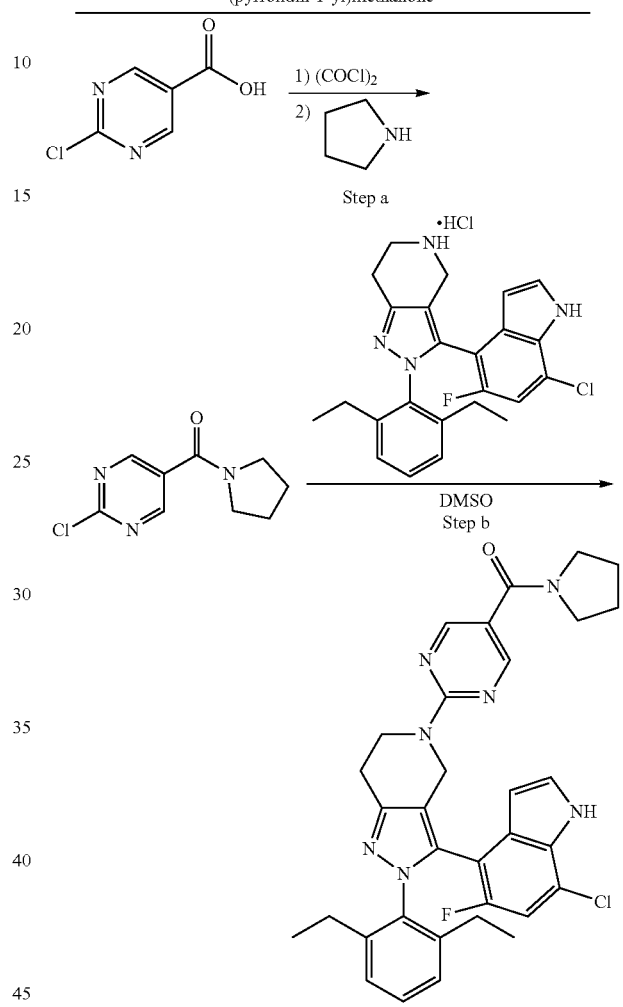

Step a: Oxalyl chloride (1 mL, 11.8 mmol) was added to a mixture of 2-chloropyrimidine-5-carboxylic acid (500 mg, 3.2 mmol) in dichloromethane (10 mL) followed by DMF (0.1 mL). The resulting mixture was stirred at room temperature for 1 h. After removal of solvent under reduced pressure, the residue was dissolved in dichloromethane (5 mL).

To above acid chloride solution was added slowly to a solution of pyrrolidine (1 mL) and DIEA (1 mL, 5.8 mmol) in dichloromethane (20 mL) at at −40° C. The resulting mixture was stirred at −40° C. for 1 h and quenched with aqueous citric acid solution. The reaction mixture was diluted with dichloromethane, washed with brine and dried over MgSO$_4$. The solvent was removed under reduced pressure to give (2-chloropyrimidin-5-yl)(pyrrolidin-1-yl)methanone. MS: (ES) m z calculated for C$_9$H$_{11}$ClN$_3$O [M+H]$^+$ 212.1, found 212.1.

N,N-diisopropylethylamine (0.1 mL, 0.58 mmol) was added to a suspension of 3-(7-chloro-5-fluoro-1H-indol-4-yl)-2-(2,6-diethylphenyl)-4,5,6,7-tetrahydro-2H-pyrazolo

[4,3-c]pyridine hydrochloride (45 mg, 0.11 mmol), (2-chloropyrimidin-5-yl)(pyrrolidin-1-yl)methanone (80 mg, 0.38 mmol), and $Li_2CO_3$ (30 mg, 0.41 mmol) in DMSO (5 mL) under magnetic stirring. The resulting mixture was stirred at 85° C. for 2 h. After cooling to room temperature, the reaction mixture was diluted with EtOAc, washed with brine and dried over $MgSO_4$. The solvent was removed under reduced pressure and the residue was purified by Preparative TLC (75% EtOAc in hexanes) followed by trituration in MeOH to afford (2-(3-(7-chloro-5-fluoro-1H-indol-4-yl)-2-(2,6-diethylphenyl)-6,7-dihydro-2H-pyrazolo[4,3-c]pyridin-5(4H)-yl)pyrimidin-5-yl)(pyrrolidin-1-yl)methanone. $^1$H NMR (400 MHz, $CDCl_3$) δ 8.56 (2, 2H), 2H), 8.54 (s, 1H), 7.13-7.32 (m, 3H), 6.84-6.90 (m, 2H), 6.44 (dd, J=2.2, 3.2 Hz, 1H), 4.87 (d, J=16.0 Hz, 1H), 4.68 (d, J=16.0 Hz, 1H), 4.24-4.47 (m, 2H), 3.48-3.63 (m, 6H), 3.05 (t, J=6.0, 2H), 2.40-2.51 (m, 2H), 1.92-2.17 (m, 4H), 1.23 (t, J=8.0 Hz, 3H), 0.76 (t, J=8.0 Hz, 3H). MS: (ES) m z calculated $C_{33}H_{34}ClFN_7O$ [M+H]$^+$ 598.2, found 598.2.

Example 45

LiAlH$_4$ in ether (2 M, 0.15 mL, 0.30 mmol). The resulting mixture was stirred for 30 min at room temperature. It was then quenched with water and diluted with EtOAc. The organic layer was separated, dried over $Na_2SO_4$, concentrated under reduced pressure and purified by silica gel flash chromatography (0 to 30% MeOH in DCM) to yield 3-(7-chloro-5-fluoro-1H-indol-4-yl)-2-(2,6-diethylphenyl)-5-[5-(pyrrolidin-1-ylmethyl)pyrimidin-2-yl]-6,7-dihydro-4H-pyrazolo[4,3-c]pyridine. $^1$H NMR (400 MHz, $CDCl_3$) δ 8.51 (br s, 1H), 8.28 (s, 2H), 7.30 (t, J=5.6 Hz, 1H), 7.19 (t, J=7.6 Hz, 1H), 7.15 (m, 1H), 6.87 (d, J=7.6 Hz, 1H), 6.84 (d, J=10 Hz, 1H), 6.46 (dd, J=2.8, 2.8 Hz, 1H), 4.80 (d, J=16 Hz, 1H),), 4.62 (d, J=15.6 Hz, 1H), 4.39 (m, 1H), 4.22 (m, 1H), 3.50 (br s, 2H),), 3.03 (t, J=5.8 Hz, 2H), 2.36-2.60 (m, 6H), 2.15 (sextet, J=7.6 Hz, 1H), 1.92 (sextet, J=7.6 Hz, 1H), 1.81 (br s, 4H), 1.22 (t, J=7.6 Hz, 3H), 0.74 (t, J=7.6 Hz, 3H). MS: (ES) m z calculated for $C_{33}H_{36}ClFN_7$ [M+H]$^+$ 584.2, found 584.2.

Example 46

Synthesis of 3-(7-chloro-5-fluoro-1H-indol-4-yl)-2-(2,6-diethylphenyl)-5-[5-(pyrrolidin-1-ylmethyl)pyrimidin-2-yl]-6,7-dihydro-4H-pyrazolo[4,3-c]pyridine Synthesis of 3-(7-methyl-1H-indol-4-yl)-2-(2,6-diethylphenyl)-5-(5-(1-methylethyl)pyridin-2-yl)-4,5,6,7-tetrahydro-2H-pyrazolo[4,3-c]pyridine

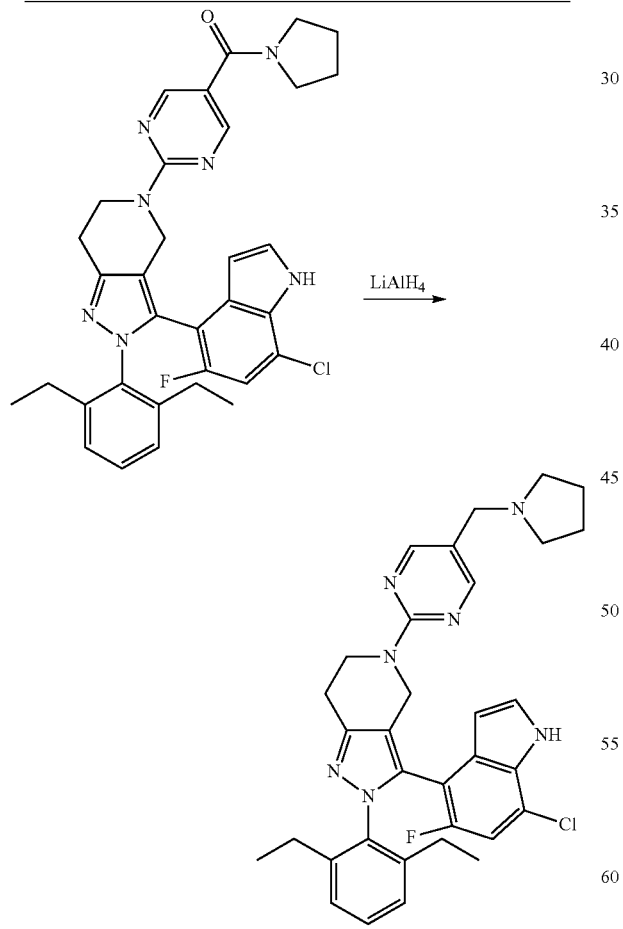

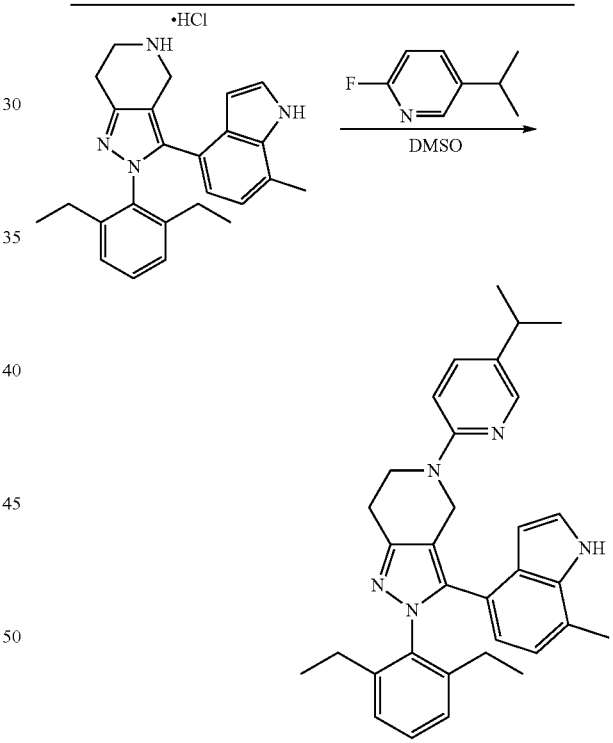

To a mixture of [2-[3-(7-chloro-5-fluoro-1H-indol-4-yl)-2-(2,6-diethylphenyl)-6,7-dihydro-4H-pyrazolo[4,3-c]pyridin-5-yl]pyrimidin-5-yl]-pyrrolidin-1-yl-methanone (0.025 g, 0.042 mmol) in THF (2 mL) was added a solution of N,N-diisopropylethylamine (0.06 mL, 0.35 mmol) was added to a suspension of 3-(7-methyl-1H-indol-4-yl)-2(2,6-diethylphenyl)-4,5,6,7-tetrahydro-2H-pyrazolo[4,3-c]pyridine hydrochloride (51 mg, 0.12 mmol), 2-fluoro-5-(1-methylethyl)pyridine (100 mg, 0.73 mmol) and $Li_2CO_3$ (24 mg, 0.32 mmol) in DMSO (0.25 mL) under magnetic stirring. The resulting mixture was stirred at 140° C. temperature for 23 h. The solvent was removed in vacuo and the residue was purified by silica gel flash chromatography (0 to 70% MTBE in hexanes) to obtain 3-(7-methyl-1H-indol-4-yl)-2-(2,6-diethylphenyl)-5-(5-(1-methylethyl)pyridin-2-yl)-4,5,6,7-tetrahydro-2H-pyrazolo[4,3-c]pyridine. $^1$H NMR (400 MHz, CD$_3$OD) δ 7.91 (s, 1H), 7.45 (d, J=8.4 Hz, 1H), 7.34 (d, J=2.9 Hz, 1H), 7.08 (br s, 2H), 6.74 (d, J=9.2 Hz, 1H), 6.68 (d, J=7.6 Hz, 1H), 6.48 (d, J=7.2 Hz, 1H), 6.40 (d, J=3.1 Hz, 1H), 4.43 (s, 2H), 4.03 (t, J=5.6 Hz, 2H), 2.99 (t, J=5.6 Hz, 2H), 2.75-2.85 (m, 1H), 2.45 (s, 3H), 2.06-2.40 (br s, 4H), 1.17-1.24 (m, 6H), 0.79-1.13 (br s, 6H). MS: (ES) m z calculated for C$_{33}$H$_{38}$N$_5$[M+H]$^+$ 504.3, found 504.3.

Example 47

Synthesis of 3-(7-methyl-1H-indol-4-yl)-2-(2,6-diethylphenyl)-5-(3-fluoro-5-(1-methylethyl)pyridin-2-yl)-4,5,6,7-tetrahydro-2H-pyrazolo[4,3-c]pyridine

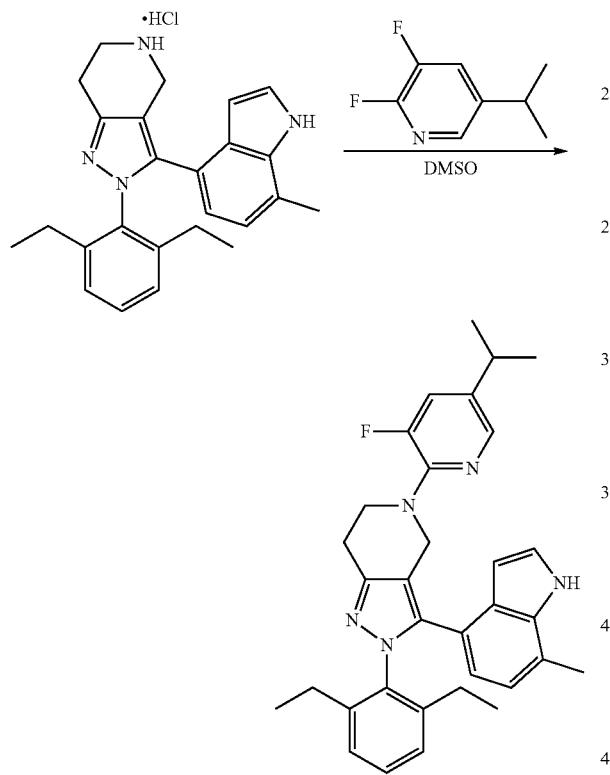

N,N-diisopropylethylamine (0.050 mL, 0.29 mmol) was added to a suspension of 3-(7-methyl-1H-indol-4-yl)-2(2,6-diethylphenyl)-4,5,6,7-tetrahydro-2H-pyrazolo[4,3-c]pyridine hydrochloride (49 mg, 0.12 mmol), 2,3-difluoro-5-(1-methylethyl)pyridine (100 mg, 0.64 mmol) and Li$_2$CO$_3$ (34 mg, 0.46 mmol) in DMSO (0.50 mL) under magnetic stirring. The resulting mixture was stirred at 130° C. temperature for 23 h. The solvent was removed in vacuo and the residue was purified by silica gel flash chromatography (0 to 70% MTBE in hexanes) to obtain 3-(7-methyl-1H-indol-4-yl)-2-(2,6-diethylphenyl)-5-(3-fluoro-5-(1-methylethyl) pyridin-2-yl)-4,5,6,7-tetrahydro-2H-pyrazolo[4,3-c]pyridine. $^1$H NMR (400 MHz, CD$_3$OD) δ 7.91 (s, 1H), 7.30-7.35 (m, 2H), 7.24 (t, J=7.6 Hz, 1H), 7.09 (br s, 2H), 6.67 (d, J=7.6 Hz, 1H), 6.48 (d, J=7.6 Hz, 1H), 6.43 (d, J=3.1 Hz, 1H), 4.38 (br s, 2H), 3.84 (t, J=5.6 Hz, 2H), 3.03 (t, J=5.6 Hz, 2H), 2.83-2.92 (m, 1H), 2.44 (s, 3H), 2.33 (br s, 4H), 1.22 (d, J=7.2 Hz, 6H), 0.99 (br s, 6H). MS: (ES) m z calculated for C$_{33}$H$_{37}$N$_5$[M+H]$^+$ 522.3, found 522.3.

Example 48

Synthesis of 3-(7-chloro-3-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine

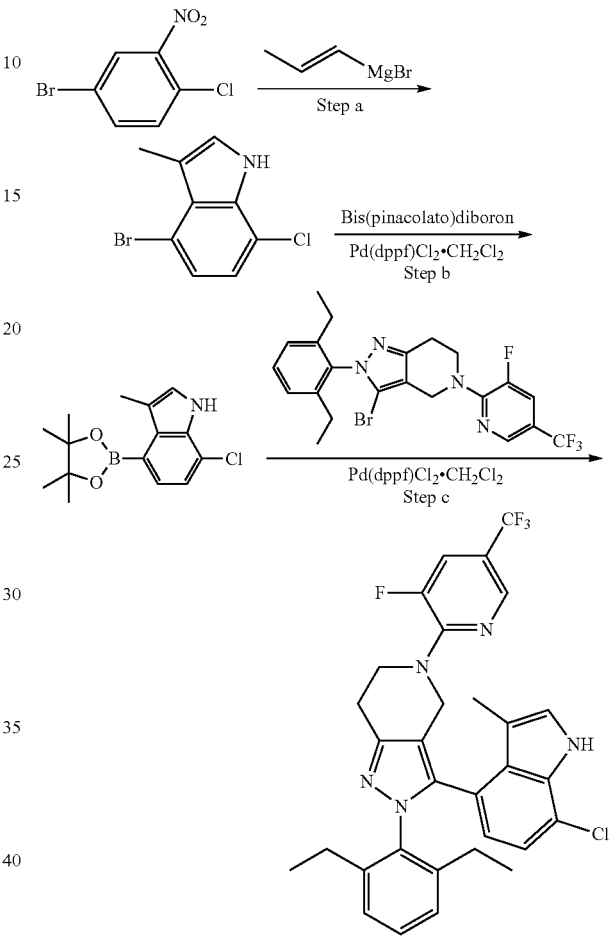

Step a: 1-Propenylmagnesium bromide solution in THF (0.5 M, 50 mL, 25 mmol) was added rapidly to a solution of 5-bromo-2-chloronitrobenzene (2.0 g, 8.5 mmol) in anhydrous THF (100 mL) under N$_2$ and vigorously stirred at −60° C. The reaction mixture was stirred at −40 to −50° C. for 35 minutes, then quenched with saturated NH$_4$Cl solution and 100 mL water and allowed to warm to room temperature. The organic phase was separated, and the aqueous phase was extracted with ether. The combined organic phases were washed with brine and the solvent was removed under reduced pressure. The residue was purified by silica gel flash chromatography (2 to 4% MTBE in hexanes) to obtain 4-bromo-7-chloro-3-methyl-1H-indole. $^1$H NMR (400 MHz, CDCl$_3$) δ 8.16 (br s, 1H), 7.17 (d, J=8.4 Hz, 1H), 7.04 (s, 1H), 6.99 (d, J=8.4 Hz, 1H), 2.54 (s, 3H).

Step b: To a suspension of 4-bromo-7-chloro-3-methyl-1H-indole (420 mg, 1.7 mmol), 4,4,4',4',5,5,5',5'-octamethyl-2,2'-bi(1,3,2-dioxaborolane) (650 mg, 2.6 mmol), and KOAc (500 mg, 5.1 mmol) in dioxane (4 mL) was added Pd(dppf)Cl$_2$ complex with dichloromethane (250 mg, 0.31 mmol). The reaction mixture was degassed (N$_2$) for 2 min and stirred at 100° C. for 3 h. The solvent was removed under reduced pressure and the residue was purified by silica gel flash chromatography (0 to 4% MTBE in hexanes) to give 7-chloro-3-methyl-4-(4,4,5,5-tetramethyl-1,3,2-dioxaborolan-2-yl)-1H-indole. MS: (ES) m z calculated for C$_{15}$H$_{20}$BClNO$_2$ [M+H]$^+$ 292.1, found 292.1.

Step c: To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (51 mg, 0.10 mmol), 7-chloro-3-methyl-4-(4,4,5,5-tetramethyl-1,3,2-dioxaborolan-2-yl)-1H-indole (52 mg, 0.18 mmol), K$_2$CO$_3$ (43 mg, 0.31 mmol) in p-dioxane (3 mL) and water (1 mL) was added Pd(dppf)Cl$_2$ complex with dichloromethane(31 mg, 0.038 mmol). The reaction mixture was degassed (N$_2$) for 2 min and stirred under N$_2$ at 100° C. for 1 h. The solvent was removed under reduced pressure and the residue was purified by silica gel flash chromatography (12% EtOAc in hexanes) followed by trituration with methanol to give 3-(7-chloro-3-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, d$_6$-DMSO) δ 11.45 (s, 1H), 8.27 (s, 1H), 7.95 (d, J=14 Hz, 1H), 7.31 (s, 1H), 7.20-7.28 (m, 2H), 6.97 (d, J=8.0 Hz, 1H), 6.93 (d, J=6.0 Hz, 1H), 6.38 (d, J=8.0 Hz, 1H), 4.49 (d, J=16 Hz, 1H), 4.18 (d, J=16 Hz, 1H), 3.85-4.04 (m, 2H), 2.90-3.16 (m, 2H), 2.11-2.45 (m, 3H), 2.01 (s, 3H), 1.89-2.00 (m, 1H), 1.20 (t, J=7.6 Hz, 3H), 0.71 (t, J=7.6 Hz, 3H). MS: (ES) m z calculated for C$_{31}$H$_{29}$ClF$_4$N$_5$[M+H]$^+$ 582.2, found 582.2.

Example 49

Synthesis of 3-(7-fluoro-3-chloro-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine

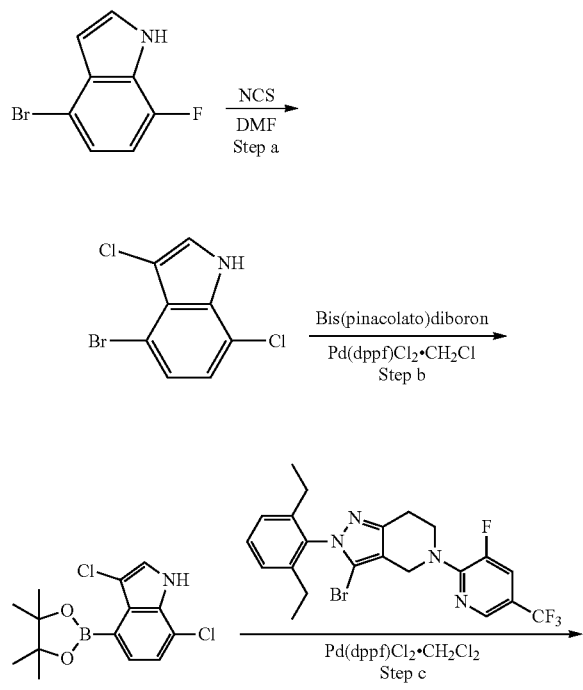

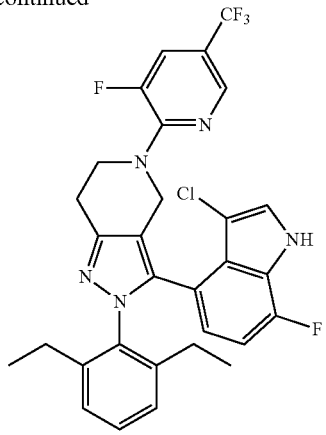

Step a: To a solution of 4-bromo-7-fluoro-1H-indole (1.0 g, 4.7 mmol) in DMF (5 mL) was added N-chlorosuccinimide (690 mg, 5.2 mmol), and the mixture was stirred for 2 h. When the reaction was complete, the mixture was diluted in EtOAc and water, the organic phase was separated and EtOAc was removed under reduced pressure. The residue was purified by silica gel flash chromatography (4 to 20% MTBE in hexanes) to give 4-bromo-3-chloro-7-fluoro-1H-indole. $^1$H NMR (400 MHz, CDCl$_3$) δ 8.34 (br s, 1H), 7.27 (d, J=2.9 Hz, 1H), 7.22 (dd, J=4.4, 8.4 Hz, 1H), 6.81 (dd, J=8.4 Hz, 10, 1H).

Step b: To a suspension of 4-bromo-3-chloro-7-fluoro-1H-indole (810 mg, 3.3 mmol), 4,4,4',4',5,5,5',5'-octamethyl-2,2'-bi(1,3,2-dioxaborolane) (920 mg, 3.6 mmol), and KOAc (980 mg, 10 mmol) in dioxane (15 mL) was added Pd(dppf)Cl$_2$ complex with dichloromethane (820 mg, 1.0 mmol). The reaction mixture was degassed (N$_2$) for 2 min and stirred at 100° C. for 1 h. The solvent was removed under reduced pressure and the residue was purified by silica gel flash chromatography (2 to 20% EtOAc in hexanes) to give 3-chloro-7-fluoro-4-(4,4,5,5-tetramethyl-1,3,2-dioxaborolan-2-yl)-1H-indole. $^1$H NMR (400 MHz, d$_6$-DMSO) δ 12.00 (s, 1H), 7.63 (d, J=2.7 Hz, 1H), 7.24 (dd, J=5.2, 8.0 Hz, 1H), 7.01 (dd, J=8.0, 12 Hz, 1H), 1.33 (s, 12H).

Step c: To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (52 mg, 0.10 mmol), 3-chloro-7-fluoro-4-(4,4,5,5-tetramethyl-1,3,2-dioxaborolan-2-yl)-1H-indole (50 mg, 0.16 mmol), K$_2$CO$_3$ (51 mg, 0.37 mmol) in p-dioxane (3 mL) and water (1 mL) was added Pd(dppf)Cl$_2$ complex with dichloromethane (39 mg, 0.048 mmol). The reaction mixture was degassed (N$_2$) for 2 min and stirred under N$_2$ at 100° C. for 1 h. The solvent was removed under reduced pressure and the residue was purified by silica gel flash chromatography (4 to 60% EtOAc in hexanes) followed by trituration with methanol to give 3-(3-chloro-7-fluoro-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, CD$_3$OD) δ 8.19 (s, 1H), 7.62 (dd, J=2.0, 13 Hz, 1H), 7.44 (s, 1H), 7.22-7.29 (m, 2H), 6.96 (dd, J=2.6, 6.8 Hz, 1H), 6.75 (dd, J=8.8, 11 Hz, 1H), 6.56 (dd, J=4.8, 8.8 Hz, 1H), 4.75 (d, J=15 Hz, 1H), 4.37 (d, J=15 Hz, 1H), 3.97-4.15 (m, 2H), 3.01-3.10 (m, 2H), 2.29-2.54 (m, 3H), 2.01-2.15 (m, 1H), 1.30 (t, J=7.2 Hz, 3H), 0.77 (t, J=7.2 Hz, 3H). MS: (ES) m z calculated for C$_{30}$H$_{26}$ClF$_5$N$_5$[M+H]$^+$ 586.2, found 586.2.

Example 50

Synthesis of 3-(3-chloro-7-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine

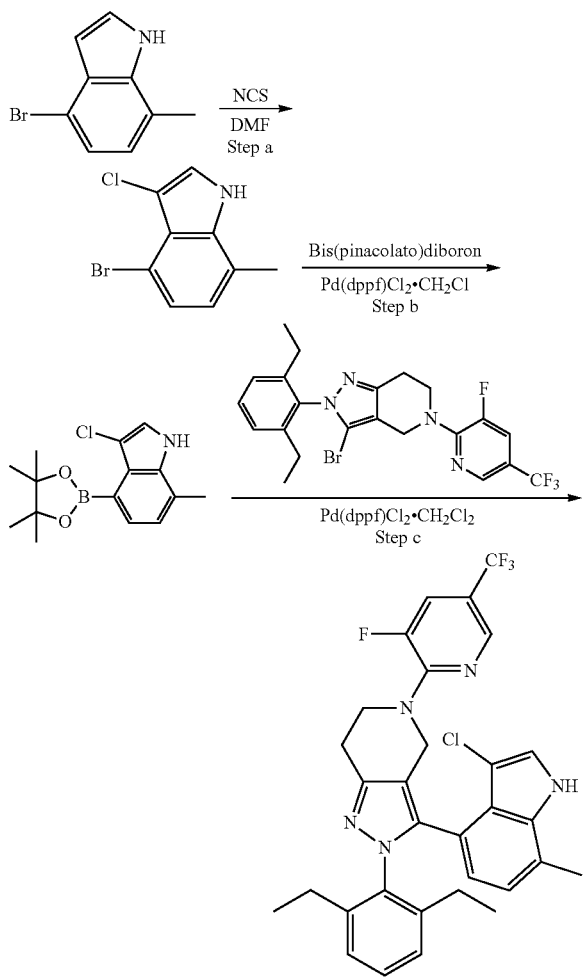

Step a: To a solution of 4-bromo-7-methyl-1H-indole (750 mg, 3.6 mmol) in DMF (5 mL) was added N-chlorosuccinimide (500 mg, 3.7 mmol), and the mixture was stirred for 3 h. When the reaction was complete, the mixture was diluted in EtOAc and water, the organic phase was separated and EtOAc was removed under reduced pressure. The residue was purified by silica gel flash chromatography (4 to 20% MTBE in hexanes) to give 4-bromo-3-chloro-7-methyl-1H-indole. $^1$H NMR (400 MHz, d$_6$-DMSO) δ 11.68 (s, 1H), 7.62 (d, J=2.8 Hz, 1H), 7.16 (d, J=8.0 Hz, 1H), 6.86 (d, J=8.0 Hz, 1H), 2.41 (s, 3H).

Step b: To a suspension of 4-bromo-3-chloro-7-methyl-1H-indole (700 mg, 2.9 mmol), 4,4,4',4',5,5,5',5'-octamethyl-2,2'-bi(1,3,2-dioxaborolane) (870 mg, 3.4 mmol), and KOAc (1.1 g, 11 mmol) in dioxane (7 mL) was added Pd(dppf)Cl$_2$ complex with dichloromethane (350 mg, 0.42 mmol). The reaction mixture was degassed (N$_2$) for 2 min and stirred at 100° C. for 14 h. The solvent was removed under reduced pressure and the residue was purified by silica gel flash chromatography (4 to 30% MTBE in hexanes) to give 3-chloro-7-methyl-4-(4,4,5,5-tetramethyl-1,3,2-dioxaborolan-2-yl)-1H-indole. $^1$H NMR (400 MHz, d$_6$-DMSO) δ 11.38 (s, 1H), 7.51 (d, J=2.6 Hz, 1H), 7.17 (d, J=7.2 Hz, 1H), 6.95 (d, J=7.2 Hz, 1H), 2.46 (s, 3H), 1.33 (s, 12H).

Step c: To a suspension of 3-bromo-2-(2,6-diethylphenyl)-5-(3-fluoro-5-(trifluoromethyl)pyridin-2-yl)-4,5,6,7-tetrahydro-2H-pyrazolo[4,3-c]pyridine (56 mg, 0.11 mmol), 3-chloro-7-methyl-4-(4,4,5,5-tetramethyl-1,3,2-dioxaborolan-2-yl)-1H-indole (60 mg, 0.21 mmol), K$_2$CO$_3$ (51 mg, 0.37 mmol) in p-dioxane (3 mL) and water (1 mL) was added Pd(dppf)Cl$_2$ complex with dichloromethane(53 mg, 0.064 mmol). The reaction mixture was degassed (N$_2$) for 2 min and stirred under N$_2$ at 100° C. for 3.5 h. The solvent was removed under reduced pressure and the residue was purified by silica gel flash chromatography (4 to 14% EtOAc in hexanes) followed by HPLC (MeCN/H$_2$O with 0.1% TFA) to give 3-(3-chloro-7-methyl-1H-indol-4-yl)-2-(2,6-diethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, CD$_3$OD) δ 8.19 (s, 1H), 7.61 (d, J=14 Hz, 1H), 7.35 (s, 1H), 7.22-7.26 (m, 2H), 6.94 (dd, J=3.4, 6.4 Hz, 1H), 6.77 (d, J=7.2 Hz, 1H), 6.51 (d, J=7.2 Hz, 1H), 4.76 (d, J=16 Hz, 1H), 4.34 (d, J=16 Hz, 1H), 3.94-4.14 (m, 2H), 2.98-3.10 (m, 2H), 2.33-2.55 (m, 3H), 2.43 (s, 3H), 2.03-2.16 (m, 1H), 1.30 (t, J=8.0 Hz, 3H), 0.77 (t, J=8.0 Hz, 3H). MS: (ES) m z calculated for C$_{31}$H$_{29}$ClF$_4$N$_5$ [M+H]$^+$ 582.2, found 582.2.

Example 51

Synthesis of 3-(7-chloro-1H-indol-4-yl)-2-(2,6-dimethylphenyl)-5-(3-fluoro-5-(trifluoromethyl)pyridin-2-yl)-4,5,6,7-tetrahydro-2H-pyrazol[4,3-c]pyridine

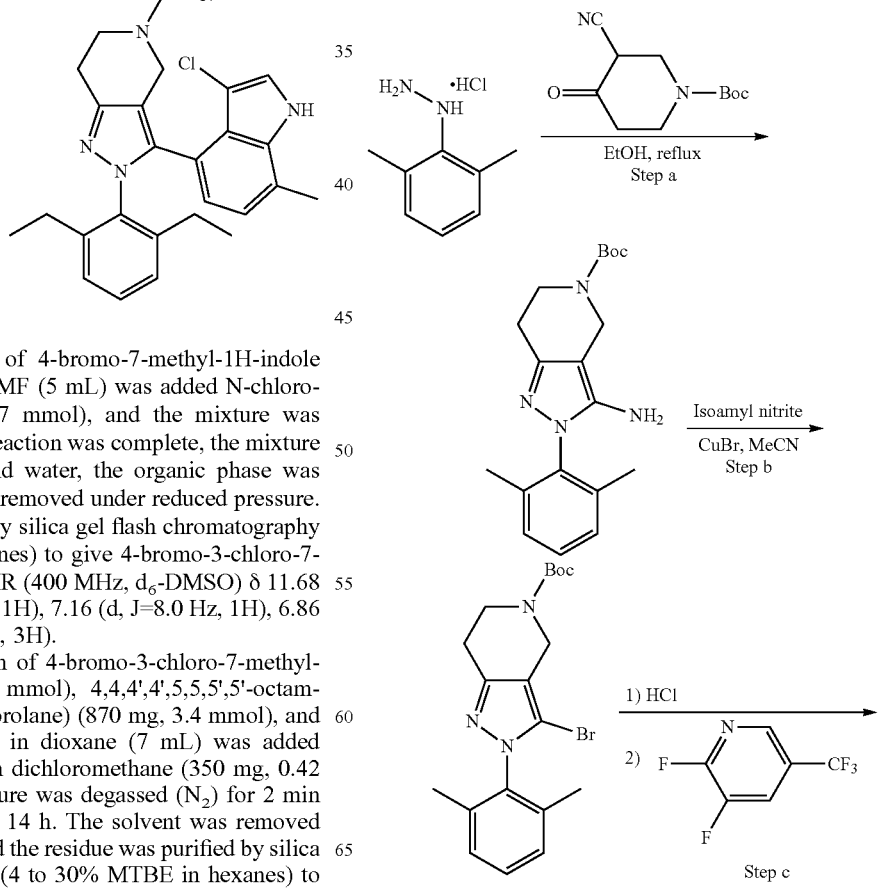

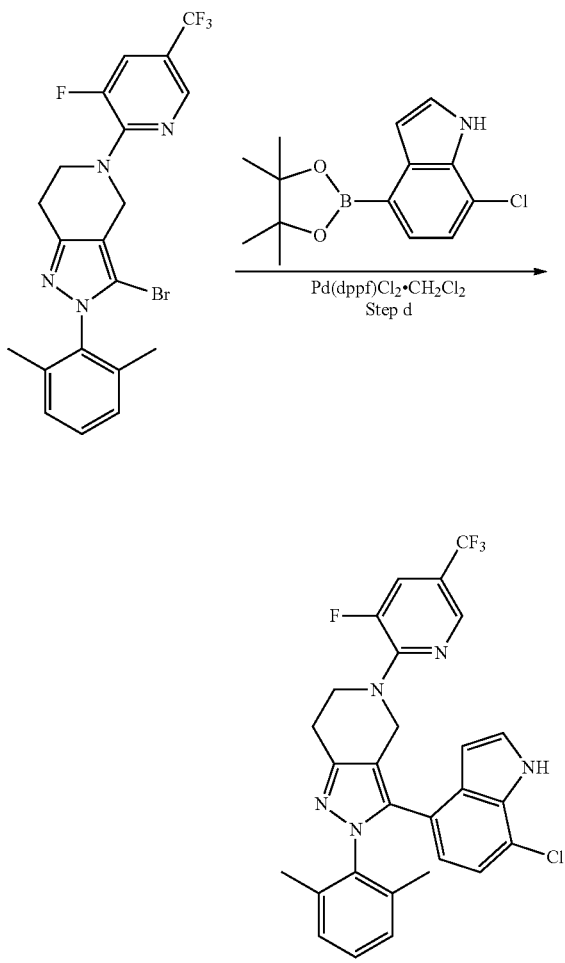

Step a: N,N-diisopropylethylamine (6 mL, 34.5 mmol) was added to a mixture of (2,6-dimethylphenyl)hydrazine hydrochloride (5 g, 28.9 mmol), tert-butyl 3-cyano-4-oxopiperidine-1-carboxylate (5 g, 22.3 mmol) and EtOH (60 mL) in a 250 mL round bottom flask under magnetic stirring. The resulting mixture was stirred under reflux for 3 h. Glacial acetic acid (6 mL, 104 mmol) was added and the mixture was stirred under reflux for another 2 h. After removal of solvent under reduced pressure, the residue was dissolved in EtOAc and washed with aqueous NaOH (2N), brine and dried over MgSO$_4$. The solvent was removed under reduced pressure and the residue was purified by silica gel flash chromatography (5 to 55% EtOAc in hexanes) to give tert-butyl 3-amino-2-(2,6-dimethylphenyl)-6,7-dihydro-2H-pyrazolo[4,3-c]pyridine-5(4H)-carboxylate. MS: (ES) m z calculated for $C_{19}H_{27}N_4O_2$ [M+H]$^+$ 343.2, found 343.2.
Caution: Diazonium formation could be potentially dangerous, please handle with care and ware proper personal protection equipment!

Step b: Isopentyl nitrite (96%, 4 mL, 28.6 mmol) was added slowly at room temperature to a mixture of tert-butyl 3-amino-2-(2,6-dimethylphenyl)-6,7-dihydro-2H-pyrazolo[4,3-c]pyridine-5(4H)-carboxylate (3 g, 8.8 mmol), CuBr (4 g, 27.9 mmol) and MeCN (50 mL) in a 250 mL round bottom flask under magnetic stirring. The resulting mixture was stirred at room temperature for 1 h, diluted with EtOAc, filtered through Celite, washed with sat NH$_4$Cl solution, and dried over MgSO$_4$. The solvent was removed under reduced pressure and the residue was purified by silica gel flash chromatography (2 to 25% EtOAc in hexanes) to give tert-butyl 3-bromo-2-(2,6-dimethylphenyl)-6,7-dihydro-2H-pyrazolo[4,3-c]pyridine-5(4H)-carboxylate. MS: (ES) m z calculated for $C_{19}H_{25}BrN_3O_2$[M+H]$^+$ 406.1, found 406.1.

Step c: tert-butyl 3-bromo-2-(2,6-dimethylphenyl)-6,7-dihydro-2H-pyrazolo[4,3-c]pyridine-5(4H)-carboxylate (1.5 g, 3.7 mmol), was dissolved in dichloromethane (10 mL) and charged with HCl in dioxane (4N, 5 mL). The resulting mixture was stirred at room temperature for 2 h. After the reaction was complete, the solvent was evaporated in vacuo to give 3-bromo-2-(2,6-dimethylphenyl)-4,5,6,7-tetrahydro-2H-pyrazolo[4,3-c]pyridine hydrochloride. MS: (ES) m z calculated for $C_{14}H_{17}BrN_3$ [M+H]$^+$ 306.1, found 306.1.

N,N-diisopropylethylamine (0.2 mL, 1.15 mmol) was added to a suspension of 3-bromo-2-(2,6-dimethylphenyl)-4,5,6,7-tetrahydro-2H-pyrazolo[4,3-c]pyridine hydrochloride (1 g, 2.9 mmol), 2,3-difluoro-5-(trifluoromethyl)pyridine (1.1 g, 6 mmol), and K$_2$CO$_3$ (1.38 g, 10 mmol) in MeCN (10 mL) under magnetic stirring. The resulting mixture was stirred at 85° C. for 2 h. After cooling to room temperature, the reaction mixture was diluted with EtOAc, washed with brine and dried over MgSO$_4$. The solvent was removed under reduced pressure and the residue was purified by silica gel flash chromatography (2 to 15% EtOAc in hexanes) to afford 3-bromo-2-(2,6-dimethylphenyl)-5-(3-fluoro-5-(trifluoromethyl)pyridin-2-yl)-4,5,6,7-tetrahydro-2H-pyrazolo[4,3-c]pyridine. MS: (ES) m z calculated for $C_{20}H_{17}BrF_4N_4$[M+H]$^+$ 469.1, found 469.1.

Step d: To a suspension of 3-bromo-2-(2,6-dimethylphenyl)-5-(3-fluoro-5-(trifluoromethyl)pyridin-2-yl)-4,5,6,7-tetrahydro-2H-pyrazolo[4,3-c]pyridine (50 mg, 0.11 mmol), 7-chloro-4-(4,4,5,5-tetramethyl-1,3,2-dioxaborolan-2-yl)-1H-indole (50 mg, 0.18 mmol), and K$_2$CO$_3$ (180 mg, 1.3 mmol) in p-dioxane (6 mL) and water (1 mL) was added Pd(dppf)Cl$_2$ complex with dichloromethane (40 mg, 0.05 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 20% EtOAc in hexanes) to give 3-(7-chloro-1H-indol-4-yl)-2-(2,6-dimethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, CD$_3$OD) δ 8.22 (d, J=1.3 Hz, 1H), 7.64 (dd, J=2.0, 13.5 Hz, 1H), 7.44 (d, J=3.2 Hz, 1H), 7.15 (t, J=7.6 Hz, 2H), 7.04 (br s, 2H), 6.94 (d, J=7.9 Hz, 1H), 6.52-6.57 (m, 2H), 4.65 (s, 2H), 4.11 (t, J=5.8 Hz, 2H), 3.29 (s, 1H), 3.06 (t, J=5.8 Hz, 2H), 1.96 (br m, 6H). MS: (ES) m z calculated $C_{28}H_{23}ClF_4N_5$[M+H]$^+$ 540.2, found 540.2.

Example 52

Synthesis of 3-(3-chloro-7-fluoro-1H-indol-4-yl)-2-(2,6-dimethylphenyl)-5-(3-fluoro-5-(trifluoromethyl)pyridin-2-yl)-4,5,6,7-tetrahydro-2H-pyrazolo[4,3-c]pyridine

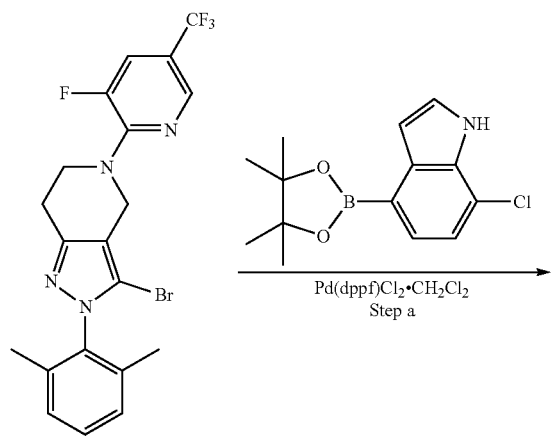

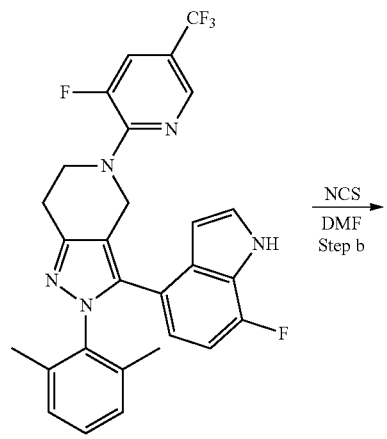

Step a: To a suspension of 3-bromo-2-(2,6-dimethylphenyl)-5-(3-fluoro-5-(trifluoromethyl)pyridin-2-yl)-4,5,6,7-tetrahydro-2H-pyrazolo[4,3-c]pyridine (100 mg, 0.22 mmol), 7-fluoro-4-(4,4,5,5-tetramethyl-1,3,2-dioxaborolan-2-yl)-1H-indole (100 mg, 0.38 mmol), K$_2$CO$_3$ (200 mg, 1.45 mmol) in p-dioxane (6 mL) and water (1 mL) was added Pd(dppf)Cl$_2$ complex with dichloromethane (50 mg, 0.06 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by by Preparative TLC (40% EtOAc in hexanes) followed by HPLC (MeCN/H$_2$O, with 0.1% TFA) to give 2-(2,6-dimethylphenyl)-3-(7-fluoro-1H-indol-4-yl)-5-(3-fluoro-5-(trifluoromethyl)pyridin-2-yl)-4,5,6,7-tetrahydro-2H-pyrazolo[4,3-c]pyridine. $^1$H NMR (400 MHz, CDCl$_3$) δ 8.52 (s, 1H), 8.19 (dt, J=1.1, 1.9 Hz, 1H), 7.39 (dd, J=2.0, 13.2 Hz, 1H), 7.26 (d, J=4.8 Hz, 1H), 7.08 (t, J=7.5 Hz, 1H), 6.96 (br, 2H), 6.70 (dd, J=8.1, 10.7 Hz, 1H), 6.50-6.59 (m, 2H), 4.64 (s, 2H), 4.07 (t, J=5.8 Hz, 2H), 3.12 (t, J=5.8 Hz, 2H), 1.96 (br m, 6H). MS: (ES) m z calculated C$_{28}$H$_{23}$F$_5$N$_5$ [M+H]$^+$ 524.2, found 524.2.

Step b: N-chlorosuccinimide (33 mg, 0.25 mmol) was added to a solution of 2-(2,6-dimethylphenyl)-3-(7-fluoro-1H-indol-4-yl)-5-(3-fluoro-5-(trifluoromethyl)pyridin-2-yl)-4,5,6,7-tetrahydro-2H-pyrazolo[4,3-c]pyridine (30 mg, 0.06 mmol) in DMF (5 mL). The resulting mixture was stirred at 60° C. for 6 h. After cooling to room temperature, the reaction mixture was diluted with EtOAc, washed with brine and dried over MgSO$_4$. The solvent was removed under reduced pressure and the residue was purified by Preparative TLC (40% EtOAc in hexanes) followed by HPLC (MeCN/H$_2$O, with 0.1% TFA) to afford 3-(3-chloro-7-fluoro-1H-indol-4-yl)-2-(2,6-dimethylphenyl)-5-(3-fluoro-5-(trifluoromethyl)pyridin-2-yl)-4,5,6,7-tetrahydro-2H-pyrazolo[4,3-c]pyridine. $^1$H NMR (400 MHz, CDCl$_3$) δ 8.56 (s, 1H), 8.16 (dt, J=1.0, 2.0 Hz, 1H), 7.18-7.41 (m, 2H), 7.03-7.13 (m, 2H), 6.70-6.86 (m, 2H), 6.58 (ddd, J=0.7, 4.6, 8.2 Hz, 1H),), 4.71 (d, J=15.5 Hz, 1H), 4.48 (d, J=15.5 Hz, 1H), 3.84-4.21 (m, 2H), 3.06-3.21 (m, 2H), 2.22 (d, J=0.7 Hz, 3H), 1.87 (d, J=0.7 Hz, 3H). MS: (ES) m z calculated C$_{28}$H$_{22}$ClF$_5$N$_5$[M+H]$^+$ 558.1, found 558.2.

Example 53

Synthesis of 2-(2,6-dimethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine

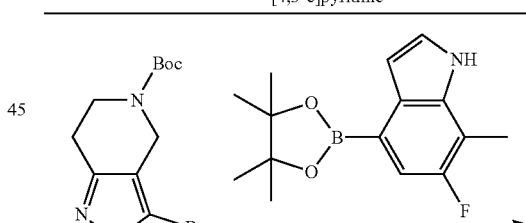

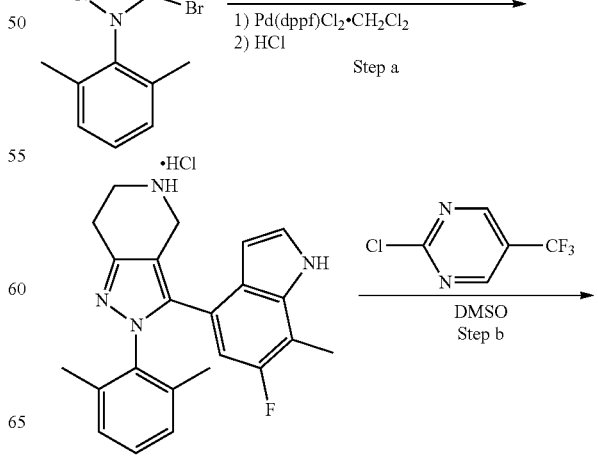

-continued

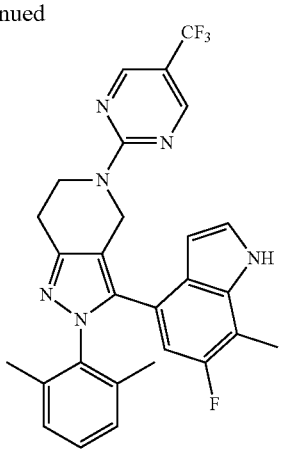

Step a: To a suspension of tert-butyl 3-bromo-2-(2,6-dimethylphenyl)-6,7-dihydro-2H-pyrazolo[4,3-c]pyridine-5(4H)-carboxylate (440 mg, 1.08 mmol), 6-fluoro-7-methyl-4-(4,4,5,5-tetramethyl-1,3,2-dioxaborolan-2-yl)-1H-indole (260 mg, 0.94 mmol), K$_2$CO$_3$ (500 mg, 3.6 mmol) in p-dioxane (6 mL) and water (1 mL) was added Pd(dppf)Cl$_2$ complex with dichloromethane (200 mg, 0.24 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 20% EtOAc in hexanes) to give tert-butyl 2-(2,6-dimethylphenyl)-3-(6-fluoro-7-methyl-1H-indol-4-yl)-6,7-dihydro-2H-pyrazolo[4,3-c]pyridine-5(4H)-carboxylate. MS: (ES) m z calculated for C$_{28}$H$_{32}$FN$_4$O$_2$[M+H]$^+$ 475.2, found 475.2.

The above tert-butyl 2-(2,6-dimethylphenyl)-3-(6-fluoro-7-methyl-1H-indol-4-yl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 2-(2,6-dimethylphenyl)-3-(6-fluoro-7-methyl-1H-indol-4-yl)-4,5,6,7-tetrahydro-2H-pyrazolo[4,3-c]pyridine hydrochloride. MS: (ES) m z calculated for C$_{23}$H$_{24}$FN$_4$ [M+H]$^+$ 375.2, found 375.2.

Step b: N,N-diisopropylethylamine (0.2 mL, 1.15 mmol) was added to a suspension of 2-(2,6-dimethylphenyl)-3-(6-fluoro-7-methyl-1H-indol-4-yl)-4,5,6,7-tetrahydro-2H-pyrazolo[4,3-c]pyridine hydrochloride (50 mg, 0.12 mmol), 2-chloro-5-(trifluoromethyl)pyrimidine (45 mg, 0.25 mmol), and Li$_2$CO$_3$ (30 mg, 0.41 mmol) in DMSO (5 mL) under magnetic stirring. The resulting mixture was stirred at 75° C. for 30 min. After cooling to room temperature, the reaction mixture was diluted with EtOAc, washed with brine and dried over MgSO$_4$. The solvent was removed under reduced pressure and the residue was purified by Preparative TLC (40% EtOAc in hexanes) followed followed by HPLC (MeCN/H$_2$O, with 0.1% TFA) to afford 2-(2,6-dimethylphenyl)-3-(6-fluoro-7-methyl-1H-indol-4-yl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.54 (s, 2H), 8.25 (s, 1H), 7.04-7.18 (m, 3H), 6.46-6.53 (m, 1H), 4.91 (s, 2H), 4.42 (br, 2H), 3.11 (t, J=5.8 Hz, 2H), 2.42 (d, J=1.7 Hz, 3H), 1.92-2.13 (br m, 6H). MS: (ES) m z calculated C$_{28}$H$_{25}$F$_4$N$_6$ [M+H]$^+$ 521.2, found 521.2.

Example 54

Synthesis of 3-(5-fluoro-7-methyl-1H-indol-4-yl)-2-(2,6-dimethylphenyl)-5-(5-(trifluoromethyl)pyrimidin-2-yl)-4,5,6,7-tetrahydro-2H-pyrazol[4,3-c]pyridine

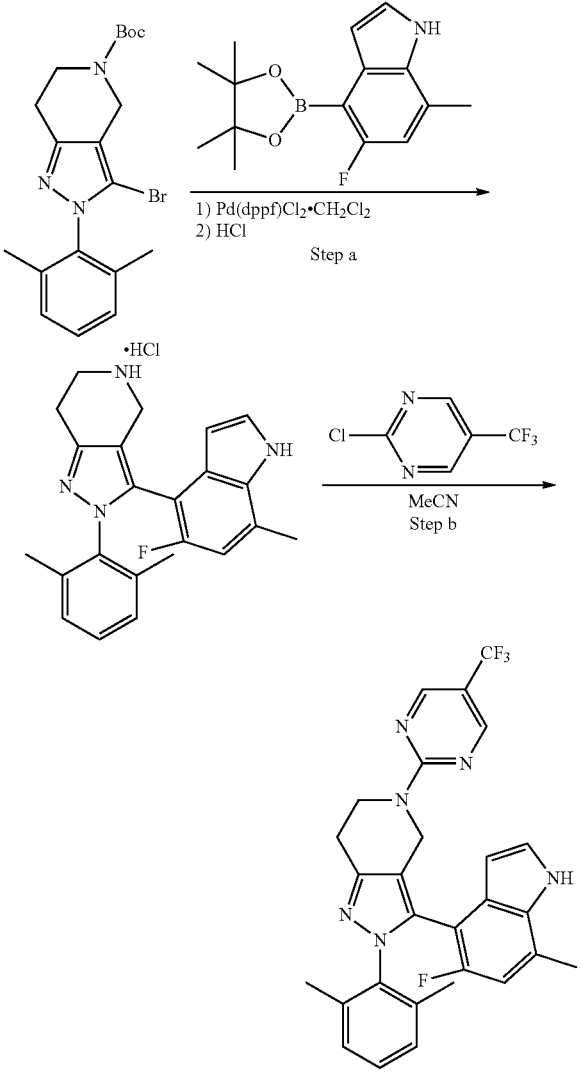

Step a: To a suspension of tert-butyl 3-bromo-2-(2,5-dimethylphenyl)-6,7-dihydro-2H-pyrazolo[4,3-c]pyridine-5(4H)-carboxylate (430 mg, 1.0 mmol), 5-fluoro-7-methyl-4-(4,4,5,5-tetramethyl-1,3,2-dioxaborolan-2-yl)-1H-indazole (220 mg, 0.80 mmol), and K$_2$CO$_3$ (420 mg, 3.0 mmol) in p-dioxane (8 mL) and water (2 mL) was added Pd(dppf)Cl$_2$ complex with dichloromethane (250 mg, 0.30 mmol). The reaction mixture was degassed (N$_2$) for 2 min and stirred under N$_2$ at 100° C. for 15 h. The reaction mixture was diluted with dichloromethane, dried over Na$_2$SO$_4$ and filtered through Celite. The solvent was removed under reduced pressure and the residue was purified by silica gel flash chromatography (10 to 60% MTBE in hexanes) to give tert-butyl 3-(5-fluoro-7-methyl-1H-indazol-4-yl)-2-(2,6-dimethylphenyl)-6,7-dihydro-2H-pyrazolo[4,3-c]pyridine-5-(4H)-carboxylate. MS: (ES) m z calculated for C$_{28}$H$_{32}$FN$_4$O$_2$[M+H]$^+$475.3, found 475.3.

The above tert-butyl 3-(5-fluoro-7-methyl-1H-indazol-4-yl)-2-(2,6-dimethylphenyl)-6,7-dihydro-2H-pyrazolo[4,3-c]pyridine-5-(4H)-carboxylate was dissolved in dichloromethane (50 mL) and treated with HCl in dioxane (4N, 4 mL). The resulting mixture was stirred at room temperature for 1 d. After the reaction was complete, the solvent was evaporated in vacuo to give 3-(5-fluoro-7-methyl-1H-indazol-4-yl)-2(2,6-dimethylphenyl)-4,5,6,7-tetrahydro-2H-pyrazolo[4,3-c]pyridine hydrochloride. MS: (ES) m z calculated for $C_{23}H_{24}FN_4$ [M+H]$^+$ 375.2, found 375.2.

Step b: N,N-diisopropylethylamine (0.040 mL, 0.23 mmol) was added to a suspension of 3-(5-fluoro-7-methyl-1H-indazol-4-yl)-2(2,6-dimethylphenyl)-4,5,6,7-tetrahydro-2H-pyrazolo[4,3-c]pyridine hydrochloride (48 mg, 0.12 mmol), 2-chloro-5-(trifluoromethyl)pyrimidine (25 mg, 0.14 mmol) and $Li_2CO_3$ (20 mg, 0.27 mmol) in acetonitrile (1 mL) under magnetic stirring. The resulting mixture was stirred at 80° C. for 4 h. The solvent was removed in vacuo and the residue was purified by silica gel flash chromatography (4 to 100% MTBE in hexanes) followed by trituration with MTBE in hexanes to obtain 3-(5-fluoro-7-methyl-1H-indazol-4-yl)-2-(2,6-dimethylphenyl)-5-(5-(trifluoromethyl)pyrimidin-2-yl)-4,5,6,7-tetrahydro-2H-pyrazolo[4,3-c]pyridine. $^1$H NMR (400 MHz, CD$_3$OD) δ 8.57 (br s, 2H), 7.38 (d, J=3.0 Hz, 1H), 7.10 (d, J=4.8 Hz, 2H), 6.84 (t, J=4.8 Hz, 1H), 6.58 (d, J=11 Hz, 1H), 6.33 (d, J=3.0 Hz, 1H), 4.3-4.5 (m, 2H), 3.00 (t, J=5.4 Hz, 2H), 2.48 (s, 3H), 2.18 (s, 3H), 1.70 (s, 3H). MS: (ES) m z calculated for $C_{28}H_{25}F_4N_6$ [M+H]$^+$ 521.2, found 521.2.

Example 55

N,N-diisopropylethylamine (0.040 mL, 0.23 mmol) was added to a suspension of 3-(5-fluoro-7-methyl-1H-indazol-4-yl)-2(2,6-dimethylphenyl)-4,5,6,7-tetrahydro-2H-pyrazolo[4,3-c]pyridine hydrochloride (48 mg, 0.12 mmol) and 2,3-difluoro-5-(trifluoromethyl)pyridine (94 mg, 0.51 mmol) in acetonitrile (1 mL) under magnetic stirring. The resulting mixture was stirred at 80° C. for 4 h. The solvent was removed in vacuo and the residue was purified by silica gel flash chromatography (0 to 60% MTBE in hexanes) followed by trituration with MTBE in hexanes to obtain 3-(5-fluoro-7-methyl-1H-indazol-4-yl)-2-(2,6-dimethylphenyl)-5-(2-fluoro-5-(trifluoromethyl)pyridin-2-yl)-4,5,6,7-tetrahydro-2H-pyrazolo[4,3-c]pyridine. $^1$H NMR (400 MHz, CD$_3$OD) δ 8.21 (s, 1H), 7.63 (dd, J=1.9, 13 Hz, 1H), 7.10 (d, J=4.8 Hz, 2H), 6.84 (t, J=4.8 Hz, 1H), 6.57 (d, J=12 Hz, 1H), 6.32 (d, J=2.9 Hz, 1H), 4.78 (d, J=16 Hz, 1H), 4.40 (d, J=16 Hz, 1H), 4.10 (t, J=5.6 Hz, 2H), 3.07 (t, J=5.6 Hz, 2H), 2.47 (s, 3H), 2.18 (s, 3H), 1.70 (s, 3H). MS: (ES) m z calculated for $C_{29}H_{25}F_5N_5$ [M+H]$^+$ 538.2, found 538.2.

Example 56

Synthesis of 3-(7-chloro-5-fluoro-1H-indol-4-yl)-2-(2,6-dimethylphenyl)-5-(3-fluoro-5-(1-methylethyl)pyridin-2-yl)-4,5,6,7-tetrahydro-2H-pyrazolo[4,3-c]pyridine Synthesis of 3-(5-fluoro-7-methyl-1H-indazol-4-yl)-2-(2,6-dimethylphenyl)-5-(3-fluoro-5-(trifluoromethyl)pyridin-2-yl)-4,5,6,7-tetrahydro-2H-pyrazolo[4,3-c]pyridine

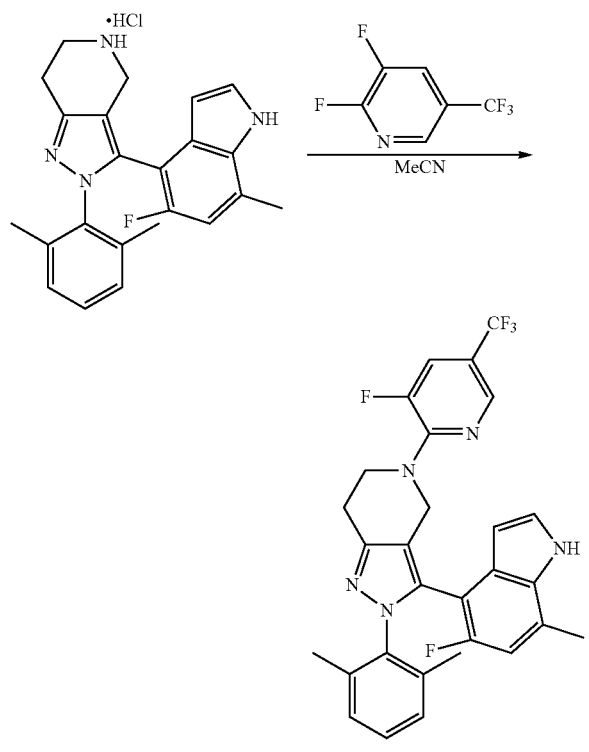

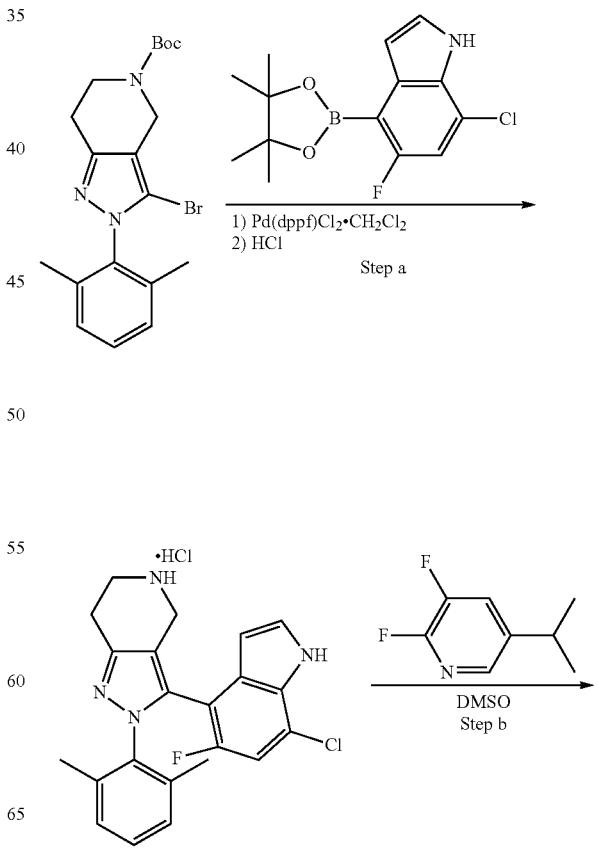

-continued

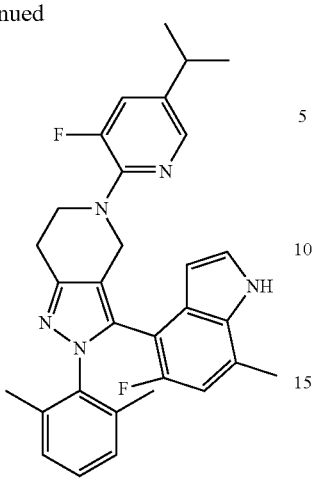

Step a: To a suspension of tert-butyl 3-bromo-2-(2,5-dimethylphenyl)-6,7-dihydro-2H-pyrazolo[4,3-c]pyridine-5(4H)-carboxylate (500 mg, 1.2 mmol), 7-chloro-5-fluoro-4-(4,4,5,5-tetramethyl-1,3,2-dioxaborolan-2-yl)-1H-indole (470 mg, 1.6 mmol), and K$_2$CO$_3$ (500 mg, 3.6 mmol) in p-dioxane (10 mL) and water (2 mL) was added Pd(dppf)Cl$_2$ complex with dichloromethane (300 mg, 0.37 mmol). The reaction mixture was degassed (N$_2$) for 2 min and stirred under N$_2$ at 100° C. for 2.5 h. The reaction mixture was diluted with EtOAc and filtered through Celite. The organic phase was separated, the solvent was removed under reduced pressure and the residue was purified by silica gel flash chromatography (10 to 60% EtOAc in hexanes) to give tert-butyl 3-(7-chloro-5-fluoro-1H-indol-4-yl)-2-(2,6-dimethylphenyl)-6,7-dihydro-2H-pyrazolo[4,3-c]pyridine-5-(4H)-carboxylate. MS: (ES) m z calculated for C$_{27}$H$_{29}$ClFN$_4$O$_2$[M+H]$^+$ 495.2, found 495.2.

The above tert-butyl 3-(7-chloro-5-fluoro-1H-indol-4-yl)-2-(2,6-dimethylphenyl)-6,7-dihydro-2H-pyrazolo[4,3-c]pyridine-5-(4H)-carboxylate was dissolved in dichloromethane (50 mL) and treated with HCl in dioxane (4N, 5 mL). The resulting mixture was stirred at room temperature for 16 h. After the reaction was complete, the solvent was evaporated in vacuo to give 3-(7-chloro-5-fluoro-1H-indol-4-yl)-2(2,6-dimethylphenyl)-4,5,6,7-tetrahydro-2H-pyrazolo[4,3-c]pyridine hydrochloride. MS: (ES) m z calculated for C$_{22}$H$_{21}$ClFN$_4$ [M+H]$^+$ 395.1, found 395.1.

Step b: N,N-diisopropylethylamine (0.04 mL, 0.23 mmol) was added to a suspension of 3-(7-chloro-5-fluoro-1H-indol-4-yl)-2(2,6-dimethylphenyl)-4,5,6,7-tetrahydro-2H-pyrazolo[4,3-c]pyridine hydrochloride (48 mg, 0.12 mmol), 2,3-difluoro-5-(1-methylethyl)pyridine (50 mg, 0.32 mmol) and Li$_2$CO$_3$ (20 mg, 0.27 mmol) in DMSO (1 mL) under magnetic stirring. The resulting mixture was stirred at 140° C. temperature for 14 h. The solvent was removed in vacuo and the residue was purified by silica gel flash chromatography (4 to 100% MTBE in hexanes) followed by HPLC (MeCN/H$_2$O with 0.1% TFA) to obtain 3-(7-chloro-5-fluoro-1H-indol-4-yl)-2-(2,6-dimethylphenyl)-5-(3-fluoro-5-(1-methylethyl)pyridin-2-yl)-4,5,6,7-tetrahydro-2H-pyrazolo[4,3-c]pyridine. $^1$H NMR (400 MHz, CD$_3$OD) S 7.19 (s, 1H), 7.54 (d, J=3.0 Hz, 1H), 7.42 (dd, J=1.8, 14 Hz, 1H), 7.21 (d, J=4.8 Hz, 2H), 6.9-7.0 (m, 2H), 6.57 (d, J=3.3 Hz, 1H), 4.64 (d, J=16 Hz, 1H), 4.23 (d, J=16 Hz, 1H), 3.8-4.1 (m, 2H), 3.13 (t, J=6.0 Hz, 2H), 2.9-3.0 (m, 1H), 2.28 (s, 3H), 1.78 (s, 3H), 1.31 (d, J=7.2 Hz, 6H). MS: (ES) m z calculated for C$_{30}$H$_{29}$ClF$_2$N$_5$ [M+H]$^+$ 532.2, found 532.2.

Example 57

Synthesis of 5-(3,5-dichloro-2-pyridyl)-2-(2,6-dimethylphenyl)-3-(1H-indol-4-yl)-6,7-dihydro-4H-pyrazolo[4,3-c]pyridine

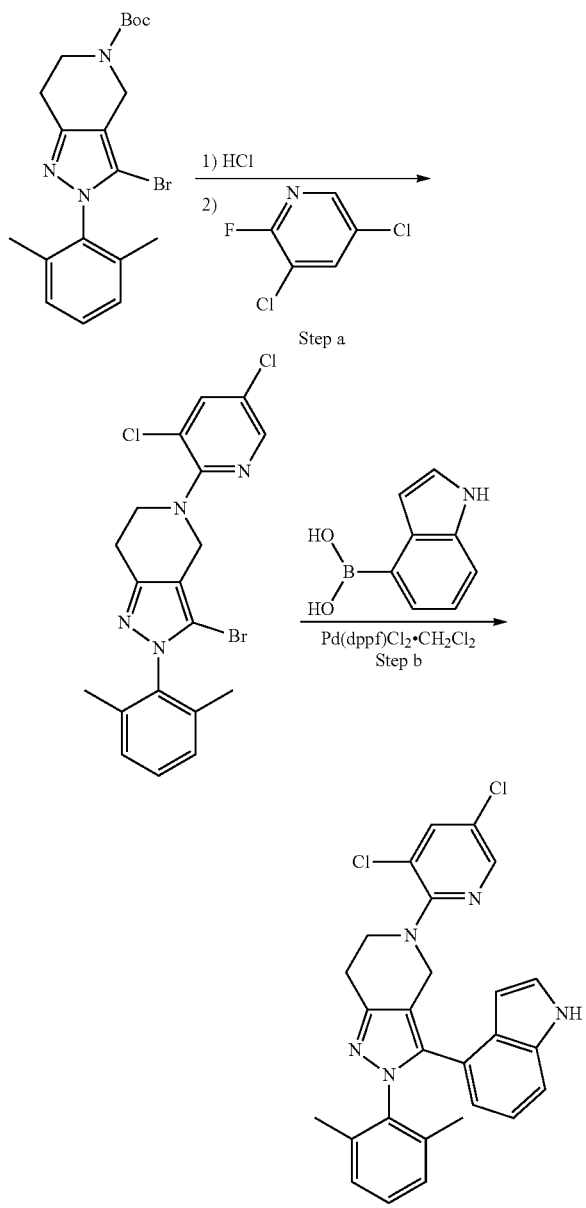

Step a: tert-butyl 3-bromo-2-(2,6-dimethylphenyl)-6,7-dihydro-2H-pyrazolo[4,3-c]pyridine-5(4H)-carboxylate (1.5 g, 3.7 mmol) was dissolved in dichloromethane (10 mL) and charged with HCl in dioxane (4N, 5 mL). The resulting mixture was stirred at room temperature for 2 h. After the reaction was complete, the solvent was evaporated in vacuo to give 3-bromo-2-(2,6-dimethylphenyl)-4,5,6,7-tetrahydro-2H-pyrazolo[4,3-c]pyridine hydrochloride. MS: (ES) m z calculated for C$_{14}$H$_{17}$BrN$_3$ [M+H]$^+$ 306.1, found 306.1.

N,N-diisopropylethylamine (0.2 mL, 1.15 mmol) was added to a suspension of 3-bromo-2-(2,6-dimethylphenyl)-

4,5,6,7-tetrahydro-2H-pyrazolo[4,3-c]pyridine hydrochloride (1 g, 2.9 mmol), 3,5-dichloro-2-fluoropyridine (1.1 g, 6.6 mmol), and $K_2CO_3$ (1.38 g, 10 mmol) in MeCN (10 mL) under magnetic stirring. The resulting mixture was stirred at 90° C. for 2 h. After cooling to room temperature, the reaction mixture was diluted with EtOAc, washed with brine and dried over $MgSO_4$. The solvent was removed under reduced pressure and the residue was purified by silica gel flash chromatography (2 to 25% EtOAc in hexanes) to afford 3-bromo-5-(3,5-dichloropyridin-2-yl)-2-(2,6-dimethylphenyl)-4,5,6,7-tetrahydro-2H-pyrazolo[4,3-c]pyridine. MS: (ES) m z calculated for $C_{19}H_{18}BrCl_2N_4[M+H]^+$ 451.0, found 451.1.

Step b: To a degassed solution of 3-bromo-5-(3,5-dichloropyridin-2-yl)-2-(2,6-dimethylphenyl)-4,5,6,7-tetrahydro-2H-pyrazolo[4,3-c]pyridine (80 mg, 0.18 mmol), indole-4-boronic acid (26 mg, 0.18 mmol), and sodium carbonate (47 mg, 0.44 mmol) in dioxane (5 mL) and water (2 mL) was added $Pd(dppf)Cl_2$ complex with dichloromethane (13 mg, 0.018 mmol). The mixture was purged with nitrogen and heated to 80° C. After 18 h, the mixture was cooled to room temperature and diluted with EtOAc (20 mL). The organic layer was washed with water (20 mL), dried over $Na_2SO_4$, filtered, and concentrated in vacuo. The crude material was passed through a silica gel plug and rinsed with EtOAc. The filtrate was concentrated and purified by reverse phase HPLC (MeCN/$H_2O$, with 0.1% TFA) to afford the titled compound. $^1$H NMR (400 MHz, $CD_3OD$) S 8.13 (ddd, J=15.9, 2.3, 0.6 Hz, 1H), 7.86 (dd, J=2.3, 0.6 Hz, 1H), 7.46 (d, J=8.2 Hz, 1H), 7.27 (t, J=7.7 Hz, 2H), 7.13 (br s, 1H), 7.01-6.94 (m, 2H), 6.69 (d, J=7.3 Hz, 2H), 4.53 (s, 2H), 3.88 (t, J=5.7 Hz, 2H), 3.21 (t, J=5.7 Hz, 2H). 2.06 (br s, 6H), MS: (ES) m z calculated for $C_{27}H_{23}Cl_2N_5$ $[M+H]^+$ 488.14, found 488.5.

Example 58

Synthesis of [4-[2-(2,6-dimethylphenyl)-5-[5-(trifluoromethyl)pyrimidin-2-yl]-6,7-dihydro-4H-pyrazolo[4,3-c]pyridin-3-yl]-5-fluoro-1H-indol-7-yl]methanol

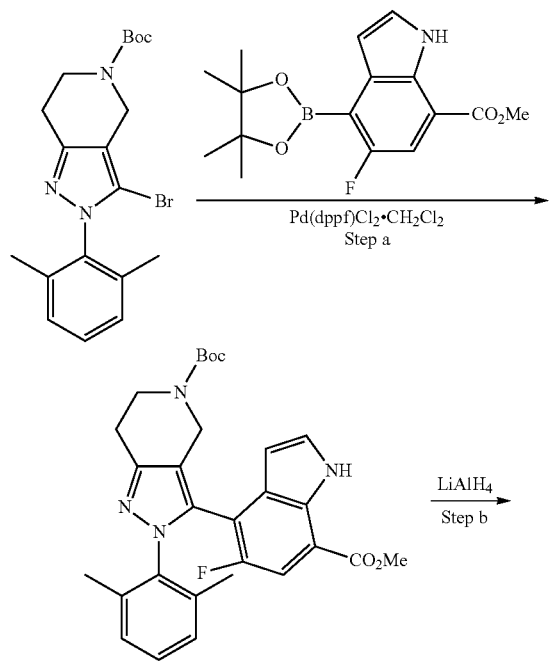

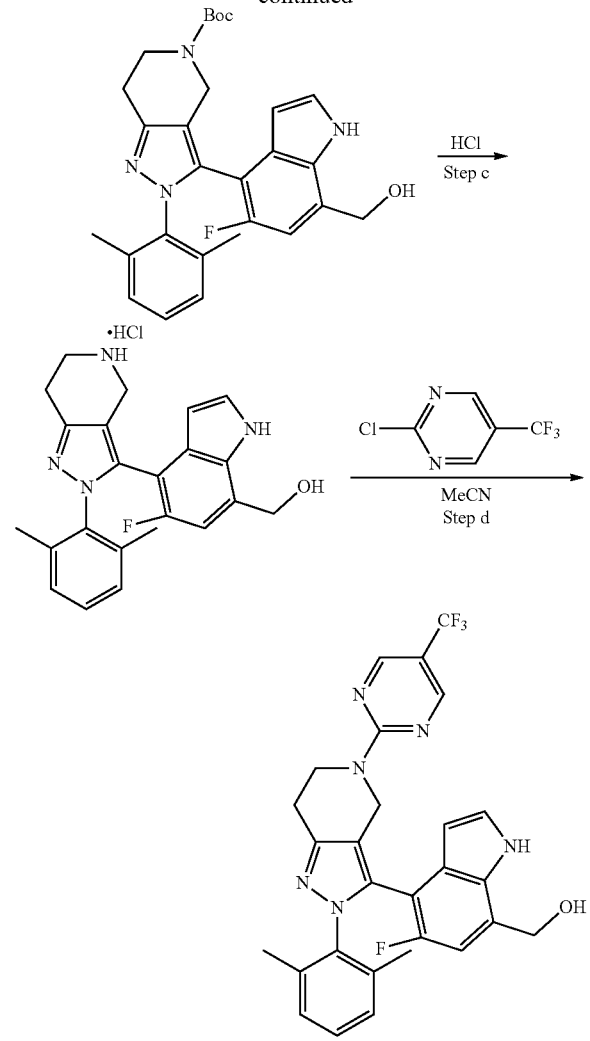

Step a: To a suspension of tert-butyl 3-bromo-2-(2,6-dimethylphenyl)-6,7-dihydro-4H-pyrazolo[4,3-c]pyridine-5-carboxylate (90 mg, 0.22 mmol), methyl 5-fluoro-4-(4,4,5,5-tetramethyl-1,3,2-dioxaborolan-2-yl)-1H-indole-7-carboxylate (70 mg, 0.22 mmol) (intermediate Example 2), and $K_2CO_3$ (150 mg, 1.1 mmol) in p-dioxane (3 mL) and water (0.5 mL) was added $Pd(dppf)Cl_2$ complex with dichloromethane (70 mg, 0.085 mmol). The reaction mixture was degassed ($N_2$) for 2 min and stirred under $N_2$ at 100° C. for 2 h. The reaction mixture was diluted with EtOAc, washed with aqueous $NaHCO_3$ and dried over $Na_2SO_4$. The solvent was removed under reduced pressure and the residue was purified by silica gel flash chromatography (0 to 80% EtOAc in hexanes) to give tert-butyl 2-(2,6-dimethylphenyl)-3-(5-fluoro-7-methoxycarbonyl-1H-indol-4-yl)-6,7-dihydro-4H-pyrazolo[4,3-c]pyridine-5-carboxylate. MS: (ES) m z calculated for $C_{29}H_{32}FN_4O_4$ $[M+H]^+$ 519.2, found 519.2.

Step b: The above tert-butyl 2-(2,6-dimethylphenyl)-3-(5-fluoro-7-methoxycarbonyl-1H-indol-4-yl)-6,7-dihydro-4H-pyrazolo[4,3-c]pyridine-5-carboxylate (38 mg, 0.073 mmol) was dissolved in THF (3 mL) and charged with a solution of $LiAlH_4$ in ether (2 M, 0.15 mL, 0.30 mmol) at 0° C. The resulting mixture was stirred at 0° C. for 20 min. It was then quenched with methanol and diluted with EtOAc and brine. The organic layer was separated, dried over $Na_2SO_4$, concentrated under reduced pressure and purified by silica gel flash chromatography (0 to 100% EtOAc in hexanes) to give tert-butyl 2-(2,6-dimethylphenyl)-3-[5-fluoro-7-(hydroxymethyl)-1H-indol-4-yl]-6,7-dihydro-4H-pyrazolo[4,3-c]pyridine-5-carboxylate. MS: (ES) m z calculated for $C_{28}H_{32}FN_4O_3[M+H]^+$ 491.2, found 491.2.

Step c: The above tert-butyl 2-(2,6-dimethylphenyl)-3-[5-fluoro-7-(hydroxymethyl)-1H-indol-4-yl]-6,7-dihydro-4H-pyrazolo[4,3-c]pyridine-5-carboxylate (21 mg, 0.042 mmol) was dissolved in dichloromethane (1 mL) and charged with HCl in dioxane (4N, 3 mL). The resulting mixture was stirred at room temperature for 1 h. The solvent was evaporated in vacuo to give [4-[2-(2,6-dimethylphenyl)-4,5,6,7-tetrahydropyrazolo[4,3-c]pyridin-3-yl]-5-fluoro-1H-indol-7-yl]methanol hydrochloride. MS: (ES) m z calculated for $C_{23}H_{24}FN_4O$ $[M+H]^+$ 391.2, found 391.2.

Step d: Triethylamine (0.12 mL, 0.85 mmol) was added to a suspension of [4-[2-(2,6-dimethylphenyl)-4,5,6,7-tetrahydropyrazolo[4,3-c]pyridin-3-yl]-5-fluoro-1H-indol-7-yl]methanol hydrochloride (20 mg, 0.044 mmol) and 2-chloro-5-(trifluoromethyl)pyrimidine (60 mg, 0.32 mmol) in MeCN (2 mL). The resulting mixture was stirred at 85° C. for 30 min. After cooling to room temperature, the reaction mixture was diluted with EtOAc, washed with aqueous $NaHCO_3$ and dried over $Na_2SO_4$. The solvent was removed under reduced pressure and the residue was purified by silica gel flash chromatography (0 to 90% EtOAc in hexanes) to afford [4-[2-(2,6-dimethylphenyl)-6-[5-(trifluoromethyl)pyrimidin-2-yl]-6,7-dihydro-4H-pyrazolo[4,3-c]pyridin-3-yl]-5-fluoro-1H-indol-7-yl]methanol. $^1$H NMR (400 MHz, $CDCl_3$) δ 8.46 (br s, 2H), 7.50 (s, 1H), 7.31 (d, J=2.8 Hz, 1H), 7.03 (m, 2H), 6.76 (m, 1H), 6.72 (d, J=11 Hz, 1H), 6.32 (d, J=3.2 Hz, 1H), 4.84 (m, 2H), 4.64 (d, J=16 Hz, 1H), 4.43 (m, 1H), 4.25 (m, 1H), 3.55-3.76 (m, 2H), 3.00 (t, J=5.6 Hz, 2H), 2.16 (s, 3H), 1.69 (s, 3H). MS: (ES) m z calculated for $C_{28}H_{25}F_4N_6O$ $[M+H]^+$537.2, found 537.2.

Example 59

Synthesis of tert-butyl 3-(6, 7-dihydro-3-(1H-indol-5-yl)-2-(2-isobutoxy-6-methylphenyl)-2H-pyrazolo[4,3-c]pyridine-5(4H)-carboxylate

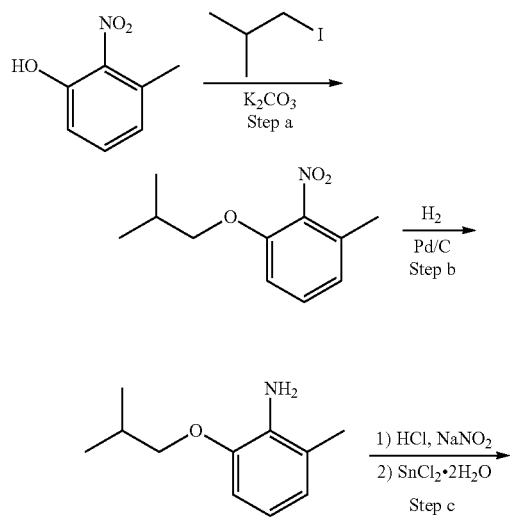

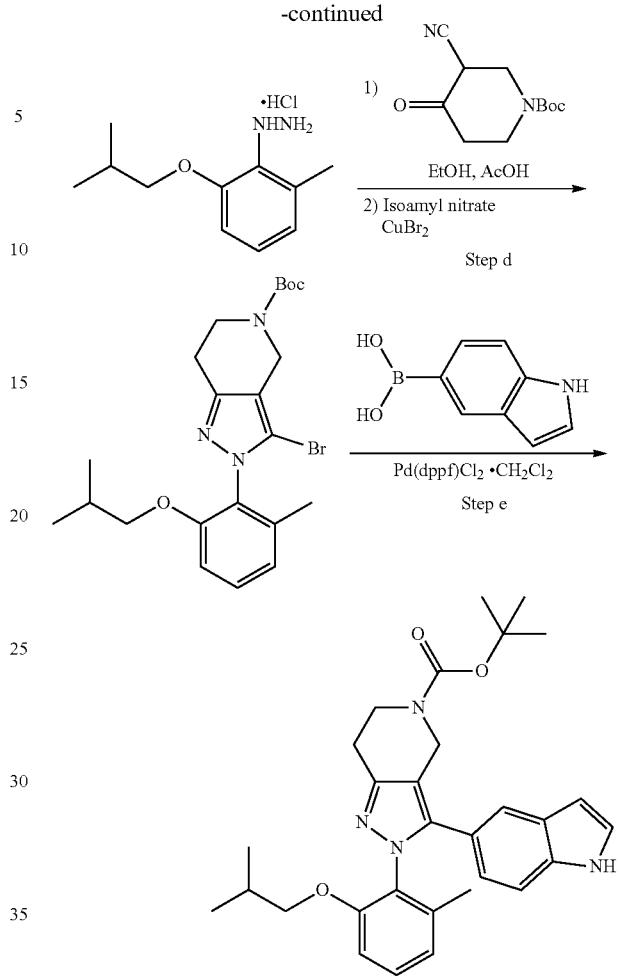

Step a: A mixture of 3-methyl-2-nitro-phenol (50 g, 326 mmol), 1-iodo-2-methyl-propane (184 g, 1 mol) and $Cs_2CO_3$ (326 g, 1 mol) in acetone (500 mL) was stirred overnight under reflux. It was then cooled to room temperature and filtered through Celite. The filtrate was collected and concentrated under reduced pressure. The obtained solid was redissolved into EtOAc, washed with brine, dried over $Na_2SO_4$ and concentrated on a rotary evaporator under reduced pressure to afford 1-isobutoxy-3-methyl-2-nitrobenzene. $^1$H NMR (400 MHz, $CDCl_3$) δ 7.26 (t, J=8.0 Hz, 1H), 6.82 (m, 2H), 3.78 (d, J=6.8 Hz, 2H), 2.94 (s, 3H), 2.07 (m, 1H), 0.98 (d, J=6.4 Hz, 6H).

Step b: A pressure vessel containing 1-isobutoxy-3-methyl-2-nitro-benzene (130.4 g, 623 mmol), 10% Pd/C (25 g, 50% wet) and EtOH (750 mL) was agitated under a hydrogen atmosphere at 45 psi for 3 h. It was then filtered through Celite. The filtrate was collected and concentrated under reduced pressure to yield 2-isobutoxy-6-methyl-aniline. $C_{11}H_{18}NO$ $[M+H]^+$ 180.2, found 180.2.

Caution: Diazonium formation could be potentially dangerous, please handle with care and ware proper personal protection equipment!

Step c: To 100 mL of conc. HCl at −10° C. was added isobutoxy-6-methyl aniline (26.4 g, 147 mmol) portionwise to obtain a stirrable suspension. After stired for 30 min at the same temperature, a solution of $NaNO_2$ (12.2 g, 176 mmol) in water (25 mL) was added dropwise within 20 min to obtain the diazonium salt.

131

To the above diazonium salt was added SnCl$_2$·2H$_2$O (83 g, 368 mmol) in conc. HCl (120 mL) portionwise. The obtained mixture was then stirred for 10 min at −10° C. followed by 1 h at room temperature. The mixture was then diluted into DCM (400 mL) and water. The organic layer was separated, dried over Na$_2$SO$_4$ and concentrated on a rotary evaporator under reduced pressure to yield (2-isobutoxy-6-methyl-phenyl)hydrazine hydrochloride. C$_{11}$H$_{19}$N$_2$O [M+H]$^+$ 195.1, found 195.1.

Step d: To a stirred suspension of (2-isobutoxy-6-methylphenyl)hydrazine hydrochloride (8 g, 39.9 mmol) in EtOH (60 mL) and glacial acetic acid (12 mL, 208 mmol) was added tert-butyl 3-cyano-4-oxopiperidine-1-carboxylate (5 g, 22.3 mmol) at room temperature. The resulting mixture was stirred under reflux for 16 h. After removal of solvent under reduced pressure, the residue was dissolved in EtOAc and washed with aqueous NaOH (2 N), brine and dried over MgSO$_4$. The solvent was removed under reduced pressure and the residue was purified by silica gel flash chromatography (5 to 55% EtOAc in hexanes) to give tert-butyl 3-amino-2-(2-isobutoxy-6-methylphenyl)-6,7-dihydro-2H-pyrazolo[4,3-c]pyridine-5(4H)-carboxylate. MS: (ES) m z calculated for C$_{22}$H$_{33}$N$_4$O$_3$ [M+H]$^+$ 401.2, found 401.2.

Caution: Diazonium formation could be potentially dangerous, please handle with care and ware proper personal protection equipment!

Isoamyl nitrite (96%, 4 mL, 28.6 mmol) was added slowly at room temperature to a mixture of tert-butyl-3-amino-2-(2-isobutoxy-6-methylphenyl)-6,7-dihydro-2H-pyrazolo[4,3-c]pyridine-5(4H)-carboxylate (3 g, 8.1 mmol), CuBr (4 g, 27.9 mmol) and MeCN (50 mL) in a 250 mL round bottom flask under magnetic stirring. The resulting mixture was stirred at room temperature for 1 h, diluted with EtOAc, filtered through Celite, washed with sat NH$_4$Cl solution, and dried over MgSO$_4$. The solvent was removed under reduced pressure and the residue was purified by silica gel flash chromatography (2 to 25% EtOAc in hexanes) to give tert-butyl 3-bromo-2-(2-isobutoxy-6-methylphenyl)-6,7-dihydro-2H-pyrazolo[4,3-c]pyridine-5(4H)-carboxylate. MS: (ES) m z calculated for C$_{22}$H$_{31}$BrN$_3$O$_3$[M+H]$^+$ 464.1, found 464.2.

Step e: To a suspension of tert-butyl 3-bromo-2-(2-isobutoxy-6-methylphenyl)-6,7-dihydro-2H-pyrazolo[4,3-c]pyridine-5(4H)-carboxylate (125 mg, 0.32 mmol), 1H-indol-5-yl-5-boronic acid (74 mg, 0.48 mmol), and Na$_2$CO$_3$ (85 mg, 0.81 mmol) in p-dioxane (4 mL) and water (1 mL) was added Pd(dppf)Cl$_2$ complex with dichloromethane (26 mg, 0.032 mmol). The reaction mixture was degassed (N$_2$) for 2 min and stirred under N$_2$ at 95° C. for 6 h. The reaction mixture was diluted with EtOAc, filtered through Celite, washed with brine and dried over MgSO$_4$. The solvent was removed under reduced pressure and the residue was purified by silica gel flash chromatography (5 to 20% to 40% EtOAc in hexanes) to give tert-butyl 3-(6, 7-dihydro-3-(1H-indol-5-yl)-2-(2-isobutoxy-6-methylphenyl)-2H-pyrazolo[4,3-c]pyridine-5(4H)-carboxylate. $^1$H NMR (400 MHz, CD$_3$OD) δ 7.40 (s, 1H), 7.20-7.26 (m, 3H), 6.92 (d, J=9.7 Hz, 1H), 6.85 (d, J=8.2 Hz, 1H), 6.78 (d, J=7.8 Hz, 1H), 6.34 (d, J=3.1 Hz, 1H), 4.54-4.65 (m, 2H), 3.80-3.95 (m, 2H), 3.67-3.70 (m, 2H), 2.85 (t, J=5.6 Hz, 2H), 1.96 (s, 3H), 1.80-1.90 (m, 1H), 1.47 (s, 9H), 0.86 (dd, J=3.5, 6.6 Hz, 6H). MS: (ES) m z calculated for C$_{30}$H$_{37}$N$_4$O$_3$ [M+H]$^+$ 501.28, found 501.2.

132

Example 60

Synthesis of tert-butyl-3-(1H-indol-5-yl)-2-(2-isobutoxy-6-methylphenyl)-6,7-dihydro-2H-pyrazolo[4,3-c]pyridine-5(4H)-carboxamide

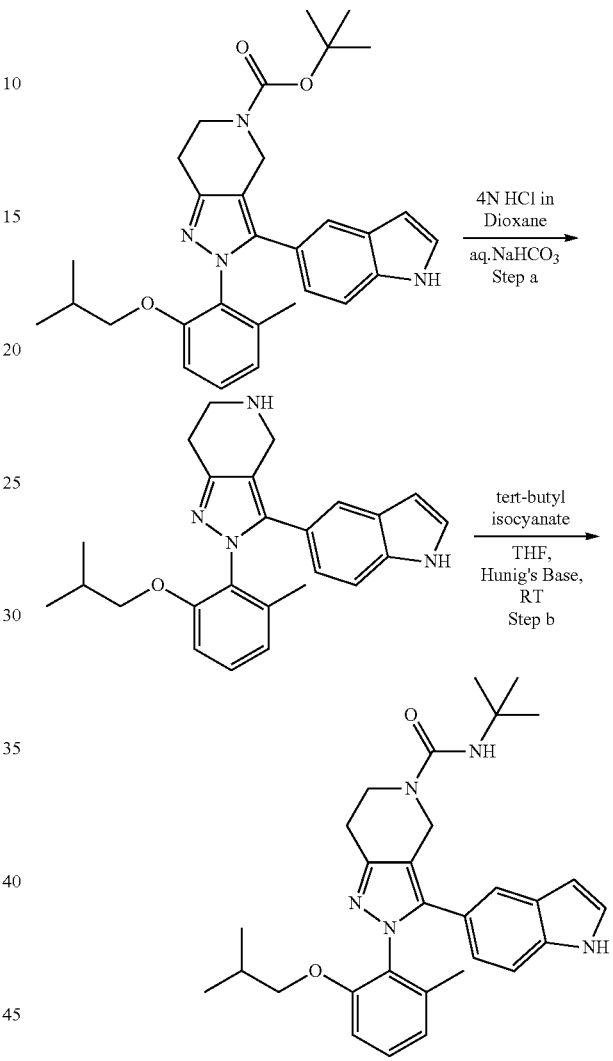

Step a: The above tert-butyl-6,7-dihydro-3-(1H-indol-5-yl)-2-(2-isobutoxy-6 methyl-phenyl)-2H-pyrazolo[4,3-c]pyridine-5(4H)-carboxylate was dissolved in dichloromethane (5 mL) and TFA (4N, 5 mL) was added. The resulting mixture was stirred at room temperature for 2 h. After completion of the reaction, the solvent was diluted with water and aqueous NaHCO$_3$ and extracted with dichloromethane (2×50 mL) washed with brine and dried over MgSO$_4$. The solvent was removed under reduced pressure and dried under vacuum to give 4,5,6,7-tetrahydro-3-(1H-indol-5-yl)-2-(2-isobutoxy-6-methylphenyl)-2H-pyrazolo[4,3-c]pyridine. MS: (ES) m z calculated for C$_{25}$H$_{29}$ClN$_4$O [M+H]$^+$ 401.2, found 401.3.

Step b: To a stirred solution of 4,5,6,7-tetrahydro-3-(1H-indol-5-yl)-2-(2-isobutoxy-6-methylphenyl)-2H-pyrazolo[4,3-c]pyridine (30 mg, 0.074 mmol) in anhydrous THF (1.5 mL) were added N,N-diisopropylethylamine (24 mg, 0.185 mmol) and tert-butyl isocyanate (10 mg, 0.089 mmol). The reaction mixture was stirred at room temperature for 16 h.

After completion, the reaction mixture was diluted with EtOAc, washed with brine, and dried over MgSO$_4$. The solvent was removed under reduced pressure and the residue was purified by Prep HPLC (20-100% H$_2$O/ACN) and lyophilized to afford N-tert-butyl-6,7-dihydro-3-(1H-indol-5-yl)-2-(2-isobutoxy-6-methylphenyl)-2H-pyrazolo[4,3-c]pyridine-5(4H)-carboxamide. $^1$H NMR (400 MHz, CD$_3$OD) δ 7.44 (d, J=1.5 Hz, 1H), 7.21-7.26 (m, 3H), 6.94 (dd, J=1.5, 8.6 Hz, 2H), 6.85 (d, J=8.2 Hz, 1H), 6.78 (d, J=7.6 Hz, 1H), 6.35 (dd, J=3.2, 10.8 Hz, 1H), 4.54 (dd, J=15.2, 29.2 Hz, 2H), 3.70-3.76 (m, 2H), 3.64-3.70 (m, 2H), 2.85 (t, J=5.6 Hz, 2H), 1.96 (s, 3H), 1.80-1.90 (m, 1H), 1.32 (s, 9H), 0.86 (dd, J=3.5, 6.6 Hz, 6H). MS: (ES) m z calculated C$_{30}$H$_{38}$N$_5$O$_2$ [M+H]$^+$ 500.29, found 500.2.

Example 61

Synthesis of tert-butyl 3-(6,7-dihydro-3-(1H-idnol-5-yl)-2-(2-methoxy-6-methylphenyl)-2H-pyrazolo[4,3-c]pyridine-5(4H)-carboxylate

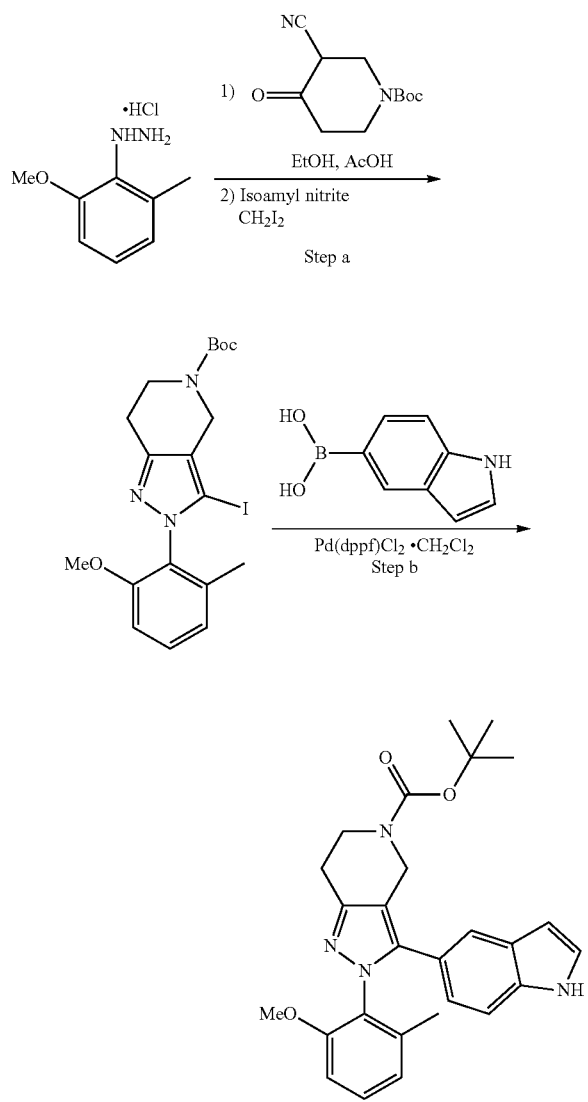

Step a: To a stirred suspension of 1-(2-methoxy-6-methylphenyl)hydrazine hydrochloride (3.77 g, 20.0 mmol) in EtOH (50 mL) and glacial acetic acid (10 mL, 208 mmol) was added tert-butyl 3-cyano-4-oxopiperidine-1-carboxylate (4.5 g, 22.0 mmol) at room temperature. The resulting mixture was stirred under reflux for 16 h. After removal of solvent under reduced pressure, the residue was dissolved in EtOAc and washed with aqueous NaOH (2 N), brine, and dried over MgSO$_4$. The solvent was removed under reduced pressure and the residue was purified by silica gel flash chromatography (5 to 55% EtOAc in hexanes) to give tert-butyl 3-amino-2-(2-methoxy-6-methylphenyl)-6,7-dihydro-2H-pyrazolo[4,3-c]pyridine-5(4H)-carboxylate. MS: (ES) m z calculated for C$_{19}$H$_{27}$N$_4$O$_3$ [M+H]$^+$ 359.2, found 359.2.

Caution: Diazonium formation could be potentially dangerous, please handle with care and ware proper personal protection equipment!

Isoamyl nitrite (3.2 g, 27.8 mmol) was added slowly at room temperature to a mixture of tert-butyl-3-amino-2-(2-methoxy-6-methylphenyl)-6,7-dihydro-2H-pyrazolo[4,3-c]pyridine-5(4H)-carboxylate (5.0 g, 13.9 mmol), CH$_2$I$_2$ (14.9 g, 55.7 mmol) and MeCN (60 mL) in a 250 mL round bottom flask under magnetic stirring. The resulting mixture was stirred at room temperature for 1 h, diluted with EtOAc, filtered through Celite, washed with sat NH$_4$Cl solution, and dried over MgSO$_4$. The solvent was removed under reduced pressure and the residue was purified by silica gel flash chromatography (2 to 25% EtOAc in hexanes) to give tert-butyl 3-iodo-2-(2-methoxy-6-methylphenyl)-6,7-dihydro-2H-pyrazolo[4,3-c]pyridine-5(4H)-carboxylate. MS: (ES) m z calculated for C$_{19}$H$_{25}$IN$_3$O$_3$[M+H]$^+$ 469.1, found 469.3.

Step b: To a suspension of tert-butyl 3-Iodo-2-(2-methoxy-6-methylphenyl)-6,7-dihydro-2H-pyrazolo[4,3-c]pyridine-5(4H)-carboxylate (250 mg, 0.53 mmol), 1H-indol-5-yl-5-boronic acid (128 mg, 1.8 mmol), Na$_2$CO$_3$ (139 mg, 3.6 mmol) in p-dioxane (4 mL) and water (1 mL) was added Pd(dppf)Cl$_2$ complex with dichloromethane (300 mg, 0.37 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 40% EtOAc in hexanes) to give tert-butyl 3-(6, 7-dihydro-3-(1H-indol-5-yl)-2-(2-methoxy-6-methylphenyl)-2H-pyrazolo[4,3-c]pyridine-5(4H)-carboxylate. $^1$H NMR (400 MHz, CD$_3$OD) S 7.35-7.40 (m, 1H), 7.26 (d, J=2.0 Hz, 1H), 7.24 (bs, 1H), 7.21-7.30 (m, 1H), 6.90 (d, J=8.4 Hz, 1H), 6.87 (d, J=8.4 Hz, 1H), 6.71 (d, J=8.4 Hz, 1H), 6.35 (dd, J=0.8, 2.8 Hz, 1H), 4.54 (dd, J=15.2, 21.6 Hz, 2H), 3.80-3.90 (m, 1H), 3.70-3.78 (m, 1H), 3.69 (s, 3H), 2.82 (t, J=6.0 Hz, 2H), 1.91 (s, 3H), 1.40-1.50 (m, 9H). MS: (ES) m z calculated for C$_{27}$H$_{31}$N$_4$O$_3$ [M+H]$^+$ 459.23, found 459.2.

Example 62

Synthesis of 5-(5-tert-butyl-2-methylphenyl)-4,5,6,7-tetrahydro-3-(1H-indol-5-yl)-2-(2-methoxy-6-methylphenyl)-2H-pyrazolo[4,3-c]pyridine

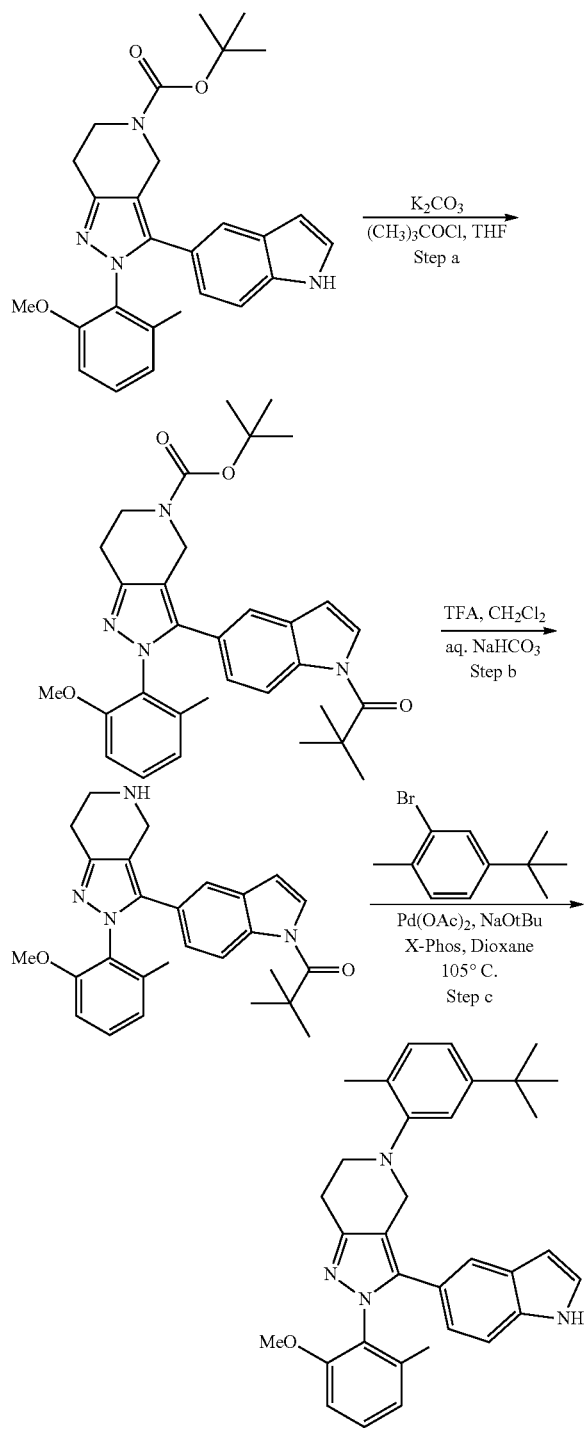

Step a: To a stirred solution of tert-butyl 3-(6, 7-dihydro-3-(1H-indol-5-yl)-2-(2-methoxy-6-methylphenyl)-2H-pyrazolo[4,3-c]pyridine-5(4H)-carboxylate (250 mg, 0.544 mmol) in anhydrous THF (4 mL) were added $K_2CO_3$ (150 mg, 1.08 mmol) and trimethylacetyl chloride (163 mg, 1.36 mmol) at 0° C. The resulting mixture was stirred for 16 h at room temperature. After completion of the reaction, the residue was dissolved in $EtOAc/H_2O$ and washed with brine and dried over $MgSO_4$. The solvent was removed under reduced pressure and the residue was purified by silica gel flash chromatography (0 to 20% EtOAc in hexanes) to give tert-butyl 6,7-dihydro-2-(2-methoxy-6-methylphenyl)-3-(1-(pivaloyl)-1H-indol-5-yl)-2H-pyrazolo[4,3-c]pyridine-5(4H)-carboxylate (220 mg). MS: (ES) m z calculated for $C_{32}H_{39}N_4O_4$ $[M+H]^+$ 542.2, found 542.2.

Step b: To a solution of tert-butyl 6,7-dihydro-2-(2-methoxy-6-methylphenyl)-3-(1-(pivaloyl)-1H-indol-5-yl)-2H-pyrazolo[4,3-c]pyridine-5(4H)-carboxylate (220 mg, 0.405 mmol) in dichloromethane (5 mL) was added TFA (115 mg, 1.01 mmol). The resulting mixture was stirred at room temperature for 2 h. After completion of the reaction, the solvent was diluted with water and aqueous $NaHCO_3$ and extracted with dichloromethane (2×50 mL) washed with brine and dried over $MgSO_4$. The solvent was removed under reduced pressure and dried under vacuum to give 1-(5-(4,5,6,7-tetrahydro-2-(2-methoxy-6-methylphenyl)-2H-pyrazolo[4,3-c]pyridin-3-yl)-1H-indol-1-yl)-2,2-dimethylpropan-1-one (125 mg). MS: (ES) m z calculated for $C_{27}H_{31}N_4O_2$ $[M+H]^+$ 443.24, found 443.2.

Step c: To a mixed 1-(5-(4,5,6,7-tetrahydro-2-(2-methoxy-6-methylphenyl)-2H-pyrazolo[4,3-c]pyridin-3-yl)-1H-indol-1-yl)-2,2-dimethylpropan-1-one (120 mg, 0.270 mmol), 4-tert-butyl-2-bromo-1-methylbenzene (93 mg, 0.406 mmol), NaOtBu (52 mg, 2.2 mmol) and X-Phos (27 mg, 2.2 mmol) in p-dioxane (6 mL) was added $Pd(OAc)_2$ (6 mg, 0.027 mmol). The reaction mixture was degassed ($N_2$) for 5 min and stirred under $N_2$ at 105° C. for 6 h. Upon completion the mixture was cooled down to room temperature, diluted with EtOAc(10 mL), filtered through Celite, washed with brine and dried over $MgSO_4$. The solvent was removed under reduced pressure and the residue was purified by silica gel flash chromatography (5 to 30% EtOAc in hexanes) and followed by prep HPLC to give 5-(5-tert-butyl-2-methylphenyl)-4,5,6,7-tetrahydro-3-(1H-indol-5-yl)-2-(2-methoxy-6-methylphenyl)-2H-pyrazolo[4,3-c]pyridine (12 mg). $^1$H NMR (400 MHz, $CD_3OD$) S 7.42-7.48 (m, 2H), 7.20-7.35 (m, 5H), 6.92-6.97 (m, 2H), 6.81 (d, J=8.0 Hz, 1H), 6.35 (d, J=3.2 Hz, 1H), 4.60 (d, J=13.6 Hz, 1H), 4.44 (d, J=13.6 Hz, 1H), 3.75-3.85 (m, 2H), 3.72 (s, 3H), 3.10-3.18 (m, 2H), 2.41 (s, 3H), 1.96 (s, 3H), 1.26 (s, 9H). MS: (ES) m z calculated for $C_{33}H_{37}N_4O$ $[M+H]^+$ 505.2, found 505.2.

Example 63

Synthesis of 5-(3,5-dichloropyridin-2-yl)-4,5,6,7-tetrahydro-3-(1H-indol-5-yl)-2-(2-isobutoxy-6-methylphenyl)-2H-pyrazolo[4,3-c]pyridine

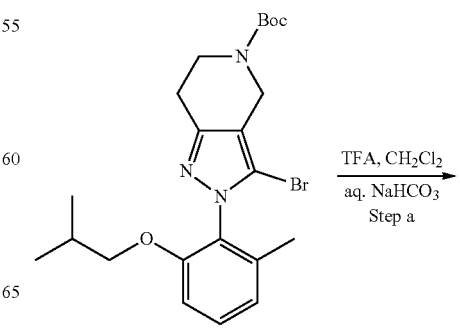

-continued

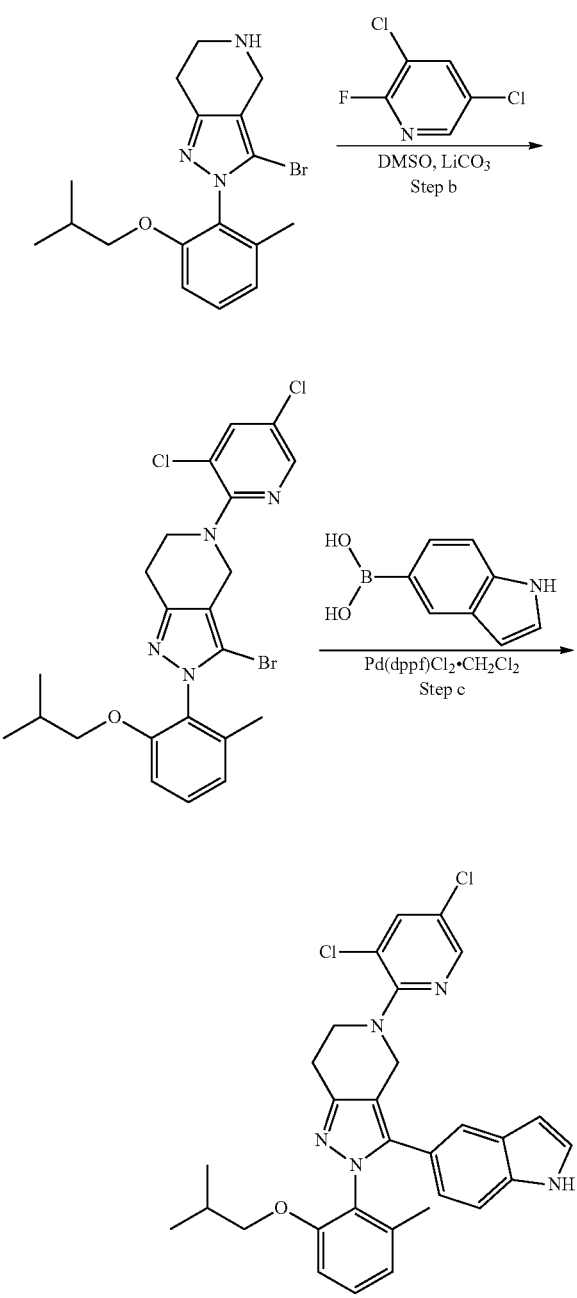

Step a: To a solution of tert-butyl 3-bromo-2-(2-isobutoxy-6-methylphenyl)-6,7-dihydro-2H-pyrazolo[4,3-c]pyridine-5(4H)-carboxylate (1.2 g, 3.6 mmol in dichloromethane (10 mL) was added TFA (1.47 g, 12.93 mmol). The resulting mixture was stirred at room temperature for 2 h. Upon completion the mixture was diluted with water and aqueous NaHCO₃ and extracted with dichloromethane, washed with brine, and dried over MgSO₄. The solvent was removed under reduced pressure and dried under vacuum to give 3-bromo-2-(2-isobutoxy-6-methylphenyl)-4,5,6,7-tetrahydro-2H-pyrazolo[4,3-c]pyridine. (1.0 g) MS: (ES) m z calculated for $C_{16}H_{22}BrN_3$ [M+H]⁺ 364.28, found 364.2.

Step b: To a mixture of 3-bromo-2-(2-isobutoxy-6-methylphenyl)-4,5,6,7-tetrahydro-2H-pyrazolo[4,3-c]pyridine (1.0 g, 2.58 mmol) in DMSO (5 mL) was added 3,5-dichloro-5-fluoro pyridine (680 mg, 4.37 mmol), and Li₂CO₃ (610 mg, 12.3 mmol) at room temperature. The resulting mixture was stirred at 100° C. for 4 h. After completion of the reaction, it was cooled down to room temperature, the reaction mixture was diluted with EtOAc (20 mL), washed with brine and dried over MgSO₄. The solvent was removed under reduced pressure and the residue was purified by silica gel flash chromatography (5 to 20% EtOAc in hexanes) to afford 3-bromo-5-(3,5-dichloropyridin-2-yl)-4,5,6,7-tetrahydro-2-(2-isobutoxy-6-methylphenyl)-2H-pyrazolo[4,3-c]pyridine (0.8 g). MS: (ES) m z calculated for $C_{22}H_{24}BrCl_2N_4O$ [M+H]⁺ 509.04, found 509.2.

Step c: To a suspension of 3-bromo-5-(3,5-dichloropyridin-2-yl)-4,5,6,7-tetrahydro-2-(2-isobutoxy-6-methylphenyl)-2H-pyrazolo[4,3-c]pyridine (600 mg, 1.4 mmol), 1H-indol-5-yl-5-boronic acid (550 mg, 1.8 mmol), Na₂CO₃ (500 mg, 3.6 mmol) in p-dioxane (6 mL) and water (1 mL) was added Pd(dppf)Cl₂ complex with dichloromethane (300 mg, 0.37 mmol). The reaction mixture was degassed (N₂) for 2 min and stirred under N₂ at 100° C. for 2 h. The reaction mixture was diluted with EtOAc, filtered through Celite, washed with brine and dried over MgSO₄. The solvent was removed under reduced pressure and the residue was purified by silica gel flash chromatography (5 to 20% EtOAc in hexanes) to give 5-(3,5-dichloropyridin-2-yl)-4,5,6,7-tetrahydro-3-(1H-indol-5-yl)-2-(2-isobutoxy-6-methylphenyl)-2H-pyrazolo[4,3-c]pyridine. ¹H NMR (400 MHz, CD₃OD) δ 8.08 (d, J=2.4 Hz, 1H), 7.80 (d, J=2.4 Hz, 1H), 7.35 (d, J=8.0 Hz, 1H), 7.29 (bs, 1H), 7.20 (t, J=8.4 Hz, 1H), 6.92 (t, J=7.2 Hz, 1H), 6.79-6.88 (m, 2H), 6.68-6.85 (m, 1H), 6.39 (d, J=3.1 Hz, 1H), 4.40-4.55 (m, 1H), 4.20-4.40 (m, 1H), 3.82 (t, J=6.0 Hz, 2H), 3.60-3.75 (m, 2H), 3.09-3.13 (m, 2H), 1.99 (m, 4H), 0.80-0.90 (m, 6H). MS: (ES) m z calculated for $C_{30}H_{30}Cl_2N_5O$ [M+H]⁺ 546.17, found 546.5

Example 64

Synthesis of 5-(3,5-dichloropyridin-2-yl)-4,5,6,7-tetrahydro-3-(1H-indol-6-yl)-2-(2-isobutoxy-6-methylphenyl)-2H-pyrazolo[4,3-c]pyridine

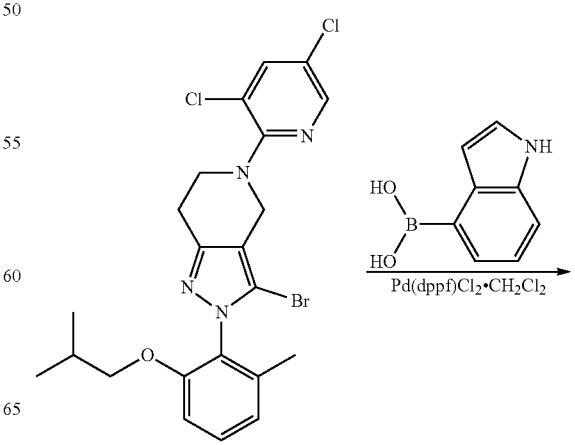

-continued

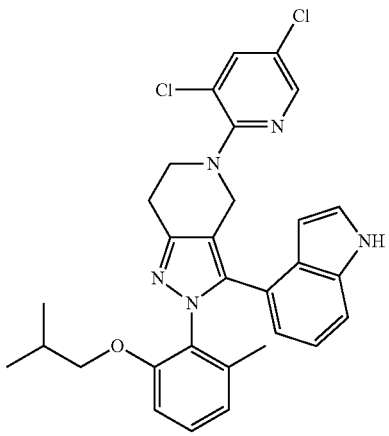

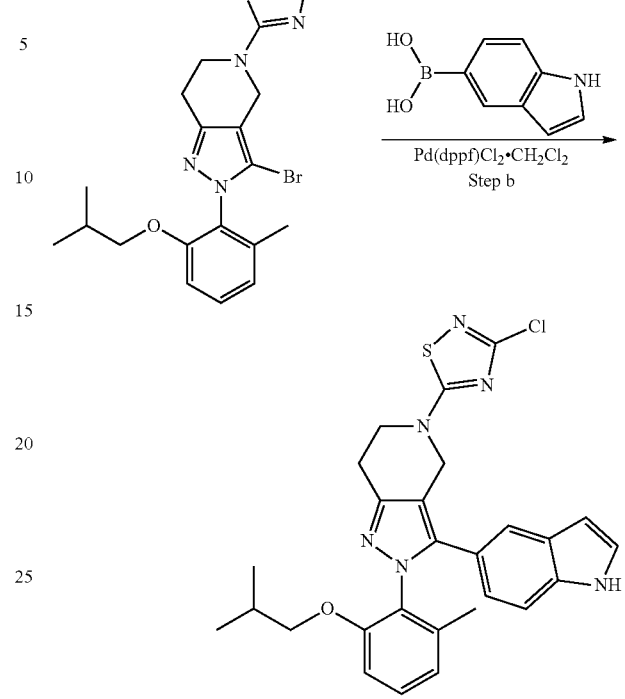

To a suspension of 3-bromo-5-(3,5-dichloropyridin-2-yl)-4,5,6,7-tetrahydro-2-(2-isobutoxy-6-methylphenyl)-2H-pyrazolo[4,3-c]pyridine (600 mg, 1.4 mmol), 1H-indol-6-yl-6-boronic acid (550 mg, 1.8 mmol), and $Na_2CO_3$ (500 mg, 3.6 mmol) in p-dioxane (6 mL) and water (1 mL) was added Pd(dppf)Cl$_2$ complex with dichloromethane (300 mg, 0.37 mmol). The reaction mixture was degassed ($N_2$) for 2 min and stirred under $N_2$ at 95° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) to give 5-(3,5-dichloropyridin-2-yl)-4,5,6,7-tetrahydro-3-(1H-indol-6-yl)-2-(2-isobutoxy-6-methylphenyl)-2H-pyrazolo[4,3-c]pyridine. $^1$H NMR (400 MHz, CD$_3$OD) δ 8.14 (d, J=2.2 Hz, 1H), 7.81 (d, J=2.3 Hz, 1H), 7.45 (d, J=1.6 Hz, 1H), 7.22-7.28 (m, 4H), 6.96 (dd, J=1.6, 8.6 Hz, 1H), 6.87 (d, J=8.0 Hz, 1H), 6.81 (d, J=7.6 Hz, 1H), 4.50 (dd, J=10.9, 18.6 Hz, 2H), 3.78 (t, J=4.2 Hz, 2H), 3.66 (d, J=6.4 Hz, 2H), 3.06 (t, J=6.0 Hz, 2H), 1.99 (s, 3H), 1.83-1.90 (m, 1H), 0.85 (dd, J=3.5, 6.7 Hz, 6H). MS: (ES) m z calculated for $C_{30}H_{30}Cl_2N_5O$ [M+H]$^+$ 546.17, found 546.1.

Example 65

Synthesis of 3-chloro-5-[3-(1H-indol-5-yl)-2-(2-isobutoxy-6-methylphenyl)-6,7-dihydro-4H-pyrazolo[4,3-c]pyridin-5-yl]-1,2,4-thiadiazole

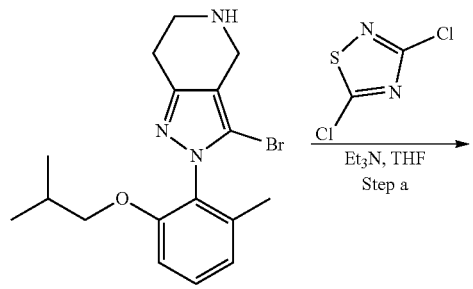

Step a: To a solution of 3-bromo-2-(2-isobutoxy-6-methyl-phenyl)-4,5,6,7-tetrahydropyrazolo[4,3-c]pyridine (363 mg, 1.0 mmol) and Et$_3$N (153 μL, 1.1 mmol) in THF (4 mL) was added 3,5-dichloro-1,2,4-thiadiazole (171 mg. 1.1 mmol) in THF (2 mL) at room temperature. After 30 min, reaction mixture was diluted with CH$_2$Cl$_2$ (20 mL) and washed with water (20 mL), dried over Na$_2$SO$_4$ and concentrated in vacuo. The obtained residue was purified by silica gel flash chromatography (50% EtOAc in hexanes) to afford 5-[3-bromo-2-(2-isobutoxy-6-methyl-phenyl)-6,7-dihydro-4H-pyrazolo[4,3-c]pyridin-5-yl]-3-chloro-1,2,4-thiadiazole. MS: (ES) m z calculated for $C_{19}H_{22}BrClN_5OS$ [M+H]$^+$ 482.8, found 482.8.

Step b: To a solution of 5-[3-bromo-2-(2-isobutoxy-6-methyl-phenyl)-6,7-dihydro-4H-pyrazolo[4,3-c]pyridin-5-yl]-3-chloro-1,2,4-thiadiazole (471 mg, 0.977 mmol) in 1,4-dioxane (8 mL) and water (2 mL) was added 1H-indol-5-ylboronic acid (157 mg, 0.977 mmol), Na$_2$CO$_3$ (155 mg, 1.465 mmol) and degassed the resulting reaction mixture for a minute with nitrogen gas. Then was added Pd(dppf)Cl$_2$ complex with dichloromethane (80 mg, 0.0977 mmol), degassed the reaction mixture for another minute with nitrogen gas and stirred at 50° C. overnight. The reaction mixture was filtered through a small pad of Celite, washed with CH$_2$Cl$_2$ (15 mL), dried over Na$_2$SO$_4$ and concentrated in vacuo. The obtained residue was purified by silica gel flash chromatography (75% EtOAc in hexanes) to get 3-chloro-5-[3-(1H-indol-5-yl)-2-(2-isobutoxy-6-methyl-phenyl)-6,7-dihydro-4H-pyrazolo[4,3-c]pyridin-5-yl]-1,2,4-thiadiazole. $^1$H NMR (400 MHz, Methanol-d$_4$) δ 7.45 (d, J=1.6 Hz, 1H), 7.32-7.20 (m, 3H), 6.97 (dd, J=8.4, 1.7 Hz, 1H), 6.83 (dd, J=8.0, 24.5 Hz, 2H), 6.41-6.35 (m, 1H), 4.77 (d, J=14.8 Hz, 1H), 4.68 (s, 1H), 4.03-3.97 (m, 2H), 3.71-3.59 (m, 2H), 3.02 (t, J=6.0 Hz, 2H), 1.97 (s, 3H), 1.88 (dt, J=6.5, 13.2 Hz, 1H), 1.28 (s, 1H), 0.85 (dd, J=3.0, 6.7 Hz, 6H).MS: (ES) m z calculated for $C_{27}H_{28}ClN_6OS$ [M+H]$^+$ 519.2, found 519.1.

Example 66

Synthesis of 5-[3-(1H-indol-5-yl)-2-(2-isobutoxy-6-methyl-phenyl)-6,7-dihydro-4H-pyrazolo[4,3-c]pyridin-5-yl]-3-isopropyl-1,2,4-thiadiazole

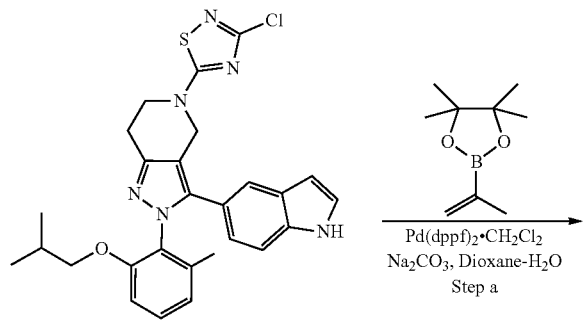

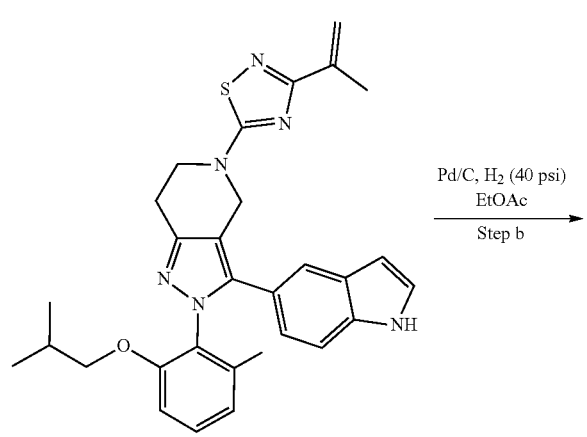

Step a: To a solution of 3-chloro-5-[3-(1H-indol-5-yl)-2-(2-isobutoxy-6-methyl-phenyl)-6,7-dihydro-4H-pyrazolo[4,3-c]pyridin-5-yl]-1,2,4-thiadiazole (100 mg, 0.193 mmol) in 1,4-dioxane (3 mL) and water (0.5 mL) was added 2-isopropenyl-4,4,5,5-tetramethyl-1,3,2-dioxaborolane (54 μL, 0.977 mmol), and $Na_2CO_3$ (155 mg, 1.465 mmol). The resulting reaction mixture was degassed for a minute with nitrogen gas. Pd(dppf)Cl$_2$ complex with dichloromethane (80 mg, 0.0977 mmol) was then added and the mixture degassed for another minute with nitrogen gas and stirred at 50° C. overnight. The reaction mixture was filtered through a small pad of Celite, washed with CH$_2$Cl$_2$(15 mL), dried over Na$_2$SO$_4$ and concentrated in vacuo. The obtained residue was purified by silica gel flash chromatography (75% EtOAc in hexanes) to get 5-[3-(1H-indol-5-yl)-2-(2-isobutoxy-6-methyl-phenyl)-6,7-dihydro-4H-pyrazolo[4,3-c]pyridin-5-yl]-3-isopropenyl-1,2,4-thiadiazole. MS: (ES) m z calculated for $C_{30}H_{33}N_6OS$ [M+H]$^+$ 525.2, found 525.2.

Step b: To a solution of 5-[3-(1H-indol-5-yl)-2-(2-isobutoxy-6-methyl-phenyl)-6,7-dihydro-4H-pyrazolo[4,3-c]pyridin-5-yl]-3-isopropenyl-1,2,4-thiadiazole (50 mg, 0.095 mmol) in EtOAc (5 mL) was added 10% Pd/C (20 mg). The resulting suspension was agitated under H$_2$ gas (40 psi) on Parr shaker at room temperature for 3 h. The reaction mixture was filtered through a small pad of Celite, washed with EtOAc (15 mL), concentrated in vacuo. The obtained residue was purified by HPLC (CH$_3$CN/H$_2$O with 0.1% TFA) to afford 5-[3-(1H-indol-5-yl)-2-(2-isobutoxy-6-methyl-phenyl)-6,7-dihydro-4H-pyrazolo[4,3-c]pyridin-5-yl]-3-isopropyl-1,2,4-thiadiazole. $^1$H NMR (400 MHz, Methanol-d$_4$) δ 7.46 (dd, J=1.6, 0.7 Hz, 1H), 7.32-7.19 (m, 3H), 6.97 (dd, J=8.5, 1.7 Hz, 1H), 6.89-6.76 (m, 2H), 6.38 (dd, J=0.9, 3.2 Hz, 1H), 4.76 (d, J=15.2 Hz, 1H), 4.67 (d, J=15.0 Hz, 1H), 4.00 (t, J=5.9 Hz, 2H), 3.71-3.59 (m, 2H), 3.00 (td, J=2.8, 6.4, 6.9 Hz, 3H), 1.97 (s, 3H), 1.88 (dt, J=6.5, 13.2 Hz, 1H), 1.27 (d, J=6.9 Hz, 6H), 0.84 (dd, J=1.7, 6.5 Hz, 6H).MS: (ES) m z calculated for $C_{30}H_{35}N_6OS$ [M+H]$^+$ 527.3, found 527.2.

Example 67

Synthesis of tert-butyl 2-(2,6-dimethylphenyl)-3-(1H-indol-5-yl)-6,7-dihydro-4H-pyrazolo[4,3-c]pyridine-5-carboxylate

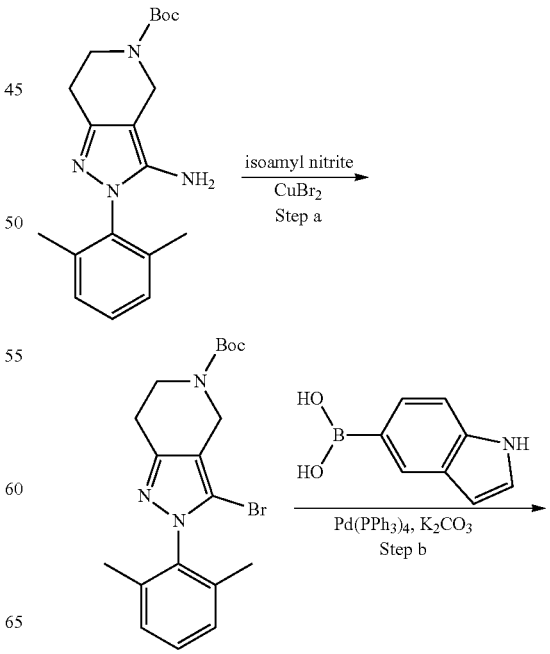

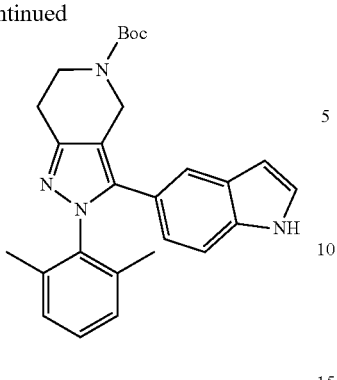

Step a: To a mixture of tert-butyl 3-amino-2-(2,6-dimethylphenyl)-6,7-dihydro-4H-pyrazolo[4,3-c]pyridine-5-carboxylate (485 mg, 1.41 mmol) and CuBr$_2$ (1.50 g, 6.7 mmol) in CH$_3$CN (30 mL) was added isopentyl nitrite (0.60 mL, 4.46 mmol) dropwise. After stirring for 1 h, the mixture was quenched with water and extracted with EtOAc. The organic layer was separated, dried over Na$_2$SO$_4$, concentrated under reduced pressure and purified by silica gel flash chromatography (0 to 35% EtOAc in hexanes) to afford tert-butyl 3-bromo-2-(2,6-dimethylphenyl)-6,7-dihydro-4H-pyrazolo[4,3-c]pyridine-5-carboxylate. MS: (ES) m z calculated for C$_{19}$H$_{25}$BrFN$_3$O$_2$[M+H]$^+$ 406.1, found 406.1.

Step b: To a suspension of tert-butyl 3-bromo-2-(2,6-dimethylphenyl)-6,7-dihydro-4H-pyrazolo[4,3-c]pyridine-5-carboxylate (35 mg, 0.086 mmol), indole-5-boronic acid (42 mg, 0.26 mmol) and K$_2$CO$_3$ (36 mg, 0.26 mmol) in toluene (1.5 mL) and water (0.2 mL) was added Pd(PPh$_3$)$_4$(30 mg, 0.026 mmol). The reaction mixture was degassed (N$_2$) for 2 min and stirred under N$_2$ at 110° C. for 3 h. The reaction mixture was cooled to room temperature, diluted with EtOAc, washed with brine and dried over Na$_2$SO$_4$. The solvent was removed under reduced pressure and the residue was purified by silica gel flash chromatography (0 to 45% EtOAc in hexanes) to afford tert-butyl 2-(2,6-dimethylphenyl)-3-(1H-indol-5-yl)-6,7-dihydro-4H-pyrazolo[4,3-c]pyridine-5-carboxylate. $^1$H NMR (400 MHz, CDCl$_3$) δ 8.27 (br s, 1H), 7.39 (s, 1H), 7.18 (m, 2H), 7.12 (dd, J=7.6, 7.6 Hz, 1H), 7.00 (d, J=7.6 Hz, 2H), 6.85 (dd, J=1.6, 8.0 Hz, 1H), 6.44 (br s, 1H), 4.66 (br s, 2H), 3.82 (br s, 2H), 2.89 (t, J=5.8 Hz, 2H), 1.99 (s, 6H), 1.50 (s, 9H). MS: (ES) m z calculated for C$_{27}$H$_{31}$N$_4$O$_2$ [M+H]$^+$ 443.2, found 443.2.

Example 68

Synthesis of 2-(2,6-dimethylphenyl)-3-(1H-indol-5-yl)-4,5,6,7-tetrahydropyrazolo[4,3-c]pyridine hydrochloride

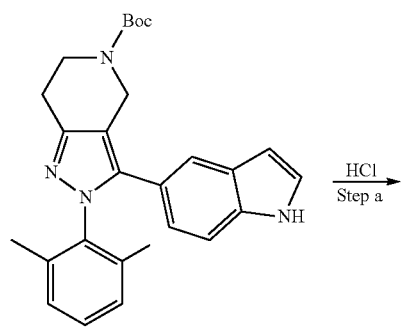

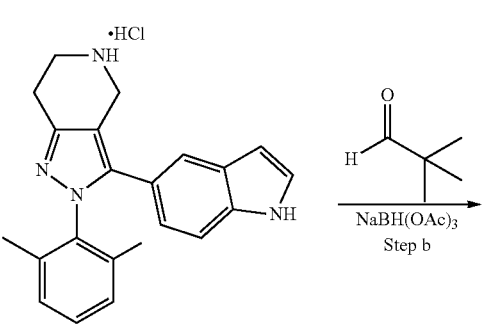

Step a: tert-butyl 2-(2,6-dimethylphenyl)-3-(1H-indol-5-yl)-6,7-dihydro-4H-pyrazolo[4,3-c]pyridine-5-carboxylate (81 mg, 0.18 mmol) was dissolved in dichloromethane (2 mL) and charged with HCl in dioxane (4N, 2 mL). The resulting mixture was stirred at room temperature for 1 h. The solvent was evaporated in vacuo to give 2-(2,6-dimethylphenyl)-3-(1H-indol-5-yl)-4,5,6,7-tetrahydropyrazolo[4,3-c]pyridine hydrochloride.

Step b: A mixture of 2-(2,6-dimethylphenyl)-3-(1H-indol-5-yl)-4,5,6,7-tetrahydropyrazolo[4,3-c]pyridine hydrochloride (25 mg, 0.066 mmol), 2,2-dimethylpropanal (100 mg, 1.16 mmol), NaBH(OAc)$_3$ (100 mg, 0.47 mmol), NEt$_3$ (0.015 mL, 0.11 mmol) and acetic acid (0.06 mL, 1 mmol) in DCM (1 mL) was stirred at 35° C. for 2 h. After cooling to room temperature, the reaction mixture was diluted with EtOAc, washed with aqueous NaHCO$_3$ and dried over Na$_2$SO$_4$. The solvent was removed under reduced pressure and the residue was purified by reverse-phased preparative HPLC to afford 2-(2,6-dimethylphenyl)-5-(2,2-dimethylpropyl)-3-(1H-indol-5-yl)-6,7-dihydro-4H-pyrazolo[4,3-c]pyridine. $^1$H NMR (400 MHz, CDCl$_3$) δ 8.35 (br s, 1H), 7.35 (s, 1H), 7.19 (d, J=8.4, 1H), 7.14 (m, 1H), 7.10 (d, J=7.6 Hz, 1H), 6.99 (d, J=7.6 Hz, 2H), 6.83 (dd, J=1.6, 8.8 Hz, 1H), 6.46 (m, 1H), 3.76 (br s, 2H), 2.93 (m, 4H), 2.33 (br s, 2H), 1.98 (br s, 6H), 0.92 (br s, 9H). MS: (ES) m z calculated for C$_{27}$H$_{33}$N$_4$ [M+H]$^+$ 413.2, found 413.2.

Example 69

Synthesis of 2-(2,6-diethylphenyl)-3-(1H-indol-5-yl)-5-(2-(trifluoromethyl)benzyl)-4,5,6,7-tetrahydro-2H-pyrazolo[4,3-c]pyridine

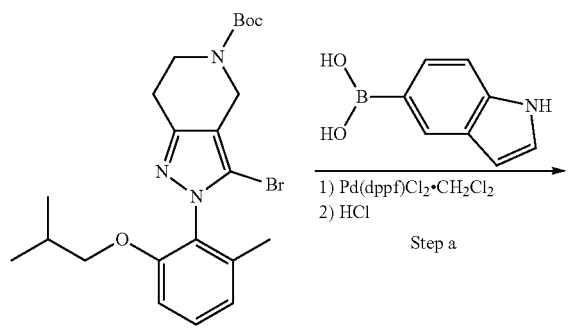

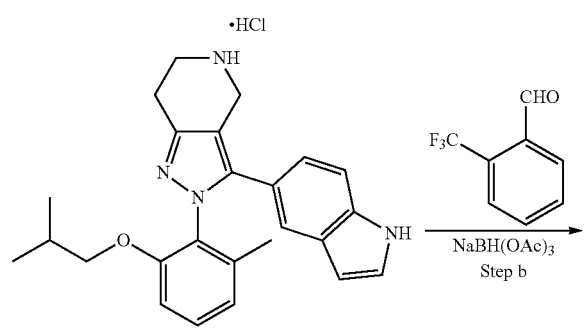

Step a: To a suspension of tert-butyl 3-bromo-2-(2-isobutoxy-6-methylphenyl)-6,7-dihydro-2H-pyrazolo[4,3-c]pyridine-5(4H)-carboxylate (500 mg, 1.08 mmol), 1H-indol-5-ylboronic acid (900 mg, 5.59 mmol), $K_2CO_3$ (2.0 g, 14.5 mmol) in p-dioxane (10 mL) and water (2 mL) was added Pd(dppf)Cl$_2$ complex with dichloromethane (200 mg, 0.24 mmol). The reaction mixture was degassed ($N_2$) for 2 min and stirred under $N_2$ at 100° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 30% EtOAc in hexanes) to give tert-butyl 3-(1H-indol-5-yl)-2-(2-isobutoxy-6-methylphenyl)-6,7-dihydro-2H-pyrazolo[4,3-c]pyridine-5(4H)-carboxylate. MS: (ES) m z calculated for $C_{30}H_{37}N_4O_3$ [M+H]$^+$ 501.2, found 501.2.

The above tert-butyl 3-(1H-indol-5-yl)-2-(2-isobutoxy-6-methylphenyl)-6,7-dihydro-2H-pyrazolo[4,3-c]pyridine-5(4H)-carboxylate was dissolved in dichloromethane (5 mL) and charged with HCl in dioxane (4N, 5 mL). The resulting mixture was stirred at room temperature for 2 h. After the reaction was complete, the solvent was evaporated in vacuo to give 3-(1H-indol-5-yl)-2-(2-isobutoxy-6-methylphenyl)-4,5,6,7-tetrahydro-2H-pyrazolo[4,3-c]pyridine hydrochloride. MS: (ES) m z calculated for $C_{25}H_{29}N_4O$ [M+H]$^+$ 401.2, found 401.2.

Step b: NaBH(OAc)$_3$ (75 mg, 0.36 mmol) was added to a mixture of 3-(1H-indol-5-yl)-2-(2-isobutoxy-6-methylphenyl)-4,5,6,7-tetrahydro-2H-pyrazolo[4,3-c]pyridine hydrochloride (30 mg, 0.07 mmol), 2-(trifluoromethyl)benzaldehyde (75 mg, 0.42 mmol), and N,N-diisopropylethylamine (0.2 mL, 1.15 mmol) in dicholomethane (10 mL) under magnetic stirring. The resulting mixture was stirred at 35° C. for 1 h. After cooling to room temperature, the reaction mixture was quenched with MeOH. The solvent was removed under reduced pressure and the residue was purified by HPLC (MeCN/H$_2$O, with 0.1% TFA) to afford 3-(7-chloro-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.17 (s, 1H), 7.94 (d, J=7.8 Hz, 1H), 7.62 (d, J=7.8 Hz, 1H), 7.51 (t, J=7.6 Hz, 1H), 7.43 (d, J=1.5 Hz, 1H), 7.08-7.35 (m, 4H), 6.95 (dt, J=1.3, 8.4 Hz, 1H), 6.44-6.77 (m, 3H), 3.92 (s, 2H), 3.81 (d, J=13.5 Hz, 1H), 3.71 (d, J=13.5 Hz, 1H), 3.57 (m, 2H), 2.82-2.91 (m, 4H), 2.04 (s, 3H), 1.92 (m, 1H), 0.83-0.88 (m, 6H). MS: (ES) m z calculated $C_{33}H_{34}F_3N_4O$ [M+H]$^+$ 559.3, found 559.3.

Example 70

Synthesis of 3-(1H-indol-5-yl)-2-(2-isobutoxy-6-methylphenyl)-5-(2-phenylpropan-2-yl)-4,5,6,7-tetrahydro-2H-pyrazolo[4,3-c]pyridine

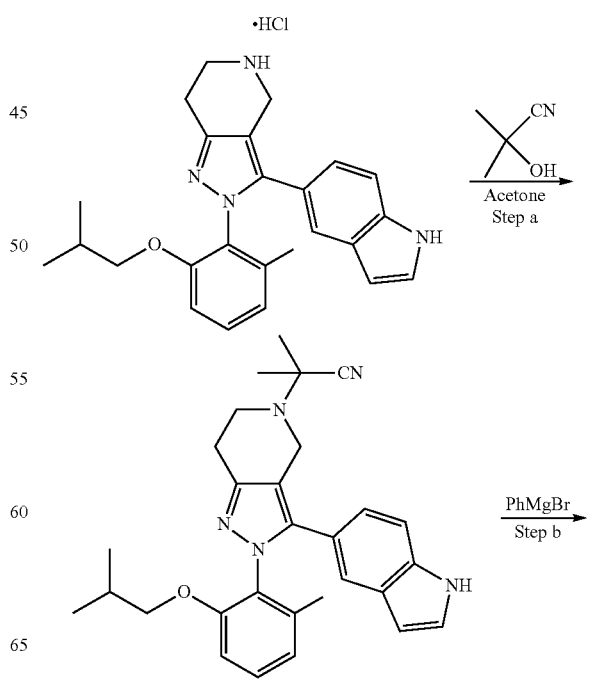

-continued

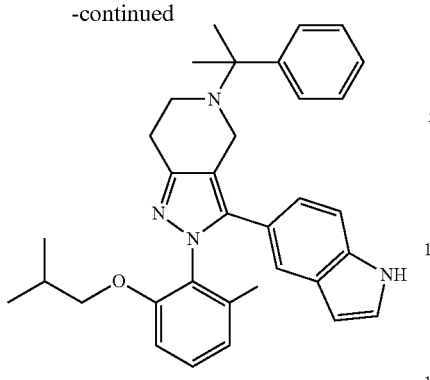

Step a: To a suspension of 3-(7-chloro-1H-indazol-4-yl)-2-(2,6-diethylphenyl)-4,5,6,7-tetrahydro-2H-pyrazolo[4,3-c]pyridine hydrochloride (50 mg, 0.11 mmol) in acetone (5 mL) under magnetic stirring was added N,N-diisopropylethylamine (0.1 mL, 0.58 mmol), followed by acetone cyanohydrin (1 mL, 10.95 mmol). The resulting mixture was stirred at room temperature overnight. The solvent was removed under reduced pressure and the residue was purified by silica gel flash chromatography (10 to 75% EtOAc in hexanes) to give 2-(3-(1H-indol-5-yl)-2-(2-isobutoxy-6-methylphenyl)-6,7-dihydro-2H-pyrazolo[4,3-c]pyridin-5(4H)-yl)-2-methylpropanenitrile. MS: (ES) m z calculated for $C_{29}H_{34}N_5O$ $[M+H]^+$ 468.3, found 468.2.

Step b: The above 2-(3-(1H-indol-5-yl)-2-(2-isobutoxy-6-methylphenyl)-6,7-dihydro-2H-pyrazolo[4,3-c]pyridin-5(4H)-yl)-2-methylpropanenitrile (25 mg, 0.05 mmol) was dissolved in THF (5 mL) and charged with a solution of phenylmagnesium bromide in THF (1 M, 1 mL, 1 mmol). The resulting mixture was stirred at room temperature overnight and quenched with aqueous $NH_4Cl$ solution. The reaction mixture was diluted with EtOAc, washed with brine and dried over $MgSO_4$. The solvent was removed under reduced pressure and and the residue was purified by Preparative TLC (45% EtOAc in hexanes) followed by HPLC (MeCN/$H_2O$, with 0.1% TFA) to afford 3-(1H-indol-5-yl)-2-(2-isobutoxy-6-methylphenyl)-5-(2-phenylpropan-2-yl)-4,5,6,7-tetrahydro-2H-pyrazolo[4,3-c]pyridine. $^1H$ NMR (400 MHz, $CDCl_3$) δ 8.13 (s, 1H), 7.61-7.68 (m, 2H), 7.47 (d, J=0.9 Hz, 1H), 7.07-7.37 (m, 5H), 7.00 (dd, J=1.7, 8.5 Hz, 1H), 6.63-6.76 (m, 2H), 6.48 (t, J=2.7 Hz, 1H), 3.91 (d, J=13.0 Hz, 1H), 3.82 (d, J=13.0 Hz, 1H), 3.52-3.64 (m, 2H), 2.62-2.80 (m, 4H), 2.04 (s, 3H), 1.93 (dq, J=6.8 Hz, 13.6, 1H), 1.45 (d, J=3.5 Hz, 6H), 0.86 (dd, J=3.5, 6.8 Hz, 6H). MS: (ES) m z calculated $C_{34}H_{39}N_4O$ $[M+H]^+$ 519.3, found 519.3.

Example 71

Synthesis of 3-(1H-indol-5-yl)-2-(2-isobutoxy-6-methylphenyl)-5-(1-(2-(trifluoromethyl)phenyl)ethyl)-4,5,6,7-tetrahydro-2H-pyrazolo[4,3-c]pyridine

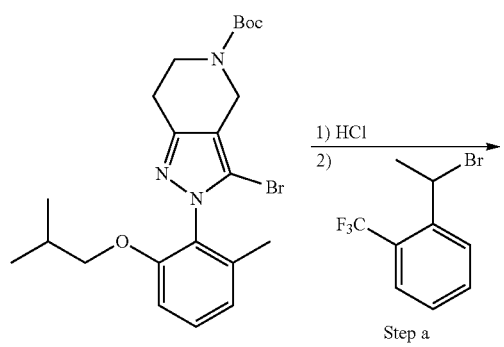

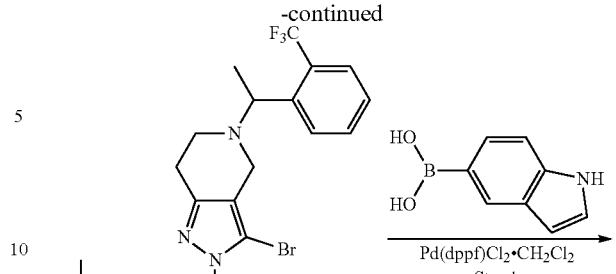

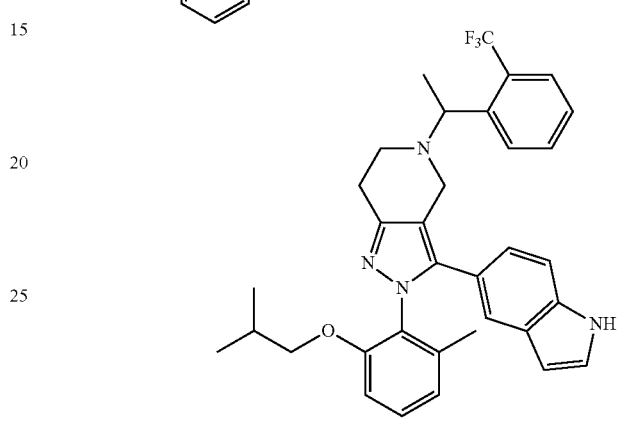

Step a: To a suspension of tert-butyl 3-bromo-2-(2-isobutoxy-6-methylphenyl)-6,7-dihydro-2H-pyrazolo[4,3-c]pyridine-5(4H)-carboxylate (1 g, 2.16 mmol) in dichloromethane (5 mL) was added a solution of HCl in dioxane (4N, 5 mL). The resulting mixture was stirred at room temperature for 2 h. The solvent was removed under reduced pressure and the residue was purified by silica gel flash chromatography (2 to 10% MeOH in dichloromethane with 1% $NH_4OH$) to give 3-bromo-2-(2-isobutoxy-6-methylphenyl)-4,5,6,7-tetrahydro-2H-pyrazolo[4,3-c]pyridine. MS: (ES) m z calculated for $C_{17}H_{23}BrN_3O$ $[M+H]^+$ 364.1, found 364.3.

The above 3-bromo-2-(2-isobutoxy-6-methylphenyl)-4,5,6,7-tetrahydro-2H-pyrazolo[4,3-c]pyridine (100 mg, 0.27 mmol) was dissolved in DMF (5 mL) and charged with $K_2CO_3$ (300 mg, 2.17 mmol) and 1-(1-bromoethyl)-2-(trifluoromethyl)benzene (100 mg, 0.40 mmol). The reaction mixture was stirred under $N_2$ at 50° C. for 14 h. The reaction mixture was diluted with EtOAc, washed with brine and dried over $MgSO_4$. The solvent was removed under reduced pressure and the residue was purified by silica gel flash chromatography (10 to 35% EtOAc in hexanes) to give 3-bromo-2-(2-isobutoxy-6-methylphenyl)-5-(1-(2-(trifluoromethyl)phenyl)ethyl)-4,5,6,7-tetrahydro-2H-pyrazolo[4,3-c]pyridine. MS: (ES) m z calculated for $C_{26}H_{30}BrF_3N_3O$ $[M+H]^+$ 536.1, found 536.4.

To a suspension of 3-bromo-2-(2-isobutoxy-6-methylphenyl)-5-(1-(2-(trifluoromethyl)phenyl)ethyl)-4,5,6,7-tetrahydro-2H-pyrazolo[4,3-c]pyridine (50 mg, 0.09 mmol), 1H-indol-5-ylboronic acid (150 mg, 0.93 mmol), and $K_2CO_3$ (300 mg, 2.17 mmol) in p-dioxane (6 mL) and water (1 mL) was added Pd(dppf)$Cl_2$ complex with dichloromethane (35 mg, 0.04 mmol). The reaction mixture was degassed ($N_2$) for 2 min and stirred under $N_2$ at 100° C. for 2 h. The reaction mixture was diluted with EtOAc, filtered through Celite, washed with brine and dried over $MgSO_4$. The solvent was removed under reduced pressure and the residue was purified by Preparative TLC (50% EtOAc in hexanes) followed by HPLC (MeCN/H$_2$O, with 1% TFA) to afford 3-(1H-indol-5-yl)-2-(2-isobutoxy-6-methylphenyl)-5-(1-(2-(trifluoromethyl)phenyl)ethyl)-4,5,6,7-tetrahydro-2H-pyrazolo[4,3-c]pyridine as a mixture of rotamers. $^1$H NMR (400 MHz, CDCl$_3$) δ 8.84 (m, 1H), 8.20-8.45 (m, 1H) 7.40-7.75 (m, 3H) 7.14-7.35 (m, 5H), 6.44-6.77 (m, 3H), 4.45-5.04 (m, 4H), 3.25-3.92 (m, 5H), 2.17 (s, 3H), 1.85 (m, 1H), 1.28 (s, 3H), 0.83-0.88 (m, 6H). MS: (ES) m z calculated C$_{34}$H$_{36}$F$_3$N$_4$O [M+H]$^+$ 573.3, found 573.3.

Example 72

Synthesis of 2-(2,6-diethylphenyl)-3-(1H-indol-5-yl)-5-(2-(trifluoromethyl)benzyl)-4,5,6,7-tetrahydro-2H-pyrazolo[4,3-c]pyridine

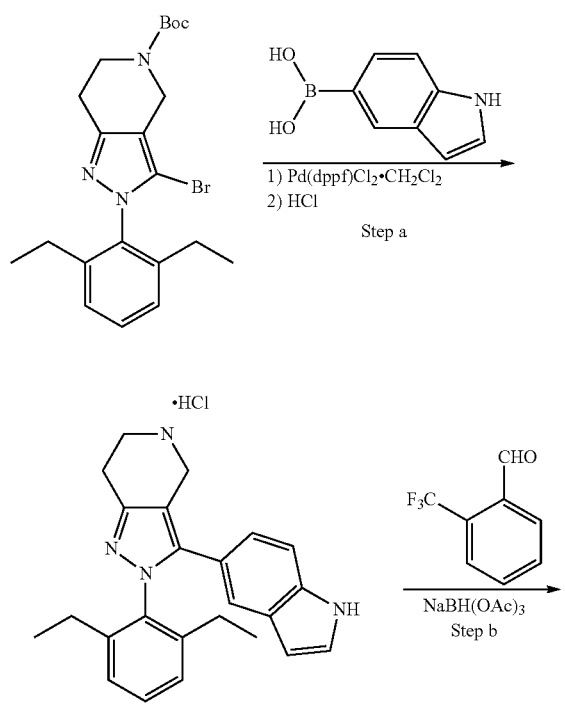

in p-dioxane (8 mL) and water (1 mL) was added Pd(dppf)Cl$_2$ complex with dichloromethane (200 mg, 0.24 mmol). The reaction mixture was degassed (N$_2$) for 2 min and stirred under N$_2$ at 100° C. for 2 h. The reaction mixture was diluted with EtOAc, filtered through Celite, washed with brine and dried over MgSO$_4$. The solvent was removed under reduced pressure and the residue was purified by silica gel flash chromatography (5 to 30% EtOAc in hexanes) to give tert-butyl 2-(2,6-diethylphenyl)-3-(1H-indol-5-yl)-6,7-dihydro-2H-pyrazolo[4,3-c]pyridine-5(4H)-carboxylate.
MS: (ES) m z calculated for C$_{29}$H$_{35}$N$_4$O$_2$ [M+H]$^+$ 471.2, found 471.2.

The above tert-butyl 2-(2,6-diethylphenyl)-3-(1H-indol-5-yl)-6,7-dihydro-2H-pyrazolo[4,3-c]pyridine-5(4H)-carboxylate was dissolved in dichloromethane (5 mL) and charged with a solution of HCl in dioxane (4N, 5 mL). The resulting mixture was stirred at room temperature for 2 h. After the reaction was complete, the solvent was evaporated in vacuo to give 2-(2,6-diethylphenyl)-3-(1H-indol-5-yl)-4,5,6,7-tetrahydro-2H-pyrazolo[4,3-c]pyridine hydrochloride.
MS: (ES) m z calculated for C$_{24}$H$_{27}$N$_4$[M+H]$^+$ 371.2, found 371.2.

Step b: NaBH(OAc)$_3$ (150 mg, 0.71 mmol) was added to a mixture of 2-(2,6-diethylphenyl)-3-(1H-indol-5-yl)-4,5,6,7-tetrahydro-2H-pyrazolo[4,3-c]pyridine hydrochloride (50 mg, 0.12 mmol), 2-(trifluoromethyl)benzaldehyde (100 mg, 0.57 mmol), and N,N-diisopropylethylamine (0.2 mL, 1.15 mmol) in dicholomethane (10 mL) under magnetic stirring. The resulting mixture was stirred at 35° C. for 1 h. After cooling to room temperature, the reaction mixture was quenched with MeOH. The solvent was removed under reduced pressure and the residue was purified by HPLC (MeCN/H$_2$O, with 0.1% TFA) to afford 3-(7-chloro-1H-indazol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.20 (s, 1H), 7.91-7.98 (m, 1H), 7.62 (dd, J=1.2, 7.6 Hz, 1H), 7.52 (t, J=7.6 Hz, 1H), 7.14-7.38 (m, 5H), 7.08 (d, J=7.6 Hz, 2H), 6.83 (dd, J=1.7, 8.5 Hz, 1H), 6.44 (m, 1H), 3.94 (s, 2H), 3.79 (s, 2H), 2.84-2.95 (m, 4H), 2.21-2.39 (m, 4H), 1.04 (dt, J=0.7, 7.6 Hz, 6H). MS: (ES) m z calculated C$_{32}$H$_{32}$F$_3$N$_4$ [M+H]$^+$ 529.3, found 529.3.

Example 73

Synthesis of 2-(2,6-diethylphenyl)-3-(1H-indol-5-yl)-5-(5-(trifluoromethyl)pyrimidin-2-yl)-4,5,6,7-tetrahydro-2H-pyrazolo[4,3-c]pyridine

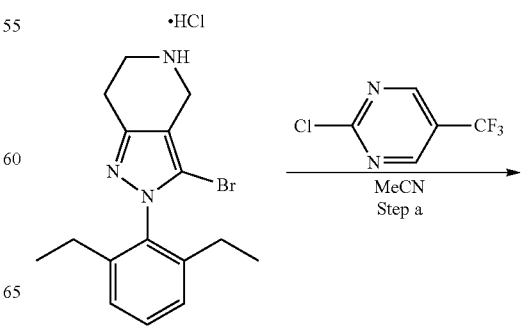

Step a: To a suspension of tert-butyl 3-bromo-2-(2,6-diethylphenyl)-6,7-dihydro-2H-pyrazolo[4,3-c]pyridine-5(4H)-carboxylate (500 mg, 1.2 mmol), 1H-indol-5-ylboronic acid (650 mg, 4.04 mmol), K$_2$CO$_3$ (1.2 g, 8.8 mmol)

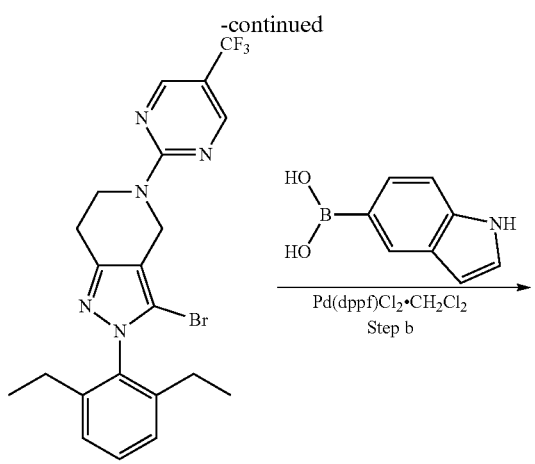

Step a: A mixture of 3-bromo-2-(2,6-diethylphenyl)-4,5,6,7-tetrahydropyrazolo[4,3-c]pyridine hydrochloride (700 mg, 1.89 mmol), 2-chloro-5-(trifluoromethyl)pyrimidine (420 mg, 2.30 mmol) and TEA (1 mL, 7.11 mmol) in CH$_3$CN (10 mL) was stirred at 80° C. for 1 h. After cooling to room temperature, the reaction mixture was diluted with EtOAc, washed with aqueous NaHCO$_3$ and dried over Na$_2$SO$_4$. The solvent was removed under reduced pressure and the residue was purified by silica gel flash chromatography (0 to 40% EtOAc in hexanes) to afford 3-bromo-2-(2,6-diethylphenyl)-5-(5-(trifluoromethyl)pyrimidin-2-yl)-4,5,6,7-tetrahydro-2H-pyrazolo[4,3-c]pyridine. MS: (ES) m z calculated for C$_{21}$H$_{22}$BrF$_3$N$_5$[M+H]$^+$ 480.1, found 480.1.

Step b: To a suspension of 3-bromo-2-(2,6-diethylphenyl)-5-(5-(trifluoromethyl)pyrimidin-2-yl)-4,5,6,7-tetrahydro-2H-pyrazolo[4,3-c]pyridine (70 mg, 0.15 mmol), 1H-indol-5-ylboronic acid (70 mg, 0.43 mmol), and K$_2$CO$_3$ (240 mg, 1.72 mmol) in p-dioxane (6 mL) and water (1 mL) was added Pd(dppf)Cl$_2$ complex with dichloromethane (50 mg, 0.06 mmol). The reaction mixture was degassed (N$_2$) for 2 min and stirred under N$_2$ at 100° C. for 1 h. The reaction mixture was cooled to room temperature, diluted with EtOAc, washed with brine, and dried over Na$_2$SO$_4$. The solvent was removed under reduced pressure and the residue was purified by preparative TLC (30% EtOAc in hexanes) followed by trituration in MeOH to give 2-(2,6-diethylphenyl)-3-(1H-indol-5-yl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.50 (s, 2H), 8.20 (s, 1H), 7.43 (s, 1H), 7.08-7.27 (m, 4H), 6.90 (dd, J=1.6, 8.8 Hz, 2H), 6.44-6.50 (m, 1H), 5.08 (s, 2H), 4.35 (t, J=6.0 Hz, 2H), 3.00 (t, J=6.0 Hz, 2H), 2.16-2.40 (m, 4H), 1.04 (t, J=7.2 Hz, 6H). MS: (ES) m z calculated for C$_{29}$H$_{28}$F$_3$N$_6$ [M+H]$^+$ 517.2, found 517.3.

Example 74

Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-1H-benzo[d]imidazol-7-yl)methanol

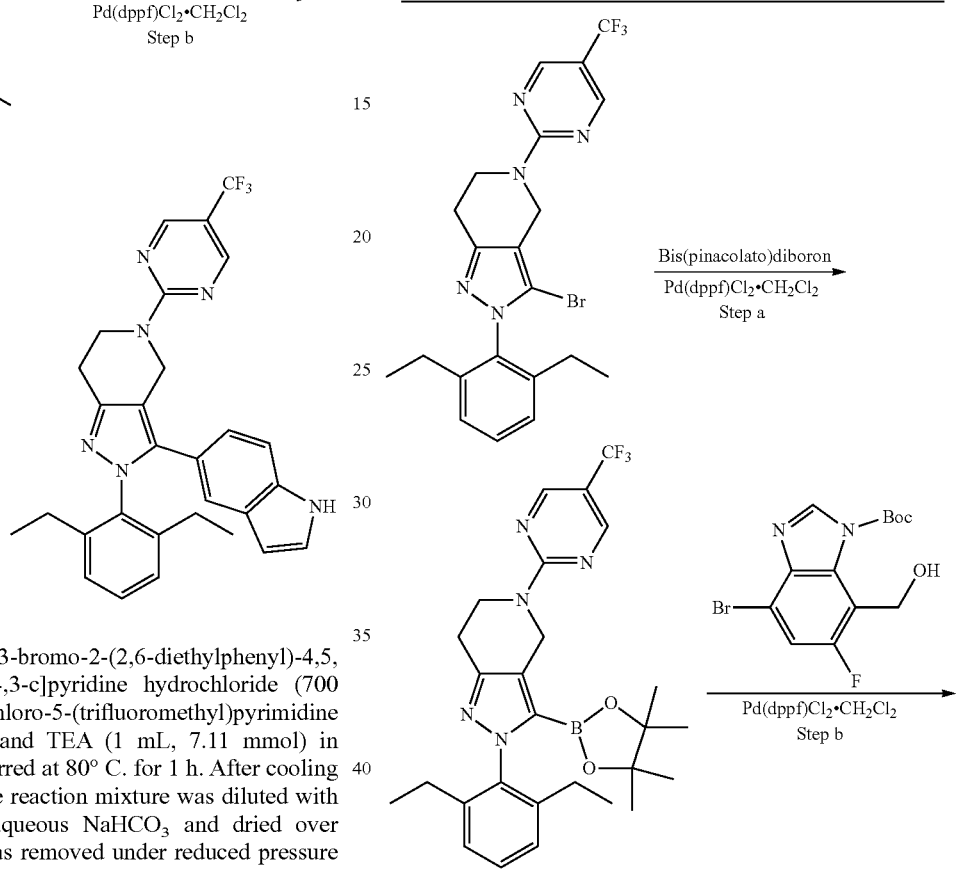

Step a: A mixture of 3-bromo-2-(2,6-diethylphenyl)-5-(5-(trifluoromethyl)pyrimidin-2-yl)-4,5,6,7-tetrahydro-2H-pyrazolo[4,3-c]pyridine (1.00 g, 2.08 mmol), 4,4,4',4',5,5,5',5'-octamethyl-2,2'-bi(1,3,2-dioxaborolane) (1.32 g, 5.2 mmol), K$_2$CO$_3$ (1.15 g, 8.3 mmol) and Pd(dppf)Cl$_2$ complex with dichloromethane (0.25 g, 0.3 mmol) in dioxane (12 mL) and water (0.7 mL) was stirred at 100° C. for 7 hours under nitrogen. It was then cooled to room temperature, diluted with 20% MeOH/DCM and filtered through celite. The filtrate was collected, dried over $Na_2SO_4$, concentrated on a rotary evaporator under reduced pressure. The residue was purified by silica gel flash chromatograph (0 to 100% EtOAc/hexanes) to give 2-(2,6-diethylphenyl)-3-(4,4,5,5-tetramethyl-1,3,2-dioxaborolan-2-yl)-5-(5-(trifluoromethyl) pyrimidin-2-yl)-4,5,6,7-tetrahydro-2H-pyrazolo[4,3-c]pyridine. MS: (ES) m z calculated for $C_{27}H_{33}BF_3N_5O_2$ [M+H]$^+$ 527.6, found 527.6.

Step b: A mixture of 2-(2,6-diethylphenyl)-3-(4,4,5,5-tetramethyl-1,3,2-dioxaborolan-2-yl)-5-(5-(trifluoromethyl) pyrimidin-2-yl)-4,5,6,7-tetrahydro-2H-pyrazolo[4,3-c]pyridine (0.400 g, 0.76 mmol), tert-butyl 4-bromo-6-fluoro-7-(hydroxymethyl)-1H-benzo[d]imidazole-1-carboxylate (0.345 g, 1 mmol), $K_2CO_3$ (0.368 g, 2.66 mmol) and Pd(dppf)Cl$_2$ complex with dichloromethane (0.15 g, 0.18 mmol) in dioxane (5 mL) and water (0.7 mL) was stirred at 100° C. for 3.5 hours under nitrogen. It was then cooled to room temperature, diluted with 20% MeOH/DCM and filtered through a plug of $Na_2SO_4$/celite. The filtrate was collected, dried over $Na_2SO_4$, concentrated on a rotary evaporator under reduced pressure. The obtained crude was stirred with a mixture of TFA (1 mL) and DCM (5 mL) for 1.5 hours. The mixture was basicified with aq. $NH_4OH$, extracted with IPA/CHCl$_3$ and purified by silica gel flash chromatograph (0 to 100% EtOAc/hexanes), followed by reverse phase HPLC to yield (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-1H-benzo[d]imidazol-7-yl)methanol. $^1$H NMR (400 MHz, CDCl$_3$) δ 7.53 (br s, 2H), 7.06 (s, 1H), 6.30 (m, 2H), 6.10 (m, 2H), 5.46 (d, J=11.6, 1H), 4.00 (m, 4H), 3.41 (m, 2H), 2.05 (m, 2H), 1.26 (m, 4H), 0.01 (br s, 6H). MS: (ES) m z calculated for $C_{29}H_{27}F_4N_7O$ [M+H]$^+$ 565.2, found 565.2.

Example 75

Synthesis of 3-(7-chloro-1H-pyrrolo[3,2-c]pyridin-4-yl)-2-(2,6-diethylphenyl)-5-(5-(trifluoromethyl)pyrimidin-2-yl)-4,5,6,7-tetrahydro-2H-pyrazolo[4,3-c]pyridine

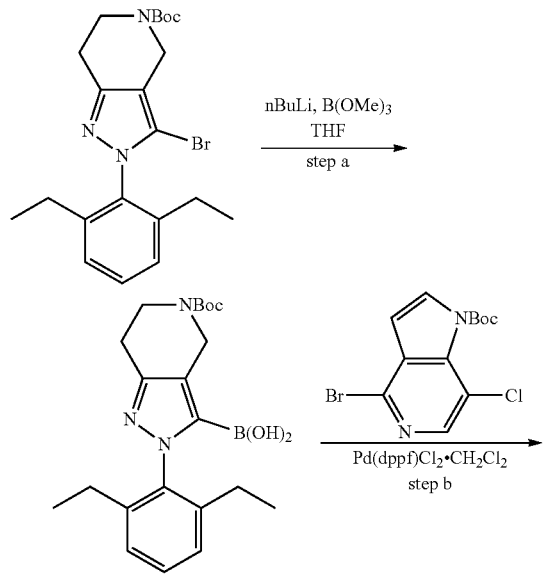

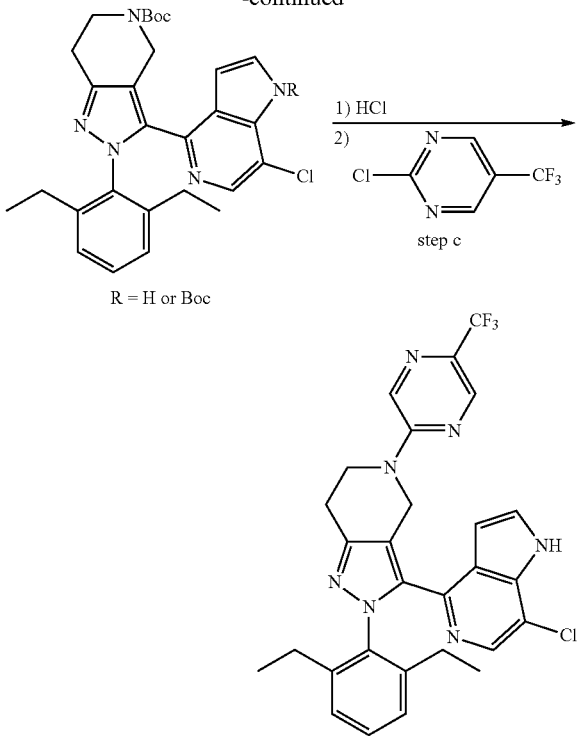

R = H or Boc

Step a: To a solution of tert-butyl 3-bromo-2-(2,6-diethylphenyl)-2,4,6,7-tetrahydro-5H-pyrazolo[4,3-c]pyridine-5-carboxylate (6.2 g, 14.3 mmol) in 56 mL of THF at –78° C. was added dropwise a 1.85 M solution of nBuLi in hexanes (9.9 mL, 18.3 mmol). After stirring at –78° C. for 1 hr, trimethyl borate (5 mL, 44.3 mmol) was added and the solution was warmed to room temperature and left stirring for 16 hrs. The reaction was quenched with 1 N HCl and the aqueous and organic layers were separated. The aqueous layer was extracted with ethyl acetate and the combined organic layers were dried with sodium sulfate, filtered and concentrated. The residue was purified by silica gel column chromatography (80% ethyl acetate in hexanes) to yield (5-(tert-butoxycarbonyl)-2-(2,6-diethylphenyl)-4,5,6,7-tetrahydro-2H-pyrazolo[4,3-c]pyridin-3-yl)boronic acid. MS: (ES) m z calculated for $C_{21}H_{30}BN_3O_4$[M+H]$^+$ 400.2, found 400.5.

Step b: To a solution of (5-(tert-butoxycarbonyl)-2-(2,6-diethylphenyl)-4,5,6,7-tetrahydro-2H-pyrazolo[4,3-c]pyridin-3-yl)boronic acid (0.42 g, 1.1 mmol) and tert-butyl 4-bromo-7-chloro-1H-pyrrolo[3,2-c]pyridine-1-carboxylate (0.35 g, 1.1 mmol) in 3.5 mL of dioxane was added a solution of potassium carbonate (0.58 g, 4.2 mmol) in 0.5 mL of H$_2$O followed by Pd(dppf)Cl$_2$ complex with dichloromethane (0.17 g, 0.2 mmol). The mixture was degassed with N$_2$ for five minutes then heated at 100° C. for 16 hrs. The contents were filtered and the filtrate was concentrated. The residue was purified by silica gel column chromatography (40% ethyl acetate in hexanes) to give tert-butyl 3-(7-chloro-1H-pyrrolo[3,2-c]pyridin-4-yl)-2-(2,6-diethylphenyl)-2,4,6,7-tetrahydro-5H-pyrazolo[4,3-c]pyridine-5-carboxylate (0.18 g, 0.35 mmol, 34%) and tert-butyl 3-(1-(tert-butoxycarbonyl)-7-chloro-1H-pyrrolo[3,2-c]pyridin-4-yl)-2-(2,6-diethylphenyl)-2,4,6,7-tetrahydro-5H-pyrazolo[4,3-c]pyridine-5-carboxylate. MS: (ES) m z calculated for $C_{29}H_{33}ClN_4O_2$ [M+H]$^+$ 506.2, found 506.2 and MS: (ES) m z calculated for $C_{33}H_{40}ClN_5O_4$[M+H]$^+$ 606.3, found 606.2.

Step c: To a solution of tert-butyl 3-(7-chloro-1H-pyrrolo[3,2-c]pyridin-4-yl)-2-(2,6-diethylphenyl)-2,4,6,7-tetrahydro-5H-pyrazolo[4,3-c]pyridine-5-carboxylate (0.18 g, 0.35 mmol) and tert-butyl 3-(1-(tert-butoxycarbonyl)-7-chloro-1H-pyrrolo[3,2-c]pyridin-4-yl)-2-(2,6-diethylphenyl)-2,4,6,7-tetrahydro-5H-pyrazolo[4,3-c]pyridine-5-carboxylate (0.79 g, 0.13 mmol) in 2 mL of dioxane was added a solution of 4.0 M HCl in dioxane (1 mL, 4 mmol). The solution was stirred at room temperature for 16 hrs and then heated to 50° C. for 2 hrs. The solvents were removed in vacuo and the residue was carried forward without further purification.

The crude material, 3-(7-chloro-1H-indol-4-yl)-2-(2,6-diethylphenyl)-4,5,6,7-tetrahydro-2H-pyrazolo[4,3-c]pyridine hydrochloride was re-dissolved in 2 mL of acetonitrile. To the solution was added Et$_3$N (0.27 mL, 1.9 mmol) followed by 2-chloro-5-(trifluoromethyl)pyrimidine (0.11 g, 0.6 mmol). The mixture was stirred as room temperature for 2 hrs then concentrated in vacuo. The residue was purified by silica gel column chromatography and the resultant solid was triturated with methanol to produce 3-(7-chloro-1H-pyrrolo[3,2-c]pyridin-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.69 (s, 1H), 8.42 (s, 2H), 8.06 (s, 1H), 7.21 (dd, J=2.7, 2.7 Hz, 1H), 7.12 (dd, J=7.7, 7.7 Hz, 1H), 6.94 (d, J=7.7 Hz, 2H), 6.44 (dd, J=3.3, 2.0 Hz, 1H), 4.85 (s, 2H), 4.28 (t, J=5.9 Hz, 2H), 2.97 (t, J=5.9 Hz, 2H), 2.34-2.16 (m, 4H) 0.95 (t, J=7.5 Hz, 6H). MS: (ES) m z calculated for C$_{28}$H$_{25}$ClF$_3$N$_7$[M+H]$^+$ 552.2, found 552.5.

Example 76

2-(2,6-diethylphenyl)-3-(3,6-difluoro-7-methoxy-1H-indol-4-yl)-5-(5-(trifluoromethyl)pyrimidin-2-yl)-4,5,6,7-tetrahydro-2H-pyrazolo[4,3-c]pyridine

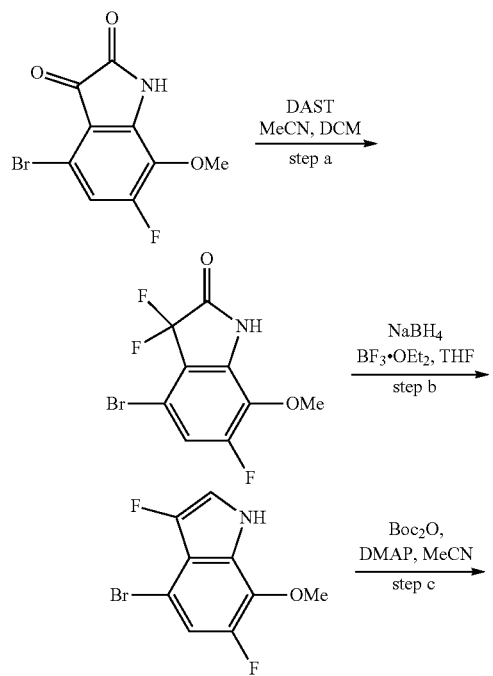

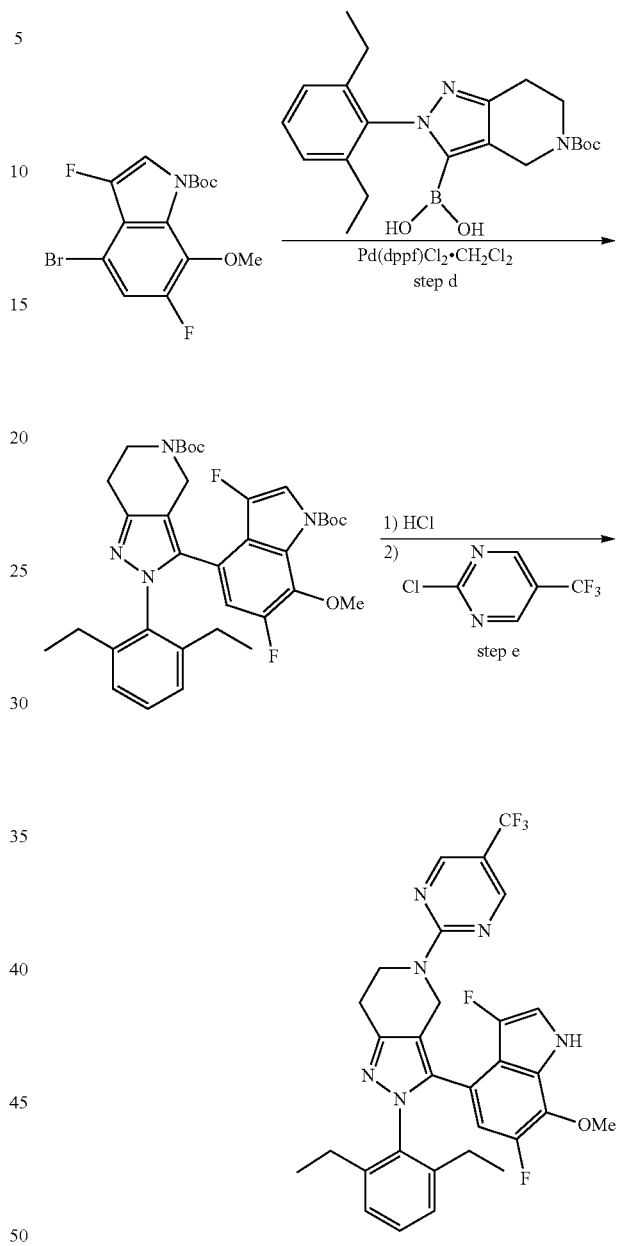

Step a: To a solution of 4-bromo-6-fluoro-7-methoxyindoline-2,3-dione (0.2 g, 0.73 mmol) in 4.9 mL acetonitrile was added a solution of DAST (0.24 mL, 1.8 mmol) in 0.5 mL of dichloromethane. The solution was heated at 60° C. for 16 hrs and another portion of DAST (0.24 mL, 1.8 mmol) was added and heating at 75° C. continued for another 24 hrs. The mixture was washed with water then the organic layer was dried with sodium sulfate, filtered and concentrated. The residue was purified on silica gel column chromatography to afford 4-bromo-3,3,6-trifluoro-7-methoxyindolin-2-one. MS: (ES) m z calculated for C$_9$H$_5$BrF$_3$NO$_2$ [M+H]$^+$ 296.0, found 296.2.

Step b: To a solution of 4-bromo-3,3,6-trifluoro-7-methoxyindolin-2-one (0.05 g, 0.17 mmol) in 0.9 mL of THF at 0° C. was added NaBH₄ (0.03 g, 0.7 mmol) followed by BF₃₀Et₂ (0.16 mL, 1.3 mmol). The mixture was stirred at room for 16 hrs then heated at 75° C. for 24 hrs. The reaction was quenched with 1 N HCl then neutralized with NaOH. The organic and aqueous layers were separated and the aqueous layer was extracted with dichloromethane. The combined organic layers were dried with sodium sulfate, filtered and concentrated. The residue was purified by silica gel column chromatography to provide 4-bromo-3,6-difluoro-7-methoxy-1H-indole.

Step c: To a solution of 4-bromo-3,6-difluoro-7-methoxy-1H-indole (0.03 g, 0.12 mmol) in 1 mL of acetonitrile was added di-tert-butyl dicarbonate (0.1 mL, 0.44 mmol) followed by DMAP (0.02 g, 13 mmol). The solution was stirred at room temperature for 30 min then concentrated in vacuo. The residue was purified by silica gel column chromatography (100% hexanes) to give tert-butyl 4-bromo-3,6-difluoro-7-methoxy-1H-indole-1-carboxylate.

Step d: To a solution of (5-(tert-butoxycarbonyl)-2-(2,6-diethylphenyl)-4,5,6,7-tetrahydro-2H-pyrazolo[4,3-c]pyridin-3-yl)boronic acid (0.03 g, 0.08 mmol) and tert-butyl 4-bromo-3,6-difluoro-7-methoxy-1H-indole-1-carboxylate (0.03 g, 0.08 mmol) in 0.3 mL of dioxane was added a solution of potassium carbonate (0.03 g, 0.23 mmol) in 0.05 mL of H₂O followed by Pd(dppf)Cl₂ complex with dichloromethane (0.02 g, 0.02 mmol). The mixture was degassed with N₂ for five minutes then heated at 100° C. for 2 hrs. The contents were filtered and the filtrate was concentrated. The residue was purified by silica gel column chromatography (40% ethyl acetate in hexanes) to provide tert-butyl 3-(1-(tert-butoxycarbonyl)-3,6-difluoro-7-methoxy-1H-indol-4-yl)-2-(2,6-diethylphenyl)-2,4,6,7-tetrahydro-5H-pyrazolo[4,3-c]pyridine-5-carboxylate. MS: (ES) m z calculated for C₃₅H₄₂F₂N₄O₅[M+H]⁺ 637.3, found 637.6.

Step e: To a solution of tert-butyl 3-(1-(tert-butoxycarbonyl)-3,6-difluoro-7-methoxy-1H-indol-4-yl)-2-(2,6-diethylphenyl)-2,4,6,7-tetrahydro-5H-pyrazolo[4,3-c]pyridine-5-carboxylate (0.027 g, 0.04 mmol) in 1 mL of dioxane was added a solution of 4.0 M HCl in dioxane (1 mL, 4 mmol). The solution was stirred at room temperature for 1 hr then heated at 50° C. for 16 hrs. The solvents were removed in vacuo and the residue was carried forward without further purification.

The crude material, 2-(2,6-diethylphenyl)-3-(3,6-difluoro-7-methoxy-1H-indol-4-yl)-4,5,6,7-tetrahydro-2H-pyrazolo[4,3-c]pyridine was re-dissolved in 0.5 mL of acetonitrile. To the solution was added Et₃N (0.03 mL, 0.17 mmol) followed by 2-chloro-5-(trifluoromethyl)pyrimidine (0.009 g, 0.05 mmol). The mixture was stirred as room temperature for 2 hrs then concentrated in vacuo. The residue was purified by preparatory HPLC to yield 2-(2,6-diethylphenyl)-3-(3,6-difluoro-7-methoxy-1H-indol-4-yl)-5-(5-(trifluoromethyl)pyrimidin-2-yl)-4,5,6,7-tetrahydro-2H-pyrazolo[4,3-c]pyridine (12 mg, 0.02 mmol, 49%). ¹H NMR (400 MHz, CDCl₃) δ 8.47 (s, 1H), 7.94 (s, 1H), 7.26-7.19 (m, 3H), 7.02 (d, J=2.1 Hz, 1H), 6.91 (d, J=7.1 Hz, 1H), 6.40 (d, J=13.3 Hz, 1H), 4.89 (d, J=15.8 Hz, 1H), 4.80-4.65 (m, 1H), 4.70 (d, J=15.8 Hz, 1H), 4.07 (d, J=2.8, 3H), 4.04-3.89 (m, 1H), 3.08-2.93 (m, 2H), 2.61-2.50 (m, 2H), 2.23-2.14 (m, 1H), 1.99-1.89 (m, 1H), 1.31 (t, J=7.5 Hz, 3H), 0.78 (t, J=7.5 Hz). MS: (ES) m z calculated for C₃₀H₂₇F₅N₆O [M+H]⁺ 583.2, found 583.5.

Example 77

The compounds in Table 1 and Table 2, below, were prepared using the methods described above. Characterization data (MS and/or NMR) is provided for each compound listed.

TABLE 1

| Structure & NMR/MS Characterization Data of Specific Embodiments | | |
|---|---|---|
| Structure | ¹H NMR | MS |
| 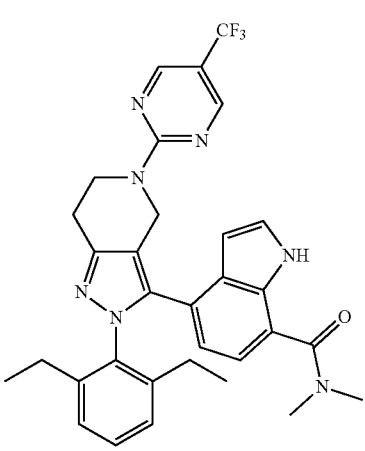 [SMILES: CCc1cccc(CC)c1-n1nc2c(c1-c1ccc(C(=O)N(C)C)c3[nH]ccc13)CN(c1ncc(C(F)(F)F)cn1)CC2]<br>Ex. 77.001 | ¹H NMR (400 MHZ, CDCl₃) δ 9.29 (s, 1H), 8.48 (s, 2H), 7.07-7.37 (m, 2H), 6.99-7.07 (m, 3H), 6.59 (dd, J = 0.9, 7.7, 1H), 6.50 (td, J = 1.3, 2.3, 1H), 4.86 (br s, 2H), 4.37 (br s, 2H), 3.14 (d, J = 0.9, 6H), 3.05 (t, J = 5.9, 2H), 2.15-2.44 (m, 4H), 0.87-1.08 (m, 6H). | MS: (ES) m/z calculated C₃₂H₃₃F₃N₇O [M + H]⁺ 588.3, found 588.2. |

TABLE 1-continued

Structure & NMR/MS Characterization Data of Specific Embodiments

| Structure | ¹H NMR | MS |
|---|---|---|
| 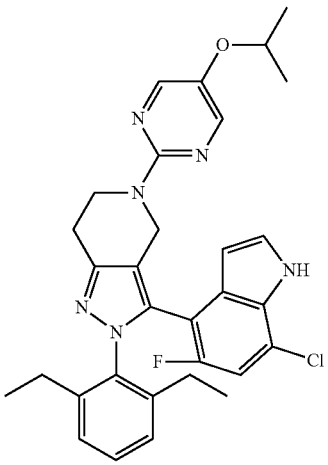<br>Ex. 77.002 | ¹H NMR (400 MHZ, CDCl₃) δ 8.51 (br s, 1H), 8.07 (s, 2H), 7.28 (t, J = 6.0, 1H), 7.19 (t, J = 7.6, 1H), 7.15 (m, 1H), 6.88 (dd, J = 6.4, 1.2, 1H), 6.83 (d, J = 10, 1H), 6.45 (dd, J = 2.6, 2.6, 1H), 4.71 (d, J = 16, 1H), 4.57 (d, J = 16, 1H), 4.34 (m, 1H), 4.28 (m, 1H), 4.15 (m, 1H), 3.03 (dd, J = 5.8, 5.8, 2H), 2.50 (sextet, J = 7.2, 1H), 2.43 (sextet, J = 7.6, 1H), 2.16 (sextet, J = 7.5, 1H), 1.92 (sextet, J = 7.6, 1H), 1.29 (d, J = 6.0, 6H), 1.21 (t, J = 7.6, 3H), 0.75 (t, J = 7.6, 3H). | MS: (ES) m/z calculated for $C_{31}H_{32}ClFN_6O[M + H]^+$ 559.2, found 559.2. |
| 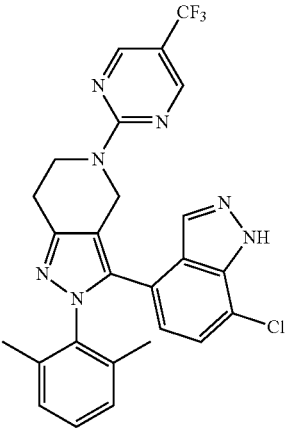 [SMILES: Cc1cccc(C)c1-n1nc2c(c1-c1ccc(Cl)c3[nH]ncc13)CN(c1ncc(C(F)(F)F)cn1)CC2]<br>Ex. 77.003 | ¹H NMR (400 MHz, d₆-DMSO) δ 8.69 (br s, 2H), 8.19 (s, 1H), 7.35 (d, J = 8.0, 1H), 7.17 (t, J = 8.0, 1H), 7.06 (d, J = 8.0, 2H), 6.60 (d, J = 8.0, 1H), 4.84 (s, 2H), 4.34 (t, J = 5.2, 2H), 2.94 (t, J = 5.2, 2H), 1.88 (s, 6H). | MS: (ES) m/z calculated for $C_{26}H_{22}ClF_3N_7 [M + H]^+$ 524.2, found 524.2. |
| 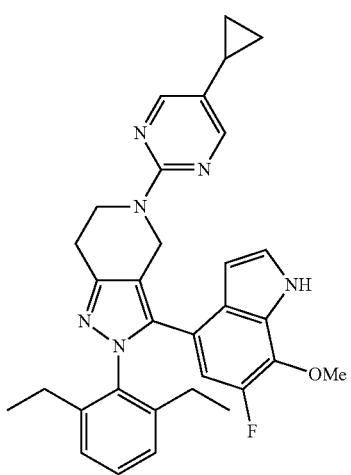 [SMILES: CCc1cccc(CC)c1-n1nc2c(c1-c1cc(F)c(OC)c3[nH]ccc13)CN(c1ncc(C3CC3)cn1)CC2]<br>Ex. 77.004 | ¹H NMR (400 MHz, CDCl₃) δ 8.41 (s, 1H), 8.11 (s, 2H), 7.17-7.30 (m, 2H), 7.04 (d, J = 7.7, 2H), 6.36-6.47 (m, 2H), 4.72 (s, 2H), 4.26 (t, J = 5.6, 2H), 4.05 (d, J = 2.5, 2H), 3.00 (t, J = 5.9, 2H), 2.10-2.36 (m, 4H), 1.69 (m, 1H), 0.91 (m, 6H), 0.88 (m, 2H), 0.59 (m, 2H). | MS: (ES) m/z calculated $C_{32}H_{34}FN_6O [M + H]^+$ 537.3, found 537.2. |

TABLE 1-continued

Structure & NMR/MS Characterization Data of Specific Embodiments

| Structure | ¹H NMR | MS |
|---|---|---|
| Ex. 77.005 | ¹H NMR (400 MHz, d₆-DMSO) δ 13.5 (s, 1H), 8.27 (s, 1H), 7.97 (s, 1H), 7.93 (dd, J = 1.6, 14, 1H), 7.25 (t, J = 8.4, 1H), 7.09 (d, J = 8.4, 2H), 6.68 (d, J = 8.0, 1H), 6.48 (d, J = 8.0, 1H), 4.57 (s, 2H), 4.04 (t, J = 5.2, 2H), 3.87 (s, 3H), 2.96 (t, J = 5.2, 2H), 2.02-2.26 (m, 4H), 0.89 (t, J = 7.2, 6H). | MS: (ES) m/z calculated for $C_{30}H_{29}F_4N_6O$ [M + H]⁺ 565.2, found 565.2. |
| Ex. 77.006 | ¹H NMR (400 MHz, CDCl₃) δ 8.47 (br s, 1H), 8.07 (s, 2H), 7.21 (t, J = 7.6, 1H), 7.18 (dd, J = 2.8, 2.8, 1H), 7.04 (d, J = 7.6, 2H), 6.43 (dd, J = 2.4, 2.4, 1H), 6.40 (d, J = 13.6, 1H), 4.69 (s, 2H), 4.20-4.32 (m, 3H), 4.04 (d, J = 2.8, 3H), 3.01 (t, J = 5.8, 2H), 2.12-2.40 (2 br s, 4H), 1.29 (d, J = 6.0, 6H), 1.00 (br s, 6H). | MS: (ES) m/z calculated for $C_{32}H_{35}FN_6O_2$[M + H]⁺ 555.3, found 555.3. |
| Ex. 77.007 | ¹H NMR (400 MHZ, CDCl₃) δ 8.64 (br s, 1H), 8.13 (d, J = 1.2, 1H), 8.05 (dd, J = 2.2, 1H), 7.82 (d, J = 2.8, 1H), 7.32 (dd, J = 2.8, 2.8, 1H), 7.22 (d, J = 7.6, 1H), 7.03 (br d, J = 7.2, 2H), 6.98 (d, J = 8.0, 1H), 6.56 (d, J = 7.6, 1H), 6.53 (dd, J = 2.8, 2.8, 1H), 4.56 (s, 2H), 4.15 (t, J = 5.8, 2H), 3.07 (t, J = 5.8, 2H), 2.15-2.40 (2 br s, 4H), 0.99 (br s, 6H). | MS: (ES) m/z calculated for $C_{28}H_{27}ClN_6$ [M + H]⁺ 483.2, found 483.2. |

TABLE 1-continued

Structure & NMR/MS Characterization Data of Specific Embodiments

| Structure | ¹H NMR | MS |
|---|---|---|
| 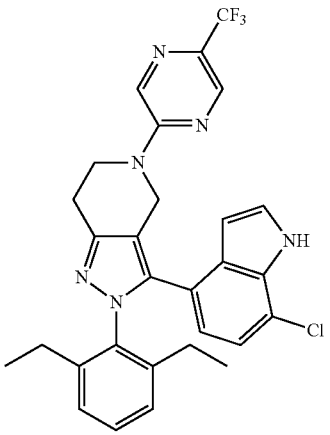 [SMILES: CCc1cccc(CC)c1-n1nc2c(c1-c1ccc(Cl)c3[nH]ccc13)CN(c1cnc(C(F)(F)F)cn1)CC2]<br>Ex. 77.008 | ¹H NMR (400 MHZ, CDCl₃) δ 8.58 (br s, 1H), 8.37 (s, 1H), 8.13 (d, J = 1.2, 1H), 7.35 (dd, J = 5.8, 1H), 7.23 (t, J = 7.8, 1H), 7.04 (br d, J = 6.4, 2H), 6.98 (d, J = 8.0, 1H), ), 6.56 (d, J = 7.6, 1H), ), 6.50 (dd, J = 2.6, 2.6, 1H), 4.66 (br s, 2H), 4.22 (t, J = 5.6, 2H), 3.09 (t, J = 5.8, 2H), 2.15-2.40 (2 br s, 4H), 0.99 (br s, 6H). | MS: (ES) m/z calculated for $C_{29}H_{26}ClF_3N_6$ [M + H]⁺ 551.1, found 551.1. |
| 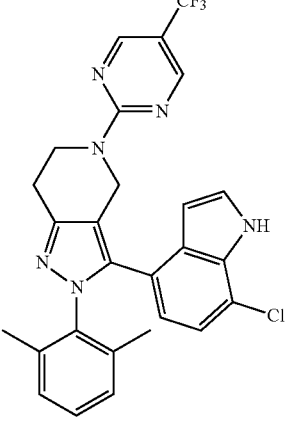<br>Ex. 77.009 | ¹H NMR (400 MHZ, d₆-DMSO) δ 11.74 (s, 1H), 8.67 (br s, 2H), 7.54 (t, J = 2.8, 1H), 7.13 (t, J = 7.6, 1H), 7.02 (d, J = 8.0, 2H), 6.46-6.54 (m, 2H), 4.76 (br s, 2H), 4.30 (br s, 2H), 2.91 (t, J = 5.6), 1.88 (br s, 6H). | MS: (ES) m/z calculated for $C_{27}H_{23}ClF_3N_6$ [M + H]⁺ 523.2, found 523.2. |
| 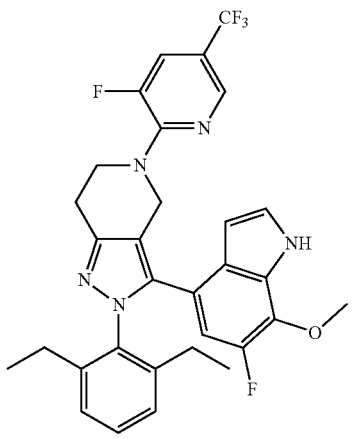 [SMILES: CCc1cccc(CC)c1-n1nc2c(c1-c1cc(F)c(OC)c3[nH]ccc13)CN(c1ncc(C(F)(F)F)cc1F)CC2]<br>Ex. 77.010 | ¹H NMR (400 MHz, CDCl₃) δ 8.38 (br s, 1H), 8.11 (br s, 1H), 7.30 (dd, J = 13.2, 2.0, 1H), 7.10-7.18 (m, 2H), 6.97 (d, J = 7.6, 2H), 6.30-7.36 (m, 2H), 4.55 (br s, 2H), 3.97 (m, 5H), 3.02 (t, J = 5.6, 2H), 2.18 (m, 4H), 0.92 (br s, 6H). | MS: (ES) m/z calculated for $C_{31}H_{28}F_5N_5O$ [M + H]⁺ 582.2, found 582.2. |

TABLE 1-continued

Structure & NMR/MS Characterization Data of Specific Embodiments

| Structure | ¹H NMR | MS |
|---|---|---|
| 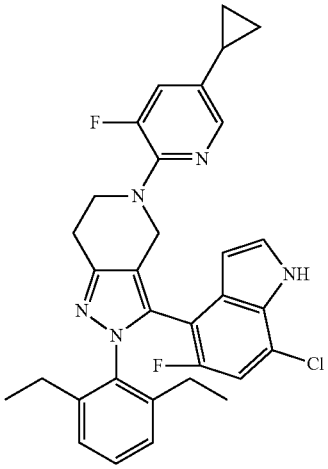 [SMILES: CCc1cccc(CC)c1-n1nc2c(c1-c1c(F)cc(Cl)c3[nH]ccc13)CN(c1ncc(C3CC3)cc1F)CC2]<br>Ex. 77.011 | ¹H NMR (400 MHz, CDCl₃) δ 8.43 (br s, 1H), 7.72 (s, 1H), 7.17 (m, 1H), 7.11 (dd, J = 7.8, 7.8, 1H), 7.08 (m, 1H), 6.84 (dd, J = 13.6, 1.2, 1H), 6.80 (dd, J = 7.6, 1.6, 1H), 6.74 (d, J = 10, 1H), 6.41 (dd, J = 2.8, 2.8, 1H), 4.41 (d, J = 15.2, 1H), 4.15 (d, J = 15.2, 1H), 3.75 (m, 2H), 3.04 (dd, J = 5.6, 5.6, 2H), 2.45 (sextet, J = 7.2, 1H), 2.35 (sextet, J = 7.6, 1H), 2.08 (sextet, J = 7.6, 1H), 1.85 (sextet, J = 7.2, 1H), 1.73 (m, 1H), 1.15 (t, J = 7.4, 3H), 0.84 (m, 2H), 0.67 (t, J = 7.6, 3H), 0.52 (m, 2H). | MS: (ES) m/z calculated for $C_{32}H_{30}ClF_2N_5$ [M + H]⁺ 558.1, found 558.2. |
| 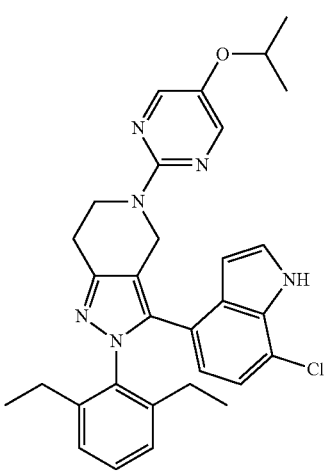 [SMILES: CCc1cccc(CC)c1-n1nc2c(c1-c1ccc(Cl)c3[nH]ccc13)CN(c1ncc(OC(C)C)cn1)CC2]<br>Ex. 77.012 | ¹H NMR (400 MHz, CDCl₃) δ 8.45 (br s, 1H), 7.98 (s, 2H), 7.19 (t, J = 2.8, 1H), 7.12 (t, J = 7.6, 1H), 6.94 (br d, J = 7.2, 2H), 6.85 (d, J = 7.6, 1H), 6.46 (m, 2H), 4.61 (br s, 2H), 4.18 (m, 3H), 2.94 (t, J = 5.8, 2H), 2.00-2.38 (2 br s, 4H), 1.20 (d, J = 6.0, 6H), 0.90 (br s, 6H). | MS: (ES) m/z calculated for $C_{31}H_{33}ClN_6O$ [M + H]⁺ 541.2, found 541.2. |
| 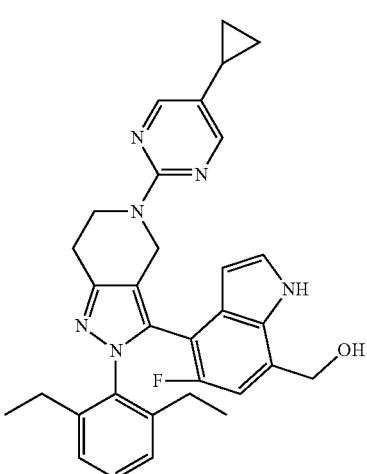<br>Ex. 77.013 | ¹H NMR (400 MHz, CDCl₃) δ 8.96 (br s, 1H), 8.10 (s, 2H), 7.22 (t, J = 2.8, 1H), 7.17 (t, J = 7.8, 1H), 7.13 (m, 1H), 6.79 (d, J = 10, 1H), 6.49 (d, J = 10, 1H), 6.37 (t, J = 5.2, 1H), 4.72 (m, 2H), 4.62 (m, 2H), 4.44 (m, 1H), 4.12 (quint, J = 6.4, 1H), 3.10 (br s, 1H), 3.02 (t, J = 5.8, 2H), 2.52 (sextet, J = 7.3, 1H), 2.42 (sextet, J = 7.6, 1H), 2.17 (m, 1H), 1.95 (sextet, J = 7.6, 1H), 1.68 (m, 1H), 1.21 (t, J = 7.6, 3H), 0.87 (m, 2H), 0.76 (t, J = 7.4, 3H), 0.55 (m, 2H). | MS: (ES) m/z calculated for $C_{32}H_{33}FN_6O$ [M + H]⁺ 537.2, found 537.2. |

TABLE 1-continued

Structure & NMR/MS Characterization Data of Specific Embodiments

| Structure | ¹H NMR | MS |
| --- | --- | --- |
| Ex. 77.014 | ¹H NMR (400 MHz, CDCl₃) δ 8.51 (br s, 1H), 7.11 (m, 1H), 7.05 (t, J = 7.6, 1H), 6.86 (m, 3H), 6.79 (d, J = 8.4, 1H), 6.69 (d, J = 9.6, 1H), 6.39 (d, J = 7.6, 1H), 6.35 (m, 1H), 4.40 (br s, 2H), 3.96 (m, 3H), 2.93 (t, J = 5.8, 2H), 1.95-2.30 (2 br s, 4H), 1.80-1.93 (m, 2H), 1.10 (t, J = 7.2, 2H), 0.83 (m, 6H). | MS: (ES) m/z calculated for $C_{31}H_{31}ClN_6$ [M + H]⁺ |
| Ex. 77.015 | ¹H NMR (400 MHZ, CDCl₃) δ 8.33 (br s, 1H), 7.78 (d, J = 1.6, 1H), 7.08-7.16 (m, 2H), 7.05 (t, J = 7.6, 1H), 6.88 (br s, 2H), 6.78 (d, J = 8.0, 1H), 6.40 (m, 2H), 4.13 (br s, 2H), 3.57 (t, J = 5.6, 2H), 3.00 (t, J = 5.6, 2H), 1.95-2.30 (2 br s, 4H), 1.65 b(m, 1H), 1.70-1.00 (m, 8H), 0.47 (m, 2H). | MS: (ES) m/z calculated for $C_{32}H_{31}Cl_2N_5$ [M + H]⁺ 556.2, found 556.2. |
| Ex. 77.016 | ¹H NMR (400 MHz, CDCl₃) δ 9.15 (br s, 1H), 8.18 (s, 1H), 7.38 (dd, J = 13.2, 2.0, 1H), 7.26 (m, 1H), 7.22 (t, J = 7.6, 1H), 7.04 (br d, J = 6.8, 2H), 6.46 (m, 1H), 6.37 (d, J = 11.2, 1H), 5.07 (d, J = 5.6, 2H), 4.64 (br s, 2H), 4.07 (t, J = 5.6, 2H), 3.11 (t, J = 5.6, 2H), 2.10-2.40 (2 br s, 4H), 2.00 (t, J = 5.6, 1H), 1.02 (br s, 6H). | MS: (ES) m/z calculated for $C_{31}H_{28}F_5N_5O$ [M + H]⁺ 582.2, found 582.2. |

TABLE 1-continued

Structure & NMR/MS Characterization Data of Specific Embodiments

| Structure | ¹H NMR | MS |
|---|---|---|
| Ex. 77.017 | ¹H NMR (400 MHZ, CD₃OD) δ 8.27 (s, 1H), 8.22 (d, J = 3.2, 1H), 7.66 (dd, J = 1.7, 14, 1H), 7.29 (t, J = 7.6, 1H), 7.12 (d, J = 7.6, 2H), 6.96 (dd, J = 7.6, 10, 1H), 6.65 (dd, J = 4.4, 8.0, 1H), 4.71 (s, 2H), 4.15 (t, J = 5.6, 2H), 3.04 (t, J = 5.6, 2H), 2.12-2.36 (m, 4H), 0.99 (t, J = 7.6, 6H). | MS: (ES) m/z calculated for $C_{29}H_{26}F_5N_6$ [M + H]⁺ 553.2, found 553.2. |
| Ex. 77.018 | ¹H NMR (400 MHZ, CD₃OD) δ 8.25 (s, 1H), 7.64 (dd, J = 2.2, 14, 1H), 7.36 (s, 1H), 7.33 (t, J = 8.4, 1H), 7.26 (d, J = 8.4, 1H), 7.21-7.24 (m, 1H), 7.16 (d, J = 7.6, 2H), 6.87 (dd, J = 1.6, 8.4, 1H), 6.36 (d, J = 3.2, 1H), 4.10 (T, J = 6.0, 2H), 3.64 (s, 2H), 3.02 (t, J = 6.0, 2H), 2.17-2.37 (m, 4H), 1.03 (t, J = 8.0, 6H). | MS: (ES) m/z calculated for $C_{30}H_{28}F_4N_5$ [M + H]+ 534.2, found 534.2. |
| Ex. 77.019 | ¹H NMR (400 MHZ, CD₃OD) δ 8.26 (s, 1H), 7.65 (dd, J = 2.1, 14, 1H), 7.37 (t, J = 7.6, 1H), 7.29 (d, J = 3.2, 1H), 7.18-7.23 (m, 3H), 6.57 (dd, J = 1.0, 12, 1H), 6.45 (t, J = 3.4, 1H), 4.10 (t, J = 5.6, 2H), 3.02 (t, J = 5.6, 2H), 2.18-2.39 (m, 4H), 1.04 (t, J = 7.6, 6H). | MS: (ES) m/z calculated for $C_{30}H_{27}F_5N_5$ [M + H]⁺ 552.2, found 552.2. |

TABLE 1-continued

Structure & NMR/MS Characterization Data of Specific Embodiments

| Structure | ¹H NMR | MS |
|---|---|---|
| 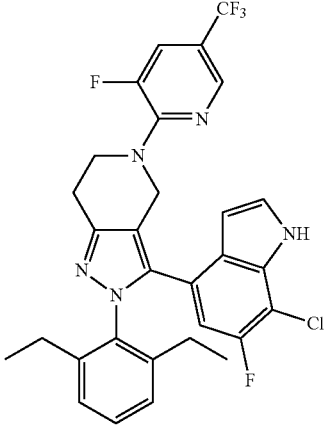 [SMILES: CCc1cccc(CC)c1-n1nc2c(c1-c1cc(F)c(Cl)c3[nH]ccc13)CN(c1ncc(C(F)(F)F)cc1F)CC2]<br>Ex. 77.020 | ¹H NMR (400 MHz, CDCl$_3$) δ 8.56 (br s, 1H), 8.19 (s, 1H), 7.40 (dd, J = 13.2, 2.0, 1H), 7.28 (t, J = 2.8, 1H), 7.24 (t, J = 7.2, 1H), 7.06 (d, J = 6.8, 2H), 6.53 (dd, J = 2.6, 2.6, 1H), 6.49 (d, J = 10.4, 1H), 4.63 (br s, 2H), 4.07 (t, J = 5.6, 2H), 3.11 (t, J = 5.6, 2H), 2.05-2.40 (2 br s, 4H), 1.02 (br s, 6H). | MS: (ES) m/z calculated for C$_{30}$H$_{25}$ClF$_5$N$_5$ [M + H]$^+$ 586.2, found 586.2. |
| 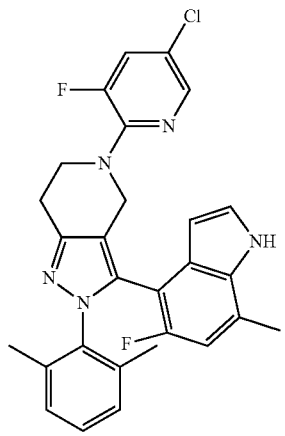<br>Ex. 77.021 | ¹H NMR (400 MHz, CDCl$_3$) δ 8.15 (s, 1H), 7.91 (dd, J = 0.8, 2.2, 1H), 7.19-7.30 (m, 2H), 7.00-7.10 (m, 2H), 6.79 (dd, J = 2.8, 6.1, 1H), 6.61 (d, J = 10.8, 1H), 6.43 (dd, J = 2.1, 3.2, 1H), 4.58 (d, J = 15.4, 1H), 4.28 (d, J = 15.4, 1H), 3.82-3.92 (m, 2H), 3.15 (t, J = 5.7, 2H), 2.43 (d, J = 0.9, 3H), 2.22 (s, 3H), 1.74 (s, 3H). | MS: (ES) m/z calculated C$_{28}$H$_{25}$ClF$_2$N$_5$ [M + H]$^+$ 504.2, found 504.2. |
| 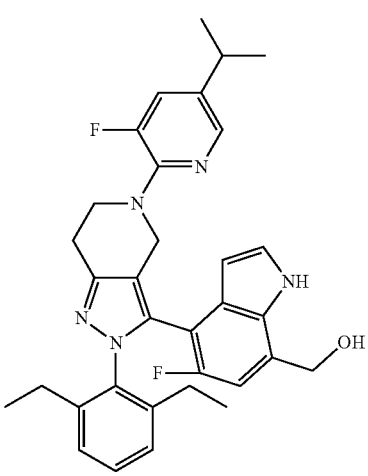 [SMILES: CCc1cccc(CC)c1-n1nc2c(c1-c1c(F)cc(CO)c3[nH]ccc13)CN(c1ncc(C(C)C)cc1F)CC2]<br>Ex. 77.022 | ¹H NMR (400 MHZ, CDCl$_3$) δ 8.95 (br s, 1H), 7.80 (s, 1H), 7.22 (t, J = 2.8, 1H), 7.10-7.20 (m, 3H), 6.86 (dd, J = 7.2, 1.6, 1H), 6.52 (t, J = 10.4, 1H), 7.22 (dd, J = 2.8, 2.8 1H), 4.79 (m, 2H), 4.51 (d, J = 15.2, 1H), 4.24 (d, J = 15.2, 1H), 3.84 (m, 2H), 3.12 (t, J = 6.2, 2H), 2.84 (quint, J = 6.8, 1H), 2.62 (br s, 1H), 2.55 (sextet, J = 7.8, 1H), 2.45 (sextet, J = 7.6, 1H), 2.20 (sextet, J = 7.4, 1H), 1.95 (sextet, J = 7.4, 1H), 1.21 (m, 9H), 0.76 (t, J = 7.6, 3H). | MS: (ES) m/z calculated for C$_{33}$H$_{35}$F$_2$N$_5$O [M + H]$^+$ 556.3, found 556.3. |

TABLE 1-continued

Structure & NMR/MS Characterization Data of Specific Embodiments

| Structure | ¹H NMR | MS |
|---|---|---|
| 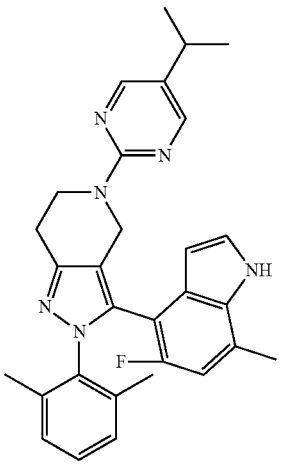<br>Ex. 77.023 | ¹H NMR (400 MHZ, CD₃OD) δ 8.23 (s, 2H), 7.37 (d, J = 3.2, 1H), 7.10 (d, J = 5.2, 2H), 6.83 (t, J = 4.0, 1H), 6.58 (d, J = 12, 1H), 6.34 (d, J = 3.0, 1H), 4.81 (d, J = 17, 1H), 4.51 (d, J = 17, 1H), 4.13-4.37 (m, 2H), 2.97 (t, J = 5.6, 2H), 2.73-2.85 (m, 1H), 2.47 (s, 3H), 2.17 (s, 3H), 1.70 (s, 3H), 1.23 (d, J = 6.8, 6H). | MS: (ES) m/z calculated for $C_{30}H_{32}FN_6$ [M + H]⁺ 495.3, found 495.3. |
| 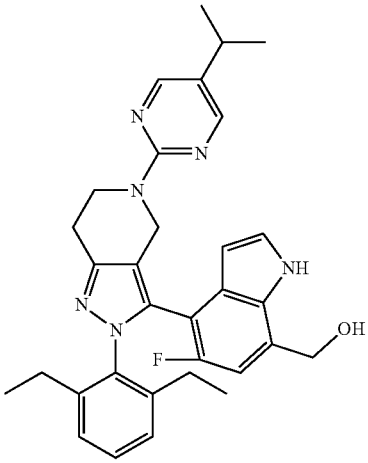 [SMILES: CCc1cccc(CC)c1-n1nc2c(c1-c1c(F)cc(CO)c3[nH]ccc13)CN(c1ncc(C(C)C)cn1)CC2]<br>Ex. 77.024 | ¹H NMR (400 MHz, CDCl₃) δ 8.96 (br s, 1H), 8.18 (s, 2H), 7.23 (t, J = 2.8, 1H), 7.23 (t, J = 2.8, 1H), 7.17 (t, J = 7.6, 1H), 7.13 (dd, J = 7.6, 1.6, 1H), 6.86 (dd, J = 7.6, 1.2, 1H), 8.50 (d, J = 10.4, 1H), 6.38 (t, J = 2.6, 1H), 4.74 (m, 2H), 4.64 (m, 2H), 4.46 (m, 1H), 4.47 (m, 1H), 3.03 (m, 2H), 3.60-3.80 (m, 1H), 2.74 (quint, J = 6.8, 1H), 2.48 (m, 2H), 2.19 (sextet, J = 7.4, 1H), 1.96 (sextet, J = 7.6, 1H), 1.21 (m, 9H), 0.76 (t, J = 7.6, 3H). | MS: (ES) m/z calculated for $C_{32}H_{35}FN_6O$ [M + H]⁺ 539.3, found 539.3. |
| 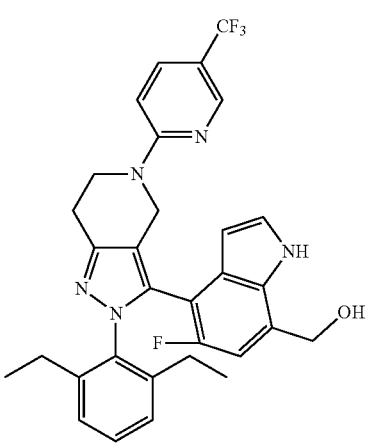 [SMILES: CCc1cccc(CC)c1-n1nc2c(c1-c1c(F)cc(CO)c3[nH]ccc13)CN(c1ccc(C(F)(F)F)cn1)CC2]<br>Ex. 77.025 | ¹H NMR (400 MHz, CDCl₃) δ 9.07 (br s, 1H), 8.38 (s, 1H), 7.59 (dd, J = 8.8, 2.8, 1H), 7.29 (t, J = 6.0, 1H), 7.19 (t, J = 7.6, 1H), 7.15 (dd, J = 8.0, 8.0, 1H), 6.87 (d, J = 7.6, 1H), 6.62 (m, 2H), 6.38 (t, J = 2.6, 1H), 4.94 (s, 2H), 4.70 (d, J = 15.2, 1H), 4.40 (d, J = 15.6, 1H), 4.18 (d, J = 5.6, 2H), ), 3.06 (dd, J = 5.6, 5.6, 2H), 2.52 (sextet, J = 7.6, 1H), 2.43 (sextet, J = 7.4, 1H), 2.16 (sextet, J = 7.6, 1H), 1.94 (sextet, J = 7.2, 1H), 1.22 (d, J = 11, 3H), 0.75 (d, J = 7.6, 3H). | MS: (ES) m/z calculated for $C_{31}H_{29}F_4N_5O$ [M + H]⁺ 564.2, found 564.2. |

TABLE 1-continued

Structure & NMR/MS Characterization Data of Specific Embodiments

| Structure | ¹H NMR | MS |
|---|---|---|
| 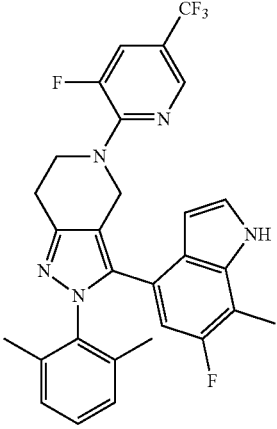<br>Ex. 77.026 | ¹H NMR (400 MHz, CDCl₃) δ 8.17-8.22 (m, 2H), 7.10-7.40 (m, 3H), 6.98 (br, 2H), 6.39-6.54 (m, 2H), 4.62-4.68 (m, 2H), 4.08 (t, J = 5.7, 2H), 3.13 (t, J = 5.8, 2H), 2.36 (J = 1.8, 3H), 2.00 (br, 6H). | MS: (ES) m/z calculated $C_{29}H_{25}F_5N_5$ [M + H]⁺ 538.2, found 538.2. |
| 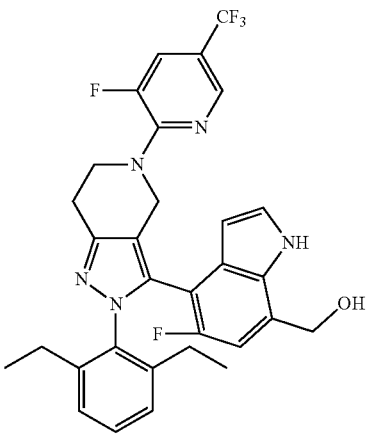 [SMILES: CCc1cccc(CC)c1-n1nc2c(c1-c1c(F)cc(CO)c3[nH]ccc13)CN(c1ncc(C(F)(F)F)cc1F)CC2]<br>Ex. 77.027 | ¹H NMR (400 MHz, CDCl₃) δ 8.85 (br s, 1H), 7.98 (s, 1H), 7.19 (d, J = 12.8, 1H), 7.06 (m, 1H), 6.99 (t, J = 7.2, 1H), 6.95 (t, J = 6.8, 1H), 6.67 (d, J = 7.2, 1H), 6.38 (d, J = 5.2, 1H), 6.20 (m, 1H), 4.72 (d, J = 5.2, 2H), 4.55 (d, J = 15.6, 1H), 4.25 (d, J = 16.4, 1H), 3.87 (m, 2H), 2.92 (dd, J = 5.6, 5.6, 2H), 2.33 (sextet, J = 7.4, 1H), 2.25 (sextet, J = 7.8, 1H), 2.09 (dd, J = 5.6, 5.6, 1H), 1.98 (sextet, J = 7.4, 1H), 1.75 (sextet, J = 7.4, 1H), 1.02 (d, J = 7.6, 3H), 0.75 (d, J = 7.4, 3H). | MS: (ES) m/z calculated for $C_{31}H_{28}F_5N_5O$ [M + H]⁺ 582.2, found 582.2. |
| 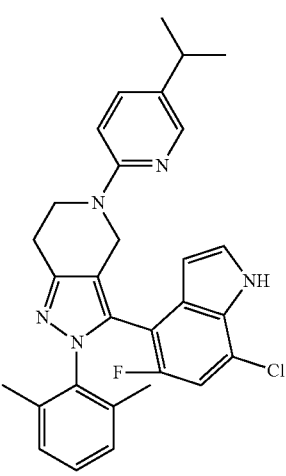 [SMILES: Cc1cccc(C)c1-n1nc2c(c1-c1c(F)cc(Cl)c3[nH]ccc13)CN(c1ccc(C(C)C)cn1)CC2]<br>Ex. 77.028 | ¹H NMR (400 MHZ, CD₃OD) δ 8.01 (d, J = 2.3, 1H), 7.54-7.58 (m, 2H), 7.18-7.22 (m, 2H), 6.93-7.00 (m, 2H), 6.90 (d, J = 9.6, 1H), 6.53 (d, J = 3.0, 1H), 4.67 (d, J = 15, 1H), 4.35 (d, J = 15, 1H), 4.07-4.15 (m, 2H), 3.10 (t, J = 5.2, 2H), 2.84-2.94 (m, 1H), 2.25 (s, 3H), 1.78 (s, 3H), 1.29 (d, J = 6.8, 6H). | MS: (ES) m/z calculated for $C_{30}H_{30}ClFN_5$ [M + H]⁺ 514.2, found 514.2. |

TABLE 1-continued

Structure & NMR/MS Characterization Data of Specific Embodiments

| Structure | ¹H NMR | MS |
|---|---|---|
| Ex. 77.029 | ¹H NMR (400 MHz, CDCl$_3$) δ 8.33 (br s, 2H), 8.07 (br s, 1H), 7.13 (m, 2H), 6.93 (t, J = 7.4, 1H), 6.81 (br s, 2H), 6.64 (d, J = 6.8, 1H), 6.43 (d, J = 7.2, 1H), 6.36 (s, 1H), 4.71 (br s, 2H), 4.22 (br s, 2H), 2.90 (t, J = 5.8, 1H), 2.30 (s, 3H), 1.85 (br s, 6H). | MS: (ES) m/z calculated for C$_{28}$H$_{25}$F$_3$N$_6$ [M + H]$^+$ 582.2, found 503.2. |
| Ex. 77.030 | ¹H NMR (400 MHZ, CDCl$_3$) δ 8.26 (br s, 1H), 8.18 (s, 1H), 7.37 (dd, J = 13.6, 2.0, 1H), 7.24 (t, J = 2.8, 1H), 7.06 (t, J = 7.6, 1H), 6.94 (br s, 2H), 6.77 (d, J = 7.2, 1H), 6.57 (d, J = 7.2, 1H), 6.51 (m, 1H), 4.66 (br s, 2H), 4.08 (t, J = 5.6, 2H), 3.13 (t, J = 5.8, 2H), 2.42 (s, 3H), 2.00 (br s, 6H). | MS: (ES) m/z calculated for C$_{29}$H$_{25}$F$_4$N$_5$ [M + H]$^+$ 520.2, found 520.2. |
| Ex. 77.031 | ¹H NMR (400 MHz, CDCl$_3$) δ 8.62 (br s, 1H), 8.16 (d, J = 5.2, 1H), 7.25 (m, 1H), 7.20 (t, J = 7.8, 1H), 7.02 (d, J = 7.2, 2H), 6.94 (d, J = 8.0, 1H), 6.59 (dd, J = 2.8, 2.8, 1H), 6.54 (d, J = 8.0, 1H), 6.36 (d, J = 4.8, 1H), 4.80 (s, 2H), 4.31 (s, 2H), 3.02 (t, J = 5.8, 2H), 2.33 (s, 3H), 2.10-2.40 (2 br s, 4H), 0.99 (br s, 6H). | MS: (ES) m/z calculated for C$_{29}$H$_{29}$ClN$_6$ [M + H]$^+$ 497.2, found 497.2. |

TABLE 1-continued

Structure & NMR/MS Characterization Data of Specific Embodiments

| Structure | ¹H NMR | MS |
|---|---|---|
| Ex. 77.032 | ¹H NMR (400 MHz, CDCl₃) δ 8.54 (br s, 1H), 8.09 (s, 2H), 7.29 (t, J = 2.8, 1H), 7.06 (d, J = 4.8, 2H), 6.85 (d, J = 9.6, 1H), 6.80 (dd, J = 4.4, 4.4, 1H), 6.47 (dd, J = 2.8, 2.8, 1H), 4.71 (d, J = 15.6, 1H), 4.57 (d, J = 16, 1H), 4.35 (m, 1H), 4.11 (m, 1H), 2.79 (s, 3H), 3.04 (t, J = 5.8, 2H), 2.20 (d, J = 1.6, 3H), 1.72 (s, 3H). | MS: (ES) m/z calculated for C₂₇H₂₄ClFN₆O [M + H]⁺ 503.2, found 503.2. |
| Ex. 77.033 | ¹H NMR (400 MHZ, CDCl₃) δ 8.50 (br s, 1H), 8.09 (s, 2H), 7.30 (t, J = 2.8, 1H), 7.08 (t, J = 7.6, 1H), 6.97 (d, J = 7.6, 1H), 6.95 (m, 2H), 6.57 (m, 2H), 4.70 (s, 2H), 4.24 (br s, 2H), 3.79 (s, 3H), 3.03 (t, J = 5.8, 2H), 1.98 (s, 6H). | MS: (ES) m/z calculated for C₂₇H₂₅ClN₆O [M + H]⁺ 485.1, found 485.1. |
| Ex. 77.034 | ¹H NMR (400 MHZ, CDCl₃) δ 8.58 (br s, 1H), 8.04 (d, J = 5.6, 1H), 7.25 (m, 1H), 7.21 (t, J = 7.6, 1H), 7.02 (d, J = 7.2, 2H), 6.94 (d, J = 8.0, 1H), 6.56 (t, J = 2.4, 1H), 6.55 (d, J = 8.0, 1H), 5.97 (d, J = 5.2, 1H), 4.80 (br s, 2H), 4.29 (br s, 2H), 3.88 (s, 3H), 3.02 (t, J = 5.8, 2H), 2.15-2.42 (2 br s, 4H), 1.00 (s, 6H). | MS: (ES) m/z calculated for C₂₉H₂₉ClN₆O [M + H]⁺ 513.2, found 513.2. |

TABLE 1-continued

Structure & NMR/MS Characterization Data of Specific Embodiments

| Structure | ¹H NMR | MS |
| --- | --- | --- |
| Ex. 77.035 | ¹H NMR (400 MHZ, CDCl₃) δ 8.18 (br s, 1H), 8.08 (s, 2H), 7.25 (t, J = 2.8, 1H), 7.06 (t, J = 7.6, 1H), 6.94 (br s, 2H), 6.76 (d, J = 7.2, 1H), 6.56 (d, J = 7.2, 1H), 6.53 (dd, J = 2.6, 2.6, 1H), 4.71 (br s, 2H), 4.23 (br s, 2H), 3.78 (s, 3H), 3.03 (t, J = 5.8, 2H), 2.43 (s, 3H), 1.99 (br s, 6H). | MS: (ES) m/z calculated for $C_{28}H_{28}N_6O$ [M + H]⁺ 465.2, found 465.2. |
| Ex. 77.036 | ¹H NMR (400 MHZ, CDCl₃) δ 8.19-8.21 (m, 3H), 7.17-7.31 (m, 2H), 7.04 (d, J = 7.7, 2H), 6.47 (dd, J = 2.0, 3.2, 1H), 6.40 (d, J = 10.9, 1H), 4.74 (s, 2H), 4.28 (s, 2H), 3.02 (t, J = 5.8, 2H), 2.75 (h, J = 6.9, 1H), 2.10-2.33 (m, 7H), 1.21 (d, J = 6.9, 6H), 0.80-1.08 (m, 6H). | MS: (ES) m/z calculated $C_{32}H_{36}FN_6$ [M + H]⁺ 523.3, found 523.3. |
| Ex. 77.037 | ¹H NMR (TFA salt) (400 MHZ, CD₃OD) δ 11.56 (br s, 1H), 8.30 (s, 1H), 7.83 (dd, J = 9.6, 2.4, 1H), 7.44 (t, J = 2.8, 1H), 7.31 (t, J = 7.6, 1H), 7.15 (br s, 2H), 7.10 (d, J = 8.8, 1H), 6.50 (m, 1H), 6.44 (m, 1H), 4.69 (br s, 2H), 4.22 (br s, 2H), 3.05 (t, J = 5.8, 2H), 2.27 (br s, 4H), 1.00 (br s, 6H). | MS: (ES) m/z calculated for $C_{30}H_{26}F_5N_5$ [M + H]⁺ 552.2, found 552.2. |

TABLE 1-continued

Structure & NMR/MS Characterization Data of Specific Embodiments

| Structure | ¹H NMR | MS |
|---|---|---|
| Ex. 77.038 | ¹H NMR (400 MHz, CDCl₃) δ 9.01 (br s, 1H), 8.21 (s, 2H), 7.22 (t, J = 7.6, 1H), 7.14 (t, J = 2.6, 1H), 7.05 (d, J = 7.6, 2H), 6.45 (m, 2H), 4.74 (s, 2H), 4.24 (br s, 2H), 3.03 (t, J = 5.8, 2H), 2.76 (septet, J = 7.0, 1H), 2.00-2.40 (2 br s, 4H), 1.21 (d, J = 7.2, 6H), 1.00 (br s, 6H). | MS: (ES) m/z calculated for $C_{31}H_{32}F_2N_6$ [M + H]⁺ 527.2, found 527.2. |
| Ex. 77.039 | ¹H NMR (400 MHZ, CD₃OD) δ 8.28 (s, 1H), 8.25 (s, 1H), 7.67 (dd, J = 2.2, 14, 1H), 7.30 (t, J = 8.4, 1H), 7.24 (d, J = 8.0, 1H), 7.13 (d, J = 8.0, 2H), 6.66 (d, J = 7.6, 1H), 4.72 (s, 2H), 4.16 (t, J = 5.6, 2H), 3.05 (t, J = 5.6, 2H), 2.14-2.37 (m, 4H), 0.99 (t, J = 7.6, 6H). | MS: (ES) m/z calculated for $C_{29}H_{26}ClF_4N_6$ [M + H]⁺ 569.2, found 569.2. |
| Ex. 77.040 | ¹H NMR (TFA salt) (400 MHz, CD₃OD) δ 8.71 (br s, 1H), 8.19 (s, 1H), 7.40 (dd, J = 13.2, 2.0, 1H), 7.24 (t, J = 7.2, 1H), 7.20 (t, J = 2.8, 1H), ), 7.06 (d, J = 6.8, 2H), 6.47 (m, 2H), 4.62 (br s, 2H), 4.07 (t, J = 5.6, 2H), 3.11 (t, J = 5.6, 2H), 2.15-2.40 (2 br s, 4H), 1.00 (br s, 6H). | MS: (ES) m/z calculated for $C_{30}H_{25}F_6N_5$ [M + H]⁺ 570.2, found 570.2. |

TABLE 1-continued

Structure & NMR/MS Characterization Data of Specific Embodiments

| Structure | ¹H NMR | MS |
|---|---|---|
| Ex. 77.041 | ¹H NMR (400 MHz, CDCl₃) δ 8.47 (d, J = 3.0, 1H), 8.03 (s, 1H), 7.25-7.34 (m, 1H), 7.21 (t, J = 7.7, 1H), 6.96-7.04 (m, 3H), 6.52-6.59 (m, 2H), 4.76 (s, 2H), 4.25 (s, 2H), 3.97 (s, 3H), 3.02 (t, J = 5.9, 2H), 2.10-2.38 (br, m, 4H), 0.88-1.08 (br, m, 6H). | MS: (ES) m/z calculated $C_{29}H_{29}Cl_2N_6O$ [M + H]⁺ 547.2, found 547.1. |
| Ex. 77.042 | ¹H NMR (400 MHZ, CDCl₃) δ 8.47 (d, J = 9.7, 3H), 7.34 (t, J = 2.9, 1H), 7.04-7.10 (m, 2H), 6.89 (d, J = 9.7, 1H), 6.78-6.85 (m, 1H), 6.43-6.46 (m, 1H), 4.90 (d, J = 16.1, 1H), 4.68 (d, J = 16.1, 1H), 4.29-4.42 (m, 2H), 3.06 (t, J = 5.9, 2H), 2.19 (d, J = 1.8, 3H), 1.73 (s, 3H). | MS: (ES) m/z calculated $C_{27}H_{22}ClF_4N_6$ [M + H]⁺ 541.1, found 541.2. |
| Ex. 77.043 | ¹H NMR (400 MHZ, CDCl₃) δ 8.18 (d, J = 2.2, 2H), 7.38 (dd, J = 2.0, 13.1, 1H), 7.18-7.34 (m, 2H), 7.04 (d, J = 7.7, 2H), 6.36-6.50 (m, 2H), 4.64 (s, 2H), 4.07 (t, J = 5.8, 2H), 3.11 (t, J = 5.8, 2H), 2.10-2.40 (m, 7H), 2.00 (br, 6H), 0.88-1.08 (m, 6H).. | MS: (ES) m/z calculated $C_{31}H_{29}F_5N_5$ [M + H]⁺ 566.2, found 566.2. |

TABLE 1-continued

Structure & NMR/MS Characterization Data of Specific Embodiments

| Structure | ¹H NMR | MS |
|---|---|---|
| Ex. 77.044 | ¹H NMR (400 MHz, CDCl₃) δ 8.46 (s, 1H), 8.18 (dt, J = 1.1, 2.1, 1H), 7.18-7.47 (m, 2H), 7.07 (dd, J = 0.7, 4.5, 2H), 6.78-6.92 (m, 2H), 6.48 (ddd, J = 0.6, 2.2, 3.1, 1H), 4.74 (d, J = 15.7, 1H), 4.44 (d, J = 15.7, 1H), 3.99-4.14 (m, 2H), 3.13 (t, J = 5.8, 2H), 2.20 (d, J = 1.7, 3H), 1.73 (s, 3H). | MS: (ES) m/z calculated $C_{28}H_{22}ClF_5N_5$ [M + H]⁺ 558.1, found 558.1. |
| Ex. 77.045 | ¹H NMR (400 MHZ, CDCl₃) δ 8.47 (br s, 1H), 8.09 (s, 2H), 7.31 (t, J = 2.8, 1H), 7.20 (t, J = 7.6, 1H), 7.03 (d, J = 7.6, 2H), 6.95 (d, J = 8.0, 1H), 6.56 (m, 2), 4.69 (br s, 2H), 4.24 (br s, 2H), 3.79 (s, 3H), 3.02 (t, J = 5.8, 2H), 2.15-2.40 (m, 4H), 0.99 (br s, 6H). | MS: (ES) m/z calculated for $C_{29}H_{29}ClN_6O$ [M + H]⁺ 513.2, found 513.2. |
| Ex. 77.046 | ¹H NMR (TFA salt) (400 MHZ, CD₃OD) δ 11.30 (br s, 1H), 7.56 (d, J = 6.8, 1H), 7.46 (t, J = 2.8, 1H), 7.29 (t, J = 7.6, 1H), 7.13 (br s, 2H), 6.94 (d, J = 7.6, 1H), 6.54 (d, J = 8.0, 1H), 6.50 (dd, J = 2.6, 1H), 6.10 (d, J = 7.2, 1H), 4.71 (br s, 2H), 4.22 (br s, 2H), 3.08 (t, J = 5.8, 2H), 2.30 (br s, 4H), 1.21 (d, J = 7.2, 6H), 1.00 (br s, 6H). | MS: (ES) m/z calculated for $C_{28}H_{28}ClN_7$ [M + H]⁺ 498.2, found 498.2. |

TABLE 1-continued

Structure & NMR/MS Characterization Data of Specific Embodiments

| Structure | ¹H NMR | MS |
|---|---|---|
| 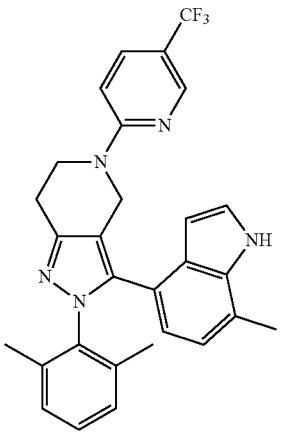<br>Ex. 77.047 | ¹H NMR (400 MHZ, CDCl₃) δ 8.38 (d, J = 2.4, 1H), 8.23 (s, 1H), 7.58 (dd, J = 2.5, 9.0, 1H), 7.24-7.32 (m, 1H), 7.07 (t, J = 7.5, 1H), 6.95 (br, 2H), 6.76-6.83 (m, 1H), 6.49-6.62 (m, 3H), 4.58 (s, 2H), 4.20 (t, J = 5.8, 2H), 3.06 (t, J = 5.8, 2H), 2.46 (s, 3H), 1.98 (br s, 6H). | MS: (ES) m/z calculated $C_{29}H_{27}F_3N_5$ [M + H]⁺ 502.2, found 502.2. |
| 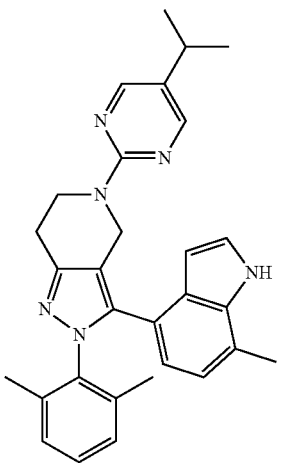<br>Ex. 77.048 | ¹H NMR (400 MHZ, CDCl₃) δ 8.18 (s, 3H), 7.24-7.26 (m, 1H), 7.06 (t, J = 7.5, 1H), 6.95 (br, 2H), 6.76 (dd, J = 1.0, 7.4, 1H), 6.50-6.60 (m, 2H), 4.75 (s, 2H), 4.28 (s, 2H), 3.03 (t, J = 5.9, 2H), 2.75 (p, J = 6.9, 2H), 2.43 (s, 3H), 1.99 (br s, 6H), 1.21 (d, J = 6.9, 6H). | MS: (ES) m/z calculated $C_{30}H_{33}N_6$ [M + H]⁺ 477.3, found 477.2. |
| 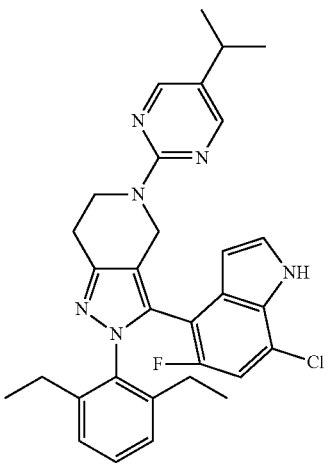<br>Ex. 77.049 | ¹H NMR (400 MHz, CDCl₃) δ 8.63 (br s, 1H), 8.19 (s, 2H), 7.25 (t, J = 2.8, 1H), 7.19 (t, J = 7.6, 1H), 7.15 (dd, J = 7.6, 7.6, 1H), 6.88 (dd, J = 7.2, 0.8, 1H), 6.83 (d, J = 9.6, 1H), 6.44 (dd, J = 2.6, 1H), 4.75 (d, J = 16, 1H), 4.63 (d, J = 16, 1H), 4.41 (quint, J = 6.6, 1H), 4.18 (quint, J = 6.6, 1H), 3.03 (t, J = 5.8 , 2H), 2.76 (sextet, J = 7.2, 1H), 2.51 (sextet, J = 7.6, 1H), 2.41 (sextet, J = 8.0, 1H), 2.16 (sextet, J = 7.2, 1H), 1.93 (sextet, J = 7.6, 1H), 1.20 (m, 9H), 0.75 (t, J = 7.4, 3H). | MS: (ES) m/z calculated for $C_{31}H_{32}ClFN_6$ [M + H]⁺ 543.2, found 543.2. |

TABLE 1-continued

Structure & NMR/MS Characterization Data of Specific Embodiments

| Structure | ¹H NMR | MS |
|---|---|---|
| 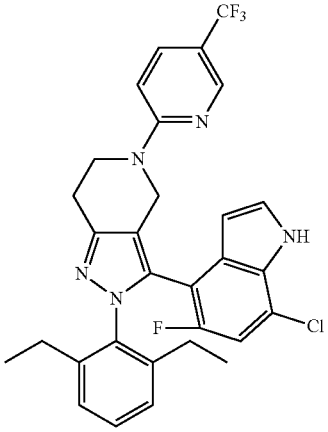 [SMILES: CCc1cccc(CC)c1-n1nc2c(c1-c1c(F)cc(Cl)c3[nH]ccc13)CN(c1ccc(C(F)(F)F)cn1)CC2]<br>Ex. 77.050 | ¹H NMR (400 MHZ, CDCl₃) δ 8.56 (br s, 1H), 8.39 (s, 1H), 7.60 (dd, J = 8.8, 2.4, 1H), 7.30 (t, J = 2.8, 1H), 7.20 (t, J = 7.6, 1H), 7.15 (t, J = 6.4, 1H), 6.88 (m, 2H), 6.64 (d, J = 8.8, 1H), 6.43 (t, J = 2.6, 1H), 4.70 (d, J = 15.2, 1H), 4.42 (d, J = 15.6, 1H), 4.17 (t, J = 5.8, 2H), 3.06 (t, J = 5.6, 2H), 2.50 (sextet, J = 8.0, 1H), 2.43 (sextet, J = 7.8, 1H), 2.15 (sextet, J = 7.4, 1H), 1.92 (sextet, J = 7.6, 1H), 1.21 (t, J = 7.4, 3H), 0.75 (t, J = 7.6, 3H). | MS: (ES) m/z calculated for $C_{30}H_{26}ClF_4N_5$ [M + H]⁺ 568.2, found 568.2. |
| 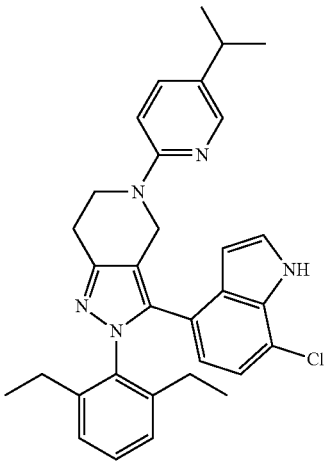<br>Ex. 77.051 | ¹H NMR (400 MHZ, CD₃OD) δ 7.92 (d, J = 2.5, 1H), 7.48 (dd, J = 2.6, 8.8, 1H), 7.44 (d, J = 3.2, 1H), 7.27 (t, J = 7.6, 1H), 7.10 (br s, 2H), 6.92 (d, J = 8.0, 1H), 6.80 (d, J = 8.8, 1H), 6.54 (d, J = 8.0, 1H), 6.51 (d, J = 3.1, 1H), 4.47 (br s, 2H), 4.04 (t, J = 5.6, 2H), 3.00 (t, J = 5.6, 2H), 2.77-2.86 (m, 1H), 2.28 (br s, 4H), 1.21 (d, J = 6.8, 6H), 0.99 (br s, 6H). | MS: (ES) m/z calculated for $C_{32}H_{35}ClN_5$ [M + H]⁺ 524.2, found 524.2. |
| 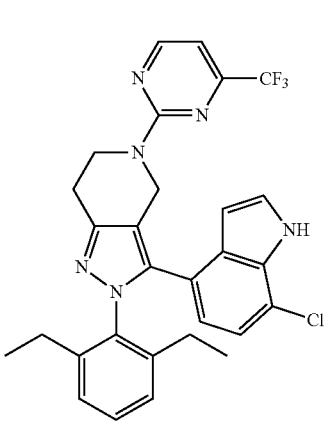 [SMILES: CCc1cccc(CC)c1-n1nc2c(c1-c1ccc(Cl)c3[nH]ccc13)CN(c1nccc(C(F)(F)F)n1)CC2]<br>Ex. 77.052 | ¹H NMR (400 MHz, CDCl₃) δ 8.54 (s, 1H), 7.60 (dd, J = 3.6, 1H), 7.31 (t, J = 2.6, 1H), 7.21 (t, J = 7.8, 1H), 7.03 (d, J = 7.2, 2H), 6.95 (d, J = 8.0, 1H), 6.76 (d, J = 4.4, 1H), 6.61 (s, 1H), 6.54 (d, J = 8.0, 1H), 4.86 (br s, 2H), 4.34 (br s, 2H), 3.04 (t, J = 6.0, 2H), 2.12-2.42 (2 br s, 4H), 0.99 (br s, 6H). | MS: (ES) m/z calculated for $C_{29}H_{26}ClF_3N_6$ [M + H]⁺ 551.2, found 551.2. |

TABLE 1-continued

Structure & NMR/MS Characterization Data of Specific Embodiments

| Structure | ¹H NMR | MS |
|---|---|---|
| 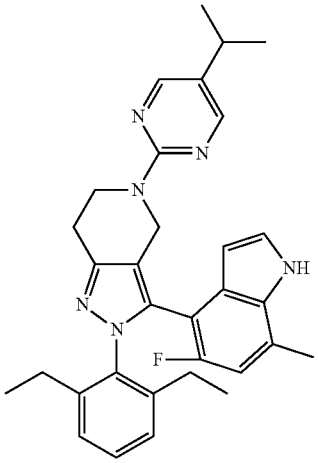 [SMILES: CCc1cccc(CC)c1-n1nc2c(c1-c1c(F)cc(C)c3[nH]ccc13)CN(c1ncc(C(C)C)cn1)CC2]<br>Ex. 77.053 | ¹H NMR (400 MHZ, CDCl₃) δ 8.19 (s, 2H), 8.13 (br s, 1H), 7.24 (t, J = 2.8, 1H), 7.18 (t, J = 7.4, 1H), 7.14 (m, 1H), 6.87 (d, J = 7.6, 1H), 6.59 (d, J = 11.2, 1H), 6.40 (t, J = 2.6, 1H), 4.76 (d, J = 16, 1H), 4.62 (d, J = 16, 1H), 4.40 (quint, J = 6.6, 1H), 4.17 (quint, J = 6.8, 1H), 3.03 (t, J = 5.6, 2H), 2.75 (sextet, J = 7.0, 1H), 2.53 (sextet, J = 7.6, 1H), 2.44 (sextet, J = 7.6, 1H), 2.41 (s, 3H), 2.19 (sextet, J = 6.8, 1H), 1.96 (sextet, J = 7.6, 1H), 1.22 (m, 9H), 0.74 (t, J = 7.6, 3H). | MS: (ES) m/z calculated for $C_{32}H_{35}FN_6$ [M + H]⁺ 523.2, found 523.2. |
| 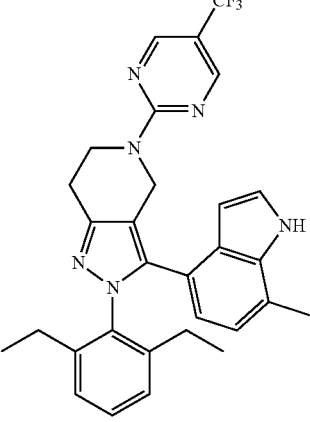<br>Ex. 77.054 | ¹H NMR (400 MHz, CDCl₃) δ 8.47 (br s, 2H), 8.23 (s, 1H), 7.26 (m, 1H), 7.20 (t, J = 7.6, 1H), 7.02 (d, J = 5.6, 2H), 6.76 (d, J = 7.6, 1H), 6.55 (d, J = 7.6, 1H) 6.49 (d, J = 2.8, 1H), 4.86 (s, 2H), 4.37 (s, 2H), 3.04 (d, J = 6.0, 2H), 2.43 (s, 3H), 2.10-2.42 (2 br s, 4H), 1.00 (s, 6H). | MS: (ES) m/z calculated for $C_{30}H_{29}F_3N_6$ [M + H]⁺ 531.2, found 531.2. |
| 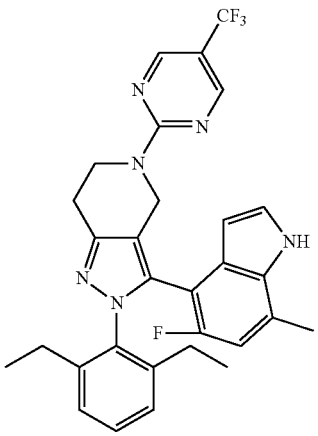 [SMILES: CCc1cccc(CC)c1-n1nc2c(c1-c1c(F)cc(C)c3[nH]ccc13)CN(c1ncc(C(F)(F)F)cn1)CC2]<br>Ex. 77.055 | ¹H NMR (400 MHZ, CDCl₃) δ 8.48 (br s, 2H), 8.19 (s, 1H), 7.25 (t, J = 3.2, 1H), 7.19 (t, J = 7.6, 1H), 7.15 (dd, J = 8.0, 8.0, 1H), 6.88 (dd, J = 7.6, 1.2, 1H), 6.61 (d, J = 10.8, 1H), 6.38 (m, 1H), 4.92 (d, J = 16, 1H), 4.69 (d, J = 16, 1H), 4.61 (quint, J = 6.4, 1H), 4.31 (quint, J = 6.6, 1H), 3.05 (t, J = 6.0, 2H), 2.50 (sextet, J = 7.6, 1H), 2.43 (sextet, J = 7.6, 1H), 2.42 (s, 3H), 2.18 (sextet, J = 8.0, 1H), 1.96 (sextet, J = 7.6, 1H), 1.21 (t, J = 7.6, 3H), 0.75 (t, J = 7.4, 3H). | MS: (ES) m/z calculated for $C_{30}H_{28}F_4N_6$ [M + H]⁺ 549.2, found 549.2. |

TABLE 1-continued

Structure & NMR/MS Characterization Data of Specific Embodiments

| Structure | ¹H NMR | MS |
|---|---|---|
| 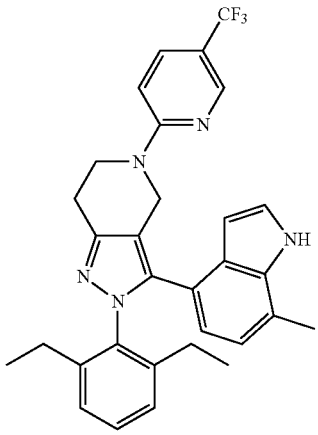 [SMILES: CCc1cccc(CC)c1-n1nc2c(c1-c1ccc(C)c3[nH]ccc13)CN(c1ccc(C(F)(F)F)cn1)CC2]<br>Ex. 77.056 | ¹H NMR (400 MHZ, CDCl₃) δ 8.36-8.42 (m, 1H), 8.22 (s, 1H), 7.58 (dd, J = 2.5, 9.0, 1H), 7.16-7.32 (m, 2H), 7.03 (br, 2H), 6.78 (dd, J = 1.0, 7.4, 1H), 6.49-6.62 (m, 3H), 4.58 (s, 2H), 4.21 (t, J = 5.9, 2H), 3.05 (t, J = 5.9, 2H), 2.10-2.45 (br m, 7H), 0.88-1.08 (br m, 6H). | MS: (ES) m/z calculated $C_{31}H_{31}F_3N_5$ [M + H]⁺ 530.3, found 530.2. |
| 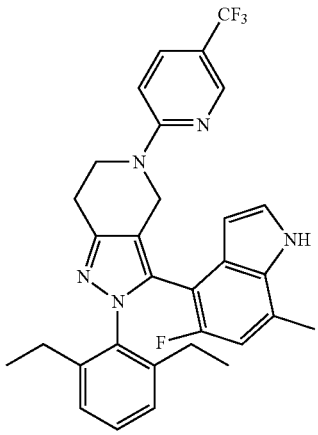 [SMILES: CCc1cccc(CC)c1-n1nc2c(c1-c1c(F)cc(C)c3[nH]ccc13)CN(c1ccc(C(F)(F)F)cn1)CC2]<br>Ex. 77.057 | ¹H NMR (400 MHz, CDCl₃) δ 8.39 (q, J = 1.3, 1H), 8.17 (s, 1H), 7.59 (dd, J = 2.5, 9.1, 1H), 7.11-7.31 (m, 3H), 6.81-6.91 (m, 1H), 6.62 (d, J = 10.2, 2H), 6.38 (dd, J = 2.1, 3.2, 1H), 4.69 (d, J = 15.4, 1H), 4.40 (d, J = 15.4, 1H), 4.13-4.25 (m, 2H), 2.99-3.10 (m, 2H), 2.38-2.55 (m, 5H), 1.90-2.20 (m, 2H), 1.22 (t, J = 7.5, 3H), 0.74 (t, J = 7.5, 3H). | MS: (ES) m/z calculated $C_{31}H_{30}F_4N_5$ [M + H]⁺ 548.2, found 548.2. |
| 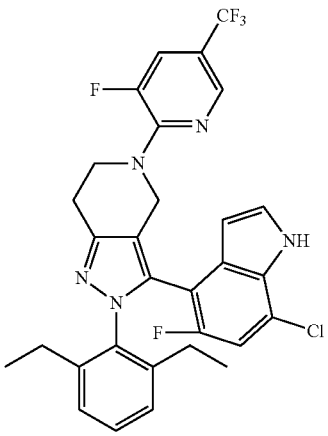<br>Ex. 77.058 | ¹H NMR (TFA salt) (400 MHZ, CD₃OD) δ 11.33 (br s, 1H), 8.22 (br s, 1H), 7.65 (dd, J = 13.2, 2.0, 1H), 7.47 (t, J = 2.8, 1H), 7.23 (m, 2H), 6.95 (d, J = 7.2, 1H), 6.85 (d, J = 10, 1H), 6.44 (dd, J = 2.4, 2.4, 1H), 4.78 (d, J = 15.6, 1H), 4.41 (d, J = 16, 1H), 4.10 (m, 2H), 3.08 (t, J = 5.6, 2H), 2.43 (m, 2.43, 2H), 2.14 (sextet, J = 7.5, 1H), 1.92 (sextet, J = 7.5, 1H), 1.23 (t, J = 7.4, 3H), 0.72 (t, J = 7.6, 3H). | MS: (ES) m/z calculated for $C_{30}H_{25}ClF_5N_5$ [M + H]⁺ 586.1, found 586.1. |

TABLE 1-continued

Structure & NMR/MS Characterization Data of Specific Embodiments

| Structure | ¹H NMR | MS |
|---|---|---|
| Ex. 77.059 | ¹H NMR (400 MHZ, CDCl₃) δ 8.13 (s, 1H), 7.82 (t, J = 1.6, 1H), 7.08-7.28 (m, 4H), 6.83-6.90 (m, 1H), 6.57 (d, J = 10.8, 1H), 6.40-6.47 (m, 1H), 4.51 (d, J = 15.2, 1H), 4.24 (d, J = 15.2, 1H), 3.82-3.85 (m, 2H), 3.12 (t, J = 5.8, 2H), 2.84 (p, J = 6.9, 2H), 2.40-2.55 (m, 5H), 1.95-2.21 (m, 2H), 1.20-1.25 (m, 9H), 0.73-0.79 (m, 3H). | MS: (ES) m/z calculated $C_{33}H_{36}F_2N_5$ [M + H]⁺ 540.3, found 540.2. |
| Ex. 77.060 | ¹H NMR (400 MHZ, CDCl₃) δ 8.24 (br s, 1H), 8.19 (s, 2H), 7.21 (t, J = 3.0, 1H), 7.18 (d, J = 7.6, 1H), 7.02 (d, J = 7.2, 2H), 6.72 (d, J = 7.2, 1H), 6.53 (d, J = 7.6, 1H), 6.50 (dd, J = 2.8, 2.8, 1H), 4.8 (br s, 2H), 4.29 (br s, 2H), 3.02 (t, J = 5.6, 2H), 2.75 (septet, J = 7.0, 1H), 2.38 (s, 3H), 2.00-2.40 (m, 4H), 1.21 (d, J = 7.2, 6H), 0.99 (br s, 6H). | MS: (ES) m/z calculated for $C_{32}H_{36}N_6$ [M + H]⁺ 505.3, found 505.3. |
| Ex. 77.061 | ¹H NMR (400 MHz, CDCl₃) δ 8.33 (br s, 1H), 8.33 (s, 1H), 7.14 (m, 1H), 7.04 (t, J = 7.8, 1H), 6.86 (d, J = 7.2, 1H), 6.79 (d, J = 8.0, 1H), 6.52 (t, J = 2.4, 1H), 6.39 (d, J = 7.6, 1H), 6.10 (s, 1H), 4.68 (br s, 2H), 4.15 (t, J = 5.6, 2H), 2.82 (t, J = 5.8, 2H), 2.12 (s, 6H), 1.90-2.15 (m 4H), 0.82 (br s, 6H). | MS: (ES) m/z calculated for $C_{30}H_{31}ClN_6$ [M + H]⁺ 510.2, found 510.2. |

TABLE 1-continued

Structure & NMR/MS Characterization Data of Specific Embodiments

| Structure | ¹H NMR | MS |
|---|---|---|
| 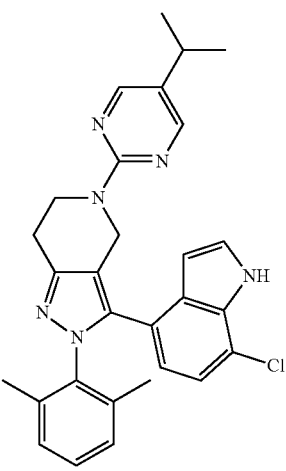 [SMILES: Cc1cccc(C)c1-n1nc2c(c1-c1ccc(Cl)c3[nH]ccc13)CN(c1ncc(C(C)C)cn1)CC2]<br>Ex. 77.062 | ¹H NMR (400 MHz, CDCl₃) δ 8.72 (br s, 1H), 8.20 (s, 2H), 7.24 (t, J = 2.8, 2H), 7.07 (t, J = 7.6, 1H), 6.95 (d, J = 8.0, 2H), 6.57 (d, J = 7.6, 1H), 6.54 (dd, J = 2.4, 2.4, 1H), 4.75 (s, 2H), 4.29 (br s, 2H), 3.04 (t, J = 5.8, 2H), 2.76 (quint, J = 7.0, 1H), 1.97 (br s, 6H), 1.2 (d, J = 7.2, 6H). | MS: (ES) m/z calculated for $C_{29}H_{29}ClN_6$ [M + H]⁺ 497.2, found 497.2 |
| 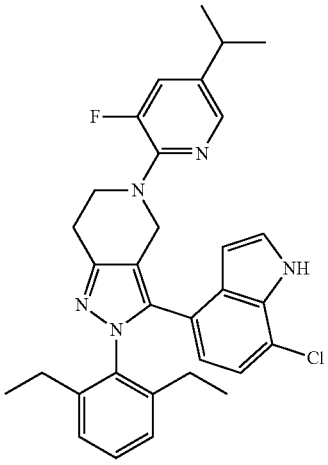 [SMILES: CCc1cccc(CC)c1-n1nc2c(c1-c1ccc(Cl)c3[nH]ccc13)CN(c1ncc(C(C)C)cc1F)CC2]<br>Ex. 77.063 | ¹H NMR (400 MHZ, CD₃OD) δ 7.80 (s, 1H), 7.42 (d, J = 3.1, 1H), 7.33 (dd, J = 1.9, 14, 1H), 7.27 (t, J = 7.6, 1H), 7.11 (br s, 2H), 6.91 (d, 7.6, 1H), 6.51-6.56, (m, 2H), 4.39 (br s, 2H), 3.85 (t, J = 5.6, 2H), 3.03 (t, J = 5.6, 2H), 2.83-2.93 (m, 1H), 2.30 (br s, 4H), 1.23 (d, J = 7.6, 6H), 1.00 (br s, 6H). | MS: (ES) m/z calculated for $C_{32}H_{34}ClFN_5$ [M + H]⁺ 542.2, found 542.2. |
| 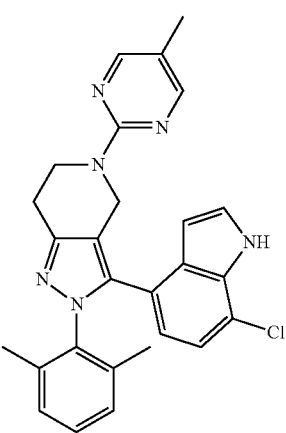 [SMILES: Cc1cnc(N2CCc3nn(-c4c(C)cccc4C)c(-c4ccc(Cl)c5[nH]ccc45)c3C2)nc1]<br>Ex. 77.064 | ¹H NMR (400 MHZ, CDCl₃) δ 8.72 (br s, 1H), 8.15 (s, 2H), 7.24 (t, J = 3.0, 1H), 7.07 (t, J = 7.4, 1H), 6.95 (d, J = 8.0, 3H), 6.55 (d, J = 2.8, 1H), 6.54 (d, J = 2.4, 1H), 4.73 (br s, 2H), 4.27 (br s, 2H), 3.03 (t, J = 5.6, 2H), 2.10 (s, 3H), 1.97 (br s, 6H). | MS: (ES) m/z calculated for $C_{27}H_{25}ClN_6$ [M + H]⁺ 469.1, found 469.1. |

TABLE 1-continued

Structure & NMR/MS Characterization Data of Specific Embodiments

| Structure | ¹H NMR | MS |
|---|---|---|
| 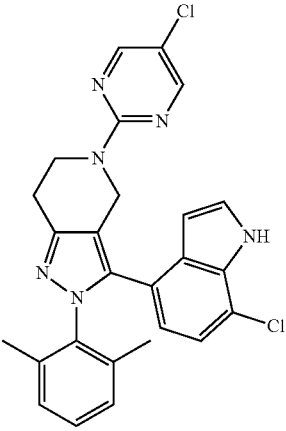 [SMILES: Cc1cccc(C)c1-n1nc2c(c1-c1ccc(Cl)c3[nH]ccc13)CN(c1ncc(Cl)cn1)CC2]<br>Ex. 77.065 | ¹H NMR (400 MHz, CD₃OD-CDCl₃) δ 8.20 (br s, 2H), 7.52 (s, 1H), 7.34 (d, J = 3.2, 1H), 7.08 (t, J = 7.6, 1H), 6.95 (2 br s, 2H), 6.90 (d, J = 8.0, 1H), 6.50 (d, J = 8.0, 1H), 6.45 (d, J = 3.2, 1H), 4.71 (br s, 2H), 4.24 (br s, 2H), 2.97 (t, J = 5.8, 2H), 1.93 (br s, 6H). | MS: (ES) m/z calculated for $C_{26}H_{22}Cl_2N_6$ [M + H]⁺ 489.1, found 489.1. |
| 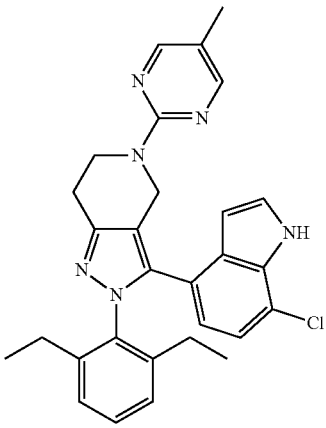 [SMILES: CCc1cccc(CC)c1-n1nc2c(c1-c1ccc(Cl)c3[nH]ccc13)CN(c1ncc(C)cn1)CC2]<br>Ex. 77.066 | ¹H NMR (400 MHz, CDCl₃) δ 8.63 (br s, 1H), 8.15 (s, 2H), 7.24 (t, J = 8.0, 1H), 7.20 (t, J = 7.6, 1H), 7.02 (d, J = 7.2, 2H), 6.93 (d, J = 7.6, 1H), 6.54 (m, 2H), 4.73 (br s, 2H), 4.28 (br s, 2H), 3.02 (t, J = 5.8, 2H), 2.07-2.42 (2 br s, 4H), 2.11 (s, 3H), 0.99 (br s, 6H). | MS: (ES) m/z calculated for $C_{29}H_{29}ClN_6$ [M + H]⁺ 497.2, found 497.2. |
| 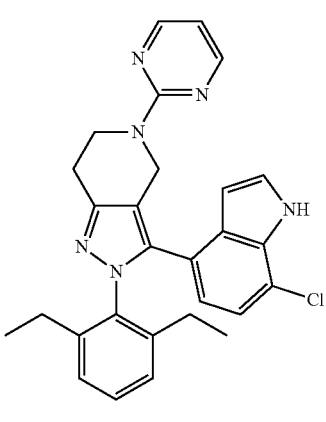 [SMILES: CCc1cccc(CC)c1-n1nc2c(c1-c1ccc(Cl)c3[nH]ccc13)CN(c1ncccn1)CC2]<br>Ex. 77.067 | ¹H NMR (400 MHz, CDCl₃) δ 8.63 (br s, 1H), 7.24 (d, J = 4.8, 2H), 7.25 (t, J = 2.8, 1H), 7.21 (d, J = 7.6, 1H), 7.03 (d, J = 7.2, 2H), 6.94 (d, J = 7.6, 2H), 6.54 (m, 2H), 6.47 (t, J = 4.6, 1H), 4.77 (br s, 2H), 4.32 (br s, 2H), 3.04 (t, J = 5.8, 2H), 2.13-2.42 (2 br s, 4H), 0.99 (br s, 6H). | MS: (ES) m/z calculated for $C_{28}H_{27}ClN_6$ [M + H]⁺ 483.2, found 483.2. |

TABLE 1-continued

Structure & NMR/MS Characterization Data of Specific Embodiments

| Structure | ¹H NMR | MS |
|---|---|---|
| 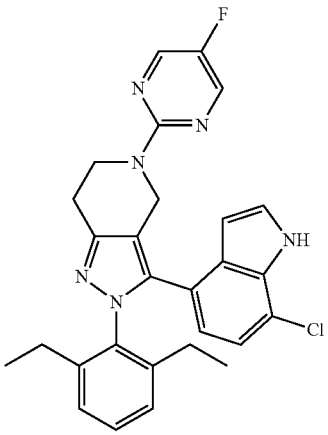 [SMILES: CCc1cccc(CC)c1-n1nc2c(c1-c1ccc(Cl)c3[nH]ccc13)CN(c1ncc(F)cn1)CC2]<br>Ex. 77.068 | ¹H NMR (400 MHZ, CDCl₃) δ 8.52 (br s, 1H), 8.19 (br s, 2H), 7.29 (t, J = 2.8, 1H), 7.21 (t, J = 7.8, 1H), 7.03 (d, J = 7.6, 2H), 6.96 (d, J = 8.0, 1H), 6.56 (d, J = 4.8, 1H), 6.55 (d, J = 2.6, 1H), 4.72 (br s, 2H), 4.26 (br s, 2H), 3.02 (t, J = 5.8, 2H), 2.15-2.42 (2 br s, 4H), 0.99 (s, 6H). | MS: (ES) m/z calculated for $C_{28}H_{26}ClFN_6$ [M + H]⁺ 501.1, found 501.1. |
| 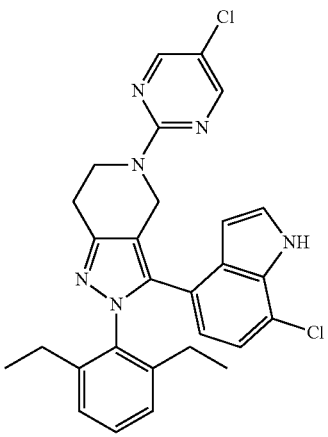 [SMILES: CCc1cccc(CC)c1-n1nc2c(c1-c1ccc(Cl)c3[nH]ccc13)CN(c1ncc(Cl)cn1)CC2]<br>Ex. 77.069 | ¹H NMR (400 MHz, CDCl₃) δ 8.49 (br s, 1H), 8.22 (s, 2H), 7.31 (t, J = 2.6, 1H), 7.21 (t, J = 7.8, 1H), 7.03 (d, J = 7.5, 2H), 6.96 (d, J = 8.0, 1H), 6.54 (m, 2H), 4.74 (br s, 2H), 4.27 (br s, 2H), 3.02 (t, J = 11.6, 2H), 2.15-2.42 (2 br s, 4H), 0.99 (s, 6H). | MS: (ES) m/z calculated for $C_{28}H_{26}Cl_2N_6$ [M + H]⁺ 517.2, found 517.2. |
| 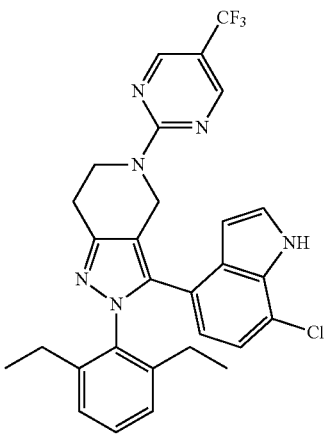 [SMILES: CCc1cccc(CC)c1-n1nc2c(c1-c1ccc(Cl)c3[nH]ccc13)CN(c1ncc(C(F)(F)F)cn1)CC2]<br>Ex. 77.070 | ¹H NMR (400 MHZ, CDCl₃) δ 8.47 (br s, 2H), 7.59 (s, 1H), 7.37 (d, J = 3.2, 1H), 7.22 (t, J = 7.8, 1H), 7.04 (br d, J = 7.2, 2H), 6.89 (d, J = 7.6, 1H), 6.49 (d, J = 7.6, 1H), 6.46 (d, J = 3.2, 1H), 4.82 (br s, 2H), 4.36 (br s, 2H), 2.99 (t, J = 5.8, 2H), 2.22 (two br s, 4H), 0.98 (br s, 6H). | MS: (ES) m/z calculated for $C_{29}H_{26}ClF_3N_6$ [M + H]⁺ 551.2, found 551.2. |

TABLE 1-continued

Structure & NMR/MS Characterization Data of Specific Embodiments

| Structure | ¹H NMR | MS |
| --- | --- | --- |
| Ex. 77.071 | ¹H NMR (400 MHZ, CDCl₃) δ 8.33 (br s, 1H), 8.61 (br s, 1H), 8.20 (s, 2H), 7.26 (t, J = 2.8, 1H), 7.20 (t, J = 7.6, 1H), 7.03 (t, J = 7.2, 2H), 7.60 (d, J = 7.6, 1H), 6.55 (m, 2H), 4.74 (br s, 2H), 4.29 (br s, 2H), 3.03 (t, J = 5.85, 2H), 2.76 (septet, J = 7.0, 1H), 2.10-2.40 (2 br s, 4H), 1.21 (d, J = 7.2, 6H), 0.99 (br s, 6H). | MS: (ES) m/z calculated for $C_{31}H_{33}ClN_6$ [M + H]⁺ 525.3, found 525.3. |
| Ex. 77.072 | ¹H NMR (400 MHZ, CD₃OD) δ 10.72 (s, 1H), 8.31 (s, 1H), 7.73 (dd, J = 2.5, 9.1, 1H), 7.40 (d, J = 3.1, 1H), 7.25 (t, J = 7.6, 1H), 7.08 (s, 2H), 6.90 (dd, J = 5.2, 8.3, 2H), 6.58 (d, J = 7.4, 1H), 6.45 (d, J = 3.2, 1H), 4.83-4.89 (m, 3H), 4.64 (s, 2H), 4.20 (s, 2H), 3.02 (t, J = 5.8, 2H), 2.11-2.46 (m, 4H), 0.85-1.08 (m, 6H). | MS: (ES) m/z calculated $C_{31}H_{31}F_3N_5O$ [M + H]⁺ 564.2, found 564.2. |
| Ex. 77.073 | ¹H NMR (400 MHz, CDCl₃) δ 8.80 (br s, 1H), 7.81 (s, 1H), 7.20 (t, J = 7.6, 1H), 7.12 (t, J = 2.8, 1H), 7.02 (br d, J = 6.0, 2H), 6.91 (dd, J = 13.6, 3.2, 1H), 6.64 (m, 1H), 6.52 (m, 2H), 4.41 (br s, 2H), 3.83 (t, J = 5.8, 2H), 3.11 (t, J = 5.8, 2H), 2.1-2.42 (2 br s, 4H), 1.81 (m, 1H), 0.86-1.10 (m, 8H), 0.60 (m, 2H). | MS: (ES) m/z calculated for $C_{32}H_{31}F_2N_5$ [M + H]⁺ 524.3, found 524.3. |

TABLE 1-continued

Structure & NMR/MS Characterization Data of Specific Embodiments

| Structure | ¹H NMR | MS |
|---|---|---|
| Ex. 77.074 | ¹H NMR (400 MHz, CDCl₃) δ 8.61 (br s, 1H), 7.93 (d, J = 2.3, 1H), 7.27 (d, J = 1.6, 1H), 7.20 (t, J = 7.6, 1H), 7.16 (t, J = 2.8, 1H), 7.02 (d, J = 6.8, 2H), 6.64 (m, 1H), 6.52 (m, 2H), 4.29 (br s, 2H), 3.72 (t, J = 5.6, 2H), 3.16 (t, J = 5.6, 2H), 2.10-2.50 (2 br s, 4H), 1.79 (m, 1H), 0.90-1.10 (m, 8H), 0.62 (m, 2H). | MS: (ES) m/z calculated for $C_{32}H_{31}ClFN_5$ [M + H]⁺ 540.2, found 540.2. |
| Ex. 77.075 | ¹H NMR (400 MHZ, CDCl₃) δ 8.79 (br s, 1H), 8.16 (s, 2H), 7.20 (t, J = 7.8, 1H), 7.17 (t, J = 2.8, 1H), 7.02 (br d, J = 6.8, 2H), 6.64 (m, 1H), 6.51 (m, 2H), 4.73 (br s, 2H), 4.28 (br s, 2H), 3.02 (t, J = 5.8, 2H), 2.11 (s, 3H), 2.10-2.44 (2 br s, 4H), 0.99 (br s, 6H). | MS: (ES) m/z calculated for $C_{29}H_{29}FN_6$ [M + H]⁺ 482.2, found 482.2. |
| Ex. 77.076 | ¹H NMR (400 MHz, CDCl₃) δ 8.65 (br s, 1H), 8.49 (br s, 2H), 7.23 (t, J = 2.6, 1H), 7.20 (t, J = 7.6, 1H), 7.03 (br d, J = 7.6, 2H), 6.68 (m, 1H), 6.51 (m, 2H), 4.84 (br s, 2H), 4.37 (br s, 2H), 3.05 (t, J = 12, 2H), 2.04-2.42 (2 br s, 4H), 0.98 (br s, 6H). | MS: (ES) m/z calculated for $C_{29}H_{26}F_4N_6$ [M + H]⁺ 535.2, found 535.2. |

TABLE 1-continued

Structure & NMR/MS Characterization Data of Specific Embodiments

| Structure | ¹H NMR | MS |
|---|---|---|
| 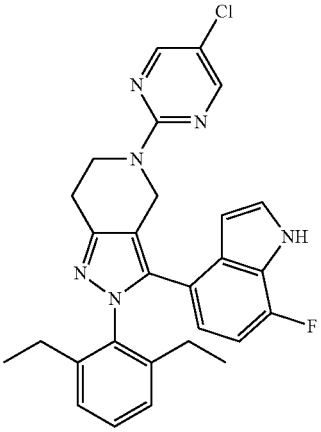 [SMILES: CCc1cccc(CC)c1-n1nc2c(c1-c1ccc(F)c3[nH]ccc13)CN(c1ncc(Cl)cn1)CC2]<br>Ex. 77.077 | ¹H NMR (400 MHZ, CDCl₃) δ 8.60 (br s, 1H), 8.22 (s, 2H), 7.23 (t, J = 6.8, 1H), 7.20 (d, J = 7.2, 1H), 7.02 (d, J = 6.8, 2H), 6.67 (m, 1H), 6.52 (m, 2H), 4.74 (s, 2H), 4.27 (br s, 2H), 3.02 (d, J = 6.0, 2H), 2.06-2.40 (two br s, 4H), 0.97 (br s, 6H). | MS: (ES) m/z calculated for $C_{28}H_{26}ClFN_6$ [M + H]⁺ 501.2, found 501.2. |
| 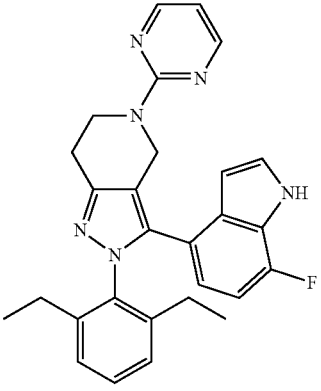 [SMILES: CCc1cccc(CC)c1-n1nc2c(c1-c1ccc(F)c3[nH]ccc13)CN(c1ncccn1)CC2]<br>Ex. 77.078 | ¹H NMR (400 MHZ, CDCl₃) δ 8.75 (br s, 1H), 8.14 (d, J = 1.6, 1H), 8.06 (m, 1H), 7.82 (d, J = 2.8, 1H), 7.25 (t, J = 2.8, 1H), 7.20 (d, J = 8.0, 1H), 7.03 ( br d, J = 7.6, 2H), 6.69 (m, 1H), 6.48-6.56 (m, 2H), 4.56 (br s, 2H), 4.15 (t, J = 5.8, 2H), 3.08 (t, J = 5.8, 2H), 2.00-2.42 (2 br s, 4H), 0.99 (br s, 6H). | MS: (ES) m/z calculated for $C_{28}H_{27}FN_6$ [M + H]⁺ 467.2, found 467.2. |
| 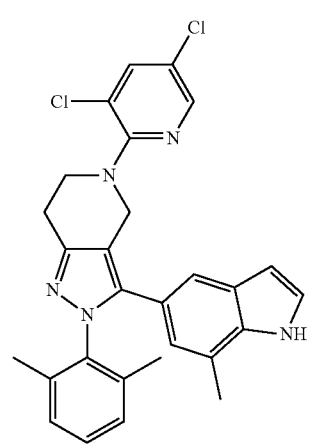<br>Ex. 77.079 | ¹H NMR (400 MHZ, d₆-DMSO) δ 11.15 (s, 1H), 8.24 (d, J = 2.6, 1H), 8.05 (d, J = 2.6, 1H), 7.31 (t, J = 2.8, 1H), 7.17 (t, J = 7.6, 1H), 7.13 (s, 1H), 7.06 (d, J = 7.6, 2H), 6.62 (s, 1H), 6.34 (m, 1H), 4.39 (s, 2H), 3.67 (t, J = 5.2, 2H), 2.97 (t, J = 6.0, 2H), 2.32 (s, 3H), 1.91 (s, 6H). | MS: (ES) m/z calculated for $C_{28}H_{26}Cl_2N_5$ [M + H]⁺ 514.2, found 514.2. |

TABLE 1-continued

Structure & NMR/MS Characterization Data of Specific Embodiments

| Structure | ¹H NMR | MS |
|---|---|---|
| Ex. 77.080 | ¹H NMR (400 MHz, d₆-DMSO) δ 12.29 (s, 1H), 8.25 (d, J = 2.2, 1H), 8.24 (d, J = 2.8, 1H), 7.49 (d, J = 8.8, 1H), 7.29 (s, 1H), 7.21 (t, J = 7.6, 1H), 7.09 (d, J = 7.6, 2H), 7.05 (dd, J = 1.2, 8.4, 1H), 4.44 (s, 2H), 2.99 (t, J = 6.0, 2H), 1.90 (s, 6H). | MS: (ES) m/z calculated for $C_{28}H_{23}Cl_2N_6$ [M + H]⁺ 513.1, found 513.1. |
| Ex. 77.081 | ¹H NMR (400 MHz, d₆-DMSO) δ 11.59 (s, 1H), 8.25 (d, J = 2.5, 1H), 8.06 (d J = 2.2, 1H), 7.41 (t, J = 2.8, 1H), 7.33 (s, 1H), 7.20 (t, J = 7.2, 1H), 7.10 (d, J = 7.2, 2H), 6.80 (d, J = 1.2, 1H), 6.49 (m, 1H), 4.41 (s, 2H), 3.68 (t, J = 6.0, 2H), 2.98 (t, J = 6.0, 2H), 1.91 (s, 6H). | MS: (ES) m/z calculated for $C_{27}H_{23}Cl_3N_5$ [M + H]⁺ 522.1, found 522.1. |
| Ex. 77.082 | ¹H NMR (400 MHz, d₆-DMSO) δ 8.26 (d, J = 2.2, 1H), 8.07 (d, J = 2.2, 1H), 8.05 (s, 1H), 7.56 (s, 1H), 7.46 (d, J = 8.8, 1H), 7.21 (t, J = 7.6, 1H), 7.10 (d, J = 7.6, 2H), 7.05 (dd, J = 1.6, 8.8, 1H), 4.43 (s, 2H), 3.70 (t, J = 5.6, 2H), 3.01 (t, J = 5.6, 2H), 1.92 (s, 6H). | MS: (ES) m/z calculated for $C_{26}H_{23}Cl_2N_6$ [M + H]⁺ 489.1, found 489.1. |

… TABLE 1-continued

Structure & NMR/MS Characterization Data of Specific Embodiments

| Structure | ¹H NMR | MS |
|---|---|---|
| 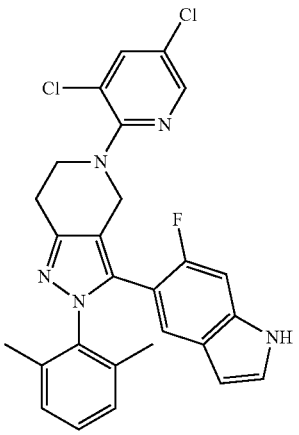 [SMILES: Cc1cccc(C)c1-n1nc2c(c1-c1cc3cc[nH]c3cc1F)CN(c1ncc(Cl)cc1Cl)CC2]<br>Ex. 77.083 | ¹H NMR (400 MHz, DMSO-d₆) δ 11.27 (s, 1H), 8.23 (d, J = 2.3, 1H), 8.07 (d, J = 2.3, 1H), 7.11-7.33 (m, 4H), 7.05 (d, J = 7.6, 2H), 6.35 (t, J = 2.4, 1H), 4.27 (s, 2H), 3.57 (t, J = 5.7, 1H), 3.01 (t, J = 5.7, 2H), 1.95 (s, 6H). | MS: (ES) m/z calculated $C_{27}H_{23}Cl_2FN_5$ [M + H]⁺ 506.1, found 506.3. |
| 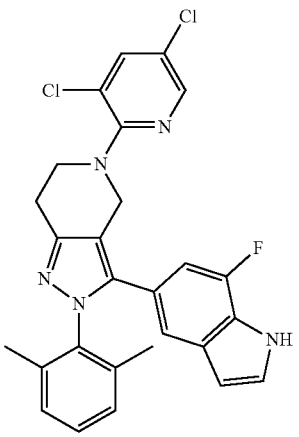 [SMILES: Cc1cccc(C)c1-n1nc2c(c1-c1cc(F)c3[nH]ccc3c1)CN(c1ncc(Cl)cc1Cl)CC2]<br>Ex. 77.084 | ¹H NMR (400 MHz, CDCl₃) δ 8.33 (s, 1H), 8.04 (dd, J = 0.4, 2.4, 1H), 8.07 (d, J = 2.3, 1H), 7.62 (dd, J = 0.4, 2.3, 1H), 7.01-7.30 (m, 4H), 6.73-6.84 (m, 2H), 6.42 (ddd, J = 0.9, 2.1, 3.1, 1H), 4.45 (d, J = 15.1, 1H), 4.16 (d, J = 15.1, 1H), 3.71-3.83 (m, 2H), 3.15-3.23 (m, 2H), 2,25 (s, 3H), 1.76 (s, 3H). | MS: (ES) m/z calculated $C_{27}H_{23}Cl_2FN_5$ [M + H]⁺ 506.1, found 506.3. |
| 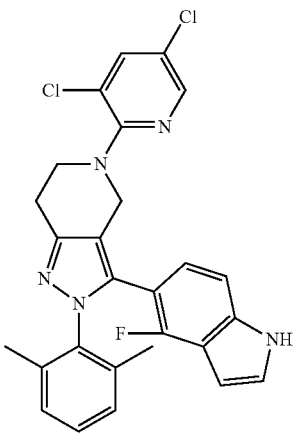 [SMILES: Cc1cccc(C)c1-n1nc2c(c1-c1ccc3[nH]ccc3c1F)CN(c1ncc(Cl)cc1Cl)CC2]<br>Ex. 77.085 | ¹H NMR (400 MHZ, CDCl₃) δ 8.35 (s, 1H), 8.10 (dd, J = 0.8, 2.3, 1H), 7.62 (dd, J = 0.8, 2.3, 1H), 7.05-7.20 (m, 4H), 6.93-7.02 (m, 3H), 6.61-6.75 (m, 2H), 4.42 (s, 2H), 3.78 (t, J = 5.7, 2H), 3.17 (t, J = 5.7, 2H), 2,05 (d, J = 3.3, 6H). | MS: (ES) m/z calculated $C_{27}H_{23}Cl_2FN_5$ [M + H]⁺ 506.1, found 506.3. |

TABLE 1-continued

Structure & NMR/MS Characterization Data of Specific Embodiments

| Structure | $^1$H NMR | MS |
|---|---|---|
| 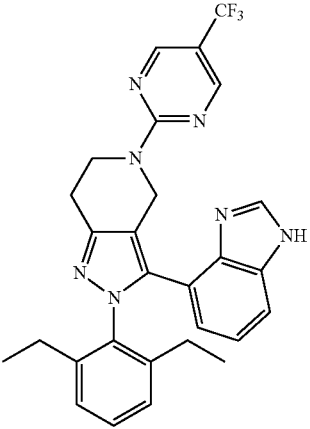<br>Ex. 77.086 | | MS: (ES) m/z calculated $C_{28}H_{27}F_3N_7[M + H]^+$ 518.2, found 518.5. |
| 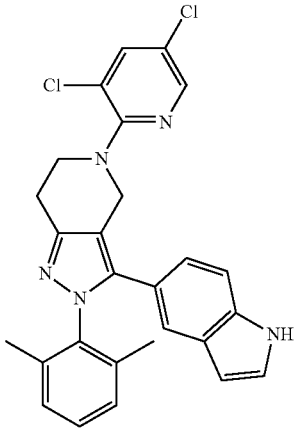 [SMILES: Cc1cccc(C)c1-n1nc2c(c1-c1ccc3[nH]ccc3c1)CN(c1ncc(Cl)cc1Cl)CC2]<br>Ex. 77.087 | $^1$H NMR (400 MHZ, CDCl$_3$) δ 8.20 (s, 1H), 8.12 (d, J = 2.3, 1H), 7.63 (d, J = 2.3, 1H), 7.42-7.47 (m, 1H), 7.09-7.28 (m, 3H), 7.02 (d, J = 7.6, 2H), 6.90 (dd, J = 8.5, 1.6, 1H), 6.50 (t, J = 2.5 Hz, 1H), 4.55 (s, 2H), 3.81-3.69 (m, 2H), 3.16 (t, J = 5.8 Hz, 2H), 2.03 (s, 6H). | MS: (ES) m/z calculated C27H24Cl2N5 [M + H]$^+$ 488.1, found 488.3. |
| 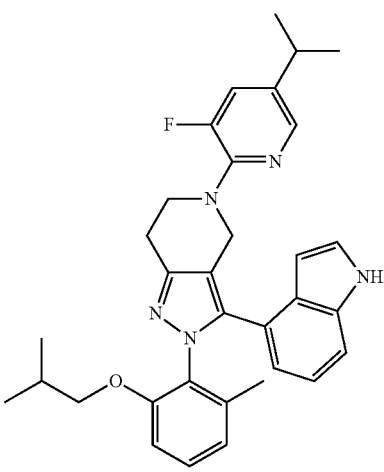 [SMILES: Cc1cccc(OCC(C)C)c1-n1nc2c(c1-c1cccc3[nH]ccc13)CN(c1ncc(C(C)C)cc1F)CC2]<br>Ex. 77.088 | $^1$H NMR (400 MHZ, Methanol-d$_4$) δ 7.73 (dd, J = 14.1, 2.0 Hz, 1H), 7.66 (dd, J = 2.0, 0.6 Hz, 1H), 7.41-7.30 (m, 2H), 7.20 (dd, J = 8.3, 7.7 Hz, 1H), 6.94 (t, J = 7.7 Hz, 1H), 6.83 (d, J = 7.9 Hz, 2H), 6.71 (s, 1H), 6.43 (dd, J = 3.1, 0.9 Hz, 1H), 4.94-4.65 (m, 2H), 4.03 (t, J = 5.7 Hz, 2H), 3.95-3.60 (m, 3H), 3.16-3.07 (m, 2H), 2.92 (p, J = 6.9 Hz, 1H), 1.8 (brs, 3H), 1.24 (d, J = 6.9 Hz, 6H), 0.88 (s, 6H). | MS: (ES) m/z calculated for C33H37FN5O [M + H]$^+$ 538.3, found 538.3. |

TABLE 1-continued

Structure & NMR/MS Characterization Data of Specific Embodiments

| Structure | ¹H NMR | MS |
|---|---|---|
| 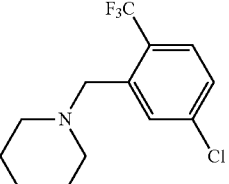<br>Ex. 77.089 | ¹H NMR (400 MHz, CDCl₃) δ 8.13 (s, 1H), 7.98 (d, J = 1.7, 1H), 7.54 (d, J = 8.4, 1H), 7.43 (dd, J = 0.8, 1.6, 1H), 7.09-7.32 (m, 4H), 6.92-6.99 (m, 1H), 6.65-6.78 (m, 2H), 6.46 (td, J = 1.1, 2.3, 1H), 3.89 (s, 2H), 3.80 (d, J = 13.6, 1H), 3.70 (d, J = 13.6, 1H), 3.52-3.64 (m, 2H), 2.79-2.98 (m, 4H), 2.05 (s, 3H), 0.85 (ddd, J = 0.8, 5.5, 6.6, 6H). | MS: (ES) m/z calculated C₃₃H₃₃ClF₃N₄O [M + H]⁺ 593.2, found 593.3. |
| 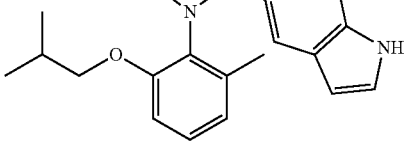<br>Ex. 77.090 | ¹H NMR (400 MHz, Methanol-d₄) δ 8.25 (d, J = 1.9 Hz, 1H), 7.64 (dd, J = 13.5, 2.1 Hz, 1H), 7.34 (dd, J = 1.7, 0.7 Hz, 1H), 7.28-7.19 (m, 2H), 7.04-6.95 (m, 2H), 6.93-6.76 (m, 2H), 4.85 (s, 2H), 4.18-4.01 (m, 2H), 3.71-3.58 (m, 2H), 3.02 (dd, J = 6.2, 2.3 Hz, 2H), 2.13 (s, 3H), 1.96 (s, 3H), 1.87 (dt, J = 13.1, 6.6 Hz, 1H), 0.82 (dd, J = 6.7, 3.6 Hz, 6H). | MS: (ES) m/z calculated for C₃₂H₃₂F₄N₅O [M + H]⁺ 578.3, found 578.2. |
| 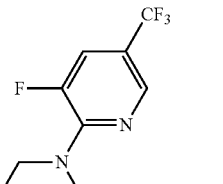<br>Ex. 77.091 | ¹H NMR (400 MHz, CDCl₃) δ 8.16 (s, 1H), 8.02 (s, 1H), 7.52 (d, J = 8.4, 1H), 7.26 (s, 4H), 7.18 (dd, J = 2.3, 3.1, 1H), 7.08 (t, J = 7.9, 1H), 6.97 (t, J = 7.7, 1H), 6.84 (s, 1H), 6.66 (s, 2H), 6.44 (s, 1H), 3.85 (s, 2H), 3.40-3.70 (m, 4H), 2.90-3.05 (m, 4H), 2.35 (s, 3H), 1.92 (m, 1H), 0.87 (m, 6H). | MS: (ES) m/z calculated C₃₃H₃₃ClF₃N₄O [M + H]⁺ 593.2, found 593.3. |

TABLE 1-continued

Structure & NMR/MS Characterization Data of Specific Embodiments

| Structure | $^1$H NMR | MS |
|---|---|---|
| 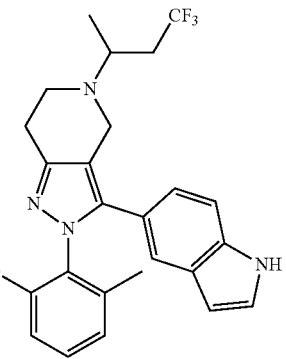<br>Ex. 77.092 | $^1$H NMR (400 MHz, CDCl$_3$) δ 8.24 (s, 1H), 7.44 (s, 1H), 7.07-7.30 (m, 3H), 6.96 (dt, J = 1.4, 8.5, 1H), 6.64-6.75 (m, 2H), 6.47 (dt, J = 1.4, 3.2, 1H), 3.51-3.82 (m, 4H), 3.25 (dtd, J = 3.3, 6.4, 9.8, 1H), 2.75-3.01 (m, 4H), 2.54 (ddd, J = 3.4, 11.7, 15.0, 1H), 2.08-2.26 (m, 1H), 1.84-2.07 (m, 4H), 1.23-1.33 (m, 3H), 0.79-0.96 (m, 6H). | MS: (ES) m/z calculated C$_{29}$H$_{34}$F$_3$N$_4$O [M + H]$^+$ 511.3, found 511.5. |
| 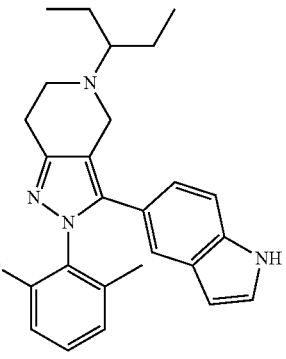<br>Ex. 77.093 | $^1$H NMR (400 MHz, CDCl$_3$) δ 8.14 (s, 1H), 7.45 (dd, J = 1.0, 1.7, 1H), 7.07-7.28 (m, 3H), 6.98 (dd, J = 1.6, 8.6, 1H), 6.64-6.76 (m, 2H), 6.47 (ddd, J = 0.9 2.0, 3.1, 1H), 3.67-3.77 (m, 2H), 3.51-3.63 (m, 2H), 2.82-2.95 (m, 4H), 2.39 (dd, J = 8.9, 15.4, 1H), 2.02 (s, 3H), 1.91 (dt, J = 6.7, 13.3, 1H), 1.42 (tt, J = 7.2, 13.9, 2H), 0.94 (td, J = 1.6, 7.4, 6H), 0.83 (dd, J = 3.9, 6.7, 6H). | MS: (ES) m/z calculated C$_{30}$H$_{39}$N$_4$O [M + H]$^+$ 471.3, found 471.5. |
| 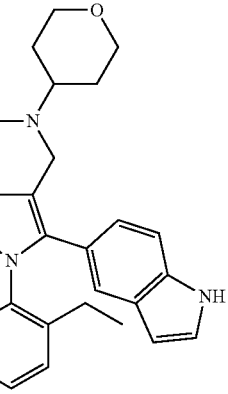<br>Ex. 77.094 | $^1$H NMR (400 MHZ, CDCl$_3$) δ 8.20 (s, 1H), 7.33-7.43 (m, 2H), 7.14-7.31 (m, 2H), 7.07 (d, J = 7.6, 2H), 6.83 (dd, J = 1.6, 8.5, 1H), 6.46 (ddd, J = 1.0, 1.9, 3.1, 1H), 4.06 (dd, J = 4.1, 11.3, 2H), 3.82 (s, 2H), 3.37-3.48 (m, 2H), 2.91-3.04 (m, 4H), 2.77 (ddd, J = 4.2, 7.8, 11.6, 1H), 2.28 (ddq, J = 7.5, 15.0, 55.2, 4H), 1.89 (d, J = 11.3 Hz, 2H), 1.75 (qd, J = 12.1, 4.3 Hz, 2H), 1.02 (td, J = 0.9, 7.6, 6H). | MS: (ES) m/z calculated C$_{29}$H$_{35}$N$_4$O [M + H]$^+$ 455.3, found 455.5. |

TABLE 1-continued

Structure & NMR/MS Characterization Data of Specific Embodiments

| Structure | ¹H NMR | MS |
|---|---|---|
| Ex. 77.095 | ¹H NMR (400 MHz, CDCl$_3$) δ 8.19 (s, 1H), 7.32-7.37 (m, 1H), 7.13-7.30 (m, 3H), 7.06 (d, J = 7.7, 2H), 6.83 (dd, J = 1.6, 8.5, 1H), 6.46 (ddd, J = 0.9, 2.1, 3.2, 1H), 3.72 (s, 2H), 2.96 (m, 4H), 2.82 (m, 1H), 2.34 (dq, J = 7.6, 15.1, 2H), 2.20 (dq, J = 15.2, 7.6 Hz, 2H), 1.99 (m, 2H), 1.50-1.72 (m, 6H), 0.93-1.06 (m, 6H). | MS: (ES) m/z calculated C$_{29}$H$_{35}$N$_4$ [M + H]$^+$ 439.3, found 439.2. |
| Ex. 77.096 | ¹H NMR (400 MHZ, CDCl$_3$) δ 8.25 (s, 1H), 7.38 (s, 1H), 7.02-7.29 (m, 5H), 6.85 (dt, J = 2.0, 8.6, 1H), 6.46 (dd, J = 1.9, 3.8, 1H), 3.84 (d, J = 12.9, 1H), 3.65 (d, J = 12.9, 1H), 2.75-3.05 (m, 4H), 2.11-2.48 (m, 5H), 1.77-1.87 (m, 1H), 1.18-1.35 (m, 3H), 0.80-1.17 (m, 12H). | MS: (ES) m/z calculated C$_{29}$H$_{37}$N$_4$ [M + H]$^+$ 441.3, found 441.2. |
| Ex. 77.097 | ¹H NMR (400 MHz, CDCl$_3$) δ 8.26-8.32 (m, 1H), 7.38 (q, J = 0.9, 1H), 7.11-7.30 (m, 3H), 7.06 (d, J = 7.7, 2H), 6.84 (dd, J = 1.6, 8.5, 1H), 6.46 (ddd, J = 0.9, 2.0, 3.1, 1H), 3.77 (s, 2H), 2.89 (dq, J = 4.6, 9.2, 4H), 2.15-2.47 (m, 5H), 1.58-1.75 (m, 2H), 1.45 (dp, J = 7.3, 14.4, 2H), 0.80-1.10 (m, 12H). | MS: (ES) m/z calculated C$_{29}$H$_{37}$N$_4$ [M + H]$^+$ 441.3, found 441.2. |

TABLE 1-continued

Structure & NMR/MS Characterization Data of Specific Embodiments

| Structure | ¹H NMR | MS |
|---|---|---|
| Ex. 77.098 | ¹H NMR (400 MHz, Methanol-$d_4$) δ 7.46 (dd, J = 1.7, 0.7 Hz, 1H), 7.33-7.19 (m, 3H), 6.98 (dd, J = 8.5, 1.7 Hz, 1H), 6.89-6.76 (m, 2H), 6.38 (dd, J = 3.2, 0.9 Hz, 1H), 6.09 (dd, J = 2.2, 1.1 Hz, 1H), 5.41 (dd, J = 2.2, 1.5 Hz, 1H), 4.80-4.64 (m, 2H), 4.04 (t, J = 5.9 Hz, 2H), 3.70-3.58 (m, 2H), 3.01 (t, J = 6.0 Hz, 2H), 2.11 (t, J = 1.2 Hz, 3H), 1.98 (s, 3H), 1.88 (dt, J = 13.1, 6.6 Hz, 1H), 1.31-1.14 (m, 1H), 0.83 (dd, J = 6.8, 1.1 Hz, 6H). | MS: (ES) m/z calculated for $C_{30}H_{33}N_6OS$ [M + H]⁺ 525.2, found 525.2. |
| Ex. 77.099 | | MS: (ES) m/z calculated for $C_{31}H_{31}F4N_6O$ [M + H]⁺ 579.2, found 579.2. |
| Ex. 77.100 | ¹H NMR (400 MHZ, Methanol-$d_4$) δ 8.44 (dd, J = 2.2, 1.0 Hz, 1H), 8.04-7.99 (m, 1H), 7.54-7.49 (m, 1H), 7.39-7.22 (m, 3H), 7.04-6.92 (m, 2H), 6.90-6.82 (m, 1H), 6.41 (dd, J = 3.2, 0.8 Hz, 1H), 4.98-4.85 (m, 1H), 4.79-4.64 (m, 2H), 4.11-3.89 (m, 2H), 3.79-3.67 (m, 2H), 3.30 (p, J = 1.7 Hz, 8H), 3.16 (t, J = 5.7 Hz, 2H), 2.00 (s, 3H), 1.97-1.85 (m, 1H), 0.85 (dd, J = 6.8, 1.2 Hz, 6H) | MS: (ES) m/z calculated for $C_{31}H_{30}ClF_3N_5O$ [M + H]⁺ 580.2, found 580.2. |

TABLE 1-continued

Structure & NMR/MS Characterization Data of Specific Embodiments

| Structure | ¹H NMR | MS |
|---|---|---|
| Ex. 77.101 | ¹H NMR (400 MHZ, CDCl₃) δ 9.03 (s, 1H), 8.20 (q, J = 1.2, 1H), 8.09-8.16 (m, 1H), 7.31-7.44 (m, 2H), 7.13 (t, J = 8.0, 1H), 6.76-6.83 (m, 1H), 6.65-6.73 (m, 2H), 6.49-6.55 (m, 1H), 4.61-4.79 (m, 2H), 4.06 (ddt, J = 6.5, 13.2, 25.4, 2H), 3.51-3.67 (m, 2H), 3.05-3.14 (m, 2H), 1.96 (s, 3H), 1.80-1.90 (m, 1H), 0.86-0.77 (m, 6H). | MS: (ES) m/z calculated $C_{30}H_{29}F_4N_6O$ [M + H]⁺ 565.2, found 565.5. |
| Ex. 77.102 | ¹H NMR (400 MHZ, CDCl₃) δ 8.35 (s, 1H), 8.21 (dd, J = 1.1, 2.2, 1H), 7.33-7.48 (m, 1H), 7.11-7.33 (m, 3H), 6.68-6.80 (m, 3H), 6.52 (qd, J = 2.0, 3.3, 1H), 4.74-4.88 (m, 2H), 3.97-4.12 (m, 2H), 3.62 (dd, J = 1.0, 6.4, 2H), 3.07 (t, J = 5.8, 2H), 2.01 (s, 3H), 1.91 (m, 1H), 0.82 (dd, J = 1.0, 6.7, 6H). | MS: (ES) m/z calculated $C_{31}H_{29}F_5N_5O$ [M + H]⁺ 582.2, found 582.5. |
| Ex. 77.103 | ¹H NMR (400 MHZ, CDCl₃) δ 8.17 (s, 1H), 7.90-7.97 (m, 1H), 7.58-7.65 (m, 1H), 7.45-7.56 (m, 2H), 7.15-7.36 (m, 6H), 7.02 (dd, J = 1.7, 8.4, 1H), 6.49 (ddd, J = 0.9, 2.0, 3.1, 1H), 3.92 (s, 2H), 3.73 (s, 2H), 2.97 (t, J = 5.6, 2H), 2.89 (t, J = 5.7, 2H). | MS: (ES) m/z calculated $C_{28}H_{22}Cl_2F_3N_4$ [M + H]⁺ 541.1, found 541.3. |

TABLE 1-continued

Structure & NMR/MS Characterization Data of Specific Embodiments

| Structure | ¹H NMR | MS |
|---|---|---|
| Ex. 77.104 | ¹H NMR (400 MHz, CDCl₃) δ 8.05 (s, 1H), 7.21-7.43 (m, 4H), 7.06-7.20 (m, 4H), 6.85-6.95 (m, 2H), 3.84 (d, J = 17.3 Hz, 4H), 2.97 (s, 4H), 2.29 (ddq, J = 7.5, 15.1, 54.9, 4H), 1.05 (td, J = 7.6, 0.7 Hz, 6H). | MS: (ES) m/z calculated C₃₁H₃₀Cl₂FN₄ [M + H]⁺ 547.2, found 547.5. |
| Ex. 77.105 | ¹H NMR (400 MHZ, CDCl₃) δ 8.19 (s, 1H), 7.94 (d, J = 7.8, 1H), 7.59-7.66 (m, 1H), 7.52 (t, J = 7.7, 1H), 7.08-7.39 (m, 5H), 6.97-7.04 (m, 2H), 6.84 (dd, J = 1.6, 8.5, 1H), 6.43-6.49 (m, 1H), 3.94 (s, 2H), 3.78 (s, 2H), 2.80-2.99 (m, 4H), 2.00 (s, 6H). | MS: (ES) m/z calculated C₃₀H₂₈F₃N₄ [M + H]⁺ 501.2, found 501.3. |
| Ex. 77.106 | ¹H NMR (400 MHz, CDCl₃) δ 8.16 (s, 1H), 7.94 (d, J = 7.8, 1H), 7.60 (d, J = 7.9, 1H), 7.51 (t, J = 7.8, 1H), 7.21-7.35 (m, 2H), 7.16 (t, J = 2.9, 1H), 7.07 (td, J = 0.9, 8.0, 1H), 6.97 (td, J = 1.0, 7.8, 1H), 6.85 (br, 1H), 6.65 (br, 2H), 6.45 (br, 1H), 3.86 (s, 2H), 3.62-3.67 (m, 2H), 3.50 (s, 2H), 3.01-2.83 (m, 4H), 1.90 (m, 1H), 1.56 (s, 3H), 0.92-0.81 (m, 6H). | MS: (ES) m/z calculated C₃₃H₃₄F₃N₄O [M + H]⁺ 559.3, found 559.3. |

TABLE 1-continued

Structure & NMR/MS Characterization Data of Specific Embodiments

| Structure | ¹H NMR | MS |
|---|---|---|
| 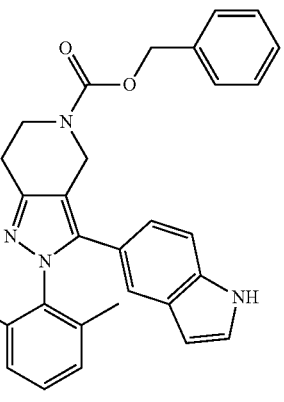<br>Ex. 77.107 | ¹H NMR (400 MHz, CDCl$_3$) δ 8.17 (s, 1H), 7.46 (s, 1H), 7.38 (br, 4H), 7.09-7.31 (m, 4H), 6.97 (d, J = 8.5, 1H), 6.66-6.76 (m, 2H), 6.42-6.49 (m, 1H), 5.18 (s, 2H), 4.62-4.75 (m, 2H), 3.83-3.93 (m, 2H), 3.54-3.67 (m, 2H), 2.90 (s, 2H), 2.03-1.86 (m, 4H), 0.79-0.92 (m, 6H). | MS: (ES) m/z calculated C$_{33}$H$_{35}$N$_4$O$_3$ [M + H]$^+$ 535.3, found 535.3. |
| 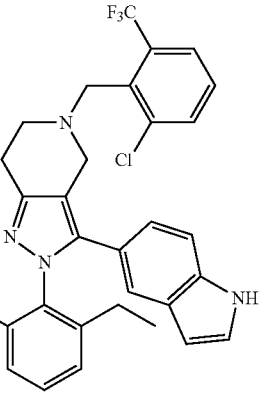<br>Ex. 77.108 | ¹H NMR (400 MHZ, CDCl$_3$) δ 8.12 (s, 1H), 7.61-7.54 (m, 2H), 7.13-7.45 (m, 5H), 7.07 (d, J = 7.7, 2H), 6.79-6.87 (m, 1H), 6.45 (dd, J = 2.1, 3.4, 1H), 4.02 (s, 2H), 3.80 (s, 2H), 2.98 (t, J = 5.9, 2H), 2.86 (t, J = 5.9, 2H), 2.42-2.14 (m, 4H), 0.93-1.06 (m, 6H). | MS: (ES) m/z calculated C$_{32}$H$_{31}$ClF$_3$N$_4$ [M + H]$^+$ 563.2, found 563.5. |
| 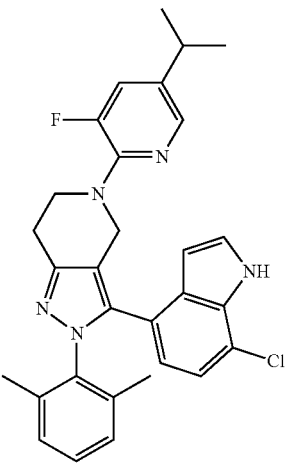 [SMILES: Cc1cccc(C)c1-n1nc2c(c1-c1ccc(Cl)c3[nH]ccc13)CN(c1ncc(C(C)C)cc1F)CC2]<br>Ex. 77.109 | 1H NMR (400 MHZ, CD$_3$OD) δ 7.80 (s, 1H), 7.42 (d, J = 3.4, 1H), 7.33 (dd, J = 2.1, 14, 1H), 7.14 (t, J = 7.6, 1H), 7.03 (br s, 2H), 6.93 (d, J = 7.6, 1H), 6.54-6.58 (m, 2H), 4.40 (br s, 2H), 3.85 (t, J = 6.0, 2H), 3.03 (t, J = 6.0, 2H), 2.82-2.92 (m, 1H), 1.95 (br s, 6H), 1.22 (d, J = 7.2, 6H). | MS: (ES) m/z calculated for C$_{30}$H$_{30}$ClFN$_5$ [M + H]$^+$ 514.2, found 514.2. |

TABLE 1-continued

Structure & NMR/MS Characterization Data of Specific Embodiments

| Structure | ¹H NMR | MS |
|---|---|---|
| 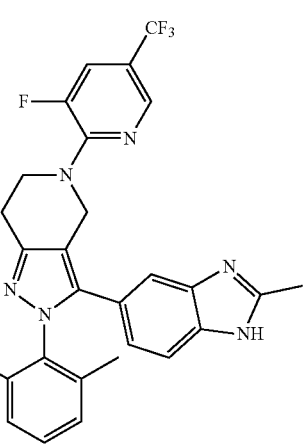<br>Ex. 77.110 | ¹H NMR (400 MHz, Methanol-$d_4$) δ 8.23 (dq, J = 2.1, 1.1 Hz, 1H), 7.68-7.52 (m, 1H), 7.40 (s, 1H), 7.33 (s, 1H), 7.23 (t, J = 8.0 Hz, 1H), 7.12 (dd, J = 8.3, 1.6 Hz, 1H), 6.87-6.76 (m, 2H), 4.90-4.77 (m, 2H), 4.17-3.99 (m, 3H), 3.62 (qd, J = 8.9, 6.2 Hz, 2H), 3.00 (t, J = 5.9 Hz, 2H), 2.52 (s, 3H), 1.99 (s, 3H), 1.83 (dp, J = 13.2, 6.7 Hz, 1H), 1.23 (t, J = 7.1 Hz, 1H), 0.89 (d, J = 6.7 Hz, 1H), 0.79 (dd, J = 6.8, 1.0 Hz, 6H). | MS: (ES) m/z calculated for $C_{31}H_{30}F_4N_6O$ [M + H]⁺ 579.2, found 579.2. |
| 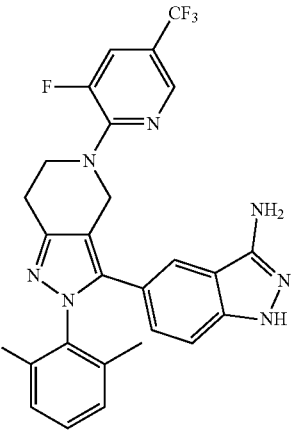<br>Ex. 77.111 | ¹H NMR (400 MHz, Methanol-$d_4$) δ 8.24 (dt, J = 2.0, 1.0 Hz, 1H), 7.69-7.60 (m, 2H), 7.24 (t, J = 8.0 Hz, 1H), 7.11 (qd, J = 8.7, 1.2 Hz, 2H), 6.88-6.78 (m, 2H), 4.84 (d, J = 1.5 Hz, 2H), 4.17-3.99 (m, 2H), 3.70-3.56 (m, 2H), 3.05-2.97 (m, 2H), 2.00 (d, J = 3.6 Hz, 3H), 1.85 (dp, J = 13.3, 6.6 Hz, 1H), 0.80 (d, J = 6.7 Hz, 6H). | MS: (ES) m/z calculated for $C_{30}H_{30}F_4N_7O$ [M + H]⁺ 580.2, found 580.2. |
| 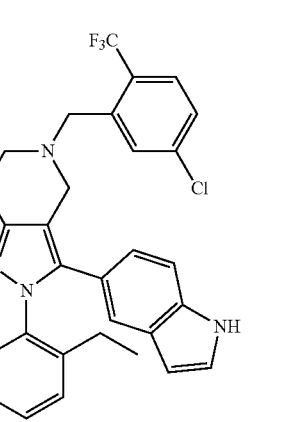<br>Ex. 77.112 | ¹H NMR (400 MHz, CDCl₃) δ 8.13 (s, 1H), 7.99 (s, 1H), 7.55 (d, J = 8.4, 1H), 7.13-7.39 (m, 5H), 7.09 (d, J = 7.7, 2H), 6.83 (dd, J = 1.7, 8.5, 1H), 6.42-6.49 (m, 1H), 3.90 (s, 2H), 3.79 (s, 2H), 2.86-3.00 (m, 4H), 2.20-2.43 (m, 4H), 1.09-1.01 (m, 6H). | MS: (ES) m/z calculated $C_{32}H_{31}ClF_3N_4$ [M + H]⁺ 563.2, found 563.5. |

TABLE 1-continued

Structure & NMR/MS Characterization Data of Specific Embodiments

| Structure | ¹H NMR | MS |
|---|---|---|
| 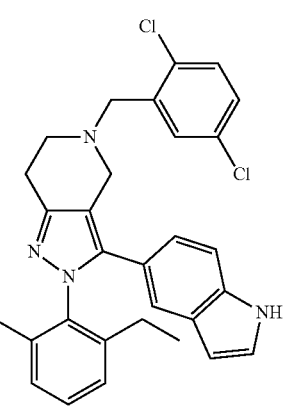<br>Ex. 77.113 | ¹H NMR (400 MHz, CDCl₃) δ 8.20 (s, 1H), 7.64 (d, J = 8.4, 1H), 7.12-7.31 (m, 6H), 7.08 (d, J = 7.7 Hz, 2H), 6.84 (dd, J = 1.7, 8.5, 1H), 6.42-6.49 (m, 1H), 3.83 (d, J = 12.5 Hz, 4H), 2.99-2.90 (m, 4H), 2.17-2.40 (m, 4H), 1.04 (td, J = 0.6, 7.6, 6H). | MS: (ES) m/z calculated $C_{31}H_{31}Cl_2N_4$ [M + H]⁺ 529.2, found 529.5. |
| 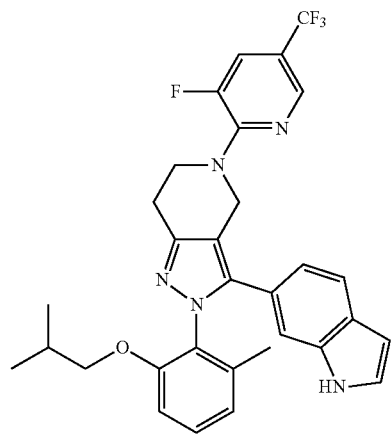 [SMILES: Cc1cccc(OCC(C)C)c1-n1nc2c(c1-c1ccc3cc[nH]c3c1)CN(c1ncc(C(F)(F)F)cc1F)CC2]<br>Ex. 77.114 | ¹H NMR (400 MHz, Methanol-d₄) δ 8.24 (dt, J = 2.0, 1.0 Hz, 1H), 7.60 (dd, J = 13.5, 2.1 Hz, 1H), 7.47 (dd, J = 8.2, 0.7 Hz, 1H), 7.30-7.20 (m, 3H), 6.95-6.78 (m, 3H), 6.41 (dd, J = 3.1, 0.9 Hz, 1H), 4.87 (d, J = 4.5 Hz, 2H), 4.10 (dtd, J = 19.7, 13.5, 5.9 Hz, 2H), 3.69-3.58 (m, 2H), 3.03 (t, J = 5.8 Hz, 2H), 2.00 (s, 3H), 1.84 (dp, J = 13.1, 6.6 Hz, 1H), 0.79 (d, J = 6.7 Hz, 6H). | MS: (ES) m/z calculated for $C_{31}H_{30}F_4N_5O$ [M + H]⁺ 564.2, found 564.2. |
| 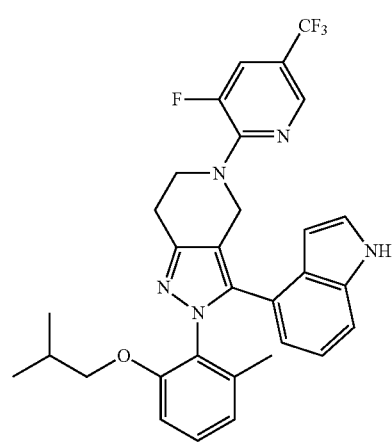 [SMILES: Cc1cccc(OCC(C)C)c1-n1nc2c(c1-c1cccc3[nH]ccc13)CN(c1ncc(C(F)(F)F)cc1F)CC2]<br>Ex. 77.115 | ¹H NMR (400 MHz, Methanol-d₄) δ 8.20 (dd, J = 2.3, 1.2 Hz, 1H), 7.58 (dd, J = 13.5, 2.1 Hz, 1H), 7.40-7.27 (m, 2H), 7.17 (t, J = 8.0 Hz, 1H), 6.97-6.88 (m, 1H), 6.85-6.77 (m, 2H), 6.69 (d, J = 7.7 Hz, 1H), 6.45-6.39 (m, 1H), 4.71 (d, J = 15.8 Hz, 1H), 4.20-4.02 (m, 2H), 3.69-3.63 (m, 2H), 3.06 (t, J = 5.9 Hz, 2H), 1.88 (s, 3H), 0.82 (d, J = 6.9 Hz, 6H). | MS: (ES) m/z calculated for $C_{31}H_{30}F_4N_5O$[M + H]⁺ 564.2, found 564.2. |

TABLE 1-continued

Structure & NMR/MS Characterization Data of Specific Embodiments

| Structure | ¹H NMR | MS |
|---|---|---|
| Ex. 77.116 | ¹H NMR (400 MHZ, CD$_3$OD) δ 7.80 (s, 1H), 7.38 (d, J = 3.4, 1H), 7.33 (dd, J = 2.0, 14, 1H), 7.26 (t, J = 8.0, 1H), 7.10 (br s, 2H), 6.63 (dd, J = 8.4, 11, 1 H), 6.49-6.53 (m, 2H), 4.38 (s, 2H), 3.85 (t, J = 6.0, 2H), 3.03 (t, J = 6.0, 2H), 2.83-2.92 (m, 1H), 2.31 (br s, 4H), 1.22 (d, J = 7.2, 6H), 0.99 (br s, 6H ). | MS: (ES) m/z calculated for C$_{32}$H$_{34}$F$_2$N$_5$ [M + H]$^+$ 526.3, found 526.3. |
| Ex. 77.117 | ¹H NMR (400 MHZ, CDCl$_3$) δ 8.20 (s, 1H), 7.43-7.13 (m, 6H), 7.08 (d, J = 7.7, 2H), 6.79-6.94 (m, 2H), 6.45 (ddd, J = 0.9, 2.0, 3.1, 1H), 3.83 (d, J = 16.1, 4H), 2.95 (t, J = 1.9, 4H), 2.11-2.45 (m, 4H), 1.32-1.21 (m, 2H), 1.04 (t, J = 7.6 Hz, 6H). | MS: (ES) m/z calculated C$_{31}$H$_{31}$ClFN$_4$ [M + H]$^+$ 513.2, found 513.3. |
| Ex. 77.118 | ¹H NMR (400 MHZ, CDCl$_3$) δ 8.11-8.20 (m, 2H), 7.87 (s, 1H), 7.77 (d, J = 8.0, 1H), 7.39-7.45 (m, 1H), 7.09-7.25 (m, 4H), 6.94 (dd, J = 1.6, 8.5, 1H), 6.65-6.77 (m, 2H), 6.45 (ddd, J = 0.9, 2.0, 3.0, 1H), 3.97 (s, 2H), 3.80 (d, J = 13.4, 1H), 3.71 (d, J = 13.4, 1H), 3.52-3.65 (m, 2H), 2.79-2.99 (m, 4H), 2.04 (s, 3H), 1.82-2.00 (m, 1H), 0.81-0.94 (m, 6H). | MS: (ES) m/z calculated C$_{34}$H$_{33}$F$_6$N$_4$O [M + H]$^+$ 627.3, found 627.3. |

TABLE 1-continued

Structure & NMR/MS Characterization Data of Specific Embodiments

| Structure | ¹H NMR | MS |
|---|---|---|
| 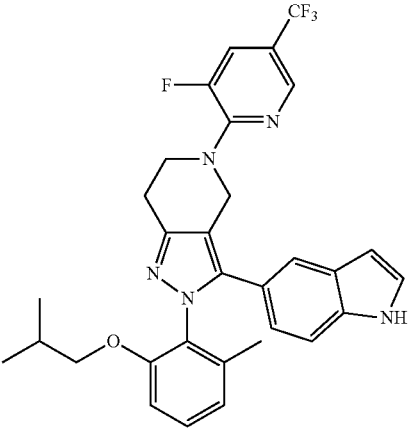 [SMILES: Cc1cccc(OCC(C)C)c1-n1nc2c(c1-c1ccc3[nH]ccc3c1)CN(c1ncc(C(F)(F)F)cc1F)CC2]<br>Ex. 77.119 | | MS: (ES) m/z calculated for $C_{31}H_{30}F_4N_5O$ [M +H] 564.2, found 564.2. |
| 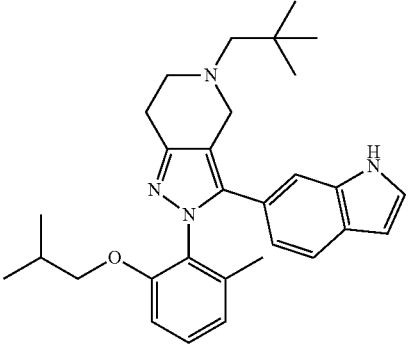 [SMILES: Cc1cccc(OCC(C)C)c1-n1nc2c(c1-c1ccc3cc[nH]c3c1)CN(CC(C)(C)C)CC2]<br>Ex. 77.120 | ¹H NMR (400 MHZ, CDCl₃) δ 8.11 (s, 1H), 7.44-7.51 (m, 1H), 7.08-7.20 (m, 3H), 6.92 (dt, J = 1.1, 8.2, 1H), 6.71-6.78 (m, 1H), 6.67 (d, J = 8.2, 1H), 6.48 (ddt, J = 0.8, 1.7, 3.0, 1H), 3.62-3.83 (m, 2H), 3.50-3.62 (m, 2H), 2.84-3.01 (m, 4H), 2.05 (s, 3H), 1.88 (dt, J = 6.9, 13.3, 1H), 0.90 (s, 9H), 0.79-0.83 (m, 6H). | MS: (ES) m/z calculated $C_{30}H_{39}N_4O$ [M + H]⁺ 471.3, found 471.5. |
| 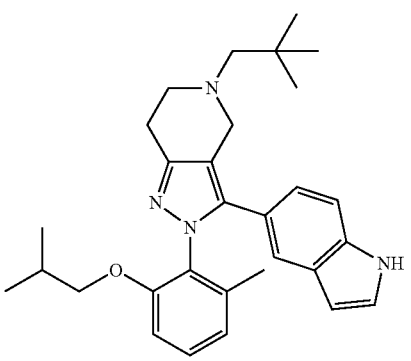 [SMILES: Cc1cccc(OCC(C)C)c1-n1nc2c(c1-c1ccc3[nH]ccc3c1)CN(CC(C)(C)C)CC2]<br>Ex. 77.121 | ¹H NMR (400 MHz, CDCl₃) δ 8.15 (s, 1H), 7.42 (dd, J = 0.8, 1.6, 1H), 7.07-7.22 (m, 3H), 6.96 (dd, J = 1.6, 8.5, 1H), 6.64-6.77 (m, 2H), 6.43-6.50 (m, 1H), 3.78 (d, J = 13.7, 1H), 3.69 (d, J = 13.7, 1H), 3.51-3.63 (m, 2H), 2.83-3.03 (m, 4H), 2.04 (s, 3H), 1.90 (dt, J = 6.6, 13.3, 1H), 0.78-0.93 (m, 15H). | MS: (ES) m/z calculated $C_{30}H_{39}N_4O$ [M + H]⁺ 471.3, found 471.2. |

TABLE 2

Structure & MS Characterization Data of Specific Embodiments

| MS | Structure |
|---|---|
| MS: (ES) m/z calculated C$_{28}$H$_{27}$ClN$_7$ [M + H]$^+$ 496.2, found 496.2. | Ex. 77.123 |
| MS: (ES) m/z calculated C$_{27}$H$_{22}$F$_5$N$_7$O [M + H]$^+$ 541.2, found 541.1. | Ex. 77.124 |
| MS: (ES) m/z calculated for C$_{31}$H$_{30}$F$_4$N$_5$O [M + H] 564.2, found 564.2. | Ex. 77.126 |

241
242
TABLE 2-continued
Structure & MS Characterization Data of Specific Embodiments
| MS | Structure |
| --- | --- |
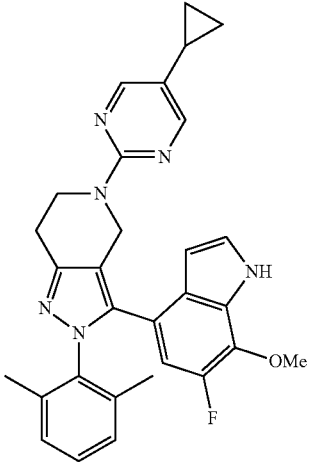 [SMILES: COc1c(F)cc(-c2c3c(nn2-c2c(C)cccc2C)CCN(c2ncc(C4CC4)cn2)C3)c2cc[nH]c12]
Ex. 77.127
MS: (ES) m/z calculated
C$_{30}$H$_{30}$FN$_6$O [M + H]$^+$ 509.2,
found 509.3.
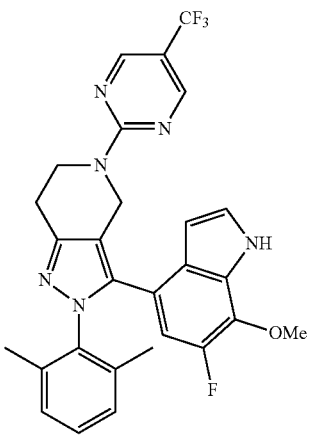 [SMILES: COc1c(F)cc(-c2c3c(nn2-c2c(C)cccc2C)CCN(c2ncc(C(F)(F)F)cn2)C3)c2cc[nH]c12]
Ex. 77.128
MS: (ES) m/z calculated
C$_{28}$H$_{25}$F$_4$N$_6$O [M + H]$^+$ 537.2,
found 537.4.
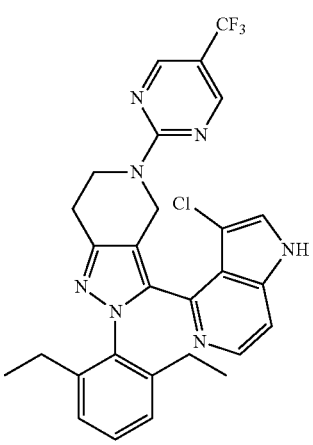 [SMILES: CCc1cccc(CC)c1-n1nc2c(c1-c1nccc3[nH]cc(Cl)c13)CN(c1ncc(C(F)(F)F)cn1)CC2]
Ex. 77.129
MS: (ES) m/z calculated
C$_{28}$H$_{26}$ClF$_3$N$_7$ [M + H]$^+$ 552.2,
found 552.5.

TABLE 2-continued
Structure & MS Characterization Data of Specific Embodiments
| MS | Structure |
|---|---|
| MS: (ES) m/z calculated for $C_{31}H_{31}F_4N_6O$ [M + H]$^+$ 579.2, found 579.2. | 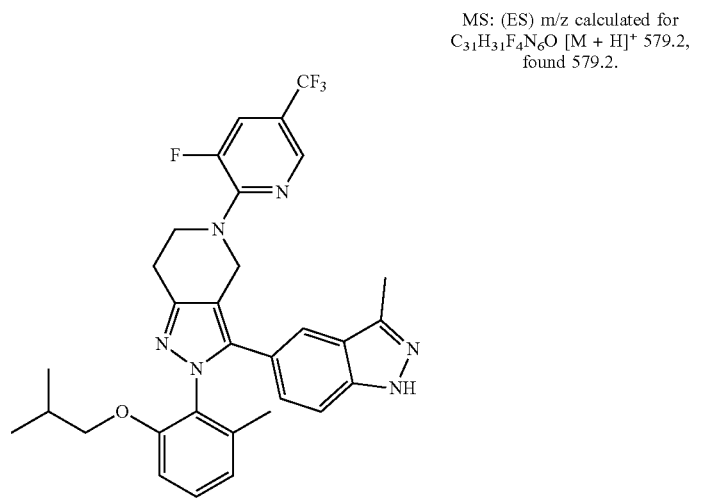<br>Ex. 77.130 |
| MS: (ES) m/z calculated $C_{29}H_{29}F_3N_7O$ [M + H]$^+$ 548.2, found 548.3. | 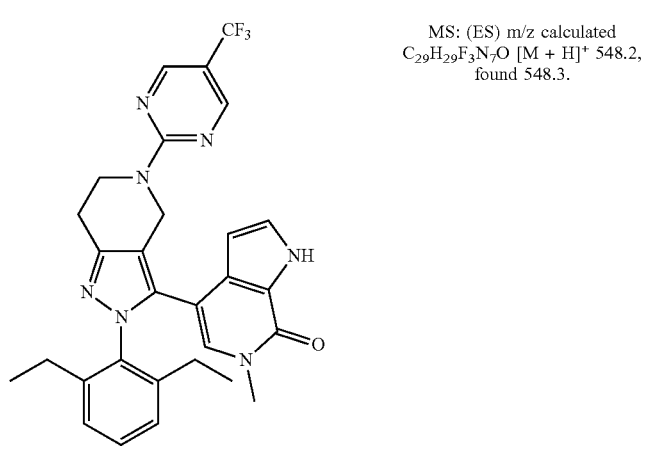<br>Ex. 77.131 |
| MS: (ES) m/z calculated $C_{28}H_{26}ClF_3N_7$ [M + H]$^+$ 552.2, found 552.5. | 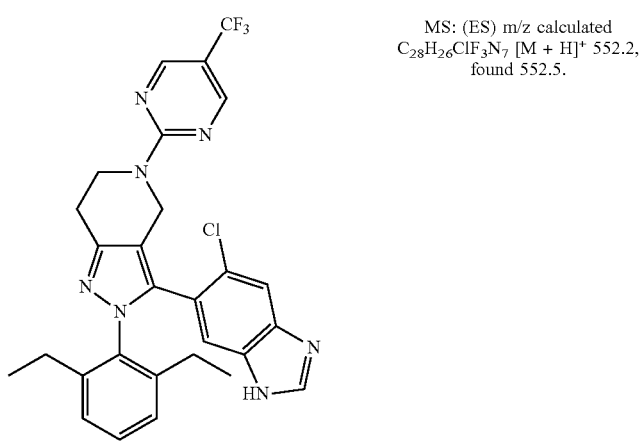<br>Ex. 77.132 |

TABLE 2-continued
Structure & MS Characterization Data of Specific Embodiments
| MS | Structure |
|---|---|
| MS: (ES) m/z calculated $C_{28}H_{27}F_3N_7$ [M + H]$^+$ 518.2, found 518.3. | 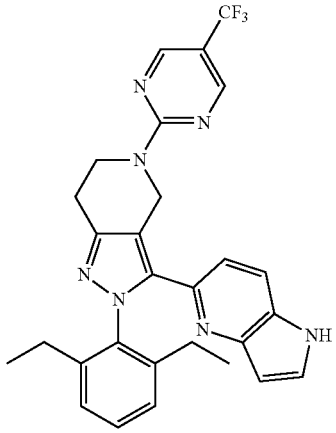<br>Ex. 77.133 |
| MS: (ES) m/z calculated $C_{28}H_{27}F_3N_7$ [M + H]$^+$ 518.2, found 518.4. | 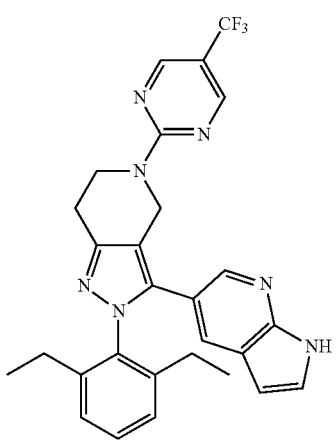 [SMILES: CCc1cccc(CC)c1-n1nc2c(c1-c1cnc3[nH]ccc3c1)CN(c1ncc(C(F)(F)F)cn1)CC2]<br>Ex. 77.134 |
| MS: (ES) m/z calculated $C_{28}H_{27}F_3N_7$ [M + H]$^+$ 518.2, found 518.5. | 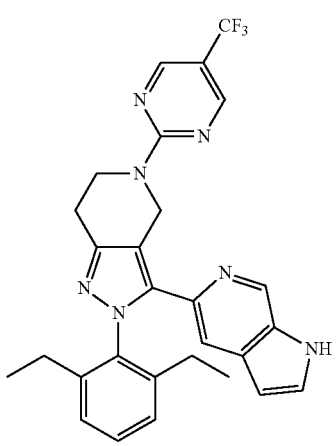 [SMILES: CCc1cccc(CC)c1-n1nc2c(c1-c1cc3cc[nH]c3cn1)CN(c1ncc(C(F)(F)F)cn1)CC2]<br>Ex. 77.135 |

TABLE 2-continued
Structure & MS Characterization Data of Specific Embodiments
| MS | Structure |
|---|---|
| MS: (ES) m/z calculated $C_{29}H_{29}F_3N_7O$ [M + H]$^+$ 548.2, found 548.5. | 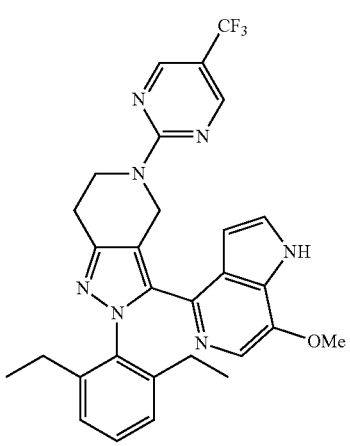 [SMILES: CCc1cccc(CC)c1-n1nc2c(c1-c1ncc(OC)c3[nH]ccc13)CN(c1ncc(C(F)(F)F)cn1)CC2] Ex. 77.136 |
| MS: (ES) m/z calculated $C_{28}H_{26}F_4N_7$ [M + H]$^+$ 536.2, found 536.5. | 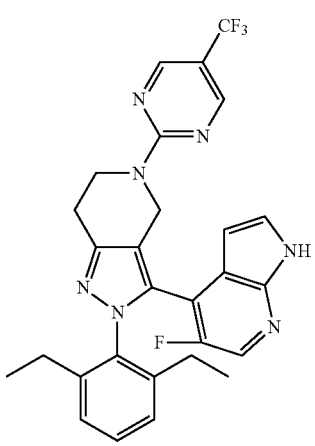 [SMILES: CCc1cccc(CC)c1-n1nc2c(c1-c1c(F)cnc3[nH]ccc13)CN(c1ncc(C(F)(F)F)cn1)CC2] Ex. 77.137 |
| MS: (ES) m/z calculated $C_{27}H_{26}F_3N_8$ [M + H]$^+$ 519.2, found 519.5. | 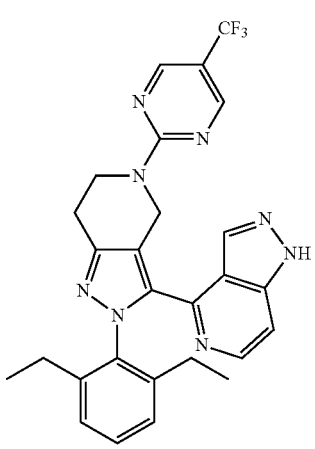 [SMILES: CCc1cccc(CC)c1-n1nc2c(c1-c1nccc3[nH]ncc13)CN(c1ncc(C(F)(F)F)cn1)CC2] Ex. 77.138 |

TABLE 2-continued

Structure & MS Characterization Data of Specific Embodiments

| MS | Structure |
|---|---|
| MS: (ES) m/z calculated $C_{29}H_{29}F_3N_7$ [M + H]$^+$ 532.2, found 532.5. | Ex. 77.139 |
| MS: (ES) m/z calculated $C_{28}H_{27}F_3N_7$ [M + H]$^+$ 518.2, found 518.5. | Ex. 77.140 |
| MS: (ES) m/z calculated $C_{29}H_{26}F_6N_7$ [M + H]$^+$ 586.2, found 586.5. | Ex. 77.141 |

251
TABLE 2-continued
Structure & MS Characterization Data of Specific Embodiments
| MS | Structure |
|---|---|
MS: (ES) m/z calculated $C_{29}H_{26}F_5N_7O[M + H]^+$ 584.2, found 584.5.
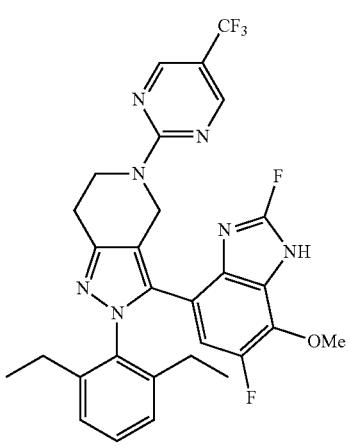 [SMILES: CCc1cccc(CC)c1-n1nc2c(c1-c1cc(F)c(OC)c3[nH]c(F)nc13)CN(c1ncc(C(F)(F)F)cn1)CC2]
Ex. 77.142
MS: (ES) m/z calculated $C_{29}H_{29}F_3N_7[M + H]^+$ 532.2, found 532.5.
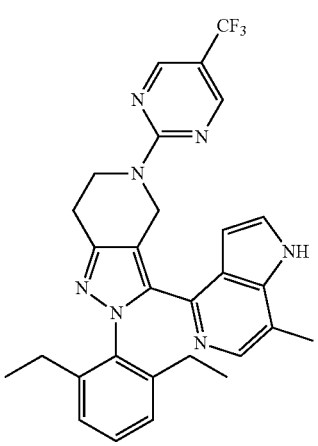
Ex. 77.143
MS: (ES) m/z calculated $C_{29}H_{26}ClF_4N_7O[M + H]^+$ 600.2, found 600.5.
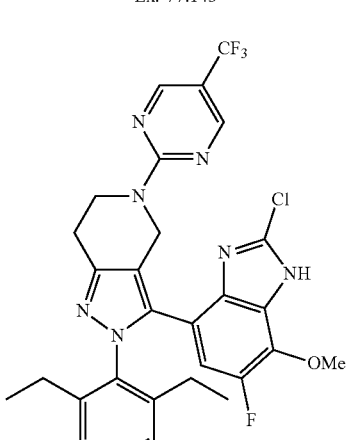
Ex. 77.144

TABLE 2-continued
Structure & MS Characterization Data of Specific Embodiments
| MS | Structure |
|---|---|
| MS: (ES) m/z calculated $C_{28}H_{27}F_3N_7 [M + H]^+$ 518.2, found 518.5. | 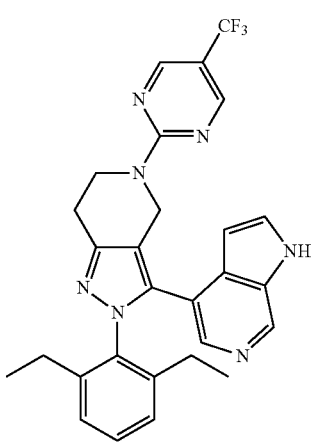 [SMILES: CCc1cccc(CC)c1-n1nc2c(c1-c1cncc3[nH]ccc13)CN(c1ncc(C(F)(F)F)cn1)CC2]<br>Ex. 77.145 |
| MS: (ES) m/z calculated $C_{31}H_{31}F_4N_6O[M + H]^+$ 579.2, found 579.5. | 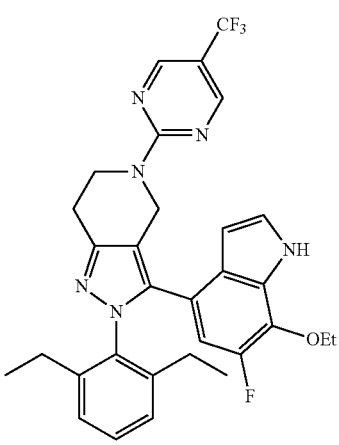 [SMILES: CCOc1c(F)cc(-c2c3c(nn2-c2c(CC)cccc2CC)CCN(c2ncc(C(F)(F)F)cn2)C3)c2cc[nH]c12]<br>Ex. 77.146 |
| MS: (ES) m/z calculated $C_{28}H_{26}ClF_3N_7[M + H]^+$ 552.2, found 552.5. | 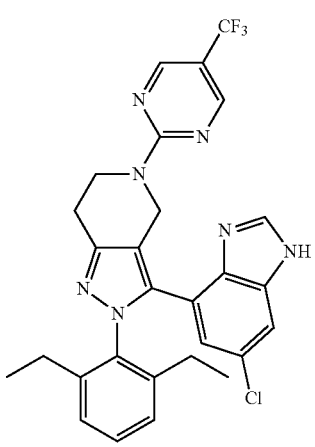 [SMILES: CCc1cccc(CC)c1-n1nc2c(c1-c1cc(Cl)cc3[nH]cnc13)CN(c1ncc(C(F)(F)F)cn1)CC2]<br>Ex. 77.147 |

TABLE 2-continued
Structure & MS Characterization Data of Specific Embodiments
| MS | Structure |
|---|---|
| MS: (ES) m/z calculated $C_{27}H_{26}F_3N_8$ [M + H]$^+$ 519.2, found 519.5. | 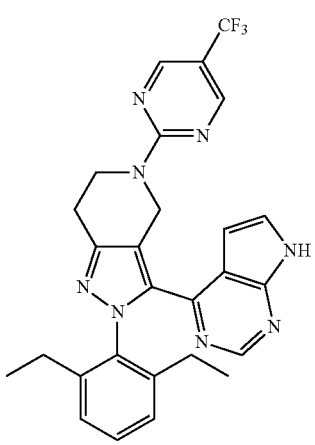<br>Ex. 77.148 |
| MS: (ES) m/z calculated $C_{29}H_{29}F_3N_7$ [M + H]$^+$ 532.2, found 532.5. | 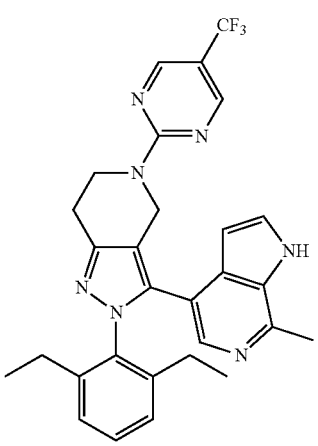 [SMILES: CCc1cccc(CC)c1-n1nc2c(c1-c1cnc(C)c3[nH]ccc13)CN(c1ncc(C(F)(F)F)cn1)CC2]<br>Ex. 77.149 |
| MS: (ES) m/z calculated $C_{30}H_{30}F_4N_7O_2$[M + H]$^+$ 596.2, found 596.5. | 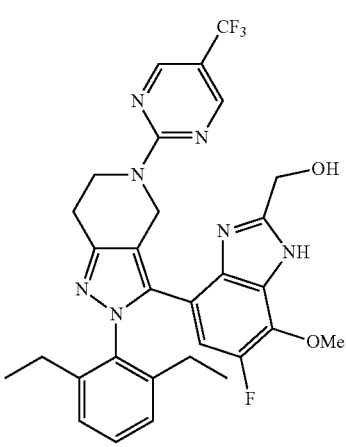 [SMILES: CCc1cccc(CC)c1-n1nc2c(c1-c1cc(F)c(OC)c3[nH]c(CO)nc13)CN(c1ncc(C(F)(F)F)cn1)CC2]<br>Ex. 77.150 |

TABLE 2-continued
Structure & MS Characterization Data of Specific Embodiments
| MS | Structure |
|---|---|
| MS: (ES) m/z calculated $C_{28}H_{27}F_3N_7$ [M + H]$^+$ 518.2, found 518.5. | 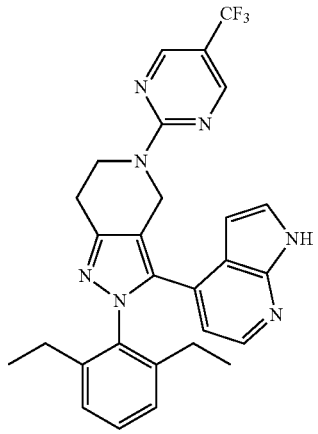 [SMILES: CCc1cccc(CC)c1-n1nc2c(c1-c1ccnc3[nH]ccc13)CN(c1ncc(C(F)(F)F)cn1)CC2]<br>Ex. 77.151 |
| MS: (ES) m/z calculated $C_{28}H_{27}F_3N_7$ [M + H]$^+$ 518.2, found 518.5. | 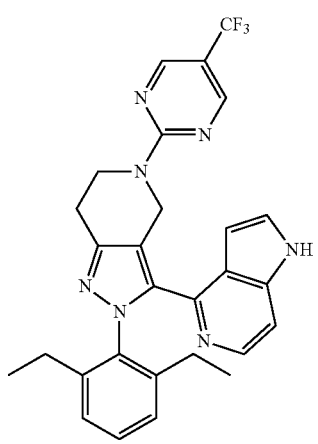 [SMILES: CCc1cccc(CC)c1-n1nc2c(c1-c1nccc3[nH]ccc13)CN(c1ncc(C(F)(F)F)cn1)CC2]<br>Ex. 77.152 |
| MS: (ES) m/z calculated $C_{30}H_{28}ClF_4N_6O$[M + H]$^+$ 599.2, found 599.5. | 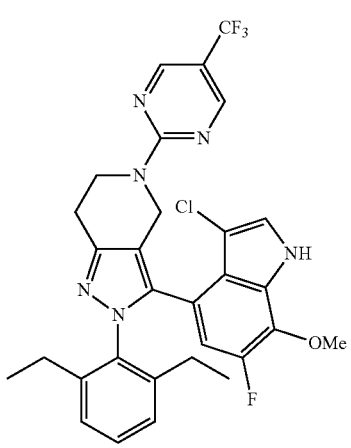 [SMILES: CCc1cccc(CC)c1-n1nc2c(c1-c1cc(F)c(OC)c3[nH]cc(Cl)c13)CN(c1ncc(C(F)(F)F)cn1)CC2]<br>Ex. 77.153 |

TABLE 2-continued
Structure & MS Characterization Data of Specific Embodiments
| MS | Structure |
|---|---|
| MS: (ES) m/z calculated $C_{30}H_{27}F_4N_6O_2[M + H]^+$ 579.2, found 579.5. | 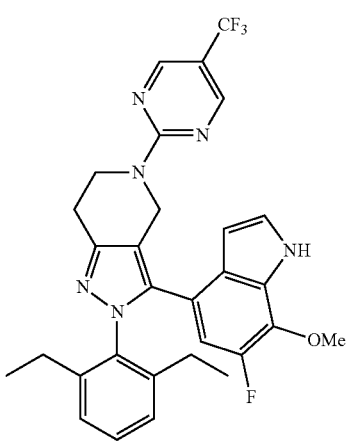 [SMILES: CCc1cccc(CC)c1-n1nc2c(c1-c1cc(F)c(OC)c3[nH]ccc13)CN(c1ncc(C(F)(F)F)cn1)CC2]<br>Ex. 77.154 |
| MS: (ES) m/z calculated $C_{28}H_{25}ClF_4N_7[M + H]^+$ 570.2, found 570.4. | 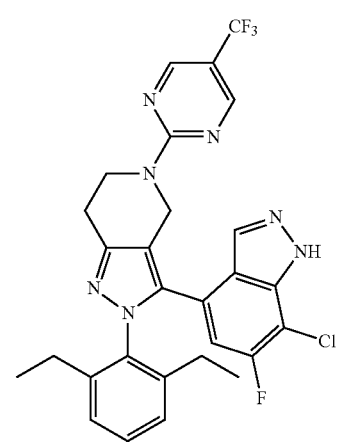 [SMILES: CCc1cccc(CC)c1-n1nc2c(c1-c1cc(F)c(Cl)c3[nH]ncc13)CN(c1ncc(C(F)(F)F)cn1)CC2]<br>Ex. 77.155 |
| MS: (ES) m/z calculated $C_{29}H_{25}ClF_3N_6O[M + H]^+$ 565.2, found 565.5. | 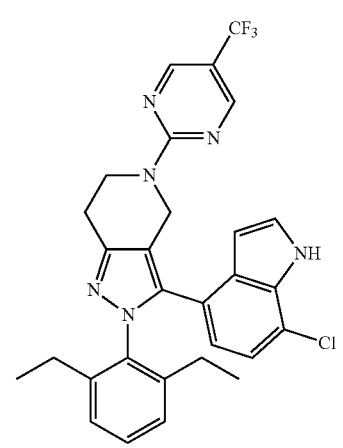<br>Ex. 77.156 |

TABLE 2-continued
Structure & MS Characterization Data of Specific Embodiments
| MS | Structure |
| --- | --- |
| MS: (ES) m/z calculated $C_{29}H_{28}F_3N_6[M + H]^+$ 517.2, found 517.3. | 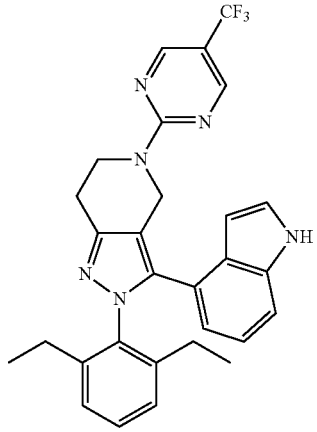 [SMILES: CCc1cccc(CC)c1-n1nc2c(c1-c1cccc3[nH]ccc13)CN(c1ncc(C(F)(F)F)cn1)CC2]<br>Ex. 77.157 |
| MS: (ES) m/z calculated $C_{29}H_{28}ClF_3N_7 [M + H]^+$ 566.2, found 566.5. | 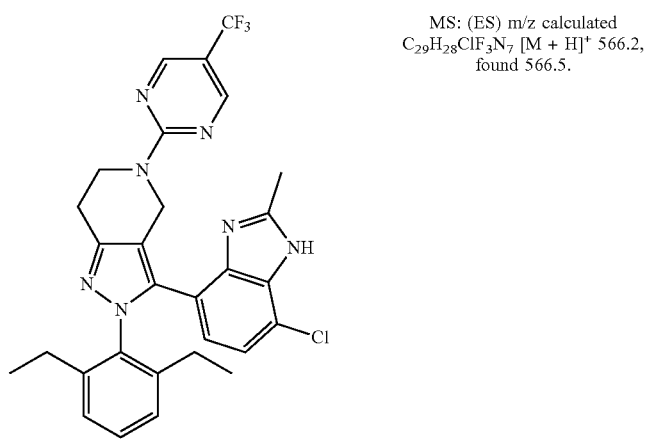<br>Ex. 77.158 |
| MS: (ES) m/z calculated $C_{28}H_{26}ClF_3N_7 [M + H]^+$ 552.2, found 552.5. | 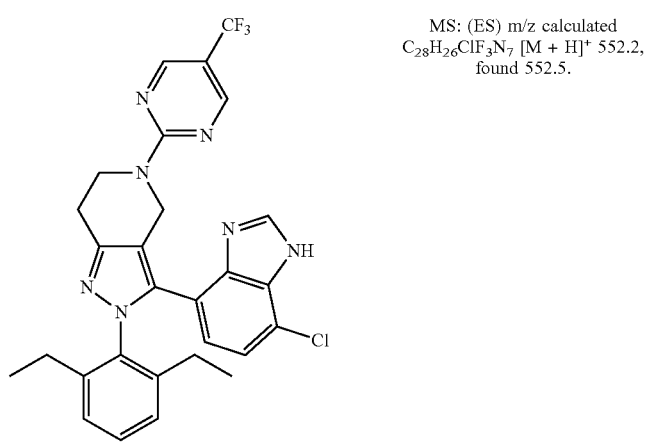<br>Ex. 77.159 |

TABLE 2-continued

Structure & MS Characterization Data of Specific Embodiments

| MS | Structure |
|---|---|
| MS: (ES) m/z calculated $C_{29}H_{28}F_4N_7O[M + H]^+$ 566.2, found 566.5. | 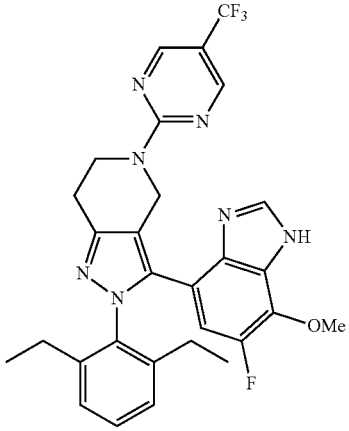 [SMILES: CCc1cccc(CC)c1-n1nc2c(c1-c1cc(F)c(OC)c3[nH]cnc13)CN(c1ncc(C(F)(F)F)cn1)CC2]<br>Ex. 77.160 |
| MS: (ES) m/z calculated $C_{29}H_{28}ClF_3N_7 [M + H]^+$ 566.2, found 566.5. | 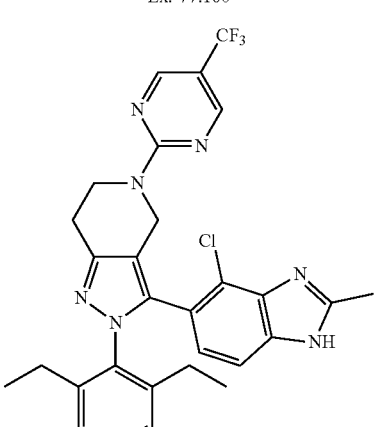<br>Ex. 77.161 |

Example 78

This example illustrates the evaluation of the biological activity associated with specific compounds of the invention.
Materials and Methods
Cells
C5a Receptor Expressing Cells
U937 Cells U937 cells are a monocytic cell line which express C5aR, and are available from ATCC (VA). These cells were cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, and 10% FBS. Cells were grown under 5% $CO_2$/95% air, 100% humidity at 37° C. and subcultured twice weekly at 1:6 (cells were cultured at a density range of $1 \times 10^5$ to $2 \times 10^6$ cells/mL) and harvested at $1 \times 10^6$ cells/mL. Prior to assay, cells are treated overnight with 0.5 mM of cyclic AMP (Sigma, OH) and washed once prior to use. cAMP treated U937 cells can be used in C5aR ligand binding and functional assays.
Isolated Human Neutrophils Optionally, human or murine neutrophils can be used to assay for compound activity. Neutrophils may be isolated from fresh human blood using density separation and centrifigation. Briefly, whole blood is incubated with equal parts 3% dextran and allowed to separate for 45 minutes. After separation, the top layer is layered on top of 15 mls of Ficoll (15 mls of Ficoll for every 30 mls of blood suspension) and centrifuged for 30 minutes at 400 x g with no brake. The pellet at the bottom of the tube is then isolated and resuspended into PharmLyse RBC Lysis Buffer (BD Biosciences, San Jose, CA) after which the sample is again centrifuged for 10 minutes at 400 x g with brake. The remaining cell pellet is resuspended as appropriate and consists of isolated neutrophils.
Assays
Inhibition of C5aR liquid binding cAMP treated U937 cells expressing C5aR were centrifuged and resuspended in assay buffer (20 mM HEPES pH 7.1, 140 mM NaCl, 1 mM $CaCl_2$, 5 mM $MgCl_2$, and with 0.1% bovine serum albumin) to a concentration of $3 \times 10^6$ cells/mL. Binding assays were set up as follows. 0.1 mL of cells was added to the assay plates containing 5 µL of the compound, giving a final concentration of ~2-10 µM each compound for screening (or part of a dose response for compound $IC_{50}$ determinations). Then 0.1 mL of $^{125}$I labeled C5a (obtained from Perkin Elmer Life Sciences, Boston, MA) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, CT). Scintillation fluid (40 µl; Microscint 20, Packard Instruments) was added to each well, the plates were sealed and radioactivity measured in a Topcount scintillation counter (Packard Instruments). Control wells containing either diluent only (for total counts) or excess C5a (1 µg/mL, for non-specific binding) were used to calculate the percent of total inhibition for compound. The computer program Prism from GraphPad, Inc. (San Diego, Ca) was used to calculate $IC_{50}$ values. $IC_{50}$ values are those concentrations required to reduce the binding of radiolabeled C5a to the receptor by 50%. (For further descriptions of ligand binding and other functional assays, see Dairaghi, et al., *J. Biol. Chem.* 274: 21569-21574 (1999), Penfold, et al., Proc. Natl. Acad. Sci. USA. 96:9839-9844 (1999), and Dairaghi et al. *J. Biol. Chem.* 272:28206-28209 (1997)).

Calcium Mobilization

Optionally, compounds may be further assayed for their ability to inhibit calcium flux in cells. To detect the release of intracellular stores of calcium, cells (e.g., cAMP stimulated U937 or neutrophils) are incubated with 3 µM of INDO-1AM dye (Molecular Probes; Eugene, OR) in cell media for 45 minutes at room temperature and washed with phosphate buffered saline (PBS). After INDO-1AM loading, the cells are resuspended in flux buffer (Hank's balanced salt solution (HBSS) and 1% FBS). Calcium mobilization is measured using a Photon Technology International spectrophotometer (Photon Technology International; New Jersey) with excitation at 350 nm and dual simultaneous recording of fluorescence emission at 400 nm and 490 nm. Relative intracellular calcium levels are expressed as the 400 nm/490 nm emission ratio. Experiments are performed at 37° C. with constant mixing in cuvettes each containing $10^6$ cells in 2 mL of flux buffer. The chemokine ligands may be used over a range from 1 to 100 nM. The emission ratio is plotted over time (typically 2-3 minutes). Candidate ligand blocking compounds (up to 10 µM) are added at 10 seconds, followed by chemokines at 60 seconds (i.e., C5a; R&D Systems; Minneapolis, MN) and control chemokine (i.e., SDF-1α; R&D Systems; Minneapolis, MN) at 150 seconds.

Chemotaxis Assays

Optionally, compounds may be further assayed for their ability to inhibit chemotaxis in cells. Chemotaxis assays are performed using 5 µm pore polycarbonate, polyvinylpyrrolidone-coated filters in 96-well chemotaxis chambers (Neuroprobe; Gaithersburg, MD) using chemotaxis buffer (Hank's balanced salt solution (HBSS) and 1% FBS). C5aR ligands (i.e., C5a, R&D Systems; Minneapolis, MN) are use to evaluate compound mediated inhibition of C5aR mediated migration. Other chemokines (i.e., SDF-1α; R&D Systems; Minneapolis, MN) are used as specificity controls. The lower chamber is loaded with 29 µl of chemokine (i.e., 0.03 nM C5a) and varying amounts of compound; the top chamber contains 100,000 U937 or neutrophil cells in 20 µl. The chambers are incubated 1.5 hours at 37° C., and the number of cells in the lower chamber quantified either by direct cell counts in five high powered fields per well or by the CyQuant assay (Molecular Probes), a fluorescent dye method that measures nucleic acid content and microscopic observation.

Identification of Inhibitors of C5aR

Assay

To evaluate small organic molecules that prevent the C5a receptor from binding ligand, an assay was employed that detected radioactive ligand (i.e, C5a) binding to cells expressing C5aR on the cell surface (for example, cAMP stimulated U937 cells or isolated human neutrophils). For compounds that inhibited binding, whether competitive or not, fewer radioactive counts are observed when compared to uninhibited controls.

Equal numbers of cells were added to each well in the plate. The cells were then incubated with radiolabeled C5a. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

% inhibition = (1 − [(sample cpm) − (nonspecific cpm)]/[(total cpm) − (nonspecific cpm)]) × 100.

Dose Response Curves

To ascertain a candidate compound's affinity for C5aR as well as confirm its ability to inhibit ligand binding, inhibitory activity was titered over a $1\times10^{10}$ to $1\times10^{-4}$ M range of compound concentrations. In the assay, the amount of compound was varied; while cell number and ligand concentration were held constant.

In Vivo Efficacy Models

The compounds of interest can be evaluated for potential efficacy in treating a C5a mediated conditions by determining the efficacy of the compound in an animal model. In addition to the models described below, other suitable animal models for studying the compound of interest can be found in Mizuno, M. et al., *Expert Opin. Investig. Drugs* (2005), 14(7), 807-821, which is incorporated herein by reference in its entirety.

Models of C5a Induced Leukopenia

C5a Induced Leukopenia in a Human C5aR Knock-In Mouse Model

To study the efficacy of compounds of the instant invention in an animal model, a recombinant mouse can be created using standard techniques, wherein the genetic sequence coding for the mouse C5aR is replaced with sequence coding for the human C5aR, to create a hC5aR-KI mouse. In this mouse, administration of hC5a leads to upregulation of adhesion molecules on blood vessel walls which bind blood leukocytes, sequestering them from the blood stream. Animals are administered 20 ug/kg of hC5a and 1 minute later leukocytes are quantified in peripheral blood by standard techniques. Pretreatment of mice with varying doses of the present compounds can almost completely block the hC5a induced leukopenia.

C5a Induced Leukopenia in a Cynomolgus Model

To study the efficacy of compounds of the instant invention in a non-human primate model model, C5a induced leucopenia is studied in a cynomolgus model. In this model administration of hC5a leads to upregulation of adhesion molecules on blood vessel walls which bind blood leukocytes, hence sequestering them from the blood stream. Animals are administered 10 ug/kg of hC5a and 1 minute later leukocytes are quantified in peripheral blood.

Mouse Model of ANCA Induced Vasculitis

On day 0 hC5aR-KI mice are intraveneously injected with 50 mg/kg purified antibody to myeloperoxidase (Xiao et al, J. Clin. Invest. 110: 955-963 (2002)). Mice are further dosed with oral daily doses of compounds of the invention or vehicle for seven days, then mice are sacrificed and kidneys collected for histological examination. Analysis of kidney sections can show significantly reduced number and severity of crescentic and necrotic lesions in the glomeruli when compared to vehicle treated animals.

Mouse Model of Choroidal Neovascularization

To study the efficacy of compounds of the instant invention in treatment of age related macular degeneration (AMD) the bruch membrane in the eyes of hC5aR-KI mice are ruptured by laser photocoagulation (Nozika et al, PNAS 103: 2328-2333 (2006). Mice are treated with vehicle or a daily oral or appropriate intra-vitreal dose of a compound of the invention for one to two weeks. Repair of laser induced damage and neovascularization are assessed by histology and angiography.

Rheumatoid Arthritis Models

Rabbit Model of Destructive Joint Inflammation

To study the effects of candidate compounds on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., J. Immunol. 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of candidate compound (dose 1=50 µM or dose 2=100 µM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1-minimal, 2-mild, 3-moderate, 4-moderate-marked.

Evaluation of a Compound in a Rat Model of Collagen Induced Arthritis

A 17 day developing type II collagen arthritis study is conducted to evaluate the effects of a candidate compound on arthritis induced clinical ankle swelling. Rat collagen arthritis is an experimental model of polyarthritis that has been widely used for preclinical testing of numerous antiarthritic agents (see Trentham, et al., J. Exp. Med. 146(3): 857-868 (1977), Bendele, et al., Toxicologic Pathol. 27:134-142 (1999), Bendele, et al., Arthritis Rheum. 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A candidate compound is dosed daily in a sub-cutaneous manner from day 0 till day 17 at a efficacious dose. Caliper measurements of the ankle joint diameter were taken, and reducing joint swelling is taken as a measure of efficacy.

Rat Model of Sepsis

To study the effect of compounds of interest on inhibiting the generalized inflammatory response that is associated with a sepsis like disease, the Cecal Ligation and Puncture (CLP) rat model of sepsis is used. A Rat CLP study is conducted essentially as described in Fujimura N, et al. (American Journal Respiratory Critical Care Medicine 2000; 161: 440-446). Briefly described here, Wistar Albino Rats of both sexes weighing between 200-250 g are fasted for twelve hours prior to experiments. Animals are kept on normal 12 hour light and dark cycles and fed standard rat chow up until 12 hours prior to experiment. Then animals are split into four groups; (i) two sham operation groups and (ii) two CLP groups. Each of these two groups (i.e., (i) and (ii)) is split into vehicle control group and test compound group. Sepsis is induced by the CLP method. Under brief anesthesia a midline laparotomy is made using minimal dissection and the cecum is ligated just below the ileocaecal valve with 3-0 silk, so the intestinal continuity is maintained. The antimesinteric surface of the cecum is perforated with an 18 gauge needle at two locations 1 cm apart and the cecum is gently squeezed until fecal matter is extruded. The bowel is then returned to the abdomen and the incision is closed. At the end of the operation, all rats are resuscitated with saline, 3 ml/100 g body weight, given subcutaneously. Postoperatively, the rats are deprived of food, but have free access to water for the next 16 hours until they are sacrificed. The sham operated groups are given a laparotomy and the cecum is manipulated but not ligated or perforated. Beneficial effects of treatment are measured by histopathological scoring of tissues and organs as well as measurement of several key indicators of hepatic function, renal function, and lipid peroxidation. To test for hepatic function aspartate transaminase (AST) and alanine transaminase (ALT) are measured. Blood urea nitrogen and creatinine concentrations are studied to assess renal function. Pro-inflammatory cytokines such as TNF-alpha and IL-1beta are also assayed by ELISA for serum levels.

Mouse SLE Model of Experimental Lupus Nephritis.

To study the effect of compounds of interest on a Systemic Lupus Erythematosus (SLE), the MRL/lpr murine SLE model is used. The MRL/Mp-Tmfrsf6$^{lpr/lpr}$ strain (MRL/lpr) is a commonly used mouse model of human SLE. To test compounds efficacy in this model male MRL/lpr mice are equally divided between control and C5aR antagonists groups at 13 weeks of age. Then over the next 6 weeks compound or vehicle is administered to the animals via osmotic pumps to maintain coverage and minimize stress effects on the animals. Serum and urine samples are collected bi-weekly during the six weeks of disease onset and progression. In a minority of these mice glomerulosclerosis develops leading to the death of the animal from renal failure. Following mortality as an indicator of renal failure is one of the measured criteria and successful treatment will usually result in a delay in the onset of sudden death among the test groups. In addition, the presence and magnitude of renal disease may also be monitored continuously with blood urea nitrogen (BUN) and albuminuria measurements. Tissues and organs were also harvested at 19 weeks and subjected to histopathology and immunohistochemistry and scored based on tissue damage and cellular infiltration.

Rat Model of COPD

Smoke induced airway inflammation in rodent models may be used to assess efficacy of compounds in Chronic Obstructive Pulmonary Disease (COPD). Selective antagonists of chemokines have shown efficacy in this model (see, Stevenson, et al., *Am. J. Physiol Lung Cell Mol Physiol.* 288 L514-L522, (2005)). An acute rat model of COPD is conducted as described by Stevenson et al. A compound of interest is administered either systemically via oral or IV dosing; or locally with nebulized compound. Male Sprague-Dawley rats (350-400 g) are placed in Perspex chambers and exposed to cigarette smoke drawn in via a pump (50 mL every 30 seconds with fresh air in between). Rats are exposed for a total period of 32 minutes. Rats are sacrificed up to 7 days after initial exposure. Any beneficial effects of treatment are assessed by a decrease inflammatory cell infiltrate, decreases in chemokine and cytokine levels.

In a chronic model, mice or rats are exposed to daily tobacco smoke exposures for up to 12 months. Compound is administered systemically via once daily oral dosing, or potentially locally via nebulized compound. In addition to the inflammation observed with the acute model (Stevensen et al.), animals may also exhibit other pathologies similar to that seen in human COPD such as emphysema (as indicated by increased mean linear intercept) as well as altered lung chemistry (see Martorana et al, *Am. J. Respir. Crit Care Med.* 172(7): 848-53.

Mouse EAE Model of Multiple Sclerosis

Experimental autoimmune encephalomyelitis (EAE) is a model of human multiple sclerosis. Variations of the model have been published, and are well known in the field. In a typical protocol, C57BL/6 (Charles River Laboratories) mice are used for the EAE model. Mice are immunized with 200 ug myelin oligodendrocyte glycoprotein (MOG) 35-55 (Peptide International) emulsified in Complete Freund's Adjuvant (CFA) containing 4 mg/ml Mycobacterium tuberculosis (Sigma-Aldrich) s.c. on day 0. In addition, on day 0 and day 2 animals are given 200 ng of pertussis toxin (Calbiochem) i.v. Clinical scoring is based on a scale of 0-5: 0, no signs of disease; 1, flaccid tail; 2, hind limb weakness; 3, hind limb paralysis; 4, forelimb weakness or paralysis; 5, moribund. Dosing of the compounds of interest to be assessed can be initiated on day 0 (prophylactic) or day 7 (therapeutic, when histological evidence of disease is present but few animals are presenting clinical signs) and dosed once or more per day at concentrations appropriate for their activity and pharmacokinetic properties, e.g. 100 mg/kg s.c. Efficacy of compounds can be assessed by comparisons of severity (maximum mean clinical score in presence of compound compared to vehicle), or by measuring a decrease in the number of macrophages (F4/80 positive) isolated from spinal cords. Spinal cord mononuclear cells can be isolated via discontinuous Percoll-gradient. Cells can be stained using rat anti-mouse F4/80-PE or rat IgG2b-PE (Caltag Laboratories) and quantitated by FACS analysis using 10 ul of Polybeads per sample (Polysciences).

Mouse Model of Kidney Transplantation

Transplantation models can be performed in mice, for instance a model of allogenic kidney transplant from C57BL/6 to BALB/c mice is described in Faikah Gueler et al, *JASN Express*, Aug. 27, 2008. Briefly, mice are anesthetized and the left donor kidney attached to a cuff of the aorta and the renal vein with a small caval cuff, and the ureters removed en block. After left nephrectomy of the recipient, the vascular cuffs are anastomosed to the recipient abdominal aorta and vena cava, respectively, below the level of the native renal vessels. The ureter is directly anastomosed into the bladder. Cold ischemia time is 60 min, and warm ischemia time is 30 min. The right native kidney can be removed at the time of allograft transplantation or at post-transplantation day 4 for long-term survival studies. General physical condition of the mice is monitored for evidence of rejection. Compound treatment of animals can be started before surgery or immediately after transplantation, eg by sub cut injection once daily. Mice are studied for renal function and survival. Serum creatinine levels are measured by an automated method (Beckman Analyzer, Krefeld, Germany).

Mouse Model of Ischemia/Reperfusion

A mouse model of ischemia/reperfusion injury can be performed as described by Xiufen Zheng et al, *Am. J. Pathol*, Vol 173:4, October, 2008. Briefly, CD1 mice aged 6-8 weeks are anesthetized and placed on a heating pad to maintain warmth during surgery. Following abdominal incisions, renal pedicles are bluntly dissected and a microvascular clamp placed on the left renal pedicle for 25-30 minutes. Following ischemia the clamps are removed along with the right kidney, incisions sutured, and the animals allowed to recover. Blood is collected for serum creatinine and BUN analysis as an indicator of kidney health. Alternatively animal survival is monitored over time. Compound can be administered to animals before and/or after the surgery and the effects on serum creatinine, BUN or animal survival used as indicators of compound efficacy.

Mouse Model of Tumor Growth

C57BL/6 mice 6-16 weeks of age are injected subcutaneously with 1×105 TC-1 cells (ATCC, VA) in the right or left rear flank. Beginning about 2 weeks after cell injection, tumors are measured with calipers every 2-4 d until the tumor size required the mice are killed. At the time of sacrifice animals are subjected to a full necropsy and spleens and tumors removed. Excised tumors are measured and weighed. Compounds may be administered before and/or after tumor injections, and a delay or inhibition of tumor growth used to assess compound efficacy.

In Table 3, below, structures and activity are provided for representative compounds described herein. Activity is provided as follows for the chemotaxis assay as described herein (Example 78 B 3): +, 500 nM≤$IC_{50}$; ++, 50 nM≤$IC_{50}$<500 nM; +++, 5 nM≤$IC_{50}$<50 nM; and ++++, $IC_{50}$<5 nM.

TABLE 3
Structure & Biological Activity of Specific Embodiments
| Compound | Structure | Mig IC50 (nM) |
| --- | --- | --- |
| 1.001 | 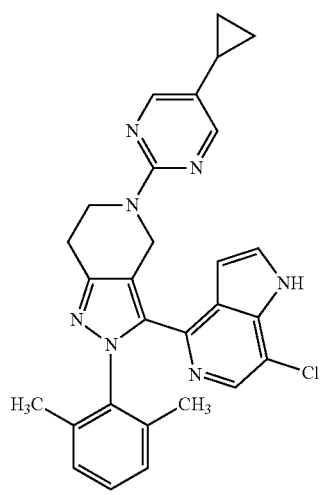 [SMILES: Cc1cccc(C)c1-n1nc2c(c1-c1ncc(Cl)c3[nH]ccc13)CN(c1ncc(C3CC3)cn1)CC2] | +++ |
| 1.002 | 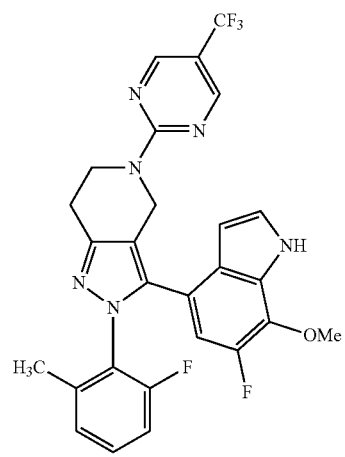 [SMILES: COc1c(F)cc(-c2c3c(nn2-c2c(C)cccc2F)CCN(c2ncc(C(F)(F)F)cn2)C3)c2cc[nH]c12] | +++ |
| 1.003 | 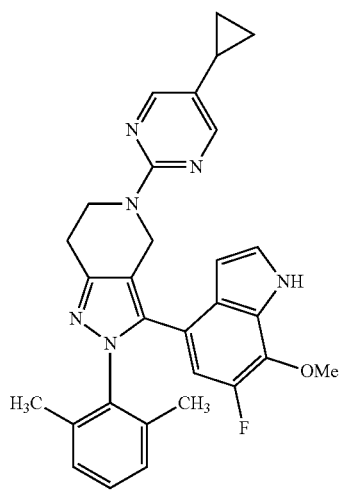 [SMILES: COc1c(F)cc(-c2c3c(nn2-c2c(C)cccc2C)CCN(c2ncc(C4CC4)cn2)C3)c2cc[nH]c12] | ++++ |

TABLE 3-continued
Structure & Biological Activity of Specific Embodiments
| Compound | Structure | Mig IC50 (nM) |
|---|---|---|
| 1.004 | 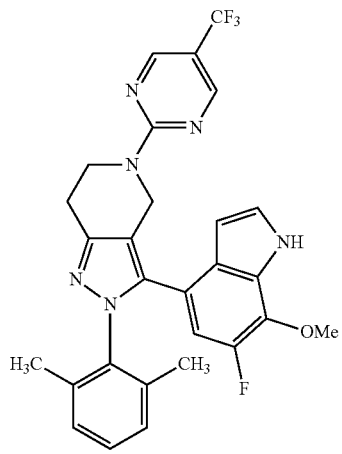 [SMILES: COc1c(F)cc(-c2c3c(nn2-c2c(C)cccc2C)CCN(c2ncc(C(F)(F)F)cn2)C3)c2cc[nH]c12] | +++ |
| 1.005 | 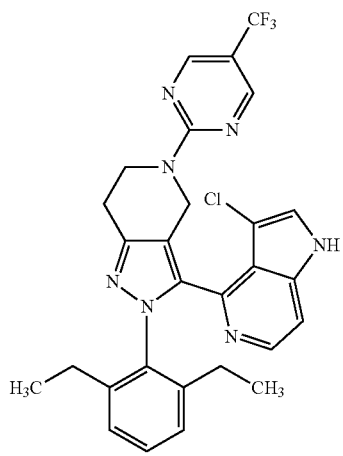 [SMILES: CCc1cccc(CC)c1-n1nc2c(c1-c1nccc3[nH]cc(Cl)c13)CN(c1ncc(C(F)(F)F)cn1)CC2] | ++++ |
| 1.006 | 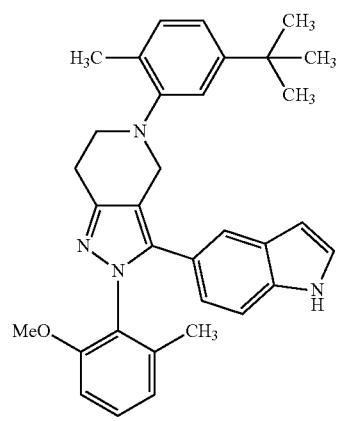 [SMILES: COc1cccc(C)c1-n1nc2c(c1-c1ccc3[nH]ccc3c1)CN(c1cc(C(C)(C)C)ccc1C)CC2] | +++ |

TABLE 3-continued
Structure & Biological Activity of Specific Embodiments
| Compound | Structure | Mig IC50 (nM) |
|---|---|---|
| 1.007 | 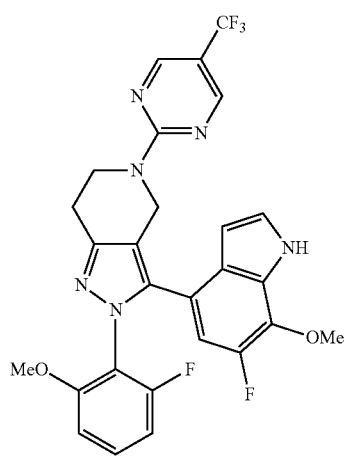 [SMILES: COc1cccc(F)c1-n1nc2c(c1-c1cc(F)c(OC)c3[nH]ccc13)CN(c1ncc(C(F)(F)F)cn1)CC2] | ++ |
| 1.008 | 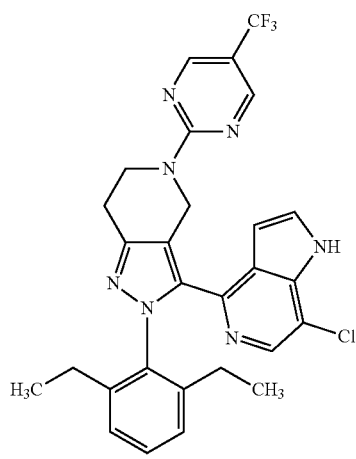 [SMILES: CCc1cccc(CC)c1-n1nc2c(c1-c1ncc(Cl)c3[nH]ccc13)CN(c1ncc(C(F)(F)F)cn1)CC2] | ++++ |
| 1.009 | 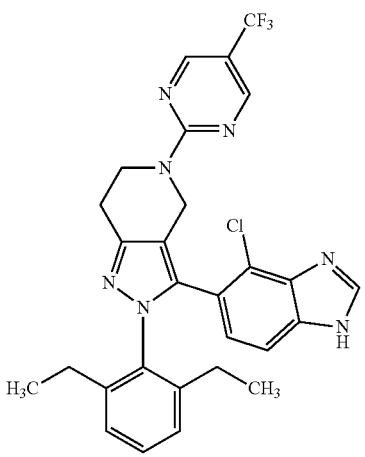 [SMILES: CCc1cccc(CC)c1-n1nc2c(c1-c1ccc3[nH]cnc3c1Cl)CN(c1ncc(C(F)(F)F)cn1)CC2] | ++ |

TABLE 3-continued

Structure & Biological Activity of Specific Embodiments

| Compound | Structure | Mig IC50 (nM) |
|---|---|---|
| 1.010 | 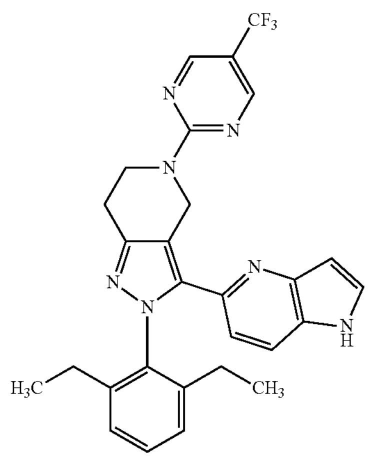 [SMILES: CCc1cccc(CC)c1-n1nc2c(c1-c1ccc3[nH]ccc3n1)CN(c1ncc(C(F)(F)F)cn1)CC2] | + |
| 1.011 | 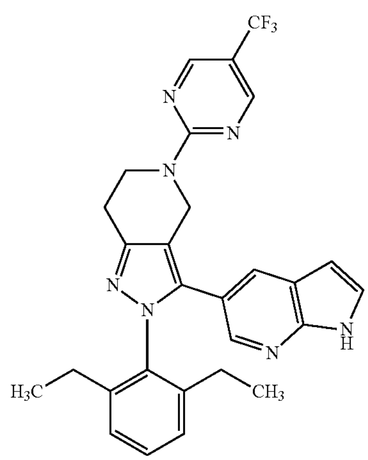 [SMILES: CCc1cccc(CC)c1-n1nc2c(c1-c1cnc3[nH]ccc3c1)CN(c1ncc(C(F)(F)F)cn1)CC2] | + |
| 1.012 | 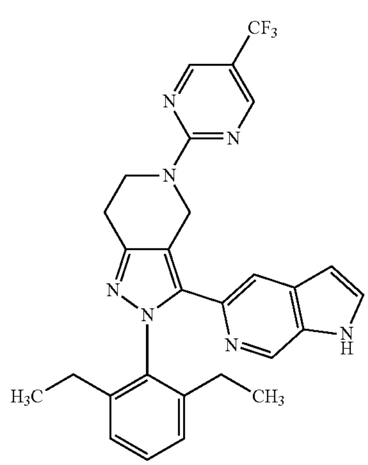 [SMILES: CCc1cccc(CC)c1-n1nc2c(c1-c1cc3cc[nH]c3cn1)CN(c1ncc(C(F)(F)F)cn1)CC2] | ++ |

TABLE 3-continued

Structure & Biological Activity of Specific Embodiments

| Compound | Structure | Mig IC50 (nM) |
|---|---|---|
| 1.013 | 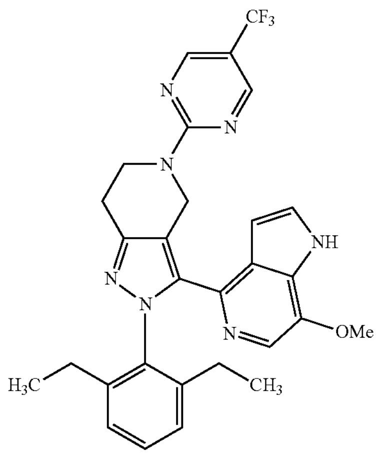 [SMILES: CCc1cccc(CC)c1-n1nc2c(c1-c1ncc(OC)c3[nH]ccc13)CN(c1ncc(C(F)(F)F)cn1)CC2] | +++ |
| 1.014 | 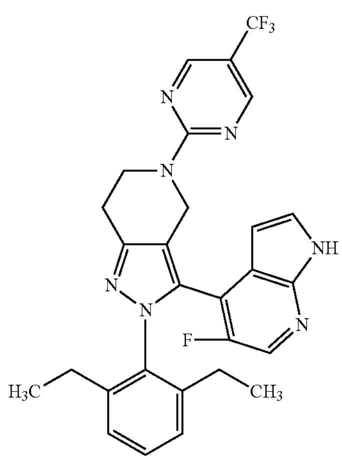 [SMILES: CCc1cccc(CC)c1-n1nc2c(c1-c1c(F)cnc3[nH]ccc13)CN(c1ncc(C(F)(F)F)cn1)CC2] | +++ |
| 1.015 | 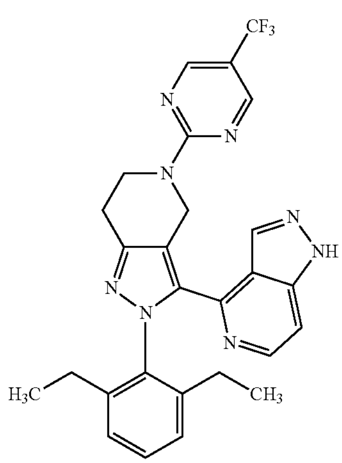 [SMILES: CCc1cccc(CC)c1-n1nc2c(c1-c1nccc3[nH]ncc13)CN(c1ncc(C(F)(F)F)cn1)CC2] | +++ |

TABLE 3-continued

Structure & Biological Activity of Specific Embodiments

| Compound | Structure | Mig IC50 (nM) |
|---|---|---|
| 1.016 | 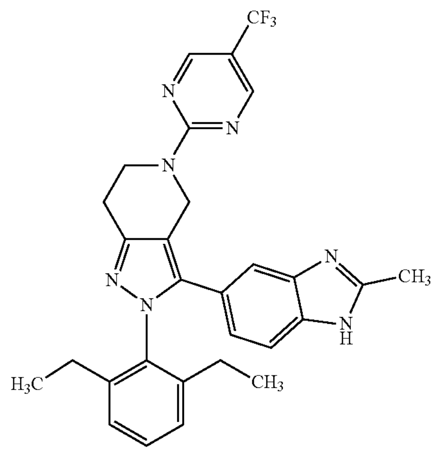 [SMILES: CCc1cccc(CC)c1-n1nc2c(c1-c1ccc3[nH]c(C)nc3c1)CN(c1ncc(C(F)(F)F)cn1)CC2] | + |
| 1.017 | 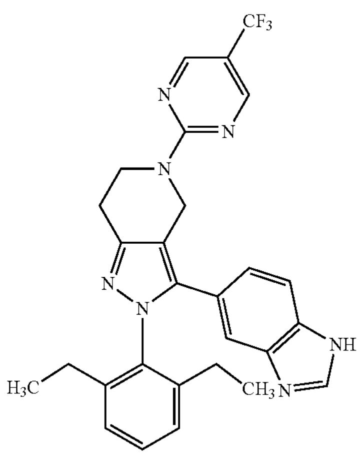 [SMILES: CCc1cccc(CC)c1-n1nc2c(c1-c1ccc3[nH]cnc3c1)CN(c1ncc(C(F)(F)F)cn1)CC2] | + |
| 1.018 | 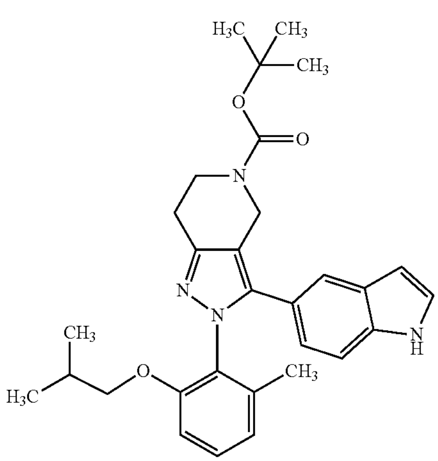 [SMILES: Cc1cccc(OCC(C)C)c1-n1nc2c(c1-c1ccc3[nH]ccc3c1)CN(C(=O)OC(C)(C)C)CC2] | +++ |

TABLE 3-continued

Structure & Biological Activity of Specific Embodiments

| Compound | Structure | Mig IC50 (nM) |
|---|---|---|
| 1.019 | 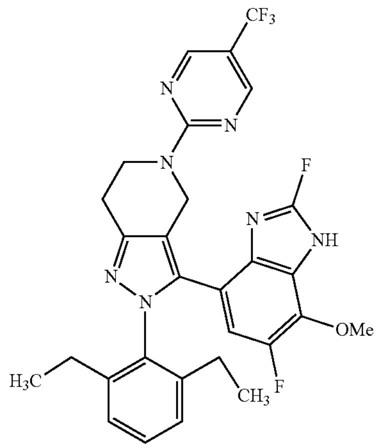 [SMILES: CCc1cccc(CC)c1-n1nc2c(c1-c1cc(F)c(OC)c3[nH]c(F)nc13)CN(c1ncc(C(F)(F)F)cn1)CC2] | +++ |
| 1.020 | 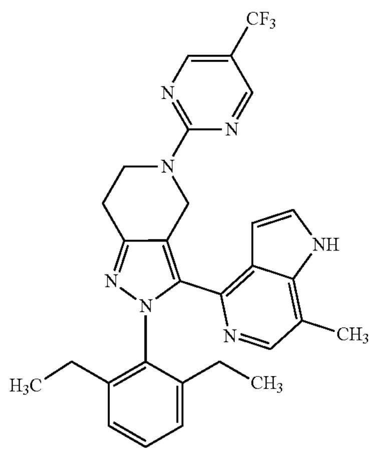 [SMILES: CCc1cccc(CC)c1-n1nc2c(c1-c1ncc(C)c3[nH]ccc13)CN(c1ncc(C(F)(F)F)cn1)CC2] | ++++ |
| 1.021 | 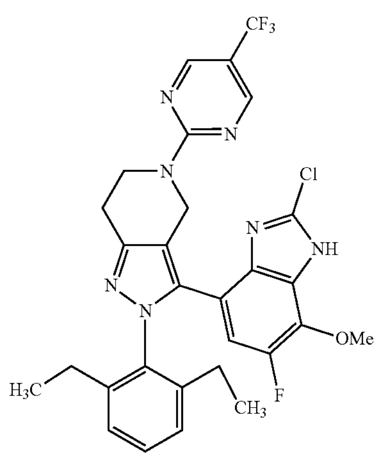 [SMILES: CCc1cccc(CC)c1-n1nc2c(c1-c1cc(F)c(OC)c3[nH]c(Cl)nc13)CN(c1ncc(C(F)(F)F)cn1)CC2] | ++ |

TABLE 3-continued
Structure & Biological Activity of Specific Embodiments
| Compound | Structure | Mig IC50 (nM) |
|---|---|---|
| 1.022 | 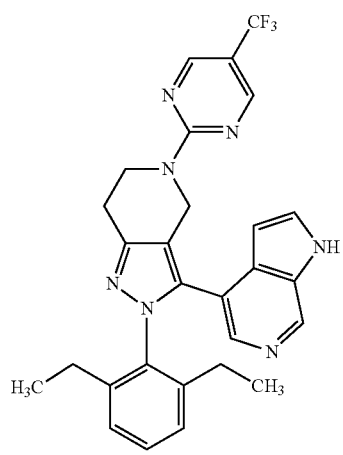 [SMILES: CCc1cccc(CC)c1-n1nc2c(c1-c1cncc3[nH]ccc13)CN(c1ncc(C(F)(F)F)cn1)CC2] | ++ |
| 1.023 | 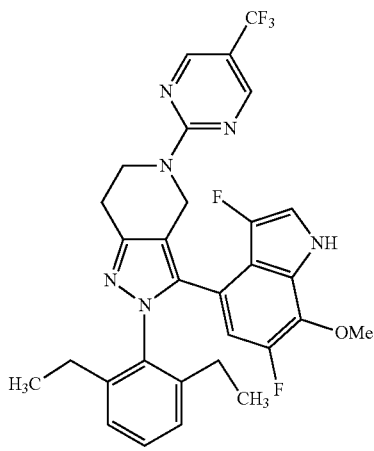 [SMILES: CCc1cccc(CC)c1-n1nc2c(c1-c1cc(F)c(OC)c3[nH]cc(F)c13)CN(c1ncc(C(F)(F)F)cn1)CC2] | ++++ |
| 1.024 | 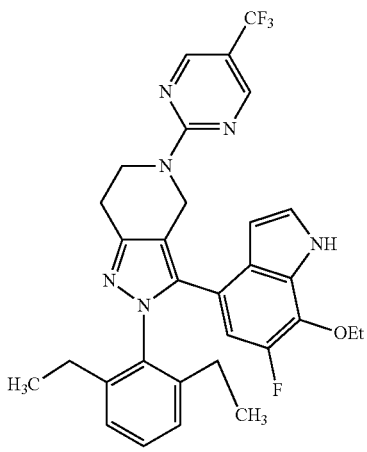 [SMILES: CCOc1c(F)cc(-c2c3c(nn2-c2c(CC)cccc2CC)CCN(c2ncc(C(F)(F)F)cn2)C3)c2cc[nH]c12] | ++++ |

TABLE 3-continued
Structure & Biological Activity of Specific Embodiments
| Compound | Structure | Mig IC50 (nM) |
|---|---|---|
| 1.025 | 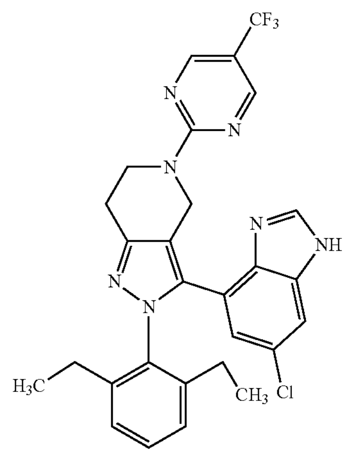 [SMILES: CCc1cccc(CC)c1-n1nc2c(c1-c1cc(Cl)cc3[nH]cnc13)CN(c1ncc(C(F)(F)F)cn1)CC2] | ++ |
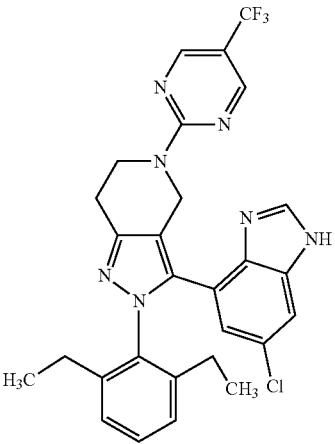
| | | |
|---|---|---|
| 1.026 | | +++ |
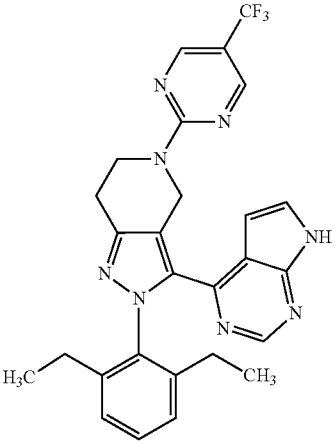 [SMILES: CCc1cccc(CC)c1-n1nc2c(c1-c1ncnc3[nH]ccc13)CN(c1ncc(C(F)(F)F)cn1)CC2]
| | | |
|---|---|---|
| 1.027 | | +++ |
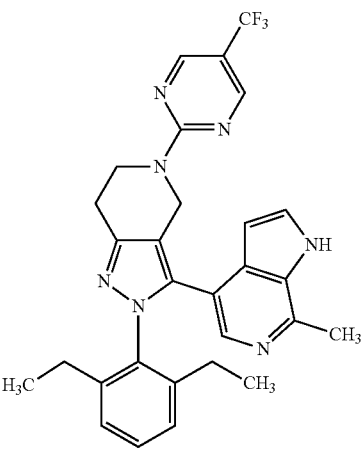 [SMILES: CCc1cccc(CC)c1-n1nc2c(c1-c1cnc(C)c3[nH]ccc13)CN(c1ncc(C(F)(F)F)cn1)CC2]

TABLE 3-continued
Structure & Biological Activity of Specific Embodiments
| Compound | Structure | Mig IC50 (nM) |
|---|---|---|
| 1.028 | 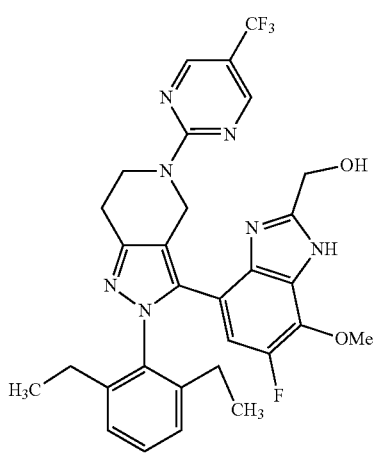 [SMILES: CCc1cccc(CC)c1-n1nc2c(c1-c1cc(F)c(OC)c3[nH]c(CO)nc13)CN(c1ncc(C(F)(F)F)cn1)CC2] | + |
| 1.029 | 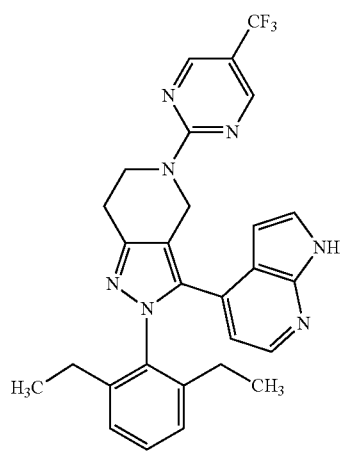 [SMILES: CCc1cccc(CC)c1-n1nc2c(c1-c1ccnc3[nH]ccc13)CN(c1ncc(C(F)(F)F)cn1)CC2] | +++ |
| 1.030 | 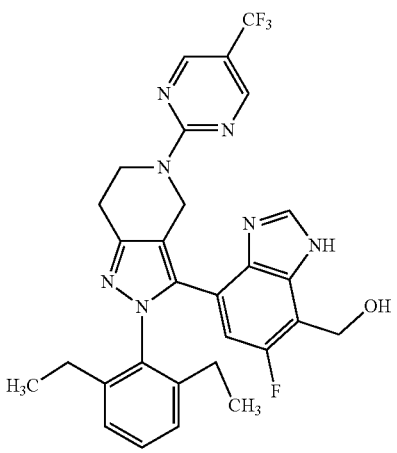 [SMILES: CCc1cccc(CC)c1-n1nc2c(c1-c1cc(F)c(CO)c3[nH]cnc13)CN(c1ncc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.031 | 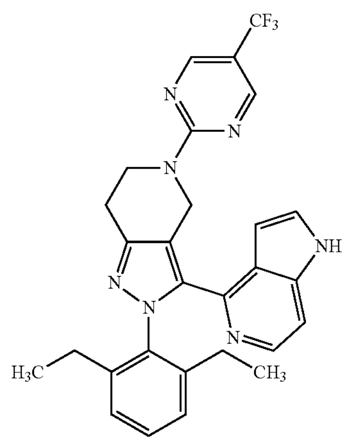 [SMILES: CCc1cccc(CC)c1-n1nc2c(c1-c1nccc3[nH]ccc13)CN(c1ncc(C(F)(F)F)cn1)CC2] | +++ |
| 1.032 | 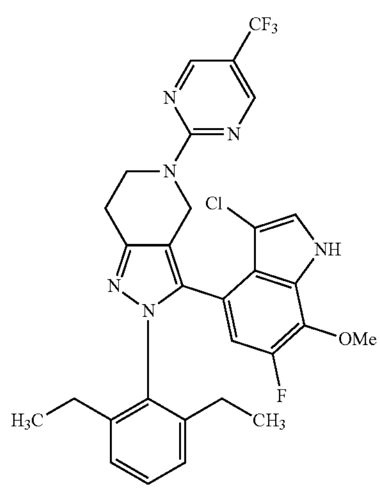 [SMILES: CCc1cccc(CC)c1-n1nc2c(c1-c1cc(F)c(OC)c3[nH]cc(Cl)c13)CN(c1ncc(C(F)(F)F)cn1)CC2] | ++++ |
| 1.033 | 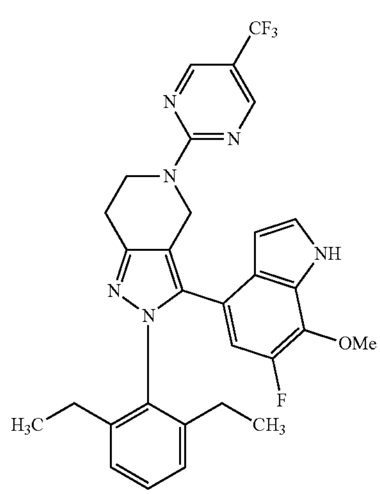 | ++ |

TABLE 3-continued

Structure & Biological Activity of Specific Embodiments

| Compound | Structure | Mig IC50 (nM) |
|---|---|---|
| 1.034 | 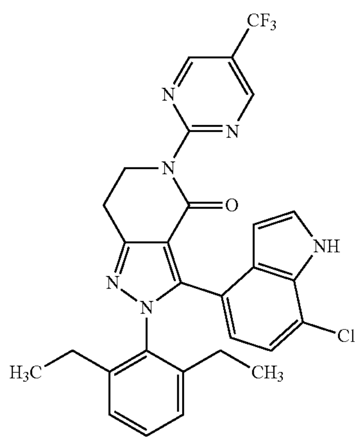 [SMILES: CCc1cccc(CC)c1-n1nc2c(c1-c1ccc(Cl)c3[nH]ccc13)C(=O)N(c1ncc(C(F)(F)F)cn1)CC2] | + |
| 1.035 | 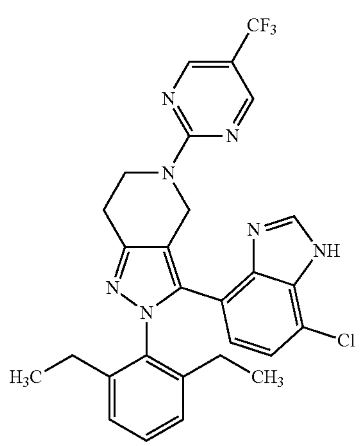 [SMILES: CCc1cccc(CC)c1-n1nc2c(c1-c1ccc(Cl)c3[nH]cnc13)CN(c1ncc(C(F)(F)F)cn1)CC2] | ++++ |
| 1.036 | 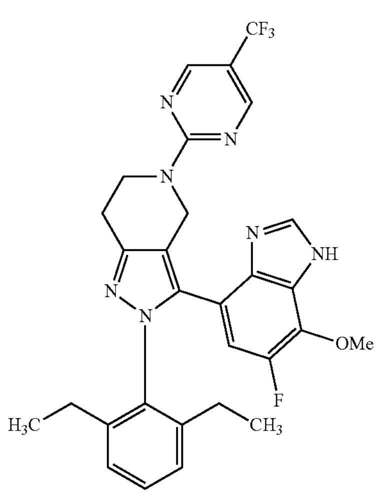 | ++++ |

TABLE 3-continued
Structure & Biological Activity of Specific Embodiments
| Compound | Structure | Mig IC50 (nM) |
|---|---|---|
| 1.037 | 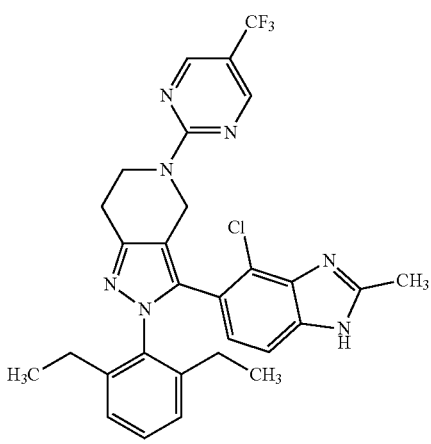 [SMILES: CCc1cccc(CC)c1-n1nc2c(c1-c1ccc3[nH]c(C)nc3c1Cl)CN(c1ncc(C(F)(F)F)cn1)CC2] | +++ |
| 1.038 | 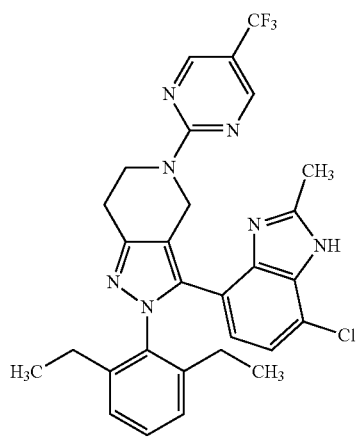 [SMILES: CCc1cccc(CC)c1-n1nc2c(c1-c1ccc(Cl)c3[nH]c(C)nc13)CN(c1ncc(C(F)(F)F)cn1)CC2] | +++ |
| 1.039 | 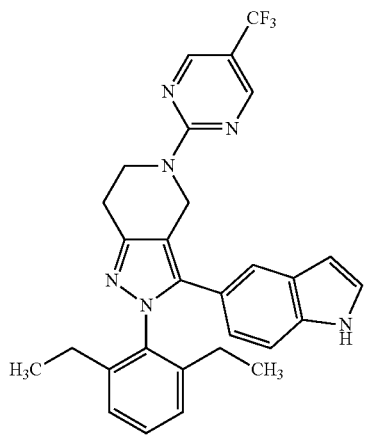 [SMILES: CCc1cccc(CC)c1-n1nc2c(c1-c1ccc3[nH]ccc3c1)CN(c1ncc(C(F)(F)F)cn1)CC2] | +++ |

TABLE 3-continued
Structure & Biological Activity of Specific Embodiments
| Compound | Structure | Mig IC50 (nM) |
|---|---|---|
| 1.040 | 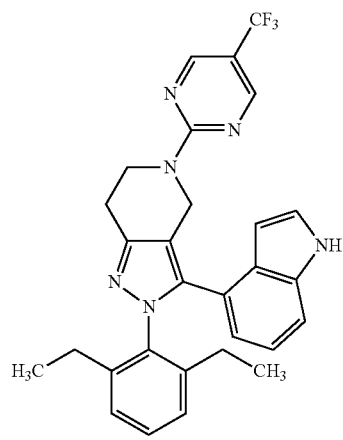 [SMILES: CCc1cccc(CC)c1-n1nc2c(c1-c1cccc3[nH]ccc13)CN(c1ncc(C(F)(F)F)cn1)CC2] | +++ |
| 1.041 | 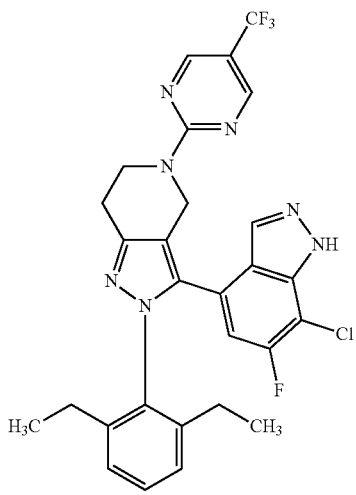 [SMILES: CCc1cccc(CC)c1-n1nc2c(c1-c1cc(F)c(Cl)c3[nH]ncc13)CN(c1ncc(C(F)(F)F)cn1)CC2] | ++++ |
| 1.042 | 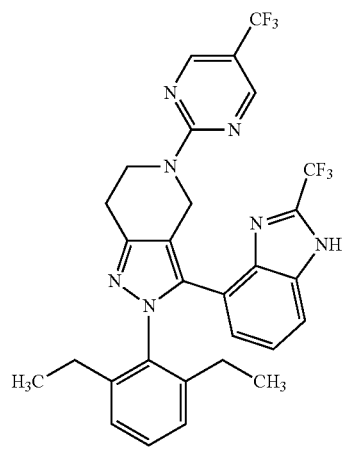 [SMILES: CCc1cccc(CC)c1-n1nc2c(c1-c1cccc3[nH]c(C(F)(F)F)nc13)CN(c1ncc(C(F)(F)F)cn1)CC2] | ++ |

TABLE 3-continued

Structure & Biological Activity of Specific Embodiments

| Compound | Structure | Mig IC50 (nM) |
|---|---|---|
| 1.043 | 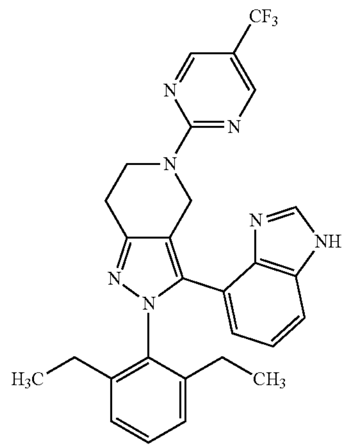 | +++ |
| 1.044 | 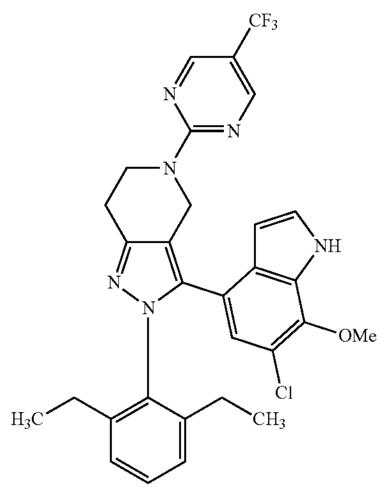 [SMILES: CCc1cccc(CC)c1-n1nc2c(c1-c1cc(Cl)c(OC)c3[nH]ccc13)CN(c1ncc(C(F)(F)F)cn1)CC2] | ++++ |
| 1.045 | 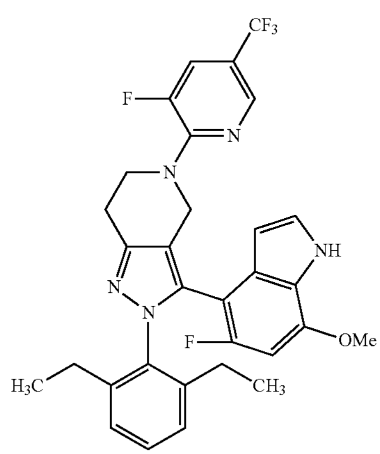 [SMILES: CCc1cccc(CC)c1-n1nc2c(c1-c1c(F)cc(OC)c3[nH]ccc13)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.046 | 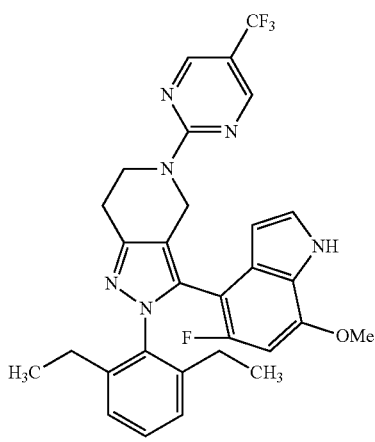 [SMILES: CCc1cccc(CC)c1-n1nc2c(c1-c1c(F)cc(OC)c3[nH]ccc13)CN(c1ncc(C(F)(F)F)cn1)CC2] | ++++ |
| 1.047 | 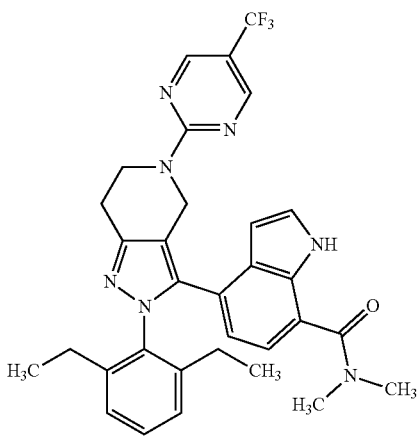 [SMILES: CCc1cccc(CC)c1-n1nc2c(c1-c1ccc(C(=O)N(C)C)c3[nH]ccc13)CN(c1ncc(C(F)(F)F)cn1)CC2] | ++ |
| 1.048 | 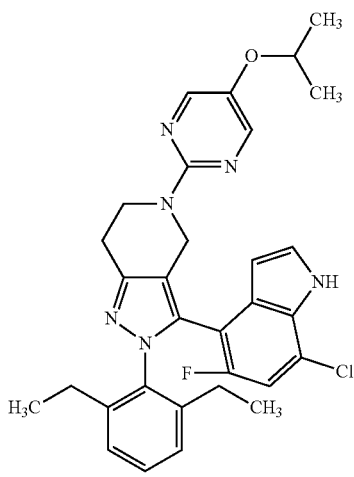 [SMILES: CCc1cccc(CC)c1-n1nc2c(c1-c1c(F)cc(Cl)c3[nH]ccc13)CN(c1ncc(OC(C)C)cn1)CC2] | ++++ |

TABLE 3-continued
Structure & Biological Activity of Specific Embodiments
| Compound | Structure | Mig IC50 (nM) |
|---|---|---|
| 1.049 | 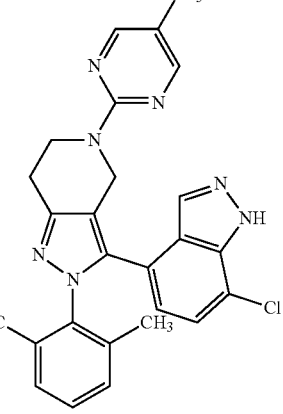 | +++ |
| 1.050 | 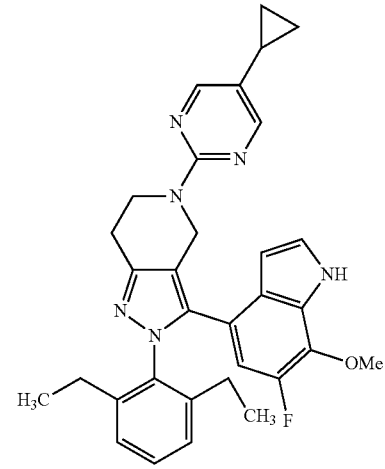 [SMILES: CCc1cccc(CC)c1-n1nc2c(c1-c1cc(F)c(OC)c3[nH]ccc13)CN(c1ncc(C3CC3)cn1)CC2] | ++++ |
| 1.051 | 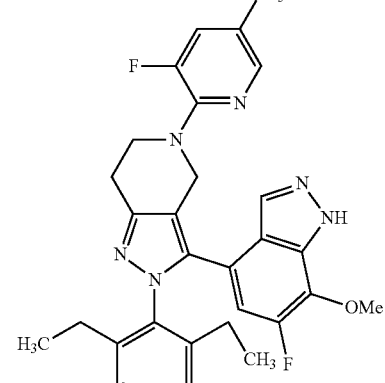 | ++++ |

TABLE 3-continued

Structure & Biological Activity of Specific Embodiments

| Compound | Structure | Mig IC50 (nM) |
|---|---|---|
| 1.052 | 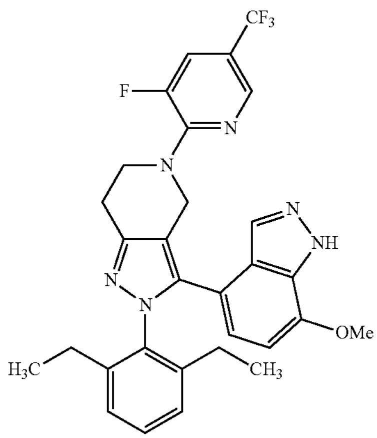 [SMILES: CCc1cccc(CC)c1-n1nc2c(c1-c1ccc(OC)c3[nH]ncc13)CN(c1ncc(C(F)(F)F)cc1F)CC2] | +++ |
| 1.053 | 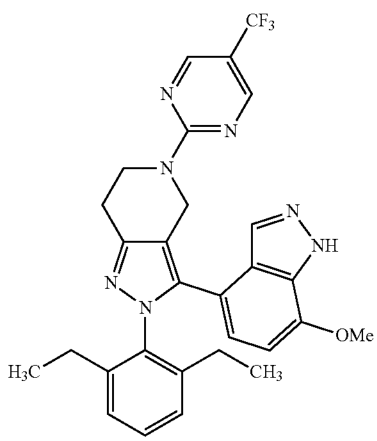 [SMILES: CCc1cccc(CC)c1-n1nc2c(c1-c1ccc(OC)c3[nH]ncc13)CN(c1ncc(C(F)(F)F)cn1)CC2] | ++++ |
| 1.054 | 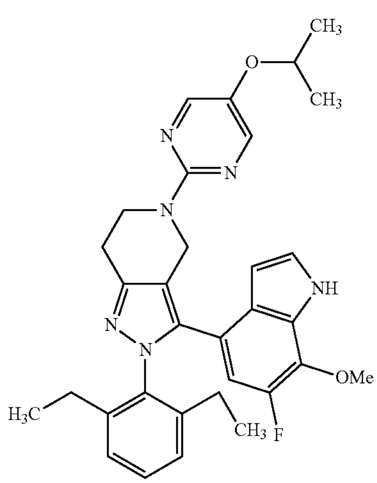 [SMILES: CCc1cccc(CC)c1-n1nc2c(c1-c1cc(F)c(OC)c3[nH]ccc13)CN(c1ncc(OC(C)C)cn1)CC2] | ++++ |

TABLE 3-continued
| Structure & Biological Activity of Specific Embodiments | | |
|---|---|---|
| Compound | Structure | Mig IC50 (nM) |
| 1.055 | 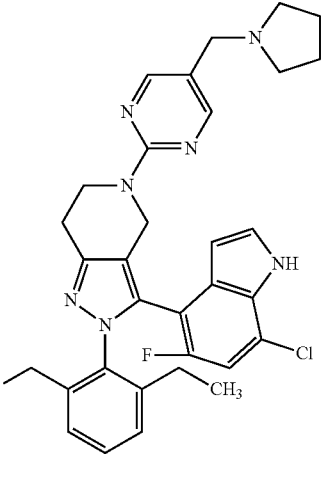 | +++ |
| 1.056 | 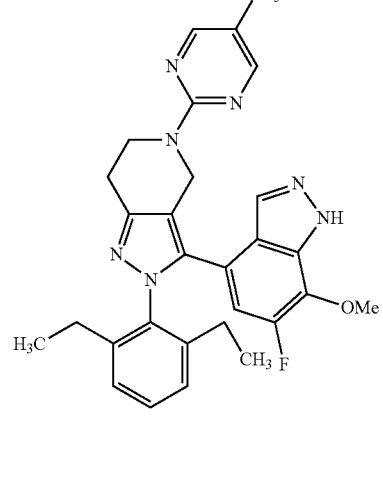 | ++++ |
| 1.057 | 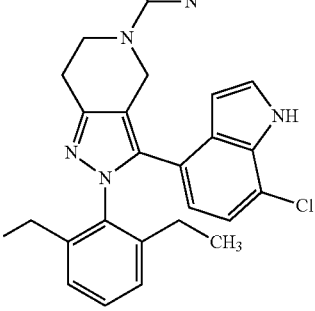 | ++++ |

TABLE 3-continued
Structure & Biological Activity of Specific Embodiments
| Compound | Structure | Mig IC50 (nM) |
|---|---|---|
| 1.058 | 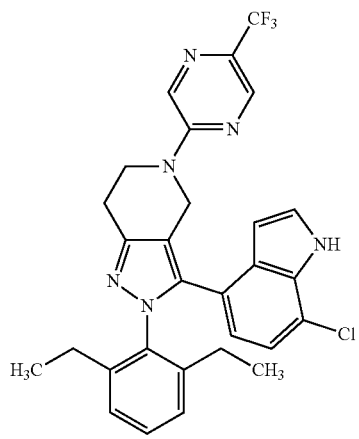 [SMILES: CCc1cccc(CC)c1-n1nc2c(c1-c1ccc(Cl)c3[nH]ccc13)CN(c1cnc(C(F)(F)F)cn1)CC2] | ++++ |
| 1.059 | 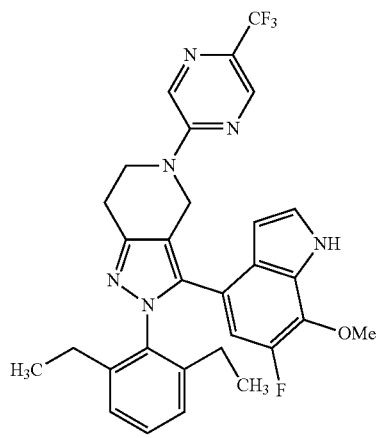 [SMILES: CCc1cccc(CC)c1-n1nc2c(c1-c1cc(F)c(OC)c3[nH]ccc13)CN(c1cnc(C(F)(F)F)cn1)CC2] | ++++ |
| 1.060 | 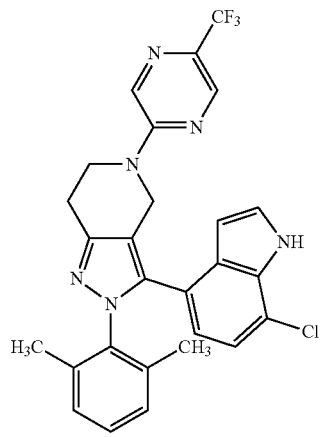 [SMILES: Cc1cccc(C)c1-n1nc2c(c1-c1ccc(Cl)c3[nH]ccc13)CN(c1cnc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.061 | 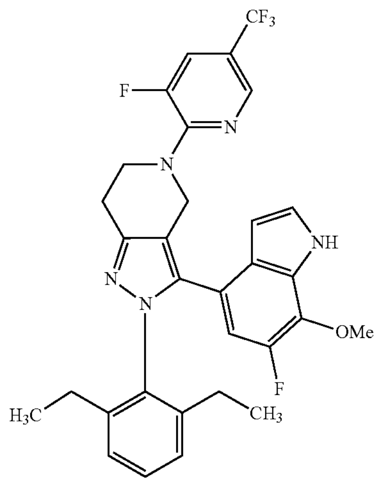 [SMILES: CCc1cccc(CC)c1-n1nc2c(c1-c1cc(F)c(OC)c3[nH]ccc13)CN(c1ncc(C(F)(F)F)cc1F)CC2] | ++++ |
| 1.062 | 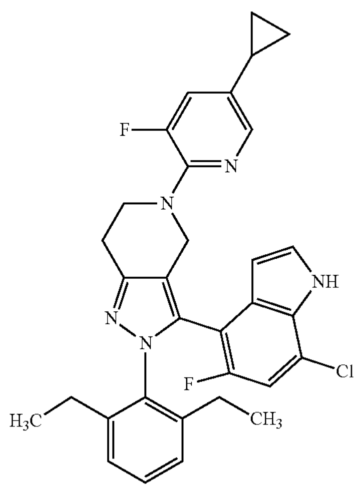 [SMILES: CCc1cccc(CC)c1-n1nc2c(c1-c1c(F)cc(Cl)c3[nH]ccc13)CN(c1ncc(C3CC3)cc1F)CC2] | ++++ |
| 1.063 | 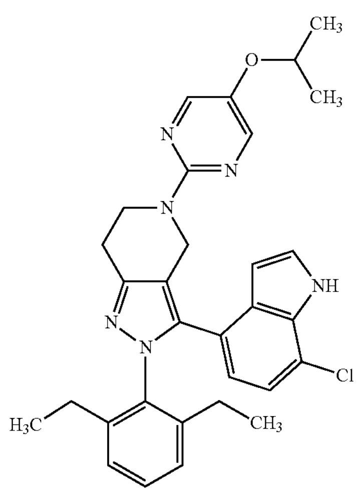 [SMILES: CCc1cccc(CC)c1-n1nc2c(c1-c1ccc(Cl)c3[nH]ccc13)CN(c1ncc(OC(C)C)cn1)CC2] | ++++ |

TABLE 3-continued

Structure & Biological Activity of Specific Embodiments

| Compound | Structure | Mig IC50 (nM) |
|---|---|---|
| 1.064 | 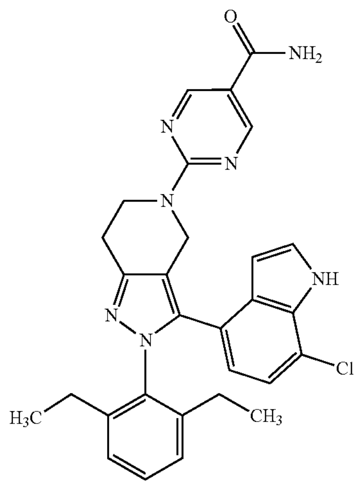 [SMILES: CCc1cccc(CC)c1-n1nc2c(c1-c1ccc(Cl)c3[nH]ccc13)CN(c1ncc(C(N)=O)cn1)CC2] | ++ |
| 1.065 | 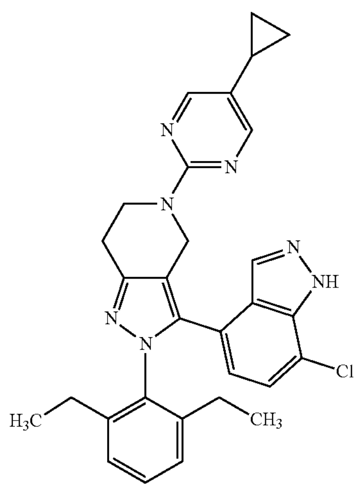 [SMILES: CCc1cccc(CC)c1-n1nc2c(c1-c1ccc(Cl)c3[nH]ncc13)CN(c1ncc(C3CC3)cn1)CC2] | ++++ |
| 1.066 | 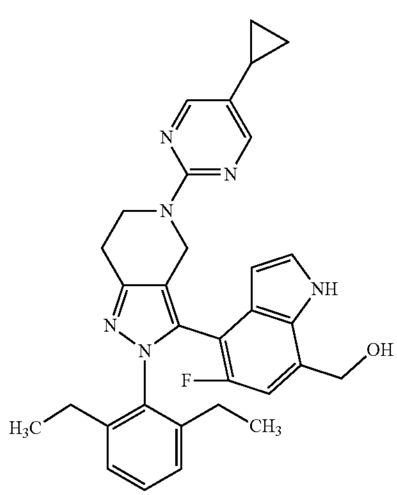 [SMILES: CCc1cccc(CC)c1-n1nc2c(c1-c1c(F)cc(CO)c3[nH]ccc13)CN(c1ncc(C3CC3)cn1)CC2] | ++++ |

TABLE 3-continued

Structure & Biological Activity of Specific Embodiments

| Compound | Structure | Mig IC50 (nM) |
|---|---|---|
| 1.067 | 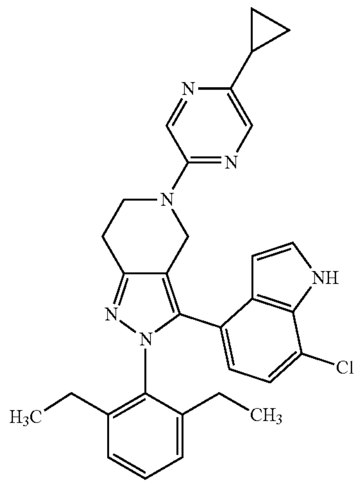 [SMILES: CCc1cccc(CC)c1-n1nc2c(c1-c1ccc(Cl)c3[nH]ccc13)CN(c1cnc(C3CC3)cn1)CC2] | +++ |
| 1.068 | 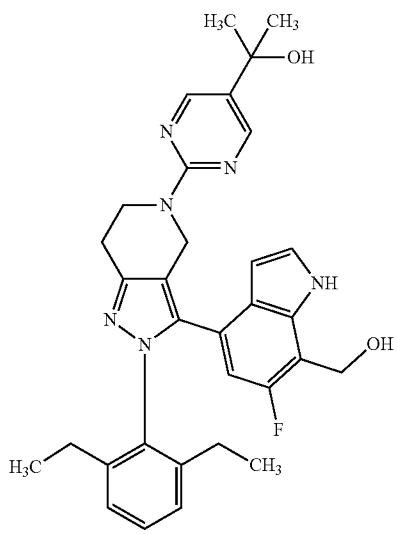 [SMILES: CCc1cccc(CC)c1-n1nc2c(c1-c1cc(F)c(CO)c3[nH]ccc13)CN(c1ncc(C(C)(C)O)cn1)CC2] | +++ |
| 1.069 | 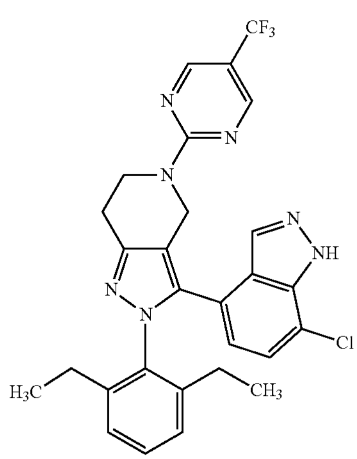 [SMILES: CCc1cccc(CC)c1-n1nc2c(c1-c1ccc(Cl)c3[nH]ncc13)CN(c1ncc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.070 | 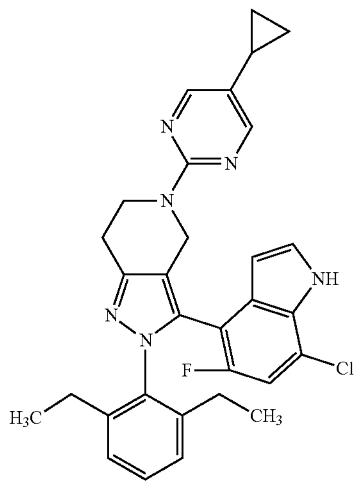 [SMILES: CCc1cccc(CC)c1-n1nc2c(c1-c1c(F)cc(Cl)c3[nH]ccc13)CN(c1ncc(C3CC3)cn1)CC2] | ++++ |
| 1.071 | 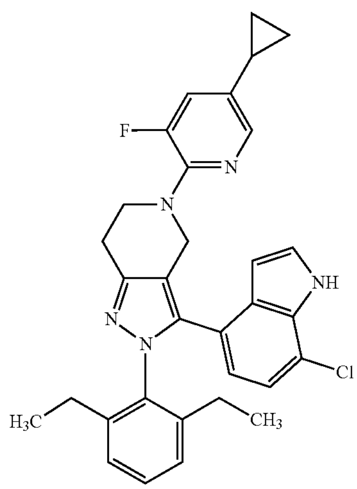 [SMILES: CCc1cccc(CC)c1-n1nc2c(c1-c1ccc(Cl)c3[nH]ccc13)CN(c1ncc(C3CC3)cc1F)CC2] | ++++ |
| 1.072 | 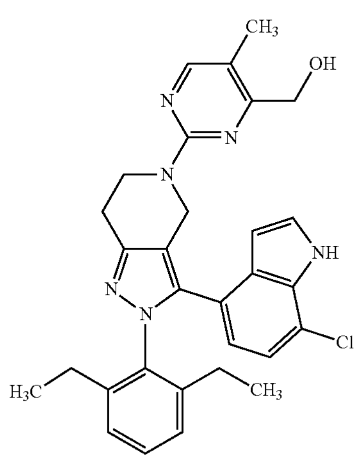 [SMILES: CCc1cccc(CC)c1-n1nc2c(c1-c1ccc(Cl)c3[nH]ccc13)CN(c1ncc(C)c(CO)n1)CC2] | +++ |

TABLE 3-continued

Structure & Biological Activity of Specific Embodiments

| Compound | Structure | Mig IC50 (nM) |
|---|---|---|
| 1.073 | 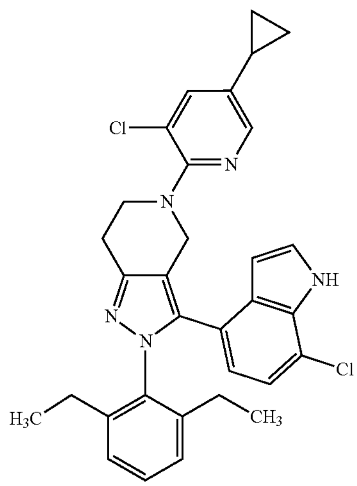 [SMILES: CCc1cccc(CC)c1-n1nc2c(c1-c1ccc(Cl)c3[nH]ccc13)CN(c1ncc(C3CC3)cc1Cl)CC2] | ++++ |
| 1.074 | 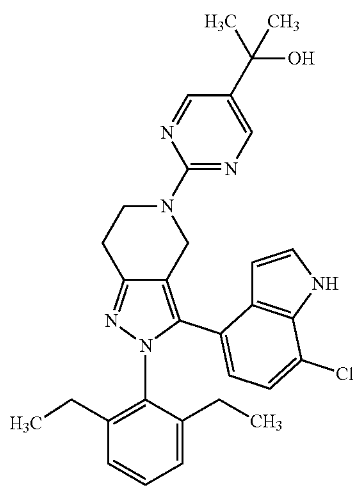 [SMILES: CCc1cccc(CC)c1-n1nc2c(c1-c1ccc(Cl)c3[nH]ccc13)CN(c1ncc(C(C)(C)O)cn1)CC2] | ++++ |
| 1.075 | 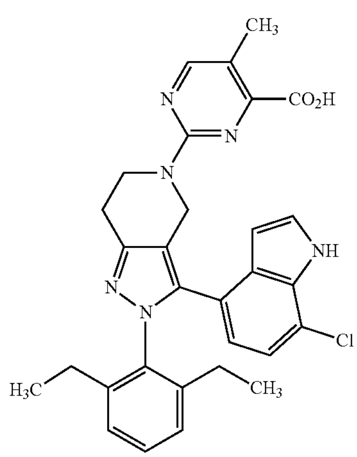 [SMILES: CCc1cccc(CC)c1-n1nc2c(c1-c1ccc(Cl)c3[nH]ccc13)CN(c1ncc(C)c(C(=O)O)n1)CC2] | ++ |

TABLE 3-continued
Structure & Biological Activity of Specific Embodiments
| Compound | Structure | Mig IC50 (nM) |
|---|---|---|
| 1.076 | 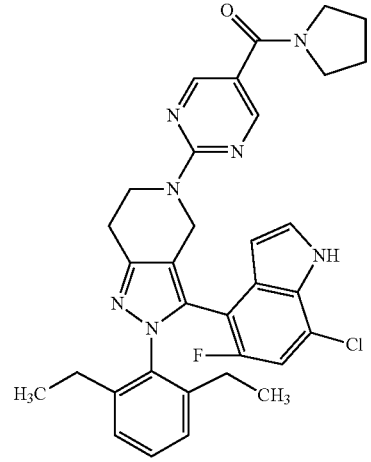 [SMILES: CCc1cccc(CC)c1-n1nc2c(c1-c1c(F)cc(Cl)c3[nH]ccc13)CN(c1ncc(C(=O)N3CCCC3)cn1)CC2] | ++++ |
| 1.077 | 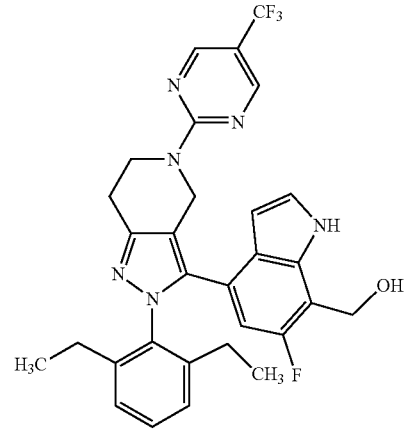 [SMILES: CCc1cccc(CC)c1-n1nc2c(c1-c1cc(F)c(CO)c3[nH]ccc13)CN(c1ncc(C(F)(F)F)cn1)CC2] | ++++ |
| 1.078 | 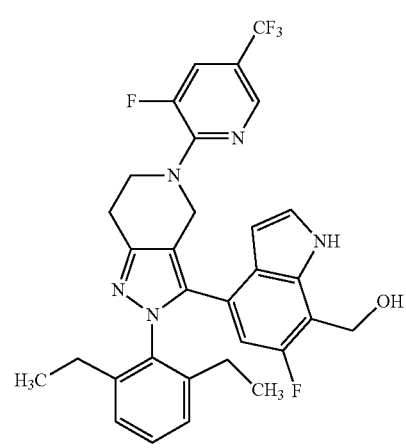 [SMILES: CCc1cccc(CC)c1-n1nc2c(c1-c1cc(F)c(CO)c3[nH]ccc13)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.079 | 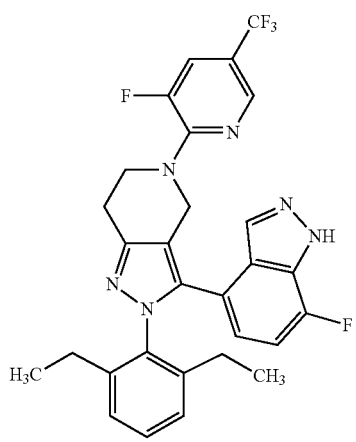 [SMILES: CCc1cccc(CC)c1-n1nc2c(c1-c1ccc(F)c3[nH]ncc13)CN(c1ncc(C(F)(F)F)cc1F)CC2] | ++ |
| 1.080 | 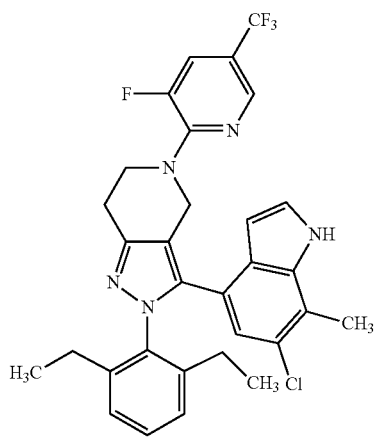 [SMILES: CCc1cccc(CC)c1-n1nc2c(c1-c1cc(Cl)c(C)c3[nH]ccc13)CN(c1ncc(C(F)(F)F)cc1F)CC2] | ++++ |
| 1.081 | 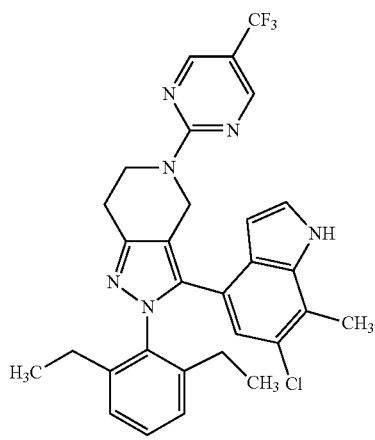 [SMILES: CCc1cccc(CC)c1-n1nc2c(c1-c1cc(Cl)c(C)c3[nH]ccc13)CN(c1ncc(C(F)(F)F)cn1)CC2] | ++++ |

TABLE 3-continued
Structure & Biological Activity of Specific Embodiments
| Compound | Structure | Mig IC50 (nM) |
|---|---|---|
| 1.082 | 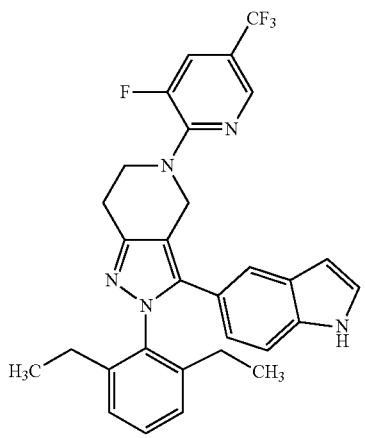 [SMILES: CCc1cccc(CC)c1-n1nc2c(c1-c1ccc3[nH]ccc3c1)CN(c1ncc(C(F)(F)F)cc1F)CC2] | +++ |
| 1.083 | 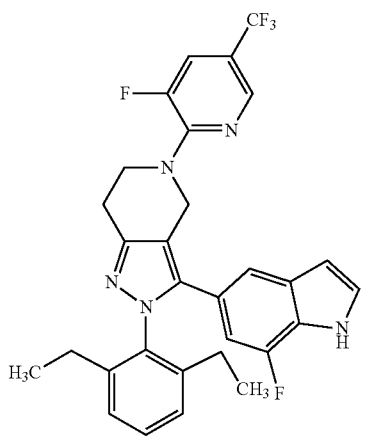 [SMILES: CCc1cccc(CC)c1-n1nc2c(c1-c1cc(F)c3[nH]ccc3c1)CN(c1ncc(C(F)(F)F)cc1F)CC2] | +++ |
| 1.084 | 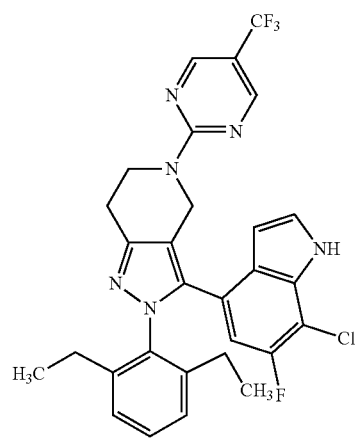 [SMILES: CCc1cccc(CC)c1-n1nc2c(c1-c1cc(F)c(Cl)c3[nH]ccc13)CN(c1ncc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.085 | 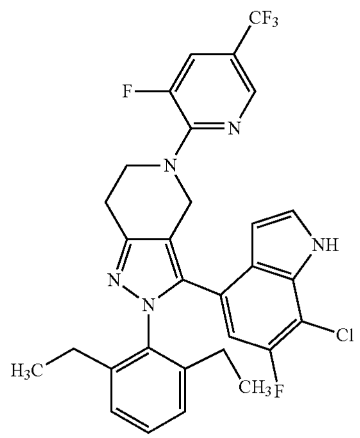 [SMILES: CCc1cccc(CC)c1-n1nc2c(c1-c1cc(F)c(Cl)c3[nH]ccc13)CN(c1ncc(C(F)(F)F)cc1F)CC2] | ++++ |
| 1.086 | 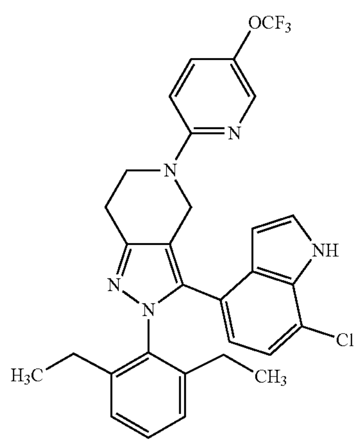 [SMILES: CCc1cccc(CC)c1-n1nc2c(c1-c1ccc(Cl)c3[nH]ccc13)CN(c1ccc(OC(F)(F)F)cn1)CC2] | ++++ |
| 1.087 | 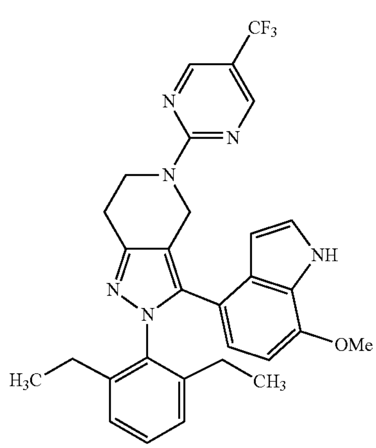 [SMILES: CCc1cccc(CC)c1-n1nc2c(c1-c1ccc(OC)c3[nH]ccc13)CN(c1ncc(C(F)(F)F)cn1)CC2] | +++ |

TABLE 3-continued
Structure & Biological Activity of Specific Embodiments
| Compound | Structure | Mig IC50 (nM) |
|---|---|---|
| 1.088 | 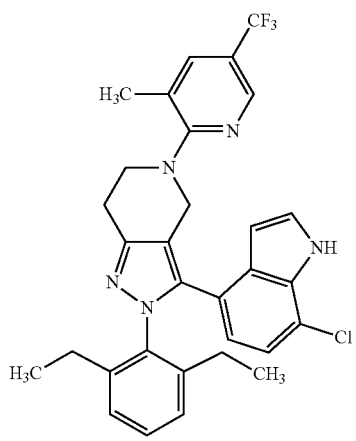 [SMILES: CCc1cccc(CC)c1-n1nc2c(c1-c1ccc(Cl)c3[nH]ccc13)CN(c1ncc(C(F)(F)F)cc1C)CC2] | ++++ |
| 1.089 | 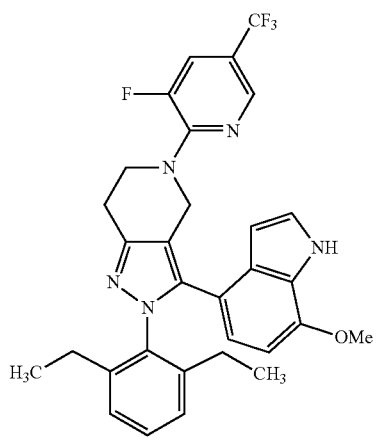 [SMILES: CCc1cccc(CC)c1-n1nc2c(c1-c1ccc(OC)c3[nH]ccc13)CN(c1ncc(C(F)(F)F)cc1F)CC2] | +++ |
| 1.090 | 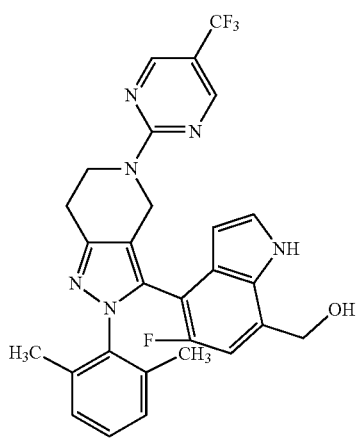 [SMILES: Cc1cccc(C)c1-n1nc2c(c1-c1c(F)cc(CO)c3[nH]ccc13)CN(c1ncc(C(F)(F)F)cn1)CC2] | +++ |

TABLE 3-continued
Structure & Biological Activity of Specific Embodiments
| Compound | Structure | Mig IC50 (nM) |
|---|---|---|
| 1.091 | 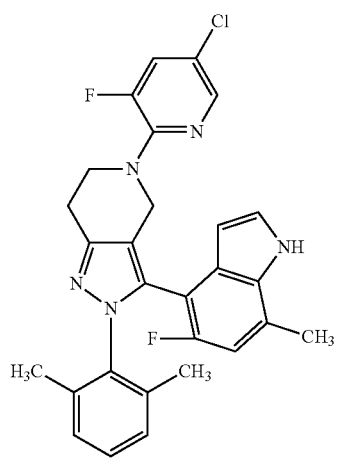 | +++ |
| 1.092 | 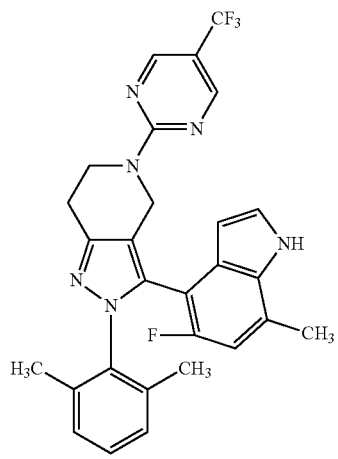 | ++++ |
| 1.093 | 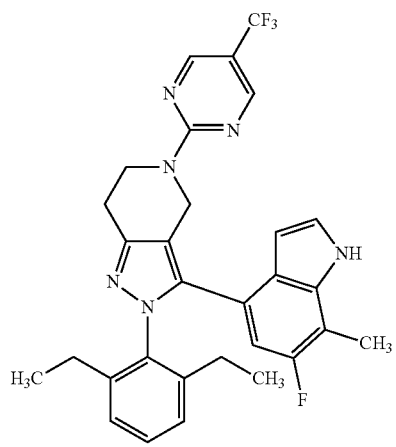 [SMILES: CCc1cccc(CC)c1-n1nc2c(c1-c1cc(F)c(C)c3[nH]ccc13)CN(c1ncc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.094 | 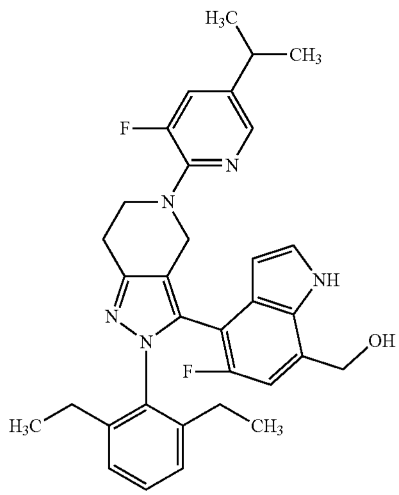 [SMILES: CCc1cccc(CC)c1-n1nc2c(c1-c1c(F)cc(CO)c3[nH]ccc13)CN(c1ncc(C(C)C)cc1F)CC2] | ++++ |
| 1.095 | 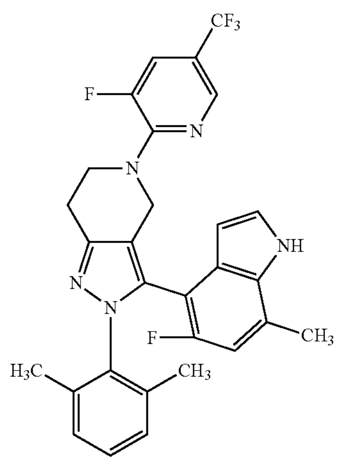 | ++++ |
| 1.096 | 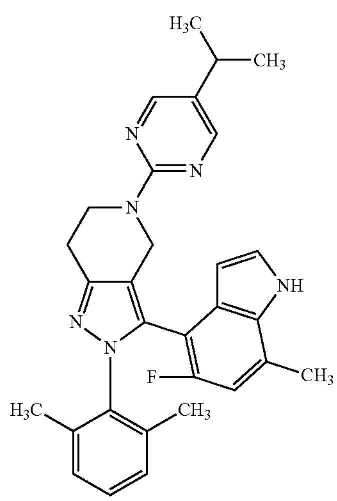 | ++++ |

TABLE 3-continued
Structure & Biological Activity of Specific Embodiments
| Compound | Structure | Mig IC50 (nM) |
|---|---|---|
| 1.097 | 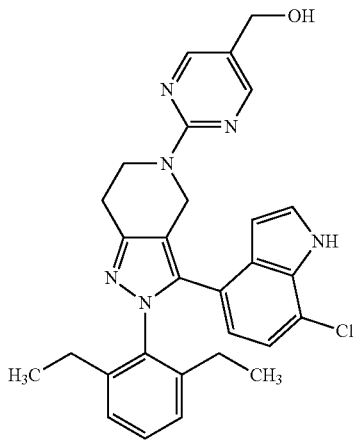 [SMILES: CCc1cccc(CC)c1-n1nc2c(c1-c1ccc(Cl)c3[nH]ccc13)CN(c1ncc(CO)cn1)CC2] | +++ |
| 1.098 | 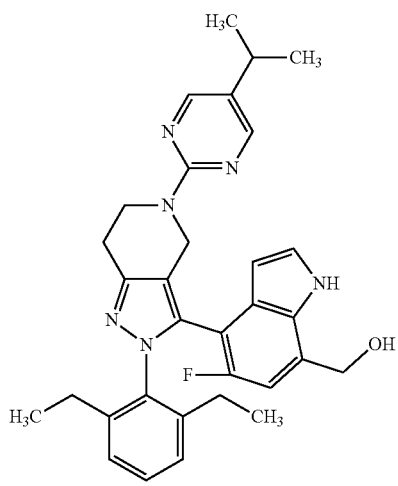 [SMILES: CCc1cccc(CC)c1-n1nc2c(c1-c1c(F)cc(CO)c3[nH]ccc13)CN(c1ncc(C(C)C)cn1)CC2] | ++++ |
| 1.099 | 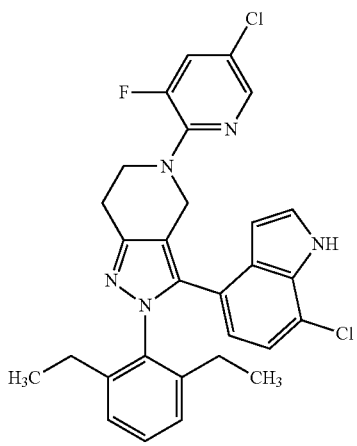 [SMILES: CCc1cccc(CC)c1-n1nc2c(c1-c1ccc(Cl)c3[nH]ccc13)CN(c1ncc(Cl)cc1F)CC2] | ++++ |

TABLE 3-continued
Structure & Biological Activity of Specific Embodiments
| Compound | Structure | Mig IC50 (nM) |
|---|---|---|
| 1.100 | 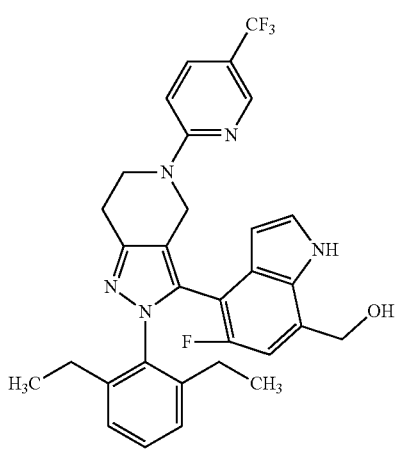 [SMILES: CCc1cccc(CC)c1-n1nc2c(c1-c1c(F)cc(CO)c3[nH]ccc13)CN(c1ccc(C(F)(F)F)cn1)CC2] | ++++ |
| 1.101 | 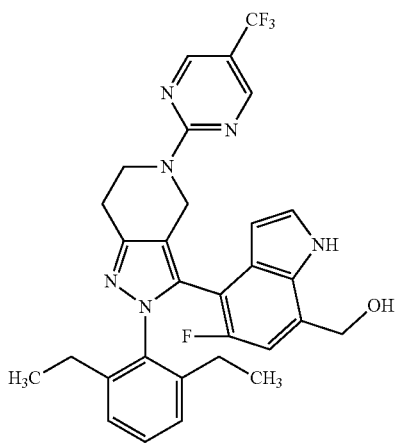 [SMILES: CCc1cccc(CC)c1-n1nc2c(c1-c1c(F)cc(CO)c3[nH]ccc13)CN(c1ncc(C(F)(F)F)cn1)CC2] | ++++ |
| 1.102 | 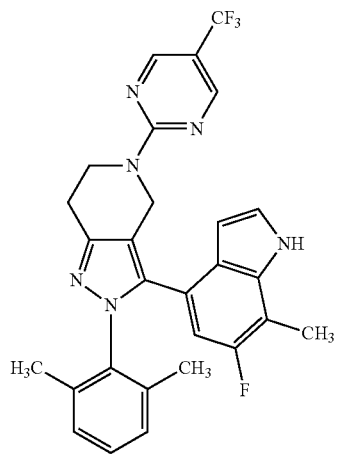 | +++ |

TABLE 3-continued

Structure & Biological Activity of Specific Embodiments

| Compound | Structure | Mig IC50 (nM) |
|---|---|---|
| 1.103 | 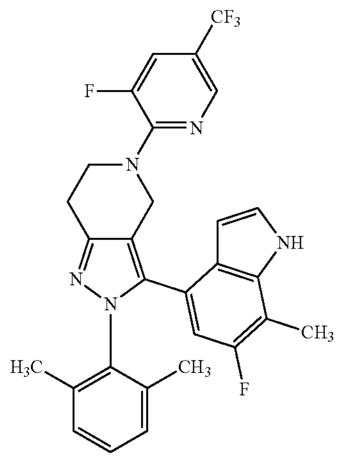 | +++ |
| 1.104 | 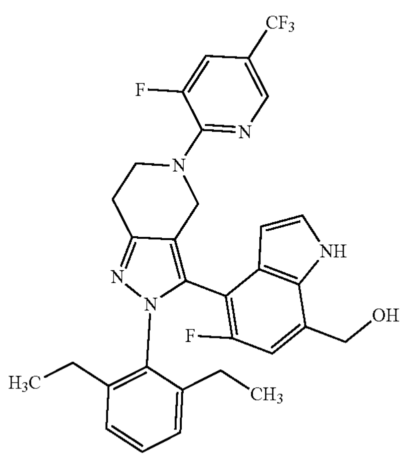 [SMILES: CCc1cccc(CC)c1-n1nc2c(c1-c1c(F)cc(CO)c3[nH]ccc13)CN(c1ncc(C(F)(F)F)cc1F)CC2] | ++++ |
| 1.105 | 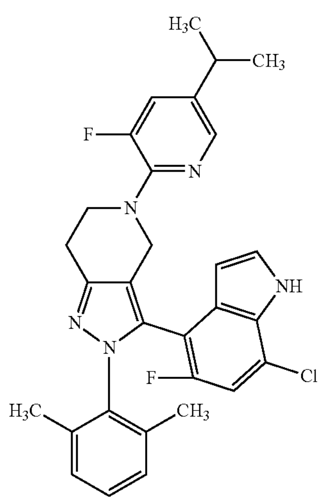 [SMILES: Cc1cccc(C)c1-n1nc2c(c1-c1c(F)cc(Cl)c3[nH]ccc13)CN(c1ncc(C(C)C)cc1F)CC2] | +++ |

TABLE 3-continued
Structure & Biological Activity of Specific Embodiments
| Compound | Structure | Mig IC50 (nM) |
|---|---|---|
| 1.106 | 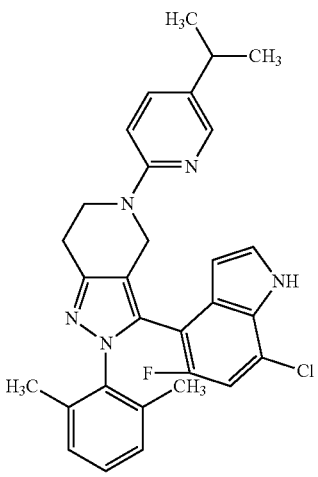 [SMILES: Cc1cccc(C)c1-n1nc2c(c1-c1c(F)cc(Cl)c3[nH]ccc13)CN(c1ccc(C(C)C)cn1)CC2] | ++++ |
| 1.107 | 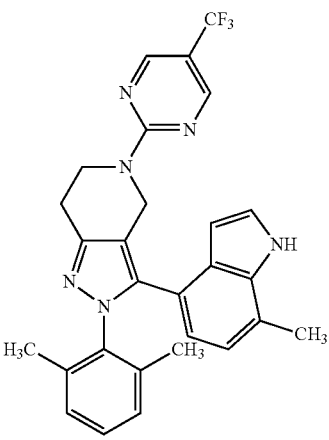 | +++ |
| 1.108 | 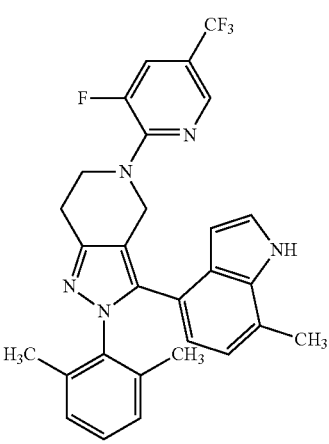 | +++ |

TABLE 3-continued
Structure & Biological Activity of Specific Embodiments
| Compound | Structure | Mig IC50 (nM) |
|---|---|---|
| 1.109 | 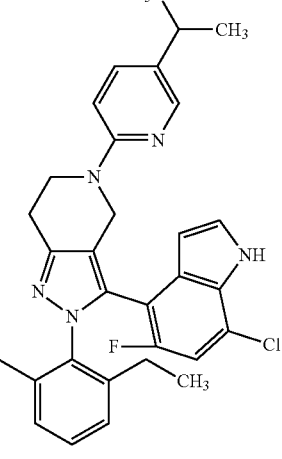 | ++++ |
| 1.110 | 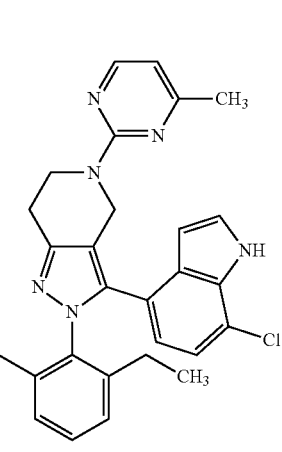 | +++ |
| 1.111 | 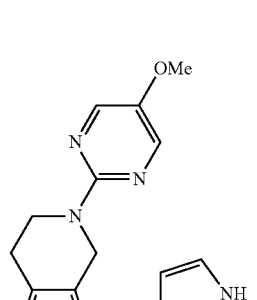 | +++ |

TABLE 3-continued
Structure & Biological Activity of Specific Embodiments
| Compound | Structure | Mig IC50 (nM) |
|---|---|---|
| 1.112 | 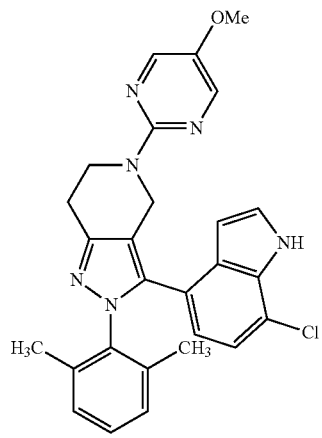 [SMILES: COc1cnc(N2CCc3nn(-c4c(C)cccc4C)c(-c4ccc(Cl)c5[nH]ccc45)c3C2)nc1] | +++ |
| 1.113 | 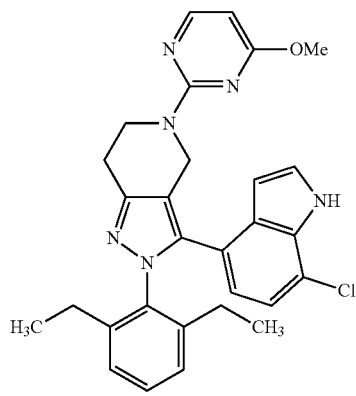 [SMILES: CCc1cccc(CC)c1-n1nc2c(c1-c1ccc(Cl)c3[nH]ccc13)CN(c1nccc(OC)n1)CC2] | ++++ |
| 1.114 | 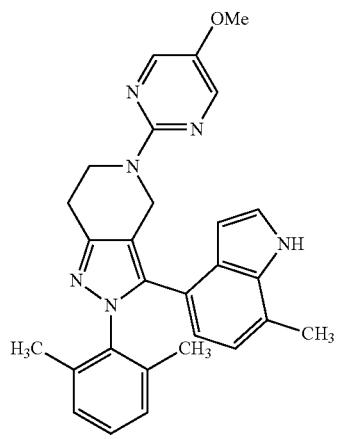 | +++ |

TABLE 3-continued

Structure & Biological Activity of Specific Embodiments

| Compound | Structure | Mig IC50 (nM) |
|---|---|---|
| 1.115 | 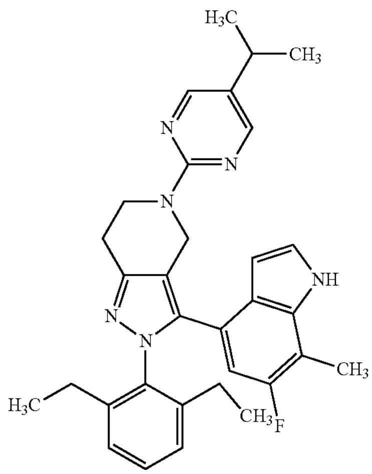 [SMILES: CCc1cccc(CC)c1-n1nc2c(c1-c1cc(F)c(C)c3[nH]ccc13)CN(c1ncc(C(C)C)cn1)CC2] | ++++ |
| 1.116 | 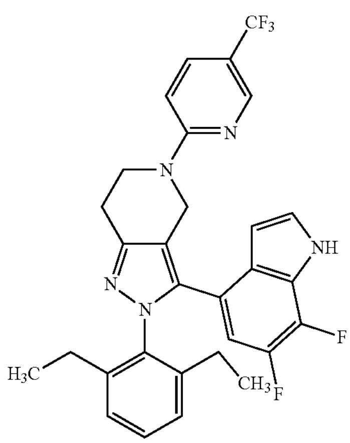 [SMILES: CCc1cccc(CC)c1-n1nc2c(c1-c1cc(F)c(F)c3[nH]ccc13)CN(c1ccc(C(F)(F)F)cn1)CC2] | +++ |
| 1.117 | 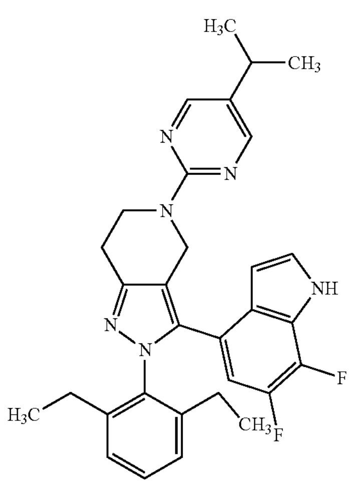 [SMILES: CCc1cccc(CC)c1-n1nc2c(c1-c1cc(F)c(F)c3[nH]ccc13)CN(c1ncc(C(C)C)cn1)CC2] | +++ |

TABLE 3-continued
Structure & Biological Activity of Specific Embodiments
| Compound | Structure | Mig IC50 (nM) |
|---|---|---|
| 1.118 | 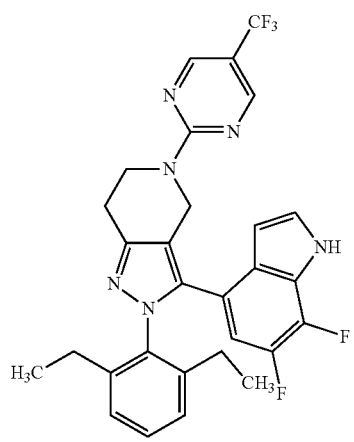 [SMILES: CCc1cccc(CC)c1-n1nc2c(c1-c1cc(F)c(F)c3[nH]ccc13)CN(c1ncc(C(F)(F)F)cn1)CC2] | +++ |
| 1.119 | 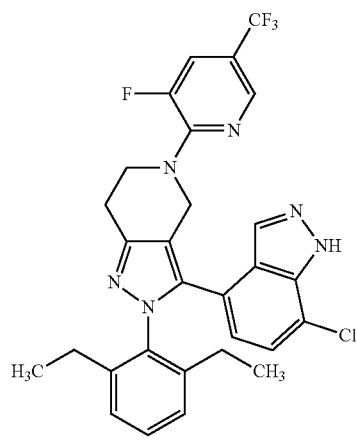 [SMILES: CCc1cccc(CC)c1-n1nc2c(c1-c1ccc(Cl)c3[nH]ncc13)CN(c1ncc(C(F)(F)F)cc1F)CC2] | +++ |
| 1.120 | 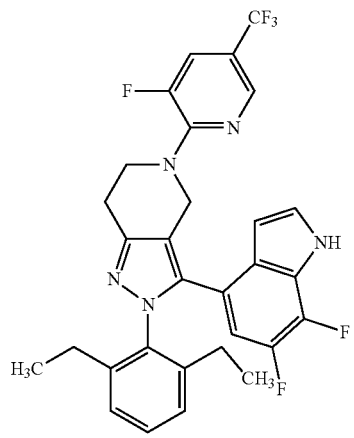 [SMILES: CCc1cccc(CC)c1-n1nc2c(c1-c1cc(F)c(F)c3[nH]ccc13)CN(c1ncc(C(F)(F)F)cc1F)CC2] | +++ |

TABLE 3-continued
Structure & Biological Activity of Specific Embodiments
| Compound | Structure | Mig IC50 (nM) |
|---|---|---|
| 1.121 | 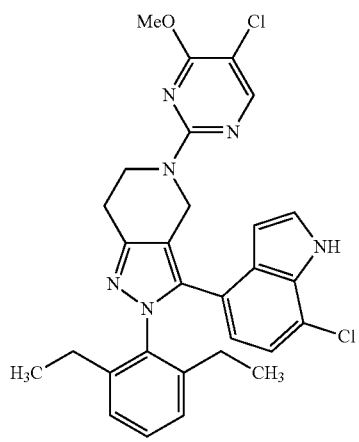 [SMILES: CCc1cccc(CC)c1-n1nc2c(c1-c1ccc(Cl)c3[nH]ccc13)CN(c1ncc(Cl)c(OC)n1)CC2] | +++ |
| 1.122 | 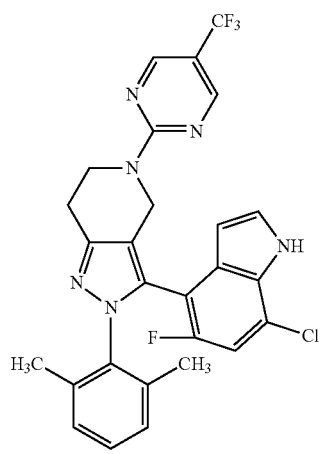 [SMILES: Cc1cccc(C)c1-n1nc2c(c1-c1c(F)cc(Cl)c3[nH]ccc13)CN(c1ncc(C(F)(F)F)cn1)CC2] | +++ |
| 1.123 | 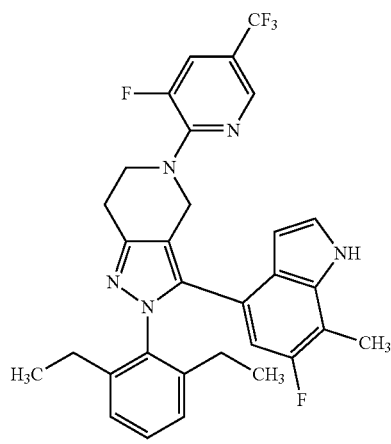 [SMILES: CCc1cccc(CC)c1-n1nc2c(c1-c1cc(F)c(C)c3[nH]ccc13)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.124 | 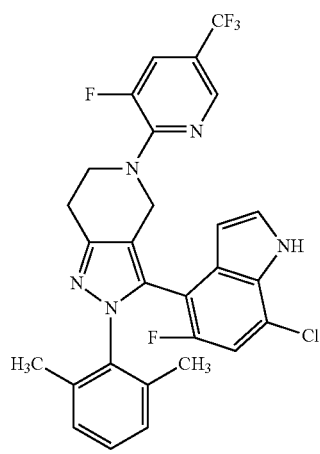 [SMILES: Cc1cccc(C)c1-n1nc2c(c1-c1c(F)cc(Cl)c3[nH]ccc13)CN(c1ncc(C(F)(F)F)cc1F)CC2] | +++ |
| 1.125 | 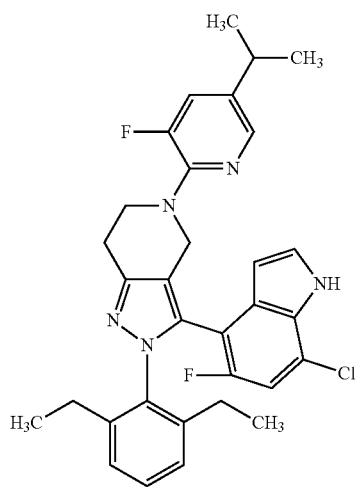 [SMILES: CCc1cccc(CC)c1-n1nc2c(c1-c1c(F)cc(Cl)c3[nH]ccc13)CN(c1ncc(C(C)C)cc1F)CC2] | ++++ |
| 1.126 | 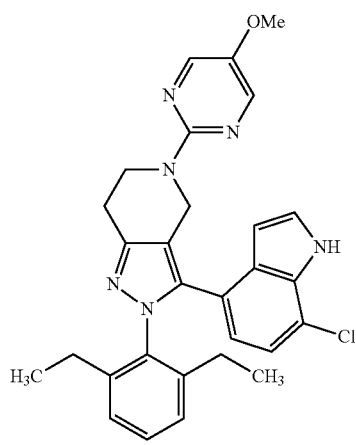 [SMILES: CCc1cccc(CC)c1-n1nc2c(c1-c1ccc(Cl)c3[nH]ccc13)CN(c1ncc(OC)cn1)CC2] | ++++ |

TABLE 3-continued
Structure & Biological Activity of Specific Embodiments
| Compound | Structure | Mig IC50 (nM) |
|---|---|---|
| 1.127 | 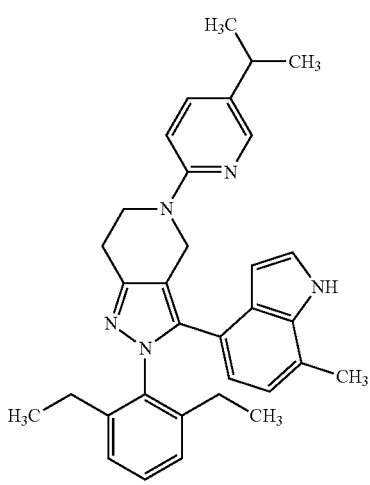 [SMILES: CCc1cccc(CC)c1-n1nc2c(c1-c1ccc(C)c3[nH]ccc13)CN(c1ccc(C(C)C)cn1)CC2] | ++++ |
| 1.128 | 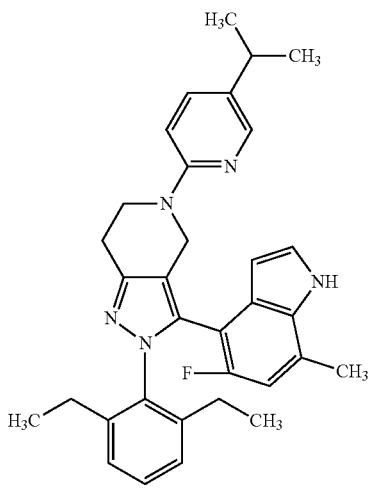 [SMILES: CCc1cccc(CC)c1-n1nc2c(c1-c1c(F)cc(C)c3[nH]ccc13)CN(c1ccc(C(C)C)cn1)CC2] | ++++ |
| 1.129 | 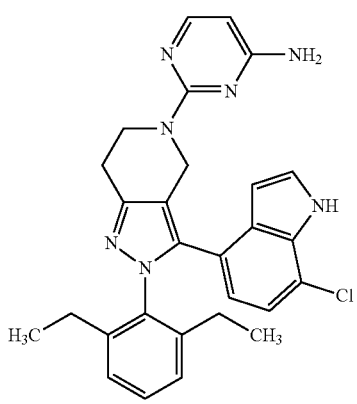 [SMILES: CCc1cccc(CC)c1-n1nc2c(c1-c1ccc(Cl)c3[nH]ccc13)CN(c1nccc(N)n1)CC2] | ++ |

TABLE 3-continued
Structure & Biological Activity of Specific Embodiments
| Compound | Structure | Mig IC50 (nM) |
|---|---|---|
| 1.130 | 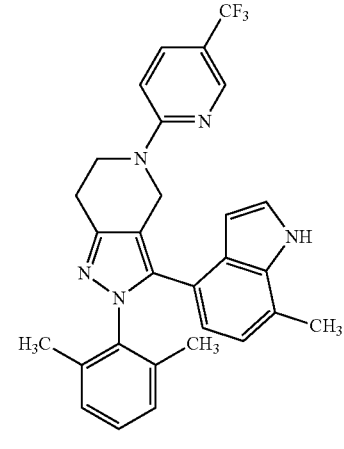 | +++ |
| 1.131 | 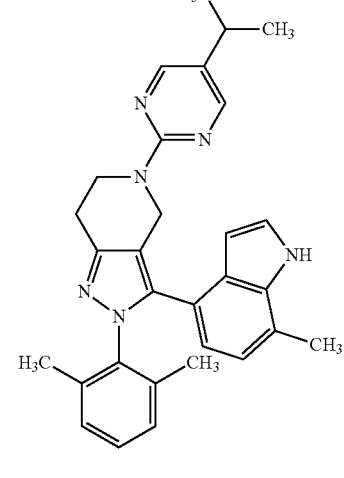 | +++ |
| 1.132 | 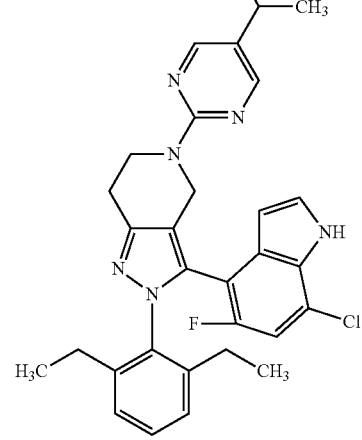 | ++++ |

TABLE 3-continued

Structure & Biological Activity of Specific Embodiments

| Compound | Structure | Mig IC50 (nM) |
|---|---|---|
| 1.133 | 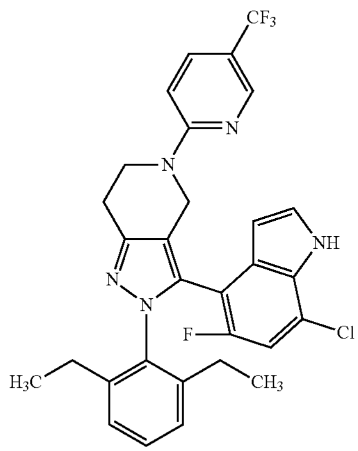 [SMILES: CCc1cccc(CC)c1-n1nc2c(c1-c1c(F)cc(Cl)c3[nH]ccc13)CN(c1ccc(C(F)(F)F)cn1)CC2] | ++++ |
| 1.134 | 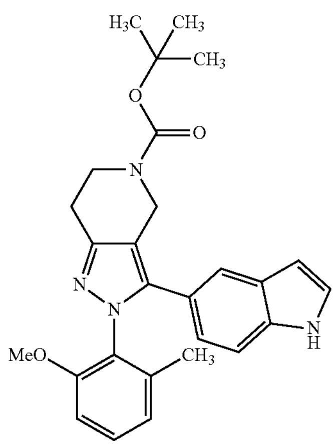 [SMILES: COc1cccc(C)c1-n1nc2c(c1-c1ccc3[nH]ccc3c1)CN(C(=O)OC(C)(C)C)CC2] | ++ |
| 1.135 | 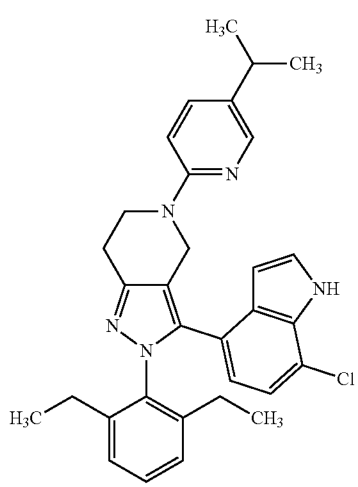 [SMILES: CCc1cccc(CC)c1-n1nc2c(c1-c1ccc(Cl)c3[nH]ccc13)CN(c1ccc(C(C)C)cn1)CC2] | ++++ |

TABLE 3-continued
Structure & Biological Activity of Specific Embodiments
| Compound | Structure | Mig IC50 (nM) |
|---|---|---|
| 1.136 | 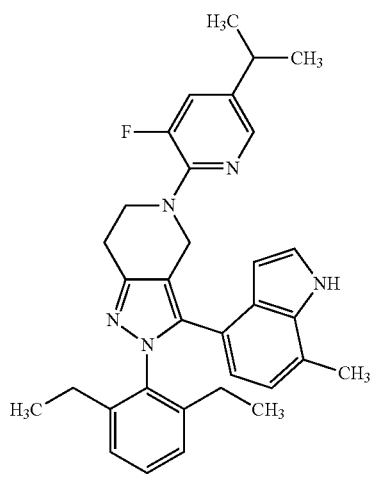 [SMILES: CCc1cccc(CC)c1-n1nc2c(c1-c1ccc(C)c3[nH]ccc13)CN(c1ncc(C(C)C)cc1F)CC2] | ++++ |
| 1.137 | 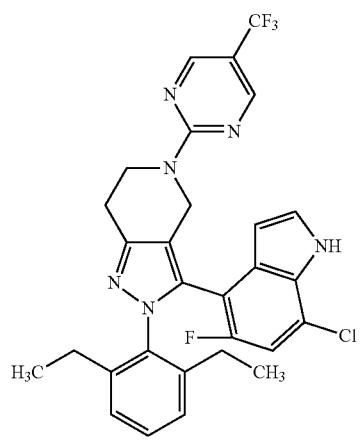 [SMILES: CCc1cccc(CC)c1-n1nc2c(c1-c1c(F)cc(Cl)c3[nH]ccc13)CN(c1ncc(C(F)(F)F)cn1)CC2] | ++++ |
| 1.138 | 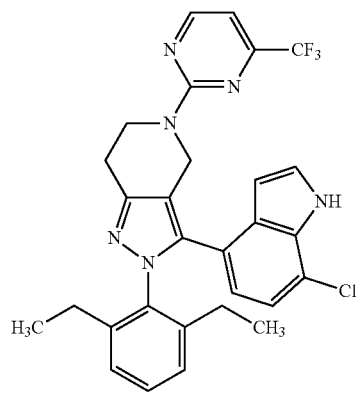 | ++++ |

TABLE 3-continued
Structure & Biological Activity of Specific Embodiments
| Compound | Structure | Mig IC50 (nM) |
|---|---|---|
| 1.139 | 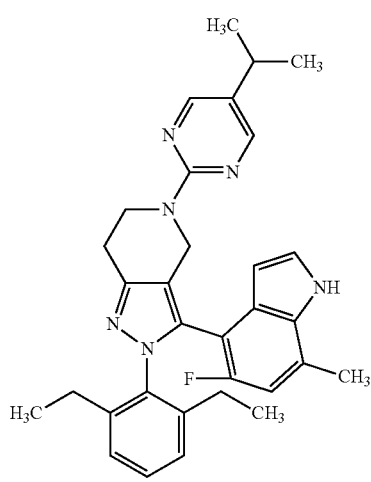 [SMILES: CCc1cccc(CC)c1-n1nc2c(c1-c1c(F)cc(C)c3[nH]ccc13)CN(c1ncc(C(C)C)cn1)CC2] | ++++ |
| 1.140 | 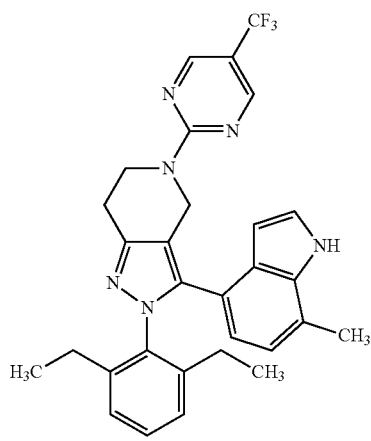 [SMILES: CCc1cccc(CC)c1-n1nc2c(c1-c1ccc(C)c3[nH]ccc13)CN(c1ncc(C(F)(F)F)cn1)CC2] | ++++ |
| 1.141 | 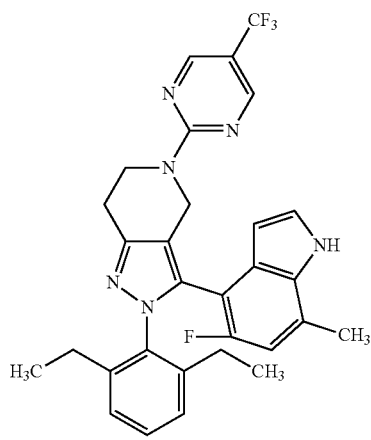 [SMILES: CCc1cccc(CC)c1-n1nc2c(c1-c1c(F)cc(C)c3[nH]ccc13)CN(c1ncc(C(F)(F)F)cn1)CC2] | ++++ |

TABLE 3-continued
Structure & Biological Activity of Specific Embodiments
| Compound | Structure | Mig IC50 (nM) |
|---|---|---|
| 1.142 | 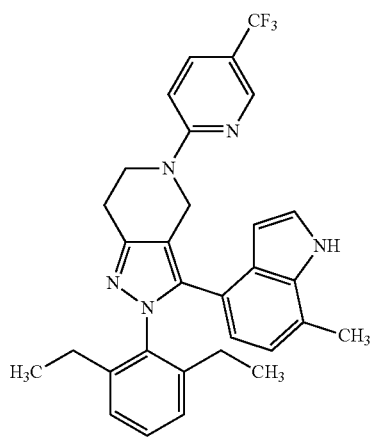 [SMILES: CCc1cccc(CC)c1-n1nc2c(c1-c1ccc(C)c3[nH]ccc13)CN(c1ccc(C(F)(F)F)cn1)CC2] | ++++ |
| 1.143 | 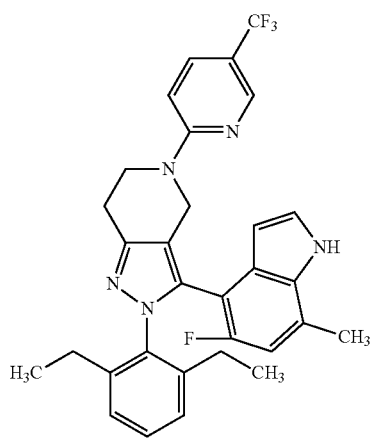 [SMILES: CCc1cccc(CC)c1-n1nc2c(c1-c1c(F)cc(C)c3[nH]ccc13)CN(c1ccc(C(F)(F)F)cn1)CC2] | ++++ |
| 1.144 | 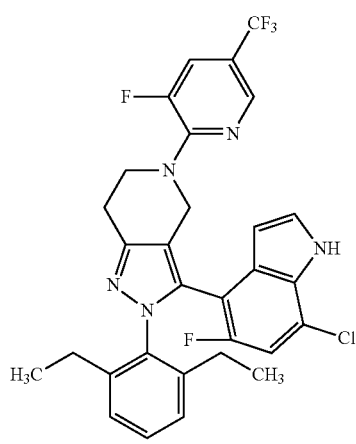 [SMILES: CCc1cccc(CC)c1-n1nc2c(c1-c1c(F)cc(Cl)c3[nH]ccc13)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.145 | 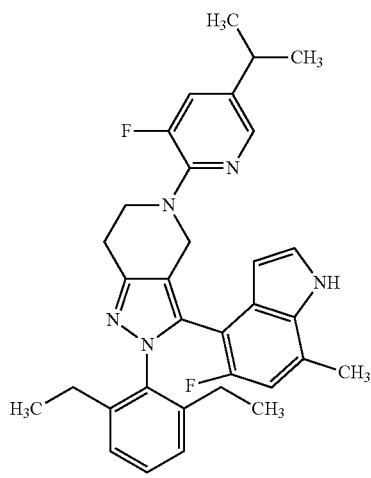 [SMILES: CCc1cccc(CC)c1-n1nc2c(c1-c1c(F)cc(C)c3[nH]ccc13)CN(c1ncc(C(C)C)cc1F)CC2] | ++++ |
| 1.146 | 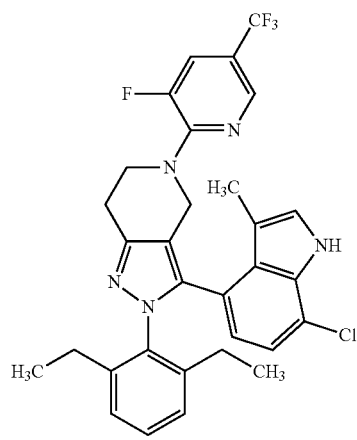 [SMILES: CCc1cccc(CC)c1-n1nc2c(c1-c1ccc(Cl)c3[nH]cc(C)c13)CN(c1ncc(C(F)(F)F)cc1F)CC2] | ++++ |
| 1.147 | 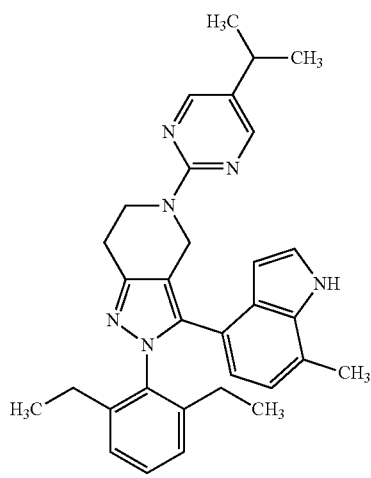 [SMILES: CCc1cccc(CC)c1-n1nc2c(c1-c1ccc(C)c3[nH]ccc13)CN(c1ncc(C(C)C)cn1)CC2] | ++++ |

TABLE 3-continued

Structure & Biological Activity of Specific Embodiments

| Compound | Structure | Mig IC50 (nM) |
|---|---|---|
| 1.148 | 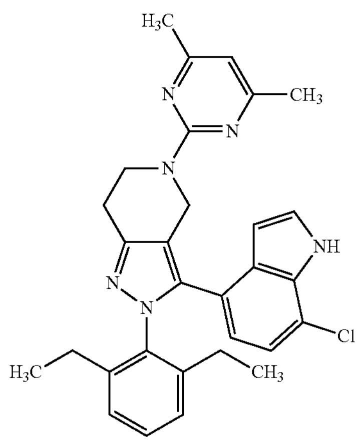 [SMILES: CCc1cccc(CC)c1-n1nc2c(c1-c1ccc(Cl)c3[nH]ccc13)CN(c1nc(C)cc(C)n1)CC2] | ++++ |
| 1.149 | 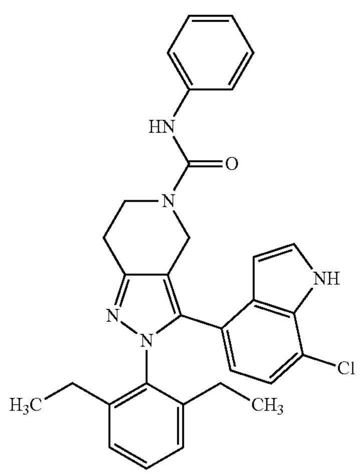 [SMILES: CCc1cccc(CC)c1-n1nc2c(c1-c1ccc(Cl)c3[nH]ccc13)CN(C(=O)Nc1ccccc1)CC2] | +++ |
| 1.150 | 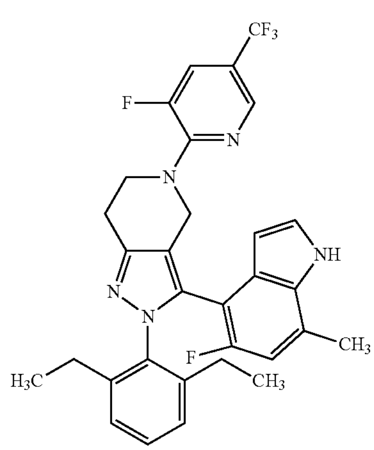 [SMILES: CCc1cccc(CC)c1-n1nc2c(c1-c1c(F)cc(C)c3[nH]ccc13)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.151 | 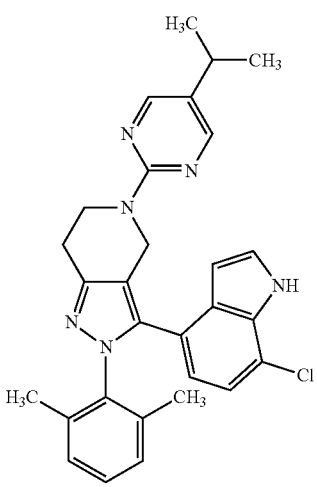 [SMILES: Cc1cccc(C)c1-n1nc2c(c1-c1ccc(Cl)c3[nH]ccc13)CN(c1ncc(C(C)C)cn1)CC2] | ++++ |
| 1.152 | 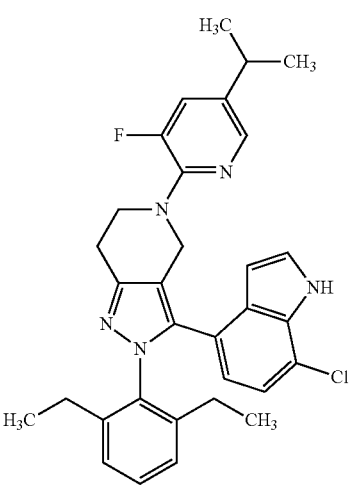 [SMILES: CCc1cccc(CC)c1-n1nc2c(c1-c1ccc(Cl)c3[nH]ccc13)CN(c1ncc(C(C)C)cc1F)CC2] | ++++ |
| 1.153 | 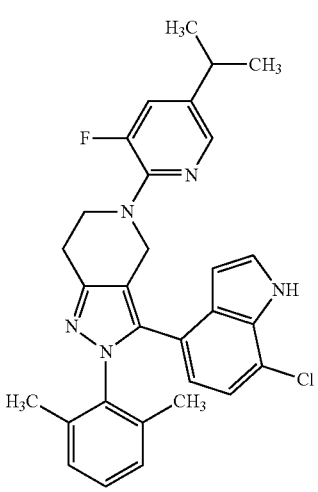 [SMILES: Cc1cccc(C)c1-n1nc2c(c1-c1ccc(Cl)c3[nH]ccc13)CN(c1ncc(C(C)C)cc1F)CC2] | +++ |

TABLE 3-continued
Structure & Biological Activity of Specific Embodiments
| Compound | Structure | Mig IC50 (nM) |
|---|---|---|
| 1.154 | 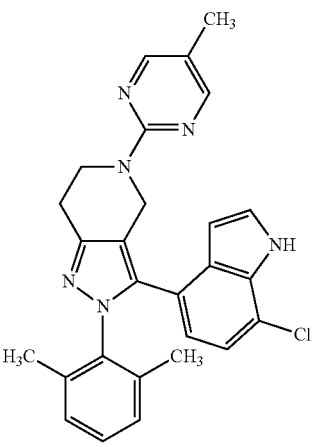 [SMILES: Cc1cnc(N2CCc3nn(-c4c(C)cccc4C)c(-c4ccc(Cl)c5[nH]ccc45)c3C2)nc1] | +++ |
| 1.155 | 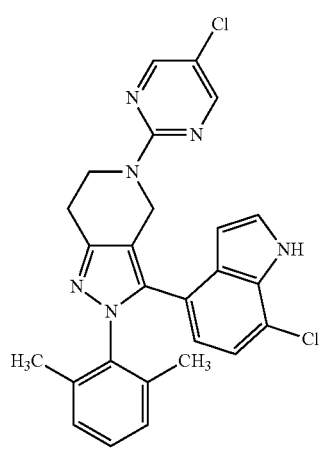 [SMILES: Cc1cccc(C)c1-n1nc2c(c1-c1ccc(Cl)c3[nH]ccc13)CN(c1ncc(Cl)cn1)CC2] | +++ |
| 1.156 | 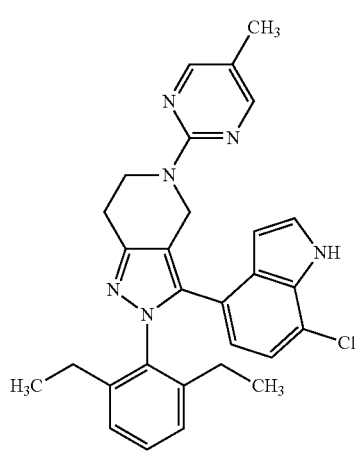 | ++++ |

TABLE 3-continued

Structure & Biological Activity of Specific Embodiments

| Compound | Structure | Mig IC50 (nM) |
|---|---|---|
| 1.157 | 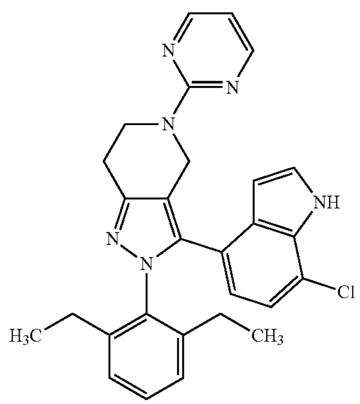 [SMILES: CCc1cccc(CC)c1-n1nc2c(c1-c1ccc(Cl)c3[nH]ccc13)CN(c1ncccn1)CC2] | ++++ |
| 1.158 | 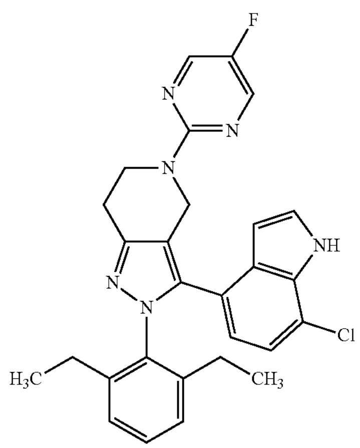 [SMILES: CCc1cccc(CC)c1-n1nc2c(c1-c1ccc(Cl)c3[nH]ccc13)CN(c1ncc(F)cn1)CC2] | ++++ |
| 1.159 | 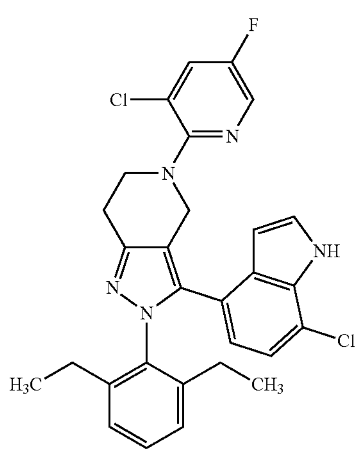 [SMILES: CCc1cccc(CC)c1-n1nc2c(c1-c1ccc(Cl)c3[nH]ccc13)CN(c1ncc(F)cc1Cl)CC2] | ++++ |

TABLE 3-continued
| Compound | Structure | Mig IC50 (nM) |
|---|---|---|
| 1.160 | 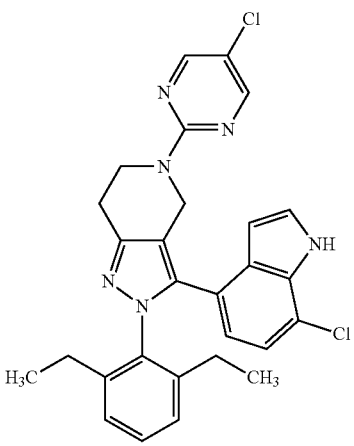 | ++++ |
| 1.161 | 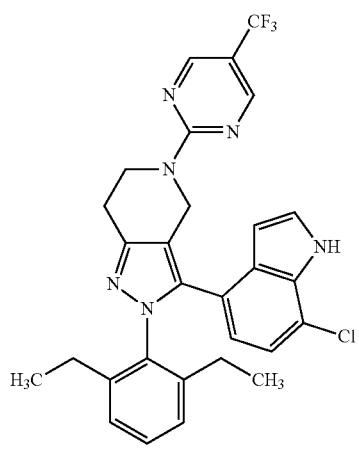 [SMILES: CCc1cccc(CC)c1-n1nc2c(c1-c1ccc(Cl)c3[nH]ccc13)CN(c1ncc(C(F)(F)F)cn1)CC2] | ++++ |
| 1.162 | 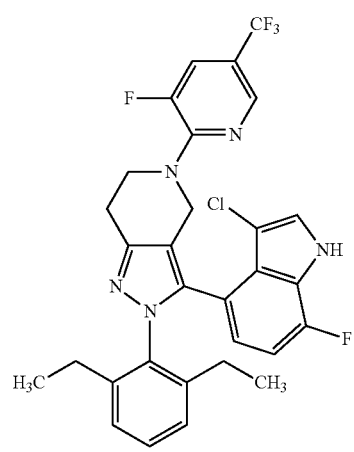 [SMILES: CCc1cccc(CC)c1-n1nc2c(c1-c1ccc(F)c3[nH]cc(Cl)c13)CN(c1ncc(C(F)(F)F)cc1F)CC2] | +++ |

TABLE 3-continued
Structure & Biological Activity of Specific Embodiments
| Compound | Structure | Mig IC50 (nM) |
| --- | --- | --- |
| 1.163 | 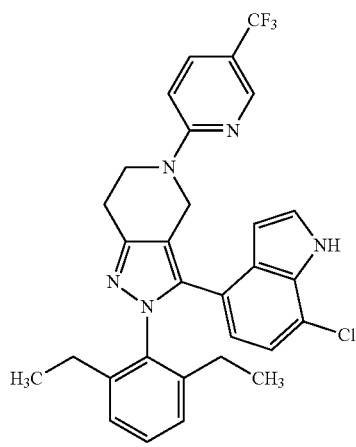 [SMILES: CCc1cccc(CC)c1-n1nc2c(c1-c1ccc(Cl)c3[nH]ccc13)CN(c1ccc(C(F)(F)F)cn1)CC2] | ++++ |
| 1.164 | 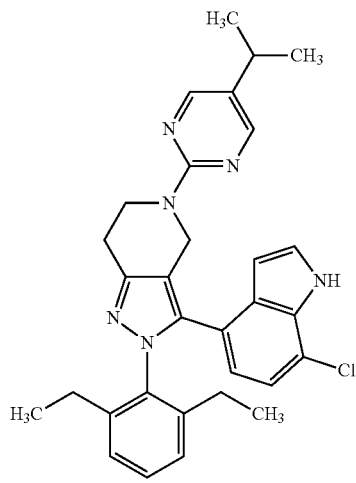 [SMILES: CCc1cccc(CC)c1-n1nc2c(c1-c1ccc(Cl)c3[nH]ccc13)CN(c1ncc(C(C)C)cn1)CC2] | ++++ |
| 1.165 | 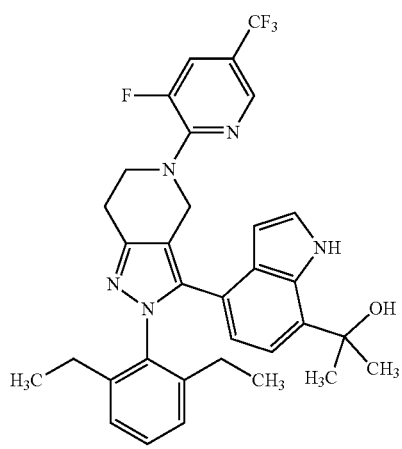 [SMILES: CCc1cccc(CC)c1-n1nc2c(c1-c1ccc(C(C)(C)O)c3[nH]ccc13)CN(c1ncc(C(F)(F)F)cc1F)CC2] | ++ |

TABLE 3-continued

Structure & Biological Activity of Specific Embodiments

| Compound | Structure | Mig IC50 (nM) |
|---|---|---|
| 1.166 | 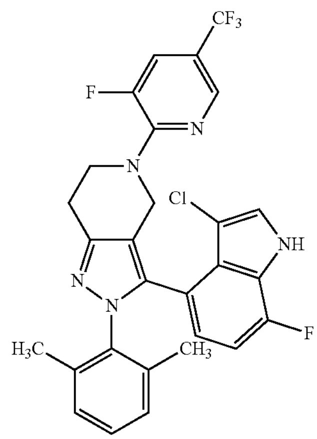 [SMILES: Cc1cccc(C)c1-n1nc2c(c1-c1ccc(F)c3[nH]cc(Cl)c13)CN(c1ncc(C(F)(F)F)cc1F)CC2] | ++ |
| 1.167 | 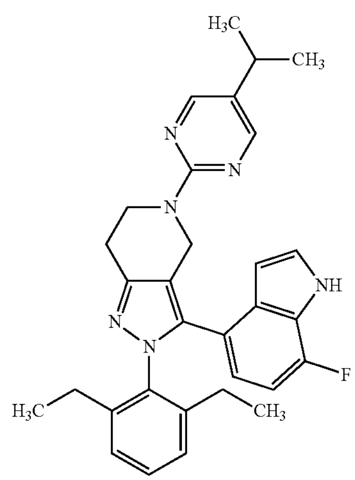 [SMILES: CCc1cccc(CC)c1-n1nc2c(c1-c1ccc(F)c3[nH]ccc13)CN(c1ncc(C(C)C)cn1)CC2] | ++++ |
| 1.168 | 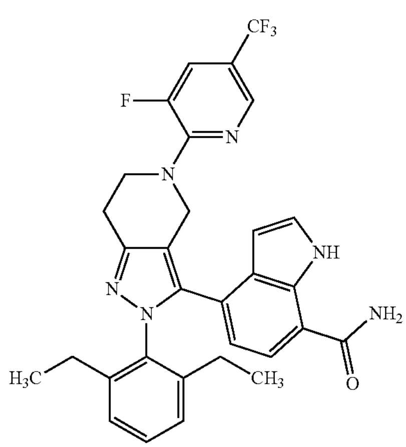 [SMILES: CCc1cccc(CC)c1-n1nc2c(c1-c1ccc(C(N)=O)c3[nH]ccc13)CN(c1ncc(C(F)(F)F)cc1F)CC2] | ++ |

TABLE 3-continued
Structure & Biological Activity of Specific Embodiments
| Compound | Structure | Mig IC50 (nM) |
|---|---|---|
| 1.169 | 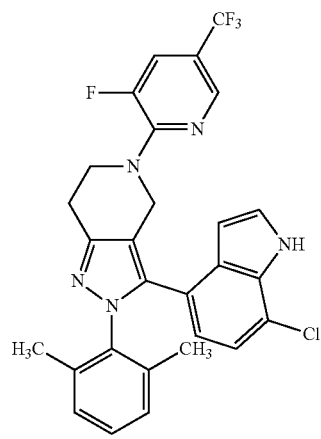 [SMILES: Cc1cccc(C)c1-n1nc2c(c1-c1ccc(Cl)c3[nH]ccc13)CN(c1ncc(C(F)(F)F)cc1F)CC2] | +++ |
| 1.170 | 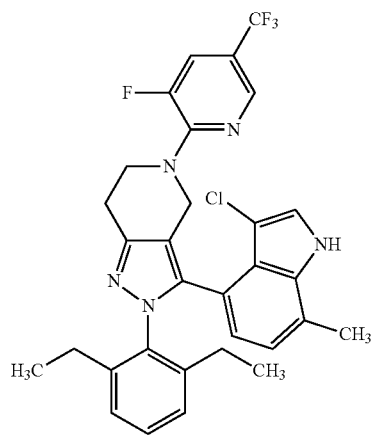 [SMILES: CCc1cccc(CC)c1-n1nc2c(c1-c1ccc(C)c3[nH]cc(Cl)c13)CN(c1ncc(C(F)(F)F)cc1F)CC2] | ++++ |
| 1.171 | 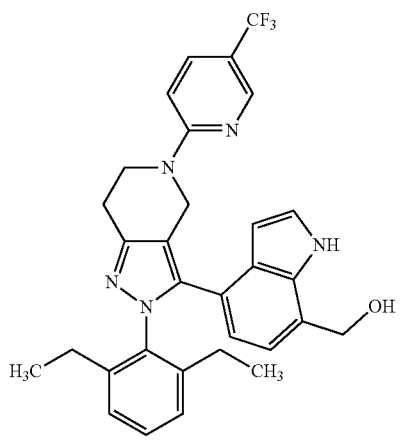 [SMILES: CCc1cccc(CC)c1-n1nc2c(c1-c1ccc(CO)c3[nH]ccc13)CN(c1ccc(C(F)(F)F)cn1)CC2] | ++++ |

TABLE 3-continued

Structure & Biological Activity of Specific Embodiments

| Compound | Structure | Mig IC50 (nM) |
|---|---|---|
| 1.172 | 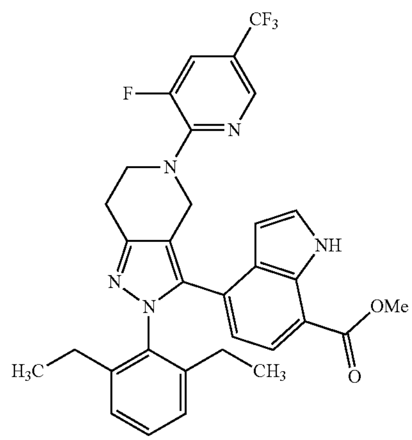 [SMILES: CCc1cccc(CC)c1-n1nc2c(c1-c1ccc(C(=O)OC)c3[nH]ccc13)CN(c1ncc(C(F)(F)F)cc1F)CC2] | ++++ |
| 1.173 | 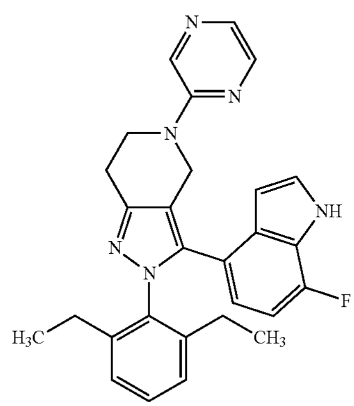 [SMILES: CCc1cccc(CC)c1-n1nc2c(c1-c1ccc(F)c3[nH]ccc13)CN(c1cnccn1)CC2] | +++ |
| 1.174 | 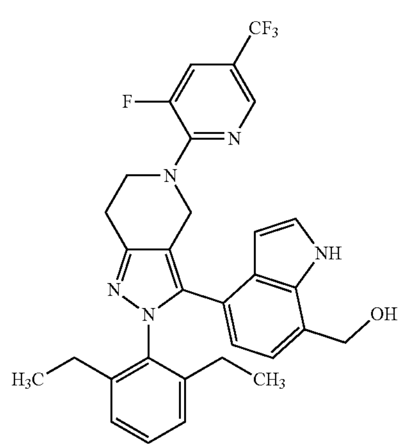 [SMILES: CCc1cccc(CC)c1-n1nc2c(c1-c1ccc(CO)c3[nH]ccc13)CN(c1ncc(C(F)(F)F)cc1F)CC2] | ++++ |

TABLE 3-continued

Structure & Biological Activity of Specific Embodiments

| Compound | Structure | Mig IC50 (nM) |
|---|---|---|
| 1.175 | 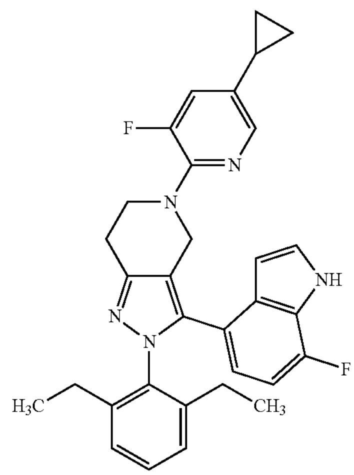 [SMILES: CCc1cccc(CC)c1-n1nc2c(c1-c1ccc(F)c3[nH]ccc13)CN(c1ncc(C3CC3)cc1F)CC2] | ++++ |
| 1.176 | 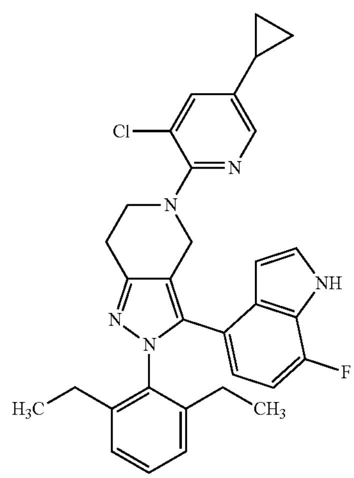 [SMILES: CCc1cccc(CC)c1-n1nc2c(c1-c1ccc(F)c3[nH]ccc13)CN(c1ncc(C3CC3)cc1Cl)CC2] | ++++ |
| 1.177 | 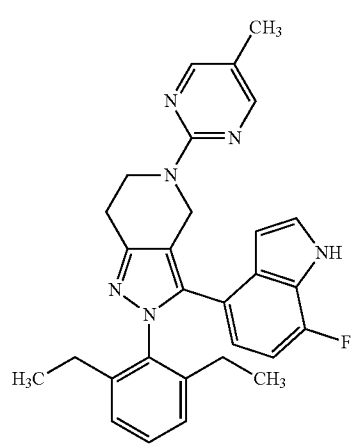 [SMILES: CCc1cccc(CC)c1-n1nc2c(c1-c1ccc(F)c3[nH]ccc13)CN(c1ncc(C)cn1)CC2] | ++++ |

TABLE 3-continued

Structure & Biological Activity of Specific Embodiments

| Compound | Structure | Mig IC50 (nM) |
|---|---|---|
| 1.178 | 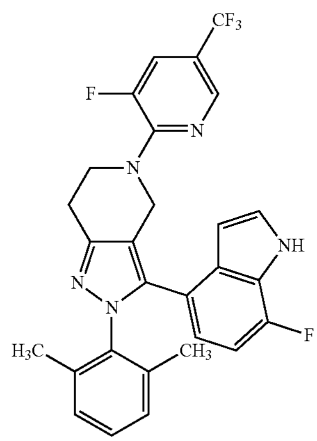 [SMILES: Cc1cccc(C)c1-n1nc2c(c1-c1ccc(F)c3[nH]ccc13)CN(c1ncc(C(F)(F)F)cc1F)CC2] | ++ |
| 1.179 | 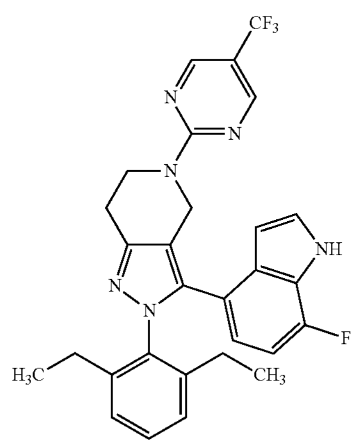 | ++++ |
| 1.180 | 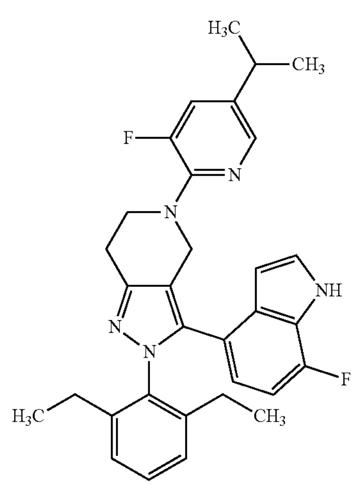 [SMILES: CCc1cccc(CC)c1-n1nc2c(c1-c1ccc(F)c3[nH]ccc13)CN(c1ncc(C(C)C)cc1F)CC2] | ++++ |

TABLE 3-continued
Structure & Biological Activity of Specific Embodiments
| Compound | Structure | Mig IC50 (nM) |
|---|---|---|
| 1.181 | 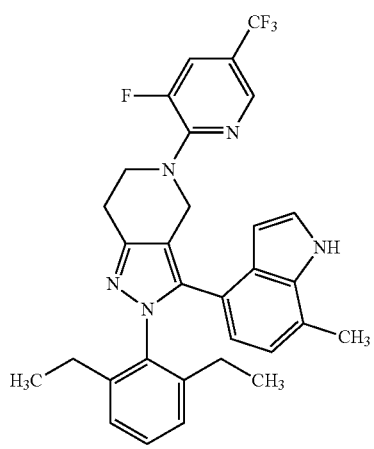 [SMILES: CCc1cccc(CC)c1-n1nc2c(c1-c1ccc(C)c3[nH]ccc13)CN(c1ncc(C(F)(F)F)cc1F)CC2] | ++++ |
| 1.182 | 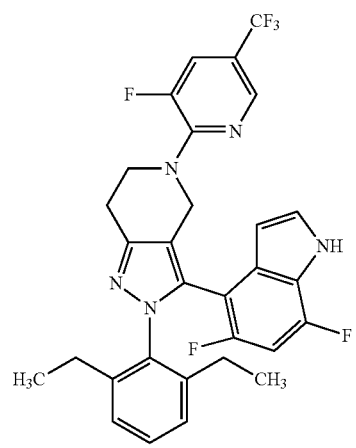 [SMILES: CCc1cccc(CC)c1-n1nc2c(c1-c1c(F)cc(F)c3[nH]ccc13)CN(c1ncc(C(F)(F)F)cc1F)CC2] | +++ |
| 1.183 | 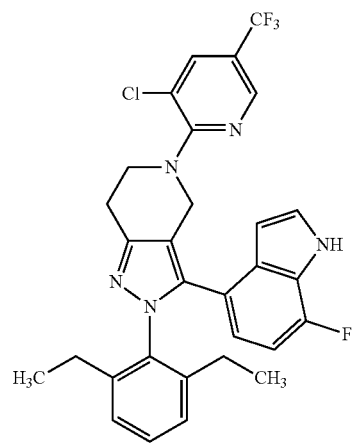 | +++ |

TABLE 3-continued

Structure & Biological Activity of Specific Embodiments

| Compound | Structure | Mig IC50 (nM) |
|---|---|---|
| 1.184 | 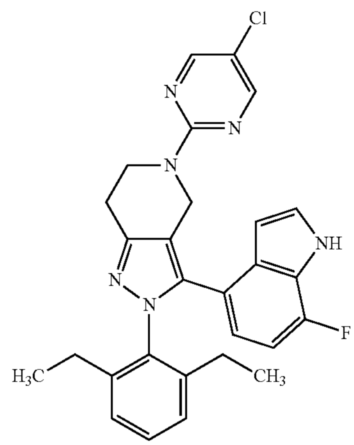 [SMILES: CCc1cccc(CC)c1-n1nc2c(c1-c1ccc(F)c3[nH]ccc13)CN(c1ncc(Cl)cn1)CC2] | ++++ |
| 1.185 | 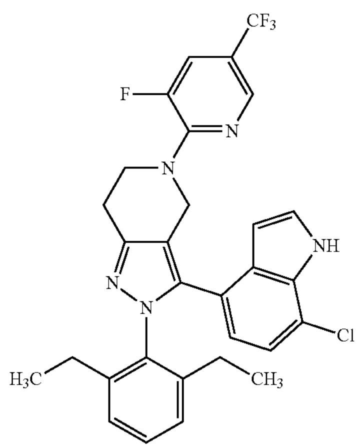 [SMILES: CCc1cccc(CC)c1-n1nc2c(c1-c1ccc(Cl)c3[nH]ccc13)CN(c1ncc(C(F)(F)F)cc1F)CC2] | ++++ |
| 1.186 | 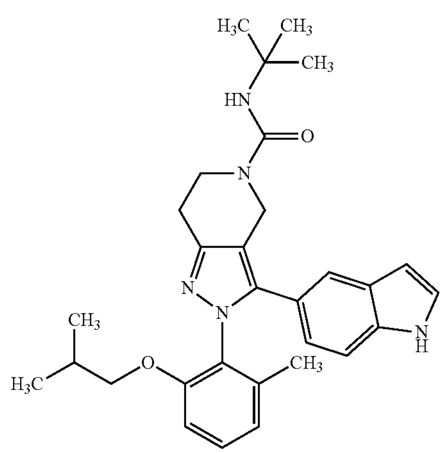 [SMILES: Cc1cccc(OCC(C)C)c1-n1nc2c(c1-c1ccc3[nH]ccc3c1)CN(C(=O)NC(C)(C)C)CC2] | ++ |

TABLE 3-continued
Structure & Biological Activity of Specific Embodiments
| Compound | Structure | Mig IC50 (nM) |
|---|---|---|
| 1.187 | 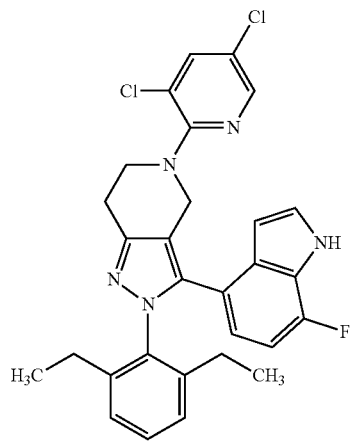 [SMILES: CCc1cccc(CC)c1-n1nc2c(c1-c1ccc(F)c3[nH]ccc13)CN(c1ncc(Cl)cc1Cl)CC2] | ++++ |
| 1.188 | 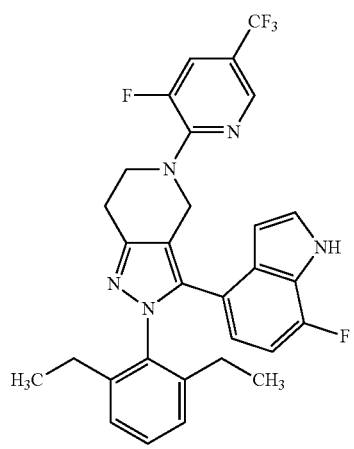 [SMILES: CCc1cccc(CC)c1-n1nc2c(c1-c1ccc(F)c3[nH]ccc13)CN(c1ncc(C(F)(F)F)cc1F)CC2] | ++++ |
| 1.189 | 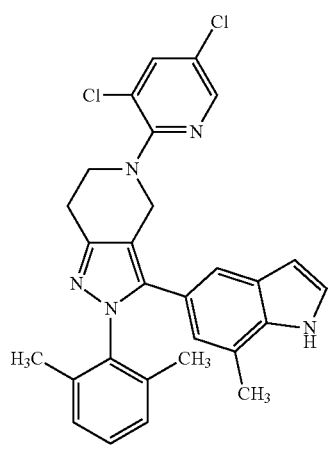 [SMILES: Cc1cccc(C)c1-n1nc2c(c1-c1cc(C)c3[nH]ccc3c1)CN(c1ncc(Cl)cc1Cl)CC2] | ++ |

TABLE 3-continued
Structure & Biological Activity of Specific Embodiments
| Compound | Structure | Mig IC50 (nM) |
|---|---|---|
| 1.190 | 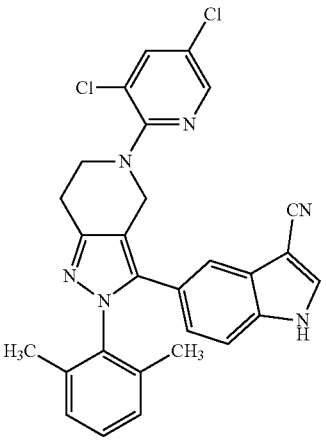 [SMILES: Cc1cccc(C)c1-n1nc2c(c1-c1ccc3[nH]cc(C#N)c3c1)CN(c1ncc(Cl)cc1Cl)CC2] | + |
| 1.191 | 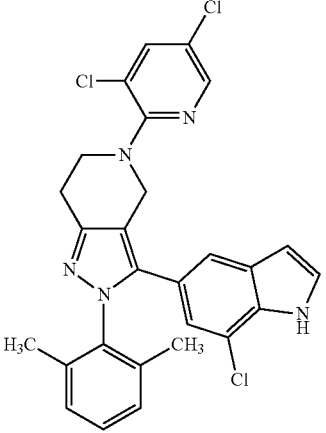 [SMILES: Cc1cccc(C)c1-n1nc2c(c1-c1cc(Cl)c3[nH]ccc3c1)CN(c1ncc(Cl)cc1Cl)CC2] | ++ |
| 1.192 | 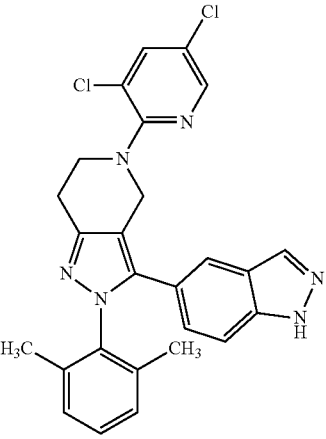 [SMILES: Cc1cccc(C)c1-n1nc2c(c1-c1ccc3[nH]ncc3c1)CN(c1ncc(Cl)cc1Cl)CC2] | + |

TABLE 3-continued

Structure & Biological Activity of Specific Embodiments

| Compound | Structure | Mig IC50 (nM) |
|---|---|---|
| 1.193 | 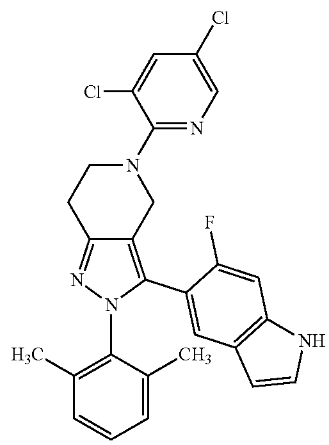 [SMILES: Cc1cccc(C)c1-n1nc2c(c1-c1cc3cc[nH]c3cc1F)CN(c1ncc(Cl)cc1Cl)CC2] | ++ |
| 1.194 | 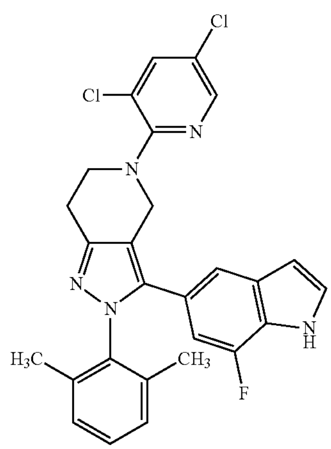 [SMILES: Cc1cccc(C)c1-n1nc2c(c1-c1cc(F)c3[nH]ccc3c1)CN(c1ncc(Cl)cc1Cl)CC2] | ++ |
| 1.195 | 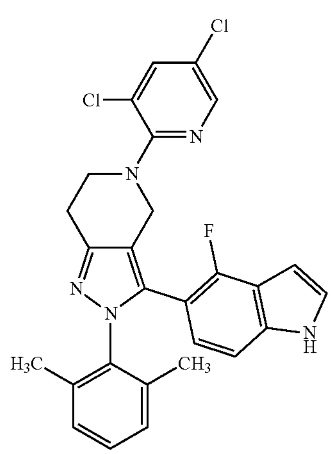 [SMILES: Cc1cccc(C)c1-n1nc2c(c1-c1ccc3[nH]ccc3c1F)CN(c1ncc(Cl)cc1Cl)CC2] | +++ |

TABLE 3-continued
Structure & Biological Activity of Specific Embodiments
| Compound | Structure | Mig IC50 (nM) |
|---|---|---|
| 1.196 | 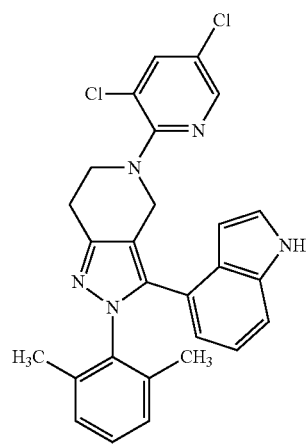 [SMILES: Cc1cccc(C)c1-n1nc2c(c1-c1cccc3[nH]ccc13)CN(c1ncc(Cl)cc1Cl)CC2] | +++ |
| 1.197 | 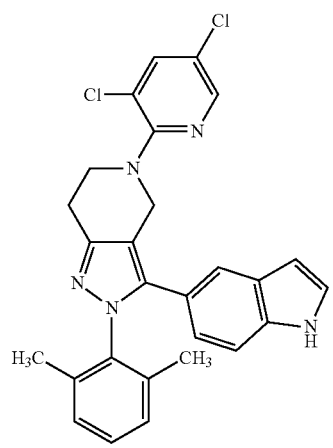 [SMILES: Cc1cccc(C)c1-n1nc2c(c1-c1ccc3[nH]ccc3c1)CN(c1ncc(Cl)cc1Cl)CC2] | +++ |
| 1.198 | 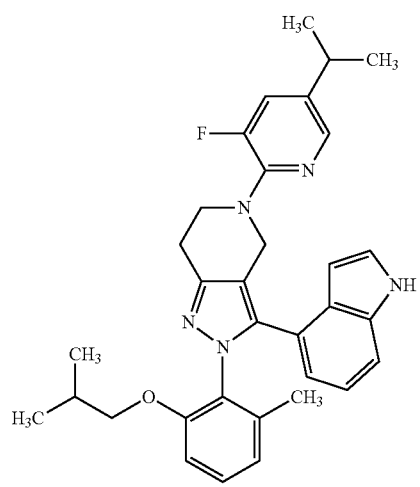 [SMILES: Cc1cccc(OCC(C)C)c1-n1nc2c(c1-c1cccc3[nH]ccc13)CN(c1ncc(C(C)C)cc1F)CC2] | +++ |

TABLE 3-continued

Structure & Biological Activity of Specific Embodiments

| Compound | Structure | Mig IC50 (nM) |
|---|---|---|
| 1.199 | 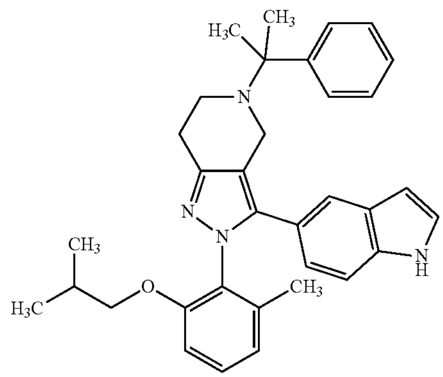 [SMILES: Cc1cccc(OCC(C)C)c1-n1nc2c(c1-c1ccc3[nH]ccc3c1)CN(C(C)(C)c1ccccc1)CC2] | ++++ |
| 1.200 | 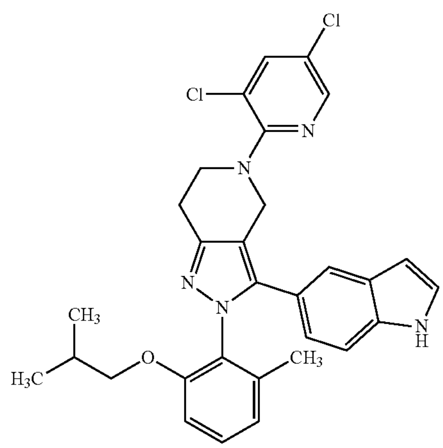 [SMILES: Cc1cccc(OCC(C)C)c1-n1nc2c(c1-c1ccc3[nH]ccc3c1)CN(c1ncc(Cl)cc1Cl)CC2] | ++++ |
| 1.201 | 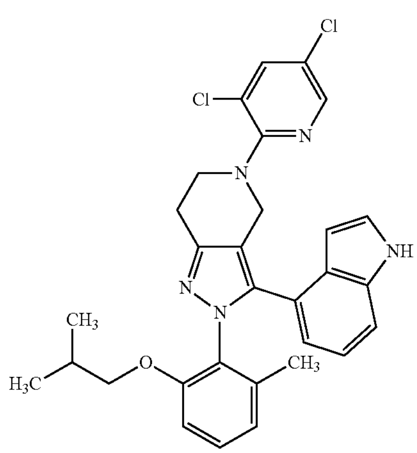 [SMILES: Cc1cccc(OCC(C)C)c1-n1nc2c(c1-c1cccc3[nH]ccc13)CN(c1ncc(Cl)cc1Cl)CC2] | +++ |

TABLE 3-continued
Structure & Biological Activity of Specific Embodiments
| Compound | Structure | Mig IC50 (nM) |
| --- | --- | --- |
| 1.202 | 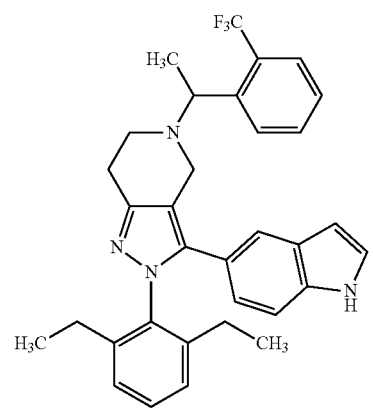 [SMILES: CCc1cccc(CC)c1-n1nc2c(c1-c1ccc3[nH]ccc3c1)CN(C(C)c1ccccc1C(F)(F)F)CC2] | +++ |
| 1.203 | 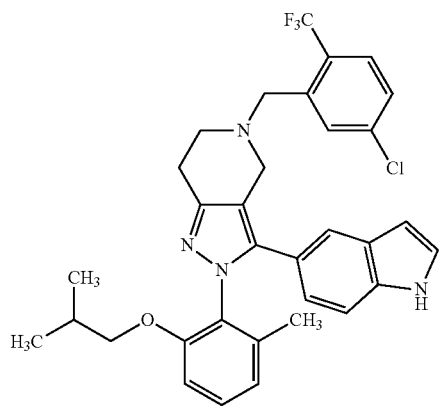 [SMILES: Cc1cccc(OCC(C)C)c1-n1nc2c(c1-c1ccc3[nH]ccc3c1)CN(Cc1cc(Cl)ccc1C(F)(F)F)CC2] | +++ |
| 1.204 | 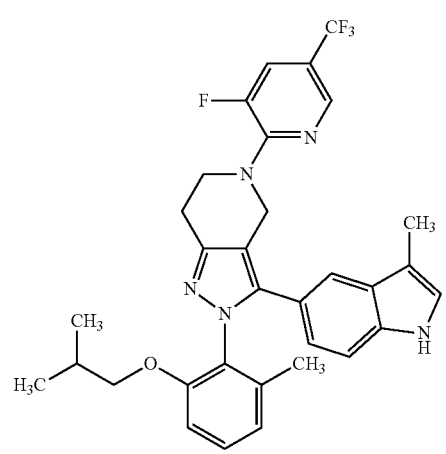 [SMILES: Cc1cccc(OCC(C)C)c1-n1nc2c(c1-c1ccc3[nH]cc(C)c3c1)CN(c1ncc(C(F)(F)F)cc1F)CC2] | ++ |

TABLE 3-continued

Structure & Biological Activity of Specific Embodiments

| Compound | Structure | Mig IC50 (nM) |
|---|---|---|
| 1.205 | 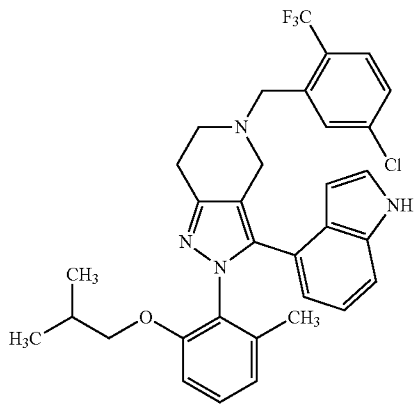 [SMILES: Cc1cccc(OCC(C)C)c1-n1nc2c(c1-c1cccc3[nH]ccc13)CN(Cc1cc(Cl)ccc1C(F)(F)F)CC2] | +++ |
| 1.206 | 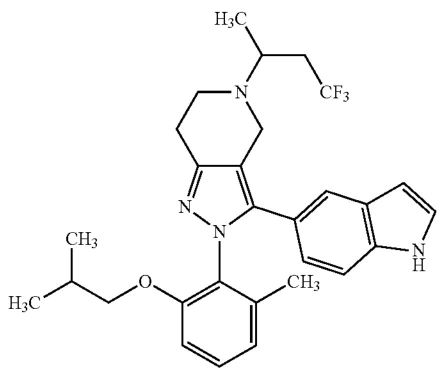 [SMILES: Cc1cccc(OCC(C)C)c1-n1nc2c(c1-c1ccc3[nH]ccc3c1)CN(C(C)CC(F)(F)F)CC2] | +++ |
| 1.207 | 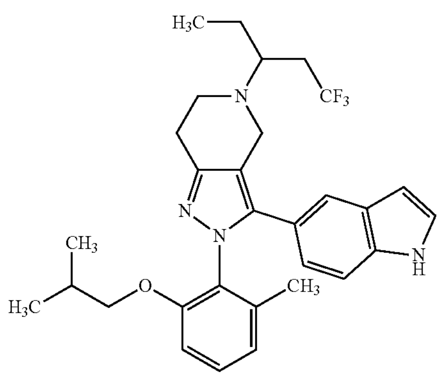 [SMILES: CCC(CC(F)(F)F)N1CCc2nn(-c3c(C)cccc3OCC(C)C)c(-c3ccc4[nH]ccc4c3)c2C1] | +++ |
| 1.208 | 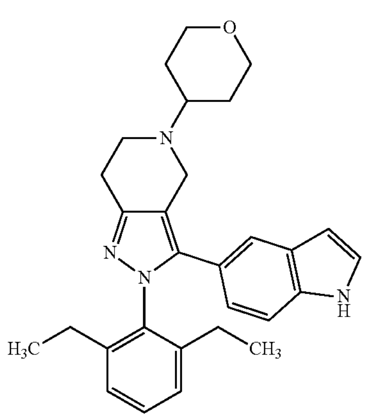 [SMILES: CCc1cccc(CC)c1-n1nc2c(c1-c1ccc3[nH]ccc3c1)CN(C1CCOCC1)CC2] | ++ |

TABLE 3-continued

Structure & Biological Activity of Specific Embodiments

| Compound | Structure | Mig IC50 (nM) |
|---|---|---|
| 1.209 | 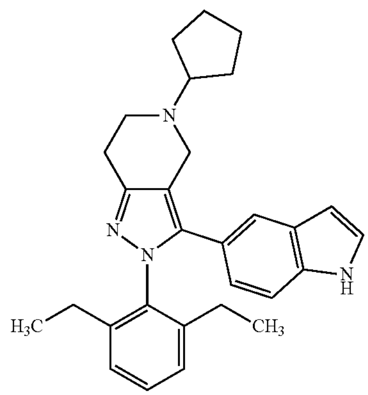 [SMILES: CCc1cccc(CC)c1-n1nc2c(c1-c1ccc3[nH]ccc3c1)CN(C1CCCC1)CC2] | +++ |
| 1.210 | 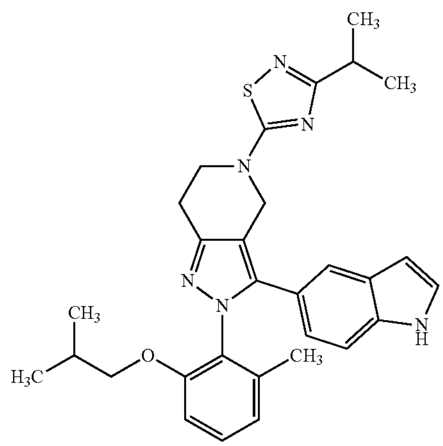 [SMILES: Cc1cccc(OCC(C)C)c1-n1nc2c(c1-c1ccc3[nH]ccc3c1)CN(c1nc(C(C)C)ns1)CC2] | +++ |
| 1.211 | 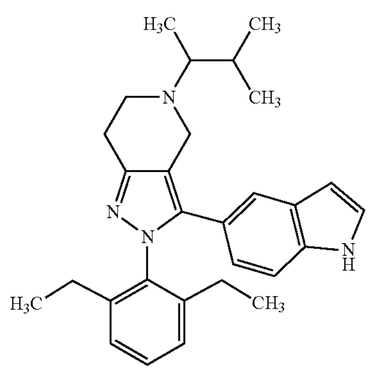 [SMILES: CCc1cccc(CC)c1-n1nc2c(c1-c1ccc3[nH]ccc3c1)CN(C(C)C(C)C)CC2] | +++ |
| 1.212 | 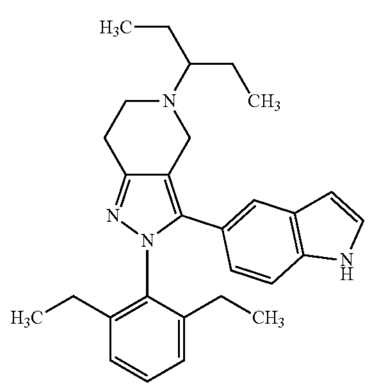 [SMILES: CCc1cccc(CC)c1-n1nc2c(c1-c1ccc3[nH]ccc3c1)CN(C(CC)CC)CC2] | ++++ |

TABLE 3-continued

Structure & Biological Activity of Specific Embodiments

| Compound | Structure | Mig IC50 (nM) |
|---|---|---|
| 1.213 | 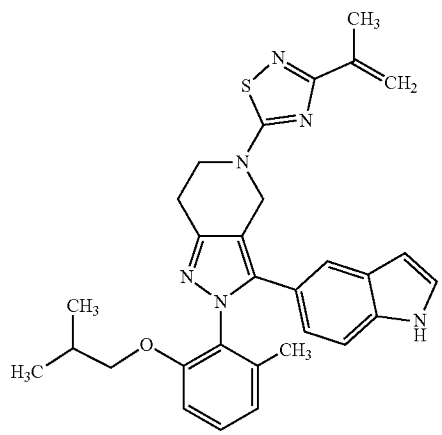 [SMILES: C=C(C)c1nsc(N2CCc3nn(-c4c(C)cccc4OCC(C)C)c(-c4ccc5[nH]ccc5c4)c3C2)n1] | +++ |
| 1.214 | 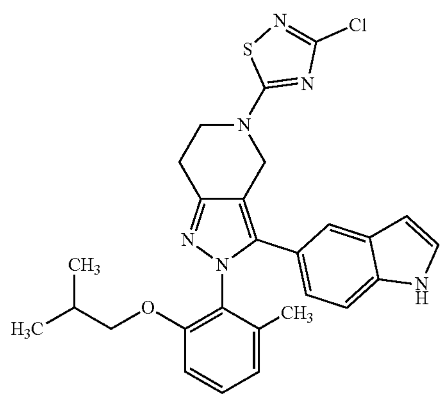 [SMILES: Cc1cccc(OCC(C)C)c1-n1nc2c(c1-c1ccc3[nH]ccc3c1)CN(c1nc(Cl)ns1)CC2] | +++ |
| 1.215 | 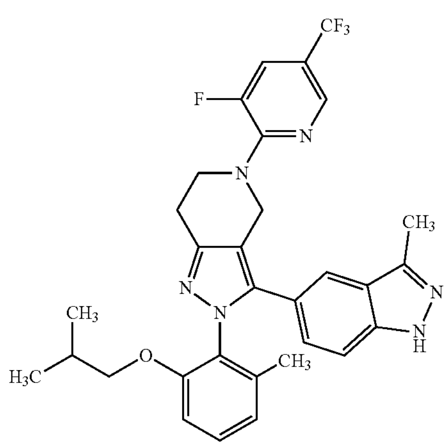 [SMILES: Cc1cccc(OCC(C)C)c1-n1nc2c(c1-c1ccc3[nH]nc(C)c3c1)CN(c1ncc(C(F)(F)F)cc1F)CC2] | + |

TABLE 3-continued
Structure & Biological Activity of Specific Embodiments
| Compound | Structure | Mig IC50 (nM) |
|---|---|---|
| 1.216 | 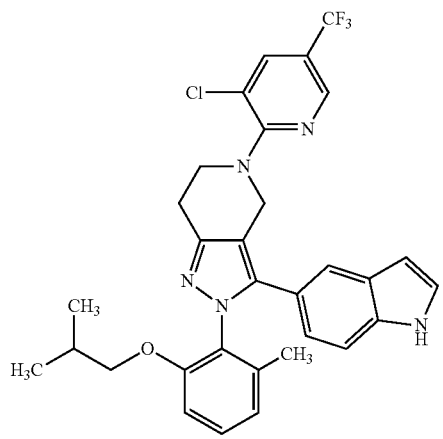 [SMILES: Cc1cccc(OCC(C)C)c1-n1nc2c(c1-c1ccc3[nH]ccc3c1)CN(c1ncc(C(F)(F)F)cc1Cl)CC2] | +++ |
| 1.217 | 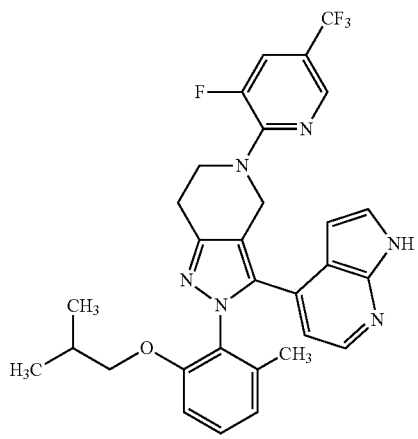 [SMILES: Cc1cccc(OCC(C)C)c1-n1nc2c(c1-c1ccnc3[nH]ccc13)CN(c1ncc(C(F)(F)F)cc1F)CC2] | ++ |
| 1.218 | 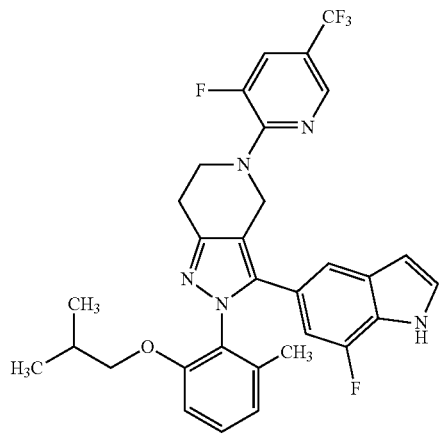 [SMILES: Cc1cccc(OCC(C)C)c1-n1nc2c(c1-c1cc(F)c3[nH]ccc3c1)CN(c1ncc(C(F)(F)F)cc1F)CC2] | ++++ |

TABLE 3-continued
Structure & Biological Activity of Specific Embodiments
| Compound | Structure | Mig IC50 (nM) |
|---|---|---|
| 1.219 | 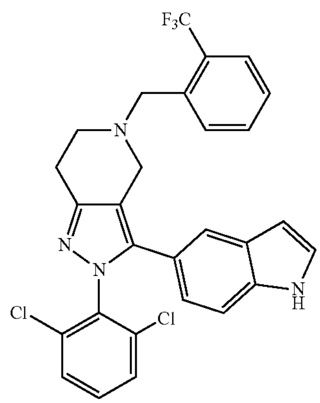 [SMILES: FC(F)(F)c1ccccc1CN1CCc2nn(-c3c(Cl)cccc3Cl)c(-c3ccc4[nH]ccc4c3)c2C1] | +++ |
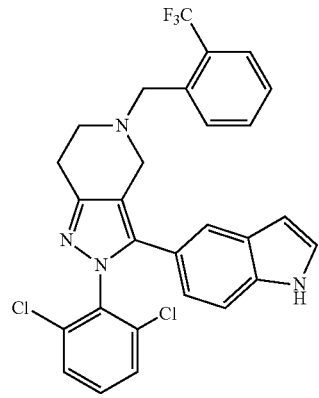
| 1.220 | | +++ |
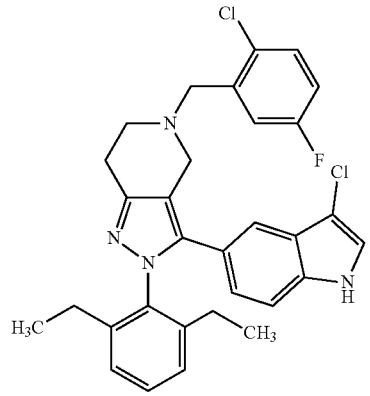 [SMILES: CCc1cccc(CC)c1-n1nc2c(c1-c1ccc3[nH]cc(Cl)c3c1)CN(Cc1cc(F)ccc1Cl)CC2]
| 1.221 | | +++ |
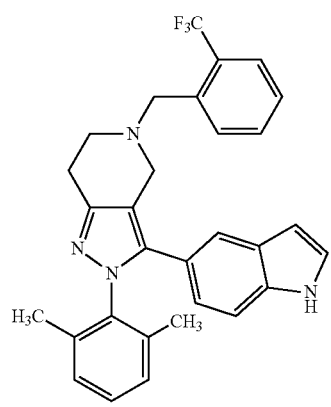 [SMILES: Cc1cccc(C)c1-n1nc2c(c1-c1ccc3[nH]ccc3c1)CN(Cc1ccccc1C(F)(F)F)CC2]

TABLE 3-continued
Structure & Biological Activity of Specific Embodiments
| Compound | Structure | Mig IC50 (nM) |
|---|---|---|
| 1.222 | 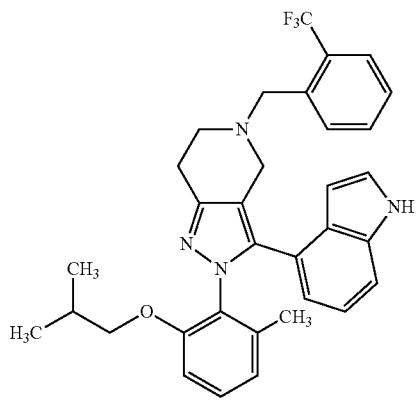 [SMILES: Cc1cccc(OCC(C)C)c1-n1nc2c(c1-c1cccc3[nH]ccc13)CN(Cc1ccccc1C(F)(F)F)CC2] | +++ |
| 1.223 | 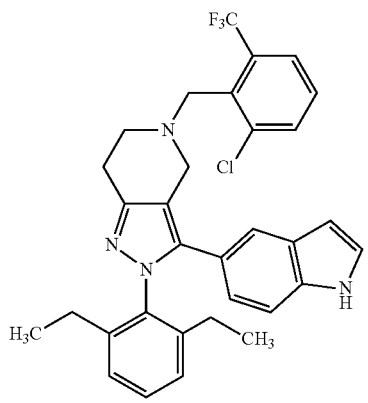 [SMILES: CCc1cccc(CC)c1-n1nc2c(c1-c1ccc3[nH]ccc3c1)CN(Cc1c(Cl)cccc1C(F)(F)F)CC2] | ++++ |
| 1.224 | 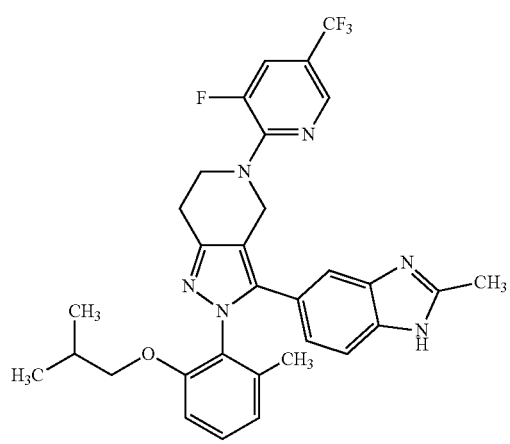 [SMILES: Cc1nc2cc(-c3c4c(nn3-c3c(C)cccc3OCC(C)C)CCN(c3ncc(C(F)(F)F)cc3F)C4)ccc2[nH]1] | + |

TABLE 3-continued
Structure & Biological Activity of Specific Embodiments
| Compound | Structure | Mig IC50 (nM) |
|---|---|---|
| 1.225 | 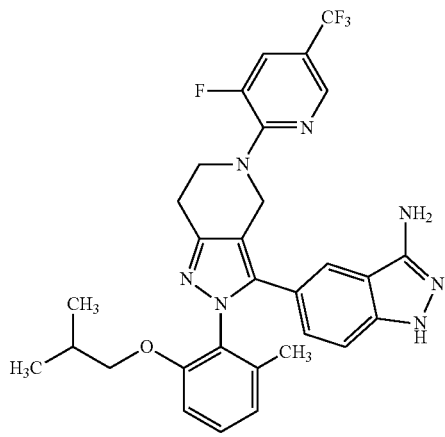 [SMILES: Cc1cccc(OCC(C)C)c1-n1nc2c(c1-c1ccc3[nH]nc(N)c3c1)CN(c1ncc(C(F)(F)F)cc1F)CC2] | + |
| 1.226 | 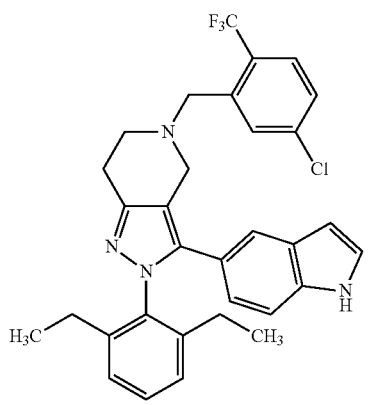 | ++++ |
| 1.227 | 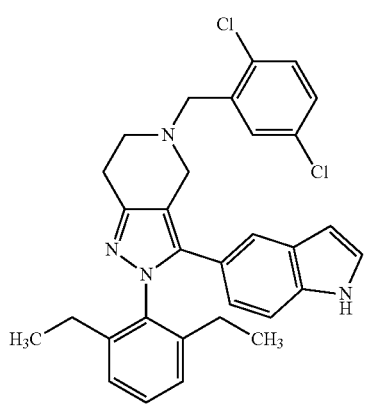 | ++++ |

TABLE 3-continued

Structure & Biological Activity of Specific Embodiments

| Compound | Structure | Mig IC50 (nM) |
|---|---|---|
| 1.228 | 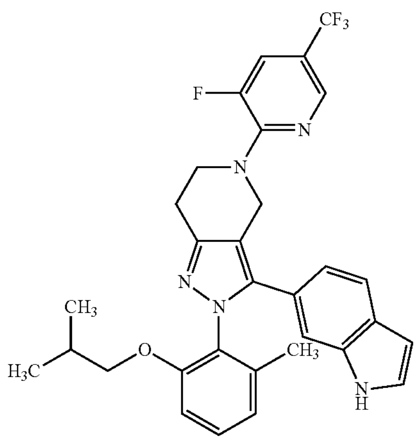 [SMILES: Cc1cccc(OCC(C)C)c1-n1nc2c(c1-c1ccc3cc[nH]c3c1)CN(c1ncc(C(F)(F)F)cc1F)CC2] | ++ |
| 1.229 | 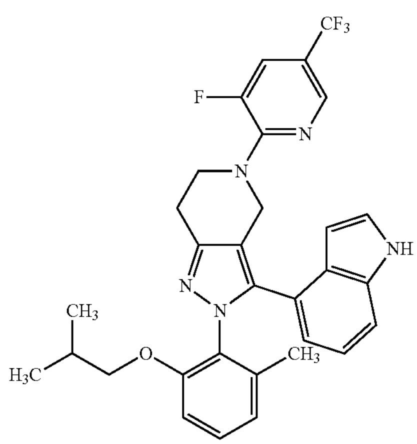 [SMILES: Cc1cccc(OCC(C)C)c1-n1nc2c(c1-c1cccc3[nH]ccc13)CN(c1ncc(C(F)(F)F)cc1F)CC2] | +++ |
| 1.230 | 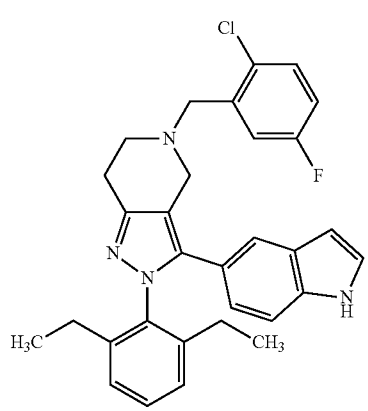 [SMILES: CCc1cccc(CC)c1-n1nc2c(c1-c1ccc3[nH]ccc3c1)CN(Cc1cc(F)ccc1Cl)CC2] | ++++ |

TABLE 3-continued
Structure & Biological Activity of Specific Embodiments
| Compound | Structure | Mig IC50 (nM) |
|---|---|---|
| 1.231 | 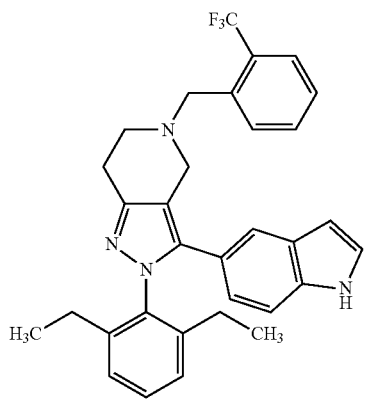 [SMILES: CCc1cccc(CC)c1-n1nc2c(c1-c1ccc3[nH]ccc3c1)CN(Cc1ccccc1C(F)(F)F)CC2] | ++++ |
| 1.232 | 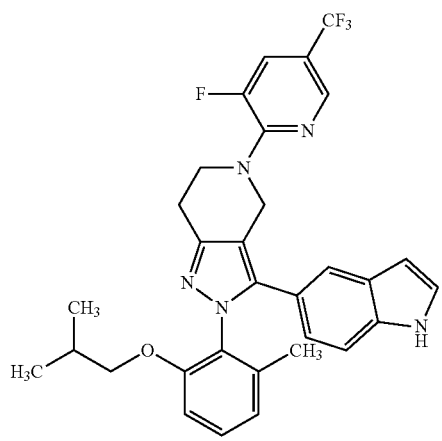 [SMILES: Cc1cccc(OCC(C)C)c1-n1nc2c(c1-c1ccc3[nH]ccc3c1)CN(c1ncc(C(F)(F)F)cc1F)CC2] | ++++ |
| 1.233 | 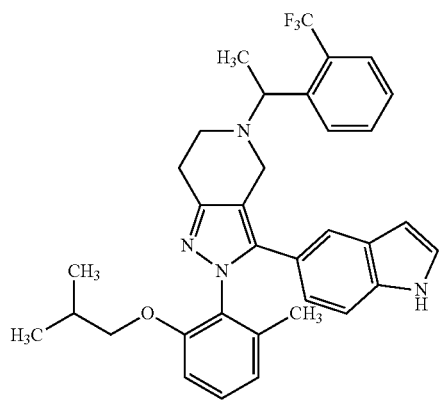 [SMILES: Cc1cccc(OCC(C)C)c1-n1nc2c(c1-c1ccc3[nH]ccc3c1)CN(C(C)c1ccccc1C(F)(F)F)CC2] | ++++ |

TABLE 3-continued

Structure & Biological Activity of Specific Embodiments

| Compound | Structure | Mig IC50 (nM) |
|---|---|---|
| 1.234 | 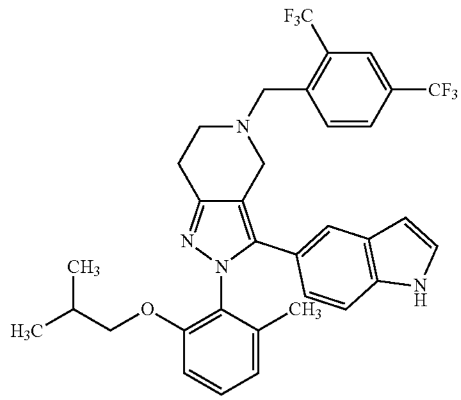 [SMILES: Cc1cccc(OCC(C)C)c1-n1nc2c(c1-c1ccc3[nH]ccc3c1)CN(Cc1ccc(C(F)(F)F)cc1C(F)(F)F)CC2] | +++ |
| 1.235 | 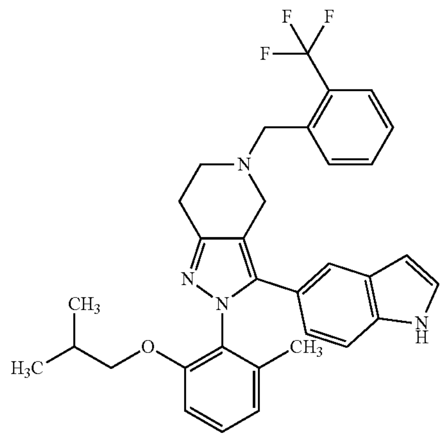 [SMILES: Cc1cccc(OCC(C)C)c1-n1nc2c(c1-c1ccc3[nH]ccc3c1)CN(Cc1ccccc1C(F)(F)F)CC2] | ++++ |
| 1.236 | 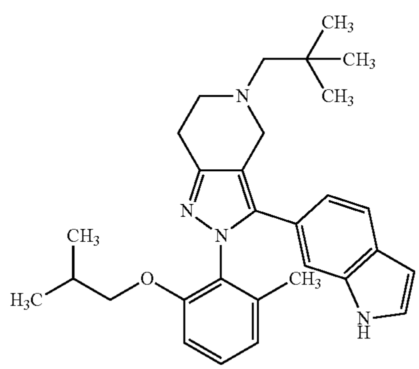 [SMILES: Cc1cccc(OCC(C)C)c1-n1nc2c(c1-c1ccc3cc[nH]c3c1)CN(CC(C)(C)C)CC2] | ++ |
| 1.237 | 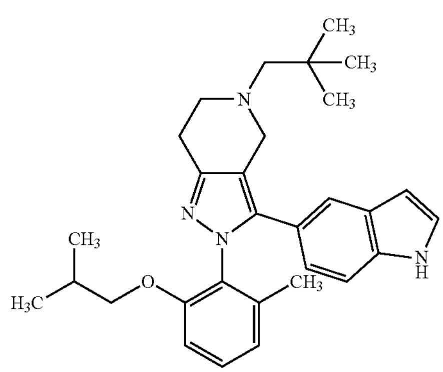 [SMILES: Cc1cccc(OCC(C)C)c1-n1nc2c(c1-c1ccc3[nH]ccc3c1)CN(CC(C)(C)C)CC2] | ++++ |

TABLE 3-continued

Structure & Biological Activity of Specific Embodiments

| Compound | Structure | Mig IC50 (nM) |
|---|---|---|
| 1.238 | 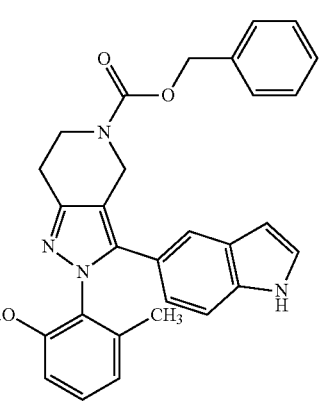 | +++ |
| 1.239 | 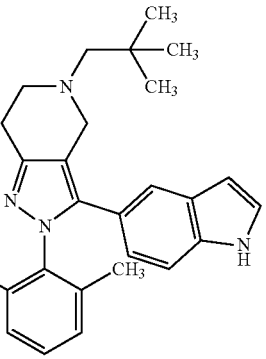 | +++ |
| 1.240 | 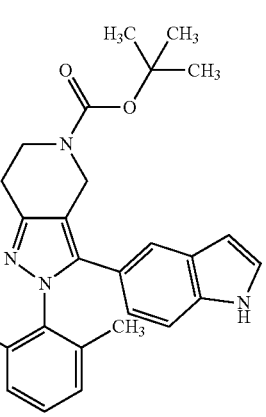 | +++ |

While particular embodiments of this invention are described herein, upon reading the description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A pharmaceutical composition comprising a pharmaceutically acceptable carrier and a compound of Formula (I)

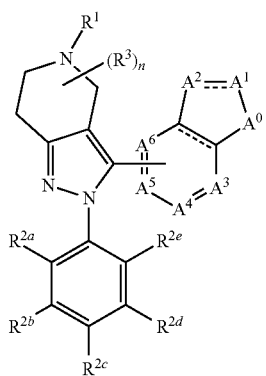

or a pharmaceutically acceptable salt thereof, wherein,
the ring portion having $A^0$, $A^1$, $A^2$, $A^3$, $A^4$, $A^5$, and $A^6$ as ring vertices is selected from the group consisting of

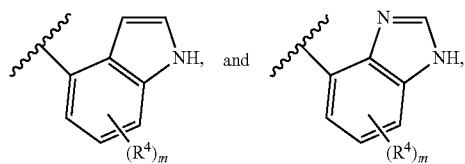

wherein m is 0, 1, 2, or 3
$R^1$ is selected from the group consisting of

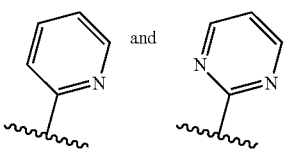

wherein $R^1$ is optionally substituted with 1 to 4 $R^5$ substituents;
$R^{2a}$ and $R^{2e}$ are each independently selected from the group consisting of $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, CN, and halogen;
$R^{2b}$, $R^{2c}$, and $R^{2d}$ are each independently selected from the group consisting of hydrogen, $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, cyano, and halogen;
each $R^3$ is independently selected from the group consisting of $C_{1-4}$ alkyl, $C_{1-4}$ haloalkyl and hydroxyl, and optionally two $R^3$ groups on the same carbon atom are combined to form oxo (=O);
each $R^4$ is independently selected from the group consisting of $C_{1-6}$ alkyl, $C_{1-6}$ alkoxy, $C_{1-6}$ hydroxyalkyl, $C_{1-6}$ haloalkyl, $C_{1-6}$ haloalkoxy, —O—$C_{1-6}$ haloalkyl, halogen, cyano, hydroxyl, —S—$C_{1-6}$ alkyl, —$C_{1-6}$ alkyl-O—$C_{1-6}$ alkyl, —$C_{1-6}$ alkyl-S—$C_{1-6}$ alkyl, —$NR^{4a}R^{4b}$, —$CONR^{4a}R^{4b}$, —$CO_2R^{4a}$, —$COR^{4a}$, —$OC(O)NR^{4a}R^{4b}$, —$NR^{4a}C(O)R^{4b}$, —$NR^{4a}C(O)_2R^{4b}$, and $NR^{4a}$—$C(O)NR^{4a}R^{4b}$;
each $R^{4a}$ and $R^{4b}$ is independently selected from the group consisting of hydrogen, $C_{1-4}$ alkyl, and $C_{1-4}$ haloalkyl;
each $R^5$ is independently selected from the group consisting of $C_{1-8}$ alkyl, $C_{1-8}$ alkoxy, $C_{1-8}$ haloalkyl, $C_{1-8}$ haloalkoxy, $C_{1-8}$ hydroxyalkyl, —$C_{1-8}$ alkyl-heterocycloalkyl, —$C_{1-8}$ alkyl-$C_{3-8}$ cycloalkyl, $C_{3-6}$ cycloalkyl, heterocycloalkyl, halogen, OH, $C_{2-8}$ alkenyl, $C_{2-8}$ alkynyl, CN, $C(O)R^{5a}$, —$NR^{5b}C(O)R^{5a}$—$CONR^{5a}R^{5b}$, $NR^{5a}R^{5b}$, —$C_{1-8}$ alkylene-$NR^{5a}R^{5b}$, —S—$C_{1-6}$alkyl, —$C_{1-6}$ alkyl-O—$C_{1-6}$ alkyl, —$C_{1-6}$ alkyl-S—$C_{1-6}$ alkyl, —$OC(O)NR^{5a}R^{5b}$, —$NR^{5a}C(O)_2R^{5b}$ —$NR^{5a}$—$C(O)NR^{5b}R^{5b}$ and $CO_2R^{5a}$; wherein the heterocycloalkyl group is a 4 to 8 membered ring having from 1 to 3 heteroatoms as ring vertices selected from N, O and S;
wherein each $R^{5a}$ and $R^{5b}$ is independently selected from the group consisting of hydrogen, $C_{1-4}$ alkyl, and $C_{1-4}$ haloalkyl, or when attached to the same nitrogen atom $R^{5a}$ and $R^{5b}$ are combined with the nitrogen atom to form a five or six-membered ring having from 0 to 1 additional heteroatoms as ring vertices selected from N, O, or S; and
the subscript n is 0, 1, 2 or 3.

2. The pharmaceutical composition of claim 1, wherein each $R^4$ is independently selected from the group consisting of $C_{1-4}$alkyl, $C_{1-4}$alkoxy, $C_{1-6}$ hydroxyalkyl, $C_{1-4}$ haloalkyl, halogen, cyano, hydroxyl, —$NH_2$, —$CONR^{4a}R^{4b}$, and —$CO_2R^{4a}$; and wherein the $R^4$ substituents, when present, are attached to any suitable carbon ring vertex of the bicyclic heteroaryl.

3. The pharmaceutical composition of claim 1, wherein the ring portion having $A^0$, $A^1$, $A^2$, $A^3$, $A^4$, $A^5$, and $A^6$ as ring vertices is selected from the group consisting of:

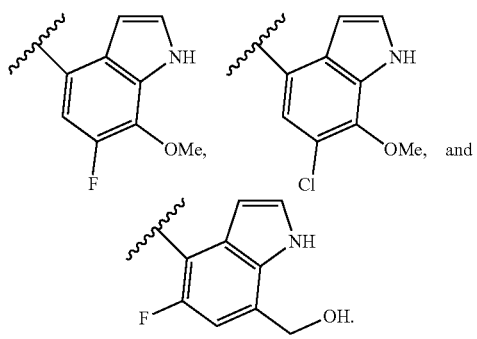

4. The pharmaceutical composition of claim 1, wherein each $R^5$ is independently selected from the group consisting of $C_{1-8}$ alkyl, $C_{1-8}$ alkoxy, $C_{1-8}$ haloalkyl, $C_{1-8}$ haloalkoxy, $C_{1-8}$ hydroxyalkyl, —$C_{1-8}$ alkyl-heterocycloalkyl, $C_{3-6}$ cycloalkyl, halogen, —$CONR^{5a}R^{5b}$, —$NR^{5a}R^{5b}$, —$C_{1-8}$ alkylene-$NR^{5a}R^{5b}$, and —$CO_2R^{5a}$, each $R^{5a}$ and $R^{5b}$ is independently selected from the group consisting of hydrogen and $C_{1-4}$ alkyl, or when attached to the same nitrogen atom can be combined with the nitrogen atom to form a 5 or 6-membered ring; and the heterocycloalkyl group is a 4 to 6 membered ring having from 1 to 3 heteroatoms as ring vertices selected from N, O and S.

5. The pharmaceutical composition of claim 1, wherein R¹ is selected from the group consisting of

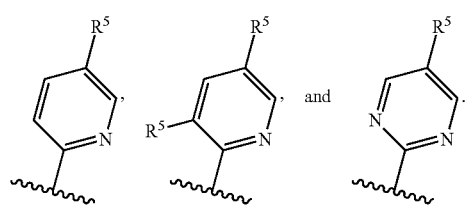

6. The pharmaceutical composition of claim 5, wherein each R⁵ is independently selected from the group consisting of cyclopropyl, isopropyl, isopropyloxy, OMe, Me, Cl, F, —CONH₂, —CF₃, —O—CF₃,

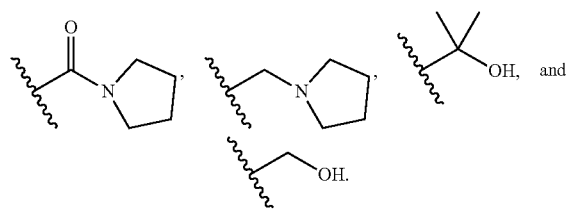

7. The pharmaceutical composition of claim 1, wherein R¹ is selected from the group consisting of

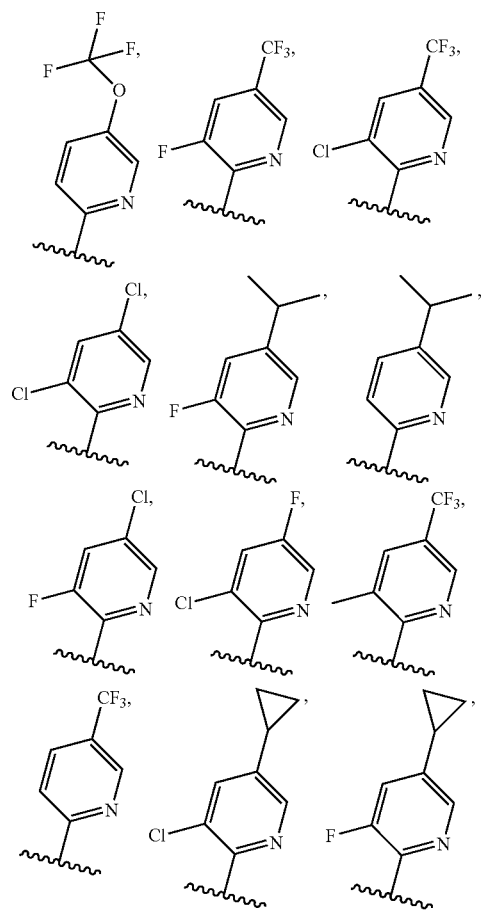

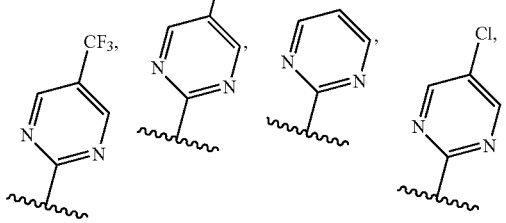

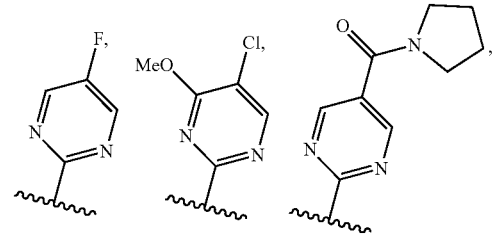

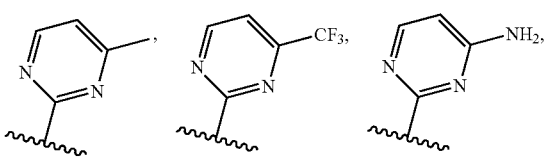

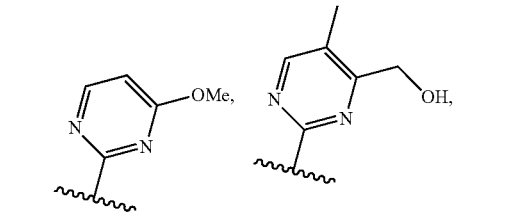

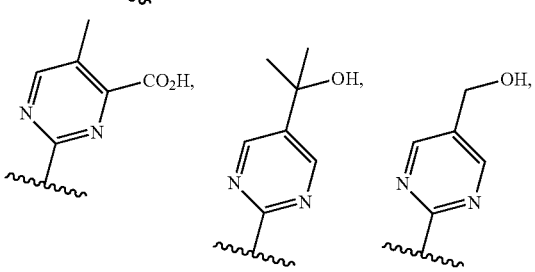

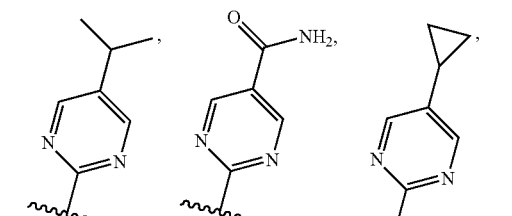

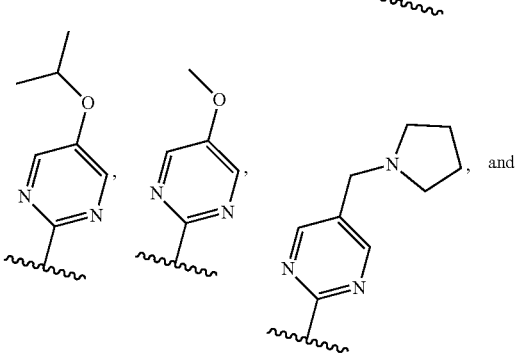

-continued

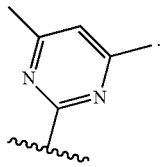

8. The pharmaceutical composition of claim 1, wherein $R^1$ is

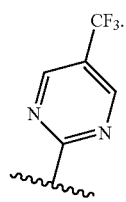

9. The pharmaceutical composition of claim 1, wherein $R^{2b}$, $R^{2d}$, and $R^{2d}$ are each H.

10. The pharmaceutical composition of claim 1, wherein $R^{2a}$ and $R^{2e}$ are each independently selected from the group consisting of $C_{1-6}$ alkyl, $C_{1-6}$ alkoxy, $C_{1-6}$ haloalkyl, —O—$C_{1-6}$ haloalkyl, and halogen.

11. The pharmaceutical composition of claim 1, wherein $R^2$a and $R^{2e}$ are each independently selected from the group consisting of Me, Et, F, Cl, OMe, OCF$_3$, and

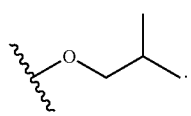

12. The pharmaceutical composition of claim 1, wherein

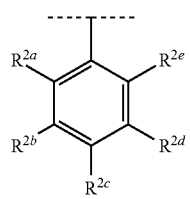

is selected from the group consisting of,

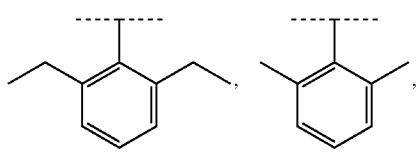

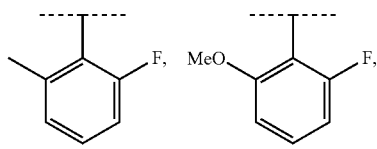

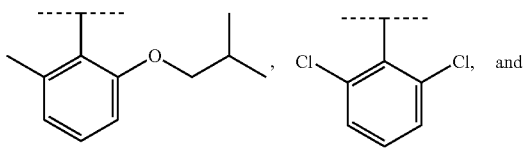

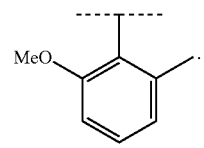

13. The pharmaceutical composition of claim 1, wherein n is 0.

14. The pharmaceutical composition of claim 1, wherein the compound has a structure represented by Formula (Ic):

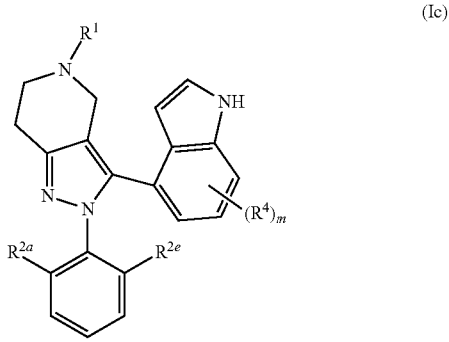

(Ic)

wherein m is 0, 1 or 2 and wherein the $R^4$ substituents may be attached to any suitable carbon ring vertex of the bicyclic heteroaryl.

15. The pharmaceutical composition of claim 14, wherein $R^{2a}$ and $R^{2e}$ are both ethyl.

16. A method for treating a mammal suffering from or susceptible to a disease selected from the group consisting of sepsis, septic shock, inflammatory bowel disease, ischemia-reperfusion injury, and lupus nephritis, comprising administering to the mammal an effective amount of a pharmaceutical composition of claim 1.

17. The pharmaceutical composition of claim 1, having the structure

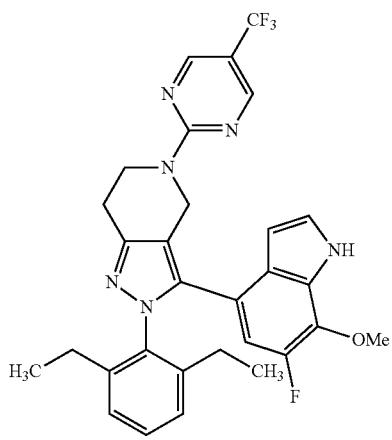 [SMILES: CCc1cccc(CC)c1-n1nc2c(c1-c1cc(F)c(OC)c3[nH]ccc13)CN(c1ncc(C(F)(F)F)cn1)CC2]

or a pharmaceutically acceptable salt thereof.

18. The pharmaceutical composition of claim 1, having the structure

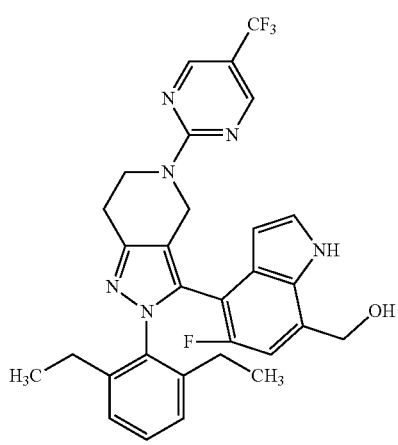 [SMILES: CCc1cccc(CC)c1-n1nc2c(c1-c1c(F)cc(CO)c3[nH]ccc13)CN(c1ncc(C(F)(F)F)cn1)CC2]

or a pharmaceutically acceptable salt thereof.

19. The pharmaceutical composition of claim 1, having the structure

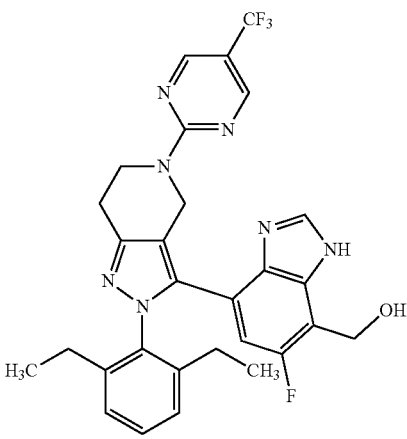 [SMILES: CCc1cccc(CC)c1-n1nc2c(c1-c1cc(F)c(CO)c3[nH]cnc13)CN(c1ncc(C(F)(F)F)cn1)CC2]

or a pharmaceutically acceptable salt thereof.

20. The pharmaceutical composition of claim 1, having the structure

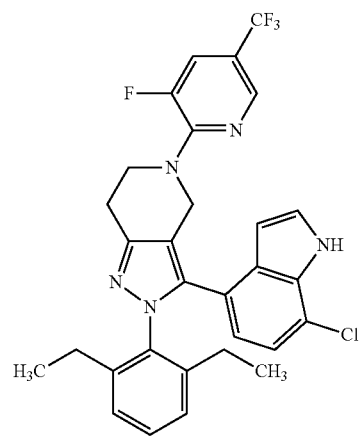 [SMILES: CCc1cccc(CC)c1-n1nc2c(c1-c1ccc(Cl)c3[nH]ccc13)CN(c1ncc(C(F)(F)F)cc1F)CC2]

or a pharmaceutically acceptable salt thereof.

* * * * *

UNITED STATES PATENT AND TRADEMARK OFFICE
CERTIFICATE OF CORRECTION

PATENT NO. : 11,773,091 B2
APPLICATION NO. : 17/735283
DATED : October 3, 2023
INVENTOR(S) : Fan et al.

It is certified that error appears in the above-identified patent and that said Letters Patent is hereby corrected as shown below:

In the Claims

Claim 1, Column 430, Line 5, please insert -- - -- after and, and before $NR^{4a}$.

Claim 1, Column 430, Lines 13 and 14, please insert -- - -- after $-CONR^{5a}R^{5b}$, and before $NR^{5a}R^{5b}$.

Signed and Sealed this
Fourteenth Day of November, 2023

Katherine Kelly Vidal
*Director of the United States Patent and Trademark Office*